US012790337B2

(12) United States Patent
Inglese et al.

(10) Patent No.: US 12,790,337 B2
(45) Date of Patent: Nov. 10, 2026

(54) METHOTREXATE ANALOGS AND METHODS OF USE

(71) Applicant: The United States of America, as represented by the Secretary, Dept. of Health and Human Services, Bethesda, MD (US)

(72) Inventors: James Inglese, Bethesda, MD (US); Ganesha Rai Bantukallu, Bethesda, MD (US); Sandeep Rana, Bethsda, MD (US); Laurence Lamy, Bethesda, MD (US)

(73) Assignee: The United States of America as represented by the Secretary, Department of Health and Human Services, Bethesda, MD (US)

( * ) Notice: Subject to any disclaimer, the term of this patent is extended or adjusted under 35 U.S.C. 154(b) by 841 days.

(21) Appl. No.: 18/011,288

(22) PCT Filed: Jun. 22, 2021

(86) PCT No.: PCT/US2021/038441

§ 371 (c)(1),
(2) Date: Dec. 19, 2022

(87) PCT Pub. No.: WO2021/262693

PCT Pub. Date: Dec. 30, 2021

(65) Prior Publication Data

US 2023/0406859 A1 Dec. 21, 2023

Related U.S. Application Data

(60) Provisional application No. 63/042,262, filed on Jun. 22, 2020.

(51) Int. Cl.

| | |
|---|---|
| ***C07D 487/04*** | (2006.01) |
| ***A61P 31/12*** | (2006.01) |
| ***A61P 35/00*** | (2006.01) |
| ***A61P 37/00*** | (2006.01) |
| ***C07D 409/14*** | (2006.01) |

(52) U.S. Cl.

CPC ............ *C07D 487/04* (2013.01); *A61P 31/12* (2018.01); *A61P 35/00* (2018.01); *A61P 37/00* (2018.01); *C07D 409/14* (2013.01)

(58) Field of Classification Search

CPC .................................................... C07D 487/04
USPC .......................................................... 514/262
See application file for complete search history.

(56) References Cited

U.S. PATENT DOCUMENTS

2021/0369853 A1 12/2021 Cao et al.

FOREIGN PATENT DOCUMENTS

| | | | |
|---|---|---|---|
| WO | WO 2016/105518 | 6/2016 | |
| WO | WO 2020/073930 | 4/2020 | |
| WO | WO-2021147697 A1 * | 7/2021 | ........... C07K 5/1013 |

OTHER PUBLICATIONS

Folic Acid (CAS 59-30-3) CAS Registry File Accessed Jun. 9, 2025 from STN, entered into STN Nov. 16, 1984 (Year: 1984).*

WO 2021147697 A1 English Translation, Google Patents, 2021 (Year: 2021).*

International Search Report from International Application No. PCT/US2021/038441 dated Aug. 30, 2021 (6 pages).

Khan et al., "Methotrexate: a detailed review on drug delivery and clinical aspects," *Expert Opinion on Drug Delivery* 9(2):151-169, 2012 [Abstract Only].

Krönke et al., "Lenalidomide Causes Selective Degradation of IKZF1 and IKZF3 in Multiple Myeloma Cells," *Science* 343(6168):301-305, Jan. 17, 2014.

Liu et al., "Cancer Selective Target Degradation by Folate-Caged PROTACs," *Journal of the American Chemical Society* 143:7380-7387, 2021.

Lu et al., "The Myeloma Drug Lenalidomide Promotes the Cereblon-Dependent Destruction of Ikaros Proteins," *Science* 343(6168):305-309, Jan. 17, 2014.

Sakamoto et al., "Protacs: Chimeric molecules that target proteins to the Skp1-Cullin-F box complex for ubiquitination and degradation," *Proceedings of the National Academy of Sciences* 98(15):8554-8559, Jul. 17, 2021.

Written Opinion from International Application No. PCT/US2021/038441 dated Aug. 30, 2021 (12 pages).

* cited by examiner

*Primary Examiner* — Jeffrey H Murray
*Assistant Examiner* — Rilla Marie Samsell
(74) *Attorney, Agent, or Firm* — Klarquist Sparkman, LLP

(57) ABSTRACT

Compounds having general formula I

Formula I

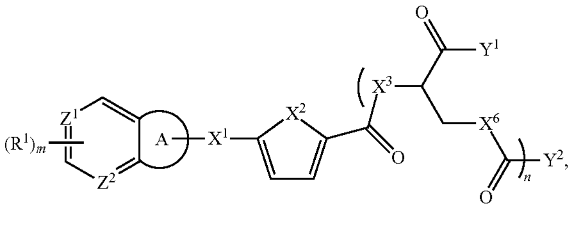

or a pharmaceutically acceptable salt, N-oxide, or hydrate thereof are provided herein. Also provided are methods of making the compounds and methods of their use, including in treatment of cancer, autoimmune disorders, and viral infections.

17 Claims, 14 Drawing Sheets

Specification includes a Sequence Listing.

SEQUENCE LISTING

```
<160> NUMBER OF SEQ ID NOS: 1

<210> SEQ ID NO 1
<211> LENGTH: 11
<212> TYPE: PRT
<213> ORGANISM: Artificial Sequence
<220> FEATURE:
<223> OTHER INFORMATION: HiBiT tag

<400> SEQUENCE: 1

Val Ser Gly Trp Arg Leu Phe Lys Lys Ile Ser
1               5                   10
```

METHOTREXATE ANALOGS AND METHODS OF USE

CROSS REFERENCE TO RELATED APPLICATIONS

This is the U.S. National Stage of International Application No. PCT/US2021/038441, filed Jun. 22, 2021, which was published in English under PCT Article 21(2), which in turn claims the benefit of U.S. Provisional Application No. 63/042,262, filed Jun. 22, 2020, which is incorporated herein by reference in its entirety.

FIELD

This disclosure relates to methotrexate analogs and methods of their use, particularly for treating cancer, autoimmune disorders, and/or viral infection.

REFERENCE TO AN ELECTRONIC SEQUENCE LISTING

The Sequence Listing is submitted as an ASCII text file in the form of the file named Sequence Listing.txt, which was created on Dec. 16, 2022, and is 578 bytes, which is incorporated by reference herein.

BACKGROUND

Dihydrofolate reductase (DHFR, EC 1.5.1.3) catalyzes the reduction of dihydrofolic acid (DHF) by NADPH to tetrahydrofolic acid (THF), an essential enzyme in the folate pathway. Tetrahydrofolate is a cofactor in several one-carbon transfer reactions which serves as a precursor in amino acid and nucleic acid synthesis. Consequently, DHFR inhibitors such as methotrexate (MTX) and its analogs have been used for several decades as potent anti-cancer agents. In addition, MTX has been used to treat autoimmune disease such as rheumatoid arthritis and psoriasis. DHFR inhibition by MTX resulted in reduced intracellular levels of tetrahydrofolate coenzymes, which resulted in inhibition of thymidylate and purine and DNA biosynthesis. Mechanistically, these folate based drugs undergo polyglutamylation by folylpolyglutamate synthetase (FPGS) in cells that leads to intracellular accumulation of these analogs (Gonen et al., *Drug Resist. Update* 15(4):183-210, 2012). The reduced levels of THF result in lower levels of serine, lower thymidylate levels, and reduced methionine synthesis, which results in arrest of DNA replication. Unfortunately, resistance to MTX has been a major issue including amplification of the gene for DHFR (Schimke *J. Biol. Chem.* 263(13): 5989-5992, 1988; Goker et al., *Blood* 86(2):677-684, 1995), decreased transport of MTX due to impaired transport intracellularly, decreased retention of MTX due to lack for polyglutamylation, and mutated DHFR, which result in weak binding to anti-folates, and increase levels of lysosomal enzymes γ-glutamyl hydrolase, that hydrolyses MTX polyglutamates (Rhee et al. *Cancer Res,* 53(10):2227-2230, 1993).

The PROteolysis TArgeting Chimeras (PROTACs) concept was first reported nearly two decades ago (Sakamoto et al., *Proc. Natl. Acad. Sci. USA* 98(15):8554-8559, 2001). The overall hypothesis was to hijack the cellular quality control machinery to degrade proteins of interest. Conceptually, this strategy involves design of heterobifunctional molecules connected by a flexible linker wherein one part of the molecule binds to the protein of interest and the other part of the molecule binds to an E3 ubiquitin ligase.

SUMMARY

Over the decades thousands of MTX analogs have been made aiming to improve the drug's efficacy and side-effect profile, though MTX remains a mainstay of treatment for highly proliferative disease (Galivan et al., *Proc. Natl. Acad. Sci. USA* 82(9):2598-2602, 1985; Inglese et al., *J. Med. Chem.* 32(5):937-940, 1989; Martinelli et al., *J. Med. Chem.* 22(7):869-874, 1979; Montgomery et al., *J. Med. Chem.* 22(7):862-868, 1979; Rahman et al., *Med. Res. Rev.* 8(1): 95-155, 1988). Provided herein are MTX analogs having the capacity to greatly reduce the cellular concentration of DHFR. The disclosed MTX analogs incorporate the proteasome-targeting properties of E3-ligase small molecule ligands to direct DHFR toward proteasomal degradation.

Disclosed herein are embodiments of MTX analog having a structure according to Formula I Formula I

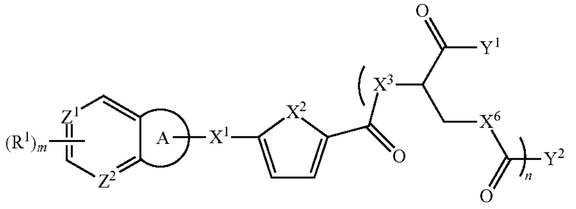

or a pharmaceutically acceptable salt, N-oxide, or hydrate thereof. With respect to Formula I, each of $Z^1$ and $Z^2$ independently is N or CH. Each $R^1$ independently is optionally substituted $C_{1-6}$alkyl, $C_{1-6}$haloalkyl, halogen, OH, cyano, amino, SH, $S(=O)R^b$, or

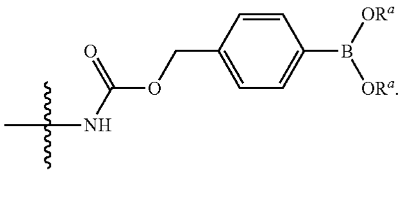

And each $R^a$ independently is H, $C_{1-6}$alkyl, or two $R^a$s together form a 5-membered heterocycloaliphatic ring, optionally substituted with 1-4 alkyl groups. $R^b$ is H, $C_{1-6}$alkyl, or $C_{1-6}$haloalkyl. m is 0, 1, 2, 3 or 4, and in some embodiments, m is 2 or 3, and may be 2. n is 1, 2, 3, 4, or 5, and in some embodiments, n is 1, but in other embodiments, n is 2, 3, 4, or 5.

Ring A is heterocyclyl or aryl, and may be a 5- or 6-membered heterocyclyl, or 6-10-membered aryl. In some embodiments, ring A is phenyl or naphthalyl, and in other embodiments, ring A is pyrazinyl, pyridinyl, pyrrolyl, furyl, or piperazinyl.

Also with respect to Formula I, $X^1$ is $—CH=N—$, $—CH_2NY^3—$, or $—CH_2CHR^2—$, and $R^2$ is H, optionally substituted aliphatic, or $R^2$ together with the atoms to which it is attached, forms a 5-membered optionally substituted heterocyclic ring that is fused to ring A. $X^2$ is S, O or $CH=CR^3$, and each $X^3$ independently is $NR^4$ or $CHR^4$. Each of $Y^1$ and $Y^2$ independently is OH, $OC_{1-6}$alkyl or -Linker-$E_3$ Ligand, and $Y^3$ is —$X^7$-Linker-$E_3$ Ligand or $R^2$, where $X^7$ is $C_{4-8}$alkyl, with the proviso that at least one of $Y^1$, $Y^2$ or $Y^3$ is or comprises -Linker-$E_3$ Ligand.

Each $X^6$ independently is $CH_2$, CHF, or

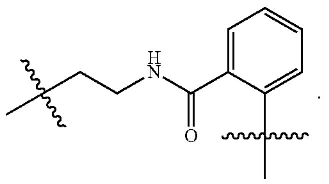 [SMILES: *CCNC(=O)c1ccccc1*]

$R^3$ is H or halogen, and each $R^4$ independently is H or optionally substituted $C_{1-6}$alkyl, $C_{3-6}$cycloalkyl, or $C_{1-6}$haloalkyl, or $R^3$ and $R^4$ together with the atoms to which they are attached, form an optionally substituted heterocyclic ring.

In any embodiments, $E_3$ Ligand is selected from

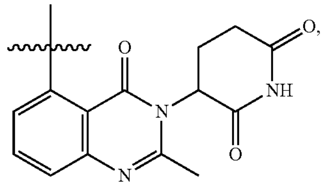

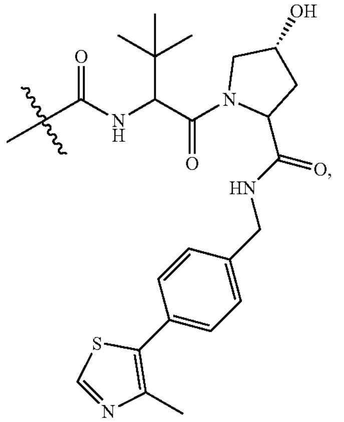

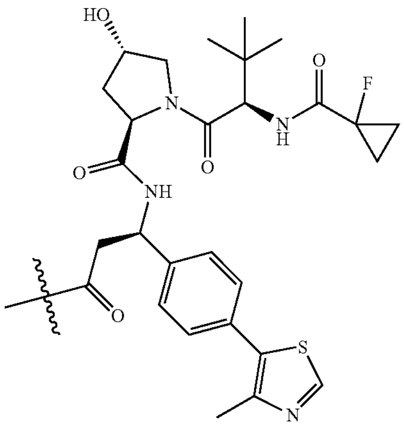

,

-continued

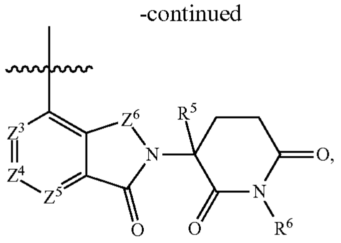

or

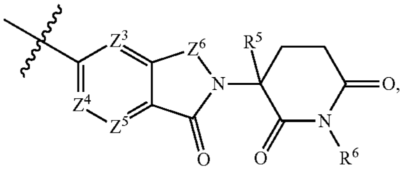

where each of $Z^3$, $Z^4$, and $Z^5$ independently is CH or N; $Z^6$ is $CH_2$ or C═O; R is H, D, $C_{1-6}$alkyl or halogen; and $R^6$ is H, $C_{1-6}$alkyl, —$CO_2B(OH)_2$,

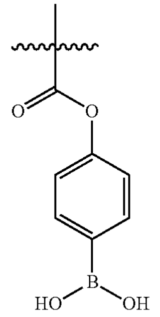

or

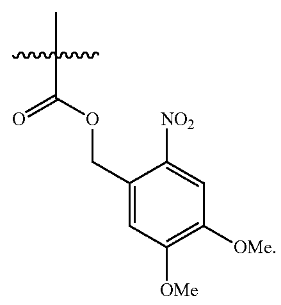

And Linker has a formula

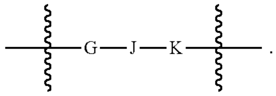

With respect to Linker, G is a bond, $NR^7$, —$NR^7C$(═O)— or $CH_2$, where $R^7$ is H, or optionally substituted $C_{1-4}$alkyl; K is a bond, O, optionally substituted $C_{1-4}$alkyl, NR, C(O)$NR^8$, NHC(O), $NHCO_2CH_2$, $CH_2C(O)NH$, $NHC(O)CH_2O$, $NHC(O)CH_2NH$, $C(O)CH_2O$, C≡C, S, or S(═O), where $R^8$ is H, or optionally substituted $C_{1-6}$alkyl; and J is optionally substituted $C_{1-12}$alkyl, $(CH_2)_n$—O—$(CH_2)_p$ where n is 1-6 and p is 1-6, $(—CH_2CH_2O—)_q$, $(—CH_2CH_2O—)_qCH_2$—, $(—CH_2CH_2O—)_qCH_2CH_2$— where q is 1-6, $(CH_2CH_2)_r$—O—$(CH_2CH_2)_s$ where r is 2-6 and s is 1-6, or —$(CH_2)_x$-M-$(CH_2)_y$— where M is optionally substituted phenyl, optionally substituted cycloalkyl, optionally substituted spirocycloalkyl, or optionally substituted heterocyclyl, where x is 0-8 and y is 0-8.

In some embodiments, each $R^1$ independently is methyl, $CF_3$, F, Cl, Br, OH, SH, S(═O)$R^b$, $CF_3$, $CF_2H$, $NH_2$,

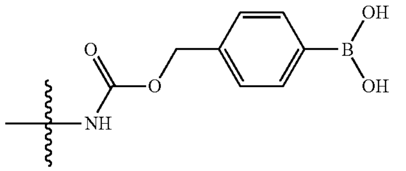

or

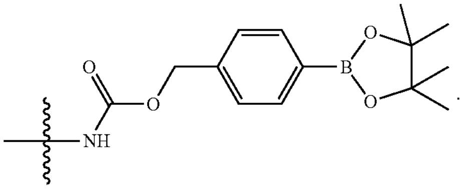

In some embodiments, $X^2$ is S, but in other embodiments, $X^2$ is $CH{=}CR^3$. And/or $R^3$ may be H or F, such as H.

In some embodiments, $X^3$ is $NR^4$ or $CHR^4$ where $R^4$ is H, $CF_3$, methyl, ethyl, or cyclopropyl, and may be H. In certain embodiments, $X^3$ is NH.

In certain embodiments, the

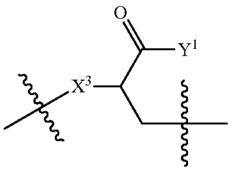

moiety is

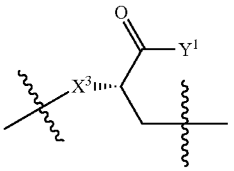

, but in other embodiments, the

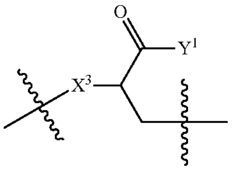

moiety may be

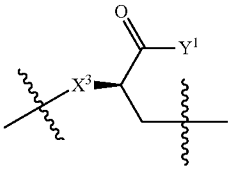

And in some embodiment, the compound is racemic.

In some embodiments, $R^2$ is H, aliphatic or haloalkyl, and may be H, methyl, ethyl, isopropyl, propargyl, cyclopropyl, or $CF_3$. Additionally, or alternatively, $X^1$ may be $—CH{=}N—$, $—CH_2NR^2—$, or $—CH_2CHR^2—$. In alternative embodiments, $X^1$ is $—CH_2NR^2—$ or $—CH_2CHR^2—$, and $R^2$ is H, methyl, ethyl or propargyl, or $R^2$ forms a 5-membered unsaturated optionally substituted heterocyclic ring with ring A.

In some embodiments, the compound has a formula selected from

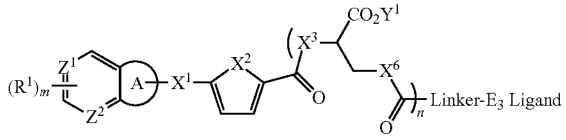

or a pharmaceutically acceptable salt, N-oxide, or hydrate thereof, where each $Y^1$ independently is OH or $OC_{1-6}$alkyl, and $X^1$ is $—CH{=}N—$, $—CH_2NR^2—$, or $—CH_2CHR^2—$.

In some such embodiments, n is 1 and optionally, $Y^1$ may be OH. In other embodiments, n is 2-5, and optionally one $Y^1$ may be OH and the remainder may be $OC_{1-6}$alkyl.

In certain other embodiments, the compound has a formula

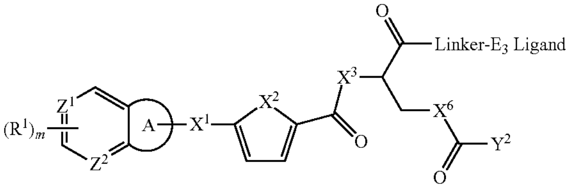

or a pharmaceutically acceptable salt, N-oxide, or hydrate thereof, where $Y^2$ is OH or $OC_{1-6}$alkyl, and $X^1$ is $—CH{=}N—$, $—CH_2NR^2—$, or $—CH_2CHR^2—$. In some embodiments, $Y^2$ is OH.

In alternative embodiments, the compound has a formula

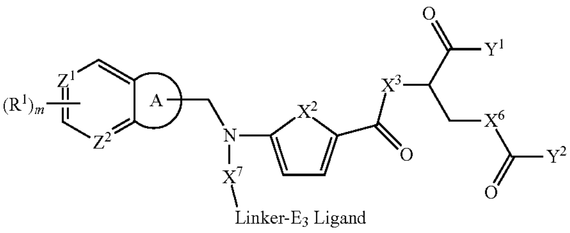

or a pharmaceutically acceptable salt, N-oxide, or hydrate thereof, where each of $Y^1$ and $Y^2$ independently is OH or $OC_{1-6}$alkyl. and $X^7$ is $C_{4-8}$alkyl. In certain embodiments, $Y^1$ and $Y^2$ are both OH, and in other examples, $Y^1$ and $Y^2$ are both $OC_{1-6}$alkyl.

In any embodiments, $X^6$ may be $CH_2$, or $X^6$ may be

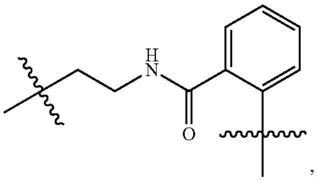 [SMILES: *CCNC(=O)c1ccccc1*]

, or $X^6$ may be a combination in embodiments where n is greater than 1. And/or $E_3$ Ligand may be

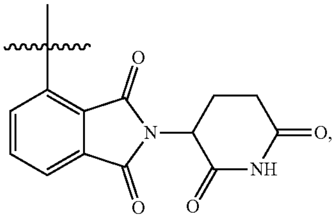

,

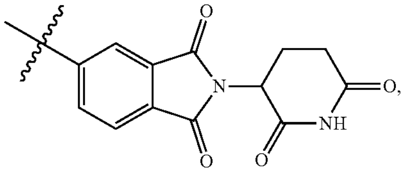

,

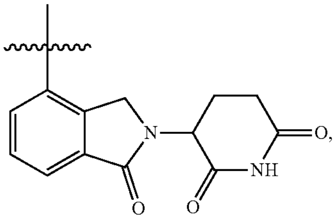

, or

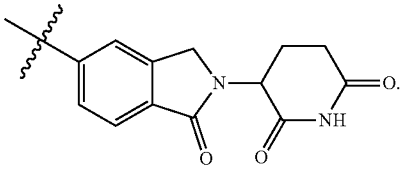

.

Also disclosed is a pharmaceutical composition, comprising an MTX analog compound according to any one of the disclosed embodiments, and a pharmaceutically acceptable excipient.

Methods of treating a subject with cancer, an autoimmune disease, or a viral infection with one or more of the disclosed compounds or pharmaceutical compositions are also provided. The methods include administering an effective amount of the compound or composition to the subject. The compound or composition in some examples may be administered orally, intravenously, intramuscularly, or subcutaneously.

In some embodiments the subject with cancer has a solid tumor or a hematological malignancy, for example, one or more of breast cancer, cancer of the head and neck, lung cancer, pancreatic cancer, bladder cancer, choriocarcinoma, hydatidiform mole, osteosarcoma, soft tissue sarcoma, mesothelioma, colorectal cancer, gestational trophoblastic tumor acute lymphoblastic leukemia, mycosis fungoides, Alibert-Bazin syndrome, or Non-Hodgkin lymphoma. In other embodiments, the subject has an autoimmune disease, for example one or more of rheumatoid arthritis, active pauciarticular juvenile rheumatoid arthritis, refractory Takayasu arteritis, psoriasis, Crohn's disease, Systemic Lupus Erythematosus (SLE), polymyositis, disseminated sclerosis, or Graft Versus Host Disease. In still further embodiments, the subject has a viral infection.

The foregoing and other features of the disclosure will become more apparent from the following detailed description, which proceeds with reference to the accompanying figures.

BRIEF DESCRIPTION OF THE DRAWINGS

FIG. 3A shows Western blot detection of DHFR levels after treatment of HBL1 cells for 16 h at the indicated concentrations of MTX or MTX-PROTAC. FIG. 3B shows quantification of protein levels in FIG. 3A as determined by densitometry and normalized to β-actin levels. Untreated control DHFR protein level was set to 1.0. MTX (□); PROTAC 13 (NCGC00685995) (●); PROTAC 11 (NCGC00685964) (▲); PROTAC 5 (NCGC00685938) (♦); PROTAC 7 (NCGC00685928) (○); PROTAC 9 (NCGC00685965) (Δ).

FIG. 4A shows Western blot detection of DHFR levels after treatment of HBL1 cells for 16 hrs at the indicated concentrations of MTX or MTX-PROTAC 9 (NCGC00685965). FIG. 4B shows quantification of protein levels in FIG. 4A as determined by densitometry and normalized to β-actin levels. Untreated control DHFR protein level was set to 1.0. $EC_{50}$ MTX-PROTAC 9 (NCGC00685965)=27 nM; $EC_{50}$ MTX~30 nM.

FIG. 5A shows 1536-well plate CellTiter-Glo assay for the detection of ATP levels after treatment of HBL1 cells for 16 h at the indicated concentrations of MTX or MTX-PROTAC 9 (NCGC00685965). FIG. 5B shows CCD-based quantification of luminescence in FIG. 5A normalized to control levels. $IC_{50}$ MTX≈200 nM.

FIG. 6A shows Western blot detection of DHFR levels after treatment of 293T, fibroblasts, and HBL1 cells for 16 h at 1 μM of MTX or the indicated MTX-PROTAC. FIG. 6B shows quantification of protein levels in FIG. 6A as determined by densitometry and normalized to β-actin levels. Untreated DMSO control DHFR protein level was set to 1.0. FIG. 6C shows ATP levels measured by CellTiter-Glo (CTG) assay from an independent experiment. Total ATP-dependent luminescence is dependent on cell type and density in 1536-well plate.

FIG. 8C is a Western blot for DHFR from a protein extract of either the HBL1 or HBL1 MTX-resistant cell line treated with 10 M of either MTX or NCGC00685965.

FIG. 9A is a schematic diagram of DHFR-HiBiT and its mechanism of action. The 11-amino acid NLuc-derived alpha helix (HiBiT) is fused to the DHFR C-terminus (triangle). Addition of the large fragment of NLuc (LgBiT, orange sector) restores the luminescence reporter function. The concentration of cellular DHFR is directly proportional to the luminescence signal. FIG. 9B shows HBL1 cells expressing HiBiT-tagged DHFR construct treated for 24 h with the indicated concentrations of MTX-PROTACs (NCGC00685965 or NCGC00687472), MTX or with DMSO as a control. HiBiT-tagged DHFR was detected using the Nano-Glo® HiBiT Blotting System (Promega), and total DHFR was detected by protein blotting with anti-DHFR antibody. β-actin was used as a loading control. FIG. 9C shows HBL1 cells expressing the HiBiT-tagged DHFR reporter incubated for 24 h with a 16-point titration of MTX (○) or MTX-PROTACs (NCGC00685965 (∇), NCGC00685928 (Δ), NCGC00687472 (■)) as a 1:2 titration, concentration ranging from 57.5 μM to 1.7 nM. DHFR-HiBiT-derived luciferase intensity was detected using the Nano-Glo® HiBiT Lytic Detection System (Promega). Data are means±s.d. of reporter activity measured as DHFR-HiBiT-derived luciferase activity normalized to DMSO control and represent the relative % of DHFR abundance. Data represent average of N=2-5 independent experiments.

SEQUENCE LISTING

Figures 1A, 1B, 1C, 1D, 1E, 1F:
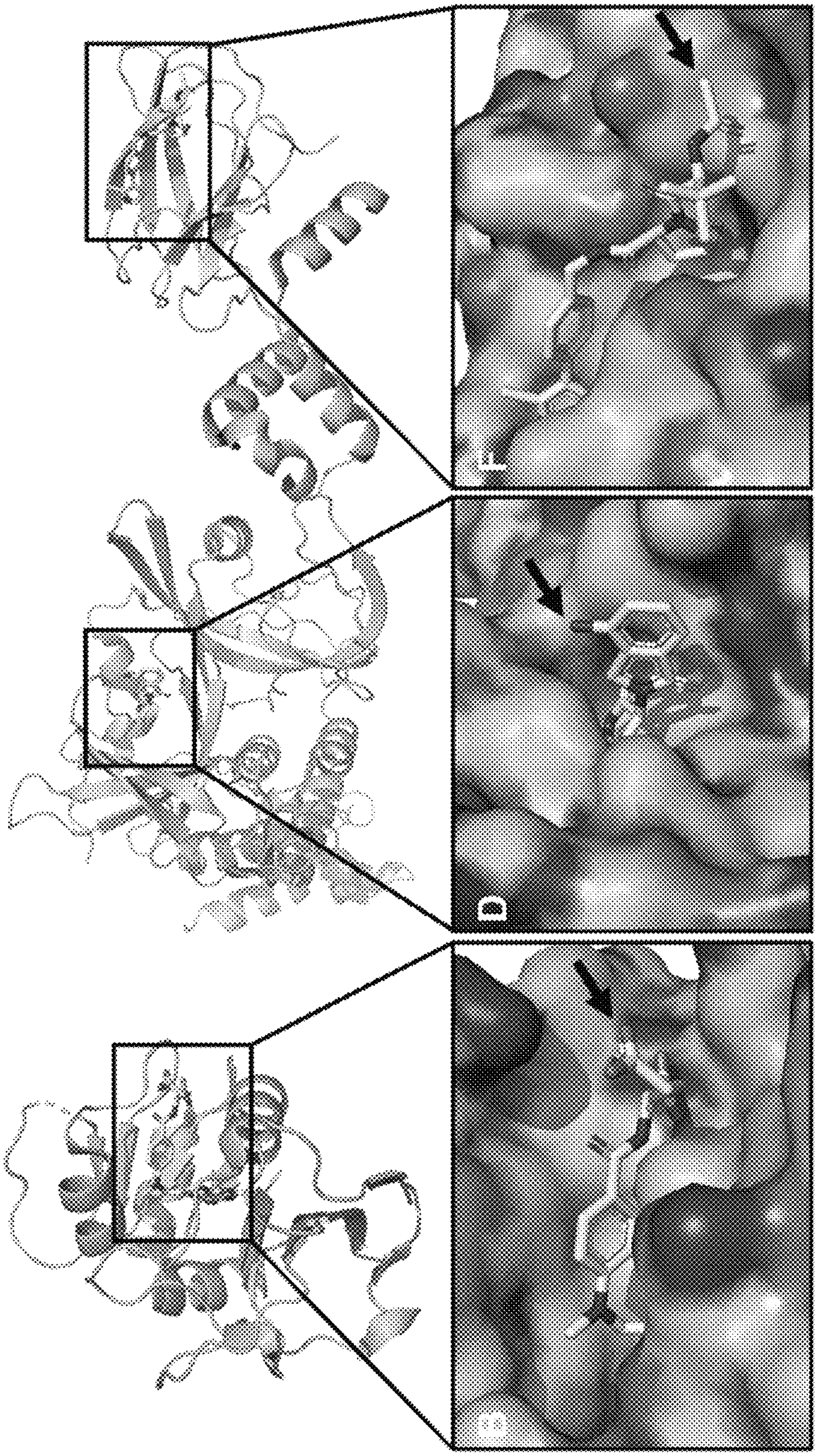
FIGS. 1A-1F show structural diagrams from co-crystal structures of DHFR (FIG. 1A, PDB ID: 2INQ), CRBN (FIG. 1C, PDB ID: 3CI2) and VHL (FIG. 1E, PDB ID: 4W9H). Possible linker tethering positions are shown in black arrows in their represented protein ligands complexes surface models, DHFR•MTX (FIG. 1B), CRBN•Lenalidomide (FIG. 1D), and VHL•VHL ligand (FIG. 1F), respectively.

Any nucleic acid and amino acid sequences listed herein or in the accompanying sequence listing are shown using standard letter abbreviations for nucleotide bases and amino acids, as defined in 37 C.F.R. § 1.822. In at least some cases, only one strand of each nucleic acid sequence is shown, but the complementary strand is understood as included by any reference to the displayed strand.

SEQ ID NO: 1 is the amino acid sequence of an 11 amino acid tag from NLuc (HiBiT):

VSGWRLFKKIS

DETAILED DESCRIPTION

As described herein, utilizing differing E3 ligase ligands and linkers to MTX resulted dramatically differential effects on the cellular turnover of DHFR in a lymphoma B-cell line (HBL1), 293T cells, and fibroblasts. Further, in comparative cell culture studies with the parent MTX the prior observation that MTX leads to an increase in cellular DHFR was confirmed, a mechanism that may allow some cancer cells to rebound from MTX administration once discontinued by leaving a high cellular concentration of active DHFR to regenerate the depleted reduced folate pool. The disappearance of DHFR from the cells treated with the disclosed MTX analogs could have a significant effect on resistance mediated by lack of drug retention which would lead to this rebound effect.

The high affinity of MTX for DHFR (and potentially other reduced folate cofactor-utilizing enzymes) results in half-life stabilization and consequent accumulation of DHFR in the cell. Increasing the level of this drug target is counterproductive to the inhibitor's purpose. However, by actively inhibiting and concurrently facilitating the cellular turnover of DHFR, MTX-PROTACs disclosed herein embody a unique property not observed in any of the thousands of MTX analogs designed to date. Because MTX-PROTACs cannot be polyglutamylated, by virtue of its blocked γ-glutamyl carboxylate, it is not subjected to retention by cells through the FPGS activity. MTX-PROTACs therefore are not subjected to mutation in FPGS, which decreases the efficacy of MTX, nor a casualty of upregulated γ-glutamyl hydrolase (GGH) activity.

The decreased negative charge owing to the lack of the γ-glutamyl carboxylate and increased lipophilicity from the linker-E3 ligase ligand may improve passive diffusion of MTX-PROTACs into cells. Without being bound by theory, MTX-PROTACs avoiding active transport across the cell membrane may circumvent mechanisms leading to tolerance of MTX and similar antifolates, which include increased efflux of MTX by upregulation of the ATP-binding cassette (ABC) family of transporters and decreased active uptake. Finally, mutations in DHFR, particularly Gly15Trp which dramatically lower the affinity of MTX for DHFR represent a significant mechanism for acquired MTX resistance. Again, without being bound by theory, it is postulated that because high affinity is not necessarily a perquisite for PROTAC engagement of the E3 ligase-proteasome machinery, MTX-PROTACs may be capable of escaping these important resistance mechanisms.

An additional surprising finding described herein of MTX-PROTACs is their ATP-sparing properties. The preservation of ATP levels may permit healthy cells to fare better during drug administration, improving the safety profile of MTX-PROTACs over MTX. Regarding side-effects of MTX, a serious and poorly understood form of cognitive impairment referred to as "chemo brain" has been described that is potentially due to CNS neurotoxicity and for which less toxic forms of MTX are critically needed. An improved safety profile would meet a critical milestone in antifolate drug development and not only be applicable to the standard indications of MTX, cancer and autoimmune disorders such as arthritis, but possibly as an antiviral.

Additionally, MTX has been reported to inhibit other reduced folate utilizing enzymes, including thymidylate synthase (TS), involved in de novo pyrimidine synthesis, 5-amino-imidazole-4-carboxide ribonucleotide (AICAR) transformylase, involved in de novo purine synthesis, and methylene $H_4F$ reductase (MTHFR) which converts 5-10-methylene $H_4F$ to the 5-methyl-$H_4F$ cofactor utilized by methionine synthase (MS). Further, MTX is a substrate for folylpolyglutamate synthetase (FPGS) and γ-glutamyl hydrolase (GGH), the enzyme pair that reversibly polyglutamylates MTX. Finally, there has been a report that deoxycytidine kinase (dCK) found in the salvage pathway of nucleotide biosynthesis is targeted by MTX, for which a recent study describes an inhibitor with some chemical similarity to MTX.

I. Definitions

The following explanations of terms and methods are provided to better describe the present disclosure and to guide those of ordinary skill in the art in the practice of the present disclosure. The singular forms "a," "an," and "the" refer to one or more than one, unless the context clearly dictates otherwise. The term "or" refers to a single element of stated alternative elements or a combination of two or more elements, unless the context clearly indicates otherwise. As used herein, "comprises" means "includes." Thus, "comprising A or B," means "including A, B, or A and B," without excluding additional elements. All references, including patents and patent applications cited herein, are incorporated by reference in their entirety, unless otherwise specified.

Unless otherwise indicated, all numbers expressing quantities of components, molecular weights, percentages, temperatures, times, and so forth, as used in the specification or claims, are to be understood as being modified by the term "about." Accordingly, unless otherwise indicated, implicitly or explicitly, the numerical parameters set forth are approximations that may depend on the desired properties sought and/or limits of detection under standard test conditions/methods. When directly and explicitly distinguishing embodiments from discussed prior art, the embodiment numbers are not approximates unless the word "about" is expressly recited.

Unless explained otherwise, all technical and scientific terms used herein have the same meaning as commonly understood by one of ordinary skill in the art to which this disclosure pertains. Although methods and materials similar or equivalent to those described herein can be used in the practice or testing of the present disclosure, suitable methods and materials are described below. The materials, methods, and examples are illustrative only and not intended to be limiting.

When chemical structures are depicted or described, unless explicitly stated otherwise, all carbons are assumed to include implicit hydrogens such that each carbon conforms to a valence of four. For example, in the structure on the left-hand side of the schematic below there are nine hydrogen atoms implied. The nine hydrogen atoms are depicted in the right-hand structure.

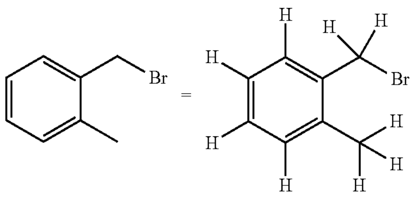

Sometimes a particular atom in a structure is described in textual formula as having a hydrogen or hydrogen atoms, for example $—CH_2CH_2—$. It will be understood by a person of ordinary skill in the art that the aforementioned descriptive techniques are common in the chemical arts to provide brevity and simplicity to description of organic structures.

If a group R is depicted as "floating" on a ring system, as for example in the group:

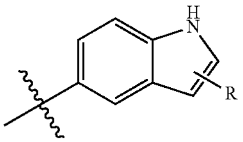

then, unless otherwise defined, a substituent R can reside on any atom of the fused bicyclic ring system, so long as a stable structure is formed that conforms to standard valence conditions as understood by a person of ordinary skill in the art. In the example depicted, the R group can reside on an atom in either the 5-membered or the 6-membered ring of the indolyl ring system, including the heteroatom by replacing the explicitly recited hydrogen, but excluding the atom carrying the bond with the "~~w" symbol and the bridging carbon atoms.

When there are more than one such depicted "floating" groups, as for example in the formulae:

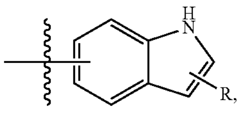 , or 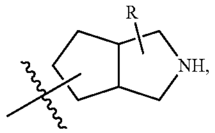 , or

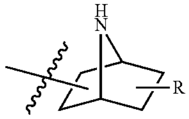

where there are two groups, namely, the R and the bond indicating attachment to a parent structure; then, unless otherwise defined, each "floating" group can reside on any atoms of the ring system, again assuming each replaces a depicted, implied, or expressly defined hydrogen on the ring system and a chemically stable compound would be formed by such an arrangement.

When a group R is depicted as existing on a ring system containing saturated carbons, for example as in the formula:

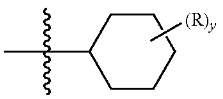

where, in this example, y can be more than one, and assuming each R replaces a currently depicted, implied, or expressly defined hydrogen on the ring; then, unless otherwise defined, two R's can reside on the same carbon. A simple example is when R is a methyl group. The depicted structure can exist as a geminal dimethyl on a carbon of the depicted ring (an "annular" carbon). In another example, two R's on the same carbon, including that same carbon, can form a ring, thus creating a spirocyclic ring (a "spirocyclyl" group) structure. For example, shown below two Rs can form a piperidine ring in a spirocyclic arrangement with the cyclohexane, as

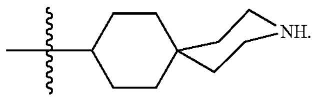 [SMILES: *C1CCC2(CCNCC2)CC1]

A person of ordinary skill in the art will appreciate that compounds may exhibit the phenomena of tautomerism, conformational isomerism, geometric isomerism, and/or optical isomerism. For example, certain disclosed compounds can include one or more chiral centers and/or double bonds and as a consequence can exist as stereoisomers, such as double-bond isomers (i.e., geometric isomers), enantiomers, diasteromers, and mixtures thereof, such as racemic mixtures. In certain embodiments the compounds disclosed herein are synthesized in or are purified to be in substantially enantiopure form, such as in an 85% enantiomeric excess (e.e.), a 90% enantiomeric excess, a 95% enantiomeric excess, a 97% enantiomeric excess, a 98% enantiomeric excess, a 99% enantiomeric excess, or even in greater than a 99% enantiomeric excess, such as in a substantially enantiopure form. In other embodiments, the compounds are in a racemic form, having substantially a 50:50 mixture of enantiomers.

As another example, certain disclosed compounds can exist in several tautomeric forms, including the enol form, the keto form, and mixtures thereof. For example, a compound may have a moiety exhibiting the following isomerization:

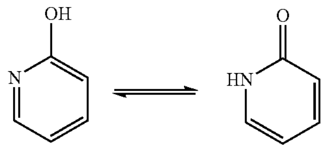 [SMILES: Oc1ccccn1 ; O=c1cccc[nH]1]

As the various compound names, formulae and compound drawings within the specification and claims can represent only one of the possible tautomeric, conformational isomeric, optical isomeric, or geometric isomeric forms, a person of ordinary skill in the art will appreciate that the disclosed compounds encompass any tautomeric, conformational isomeric, optical isomeric, and/or geometric isomeric forms of the compounds described herein, as well as mixtures of these various different isomeric forms. In cases of limited rotation, e.g. around the amide bond, atropisomers are also possible and are also specifically included in the compounds of the invention.

In any embodiments, any or all hydrogens present in the compound, or in a particular group or moiety within the compound, may be replaced by a deuterium or a tritium. Thus, a recitation of alkyl includes deuterated alkyl, where from one to the maximum number of hydrogens present may be replaced by deuterium. For example, ethyl may be $C_2H_5$ or $C_2H_5$ where from 1 to 5 hydrogens are replaced by deuterium, such as in $C_2D_xH_{5-x}$.

As used herein, the term "substituted" refers to all subsequent modifiers in a term, for example in the term "substituted aryl$C_{1-8}$alkyl," substitution may occur on the "$C_{1-8}$alkyl" portion, the "aryl" portion or both portions of the aryl$C_{1-8}$alkyl group.

"Substituted," when used to modify a specified group or moiety, means that at least one, and perhaps two or more, hydrogen atoms of the specified group or moiety is independently replaced with the same or different substituent groups as defined below. In a particular embodiment, a group, moiety or substituent may be substituted or unsubstituted, unless expressly defined as either "unsubstituted" or "substituted." Accordingly, any of the groups specified herein may be unsubstituted or substituted. In particular embodiments, the substituent may or may not be expressly defined as substituted, but is still contemplated to be optionally substituted. For example, an "alkyl" moiety may be unsubstituted or substituted, but an "unsubstituted alkyl" is not substituted.

"Substituents" or "substituent groups" for substituting for one or more hydrogen atoms the specified group or moiety are, unless otherwise specified, aliphatic, such as alkyl, alkenyl, alkynyl, cycloalkyl, or spiroalkyl, preferably $C_{1-6}$alkyl or $C_{1-4}$alkyl, $C_{3-6}$cycloalkyl, or $C_{6-15}$spiroalkyl; halogen; haloalkyl, such as $CF_3$ or $CF_2H$; aryl, such as phenyl; heterocyclyl, such as heteroaryl or heterocycloaliphatic; carboxy; carboxyl ester; or amino.

In one embodiment, a group that is substituted has at least one substituent up to the number of substituents possible for a particular moiety, such as 1 substituent, 2 substituents, 3 substituents, or 4 substituents.

Additionally, in embodiments where a group or moiety is substituted with a substituted substituent, the nesting of such substituted substituents is limited to three, thereby preventing the formation of polymers. Thus, in a group or moiety comprising a first group that is a substituent on a second group that is itself a substituent on a third group, which is attached to the parent structure, the first (outermost) group can only be substituted with unsubstituted substituents. For example, in a group comprising -(aryl-1)-(aryl-2)-(aryl-3), aryl-3 can only be substituted with substituents that are not themselves substituted.

Aliphatic: A substantially hydrocarbon-based group or moiety. An aliphatic group or moiety can be acyclic, including alkyl, alkenyl, or alkynyl groups, cyclic versions thereof, such as cycloaliphatic and/or spiroaliphatic groups or moieties including cycloalkyl, cycloalkenyl, cycloalkynyl, or spiroalkyl and further including straight- and branched-chain arrangements, and all stereo and position isomers as well. Unless expressly stated otherwise, an aliphatic group contains from one to twenty-five carbon atoms ($C_{1-25}$); for example, from one to fifteen ($C_{1-15}$), from one to ten ($C_{1-10}$) from one to six ($C_{1-6}$), or from one to four carbon atoms ($C_{1-4}$) for an acyclic aliphatic group or moiety; from three to fifteen carbon atoms ($C_{3-15}$), such as from three to ten ($C_{3-10}$), from three to six ($C_{3-6}$), or from three to four ($C_{3-4}$) carbon atoms for a cycloaliphatic group or moiety; or from three to fifteen ($C_{6-15}$) carbon atoms for a spiroaliphatic group or moiety. An aliphatic group may be substituted or unsubstituted, unless expressly referred to as an "unsubstituted aliphatic" or a "substituted aliphatic." An aliphatic group can be substituted with one or more substituents (up to two substituents for each methylene carbon in an aliphatic chain, or up to one substituent for each carbon of a —C═C— double bond in an aliphatic chain, or up to one substituent for a carbon of a terminal methine group).

Alkyl: A saturated aliphatic hydrocarbyl group having from 1 to 25 ($C_{1-25}$) or more carbon atoms, more typically 1 to 10 ($C_{1-10}$) carbon atoms such as 1 to 6 ($C_{1-6}$) carbon atoms or 1 to 4 ($C_{1-4}$) carbon atoms.

An alkyl moiety may be substituted or unsubstituted. This term includes, by way of example, linear and branched hydrocarbyl groups such as methyl ($CH_3$), ethyl ($—CH_2CH_3$), n-propyl ($—CH_2CH_2CH_3$), isopropyl ($—CH(CH_3)_2$), n-butyl ($—CH_2CH_2CH_2CH_3$), or isobutyl ($—CH_2CH_2(CH_3)_2$).

Amino: The group —$NH_2$, —NHR, or —NRR, where each R independently is selected from aliphatic, such as alkyl, alkenyl or alkynyl; aryl; heteroaryl; heterocycloaliphatic, or two R groups together with the nitrogen attached thereto form a heterocyclic ring, such as a 5-membered or 6-membered heterocycloaliphatic ring.

Aryl: An aromatic carbocyclic group of, unless specified otherwise, from 6 to 15 carbon atoms having a single ring (e.g., phenyl) or multiple condensed rings in which at least one ring is aromatic (e.g., 1,2,3,4-tetrahydroquinoline, benzodioxole, naphthylene and the like). If any aromatic ring portion contains a heteroatom, the group is heteroaryl and not aryl. Aryl groups may be, for example, monocyclic, bicyclic, tricyclic or tetracyclic. Unless otherwise stated, an aryl group may be substituted or unsubstituted.

Autoimmune disorder: A disorder in which the immune system produces an immune response (for example, a B cell or a T cell response) against an endogenous antigen, with consequent injury to tissues. For example, rheumatoid arthritis is an autoimmune disorder, as are psoriasis, juvenile rheumatoid arthritis (such as pauciarticular juvenile rheumatoid arthritis, polyarticular juvenile rheumatoid arthritis, or systemic juvenile rheumatoid arthritis), Takayasu arteritis, Hashimoto's thyroiditis, pernicious anemia, uveitis, Addison's disease, type I diabetes, Systemic Lupus Erythematosus (SLE), Sjögren's syndrome, dermatomyositis, multiple sclerosis, polymyositis, disseminated sclerosis, myasthenia gravis, Reiter's syndrome, and Grave's disease, Graft Versus Host Disease, among others. Some forms of inflammatory bowel disease, can also be of autoimmune origin, with the immune system attacking self or with the immune system attacking a harmless virus, bacteria, or food in the gut, causing inflammation that leads to bowel injury.

Cancer: A malignant neoplasm that has undergone anaplasia with loss of differentiation, increased rate of growth, invasion of surrounding tissue, and is capable of metastasis. As used herein, cancer includes both solid tumors and hematological malignancies. Residual cancer is cancer that remains in a subject after any form of treatment is given to the subject to reduce or eradicate cancer. Metastatic cancer is a cancer at one or more sites in the body other than the original site of the cancer from which the metastatic cancer is derived. Local recurrence is a reoccurrence of the cancer at or near the same site as the original cancer, for example, in the same tissue as the original cancer.

Carboxyl: A —$CO_2H$ group or moiety or salts thereof.

Carboxyl ester: A —C(O)OR group or moiety, where R is acyclic, cyclic, or spirocyclic aliphatic, heterocyclic, or aryl.

Cyano: The —CN group or moiety.

Cycloaliphatic and spiroaliphatic: A cyclic aliphatic group having a single ring (e.g., cyclobutyl), or multiple rings, such as in a fused, bridged or spirocyclic system, at least one of which is aliphatic.

Typically, the point of attachment to the parent structure is through an aliphatic portion of the multiple ring system. Cycloaliphatic includes saturated and unsaturated systems, including cycloalkyl, cycloalkenyl, cycloalkynyl, and spiroalkyl. A cycloaliphatic group may contain from three to twenty-five carbon atoms; for example, from three to fifteen, from three to ten, from three to six, or from three to four carbon atoms. Unless otherwise stated, a cycloaliphatic group may be substituted or unsubstituted. Exemplary cycloaliphatic groups include, but are not limited to, cyclopropyl, cyclobutyl, cyclopentyl, cyclohexyl, or spiro[3.3] heptan.

Halogen or halo: Fluoro, chloro, bromo or iodo.

Haloalkyl: An alkyl moiety substituted with one or more halogens, such as $C_{1-6}$alkyl substituted with 1, 2, 3 or more halogens. Exemplary haloalkyl moieties include —$CF_3$ and —$CF_2H$.

Heteroaryl: An aromatic group or moiety of, unless specified otherwise, from 5 to 15 ring atoms comprising at least one carbon atom and at least one heteroatom, such as N, S, O, P, or Si, preferably N, S or O. A heteroaryl group or moiety may comprise a single ring (e.g., pyridinyl, or pyrazine) or multiple condensed rings (e.g., indolyl). Heteroaryl groups or moiety may be, for example, monocyclic, bicyclic, tricyclic or tetracyclic. Unless otherwise stated, a heteroaryl group or moiety may be substituted or unsubstituted.

Heterocyclyl, heterocyclo or heterocycle: Aromatic and non-aromatic ring systems, and more specifically refer to a stable three- to fifteen-membered ring moiety comprising at least one carbon atom, and typically plural carbon atoms, and at least one, such as from one to five, heteroatoms. The heteroatom(s) may be nitrogen, phosphorus, oxygen, silicon or sulfur atom(s), preferably N, S or O. The heterocyclyl moiety may be a monocyclic moiety, or may comprise multiple rings, such as in a bicyclic or tricyclic ring system, provided that at least one of the rings contains a heteroatom. Such a multiple ring moiety can include fused or bridged ring systems as well as spirocyclic systems (two rings joined at a single atom) or bi-heterocyclyl systems where two heterocyclyl rings are joined by a direct bond, for example, bipiperidine; and any nitrogen, phosphorus, carbon, silicon or sulfur atoms in the heterocyclyl moiety can be optionally oxidized to various oxidation states. For convenience, nitrogens, particularly, but not exclusively, those defined as annular aromatic nitrogens, are meant to include their corresponding N-oxide form, although not explicitly defined as such in a particular example. Thus, for a compound having, for example, a pyridinyl ring, the corresponding pyridinyl-N-oxide is included as another compound of the invention, unless expressly excluded or excluded by context. In addition, annular nitrogen atoms can be optionally quaternized. Heterocycle includes heteroaryl moieties, and heterocycloaliphatic moieties, such as heterocycloalkyl moieties, which are heterocyclyl rings that are partially or fully saturated. Unless otherwise stated, a heterocyclyl group or moiety may be substituted or unsubstituted. Examples of heterocyclyl groups include, but are not limited to, azetidinyl, oxetanyl, acridinyl, benzodioxolyl, benzodioxanyl, benzofuranyl, dioxolanyl, indolizinyl, naphthyridinyl, phenazinyl, phenothiazinyl, phenoxazinyl, phthalazinyl, pteridinyl, purinyl, quinazolinyl, quinoxalinyl, quinolinyl, isoquinolinyl, tetrazoyl, tetrahydroisoquinolyl, piperidinyl, piperazinyl, 2-oxopiperazinyl, 2-oxopiperidinyl, 2-oxopyrrolidinyl, 2-oxoazepinyl, azepinyl, pyrrolyl, 4-piperidonyl, pyrrolidinyl, pyrazolyl, pyrazolidinyl, imidazolyl, imidazolinyl, imidazolidinyl, dihydropyridinyl, tetrahydropyridinyl, pyridinyl, pyrazinyl, pyrimidinyl, pyridazinyl, oxazolyl, oxazolinyl, oxazolidinyl, triazolyl, isoxazolyl, isoxazolidinyl, morpholinyl, thiazolyl, thiazolinyl, thiazolidinyl, isothiazolyl, quinuclidinyl, isothiazolidinyl, indolyl, isoindolyl, indolinyl, isoindolinyl, octahydroindolyl, octahydroisoindolyl, quinolyl, isoquinolyl, decahydroisoquinolyl, benzimidazolyl, thiadiazolyl, benzopyranyl, benzothiazolyl, benzoxazolyl, furyl, tetrahydrofuryl, tetrahydropyranyl, thienyl, benzothieliyl, thiamorpholinyl, thiamorpholinyl sulfoxide, thiamorpholinyl sulfone, and oxadiazolyl.

Pharmaceutically acceptable salt: A biologically compatible salt of a compound that can be used as a drug, which salts are derived from a variety of organic and inorganic counter ions well known in the art. Pharmaceutically acceptable salts include salts of organic or inorganic acids, such as hydrochloride, hydrobromide, tartrate, mesylate, acetate, maleate, oxalate, sulfate, nitrate, phosphate, formate, trifluoroactate, glycolate, citrate, tosylate, and the like. And pharmaceutically acceptable salts of acidic functional groups may include, by way of example only, pharmaceutically acceptable salts that are derived from inorganic bases, such as lithium, sodium, potassium, calcium, magnesium, zinc, manganese, iron, copper, ammonium, aluminum salts and the like. Salts that are derived from pharmaceutically acceptable organic bases, include, but are not limited to, salts of primary, secondary and tertiary amines, cyclic amines and the like, such as isopropylamine, trimethylamine, diethylamine, triethylamine, tripropylamine, tris(hydroxymethyl)aminomethane (Tris), ethanolamine, piperidine, piperazine, amino acids, including, but not limited to, lysine, arginine, histidine, glycine, and the like. Additional information concerning pharmaceutically acceptable salts can be found in S. M. Berge, et al., "Pharmaceutical Salts," J. Pharm. Sci., 1977; 66:1-19 which is incorporated herein by reference.

Pharmaceutically acceptable carrier: *Remington: The Science and Practice of Pharmacy*, The University of the Sciences in Philadelphia, Editor, Lippincott, Williams, & Wilkins, Philadelphia, PA, 21st Edition (2005), describes compositions and formulations suitable for pharmaceutical delivery of one or more therapeutic compounds or molecules. In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions can contain minor amounts of non-toxic auxiliary substances, such as wetting or emulsifying agents, preservatives, pH buffering agents, and the like, for example sodium acetate or sorbitan monolaurate.

Subject: A living multi-cellular vertebrate organism, a category that includes both human and veterinary subjects, including human and non-human mammals.

Therapeutically effective amount or effective amount: A quantity of a specific substance, such as a therapeutic agent, sufficient to treat, reduce, and/or ameliorate the symptoms and/or underlying causes of a disorder or disease. In some embodiments, a therapeutically effective amount is the amount necessary to reduce or eliminate a symptom of a disease, such as cancer or an autoimmune disorder. In some examples, when administered to a subject, a dosage is used that will achieve target tissue concentration that has been shown to achieve a desired effect.

II. Methotrexate Analogs

A. Compounds

Disclosed herein are compounds, methods of making the compounds and methods for using the compounds. A person of ordinary skill in the art will appreciate that salts, N-oxides and/or solvates of the disclosed compounds also may be formed, and accordingly salts, N-oxides and/or solvates are understood to be included within the scope of the disclosed general formulas. In some embodiments, the compound has a general formula I Formula I

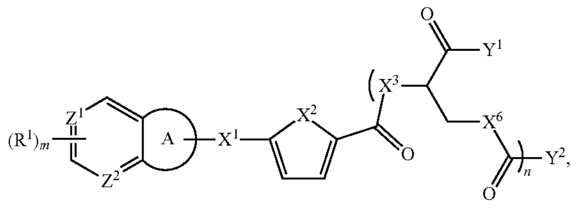

or a pharmaceutically acceptable salt, N-oxide, or hydrate thereof. A person of ordinary skill in the art understand that in any of the disclosed embodiments, the

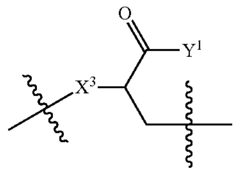

moiety is chiral, and that, unless otherwise specified in a particular embodiment, formula, structure, and/or context, in some embodiments, the

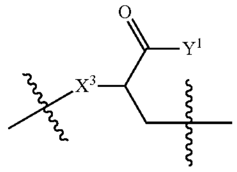

moiety may be

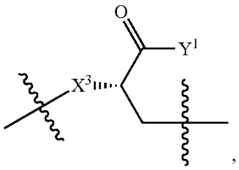

, or

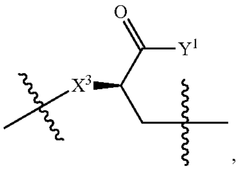

, or a combination thereof, such as a racemic mixture of the chiral centers.

With reference to Formula I, each of $Z^1$ and $Z^2$ independently is N or CH. A person of ordinary skill in the art will understand that if $Z^1$ and/or $Z^2$ is CH, they may be independently substituted by $R^1$ where $R^1$ replaces the respective hydrogen in the CH moiety.

Each $R^1$ independently is $C_{1-6}$alkyl, such as, methyl, ethyl, n-propyl or isopropyl, typically methyl; $C_{1-6}$haloalkyl, such as $CF_3$, $CF_2H$; halogen, such as F, Cl, Br or I, typically, F, Cl, or Br; —OH; —SH; —$S(O)R^b$; cyano; amino, such as $NH_2$, $NH(C_{1-6}alkyl)$, or $N(C_{1-6}alkyl)_2$; or

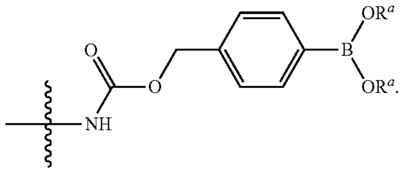

Each $R^a$ independently is H, $C_{1-6}$alkyl, or two $R^a$s together form a 5-membered heterocycloaliphatic ring, such as a 5-membered heterocycloalkyl ring, optionally substituted with 1-4 alkyl groups, such as methyl.

Each $R^b$ independently is H; $C_{1-6}$alkyl, such as methyl, ethyl, n-propyl, isopropyl, n-butyl, iso-butyl, sec-butyl, tert-butyl, pentyl, n-pentyl, neo-pentyl, or hexyl; or $C_{1-6}$haloalkyl, such as $CF_3$ or $CF_2H$.

In some embodiments, each $R^1$ independently is methyl, $CF_3$, $CF_2H$, F, Cl, Br, OH, SH, $NH_2$,

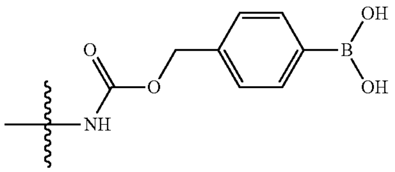

or

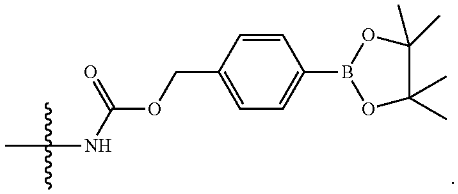

.

m is 0, 1, 2, 3 or 4, such as 2, or 3, and in some embodiments, m is 2.

n is 1, 2, 3, 4 or 5, and in some embodiments, n is 1, 2 or 3, and may be 1.

Ring A is heterocyclyl, such as 5- or 6-membered heterocyclyl, or aryl, such as a 6-10-membered aryl, for example, phenyl or naphthalyl. In some embodiments, ring A is 5- or 6-membered heteroaryl, 6-10-membered aryl, or 6-membered heterocycloaliphatic, and may be phenyl, naphthalyl, pyrazinyl, pyridinyl, pyrrolyl, furyl, naphthalyl, or piperazinyl.

$X^1$ is —CH═N—, —$CH_2NY^3$—, or —$CH_2CHR^2$—, where $R^2$ is H, aliphatic, haloalkyl, or $R^2$, together with the atoms to which it is attached, forms a 5-membered heterocyclic ring that is fused to ring A. In some embodiments, $R^2$ is H; $C_{1-6}$alkyl, for example, methyl, ethyl, or isopropyl; $C_{3-6}$cycloalkyl, such as cyclopropyl; $CF_3$; $C_{2-6}$alkynyl, such as propargyl; or forms a fused 5-membered unsaturated heterocyclic ring with ring A.

$Y^3$ is —$X^7$-Linker-$E_3$ Ligand or $R^2$, where $X^7$ is $C_{4-8}$alkyl;

each of $Y^1$ and $Y^2$ independently is OH, O-aliphatic, O-aryl, O-heterocyclic, or -Linker-$E_3$ Ligand, such as OH, O-aliphatic, or -Linker-$E_3$ Ligand, preferably, OH, $OC_{1-6}$alkyl (for example, O-methyl, O-ethyl, O-propyl, or O-isopropyl) or -Linker-$E_3$ Ligand;

wherein at least one of $Y^1$, $Y^2$ or $Y^3$ is or comprises -Linker-$E_3$ Ligand. In one embodiment, $Y^1$ is -Linker-$E_3$ Ligand, $Y^2$ is OH or $OC_{1-6}$alkyl, and $Y^3$ is $R^2$. In another embodiment, $Y^2$ is -Linker-$E_3$ Ligand, $Y^1$ is OH or $OC_{1-6}$alkyl, and $Y^3$ is $R^2$. And in a further embodiments, each of $Y^1$ and $Y^2$ independently is OH or $OC_{1-6}$alkyl, and $Y^3$ is —$X^7$-Linker-$E_3$ Ligand.

In some embodiments, each of $Y^1$ and $Y^2$ independently is OH, O-methyl or -Linker-$E_3$ Ligand.

$X^2$ is O, S or CH═$CR^3$, where $R^3$ is H or halogen, and in some embodiments, $R^3$ is H or F;

Each $X^3$ independently is $NR^4$ or $CHR^4$, where each $R^4$ independently is H; $C_{1-6}$alkyl, such as methyl, ethyl or isopropyl; $C_{3-6}$cycloalkyl, such as cyclopropyl; or $C_{1-6}$haloalkyl, such as $CF_3$ or $CF_2H$. In some embodiments, each $R^4$ independently is H or $CF_3$, and in certain embodiments, $R^4$ is H;

or $R^3$ and $R^4$, together with the atoms to which they are attached, form a heterocyclyl ring, such as a 5-membered heterocyclyl ring. A person of ordinary skill in the art understands that if n is greater than 1, only the first $R^4$ moiety combines with $R^3$ to form the heterocyclyl ring.

In embodiments where n is greater than 1, each $X^3$ may be the same, but in other embodiments, the compound comprises more than one $X^3$, such as from 1 to n $X^3$ moieties.

each $X^6$ independently is $CH_2$, CHF, or

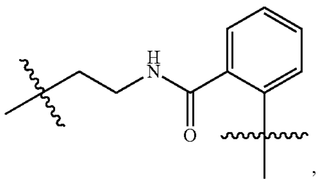 [SMILES: *CCNC(=O)c1ccccc1*]

, such as $CH_2$, or

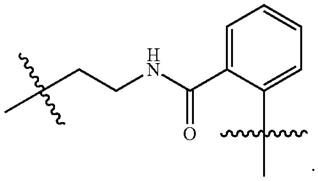 [SMILES: *CCNC(=O)c1ccccc1*]

.

In some embodiments, all $X^6$ moieties are the same, but in other embodiments, the compound comprises two different $X^6$ moieties.

$E_3$ Ligand is selected from:

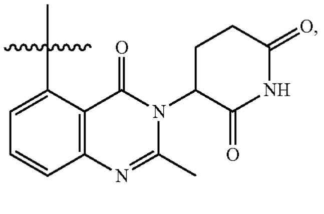

-continued

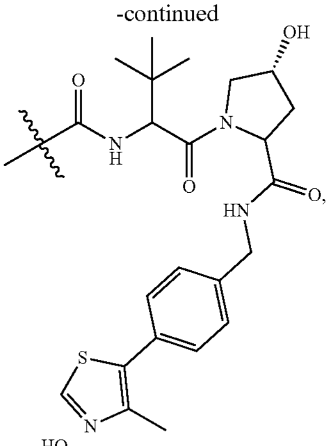

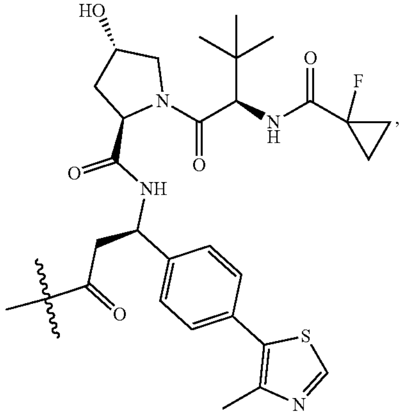

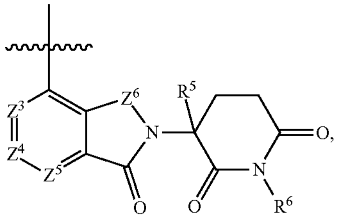

or

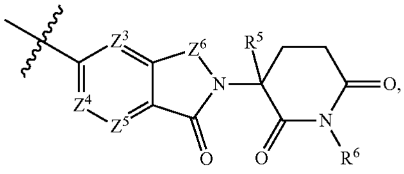

such as

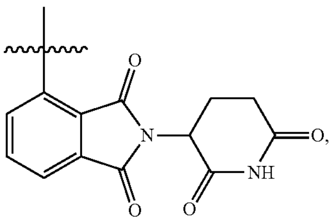

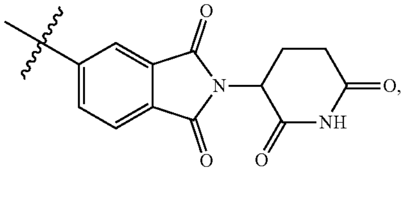

-continued

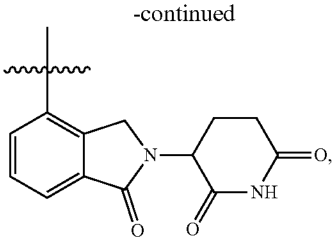

or

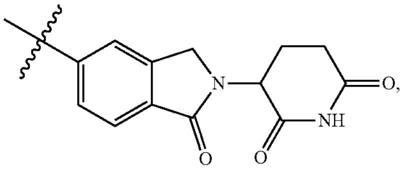

wherein each of $Z^3$, $Z^4$, and $Z^5$ independently is CH or N; $Z^6$ is $CH_2$ or C═O;

$R^5$ is H, D, $C_{1-6}$alkyl, such as methyl, or halogen, such as F; and $R^6$ is H, $C_{1-6}$alkyl (for example, methyl), —$CO_2B(OH)_2$,

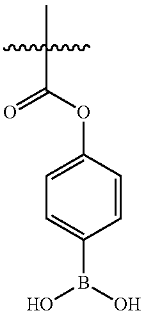

or

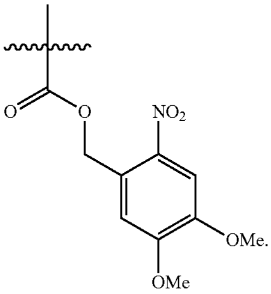

In a particular embodiment, $Z^3$, $Z^4$, and $Z^5$ are each CH, $R^5$ is H and $R^6$ is H or methyl.

Linker has a formula

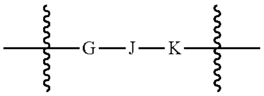

such that -Linker-$E_3$ Ligand is -G-J-K-$E_3$ Ligand, wherein:

G is a bond, $NR^7$, —$NR^7C$(═O)—, or $CH_2$, where $R^7$ is H, or $C_{1-4}$alkyl, such as methyl or ethyl;

K is a bond; O; $C_{1-4}$alkyl such as $CH_2$, or $CH_2CH_2$; $CF_2$; $NR^8$; C(O)$NR^8$; NHC(O); $NHCO_2CH_2$; $CH_2C(O)NH$; $NHC(O)CH_2O$; $NHC(O)CH_2NH$; $C(O)CH_2O$; CC; S; or S(═O); wherein $R^8$ is H; $C_{1-6}$alkyl, such as methyl, ethyl, n-propyl, isopropyl, n-butyl, iso-butyl, sec-butyl, tert-butyl, pentyl, n-pentyl, neo-pentyl, or hexyl; or $C_{1-6}$haloalkyl, such as $CF_3$ or $CF_2H$; and J is $C_{1-12}$alkyl such as $C_{2-12}$alkyl; $(CH_2)_n$—O—$(CH_2)_p$ where n is 1-6 and p is 1-6; $(—CH_2CH_2O—)_q$, $(—CH_2CH_2O—)_qCH_2$— or $(—CH_2CH_2O—)_q$ $CH_2CH_2$— where q is 1-6; $(CH_2CH_2)_r$—O—$(CH_2CH_2)_s$ where r is 2-6 and s is 1-6; or —$(CH_2)_x$-M-$(CH_2)_y$— where M is phenyl, cycloalkyl, spirocycloalkyl, heterocyclyl, such as heteroaryl or heterocycloaliphatic including spiro- and bi-heterocyclyl groups, x is from 0 to 8, such as from 1 to 8, and y is from 0 to 8, such as from 1 to 8. In some embodiments, J is

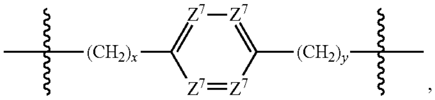
,
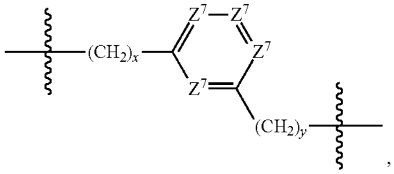
,
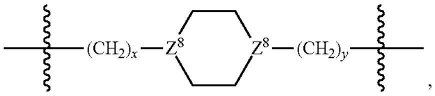
,
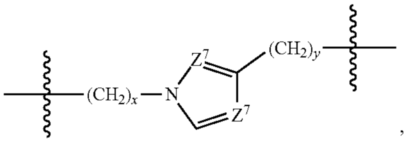
,
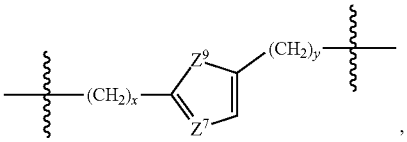
,
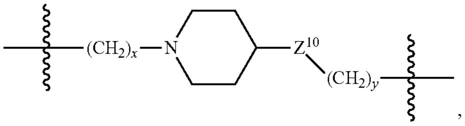
,
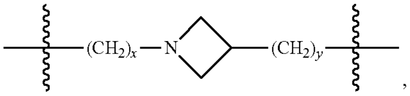
,
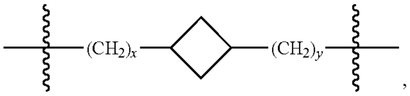
,
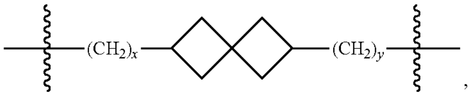
,
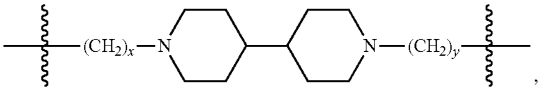
, or
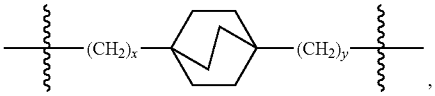
, where each $Z^7$ independently is CH or N, $Z^8$ is CH, N or NC(O), such as in

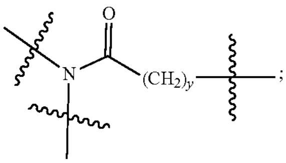
;

$Z^9$ is $CH_2$, S, NH, $NR^c$ or O, where $R^c$ is $C_{1-6}$alkyl, such as methyl, ethyl, n-propyl, or isopropyl; $C_{3-6}$cycloalkyl, such as cyclopropyl; or $C_{1-6}$haloalkyl, such as $CF_3$ or $CF_2H$; and $Z^{10}$ is O, NH, S or S(═O);

In some embodiments, the -Linker-$E_3$ Ligand moiety is selected from:

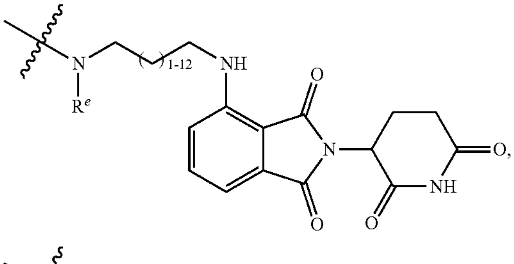
,
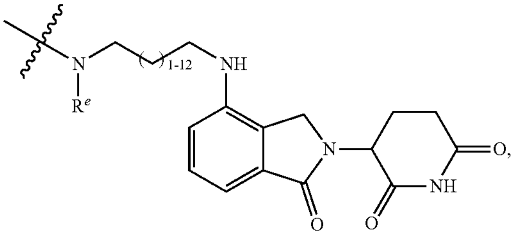
,
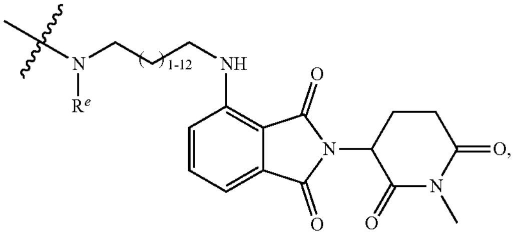
,
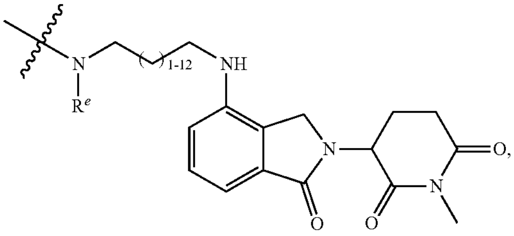
,
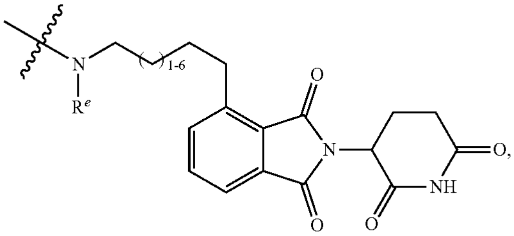
,
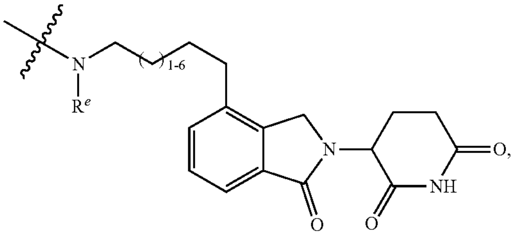
,

-continued
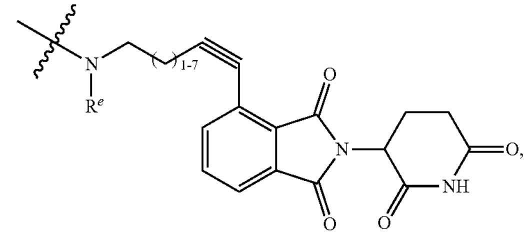
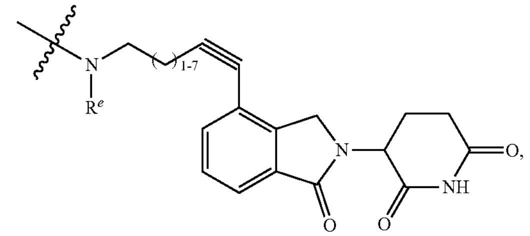
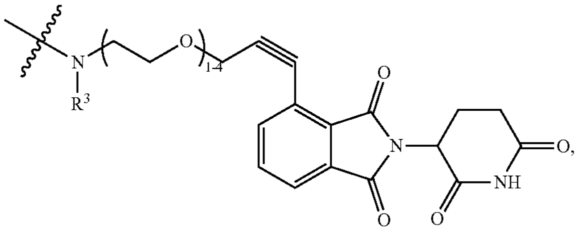
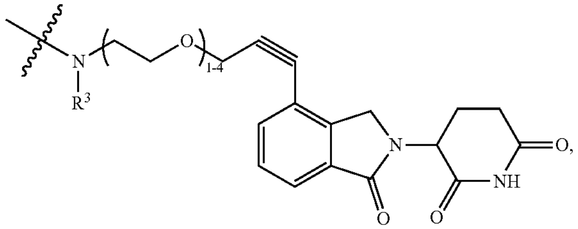
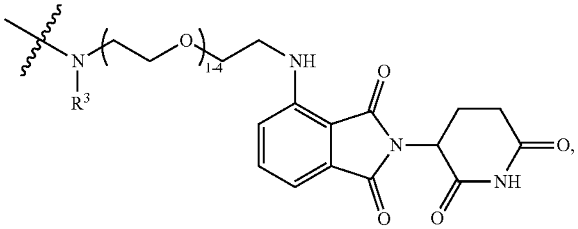
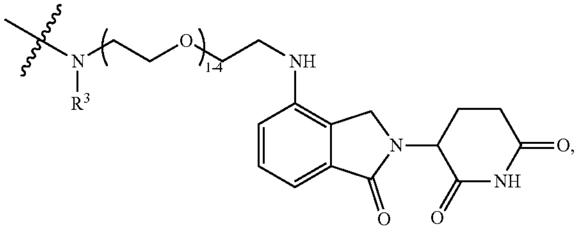
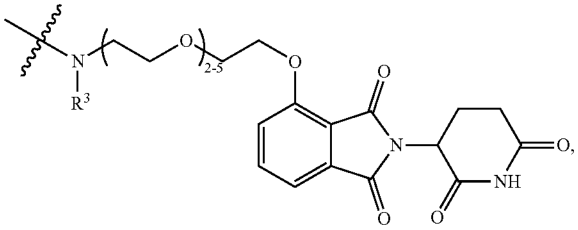
-continued
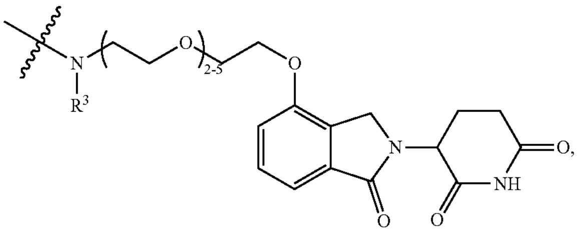
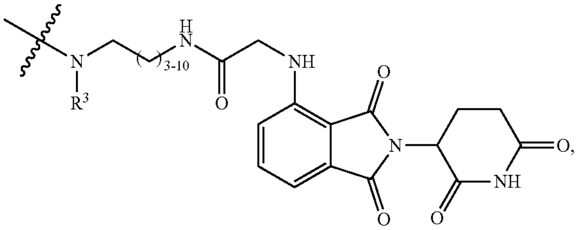
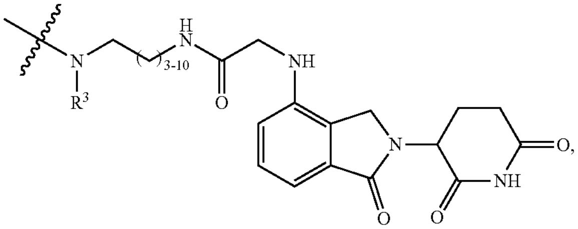
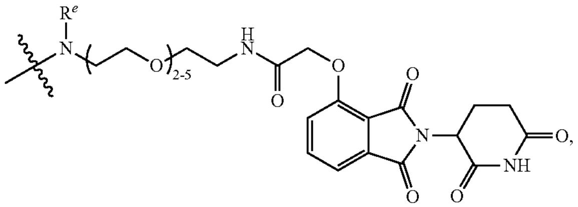
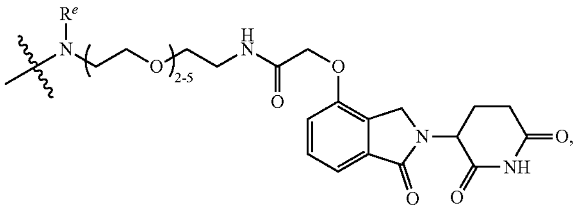
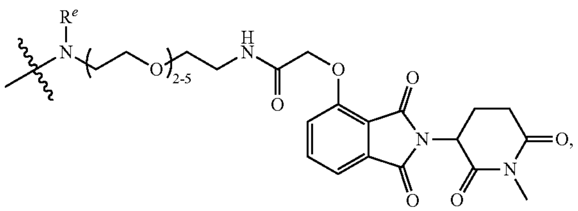
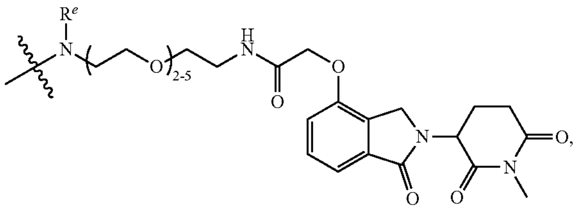

-continued
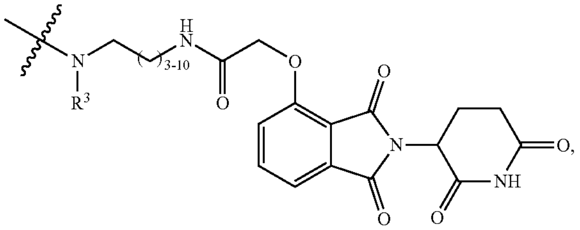
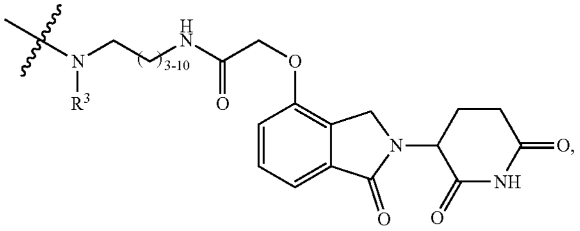
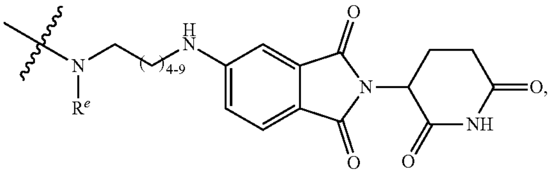
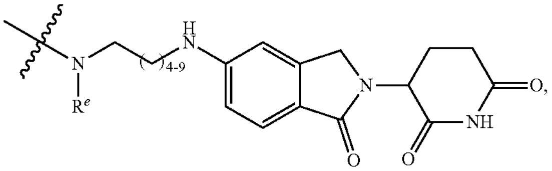
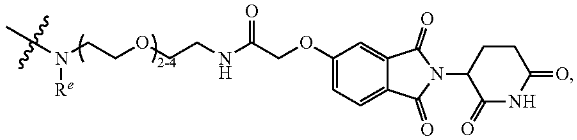
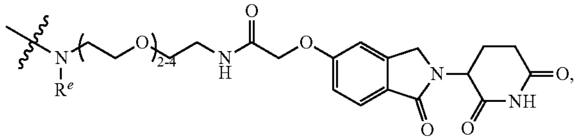
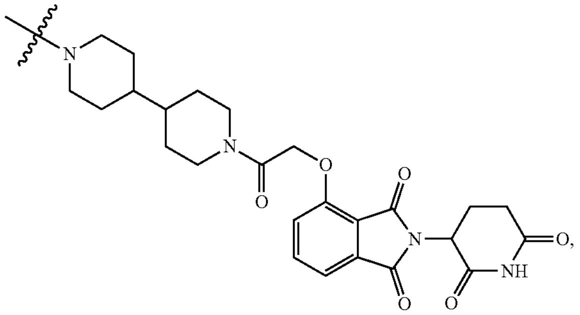
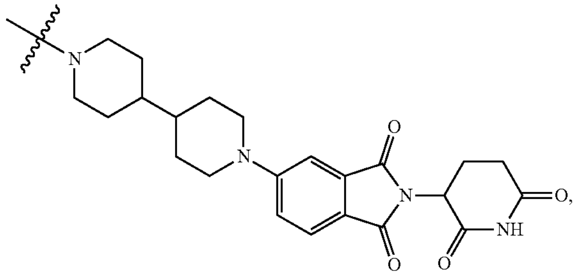
-continued
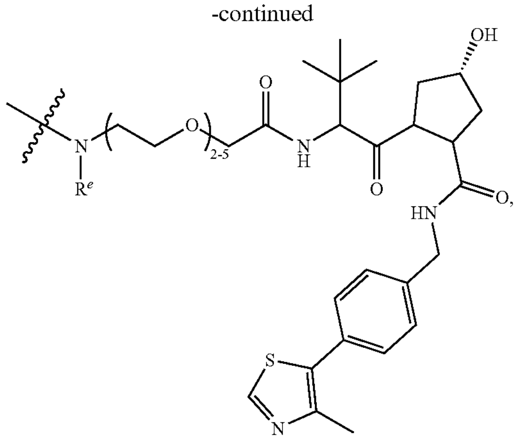
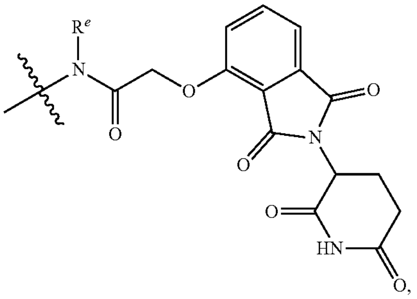
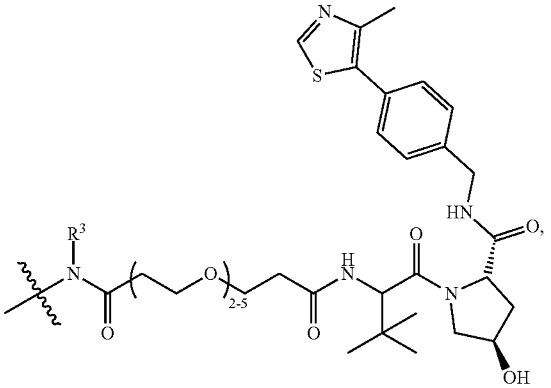
or
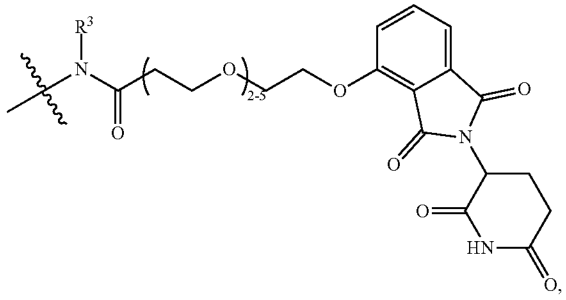
where $R^e$ is H, or $C_{1-6}$alkyl, such as methyl, ethyl, n-propyl, or isopropyl.
In some embodiments, the compound may have a formula selected from:

Formula I-A

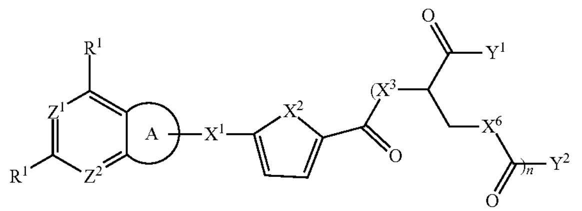

Formula I-B

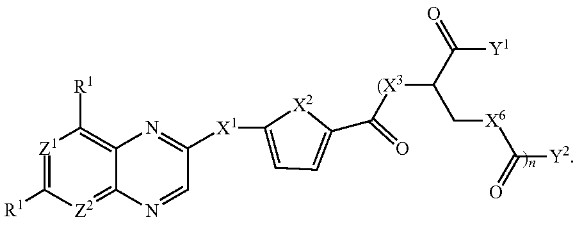

In some embodiments of Formulas I, I-A, and I-B, $X^2$ is CH═CH, and/or $X^1$ is —$CHNY^3$—. In some embodiments of Formulas I-A and I-B, each $R^1$ is $NH_2$, and in some embodiments, one $R^1$ is $NH_2$ and the other $R^1$ is OH.

i) $Y^2$ is Linker-$E_3$ Ligand

In some embodiments, $Y^1$ is OH or $OC_{1-6}$alkyl, $Y^2$ is Linker-$E_3$ Ligand, and if present, $Y^3$ is $R^2$. In some embodiments, the compound has a general Formula II Formula II

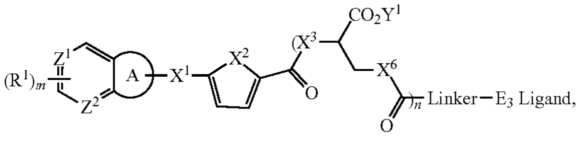

or a pharmaceutically acceptable salt, N-oxide, or hydrate thereof. With respect to Formula II and the associated Formulas III-XIV, a person of ordinary skill in the art understand that in any of the disclosed embodiments, the

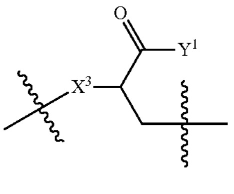

moiety is chiral, and that, unless otherwise specified in a particular embodiment, formula, structure, and/or context, in some embodiments, the

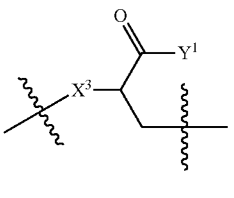

moiety may be

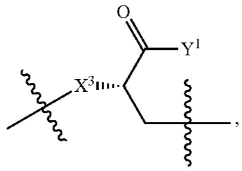

, or

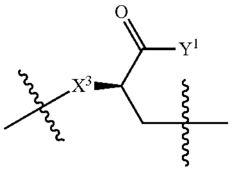

or a combination thereof, such as a racemic mixture of the chiral centers.

With reference to Formula II, $Z^1$, $Z^2$, $R^1$, m, n, ring A, $X^2$, $R^3$, $R^4$, $X^3$, $X^6$, Linker, and $E_3$ Ligand are as defined in Formula I. Each $Y^1$ independently is OH or $OC_{1-6}$alkyl. In some embodiments, at least one $Y^1$ is OH, and may be all $Y^1$ groups are OH. In other embodiments at least one $Y^1$ is $OC_{1-6}$alkyl, such as methyl or ethyl, and may be all $Y^1$ groups are $OC_{1-6}$alkyl. And in some embodiments where n is greater than 1, at least one $Y^1$ is OH and at least one $Y^1$ is $OC_{1-6}$alkyl.

$X^1$ is —CH═N—, —$CH_2NR^2$— or —$CH_2CHR^2$—, where $R^2$ is H, aliphatic, or haloalkyl, or $R^2$, together with the atom to which it is attached, forms a 5-membered heterocyclic ring that is fused to ring A. In some embodiments, $R^2$ is H; $C_{1-6}$alkyl, for example, methyl, ethyl, or isopropyl; $C_{3-6}$cycloalkyl, such as cyclopropyl; $CF_3$; $C_{2-6}$alkynyl, such as propargyl; or forms a fused 5-membered unsaturated heterocyclic ring with ring A.

In some embodiments, each $X^6$ independently is $CH_2$ or

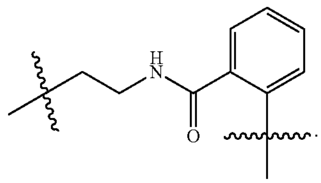 [SMILES: *CCNC(=O)c1ccccc1*]

In some embodiments, all $X^6$ moieties are the same, but in other embodiments, the compound comprises two different $X^6$ moieties.

In some embodiments of Formula II, Z and $Z^2$ are CH. And in certain embodiments, the compound has a structure according to formula III, III-a or III-b, or a pharmaceutically acceptable salt, N-oxide, or hydrate thereof:

Formula III

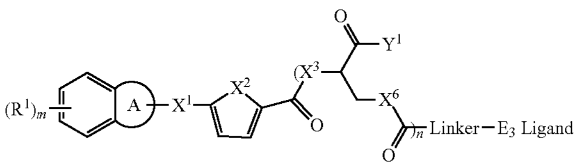

Formula III-a

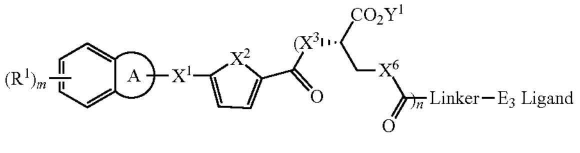

-continued

Formula III-b

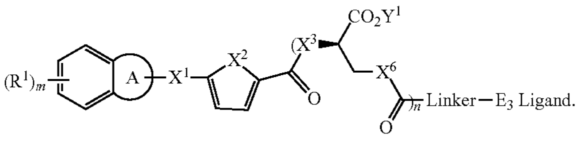

With respect to formulas III, III-a and III-b, $R^1$, m, n, $X^1$, $X^2$, $X^3$, $X^6$, $Y^1$, Linker and $E_3$ ligand are as previously defined for Formula II. And in particular embodiments, the compound has a structure according to formula IV, IV-a or IV-b:

Formula IV

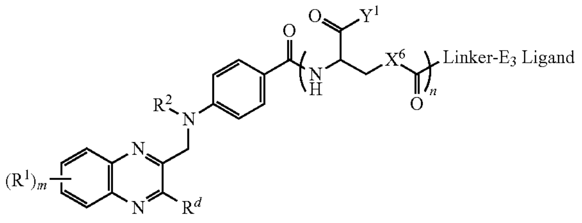

Formula IV-a

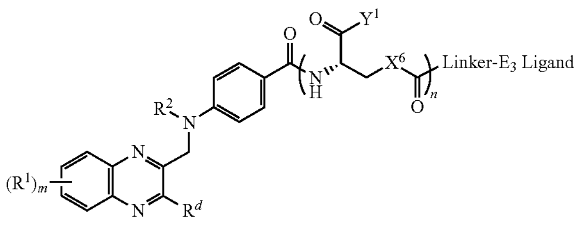

Formula IV-b

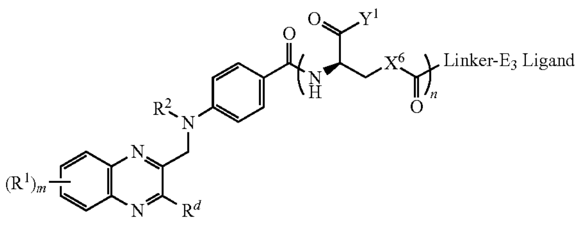

or a pharmaceutically acceptable salt, N-oxide, or hydrate thereof. With respect to Formula IV, $R^1$, n, $X^6$, $Y^1$, Linker and $E_3$ Ligand are as previously defined for Formula II; m is 0 to 4; $R^2$ is H, aliphatic, or haloalkyl; and $R^d$ is $R^1$ or H. In some embodiments, $R^2$ is H; $C_{1-6}$alkyl, such as methyl, ethyl, or isopropyl; $C_{3-6}$cycloalkyl, such as cyclopropyl; $CF_3$; or propargyl. In some embodiments, $R^d$ is H, $CH_3$ or $CF_3$. And in certain embodiments, $R^2$ is methyl or H, and $R^d$ is H.

In other embodiments of Formula II, $Z^1$ and $Z^2$ are nitrogen. In some embodiments, the compound has a structure according to Formula V or Formula VI, or a pharmaceutically acceptable salt, N-oxide, or hydrate thereof:

Formula V

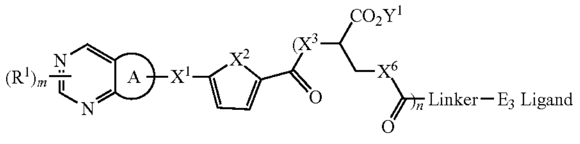

Formula VI

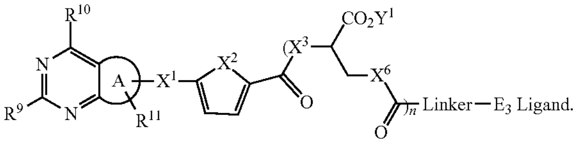

With respect to Formulas V and VI, $R^1$, m, n, $X^1$, $X^2$, $X^3$, $X^6$, $Y^1$, Linker and $E_3$ ligand, if present, are as previously defined for Formula II, and with respect to Formula VI, each of $R^9$, $R^{10}$ and $R^{11}$ independently are as previously defined for $R^1$.

In some embodiments of Formula VI, $R^9$ is $NH_2$, $CF_3$ or $CH_3$.

In some embodiments of Formula VI, $R^{10}$ is OH, $NH_2$, SH, $S(=O)R^b$, $CF_3$, $CF_2H$, or

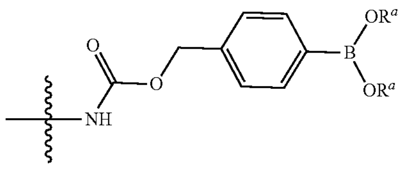

where each $R^a$ independently is H or two $R^a$s together form a 5-membered heterocycloaliphatic ring optionally substituted with 1-4 alkyl groups, such as methyl. and And in some embodiments of Formula VI, $R^{11}$ is H, $CF_3$, or $CH_3$.

In certain embodiments of Formula VI, $R^{10}$ is $NH_2$ or OH.

A person of ordinary skill in the art understands that when $R^{10}$ is OH or SH, the compound may be in a keto form, an enol form or a combination thereof, as shown below:

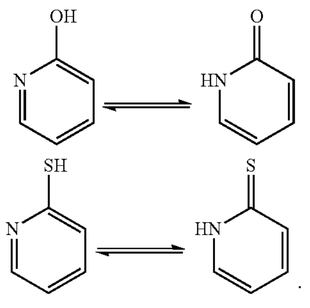

In some embodiments, the compound has a formula selected from:

Formula VII

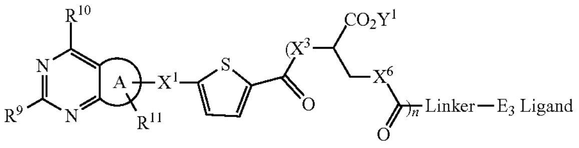

Formula VIII

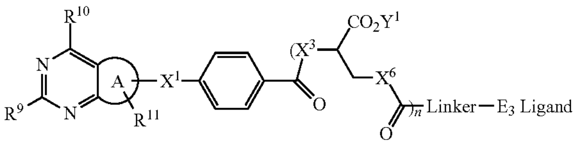

-continued

Formula IX

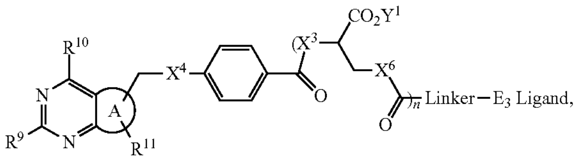

or a pharmaceutically acceptable salt, N-oxide, or hydrate thereof. With respect to Formulas VII, VIII and IX, ring A, $R^9$, $R^{10}$, $R^{11}$, $X^1$, $X^3$, $X^6$, n, $Y^1$, Linker and $E_3$ ligand are as previously defined for Formula VI, and $X^4$ is NH, $CH_2$, $CH(CH_2CH_3)$, $N(CH_3)$, $N(CF_3)$, $N(CH(CH_3)_2)$, N(cyclopropyl), $N(CH_2CH_3)$, or $N(CH_2CCH)$.

In certain embodiments of Formulas VI-IX, $R^{11}$ is H.

In other embodiments of Formula VI, the compound has a formula selected from:

Formula X

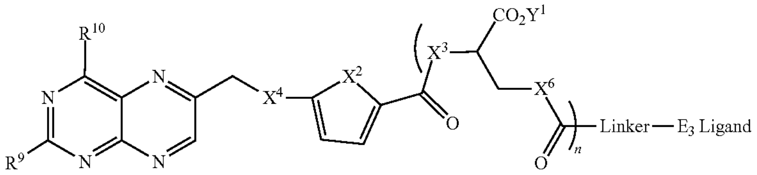

Formula XI

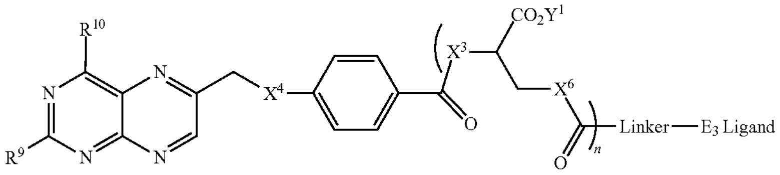

Formula XII

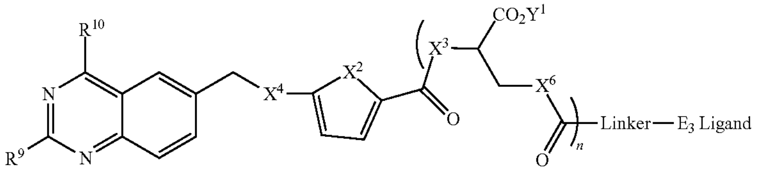

Formula XIII

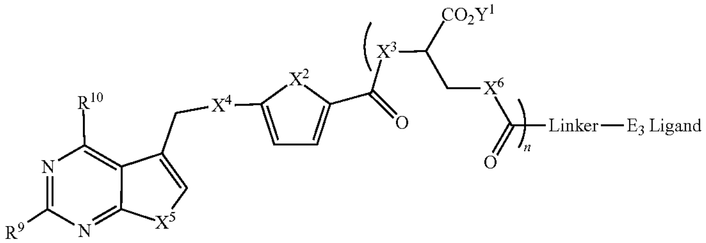

Formula XIV

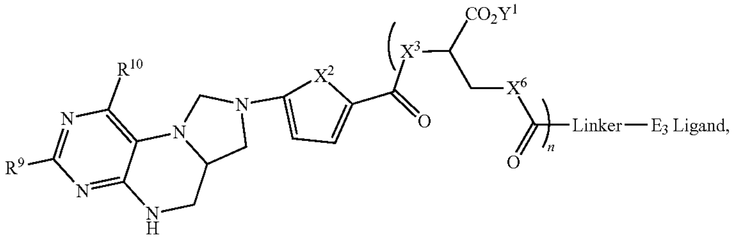

or a pharmaceutically acceptable salt, N-oxide, or hydrate thereof. With respect to Formulas X, XI, XII, XIII, and XIV, $R^9$, $R^{10}$, $X^2$, $X^3$, $X^6$, n, $Y^1$, Linker and $E_3$ Ligand are as previously defined for Formula VI, and if present, $X^4$ is NH, $CH_2$, $CH(CH_2CH_3)$, $N(CH_3)$, $N(CF_3)$, $N(CH(CH_3)_2)$, N(cyclopropyl), $N(CH_2CH_3)$, or $N(CH_2CCH)$. And with respect to Formula XII, $X^5$ is O or NH.

In certain embodiments of formulas VI-XIV, $R^9$ is $NH_2$, and/or $R^{10}$ is $NH_2$, and in particular embodiment, both $R^9$ and $R^{10}$ are $NH_2$.

In other certain embodiments of formulas VI-XIV, $R^9$ is $NH_2$ and $R^{10}$ is OH.

In some embodiments of formulas I-XIV, each $X^6$ is $CH_2$.

In other embodiments of formula I-XIV, each $X^6$ is

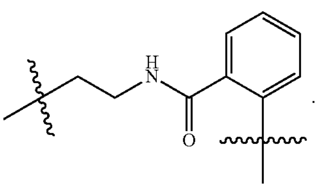 [SMILES: *CCNC(=O)c1ccccc1*]

In any embodiments, n may be 1, but in other embodiments, n is 2, 3, 4, or 5, such as 2, 3, or 4, and may be 3.

In a particular embodiment, n is 1, and $Y^1$ is OH. In an alternative embodiment, n is 1, and $Y^1$ is $OC_{1-6}$alkyl, such as O-methyl.

ii) $Y^1$ is Linker-$E_3$ Ligand

In other embodiments of Formula I, $Y^1$ is Linker-$E_3$ Ligand, $Y^2$ is OH, or $OC_{1-6}$alkyl, and if present, $Y^3$ is $R^2$. In some embodiments, the compound has a general formula XV Formula XV

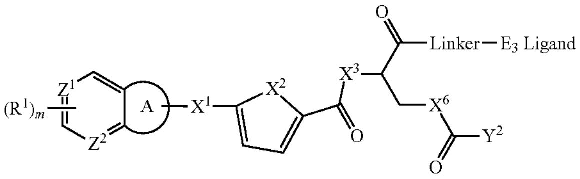

or a pharmaceutically acceptable salt, N-oxide, or hydrate thereof. With respect to Formula XV and the associated Formulas XVI-XXVII, a person of ordinary skill in the art understand that in any of the disclosed embodiments, the

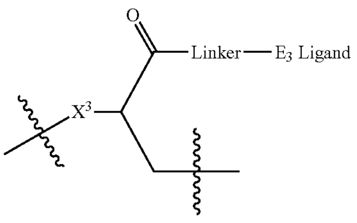

moiety is chiral, and that, unless otherwise specified in a particular embodiment, formula, structure, and/or context, in some embodiments, the

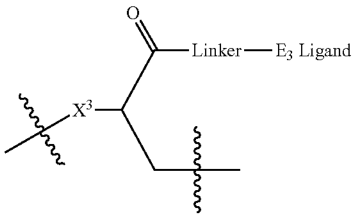

moiety may be

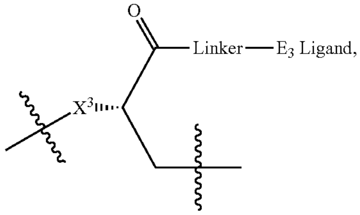

or

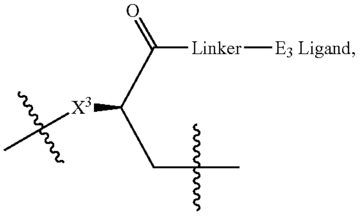

or a combination thereof, such as a racemic mixture of the chiral centers.

With reference to Formula XV, $Z^1$, $Z^2$, $R^1$, m, ring A, $X^1$, $X^2$, $R^3$, $R^4$, $X^3$, $X^6$, Linker, and $E_3$ Ligand are as previously defined for Formulas II-XIV. $Y^2$ is OH or $OC_{1-6}$alkyl, such as OH or methyl, typically OH.

The compound according to Formula XV may have a formula according to any one of Formulas XVI to XXVII, or a pharmaceutically acceptable salt, N-oxide, or hydrate thereof:

Formula XVI

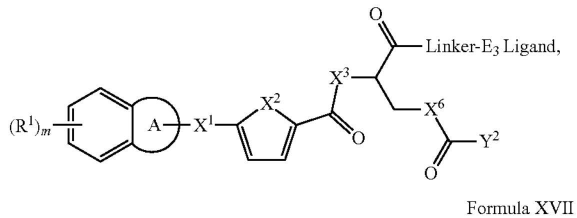

Formula XVII

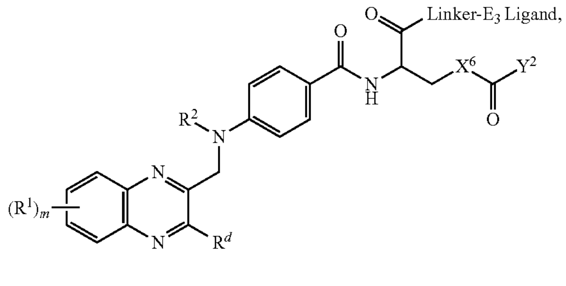

-continued

Formula XVIII

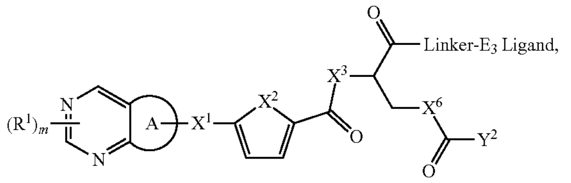

Formula XIX

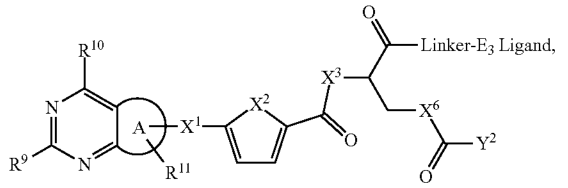

Formula XX

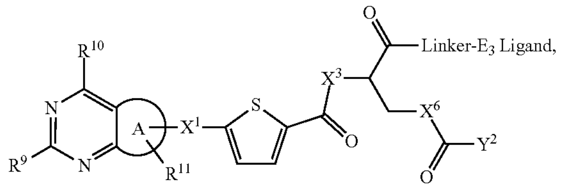

Formula XXI

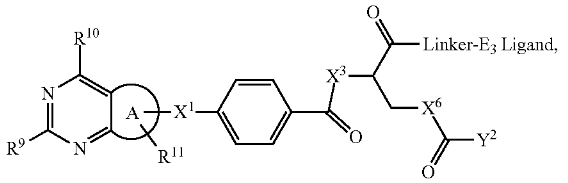

Formula XXII

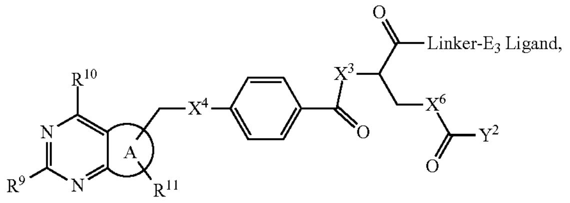

Formula XXIII

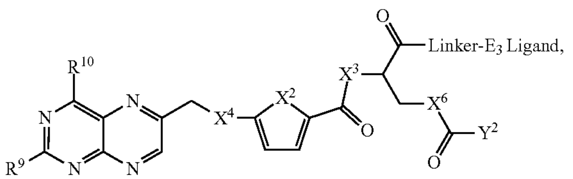

Formula XXIV

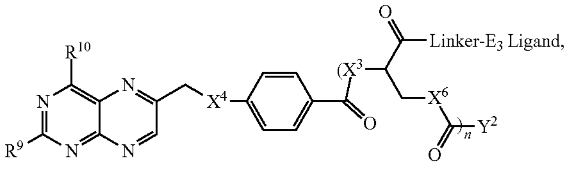

-continued

Formula XXV

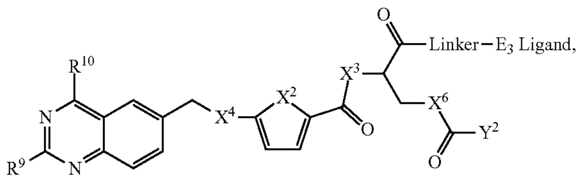

Formula XXVI

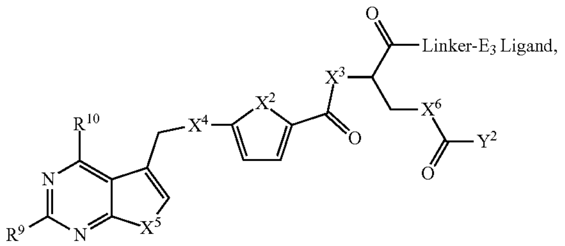

Formula XXVII

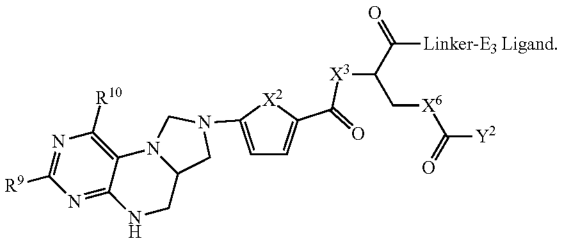

With respect to Formulas XVI to XXVII, Ring A, $R^1$, $R^2$, $R^9$, $R^{10}$, $R^{11}$, $R^d$, m, n, $X^1$, $X^2$, $X^3$, $X^4$, $X^5$, $X^6$, Linker and $E_3$ Ligand, if present, are as previously defined for Formulas II to XIV. And $Y^2$ is as previously defined for Formula XV.

In particular embodiment, $Y^2$ is OH, but in an alternative embodiment, $Y^2$ is $OC_{1-6}$alkyl, such as O-methyl.

iii) $X^1$ is —$CH_2N(Y^3)$— and $Y^3$ is $X^7$-Linker-$E_3$ Ligand

In alternative embodiments of Formula I, each of $Y^1$ and $Y^2$ independently is OH or $OC_{1-6}$alkyl, and the compound has a Formula XXVIII, or a pharmaceutically acceptable salt thereof:

Formula XXVIII

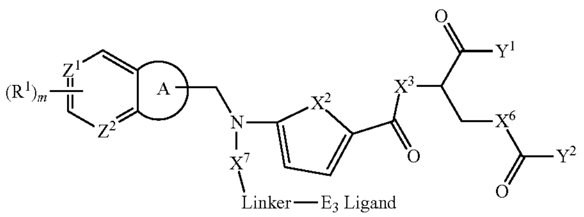

With respect to Formula XXVIII, $Z^1$, $Z^2$, $R^1$, m, ring A, $X^2$, $R^3$, $R^4$, $X^3$, $X^6$, Linker, and $E_3$ Ligand are as defined in Formula I, each of $Y^1$ and $Y^2$ independently is OH or $OC_{1-6}$alkyl, and $X^7$ is $C_{4-8}$alkyl. And with respect to Formula XXVIII and the related Formulas XXIX-XXXVIII, a person of ordinary skill in the art understand that in any of the disclosed embodiments, the

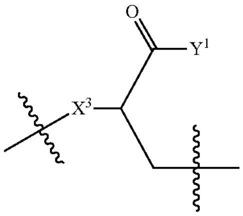

moiety is chiral, and that, unless otherwise specified in a particular embodiment, formula, structure, and/or context, in some embodiments, the

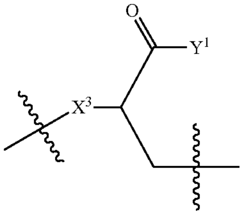

moiety may be

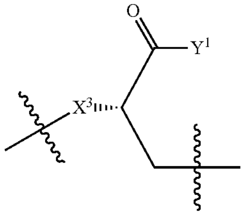

, or

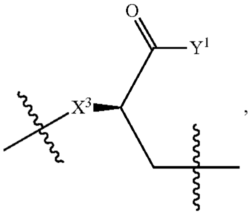

, or a combination thereof, such as a racemic mixture of the chiral centers.

The compound according to Formula XXVIII may have a formula according to any one of Formulas XXIX to XXXVIII, or a pharmaceutically acceptable salt thereof:

Formula XXIX

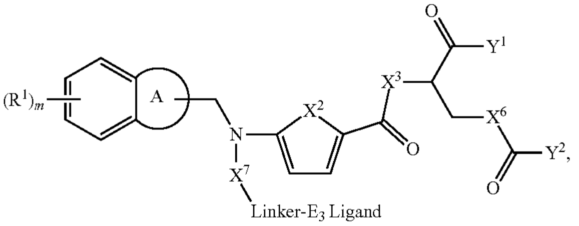

Formula XXX

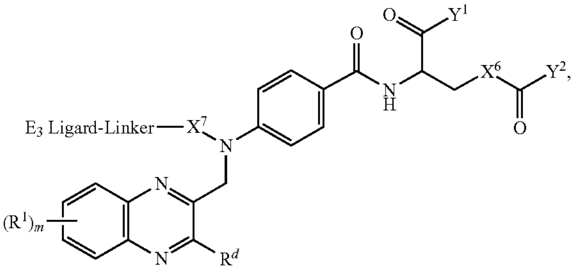

-continued

Formula XXXI

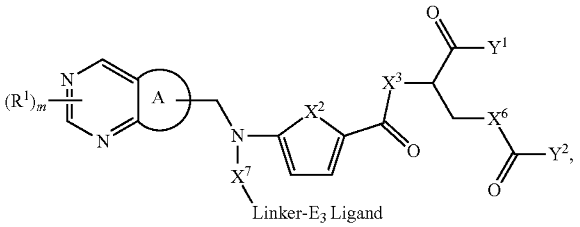

Formula XXXII

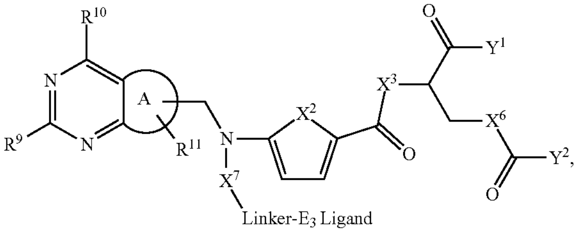

Formula XXXIII

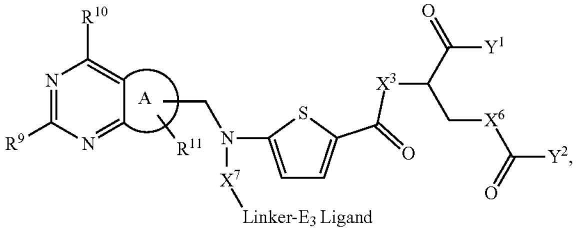

Formula XXXIV

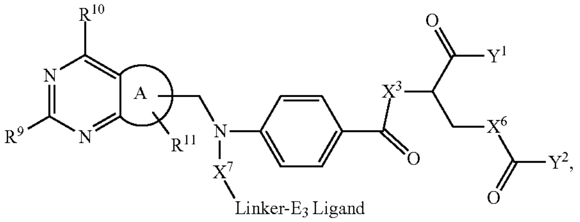

Formula XXXV

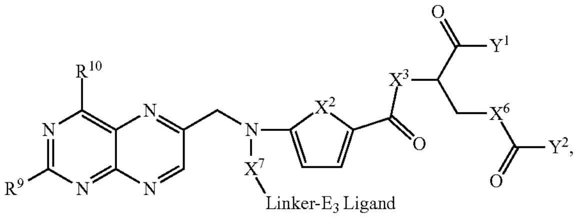

Formula XXXVI

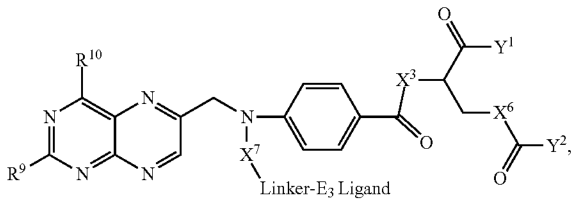

-continued

Formula XXXVII

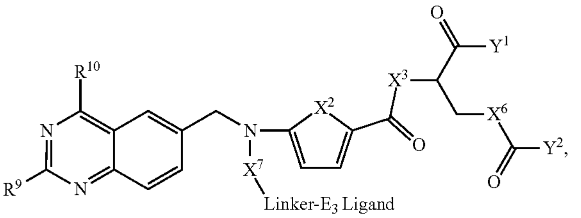

Formula XXXVIII

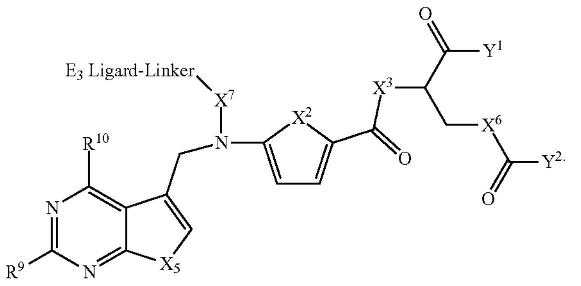

In some embodiments, each of $Y^1$ and $Y^2$ independently is OH or $OC_{1-6}$alkyl, such as O-methyl. In some embodiments, each of $Y^1$ and $Y^2$ is OH. In other embodiments, each of $Y^1$ and $Y^2$ is $OC_{1-6}$alkyl, such as O-methyl. And in further embodiments, one of $Y^1$ and $Y^2$ is OH and the other is $OC_{1-6}$alkyl, such as O-methyl, such as $Y^1$=OH and $Y^2$=$OC_{1-6}$alkyl, or $Y^1$=$OC_{1-6}$alkyl and $Y^2$=OH.

In certain embodiments of Formulas I-XXXVIII, the

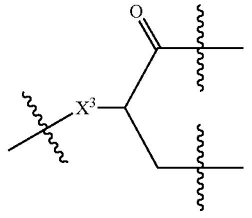

moiety is

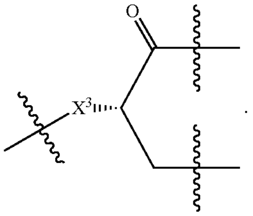

For example, a compound according to Formulas I, II, XV or XXVII may have a structure according to Formulas I-a, II-a, XV-a, or XXVII-a, or a pharmaceutically acceptable salt, N-oxide, or hydrate thereof:

Formula II-a

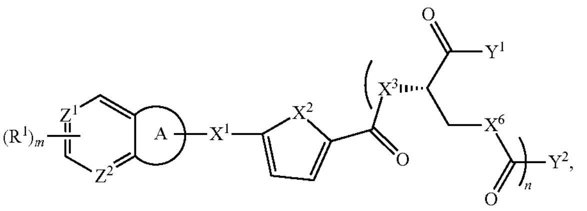

Formula I-a

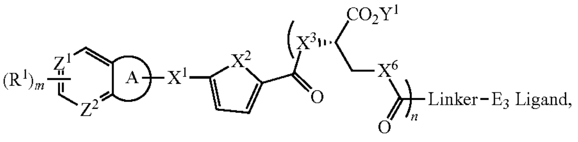

Formula XV-a

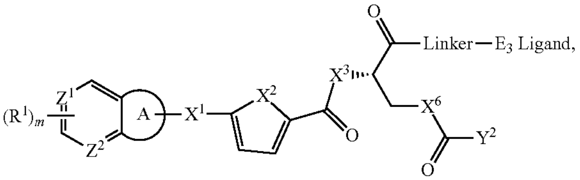

Formula XXVIII-a

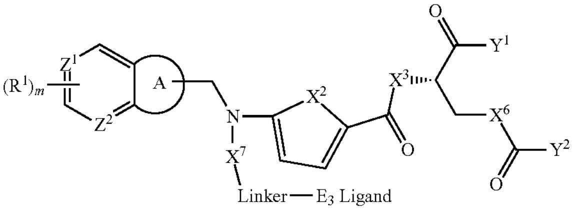

In other embodiments of Formulas I-XXXVIII, the

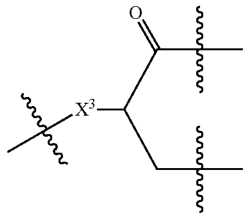

moiety is

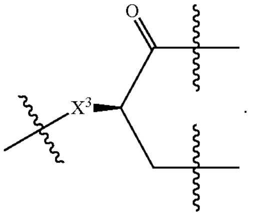

For example, a compound according to Formulas I, II, XV or XXVIII may have a structure according to Formulas I-b, II-b, XV-b, or XXVIII-b, or a pharmaceutically acceptable salt, N-oxide, or hydrate thereof:

Formula I-b
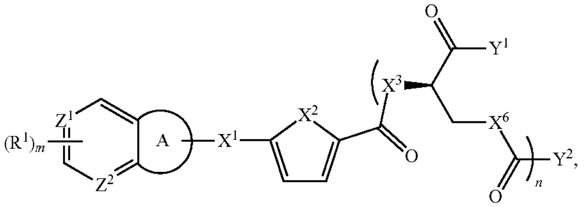
Formula II-b
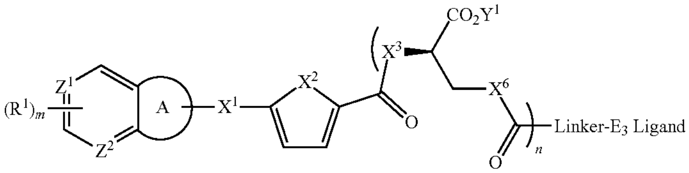
Formula XV-b
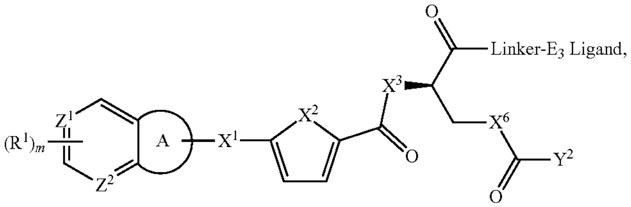
Formula XXVIII-b
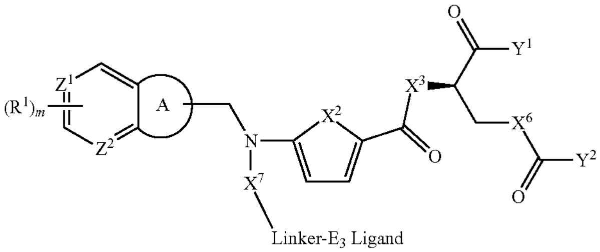
In certain embodiments of Formulas I-XXVII, the compound has a formula selected from:
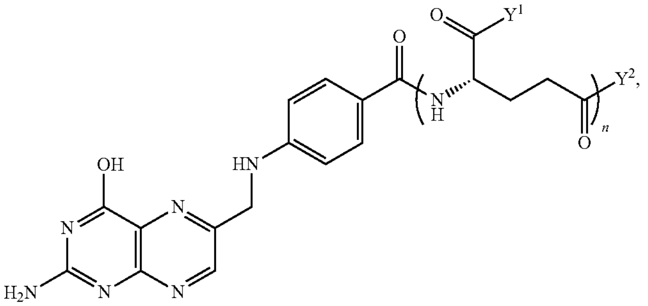
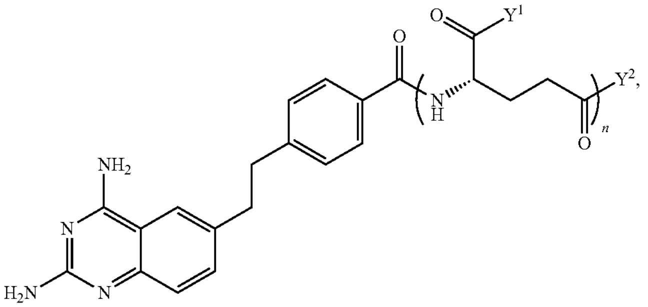

-continued
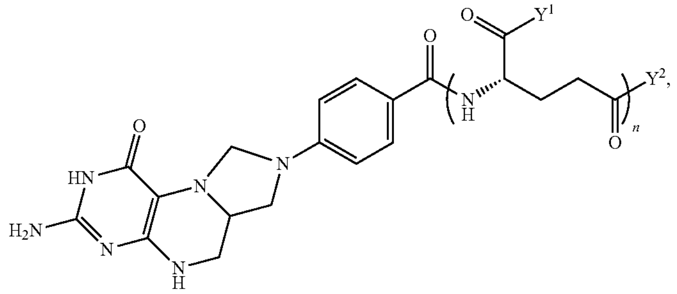
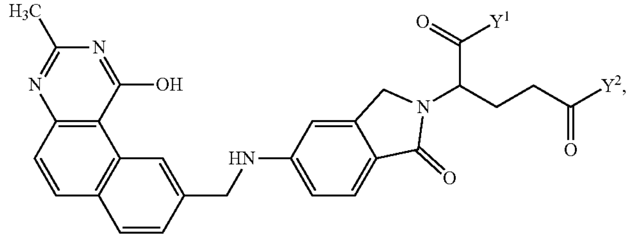
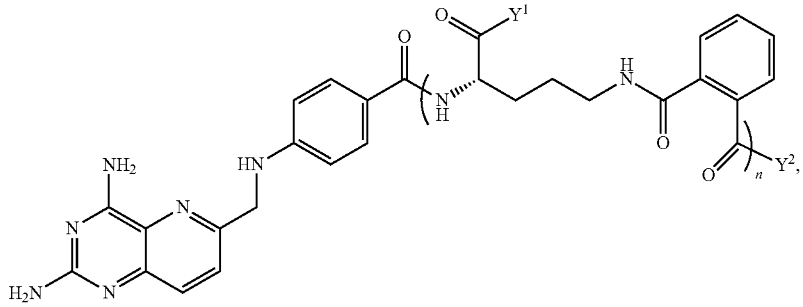
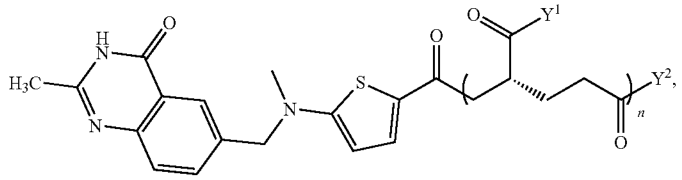
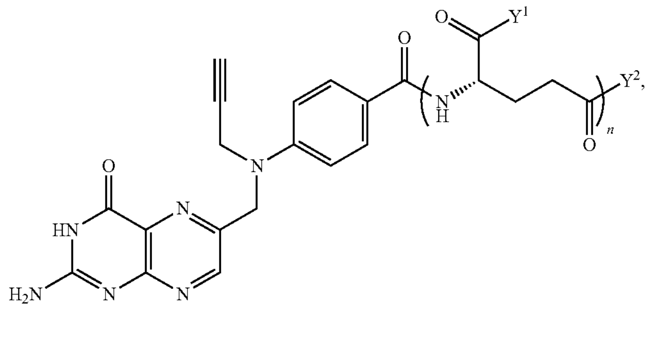

-continued
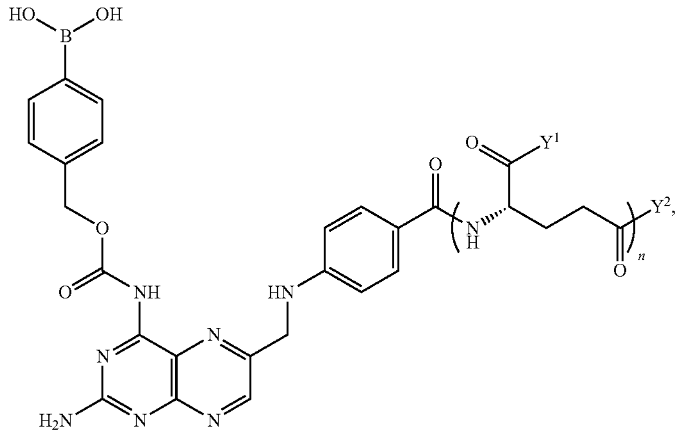
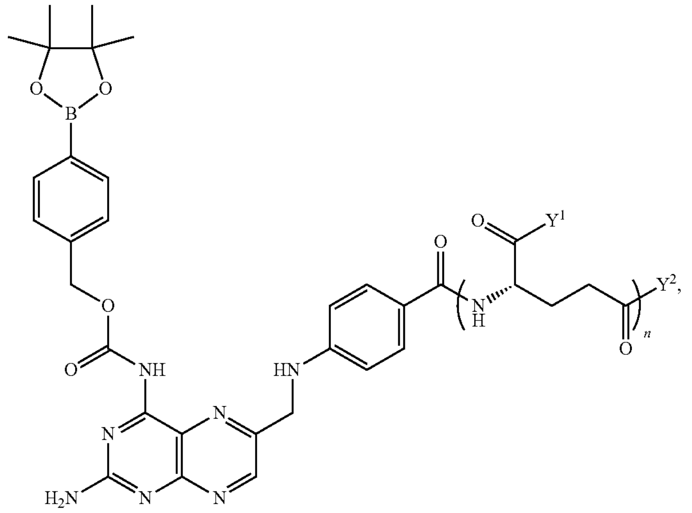
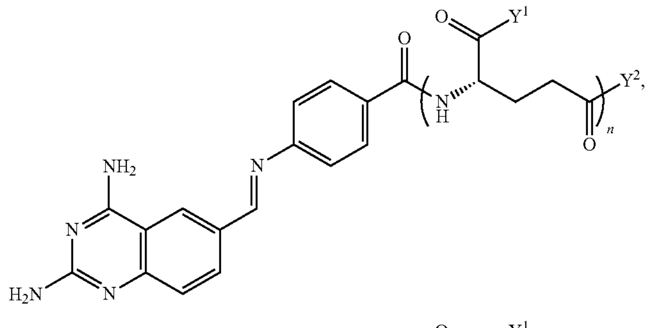
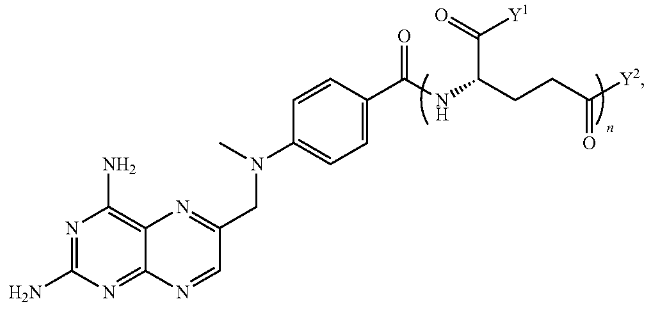

-continued
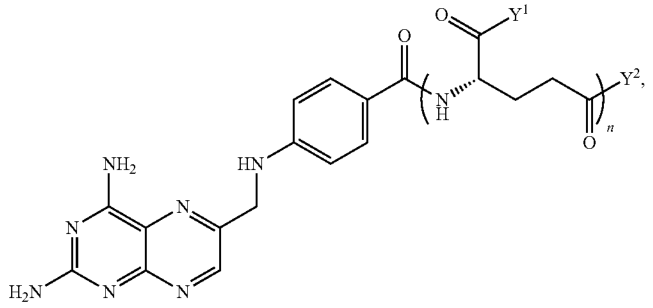
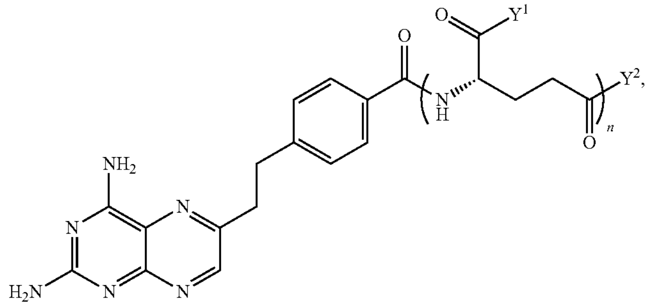
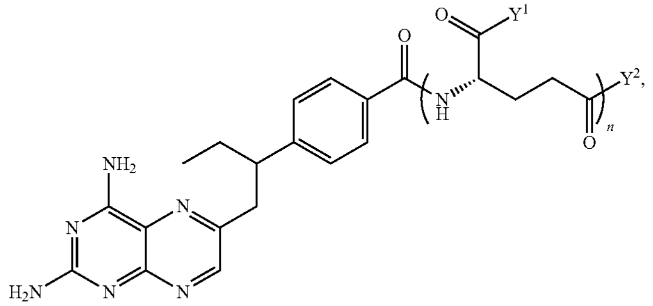
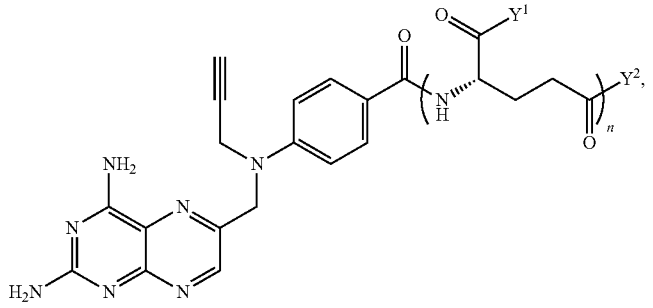
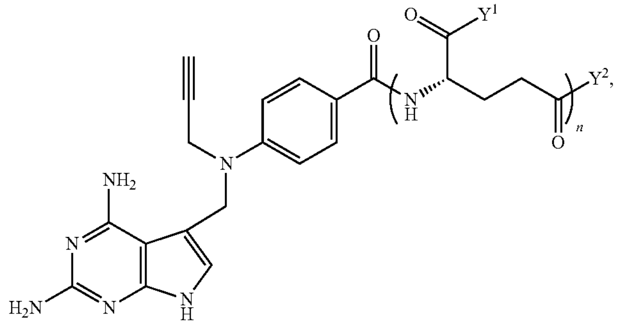

-continued
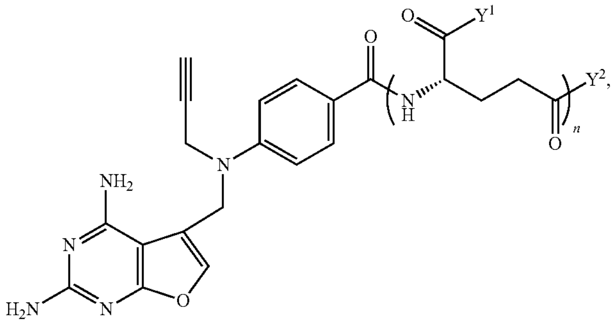
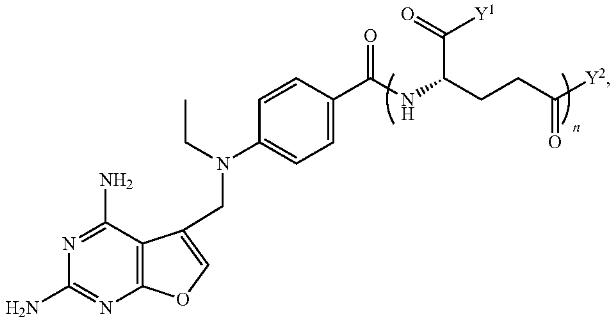
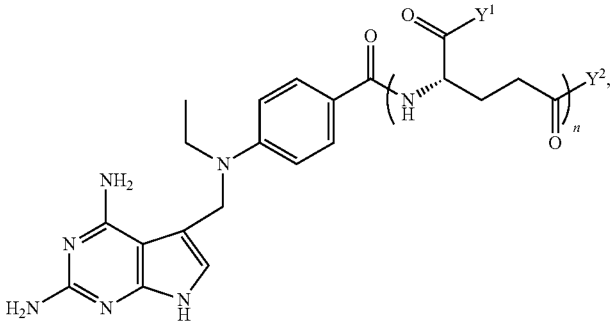
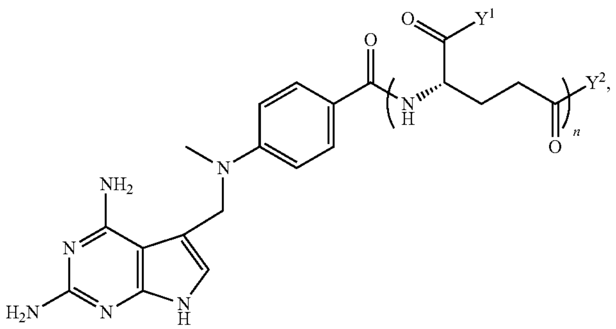
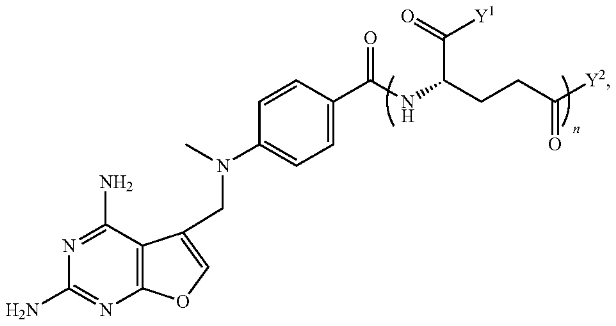

-continued
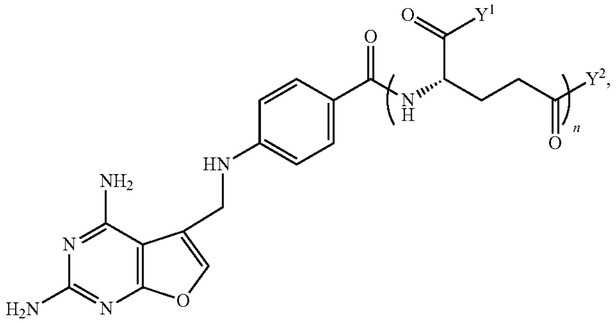
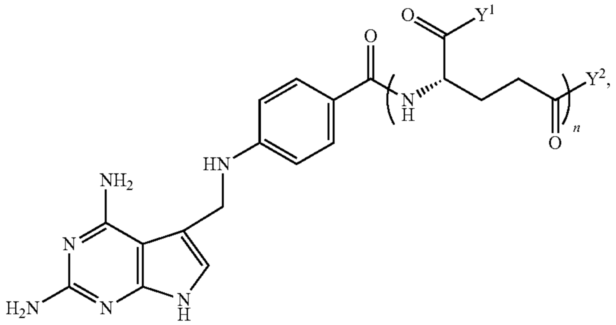
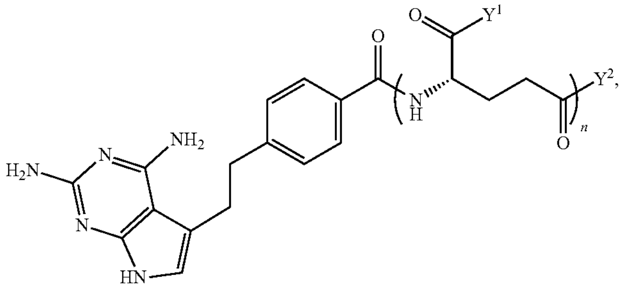
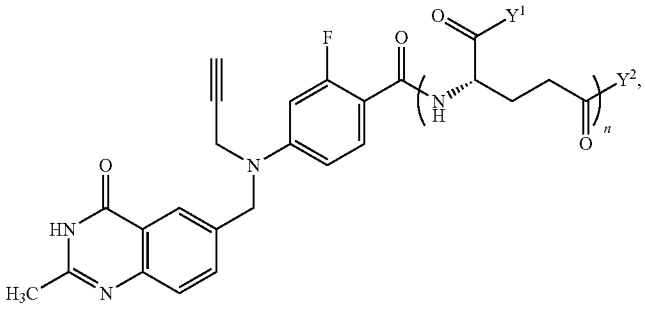
or
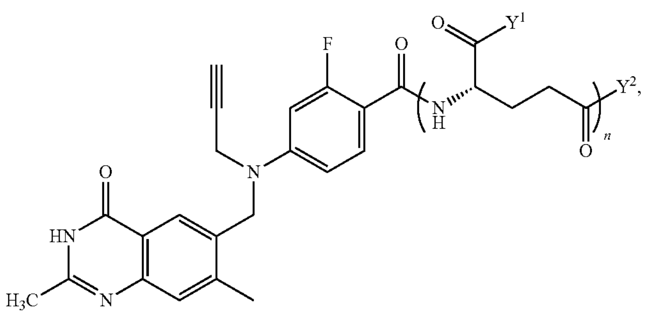

or a pharmaceutically acceptable salt, N-oxide, or hydrate thereof. With respect to the above formulas, in some embodiments, n is 1, but in other embodiments, n is 2, 3, 4, or 5. And when n is 1, one of $Y^1$ and $Y^2$ is -Linker-$E_3$ ligand, as previously defined for Formula I, and the other of $Y^1$ and $Y^2$ is OH or $OC_{1-6}$alkyl, such as O-methyl. And when n is greater than 1, $Y^2$ is -Linker-$E_3$ ligand, and each $Y^1$ independently is OH or $OC_{1-6}$alkyl, such as O-methyl.

In a particular embodiment, n is 1, $Y^1$ is OH and $Y^2$ is -Linker-$E_3$ ligand. In an alternative embodiment, n is 1, $Y^1$ is $OC_{1-6}$alkyl, such as O-methyl and $Y^2$ is -Linker-$E_3$ ligand.

In another particular embodiment, n is 1, $Y^2$ is OH and $Y^1$ is -Linker-$E_3$ ligand. In an alternative embodiment, n is 1, $Y^2$ is $OC_{1-6}$alkyl, such as O-methyl and $Y^1$ is -Linker-$E_3$ ligand.

In certain embodiments of Formulas XXVIII-XXXVIII the compound has a formula selected from:

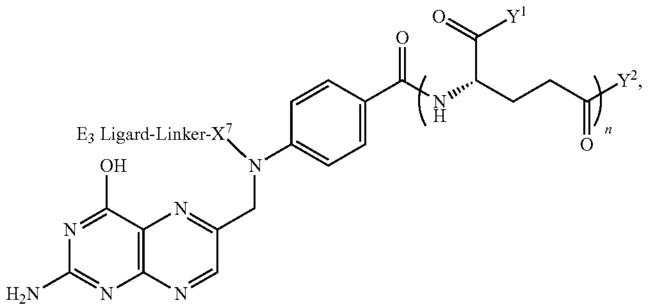

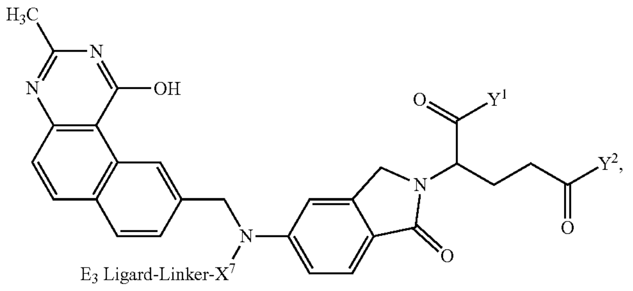

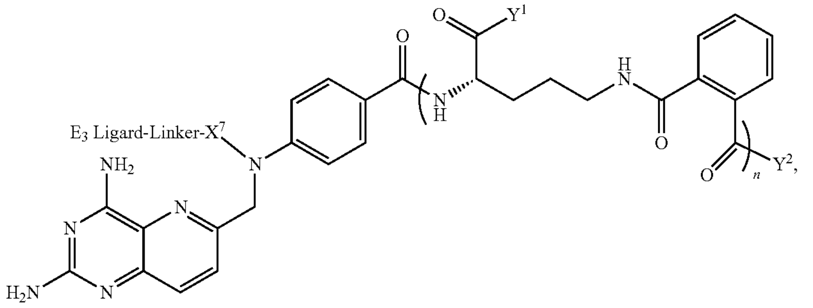

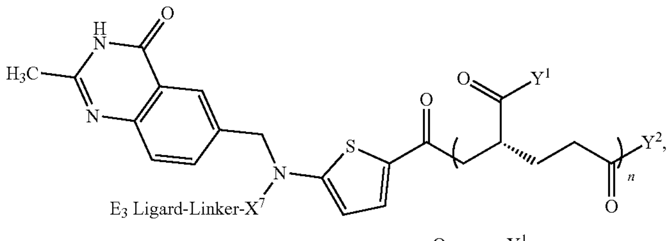

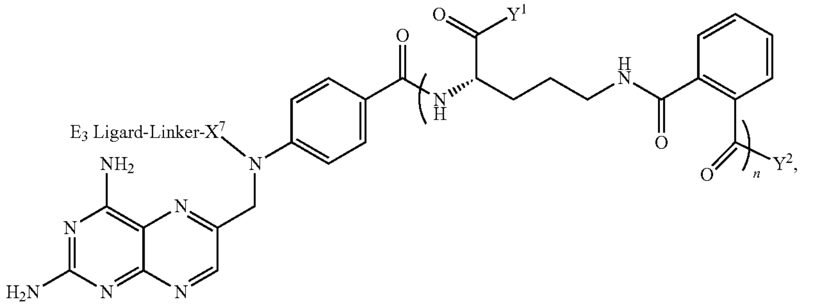

-continued
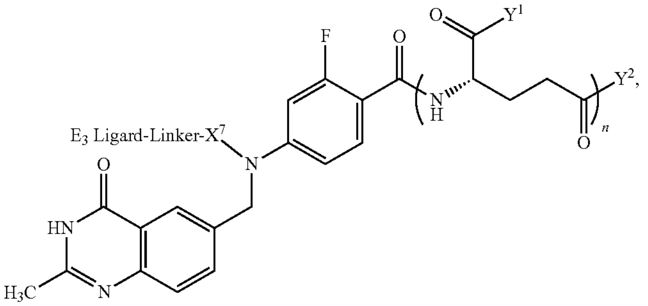
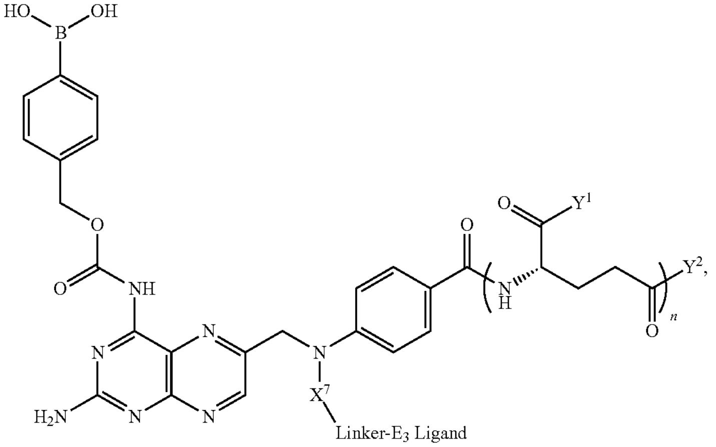
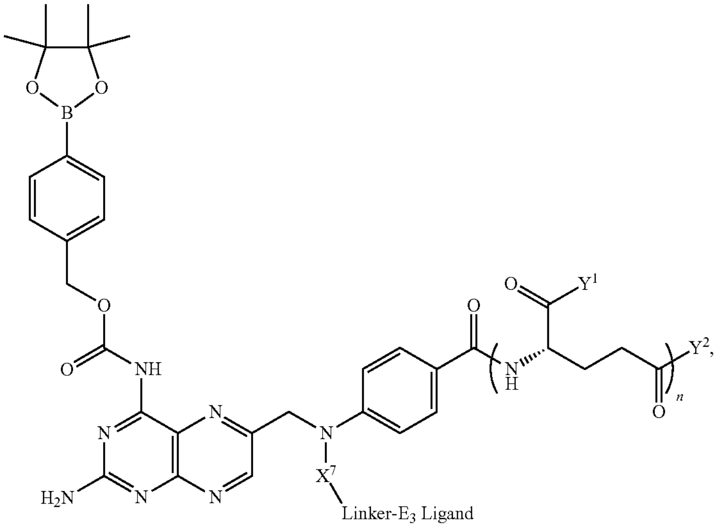
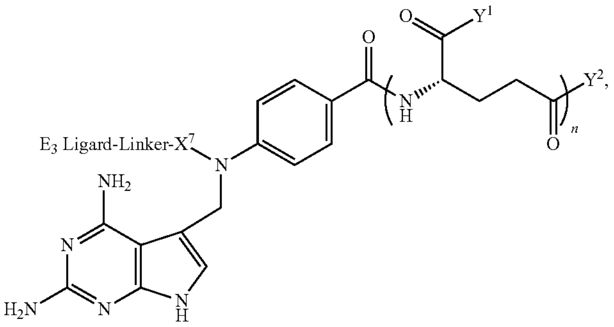
or

-continued

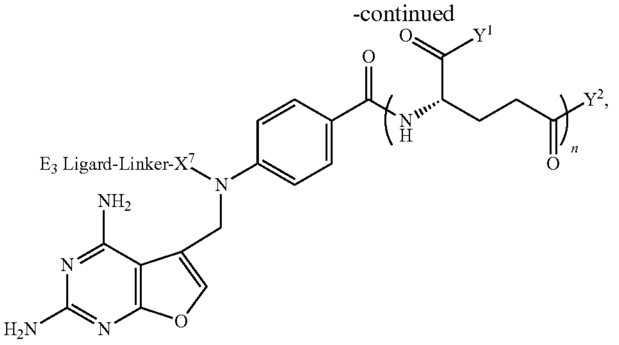

or a pharmaceutically acceptable salt, N-oxide, or hydrate thereof. With respect to the above formulas, in some embodiments, n is 1, but in other embodiments, n is 2, 3, 4, or 5. And each of $Y^1$ and $Y^2$ independently is OH or $OC_{1-6}$alkyl, and $X^7$, Linker and $E_3$ Ligand are as previously defined for Formula I.

In some of the preceding embodiments, $Y^1$, if present, is OH.

In some of the preceding embodiments, $Y^2$, if present, is OH.

In some of the preceding embodiments, if both are present, both $Y^1$ and $Y^2$ are OH.

Certain disclosed exemplary compounds within the scope of one or more of the general formulas include:

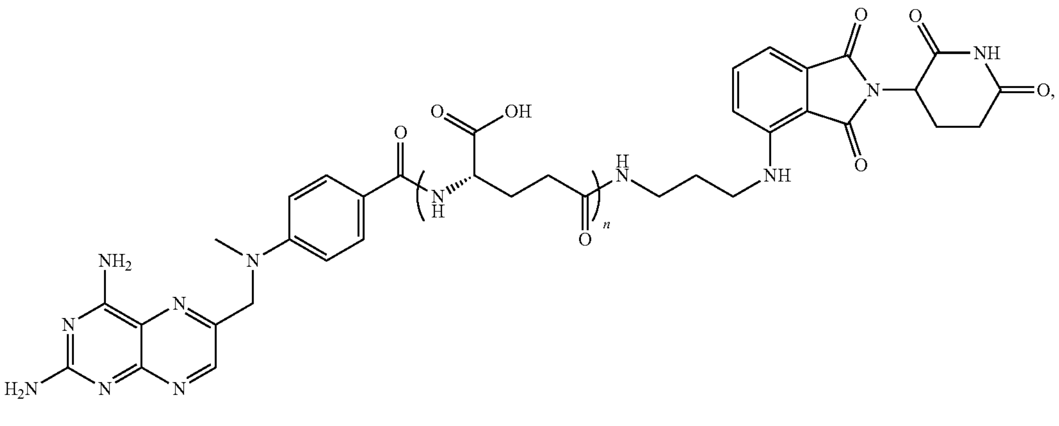

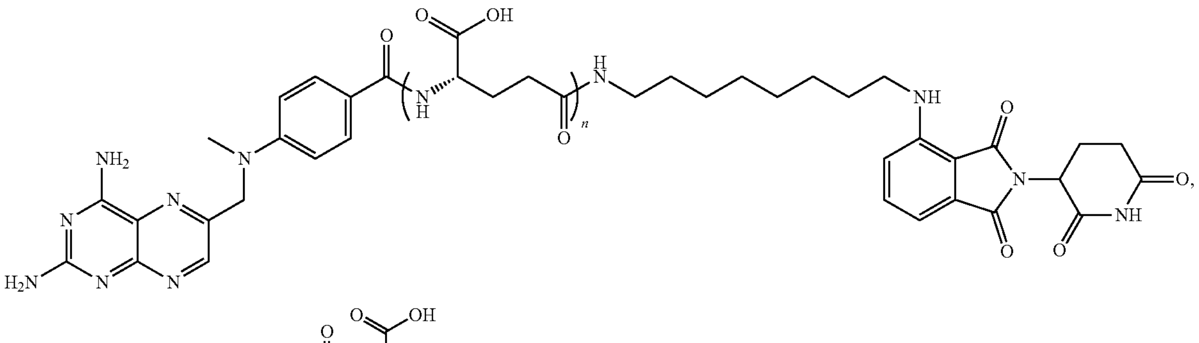

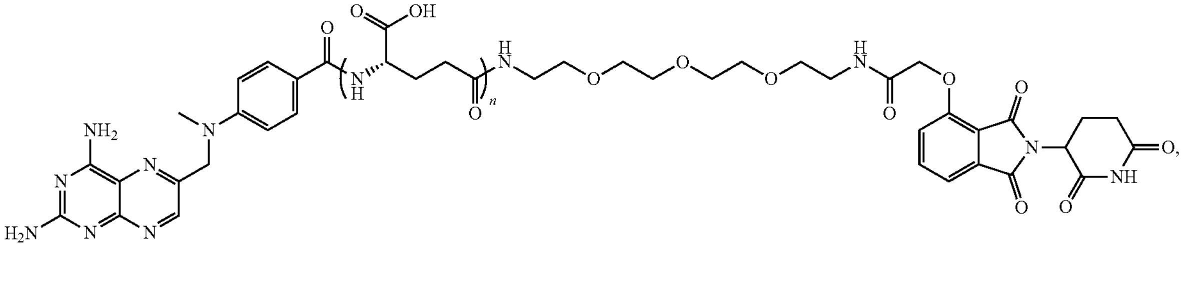

-continued
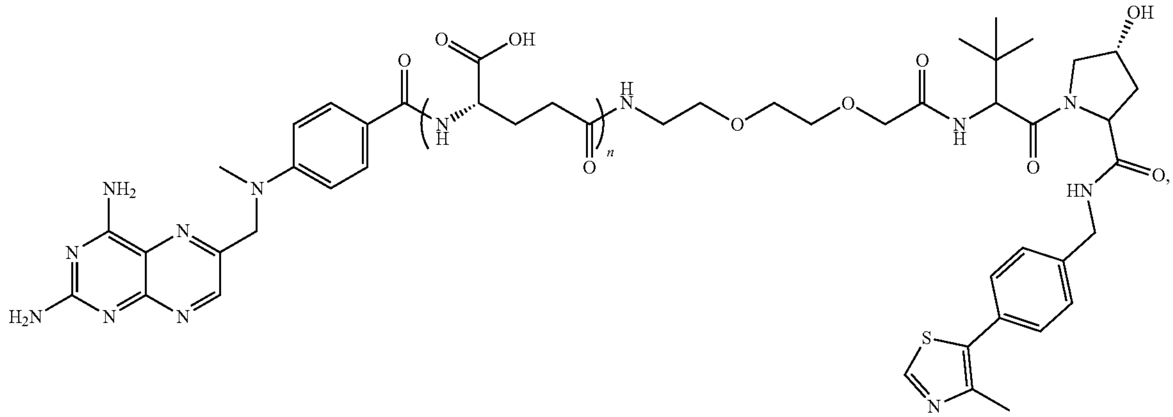
,
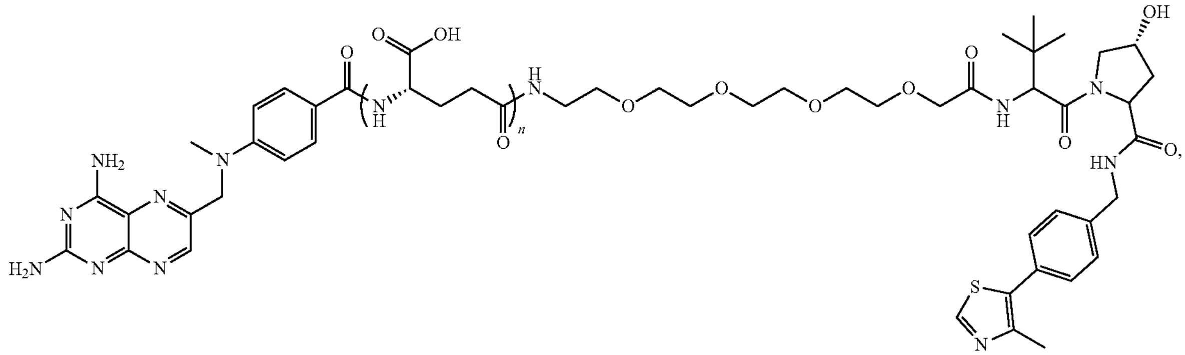
,
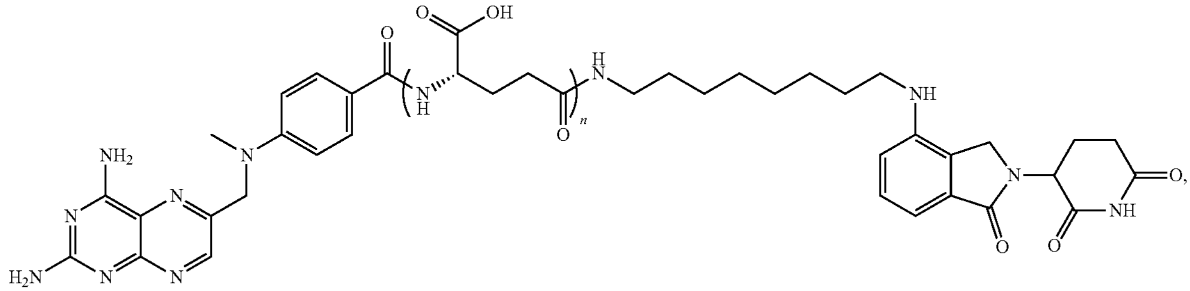
,
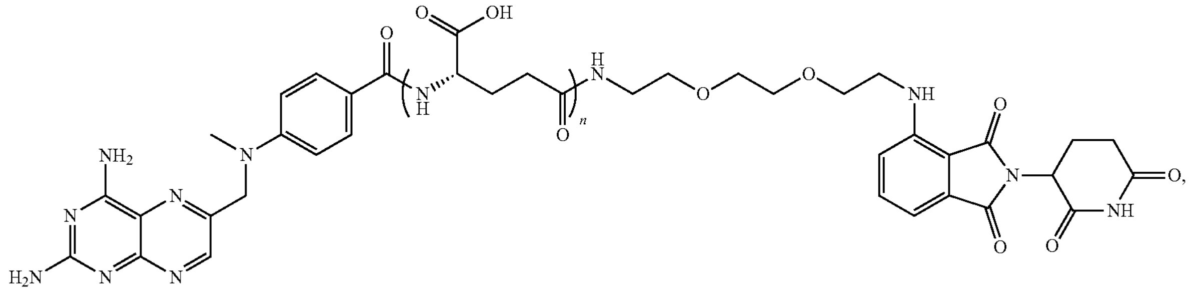
,
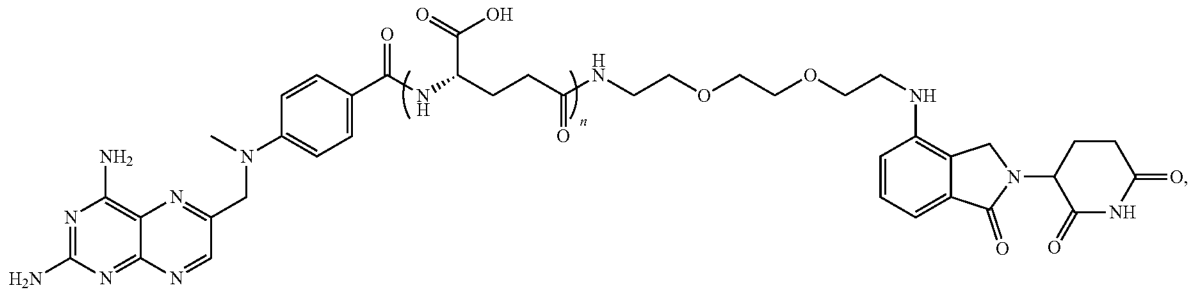
, -continued
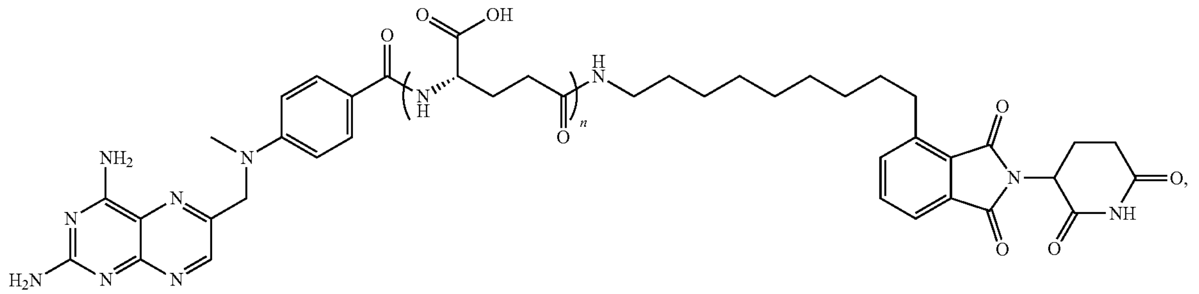
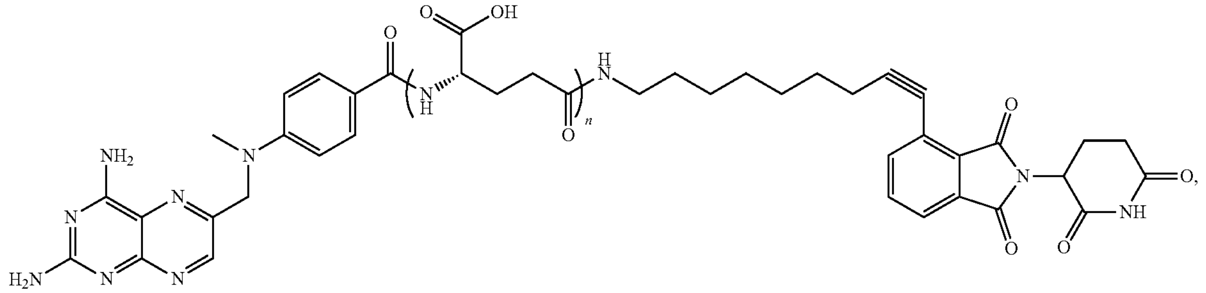
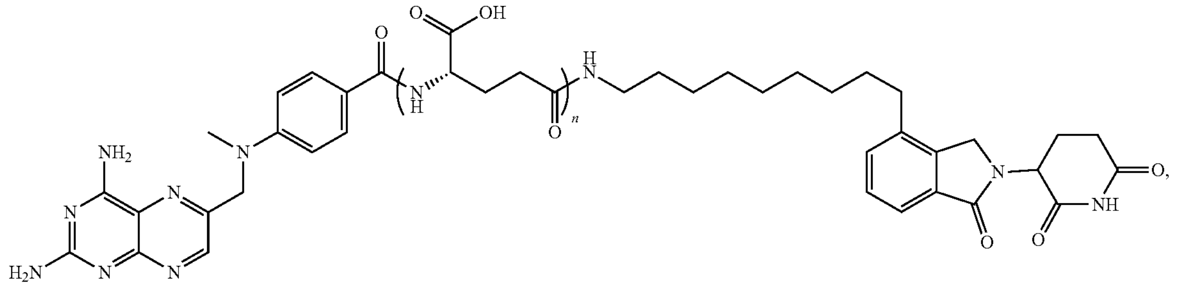
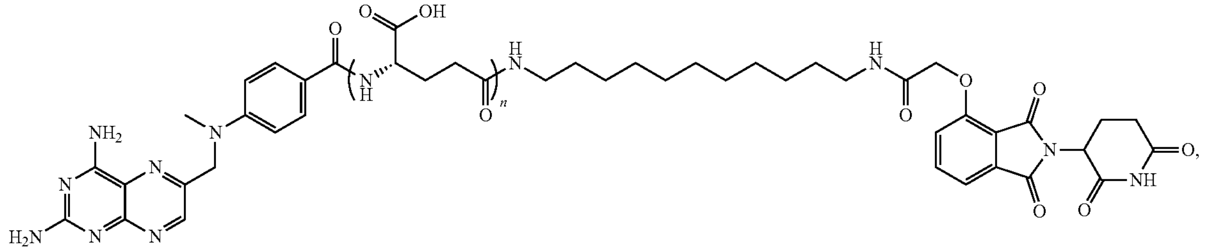
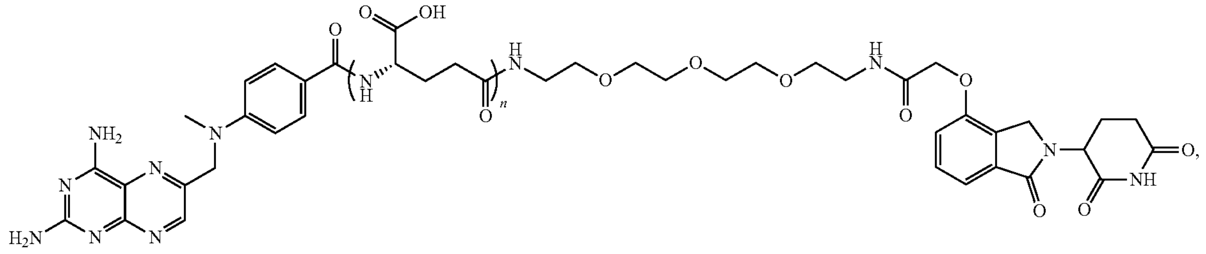
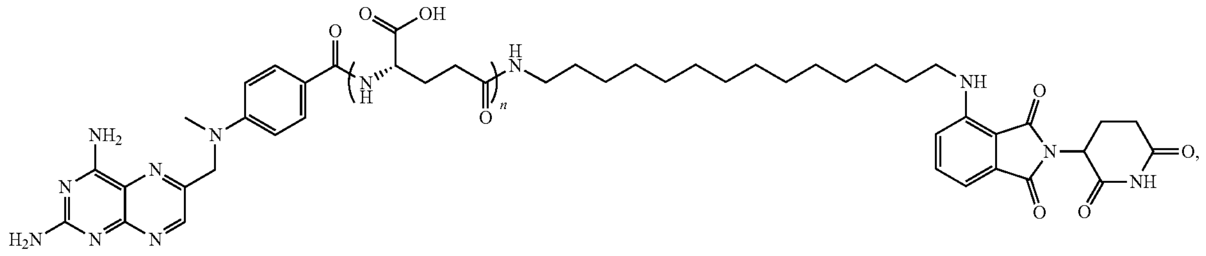

-continued
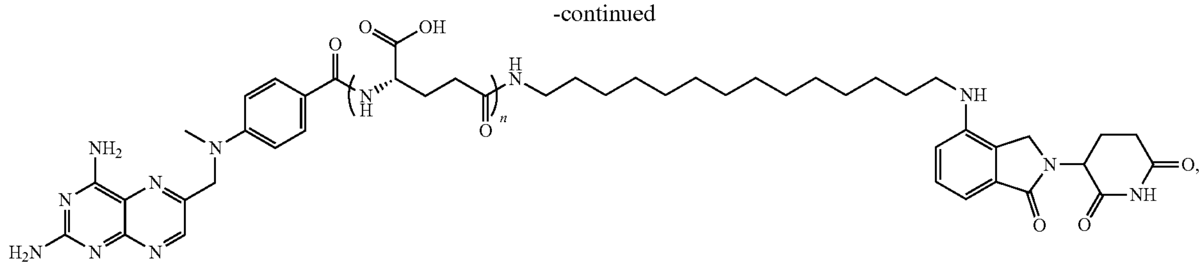
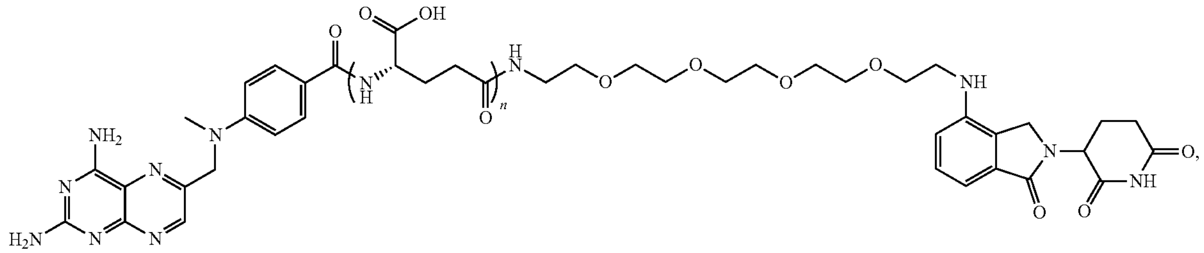
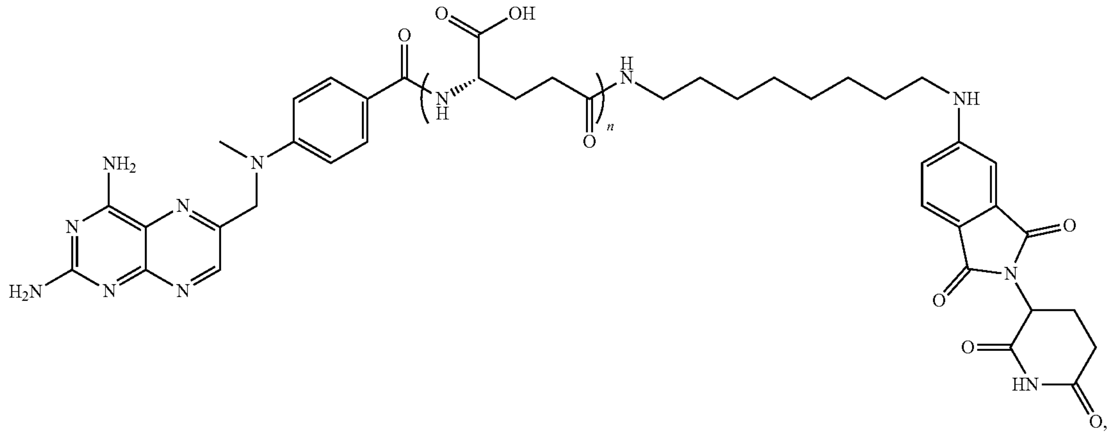
or
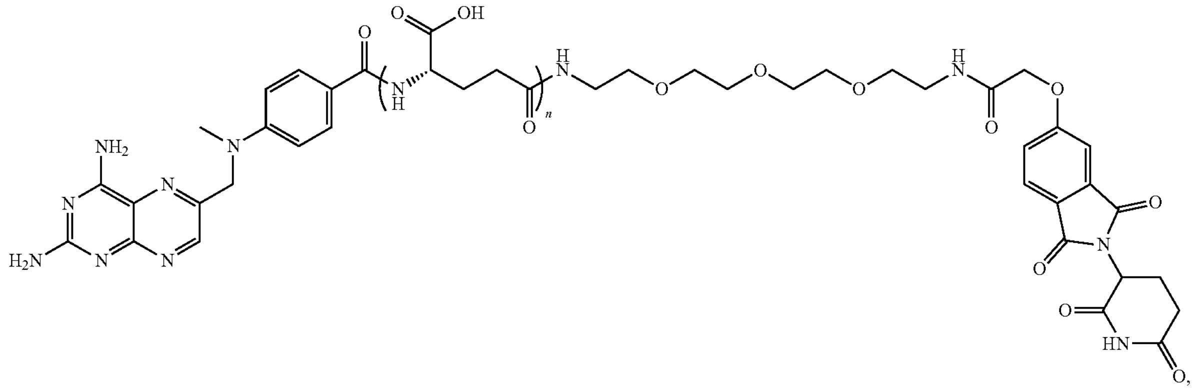
where n is 1, 2, 3, 4 or 5. In some embodiments, n is 1, but in other embodiments, n is 2, 3, 4, or 5.
Additional exemplary compounds within the scope of one or more of the general formulas include:

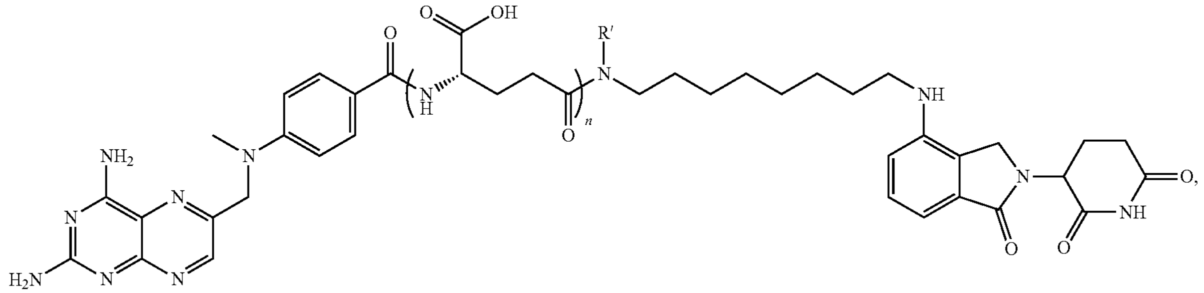
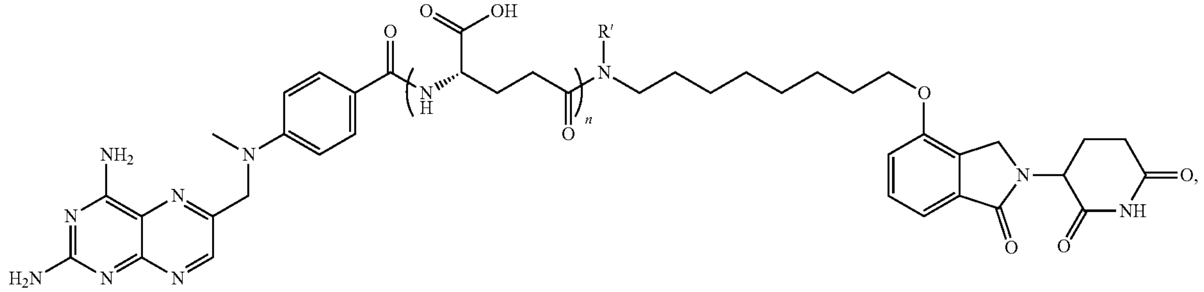
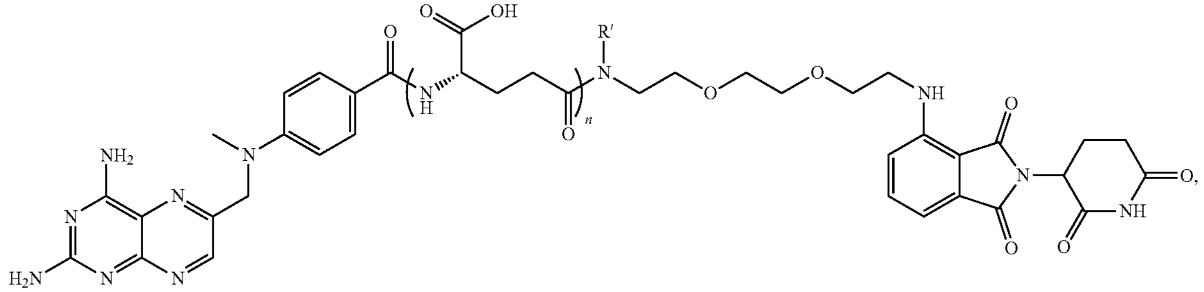
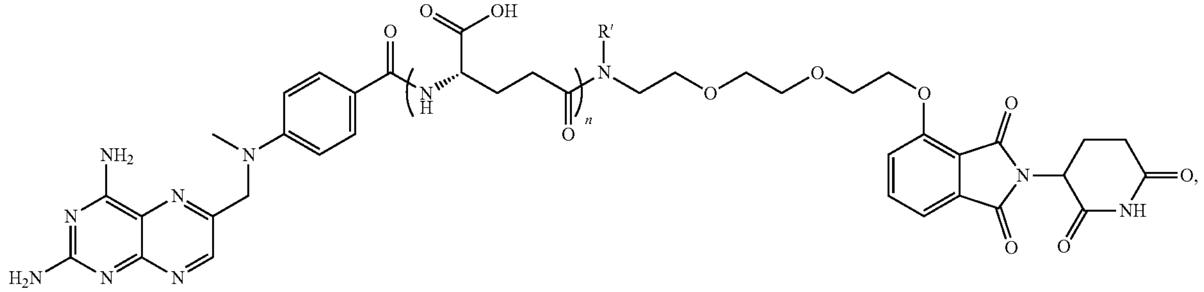
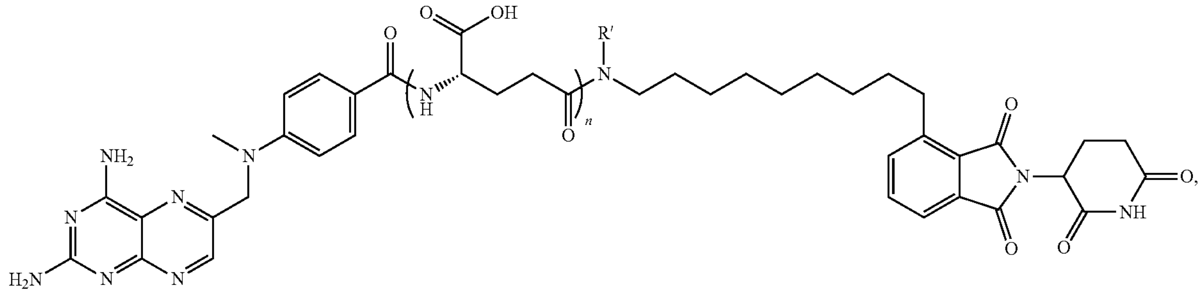
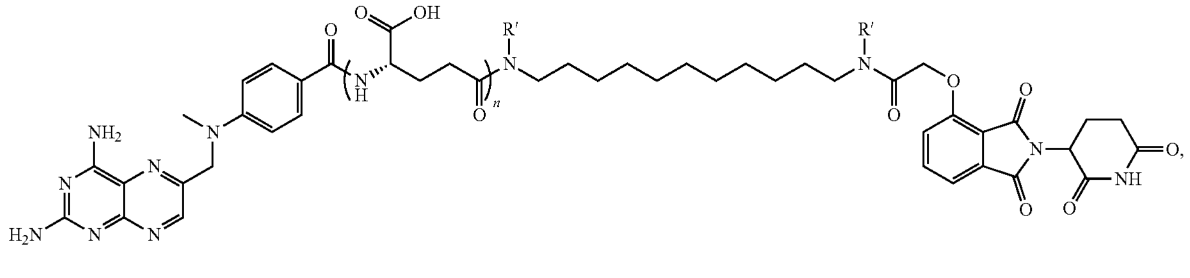

-continued
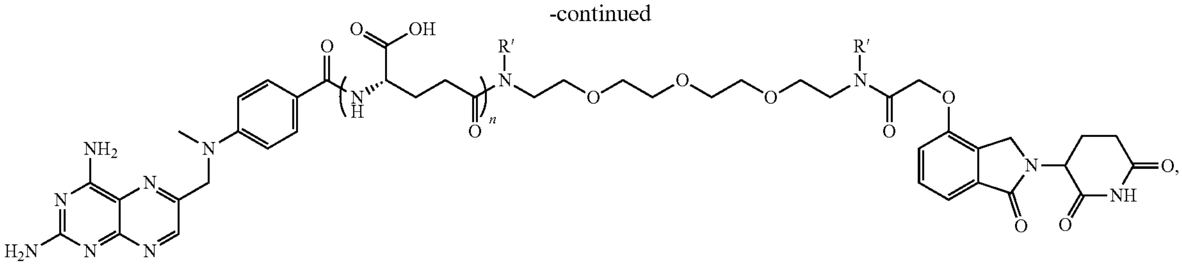
,
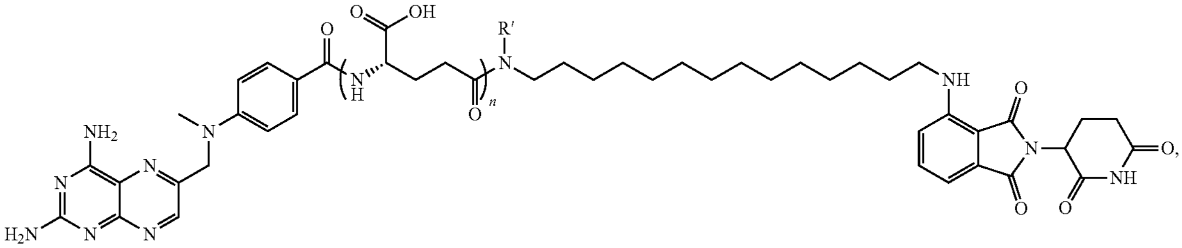
,
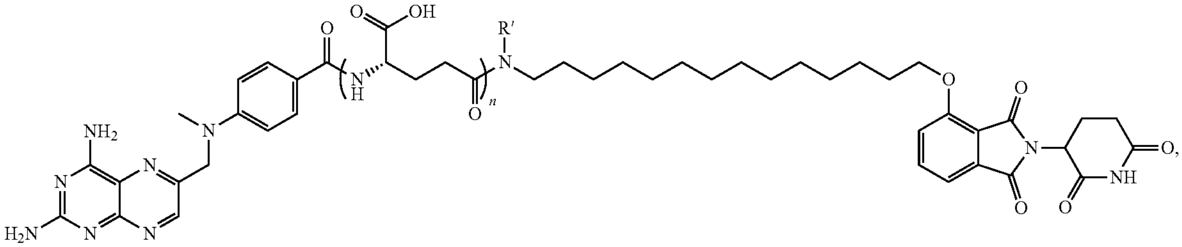
,
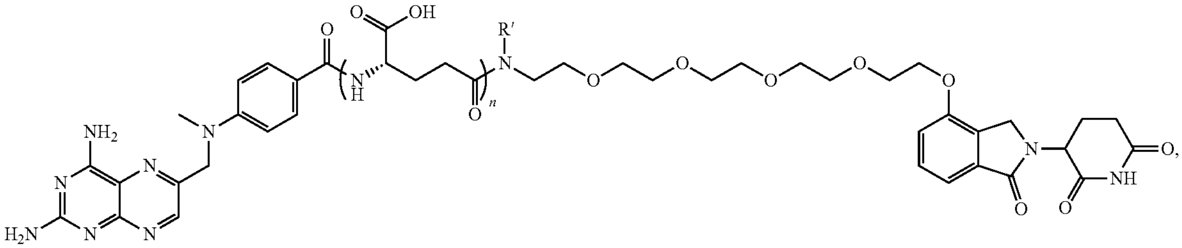
,
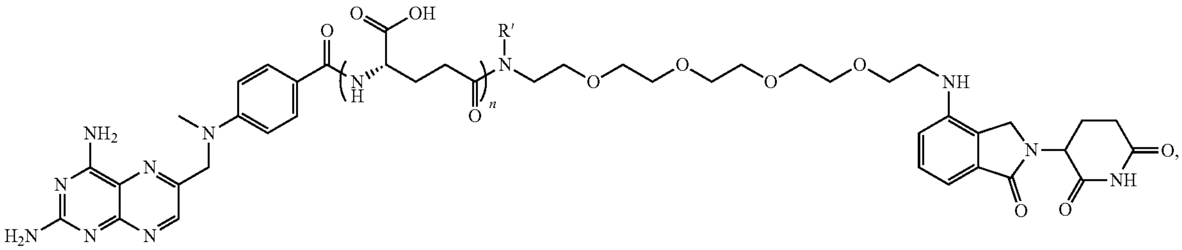
,
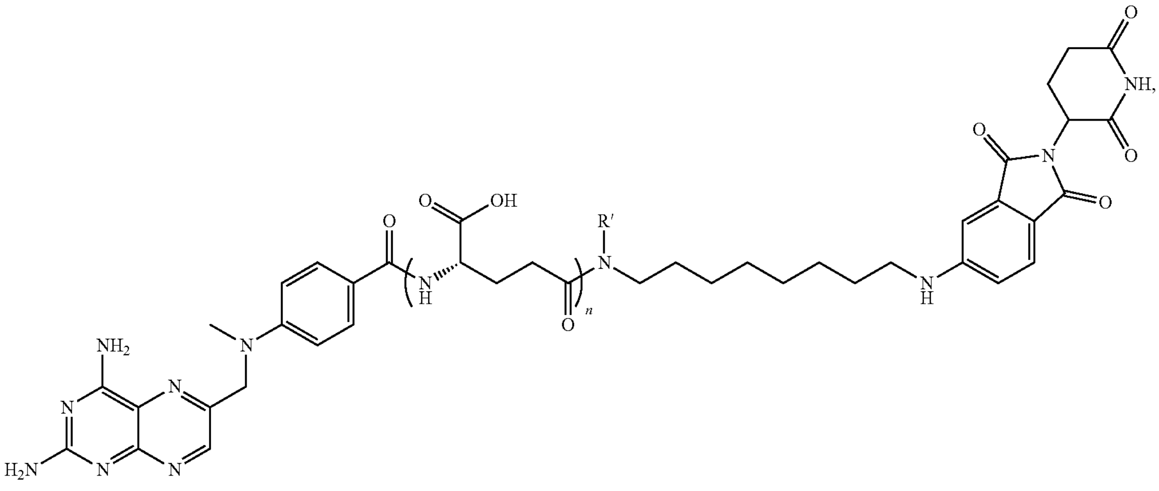
, or -continued
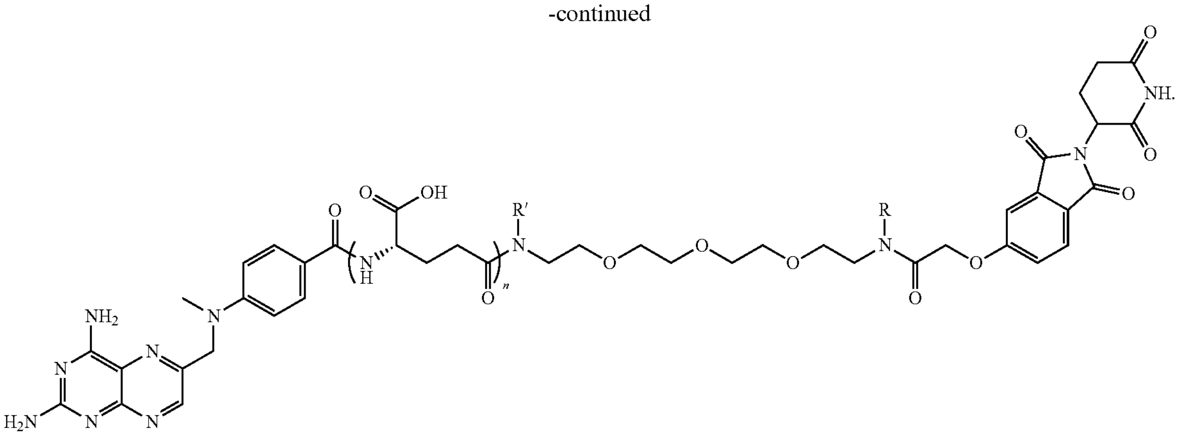
With respect to these compounds, each R' independently is H, methyl, ethyl, n-propyl, or isopropyl, and at least one R' is not H. And n is 1, 2, 3, 4, or 5. In some embodiments, n is 1, but in other embodiments, n is 2, 3, 4, or 5. Certain exemplary embodiments include:
NCGC 00842346
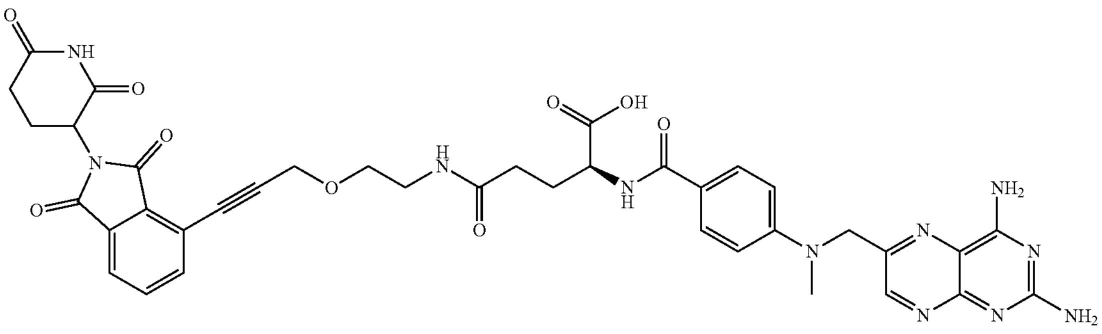
NCGC 00842349
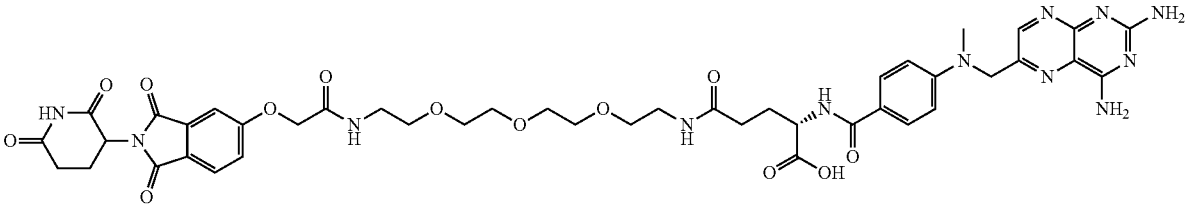
NCGC 00842343
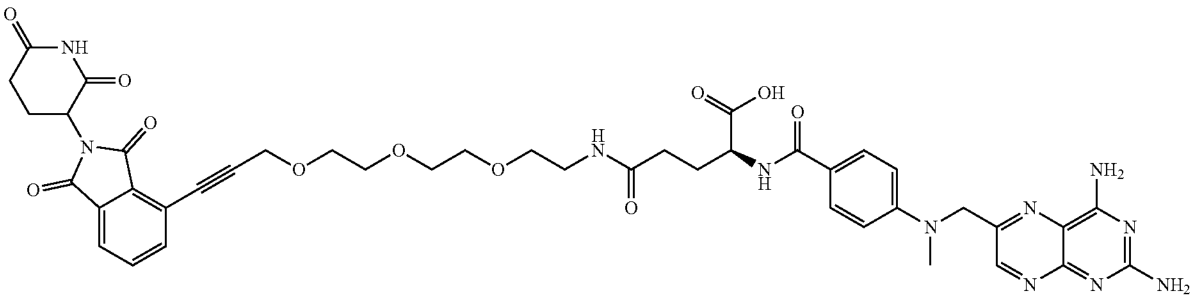

-continued
NCGC 00842356
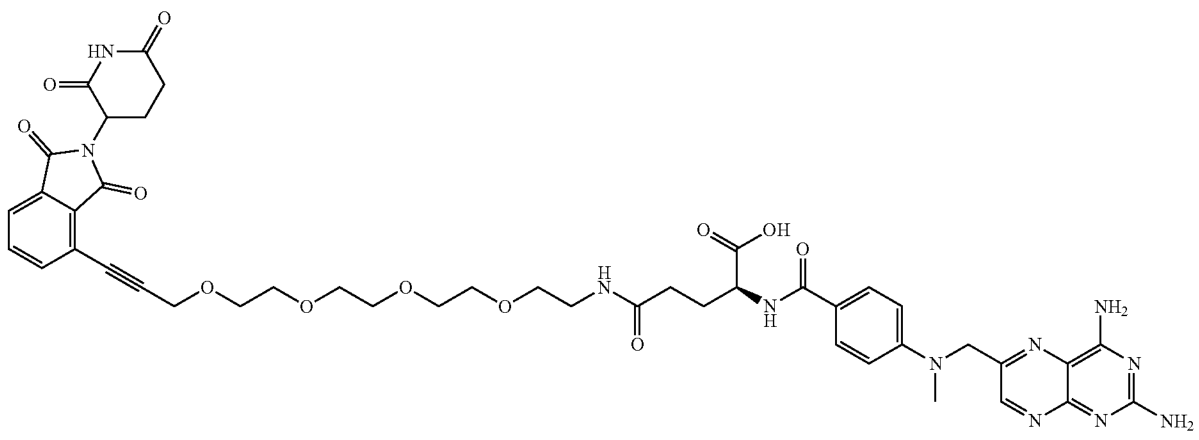
NCGC 00842342
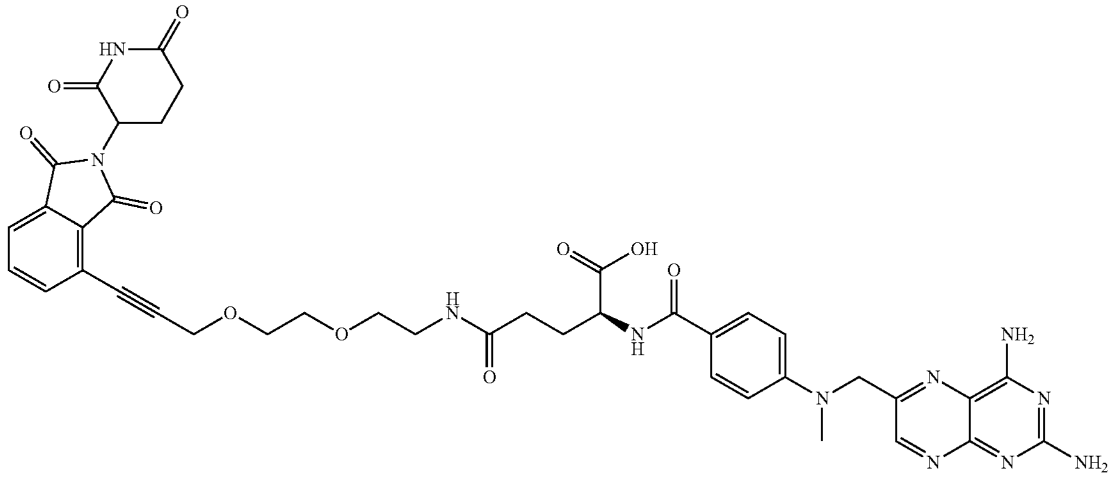
NCGC 00687572
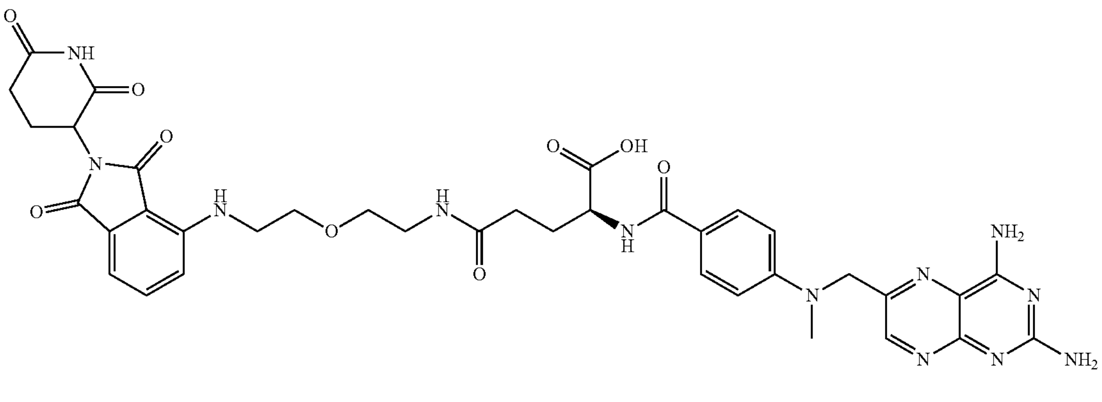

-continued
NCGC 00842350
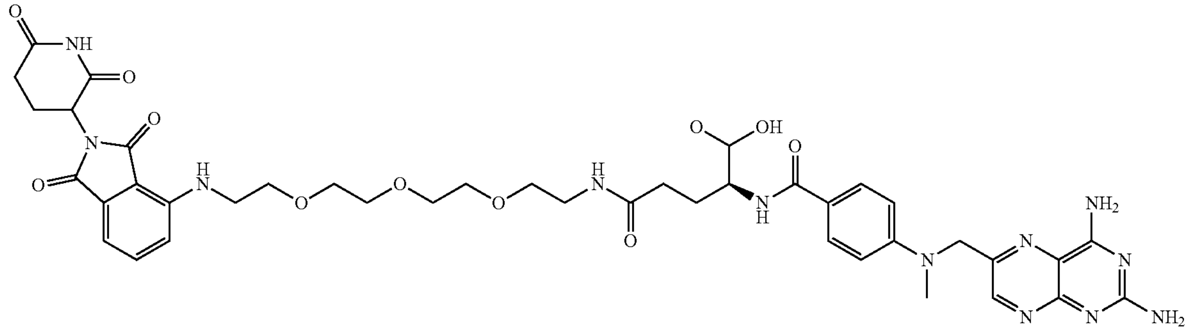
NCGC 00842354
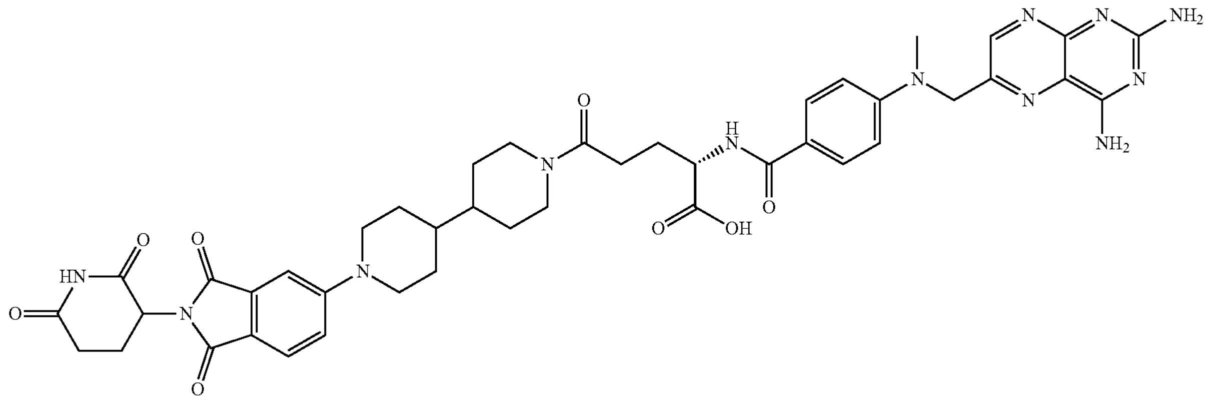
NCGC 00842344
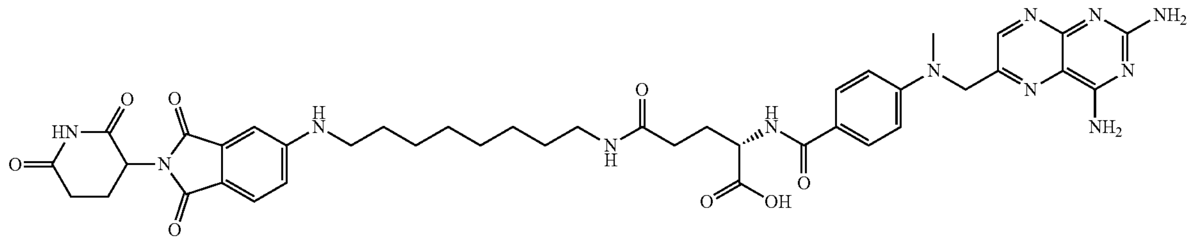
NCGC 00842353
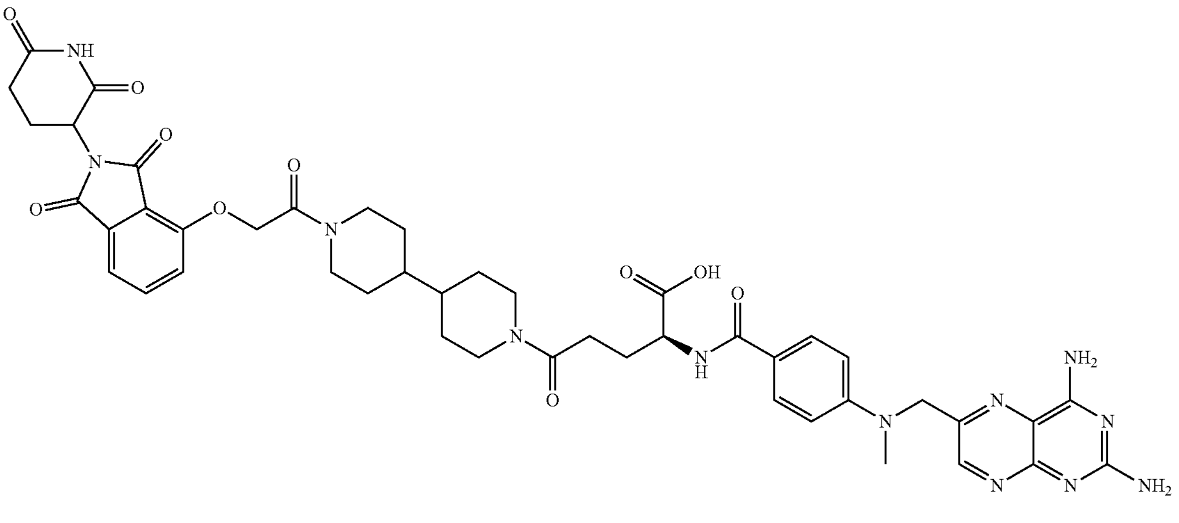

-continued
NCGC 00842358
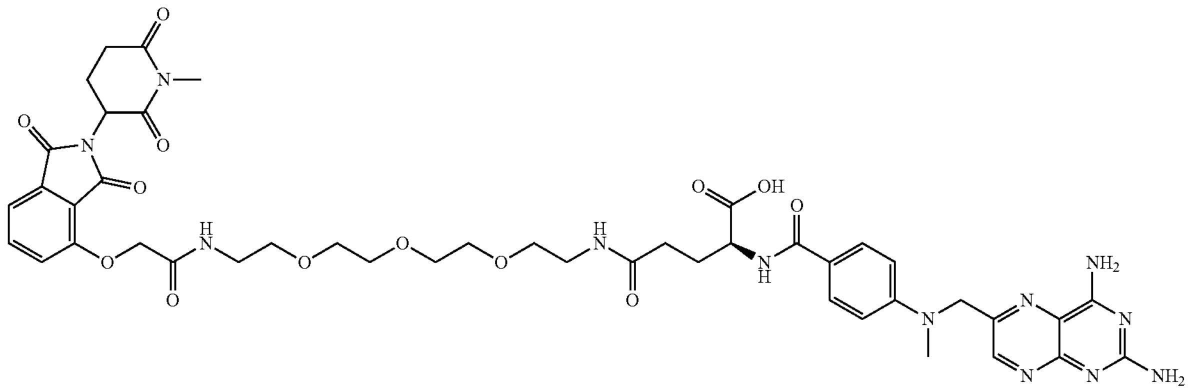
NCGC 00690398
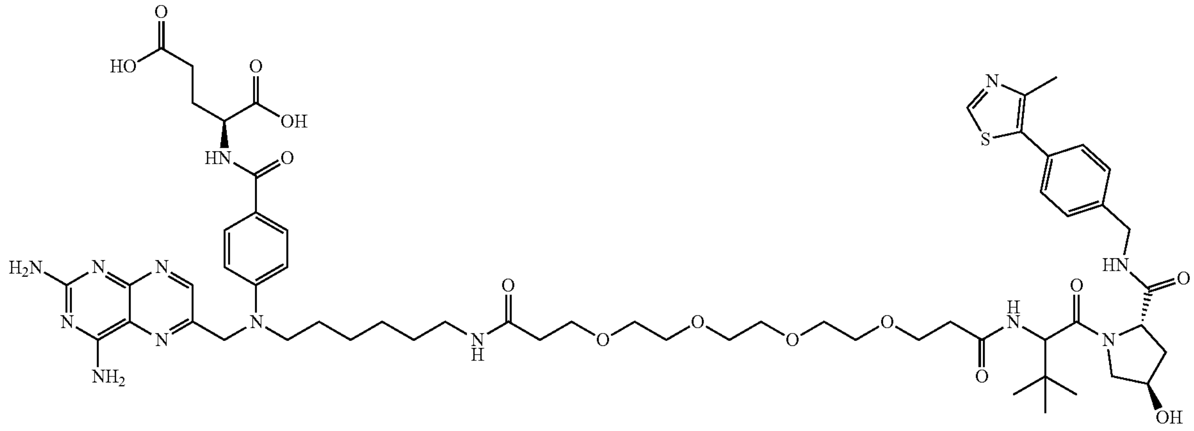
NCGC 00690397
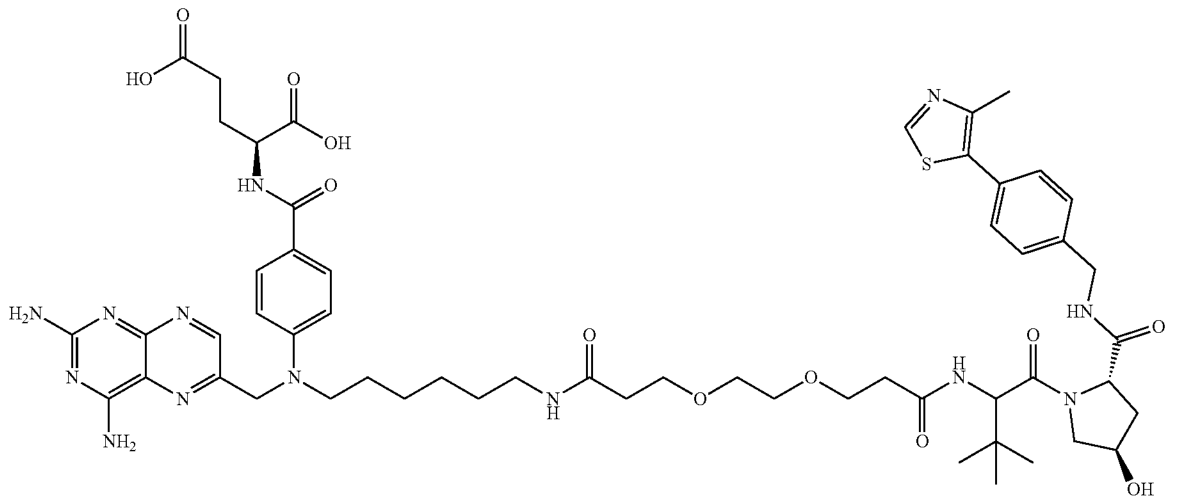

-continued
NCGC 00690396
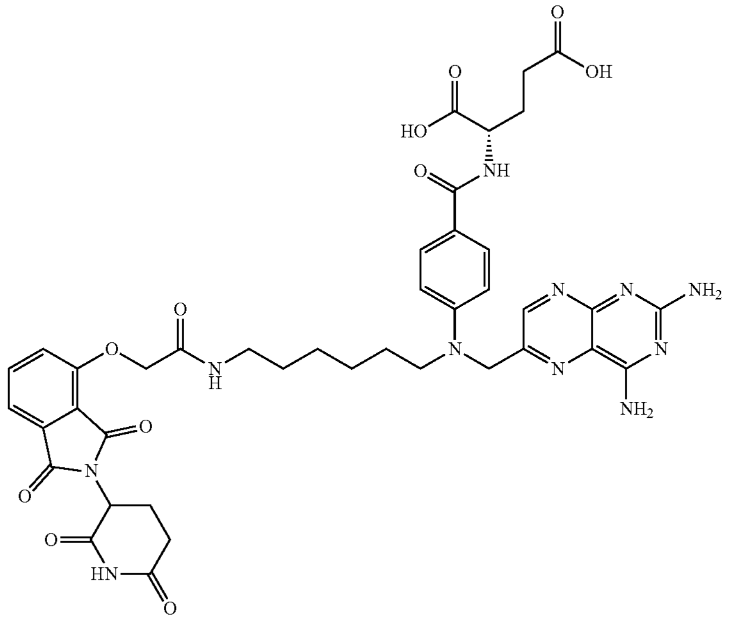
NCGC 00690395
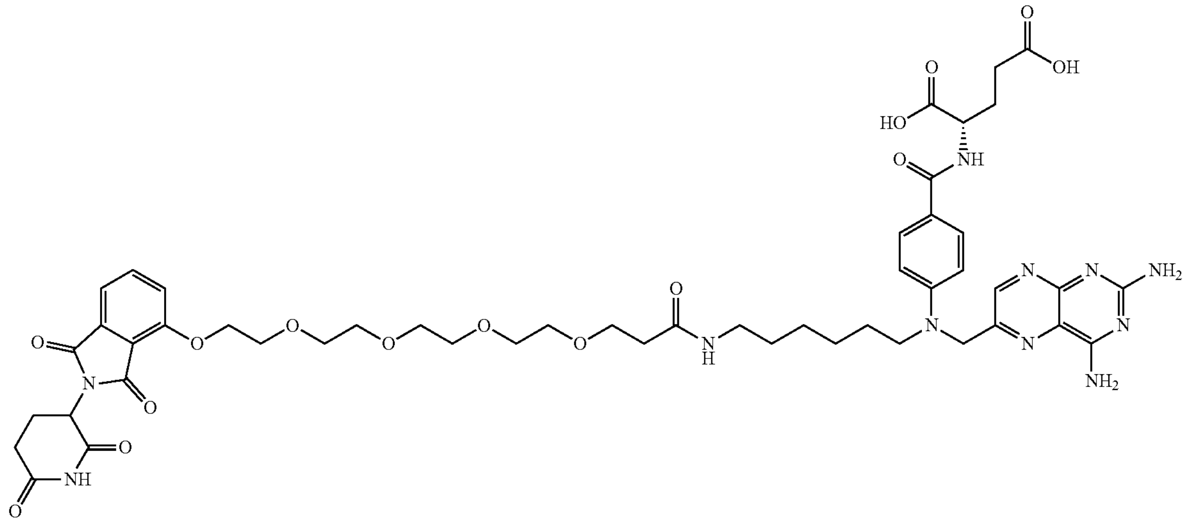

-continued
NCGC 00690069
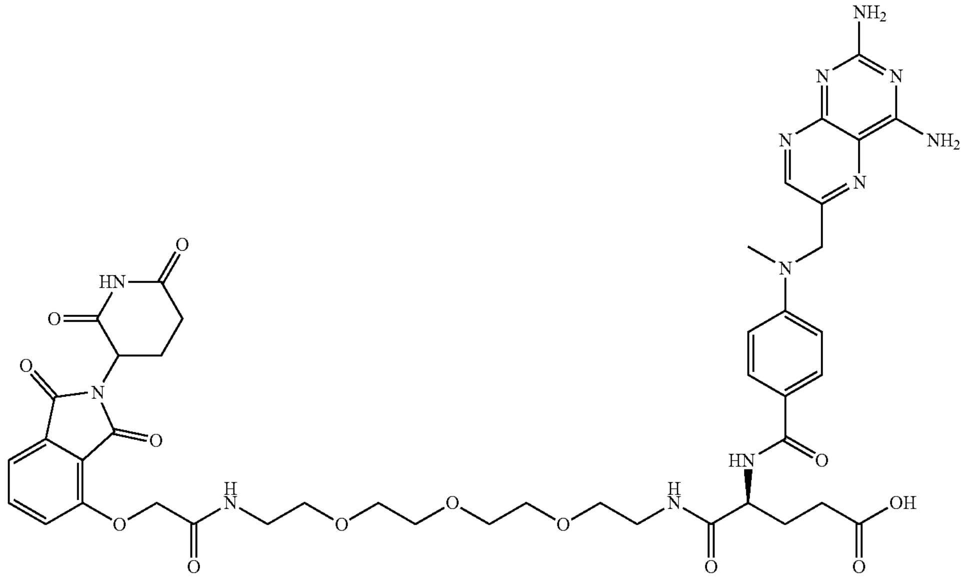
NCGC 00690412
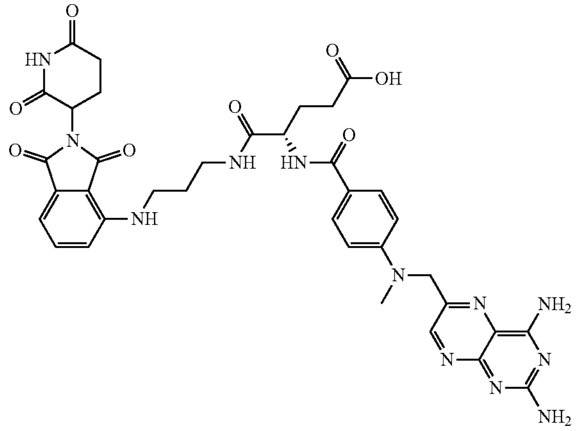
NCGC 00690407
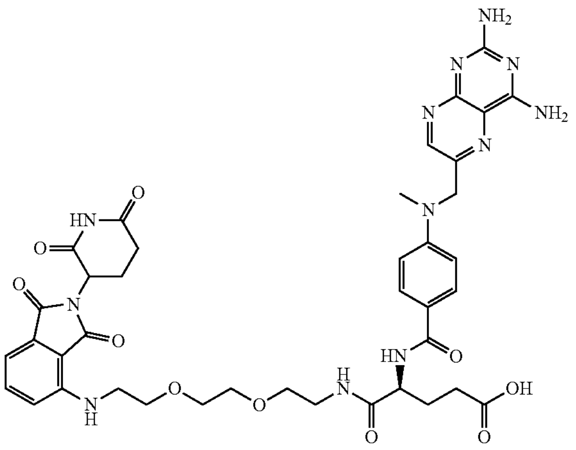
NCGC 00690075
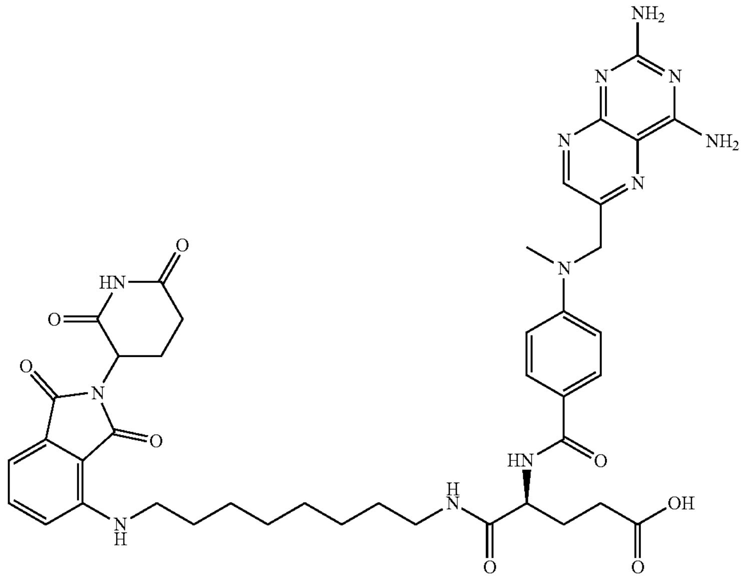

-continued
NCGC 00689630
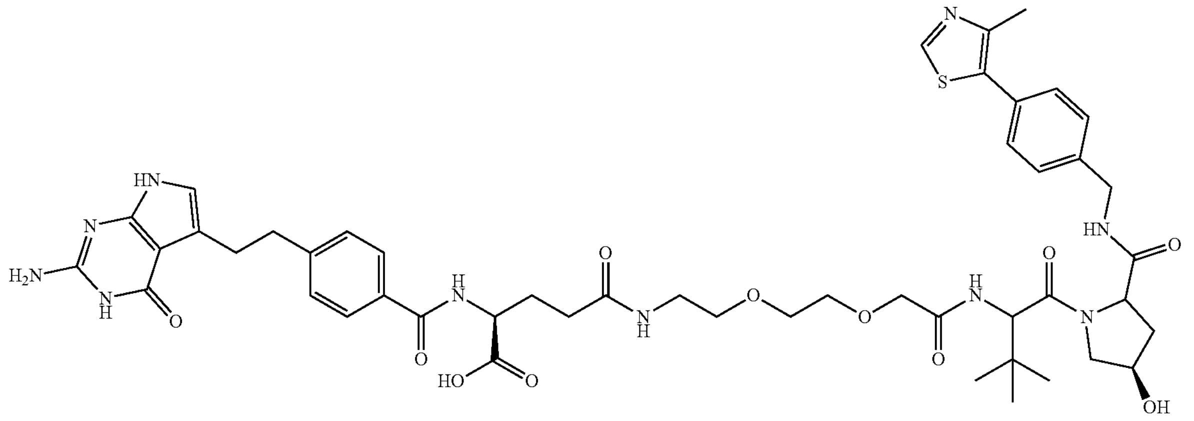
NCGC 00689208
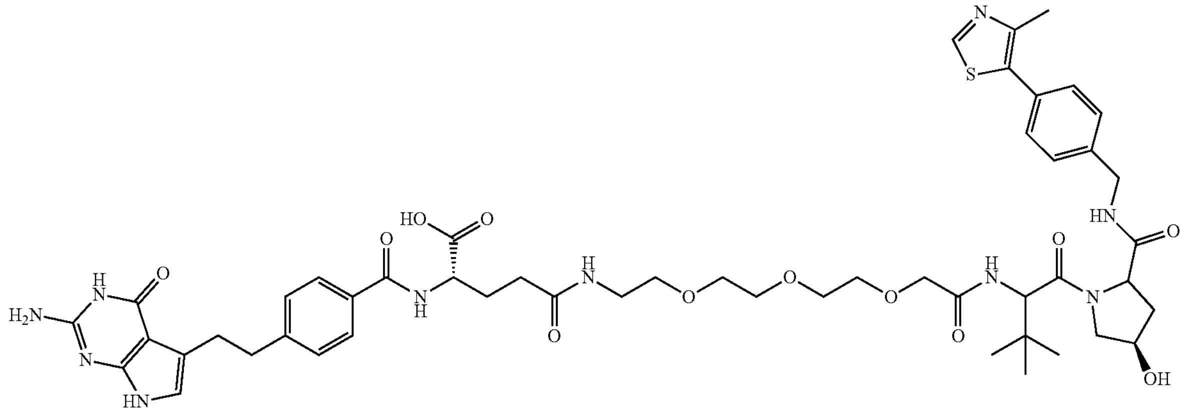
NCGC 00689137
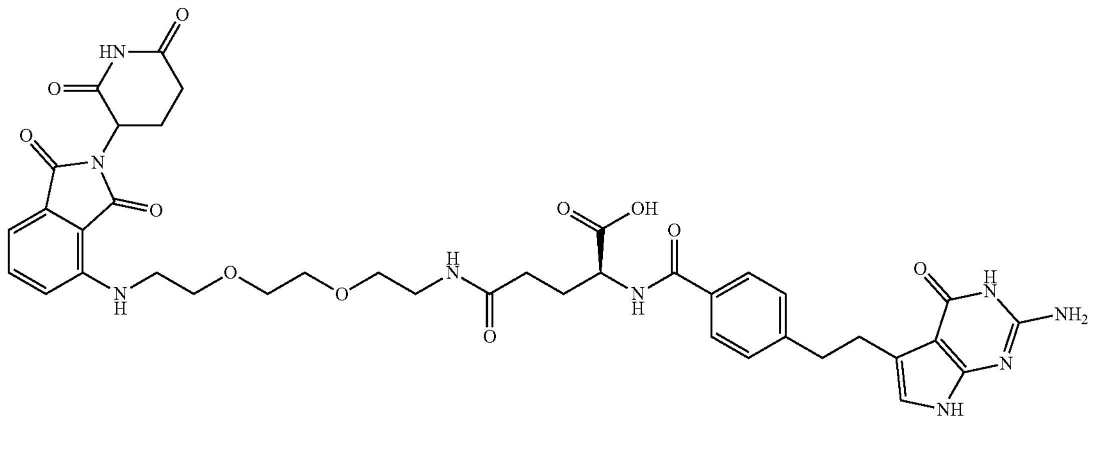

-continued
NCGC 00687877
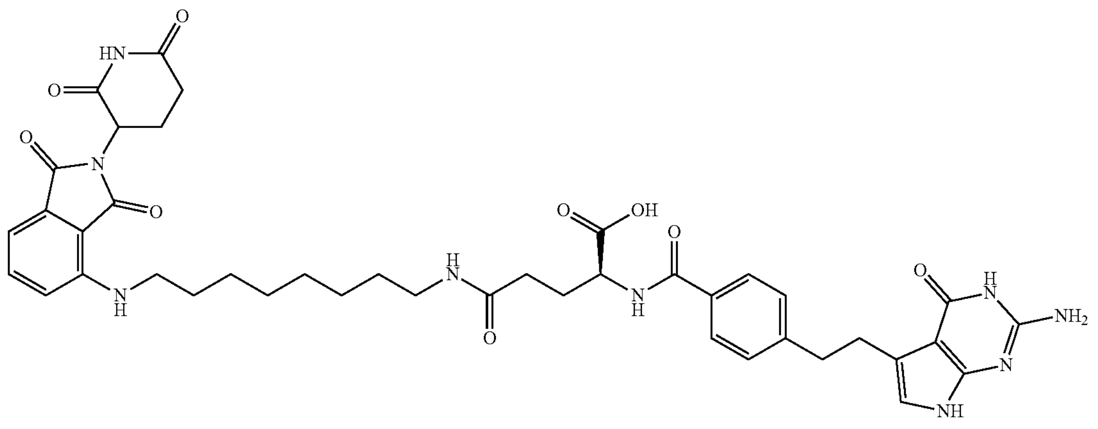
NCGC 00687847
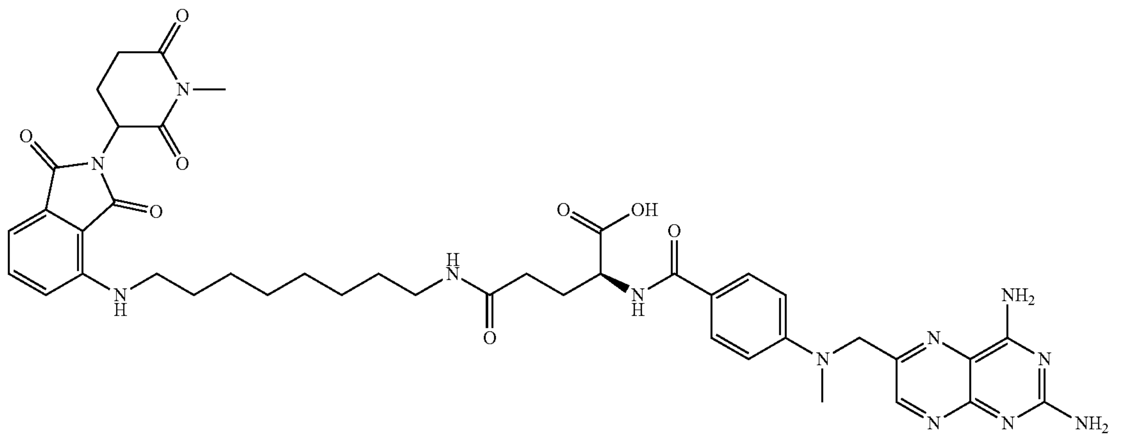
NCGC 00687807
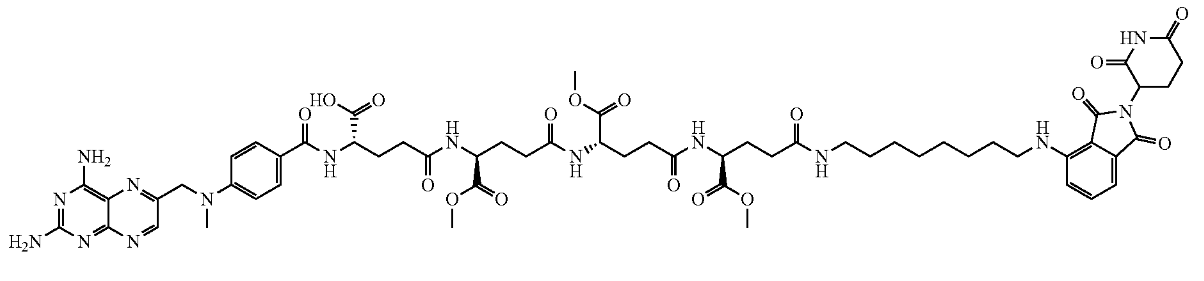
NCGC 00687811
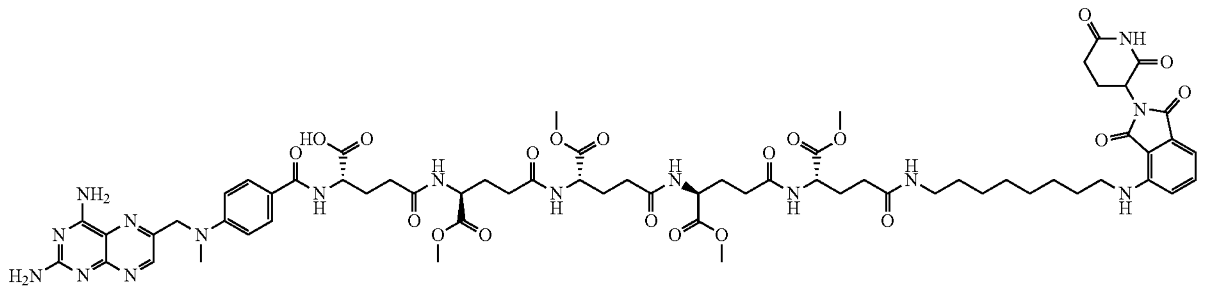

-continued
NCGC 00687576
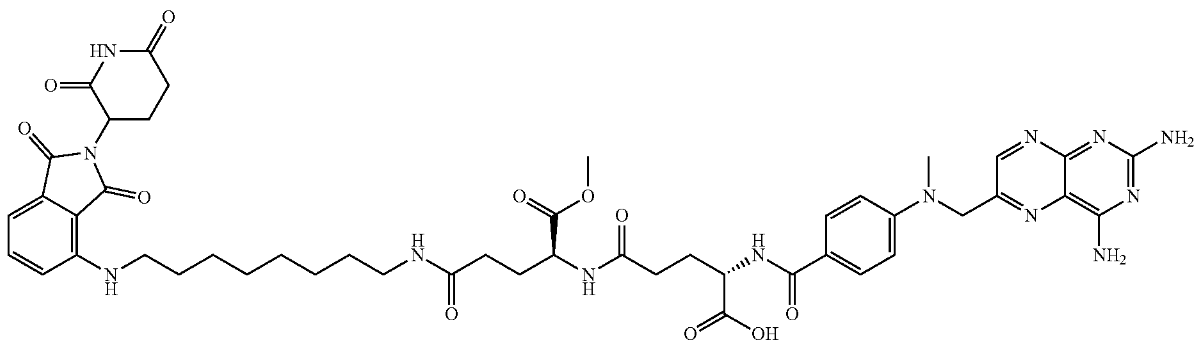
NCGC 00687555
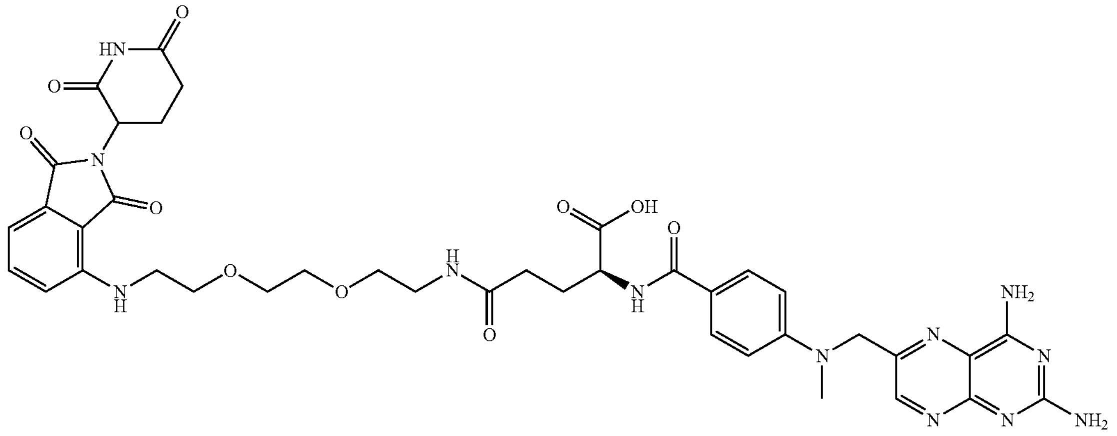
NCGC 00687567
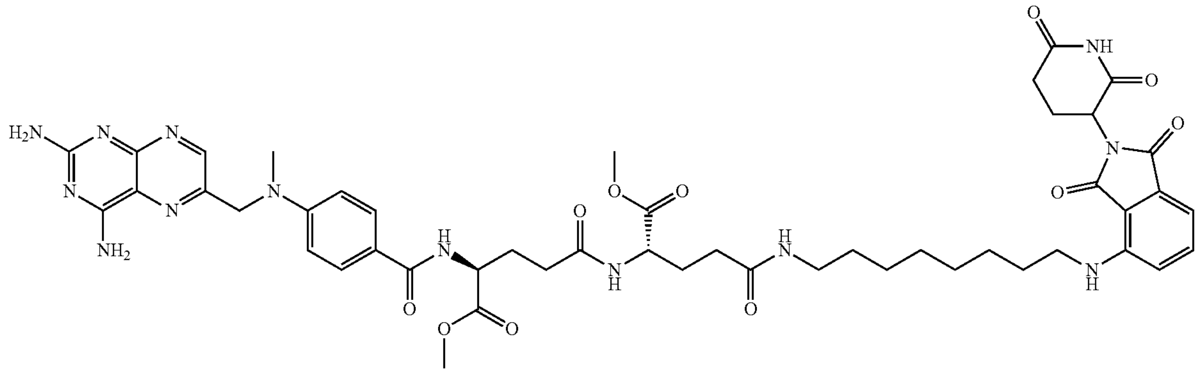
NCGC 00687569
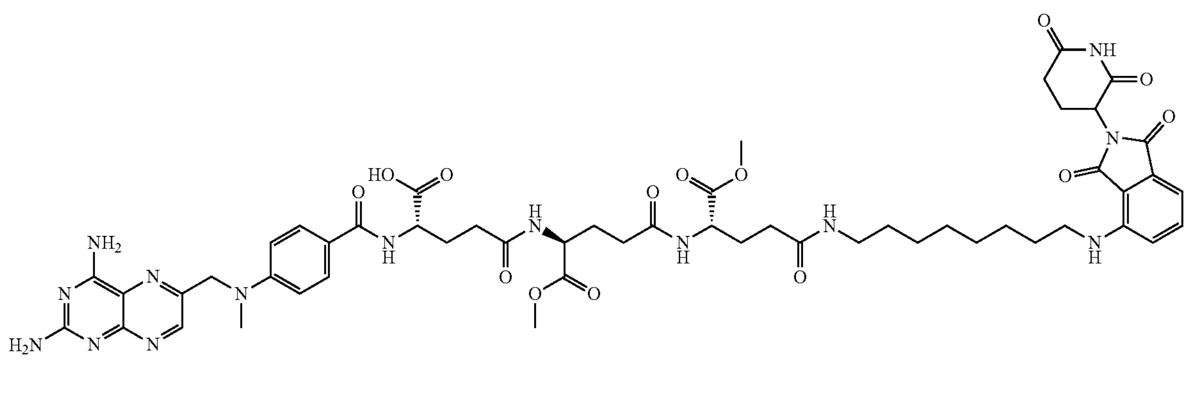

-continued
NCGC 00687472
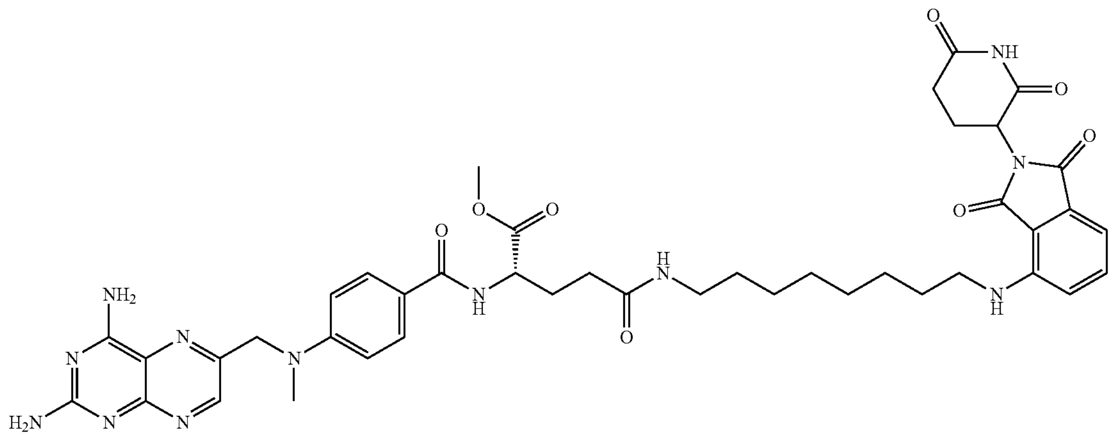
NCGC 00687415
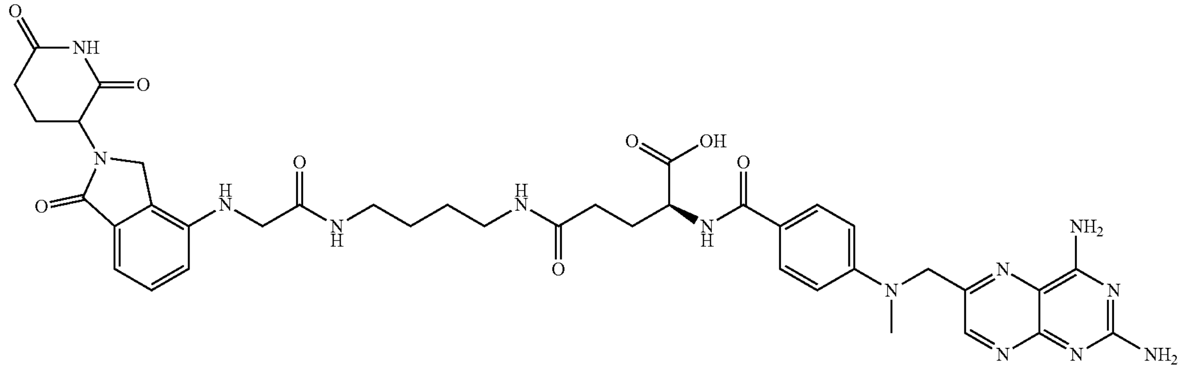
NCGC 00687417
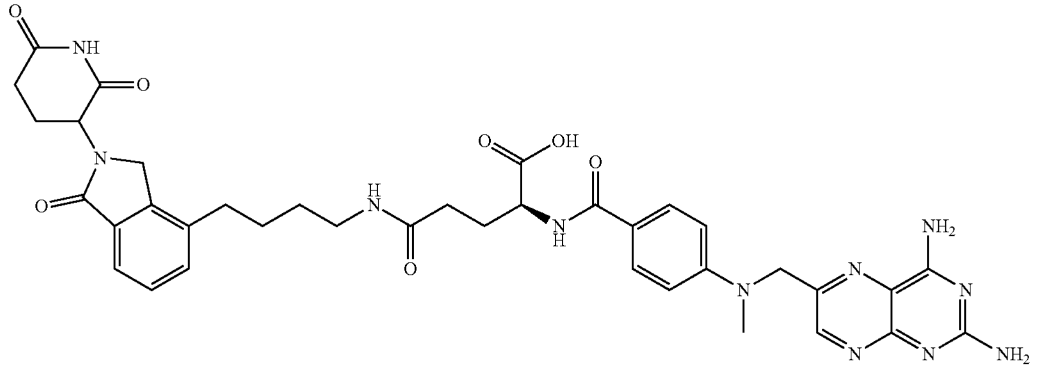
NCGC 00687414
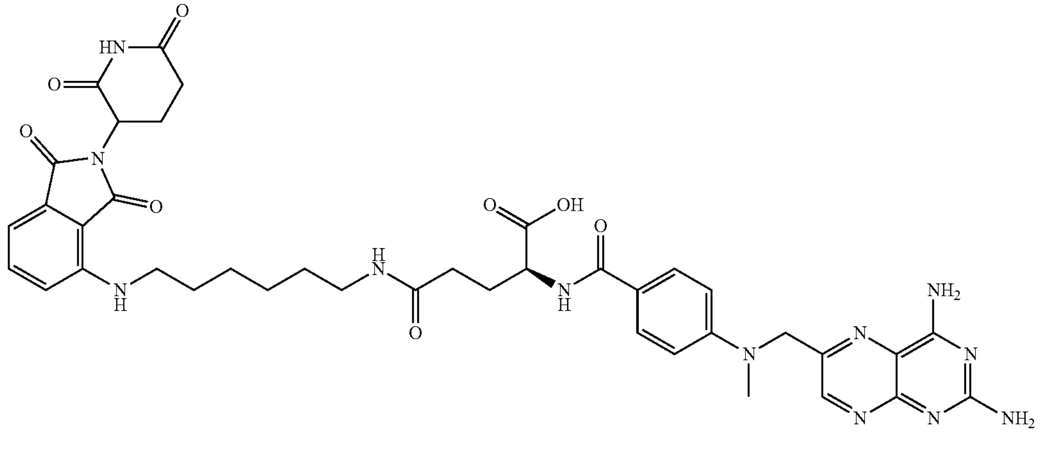

-continued
NCGC 00685928
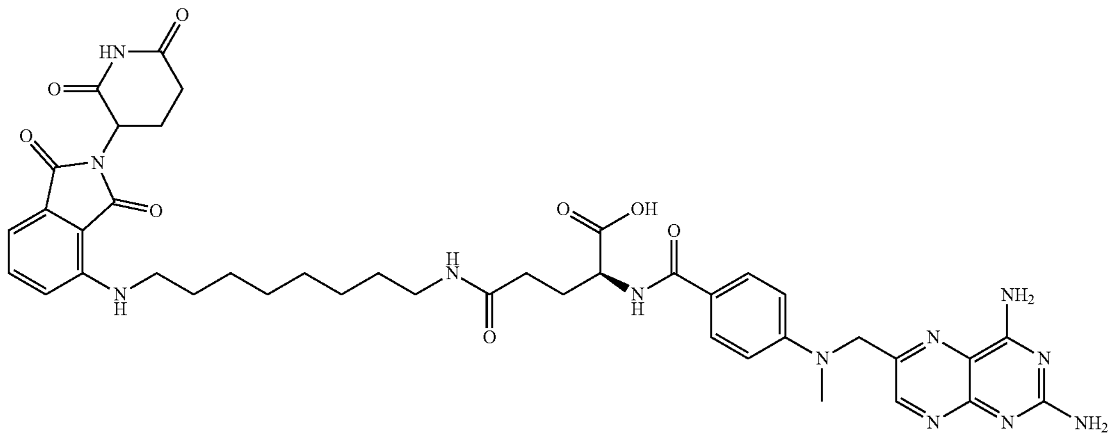
NCGC 00685938
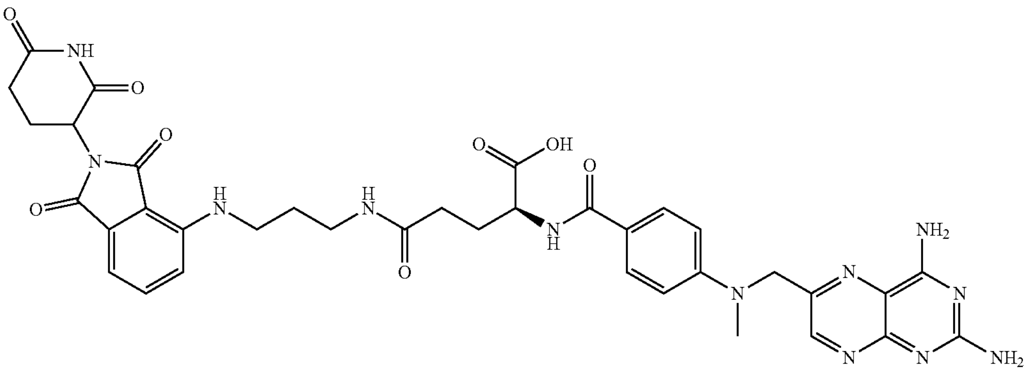
NCGC 00685995
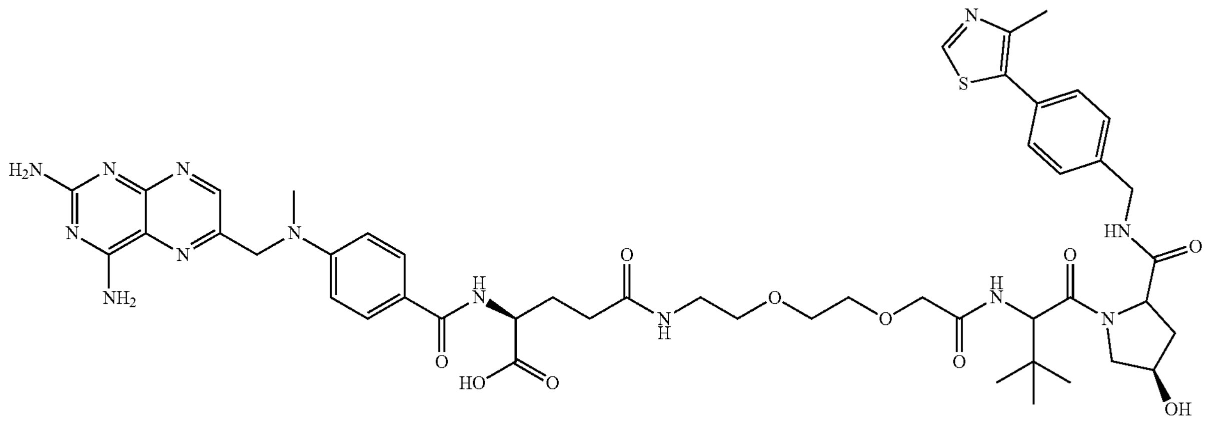

-continued
NCGC 00685965
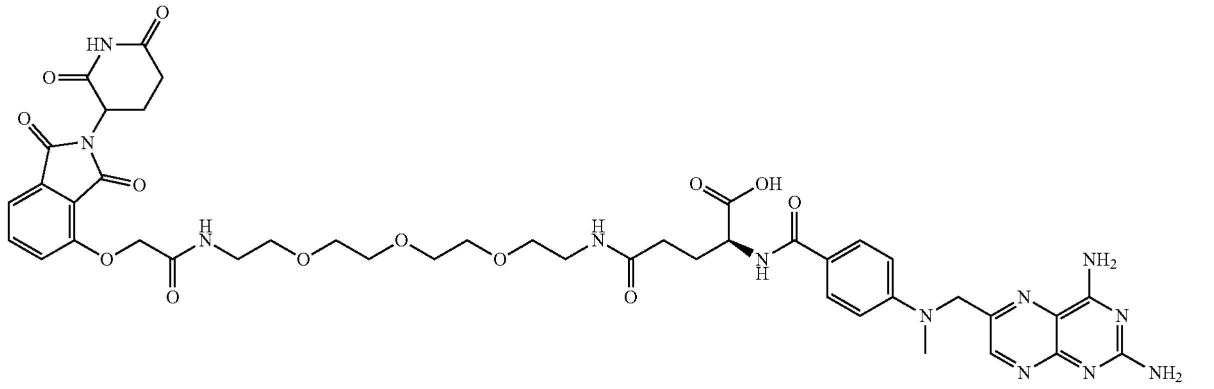
NCGC 00685964
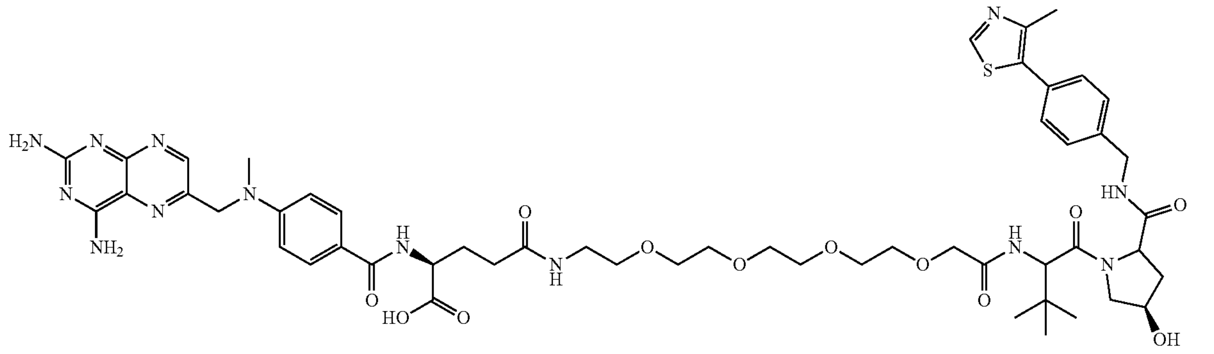
NCGC 00842394
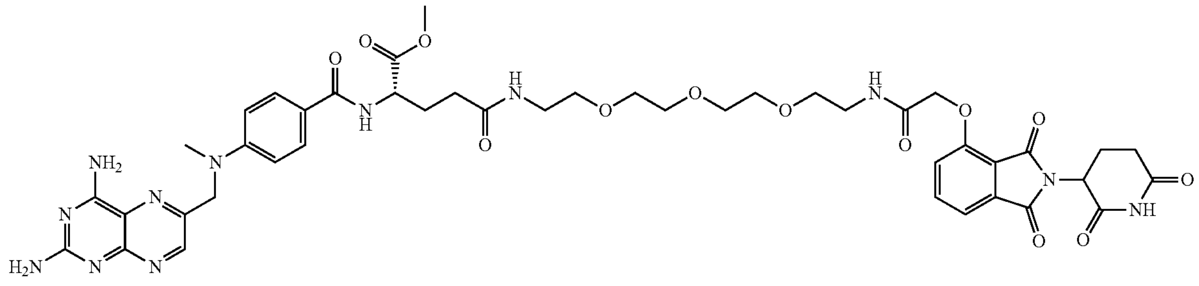
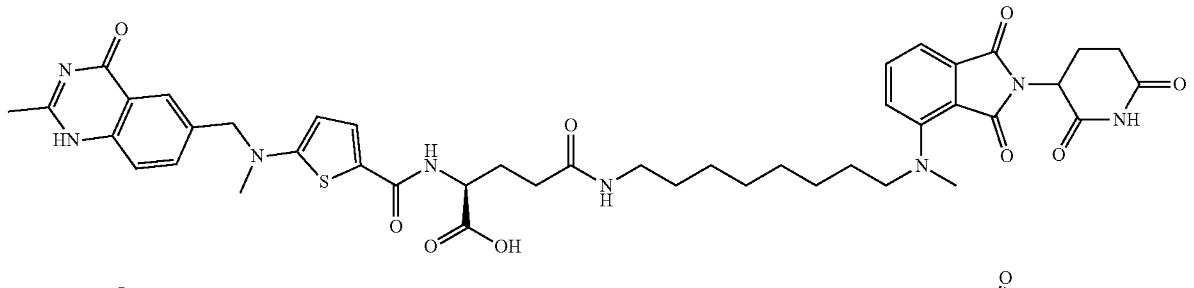
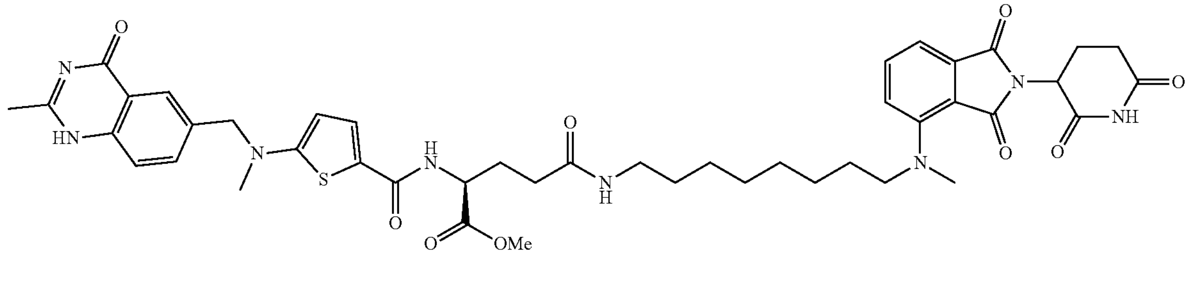

-continued
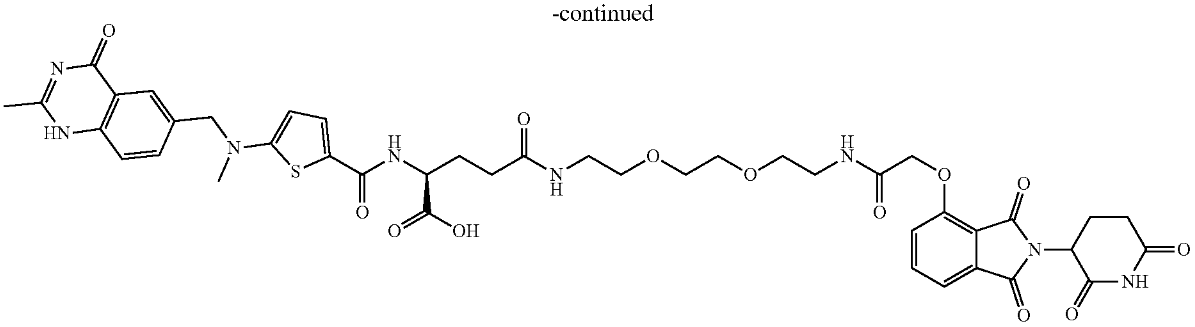
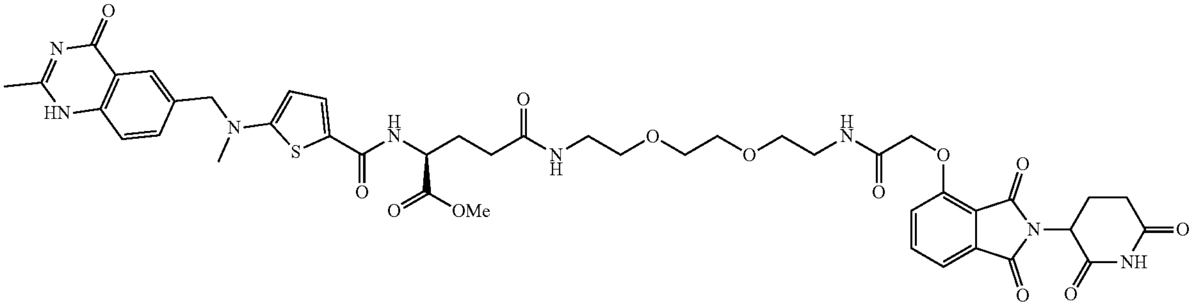
Additional exemplary compounds include, but are not limited to:
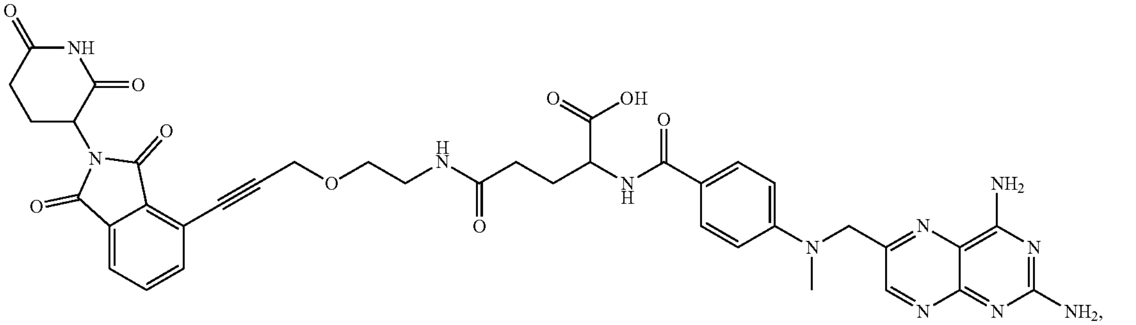
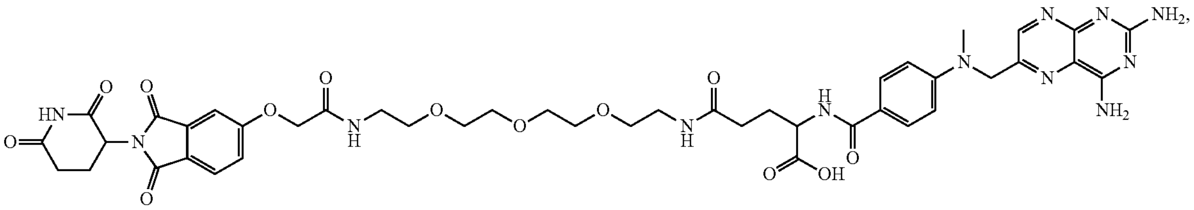
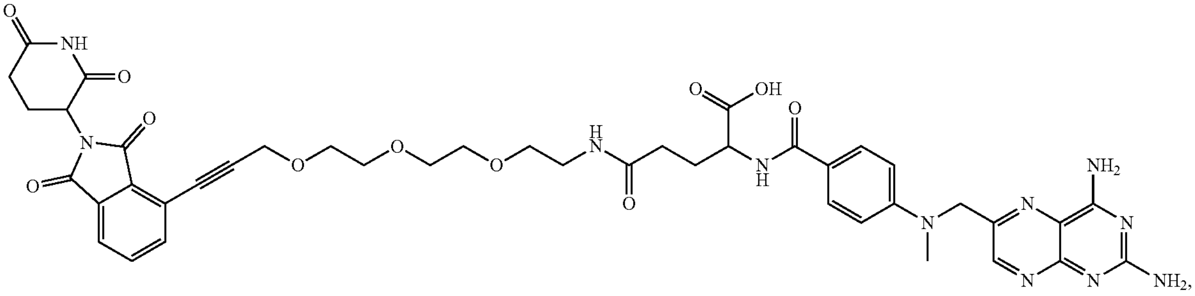

-continued
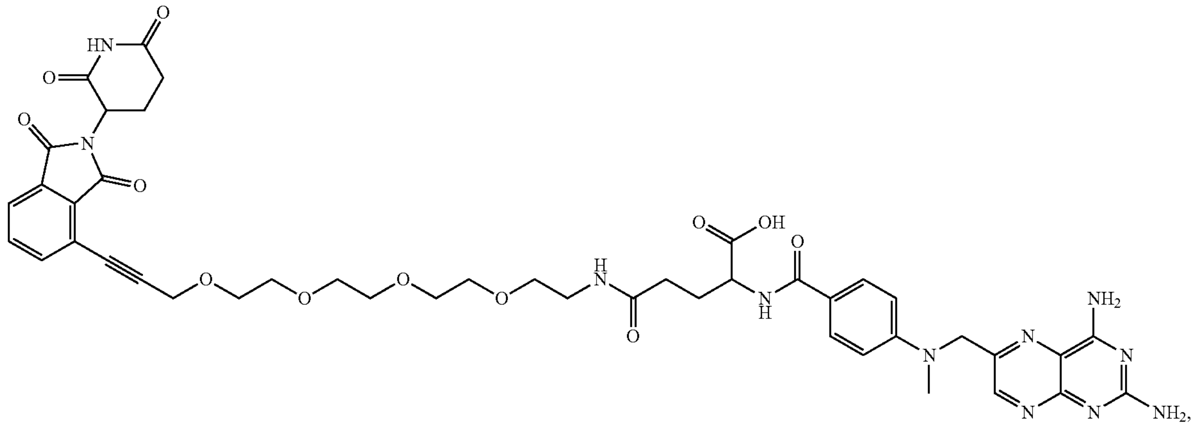
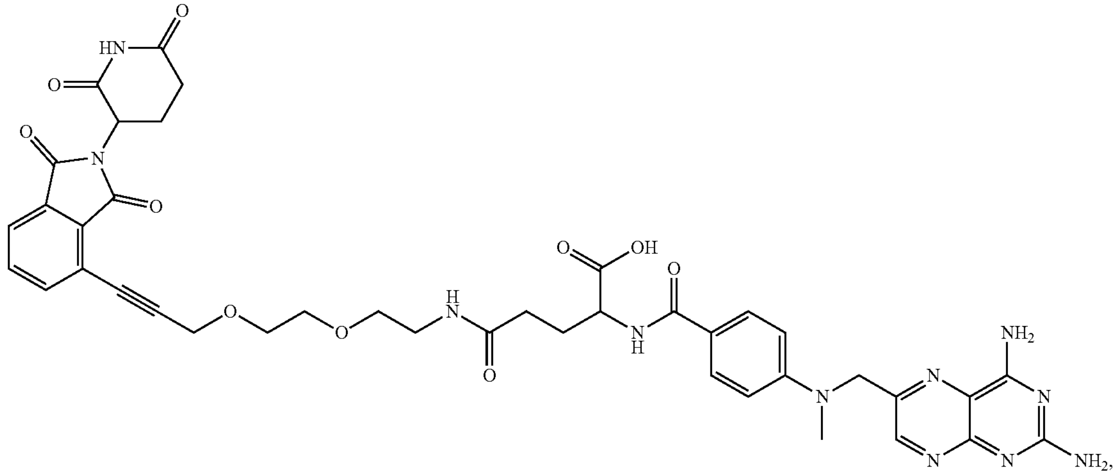
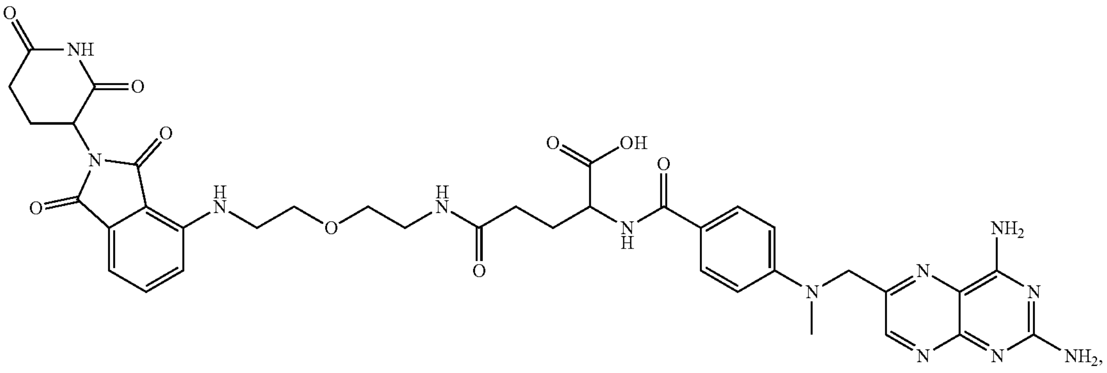
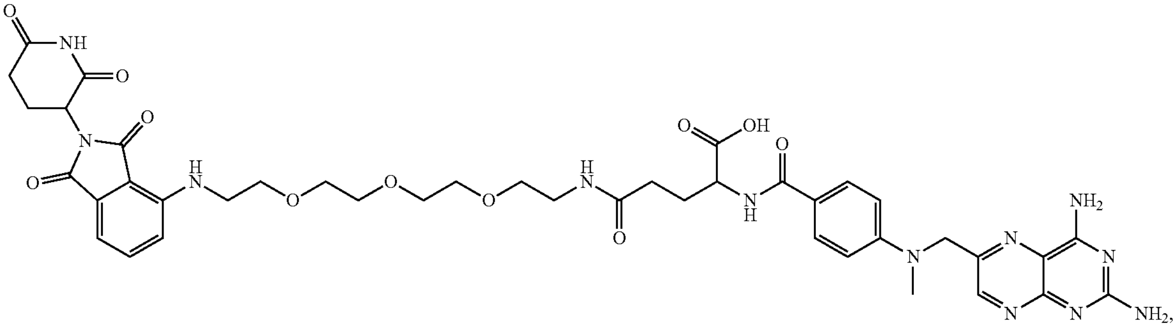

-continued
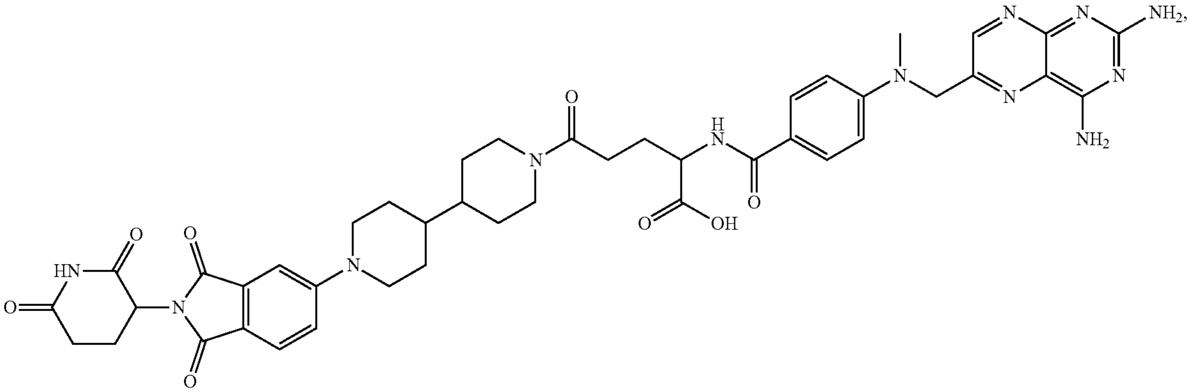
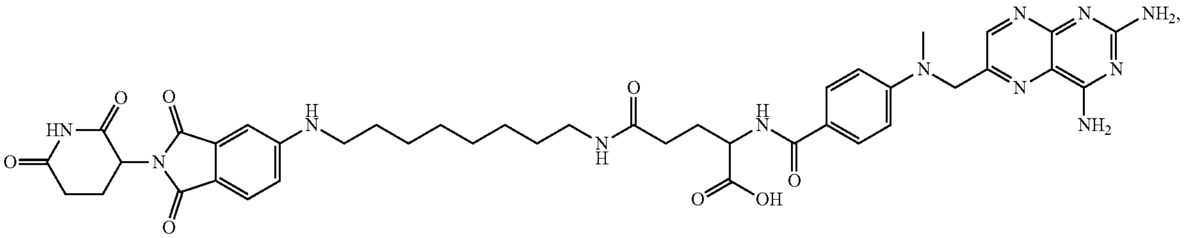
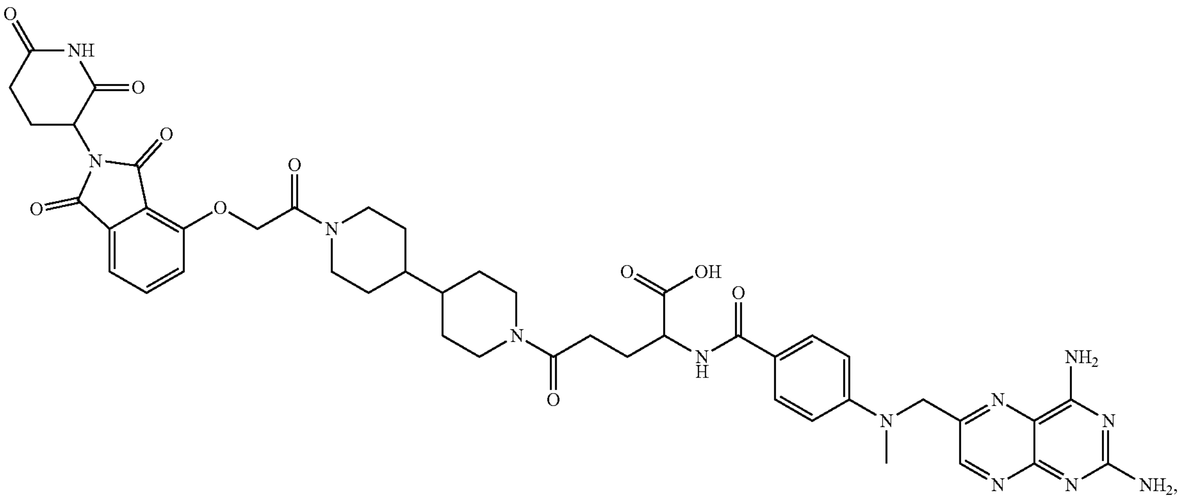
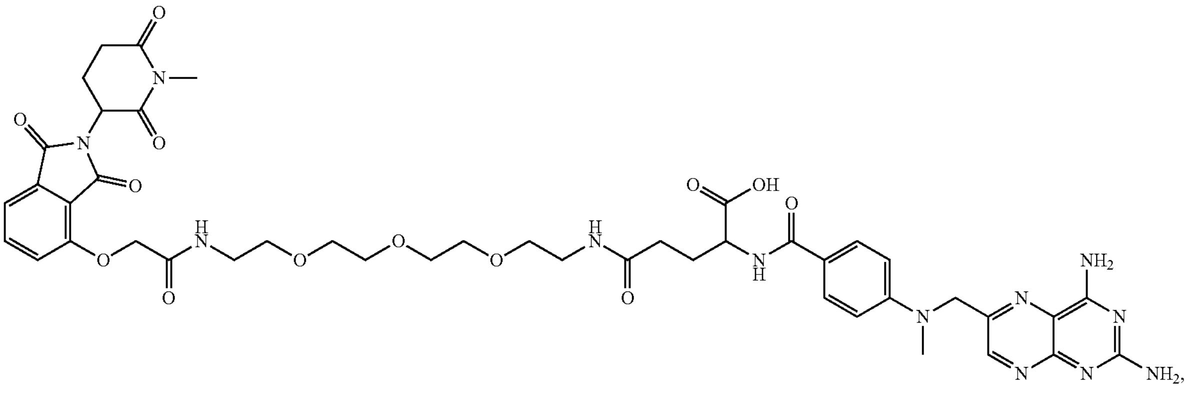

-continued
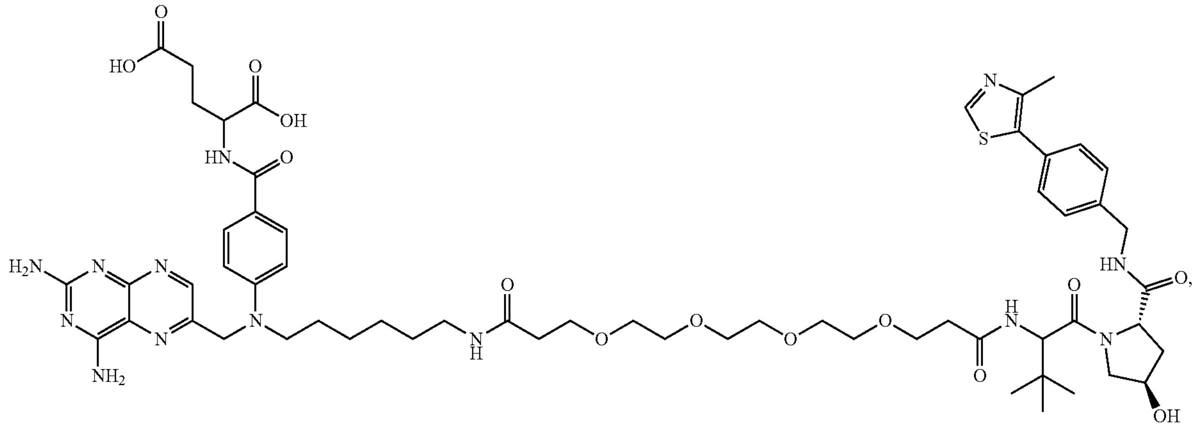
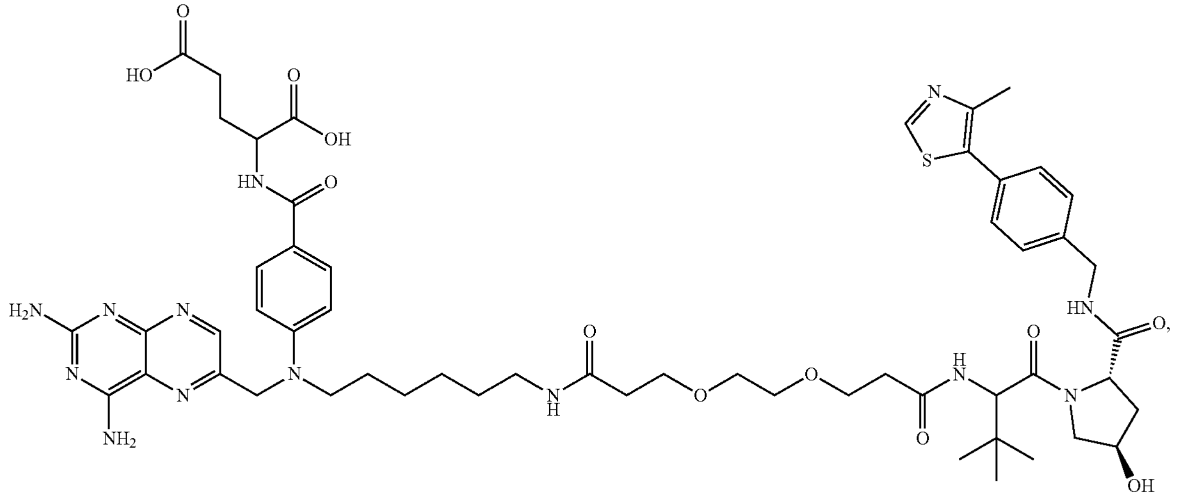
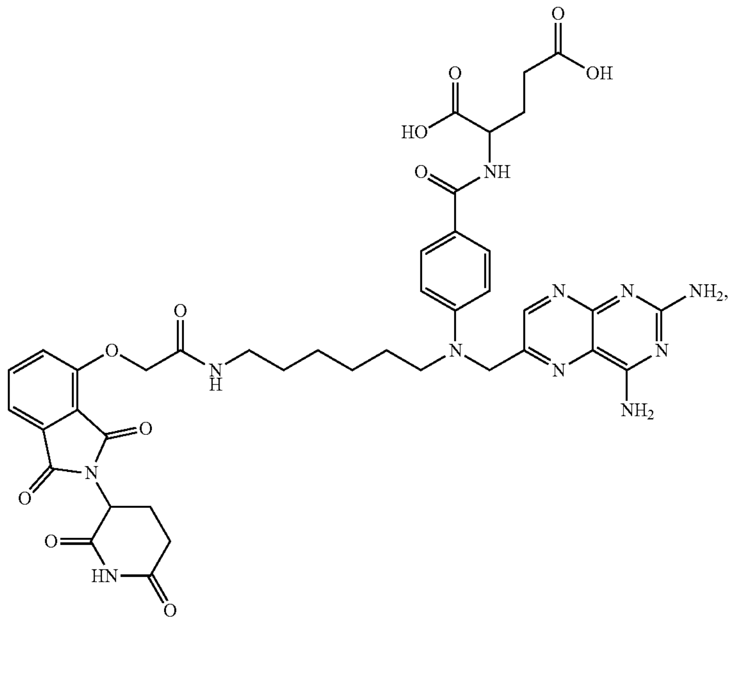

-continued
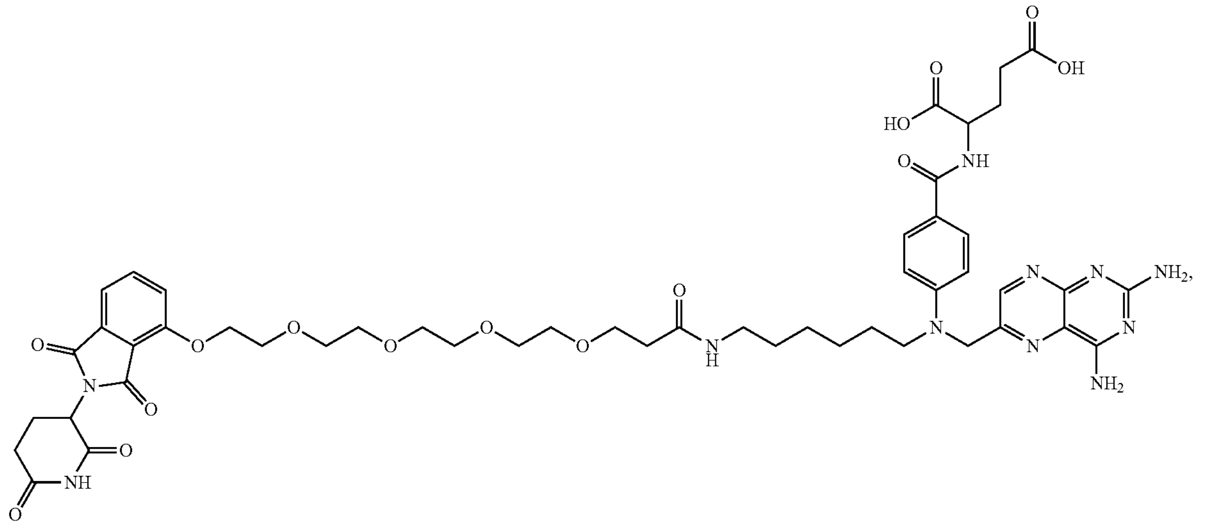
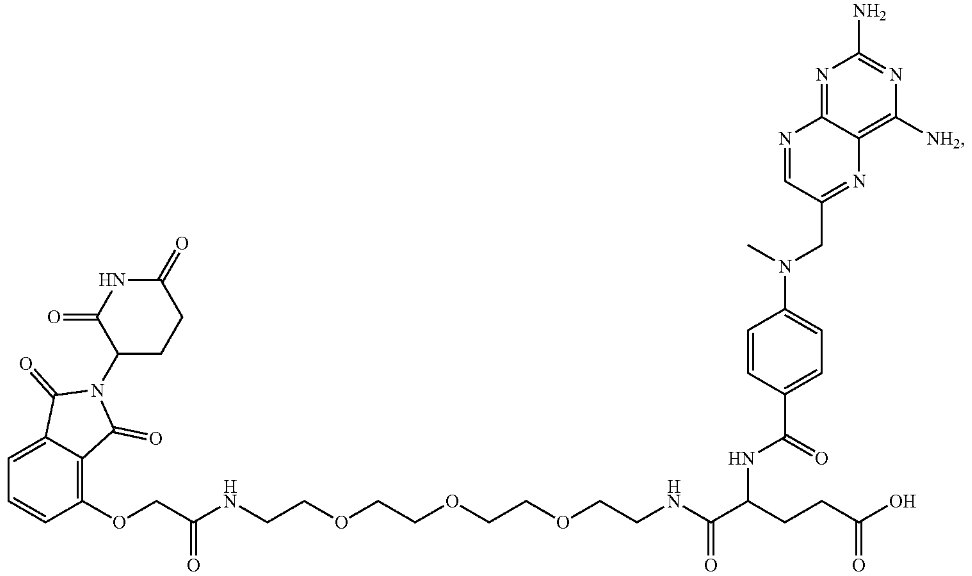
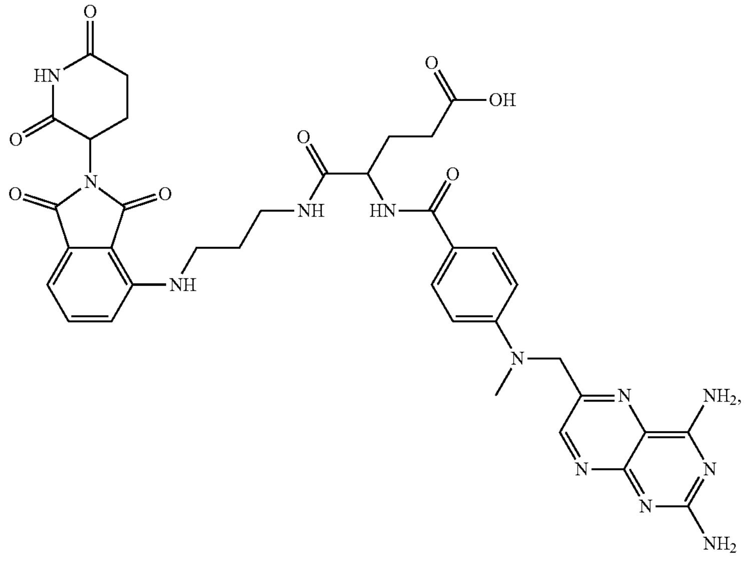

-continued
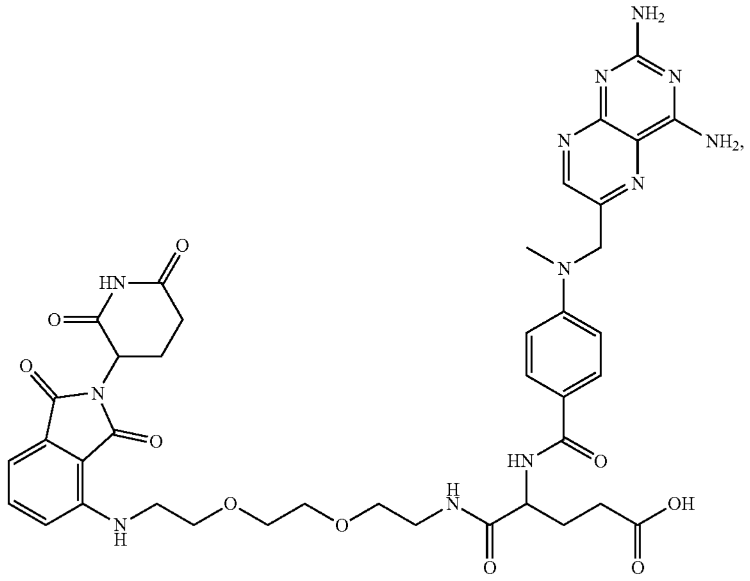
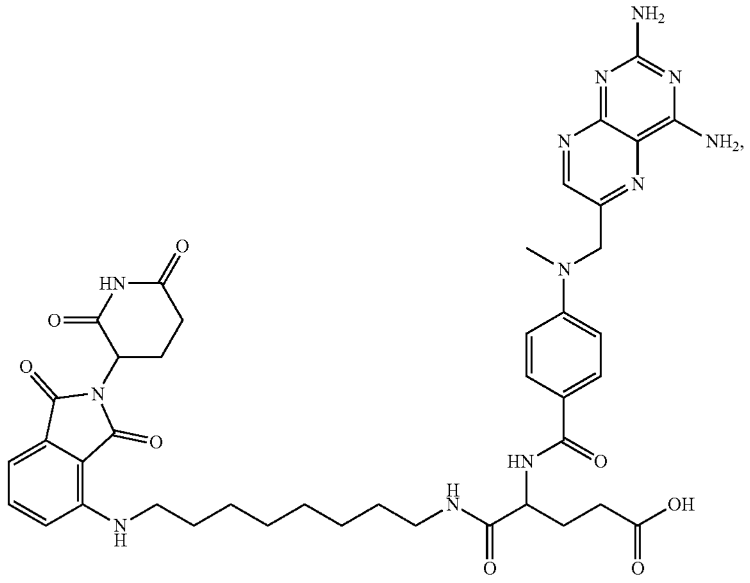
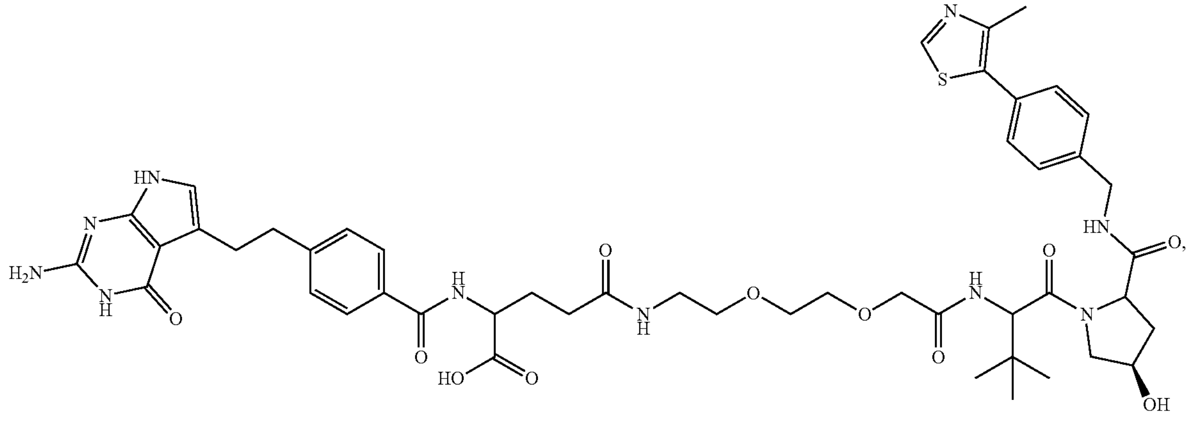

-continued
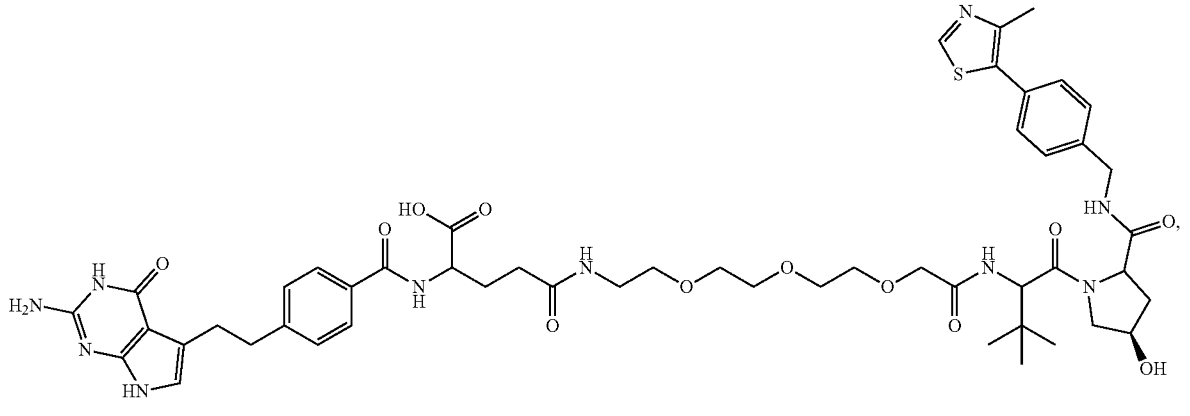
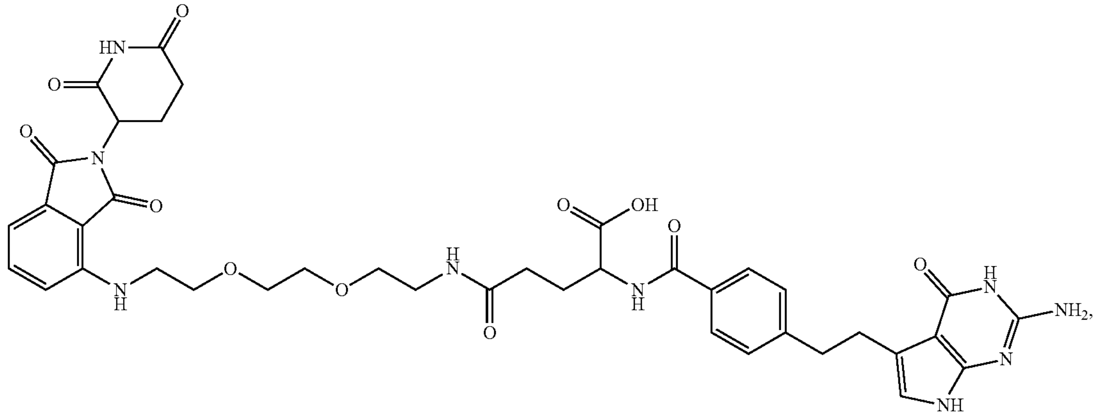
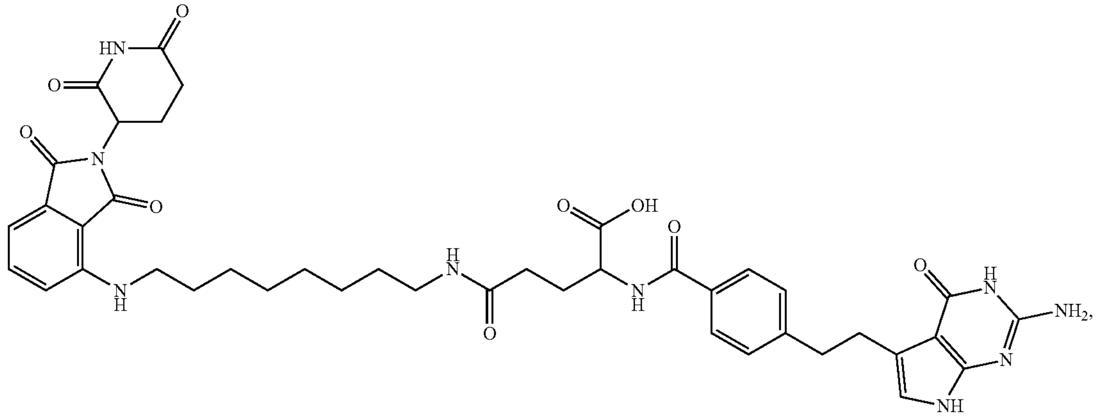
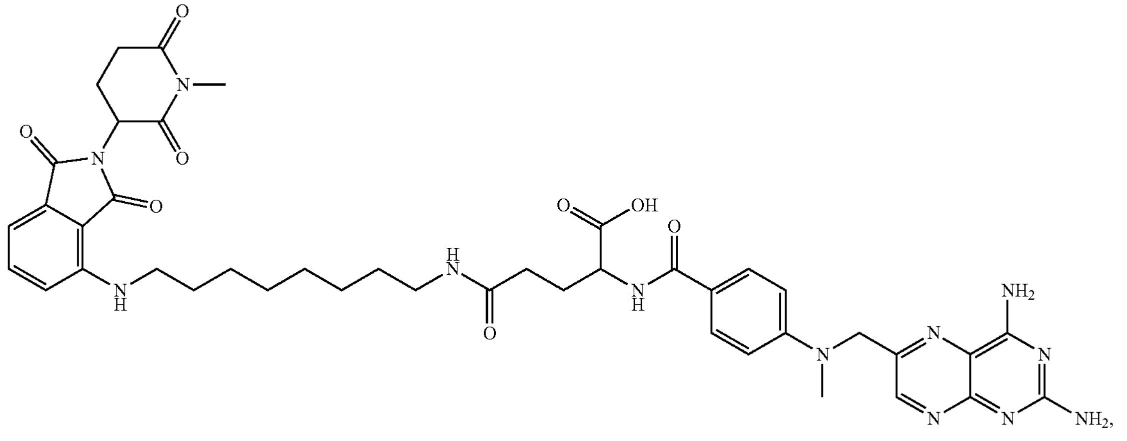

-continued
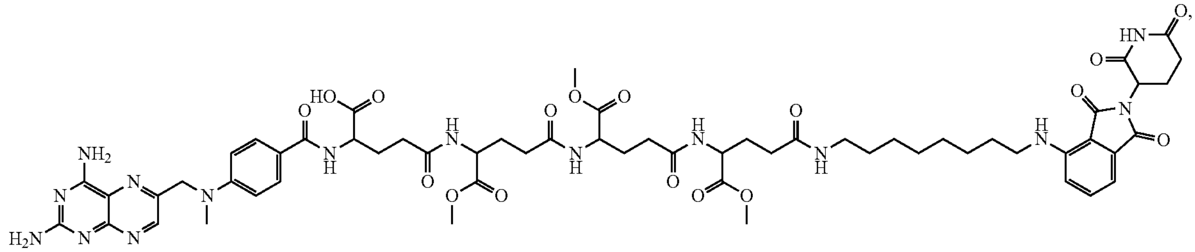
,
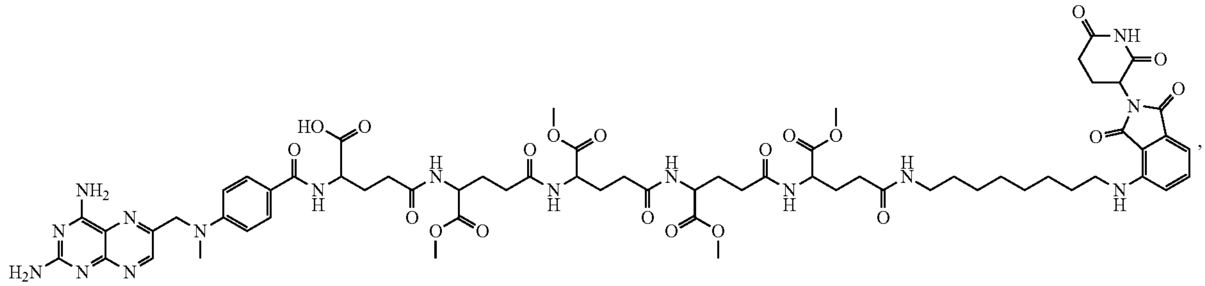
,
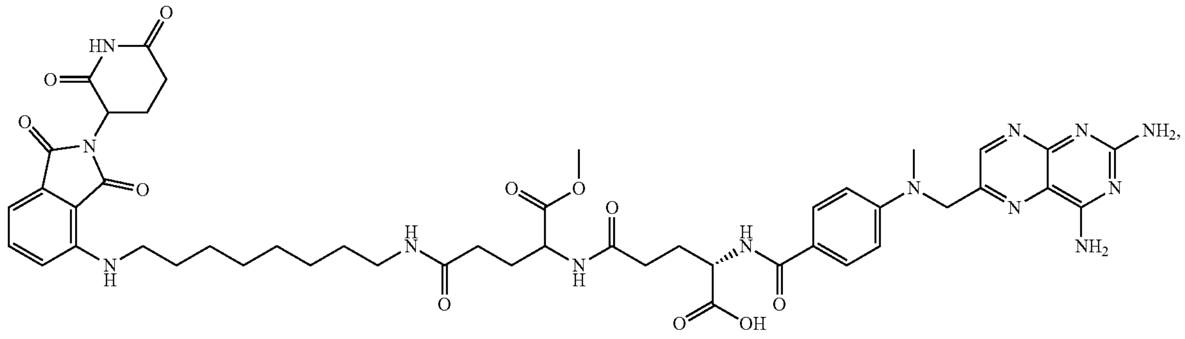
,
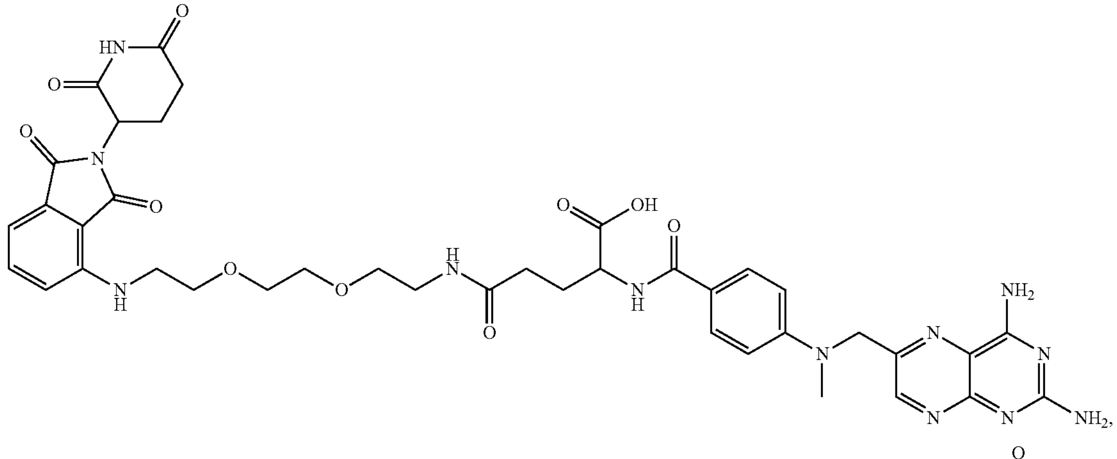
,
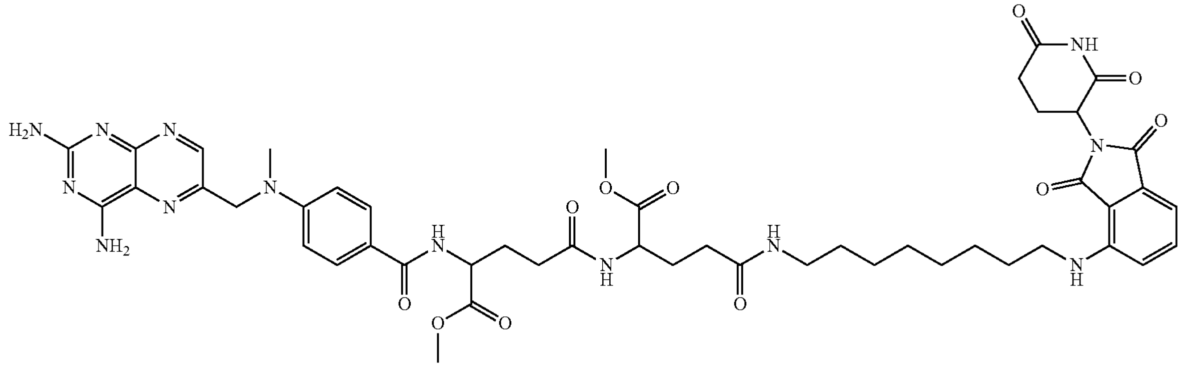
, -continued
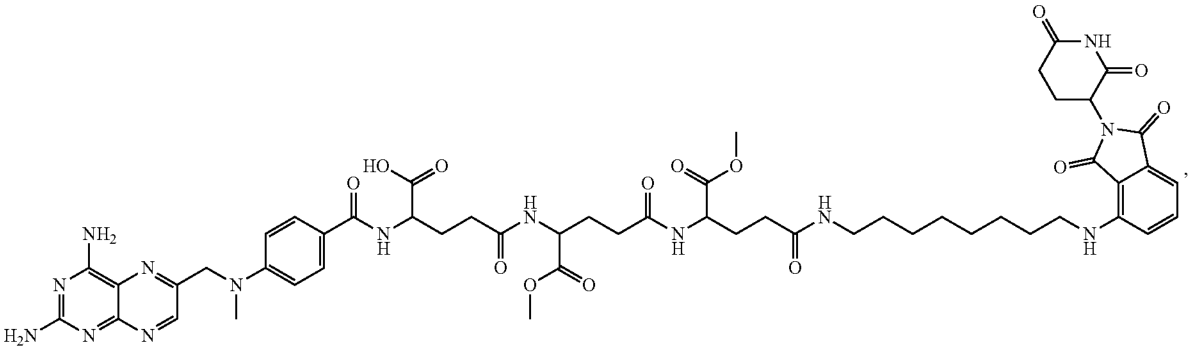
,
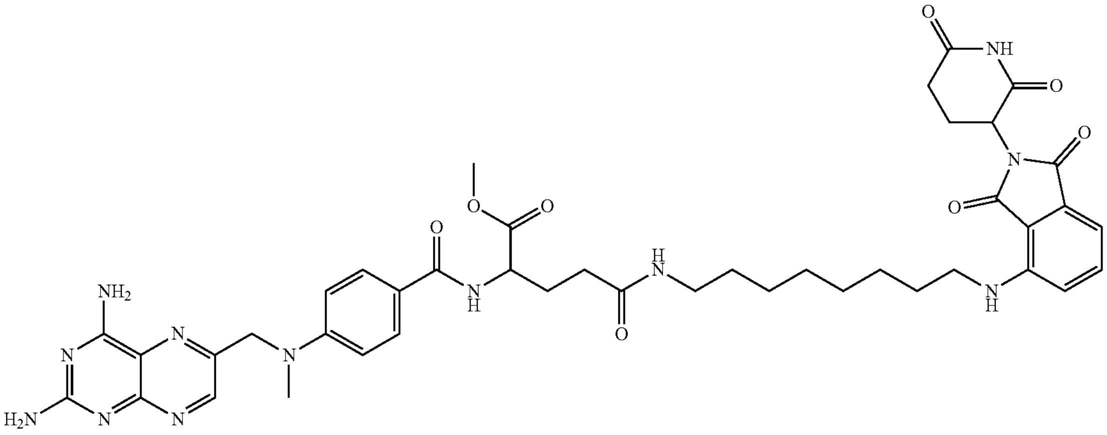
,
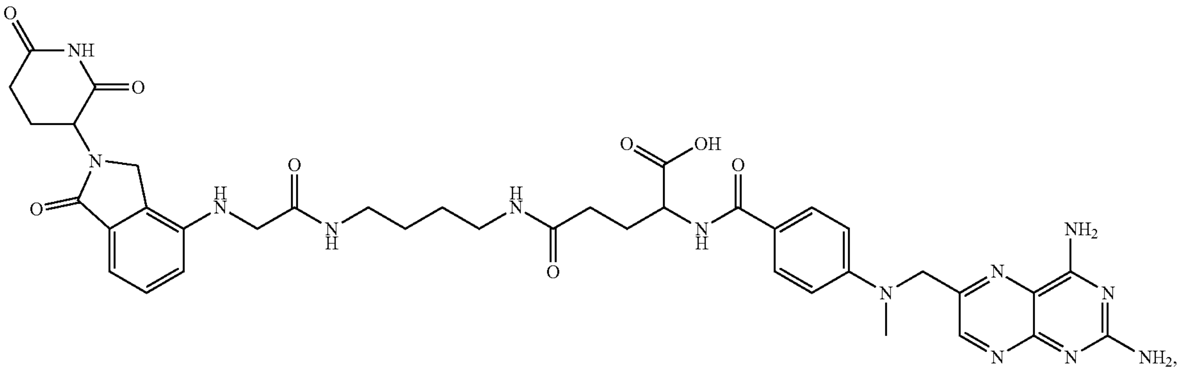
,
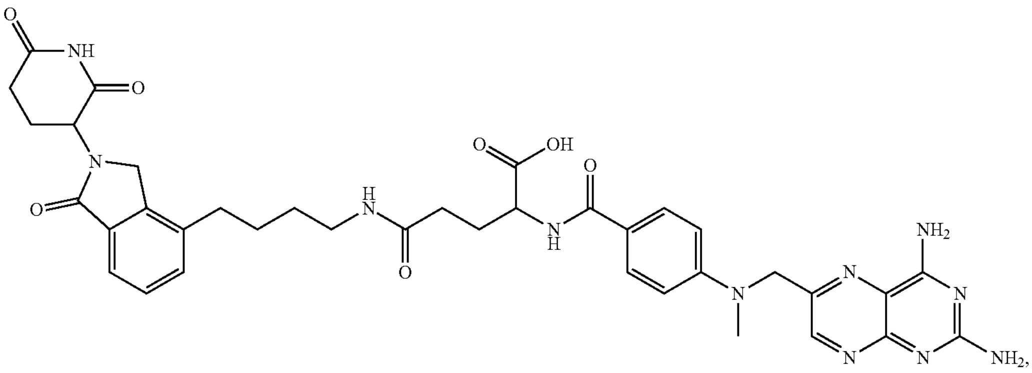
, -continued
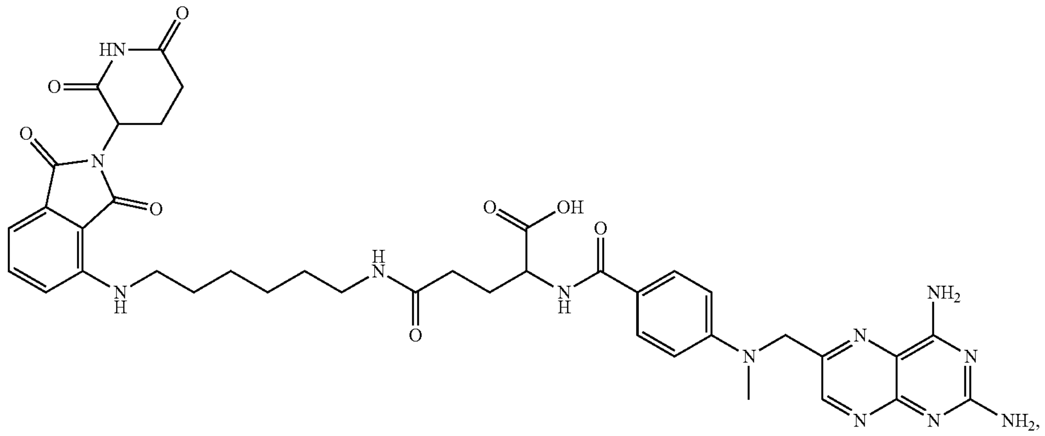
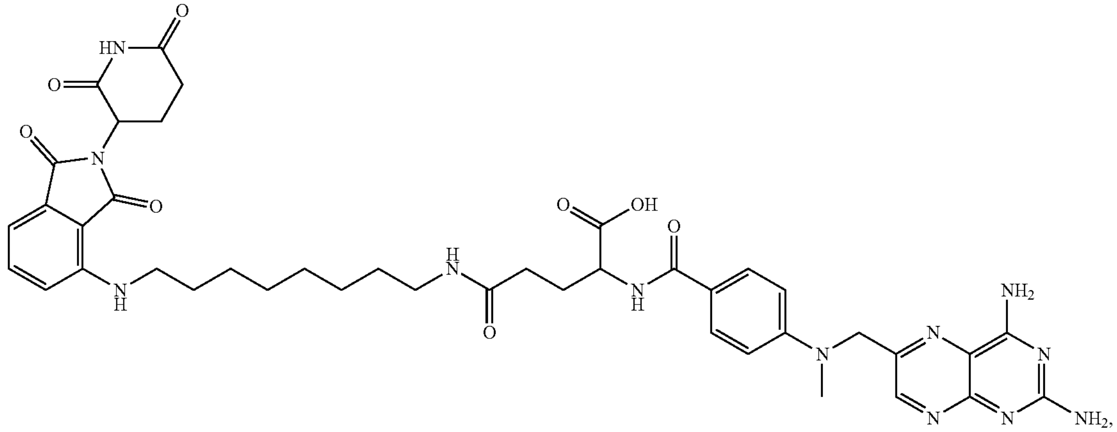
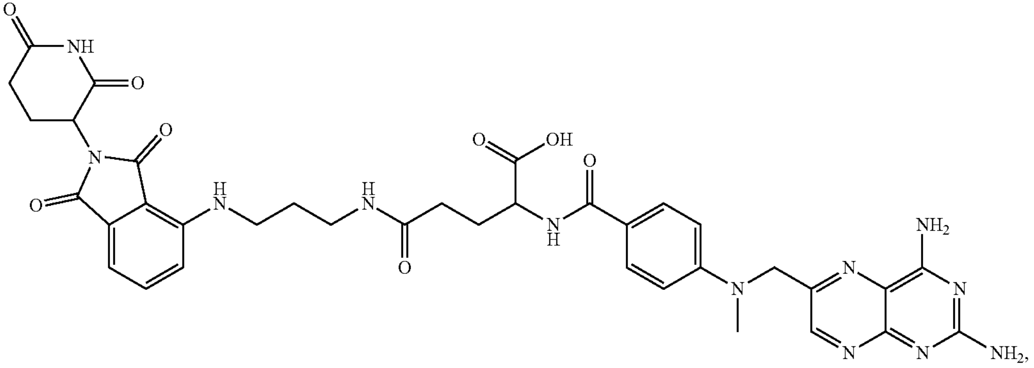
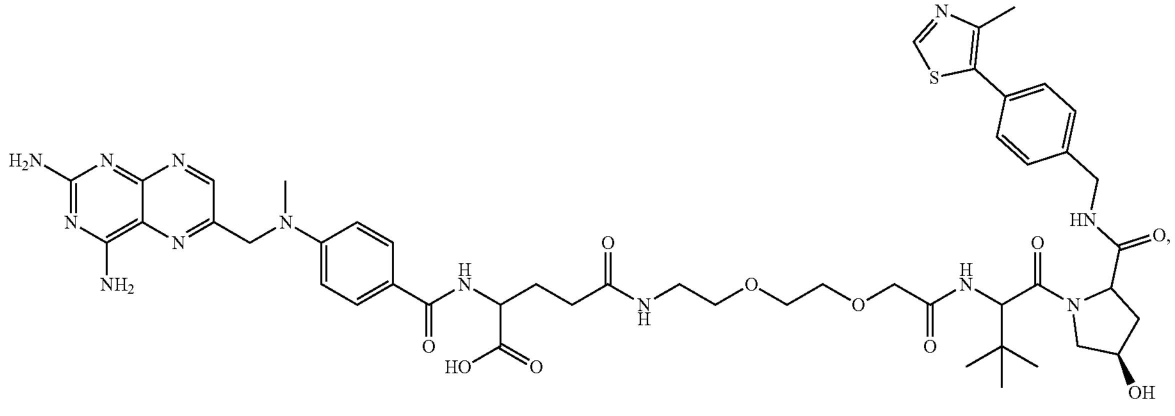

-continued
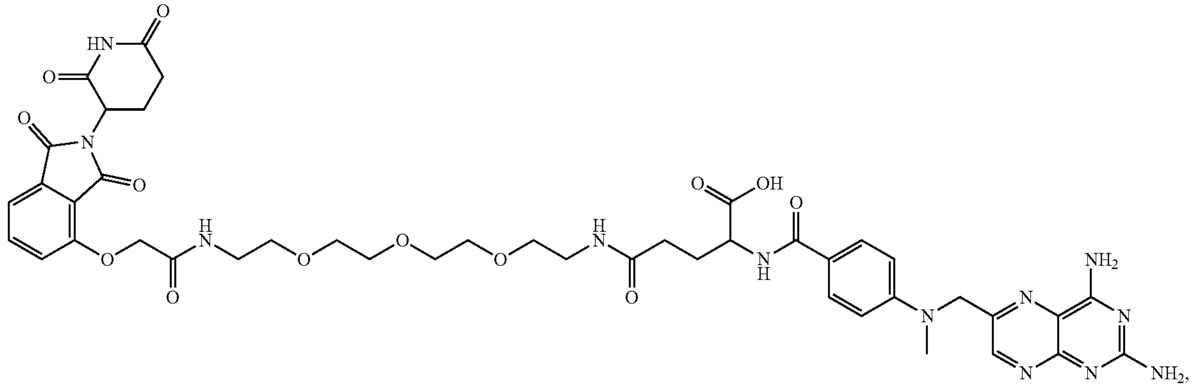
,
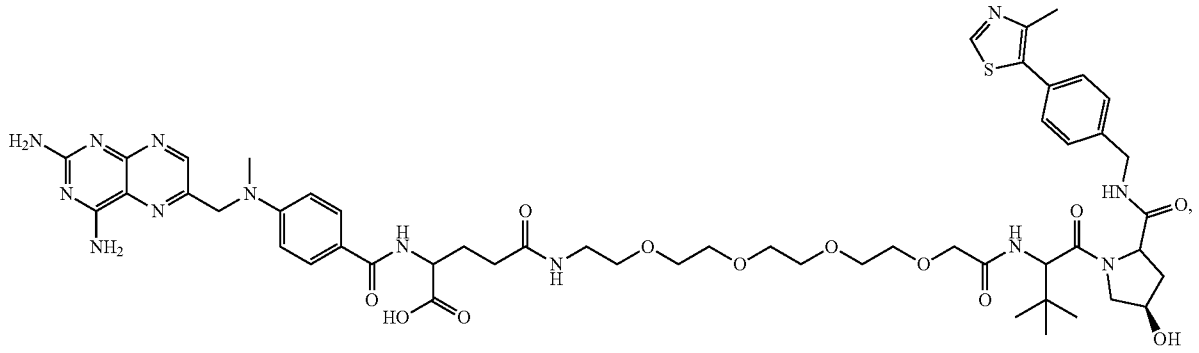
,
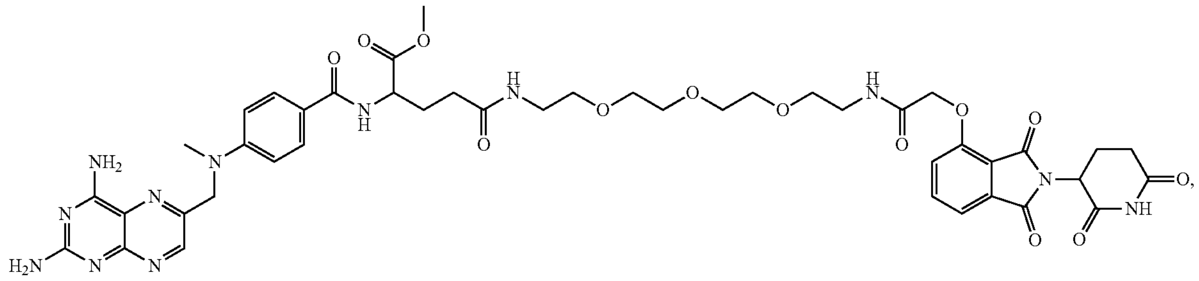
,
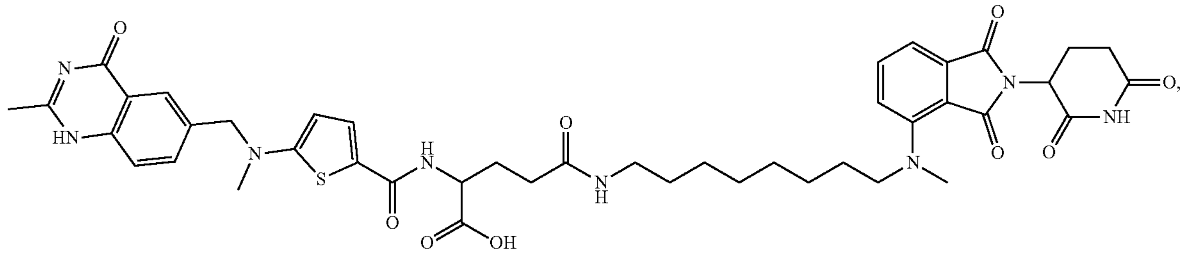
,
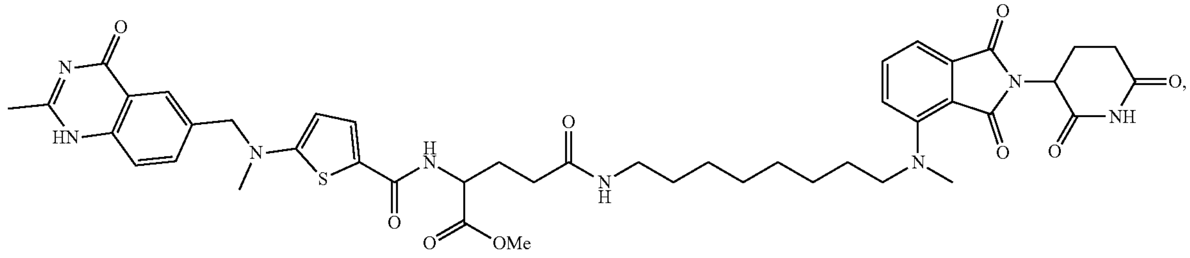
, -continued
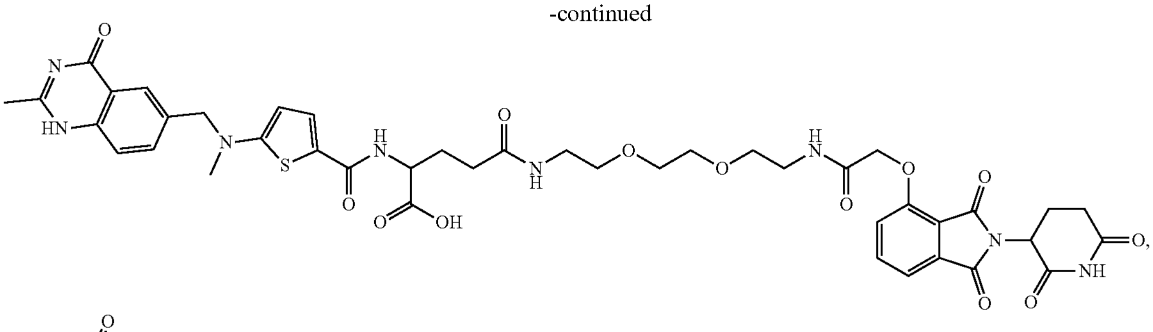
, or
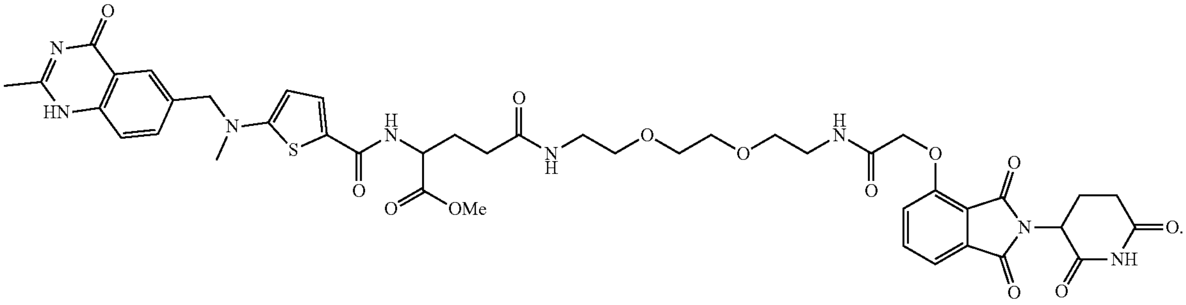
.
Additional exemplary compounds include:
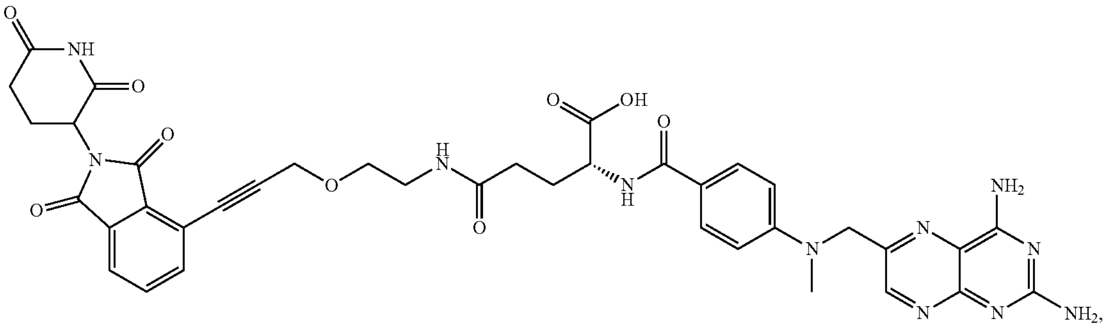
,
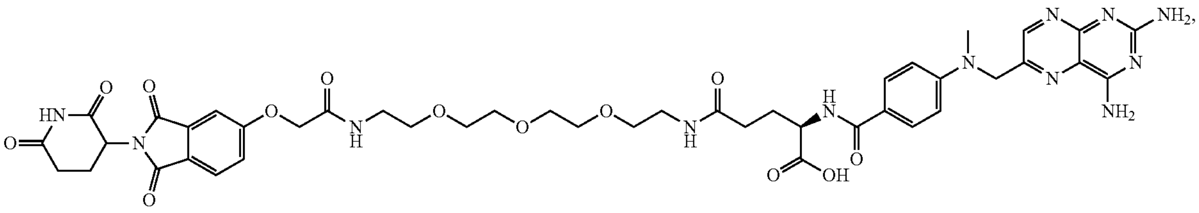
,
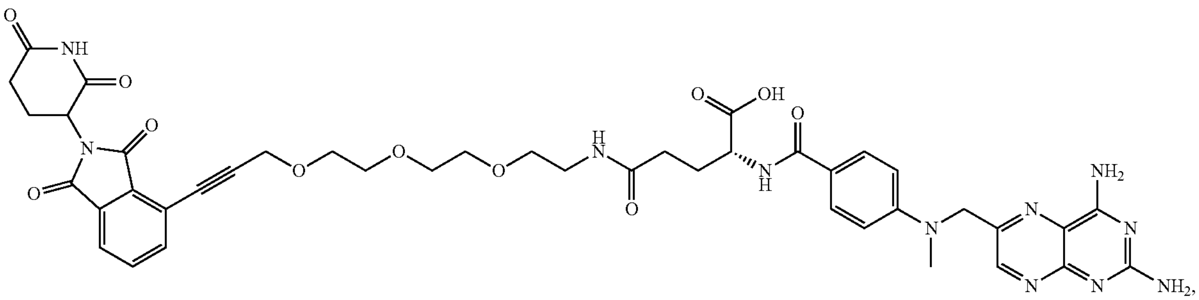
, -continued
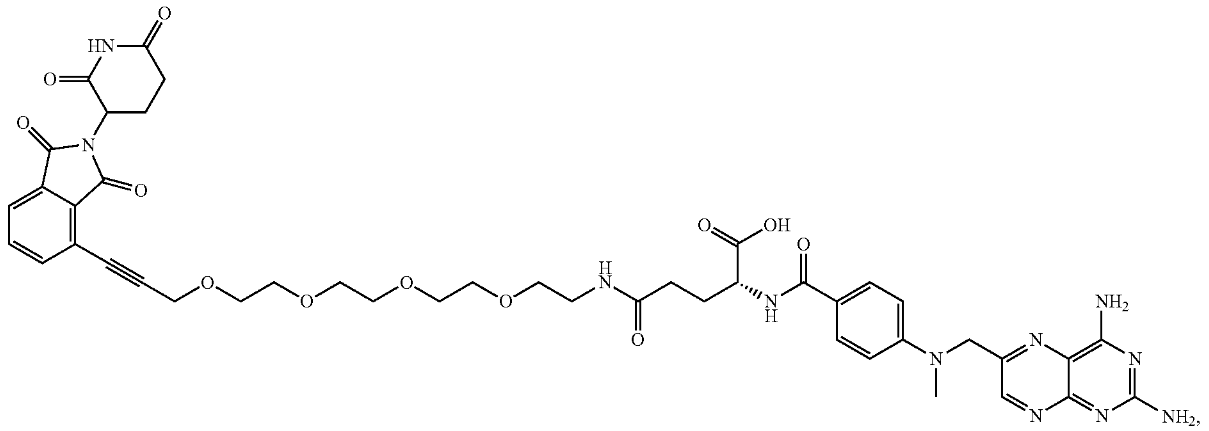
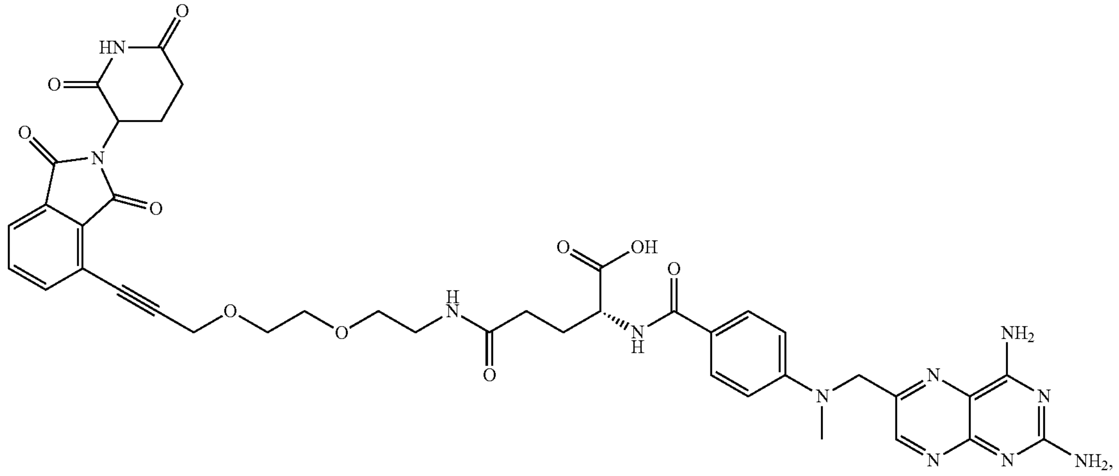
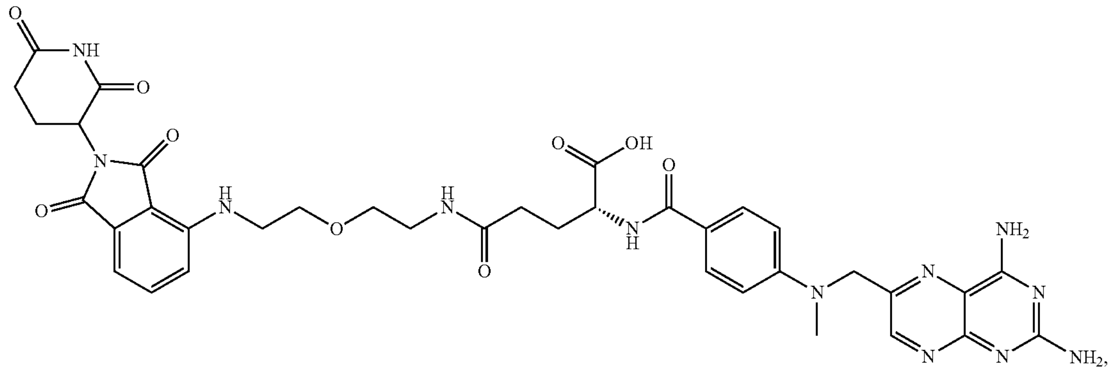
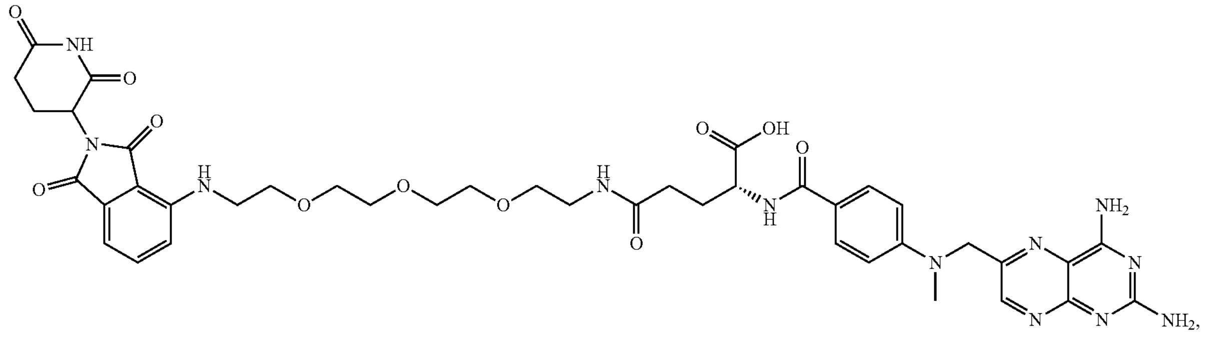

-continued
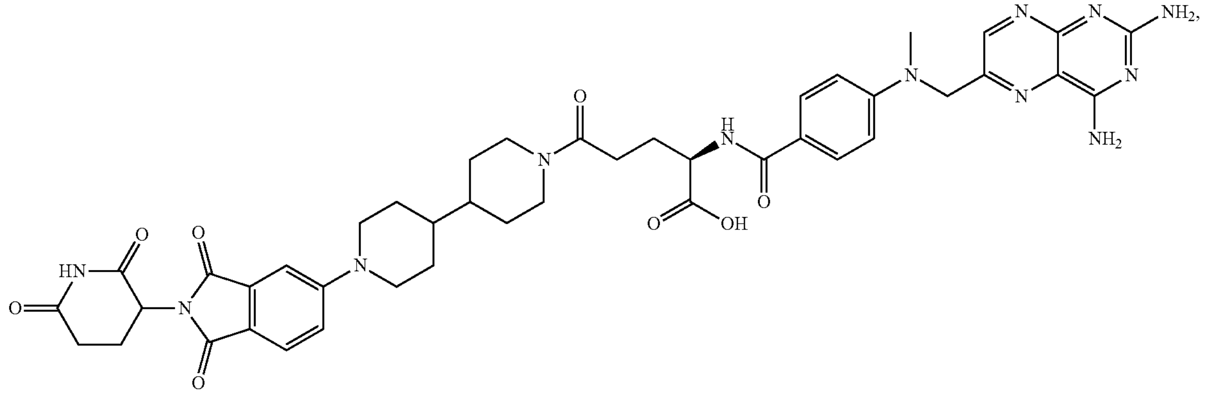
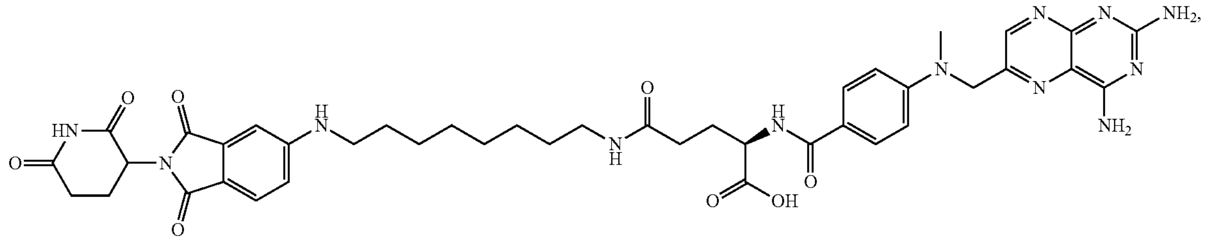
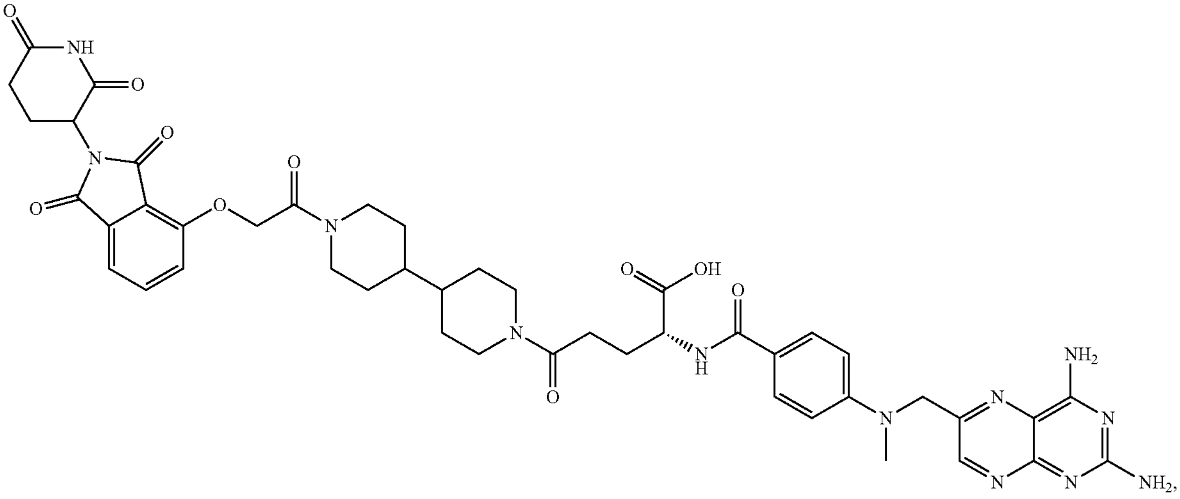
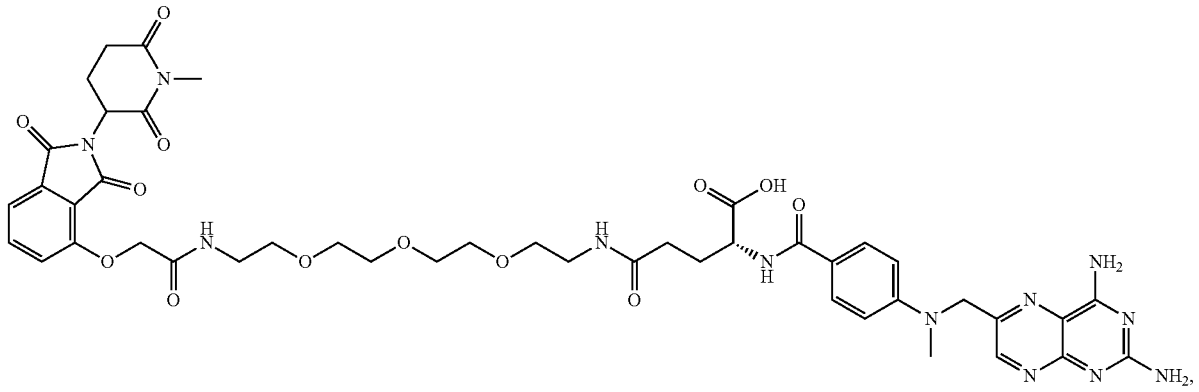

-continued
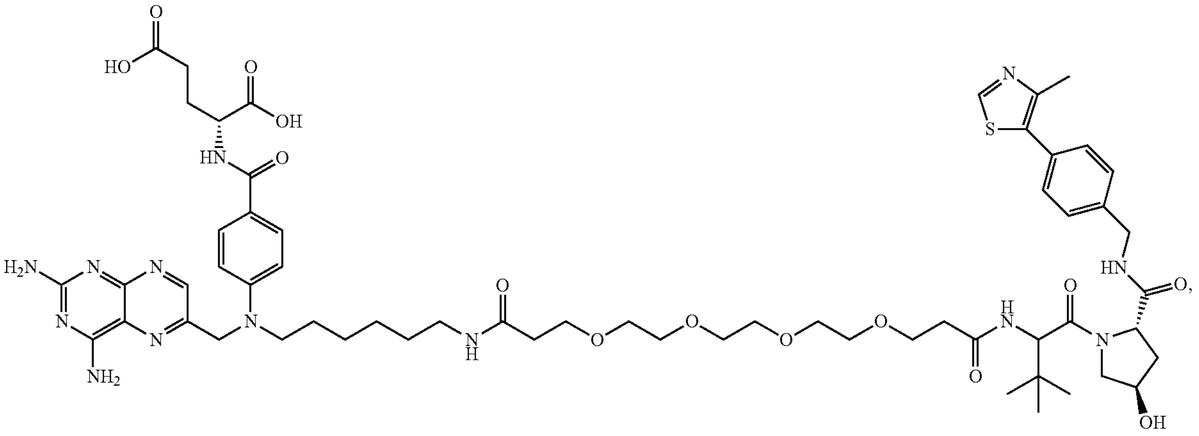
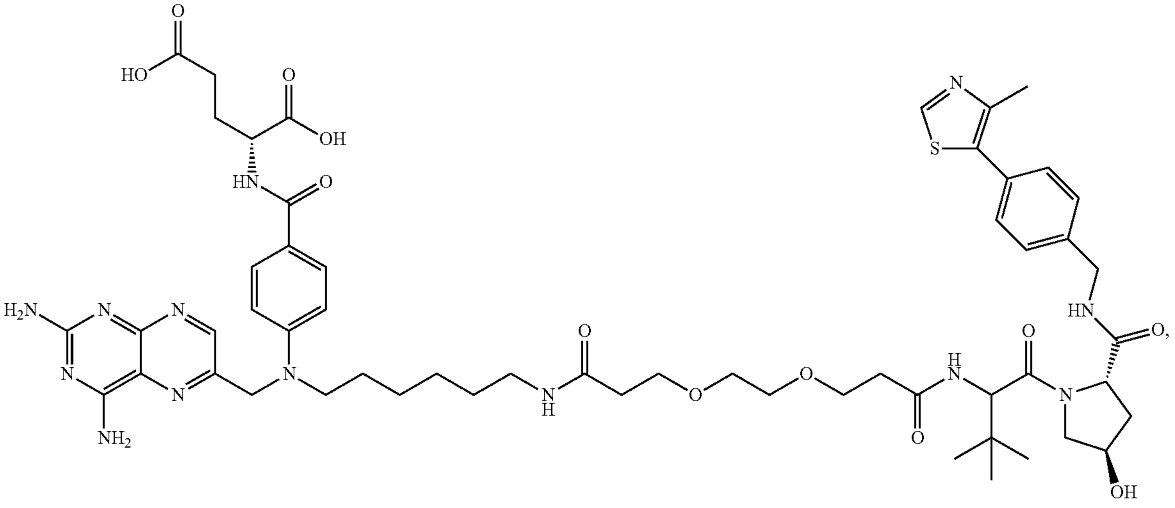
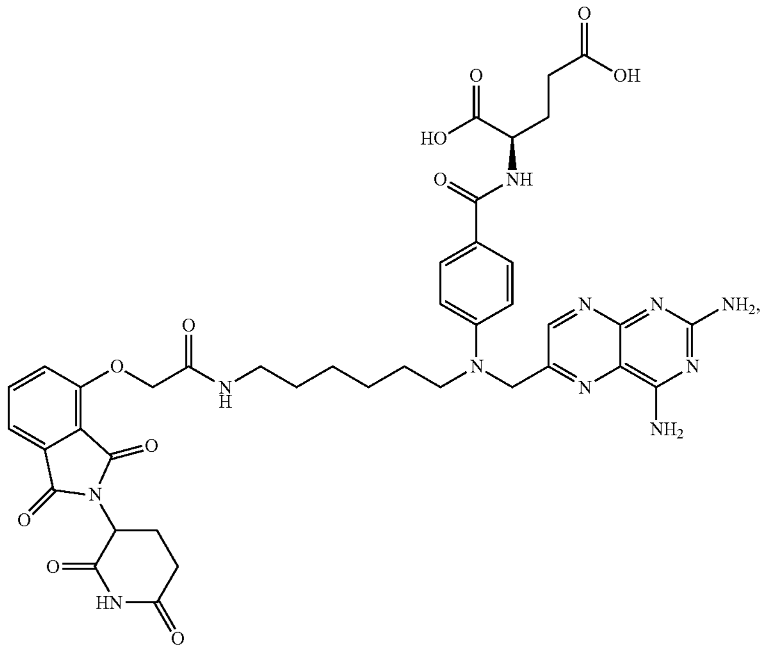

-continued
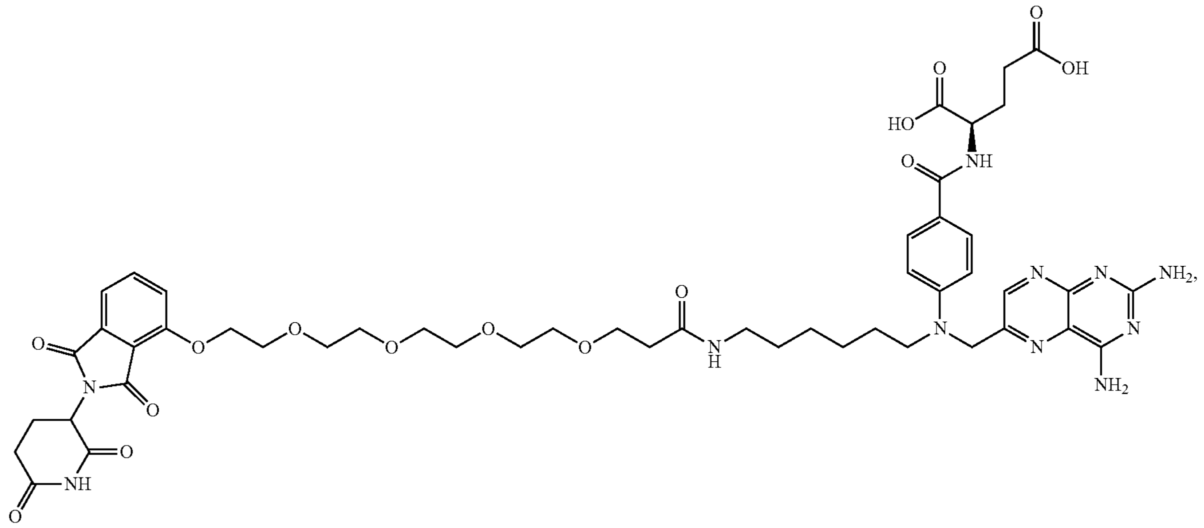
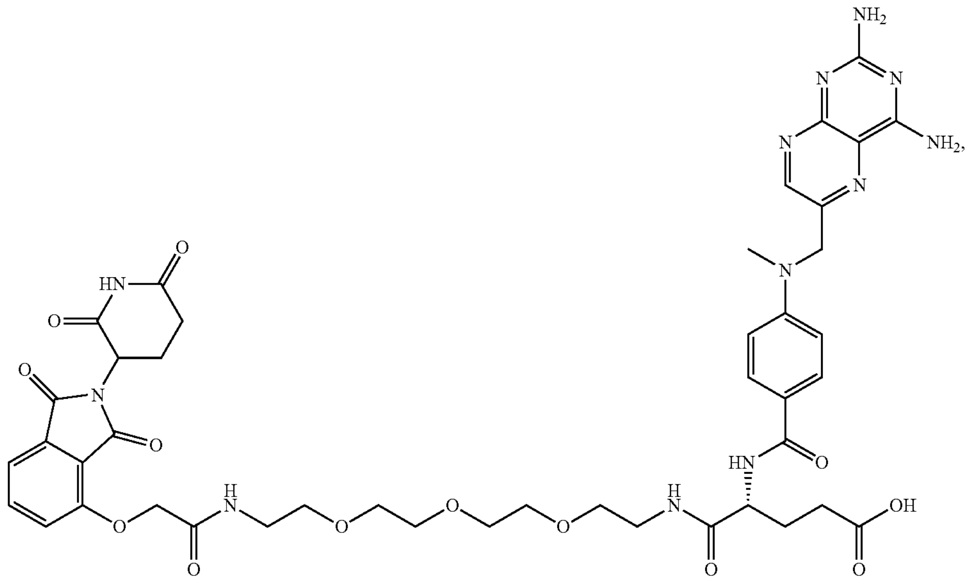
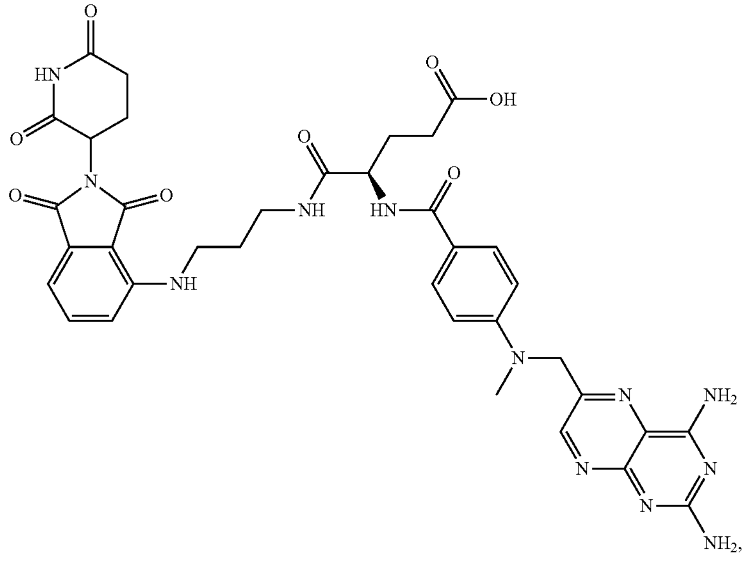

-continued
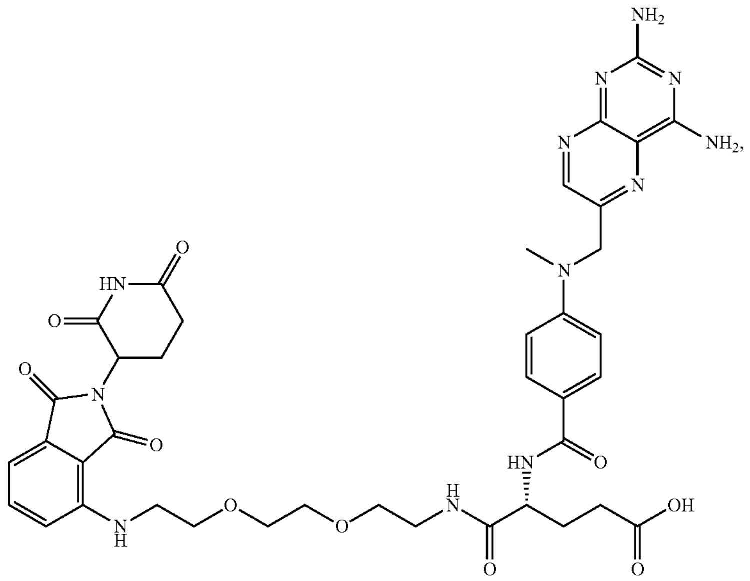
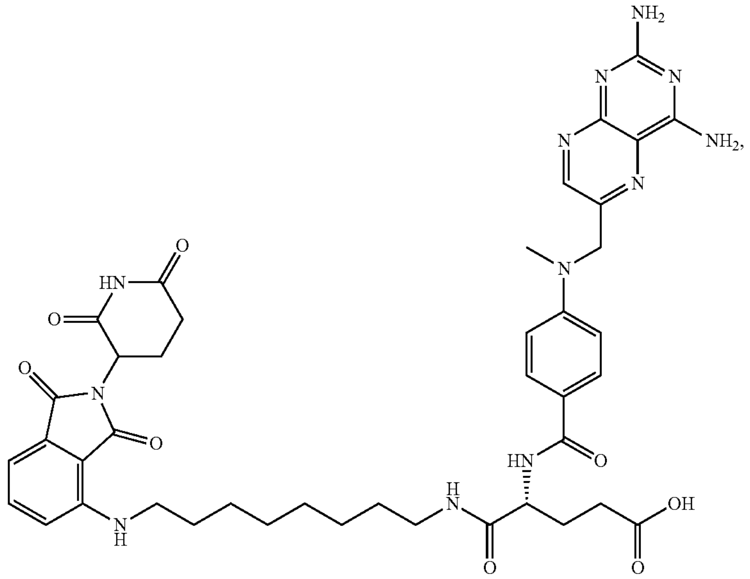
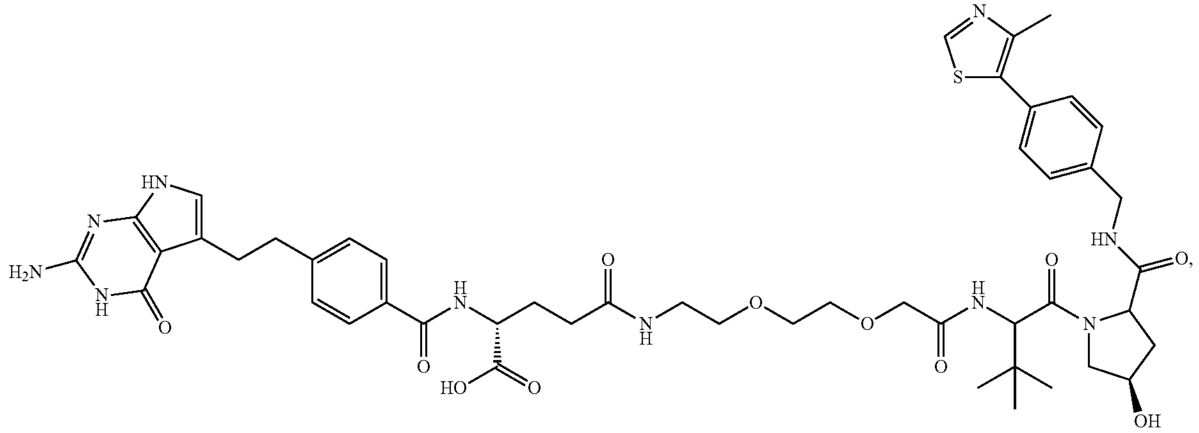

-continued
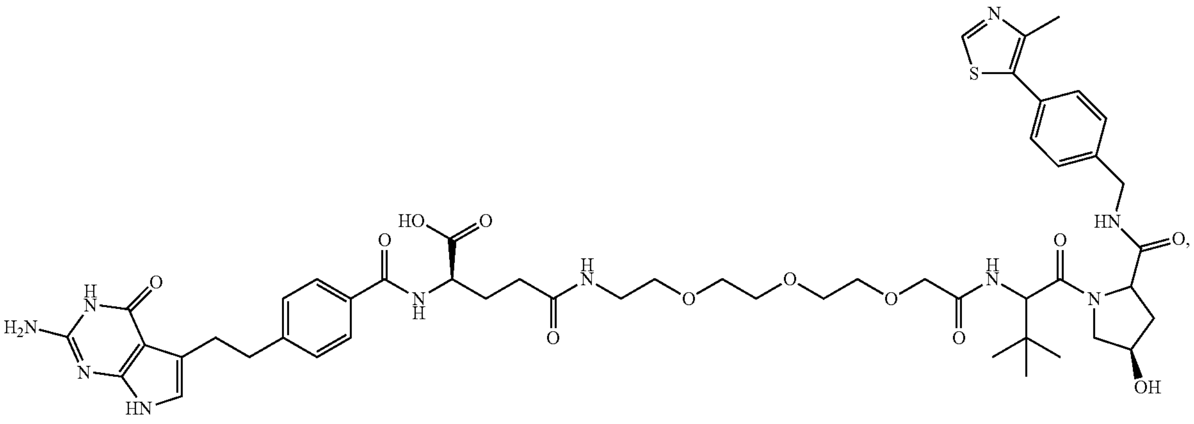
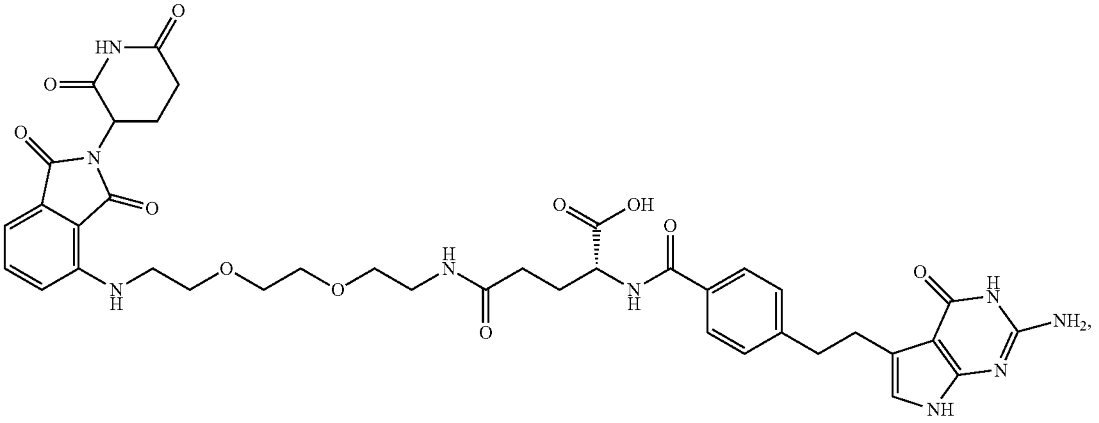
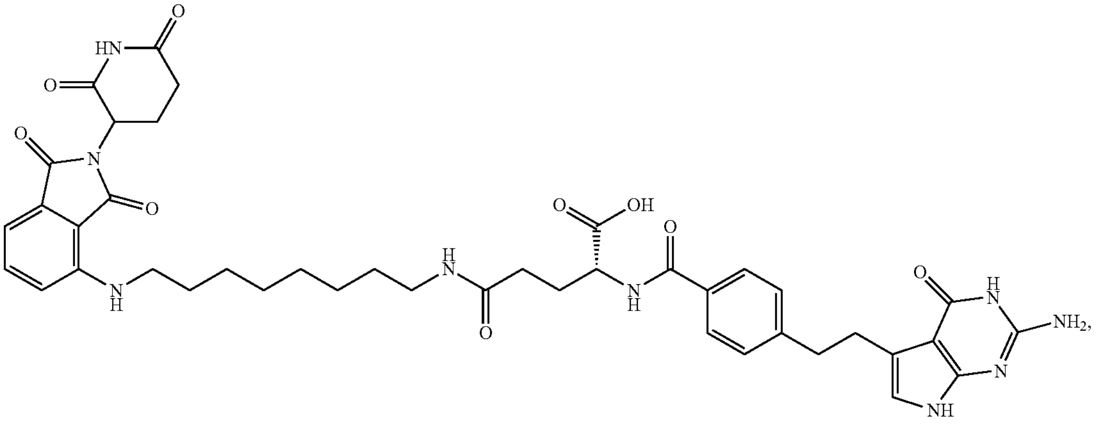
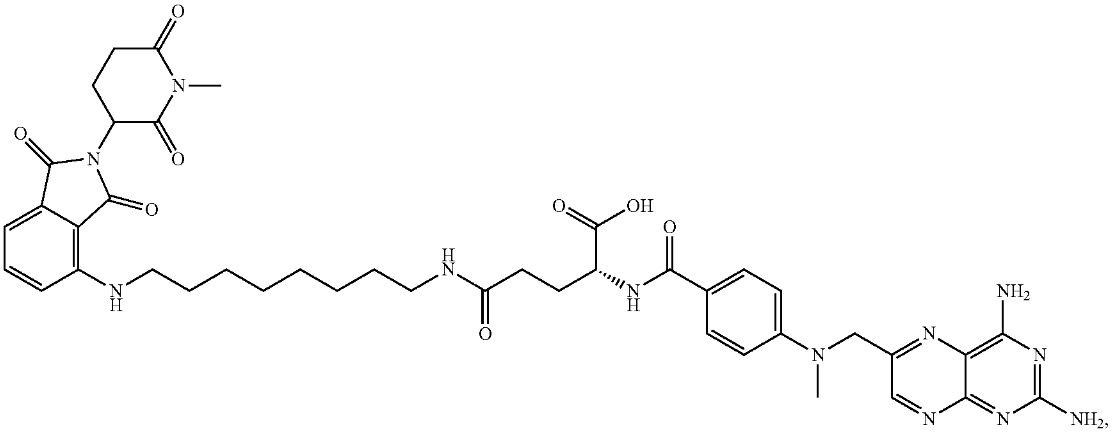

-continued
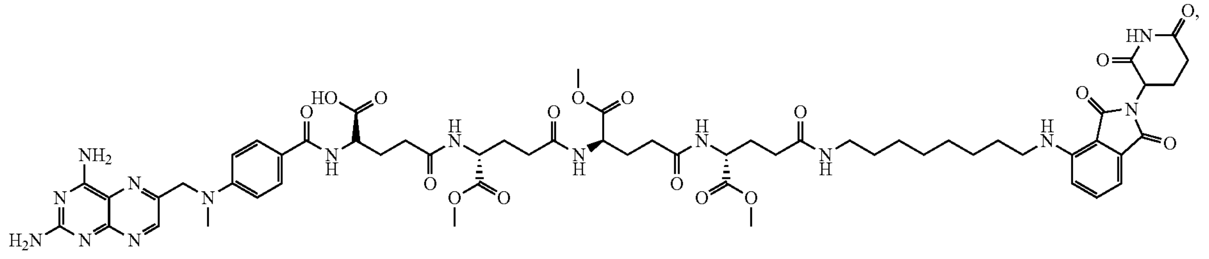
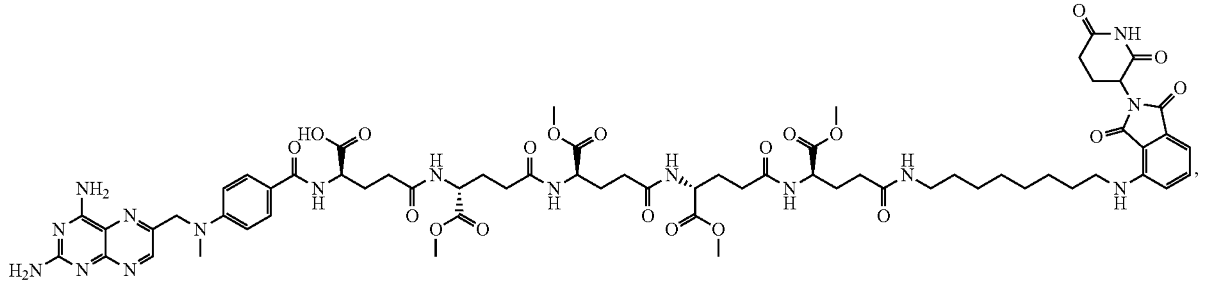
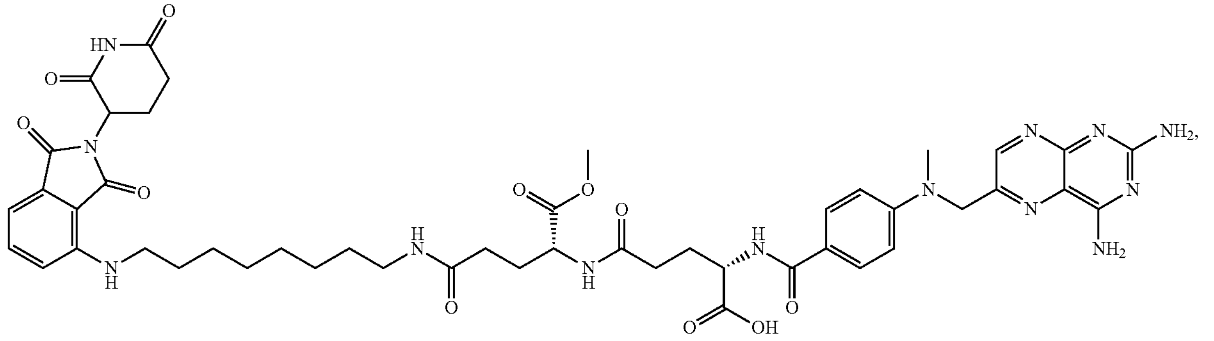
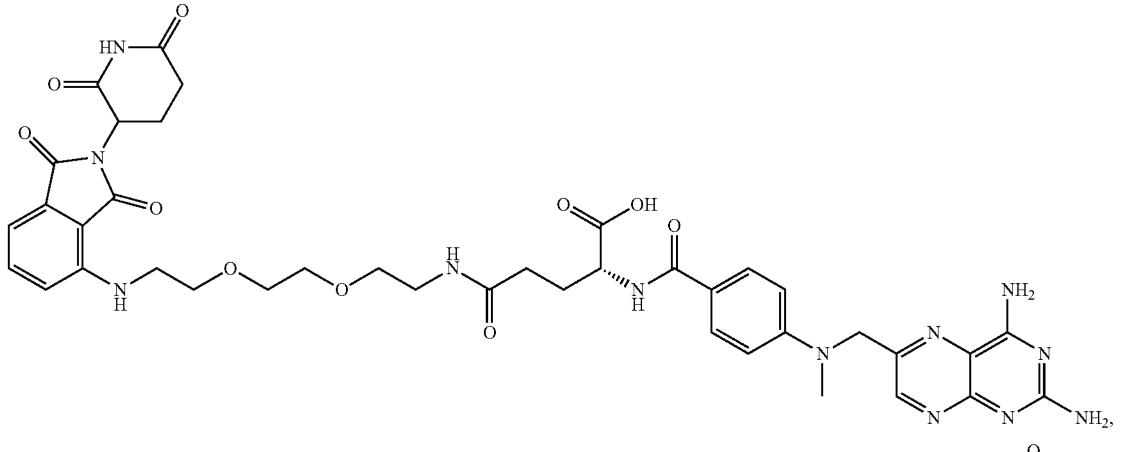
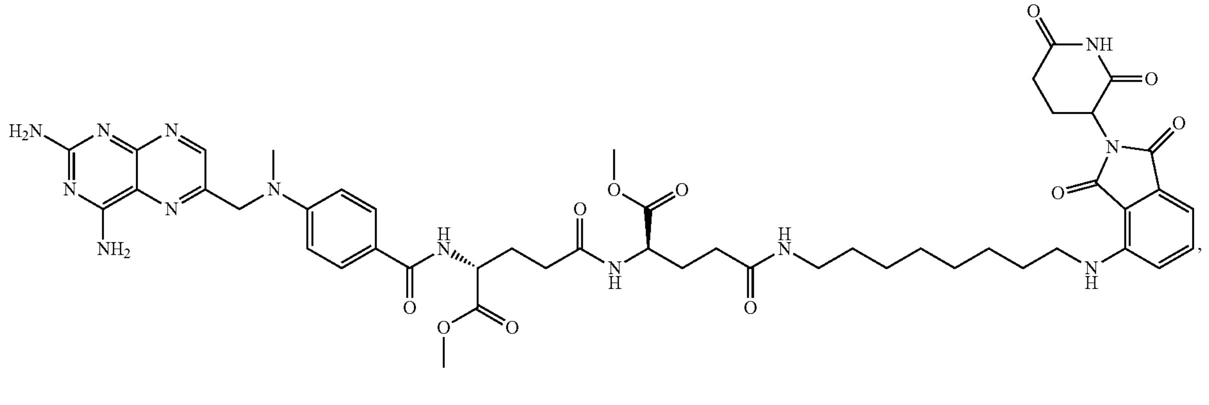

-continued
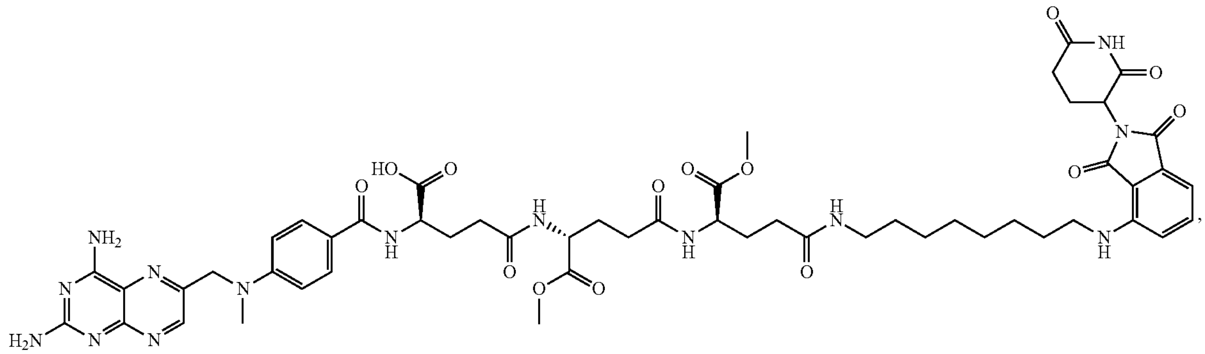
,
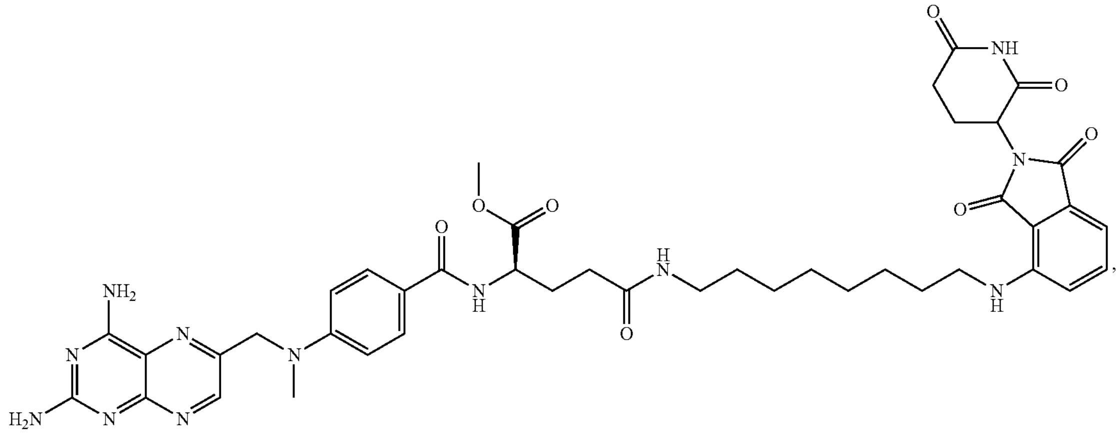
,
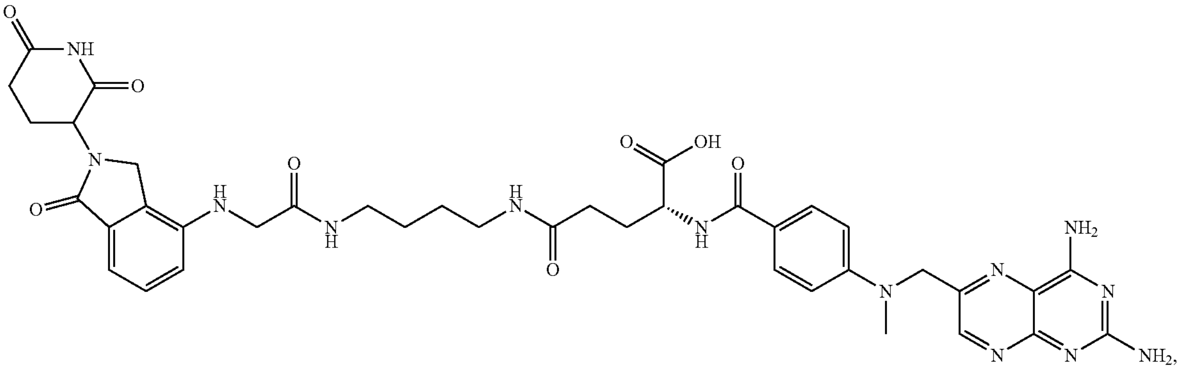
,
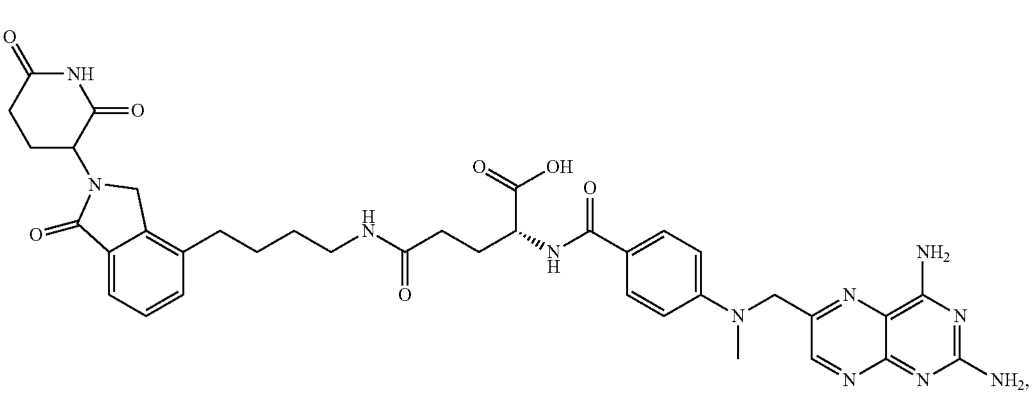
,

-continued
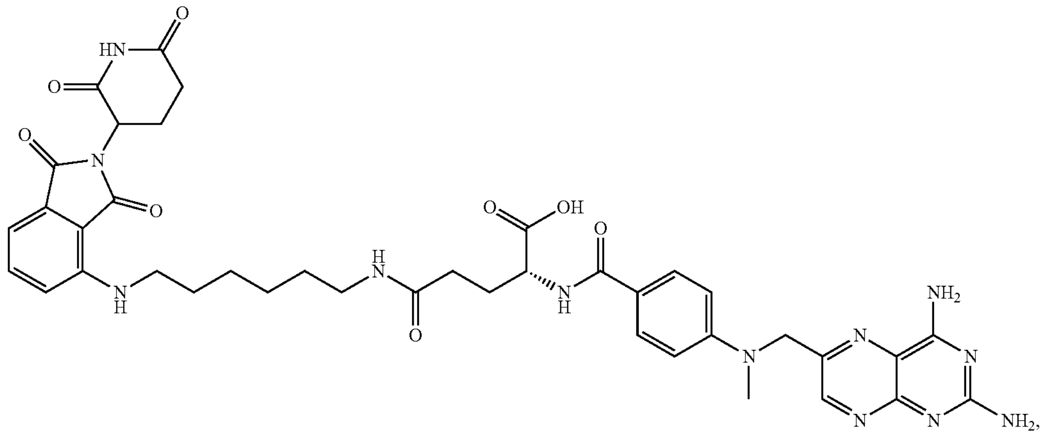
,
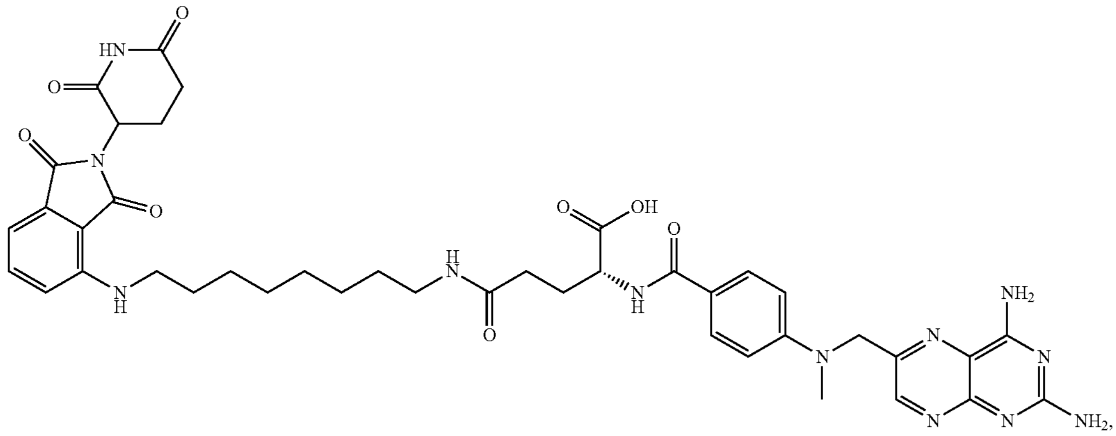
,
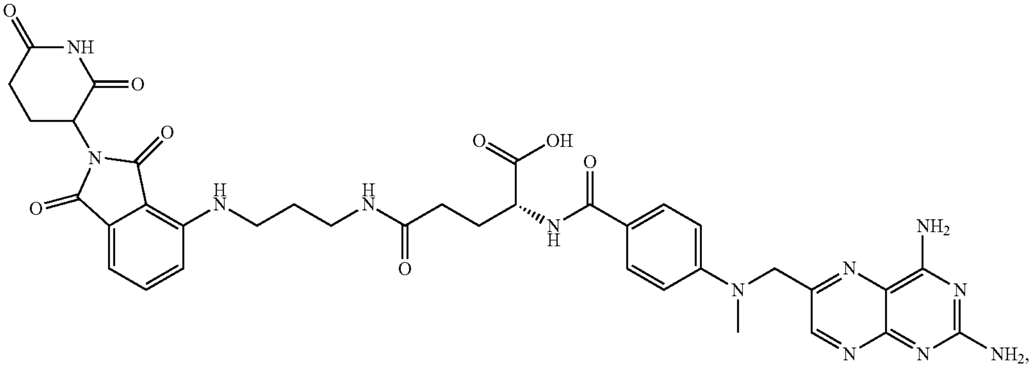
,
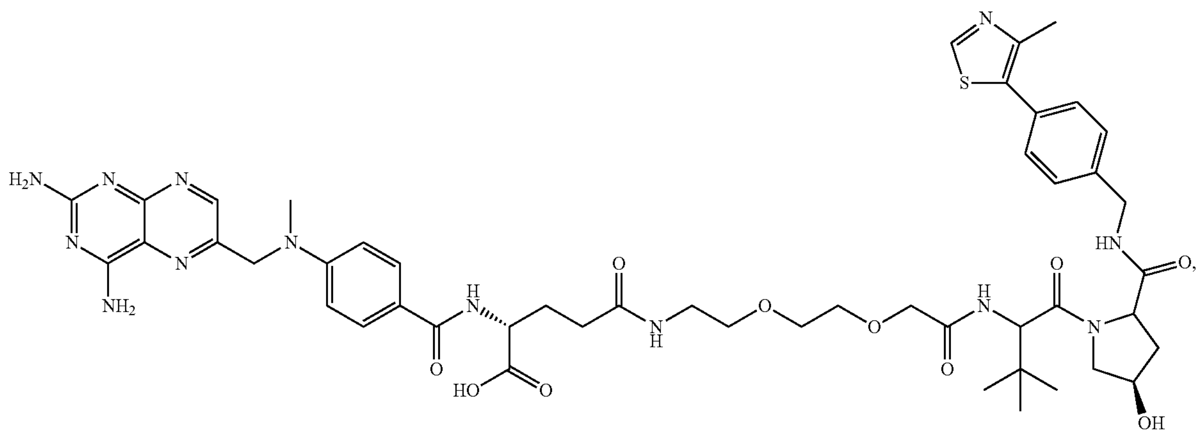
,

-continued
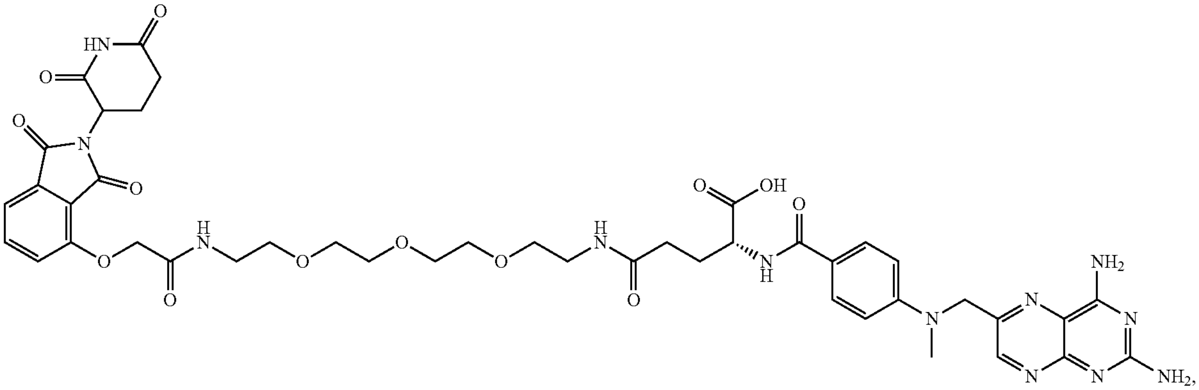
,
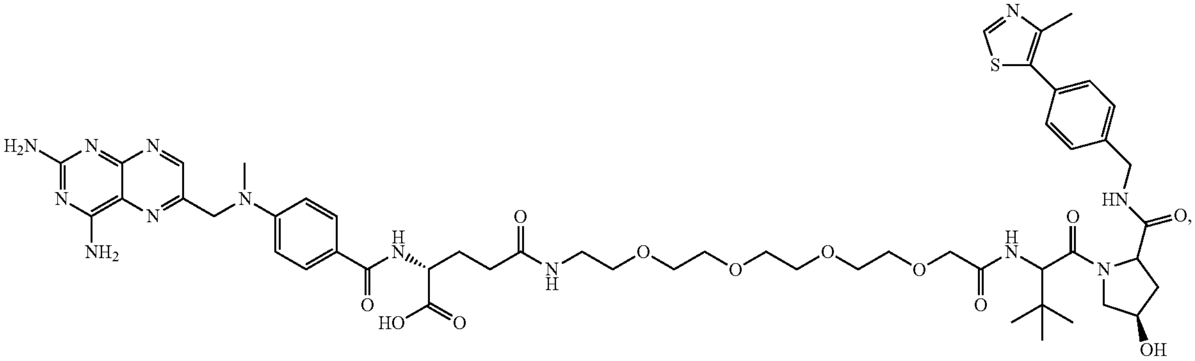
,
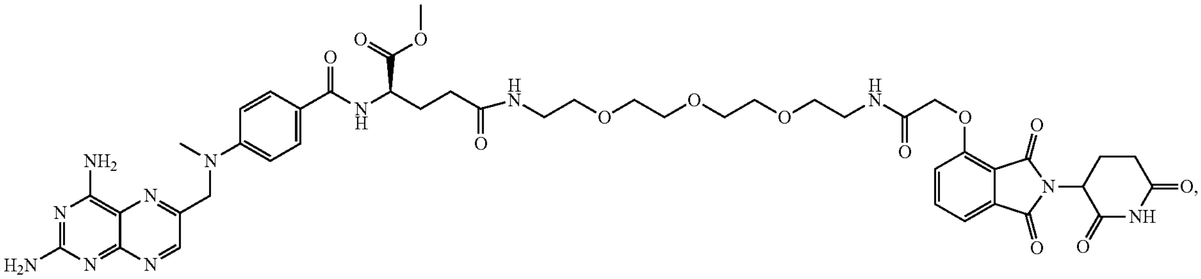
,
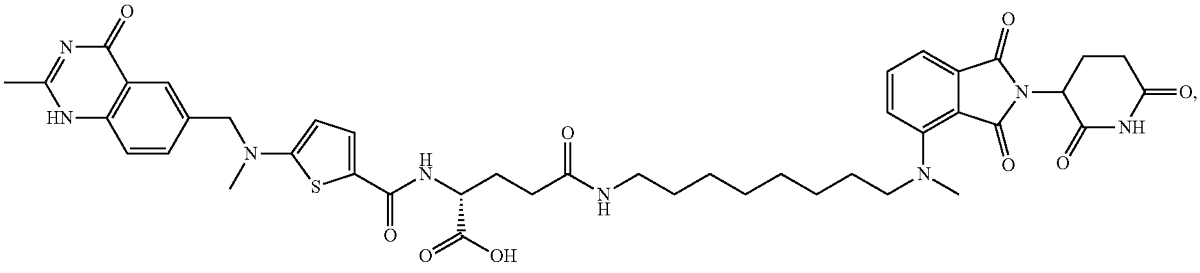
,
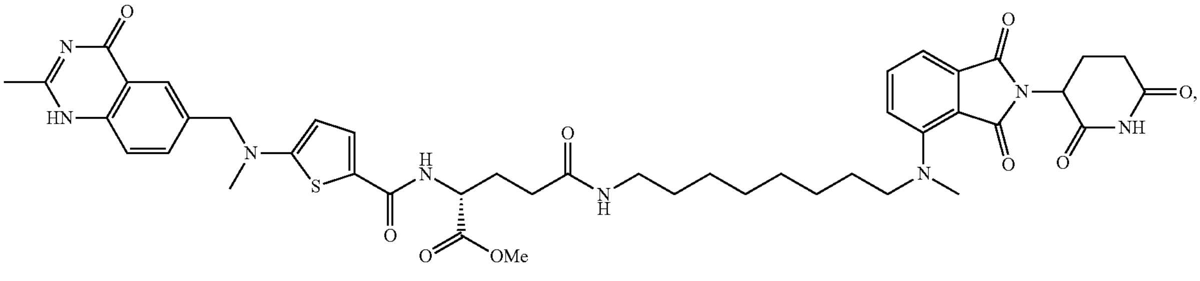
, -continued

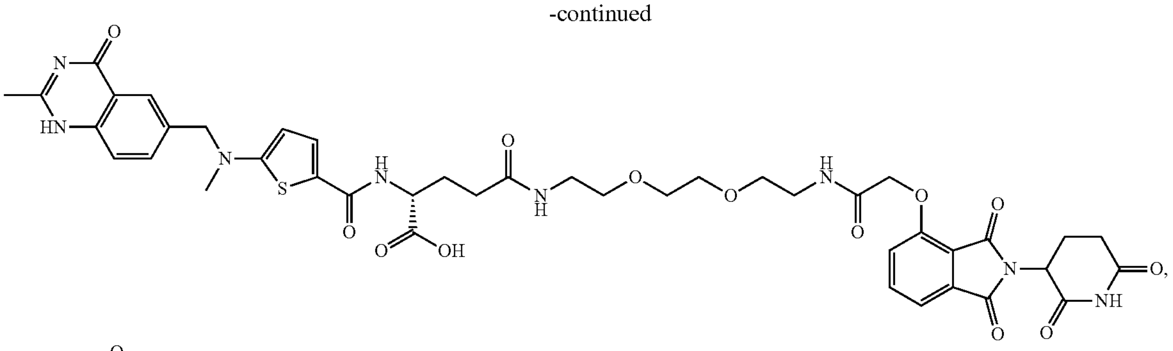

, or

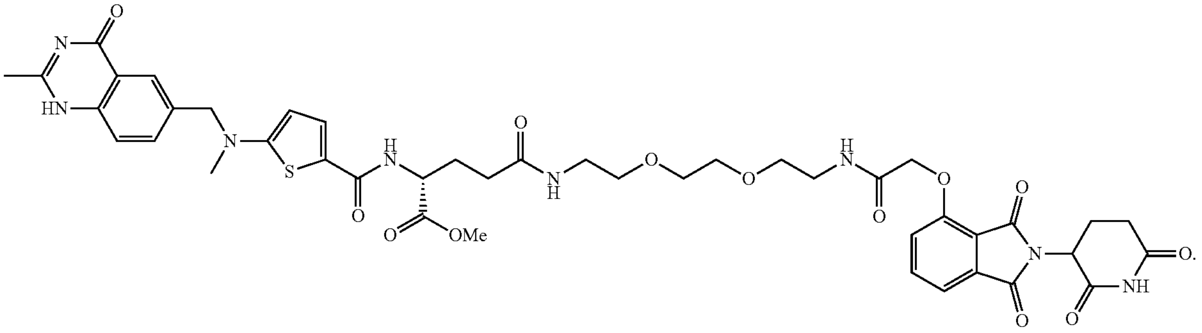

B. Methods for Making

Disclosed compounds can be prepared as exemplified below, as illustrated for specific compounds in the examples, and as will be understood by a person of ordinary skill in the art of organic synthesis. An exemplary synthesis may include the following first reaction step according to Scheme 1.

Scheme 1

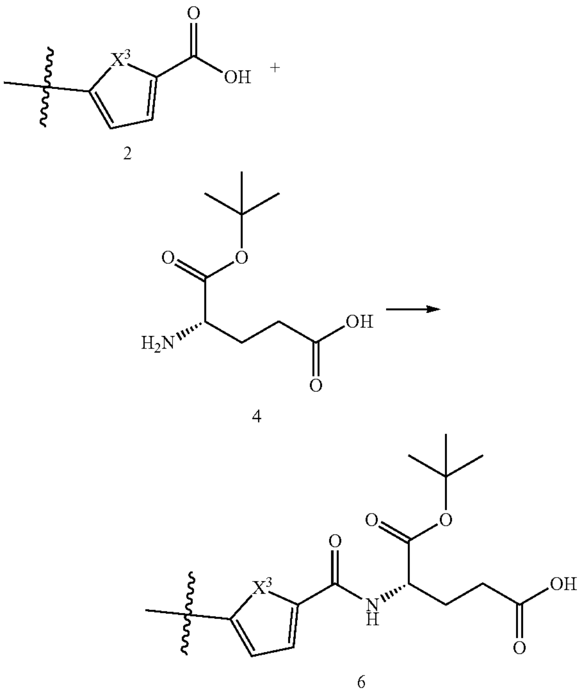

2

4

6

With respect to Scheme 1, acid 2 is dissolved in a suitable solvent, such as a non-protic solvent (for example, DMSO, DMF, pyridine, acetonitrile, THF, toluene, a chlorinated solvent, such as chloroform, dichloroethane, or dichloromethane, or any combination thereof. Acid 2 is treated with a coupling agent in the presence of a suitable base. Suitable coupling agents include any coupling agent that facilitates the formation of compound 6, such as, but not limited to, PyBOP, BOP, DCC, HATU, EDCI, or a combination thereof. Suitable bases include any base that facilitates the formation of compound 6, such as, but not limited to, a trialkylamine, for example, triethylamine, or diisopropylethylamine; pyridine; or a carbonate base, such as potassium carbonate, sodium carbonate, or lithium carbonate; or a combination thereof. Typically, the reaction mixture is agitated, such as by stirring or shaking, at a temperature suitable to facilitate the reaction, such as from 10° C. or less to 30° C. or more, and for a time of from greater than zero to 12 hours or more, such as from 1 hour to 6 hours. After isolating the crude product, such as by evaporating the solvent, and/or extraction, compound 6 is isolated by a suitable technique such as reverse phase HPLC.

A second reaction step in the exemplary synthesis is provided by Scheme 2.

Scheme 2

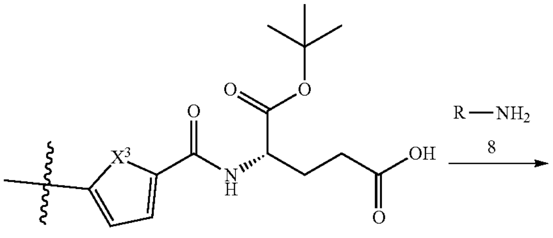

6

-continued

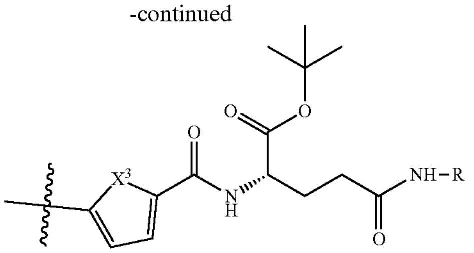

10

Compound 6 (1 eq) and amine 8 (1 eq) are treated with a base and a coupling agent in a suitable solvent, for example, a non-protic solvent, such as, but not limited to, DMF, THF, acetonitrile, toluene, pyridine, DMSO, a chlorinated solvent such as chloroform, dichloroethane, or dichloromethane, or any combination thereof. The base may be any base suitable to facilitate formation of amide 10, such as, but not limited to, a trialkylamine, for example, triethylamine, or diisopropylethylamine; pyridine; or a carbonate base, such as potassium carbonate, sodium carbonate, or lithium carbonate; or a combination thereof. The coupling agent may be any coupling agent suitable to facilitate amide formation, such as, but not limited to, PyBOP, BOP, DCC, HATU, EDCI, or a combination thereof.

The reaction proceeds at a suitable temperature, such as from 10° C. or less to 30° C. or more, and for a time period of from greater than zero to 12 hours or more, such as from 1 hour to 6 hours, after which time, amide 10 is isolated by a suitable technique such as reverse phase HPLC.

A third reaction step in the exemplary synthesis is provided below according to Scheme 3.

Scheme 3

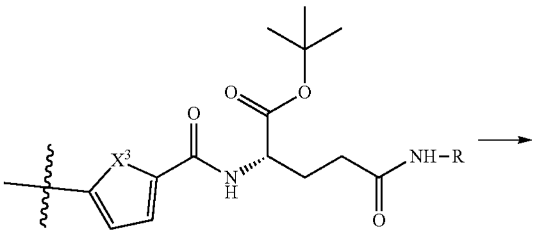

10

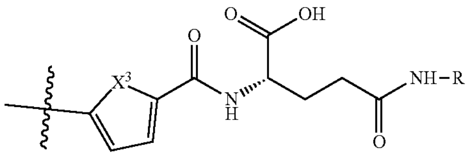

12

Amide 10 is treated by an acid suitable to remove the t-butyl group and form the acid, such as trifluoroacetic acid, in a suitable solvent. The solvent may be a non-protic solvent, such as, but not limited to, a chlorinated solvent such as chloroform, dichloroethane, or dichloromethane, DMF, THF, acetonitrile, toluene, pyridine, DMSO or any combination thereof. The progress of the reaction may be monitored by a suitable technique, such as LCMS, or TLC, and/or may proceed for a suitable time period, such as from greater than zero to 12 hours or more, or from 1 hour to 6 hours. The crude product is isolated, such as my evaporating the solvent optionally under reduced pressure, and/or extraction into a suitable solvent, and compound 12 is purified by any suitable technique, such as reverse phase preparative LCMS.

III. Pharmaceutical Compositions and Methods of Treatment

Disclosed herein are methods of treating a subject with one or more compounds provided herein. In some embodiments, the subject has cancer. In other embodiments, the subject has an auto-immune disorder, such as rheumatoid arthritis or psoriasis. In still further embodiments, the subject has a viral infection.

This disclosure includes pharmaceutical compositions comprising at least one of the compounds described herein for use in human or veterinary medicine. Embodiments of pharmaceutical compositions include a pharmaceutically acceptable carrier and at least one of the disclosed compounds. Useful pharmaceutically acceptable carriers and excipients are known in the art.

The pharmaceutical compositions comprising one or more compounds disclosed herein may be formulated in a variety of ways depending, for example, on the mode of administration and/or on the subject or disorder to be treated. For example, pharmaceutical compositions may be formulated as pharmaceutically acceptable salts. As another example, parenteral formulations may comprise injectable fluids that are pharmaceutically and physiologically acceptable fluid vehicles such as water, physiological saline, other balanced salt solutions, aqueous dextrose, glycerol or the like. Excipients may include, for example, nonionic solubilizers, such as cremophor, or proteins, such as human serum albumin or plasma preparations. In some examples, the pharmaceutical composition to be administered may also contain non-toxic auxiliary substances, such as wetting or emulsifying agents, preservatives, and pH buffering agents and the like, for example, sodium acetate or sorbitan monolaurate.

Routes of administration include but are not limited to oral and parenteral routes, such as intravenous, intraperitoneal, rectal, topical, ophthalmic, intranasal, and transdermal. The compound may also be delivered intramuscularly or subcutaneously.

The dosage form of the pharmaceutical composition can be determined, at least in part, by the mode of administration chosen. For example, in addition to injectable fluids, topical or oral formulations may be employed. Topical preparations may include eye drops, ointments, sprays and the like. Oral formulations may be liquid (e.g., syrups, solutions or suspensions), or solid (e.g., powders, pills, tablets, or capsules). For solid compositions, non-toxic solid carriers include but are not limited to pharmaceutical grade mannitol, lactose, starch, or magnesium stearate.

In some embodiments, the pharmaceutical composition is formulated in unit dosage form suitable for individual administration of precise dosages. The amount of a therapeutic compound administered will depend on the subject being treated, the type and severity of the disorder being treated, and the manner or route of administration, and is known to those skilled in the art. Within these bounds, the formulation to be administered will contain an amount of the one or more compounds disclosed herein effective to achieve the desired effect in the subject being treated (e.g., treating or inhibiting a cancer, autoimmune disease, or viral infection).

Therapeutically effective doses of a disclosed compound can be determined by one of skill in the art. In some examples, the dose of the compound is about 1 $mg/m^2$ to 15 $g/m^2$, such as about 1-5 $mg/m^2$, about 3-10 $mg/m^2$, about 5-15 $mg/m^2$, about 10-30 $mg/m^2$, about 25-50 $mg/m^2$, about 50-500 $mg/m^2$, about 100 $mg/m^2$ to 2 $g/m^2$, about 2-5 $g/m^2$, about 5-10 $g/m^2$, or about 10-15 $g/m^2$ (e.g., about 1 $mg/m^2$, 3.3 $mg/m^2$, 5 $mg/m^2$, 10 $mg/m^2$, 15 $mg/m^2$, 20 $mg/m^2$, 25 $mg/m^2$, 30 $mg/m^2$, 50 $mg/m^2$, 100 $mg/m^2$, 500 $mg/m^2$, 1 $g/m^2$, 5 $g/m^2$, 10 $g/m^2$, 12 $g/m^2$, or 15 $g/m^2$). In some examples, the dose of the compound is about 0.1 mg/kg to about 10 mg/kg, such as about 0.1-0.5 mg/kg, about 0.3-1 mg/kg, about 0.75-1.5 mg/kg, about 1-2.5 mg/kg, about 2-5 mg/kg, about 4-7.5 mg/kg, or about 7-10 mg/kg (e.g., about 0.1 mg/kg, about 0.3 mg/kg, about 0.5 mg/kg, about 1 mg/kg, about 2.5 mg/kg, about 5 mg/kg, about 7.5 mg/kg, or about 10 mg/kg). In further examples the compound is provided in a dosage form containing about 1 to 50 mg of the compound, in single or divided doses, such as about 1-15 mg, about 2.5-10 mg, about 5-20 mg, about 10-25 mg, about 15-30 mg, about 25-40 mg, or about 30-50 mg (e.g., about 1 mg, 2.5 mg, 5 mg, 7.5 mg, 10 mg, 12.5 mg, 15 mg, 20 mg, 25 mg, 30 mg, 35 mg, 40 mg, 45 mg, or 50 mg) of the compound.

One or more doses of the compound can be administered to a subject. For example, the compound can be administered three times per day, twice per day, daily, every other day, twice per week, weekly, every other week, every three weeks, monthly, or less frequently. In some examples, the compound may be administered in cycles, for example, daily for a set number of days, followed by a rest period, then repeated one or more times.

The specific dose level and frequency of dosage for any particular subject may be varied and will depend upon a variety of factors, including the disorder being treated, the specific compound being administered, the age, body weight, general health, sex and diet of the subject, mode and time of administration, and so on.

In some embodiments, the subject being treated has a solid tumor. Examples of solid tumors include sarcomas (such as fibrosarcoma, myxosarcoma, liposarcoma, chondrosarcoma, osteosarcoma, soft tissue sarcoma, and other sarcomas), synovioma, mesothelioma, Ewing sarcoma, leiomyosarcoma, rhabdomyosarcoma, colon cancer, colorectal cancer, peritoneal cancer, esophageal cancer (such as esophageal squamous cell carcinoma), pancreatic cancer, breast cancer (including basal breast carcinoma, ductal carcinoma and lobular breast carcinoma), endometrial cancer, lung cancer (such as non-small cell lung cancer), ovarian cancer, prostate cancer, liver cancer (including hepatocellular carcinoma), gastric cancer, squamous cell carcinoma (including head and neck squamous cell carcinoma), basal cell carcinoma, adenocarcinoma, sweat gland carcinoma, medullary thyroid carcinoma, papillary thyroid carcinoma, pheochromocytoma, sebaceous gland carcinoma, papillary carcinoma, papillary adenocarcinoma, medullary carcinoma, bronchogenic carcinoma, hepatoma, bile duct carcinoma, choriocarcinoma, Wilms tumor, cervical cancer, fallopian tube cancer, testicular tumor, seminoma, bladder cancer (such as renal cell cancer), melanoma, and CNS tumors (such as a glioma, glioblastoma, astrocytoma, medulloblastoma, craniopharyngioma, ependymoma, pinealoma, hemangioblastoma, acoustic neuroma, oligodendroglioma, meningioma, neuroblastoma and retinoblastoma). Solid tumors also include tumor metastases (for example, metastases to the lung, liver, brain, or bone). In particular examples, the subject has breast cancer, cancer of the head and neck, pancreatic cancer, colorectal cancer (CRC), lung cancer (including squamous cell lung cancer and non-small cell lung cancer), mesothelioma, osteosarcoma, soft tissue sarcoma (STS), glioma, gestational trophoblastic tumor, bladder cancer, choriocarcinoma, hydatidiform mole, or gestational trophoblastic disease.

In other examples, the subject has a hematological malignancy. Examples of hematological malignancies include leukemias, including acute leukemias (such as 11q23-positive acute leukemia, acute lymphocytic leukemia (ALL), T cell ALL, acute myelocytic leukemia, acute myelogenous leukemia (AML), and myeloblastic, promyelocytic, myelomonocytic, monocytic and erythroleukemia), chronic leukemias (such as chronic myelocytic (granulocytic) leukemia, chronic myelogenous leukemia, and chronic lymphocytic leukemia), lymphoblastic leukemia, polycythemia vera, Hodgkin lymphoma, non-Hodgkin lymphoma (such as T cell lymphoma and B cell lymphoma (diffuse large B cell lymphoma, Burkitt lymphoma, follicular lymphoma, mantle cell lymphoma)), multiple myeloma, Waldenstrom macroglobulinemia, heavy chain disease, myelodysplastic syndrome, hairy cell leukemia, and myelodysplasia. In particular examples, the subject has acute lymphoblastic leukemia, mycosis fungoides (a type of T cell lymphoma, also known as Alibert-Bzain syndrome), or Non-Hodgkin lymphoma.

In some embodiments, the subject has an auto-immune disorder. In particular examples, the subject has rheumatoid arthritis or juvenile rheumatoid arthritis (including but not limited to active pauciarticular juvenile rheumatoid arthritis, psoriasis, inflammatory bowel disease (such as Crohn's disease or ulcerative colitis), refractory Takayasu arteritis, dermatomyositis, disseminated sclerosis, Graft Versus Host Disease (GVHD), polymyositis, systemic lupus erythematosus (SLE), uveitis or thyroid eye disease (for example, associated with Grave's disease or Hashimoto's thyroiditis).

In additional embodiments, the subject has a viral infection, which includes, but is not limited to infection with human immunodeficiency virus (HIV), polio virus, hepatitis A virus, hepatitis B virus, hepatitis C virus, enteroviruses, human coxsackie viruses, rhinoviruses, echoviruses, foot-and-mouth disease virus, Norwalk virus, chikungunya virus, equine encephalitis viruses, Simliki Forest virus, Sindbis virus, Ross River virus, rubella viruses, dengue viruses, yellow fever viruses, West Nile virus, St. Louis encephalitis virus, Japanese encephalitis virus, Powassan virus, Zika virus, coronaviruses (e.g., alpha coronaviruses, beta coronaviruses, MERS-CoV, SARS-CoV, or SARS-CoV-2), rabies viruses, Ebola virus, Marburg virus, parainfluenza viruses, mumps virus, measles virus, respiratory syncytial virus, influenza viruses, papilloma viruses, polyoma viruses, adenoviruses, herpes simplex viruses, cytomegalovirus, Epstein-Barr virus; varicella zoster virus, and others.

EXAMPLES

The following examples are provided to illustrate certain features and/or embodiments. These examples should not be construed to limit the disclosure to the particular features or embodiments described.

Example 1

Materials and Methods

Cell Culture Methods: Cells (HBL1, immortalized fibroblasts from a healthy donor, or 293T) were seeded at the numbers indicated in a 12-well plate in 500 ul. Samples were topped with 500 ul of fresh cell culture medium with DMSO, MTX or the MTX-PROTACs at the indicated concentrations and incubated for 16 hours at 37° C. Human embryonic kidney HEK293T cells and immortalized fibroblasts were maintained in DMEM (Gibco) supplemented with 10% fetal bovine serum (Hyclone), 2 mmol/L L-glutamine, Hepes (Gibco), and 100 U/mL penicillin/streptomycin (Invitrogen). The lymphoma cell line HBL1 was maintained in RPMI (Life Technology) supplemented with 5% fetal bovine serum (Hyclone), 2 mmol/L 1-glutamine, Hepes (Gibco), and 100 U/mL penicillin/streptomycin (Invitrogen). Cells were cultured in incubators maintained at 37° C., with 5% $CO_2$ and 85% humidity.

Western blotting: Cells at confluence from 12-well plate treatments were washed with PBS and lysed in 75 μL/well NP40 lysis buffer (Cell Signaling), subjected to agitation and centrifugation. Approximately 100 μg of total protein was used per analysis. Proteins were sized on a NuPAGE 12% Bis-Tris Gel, 1.0 mm×10 wells, proteins transferred to 0.2 μm nitrocellulose membrane for 60 min followed by blocking with 5% t milk in TBS-T for 1 h at ambient temperature with gentle shaking. Blots were first incubated with 1:2000 dilution of anti-human DHFR antibody (Abcam, ab124814, host rabbit) for 16 h at 4° C. with shaking, washed 3× with TBS-T and incubated with 1:2000 dilution of anti-human β-actin primary antibody (Cell Signaling, host mouse) for 1 h at ambient temperature with shaking. Blots were then washed 3× with TBS-T and incubated with 1:5000 HRP secondary antibody (Novex, anti-Rabbit IgG raised in Goat, 1 mg/ml) for 1 h at ambient temperature, then washed with 3×TBS-T and developed with Pierce ECL Dura reagent for 5 min. Immunoreactive bands were imaged on a ChemiDoc Imaging System (Bio-Rad) with 20 s chemiluminescence exposure. The molecular weight marker ladder was imaged with colorimetric auto-exposure, and both images merged.

Cell-Titer-Glo viability assays: Five μL of cells (2500 cells) from the 12-well plate culture were plated into white 1536-well plates (Greiner, Monroe, NC, 789173-F) in 6 replicates. CellTiter-Glo Luminescent Cell Viability Assay (CTG) (Promega, G7572), 2.5 μL/well reagent was added with a BioRAPTR FRD (Beckman Coulter, Sykesville, MD), plates were incubated in the dark at ambient temperature for 10 min, and luminescence measured with a ViewLux 1430 Ultra HTS (Perkin Elmer, Waltham, MA).

Reagents and Methods: All air or moisture sensitive reactions were performed under positive pressure of nitrogen or argon with oven-dried glassware. Anhydrous solvents and bases such as dichloromethane, N,N-dimethylformamide (DMF), acetonitrile, ethanol, DMSO, dioxane DABCO were purchased from Sigma-Aldrich. Preparative purification was performed on a Waters semi-preparative HPLC system using a Phenomenex Luna C18 column (5 micron, 30×75 mm) at a flow rate of 45 mL/min. The mobile phase consisted of acetonitrile and water (each containing 0.1% trifluoroacetic acid). A gradient of 10% to 50% acetonitrile over 8 minutes was used during the purification. Fraction collection was triggered by UV detection (220 nm). Analytical analysis was performed on an Agilent LC/MS (Agilent Technologies, Santa Clara, CA).

Method 1: A 3 minute gradient of 4% to 100% Acetonitrile (containing 0.025% trifluoroacetic acid) in water (containing 0.05% trifluoroacetic acid) was used with a 4.5 minute run time at a flow rate of 1 mL/min. A Phenomenex Gemini Phenyl column (3 micron, 3×100 mm) was used at a temperature of 50° C.

Method 2: A 7 minute gradient of 4% to 100% Acetonitrile (containing 0.025% trifluoroacetic acid) in water (containing 0.05% trifluoroacetic acid) was used with an 8 minute run time at a flow rate of 1 mL/min. A Phenomenex Luna C18 column (3 micron, 3×75 mm) was used at a temperature of 50° C.

Purity determination was performed using an Agilent Diode Array Detector for both Method 1 and Method 2.

Mass determination was performed using an Agilent 6130 mass spectrometer with electrospray ionization in the positive mode. 1H NMR spectra were recorded on Varian 400 MHz spectrometers. Chemical shifts are reported in ppm with undeuterated solvent (DMSO-d6 at 2.49 ppm) as internal standard for DMSO-d6 solutions. All of the analogs tested in the biological assays have purity greater than 95%, based on both analytical methods. High resolution mass spectrometry was recorded on Agilent 6210 Time-of-Flight LC/MS system. Confirmation of molecular formula was accomplished using electrospray ionization in the positive mode with the Agilent Masshunter software (version B.02).

Method 1. Analysis was performed on an Agilent 1290 Infinity series HPLC instrument. UHPLC long gradient equivalent from 4% to 100% acetonitrile (0.05% trifluoroacetic acid) in water over 3 minute run time of 4.5 minutes with a flow rate of 0.8 mL/min. A Phenomenex Luna C18 column (3 m, 3 mm×75 mm) was used at a temperature of 50° C.

Method 2. Analysis was performed on an Agilent 1260 with a 7 minute gradient from 4% to 100% acetonitrile (containing 0.025% trifluoroacetic acid) in water (containing 0.05% trifluoroacetic acid) over 8 minute run time at a flow rate of 1 mL/min. A Phenomenex Luna C18 column (3 μm, 3 mm×75 mm) was used at a temperature of 50° C. Purity determination was performed using an Agilent diode array detector for both method 1 and method 2. Mass determination was performed using an Agilent 6130 mass spectrometer with electrospray ionization in the positive mode. All analogs for assay have purity greater than 95% based on both analytical methods.

General Synthesis Methods

A: Amide Coupling Reaction (S)-5-(tert-butoxy)-4-(4-(((2,4-diaminopteridin-6-yl)methyl)(methyl)amino)benzamido)-5-oxopentanoic acid (I-1) (1 eq) and the corresponding amine (1 eq) were dissolved in DMF (1 ml) followed by the addition of DIEA (8 eq) and HATU (2 eq). The reaction mixture was stirred for 2 hours and purified by reverse phase preparative HPLC.

B: Deprotection of t-butyl Group

The amide compound from step A (0.01-0.04 mmol) was dissolved in DCM (1 mL) followed by addition of TFA (1 mL). The progress of the reaction was monitored by LCMS (approximately 2 hours). The solvent was evaporated under reduced pressure and the crude was dissolved in DMF and purified by reverse phase preparative LCMS.

(S)-5-(tert-butoxy)-4-(4-(((2,4-diaminopteridin-6-yl)methyl)(methyl)amino)benzamido)-5-oxopentanoic acid (I-1)

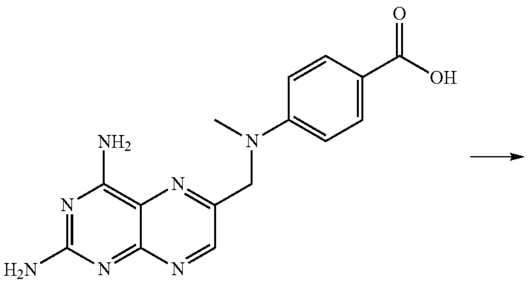

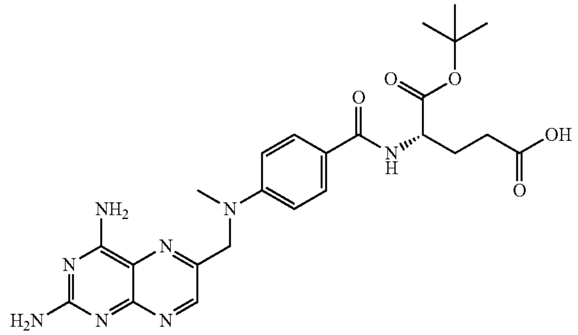

I-1

To a solution of 4-(((2,4-diaminopteridin-6-yl)methyl)(methyl)amino)benzoic acid (100 mg, 0.307 mmol) in DMSO (3 ml) was added TEA (64.3 μl, 0.461 mmol) and PyBOP (192 mg, 0.369 mmol). The mixture was stirred at room temperature for 2 hours followed by addition of (S)-4-amino-5-(tert-butoxy)-5-oxopentanoic acid (75.0 mg, 0.369 mmol) and anhydrous $K_2CO_3$ (21.24 mg, 0.154 mmol). The resultant mixture was stirred at room temperature for additional 8 hours. Solvent was removed under reduced pressure and the crude was purifies by reverse phase HPLC.

(4-(((2,4-diaminopteridin-6-yl)methyl)(methyl)amino)benzoyl)-L-glutamic acid (Methotrexate) (I-2)

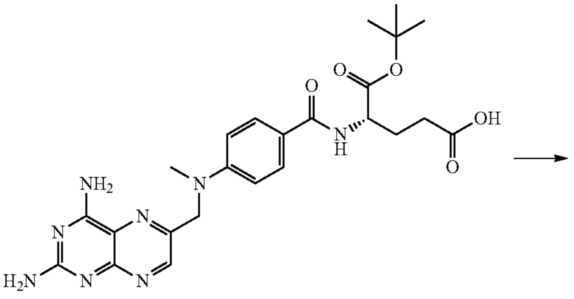

I-1

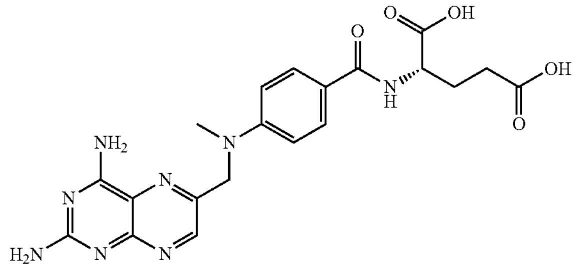

I-2

I-1 (0.01-0.04 mmol) was dissolved in DCM (1 mL) followed by addition of TFA (1 mL). The progress of the reaction was monitored by LCMS (approximately 2 hours). The solvent was evaporated under reduced pressure and the crude was dissolved in DMF and purified by reverse phase preparative LCMS to give I-2.

$^1$H NMR (400 MHz, DMSO-d6) δ 12.99 (s, 1H), 12.20 (s, 2H), 9.08 (s, 1H), 8.88 (s, 1H), 8.69 (s, 1H), 8.38-8.32 (m, 2H), 8.20 (d, J=7.8 Hz, 1H), 7.73 (d, J=8.7 Hz, 2H), 7.43 (s, 1H), 6.81 (d, J=8.9 Hz, 2H), 4.85 (s, 2H), 4.33 (ddd, J=9.9, 7.6, 4.8 Hz, 1H), 3.23 (s, 3H), 2.30 (t, J=7.4 Hz, 2H), 2.05 (ddd, J=16.1, 7.8, 4.0 Hz, 1H), 1.89 (ddt, J=14.0, 10.1, 7.2 Hz, 1H). MS (ESI); m/z $[M+H]^+$: Calcd. for $C_{20}H_{22}NO_5$, 455.17. found 455.1.

N2-(4-(((2,4-diaminopteridin-6-yl)methyl)(methyl)amino)benzoyl)-N5-(3-((2-(2,6-dioxopiperidin-3-yl)-1,3-dioxoisoindolin-4-yl)amino)propyl)-L-glutamine (I-3)

I-1 +

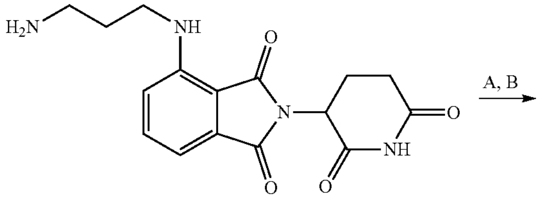

A-1

-continued

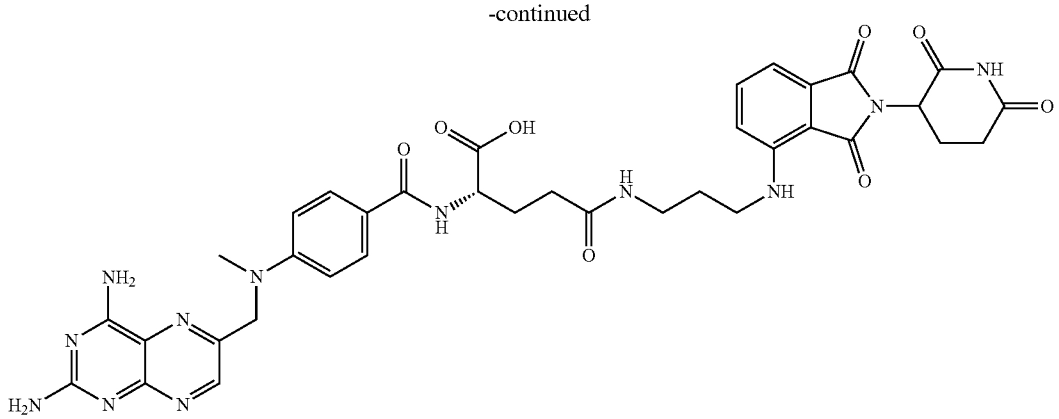

I-3

Made using 4-((3-aminopropyl)amino)-2-(2,6-dioxopiperidin-3-yl)isoindoline-1,3-dione (A-1) that was synthesized according to the method of Li, Y. et al., *J Med Chem* 2019, 62 (2), 448-466. Zhou, B. et al., *J Med Chem* 2018, 61 (2), 462-481.

MS (ESI); m/z [M+H]+: Calcd. for $C_{36}H_{38}N_{12}O_8$, 767.29. found 767.3.

N2-(4-(((2,4-diaminopteridin-6-yl)methyl)(methyl)amino)benzoyl)-N5-(8-((2-(2,6-dioxopiperidin-3-yl)-1,3-dioxoisoindolin-4-yl)amino)octyl)-L-glutamine (I-4)

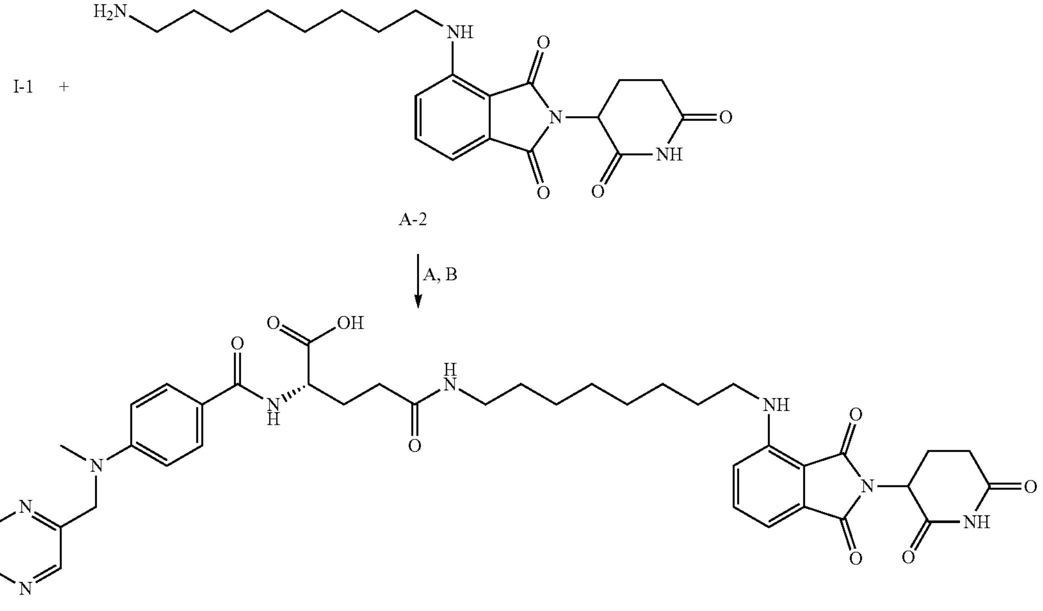

I-4

Made using 4-((8-aminooctyl)amino)-2-(2,6-dioxopiperidin-3-yl)isoindoline-1,3-dione (A-2) that was synthesized according to the method of Remillard, D et al. *Angew Chem Int Ed Engl* 2017, 56 (21), 5738-5743.

$^1$H NMR (400 MHz, DMSO-$d_6$) δ 12.98 (s, 1H), 12.44 (s, 1H), 11.07 (s, 1H), 9.21 (s, 1H), 9.00 (s, 1H), 8.69 (s, 1H), 8.28 (d, J=7.4 Hz, 1H), 7.78 (t, J=5.6 Hz, 1H), 7.72 (d, J=8.7 Hz, 2H), 7.55 (dd, J=8.6, 7.1 Hz, 1H), 7.06 (d, J=8.6 Hz, 1H), 7.00 (d, J=7.0 Hz, 1H), 6.80 (d, J=8.6 Hz, 2H), 6.49 (t, J=6.0 Hz, 1H), 5.03 (dd, J=12.8, 5.4 Hz, 1H), 4.85 (s, 2H), 4.27 (ddd, J=9.4, 7.4, 4.8 Hz, 1H), 3.26 (t, J=6.7 Hz, 2H), 3.22 (s, 3H), 2.98 (q, J=6.5 Hz, 2H), 2.86 (ddd, J=17.4, 14.0, 5.4 Hz, 1H), 2.62-2.50 (m, 2H), 2.16 (t, J=7.5 Hz, 2H), 2.06-1.98 (m, 2H), 1.96-1.83 (m, 1H), 1.57-1.50 (m, 2H), 1.37-1.20 (m, 12H). MS (ESI); m/z [M+H]$^+$: Calcd. for $C_{41}H_{48}N_{12}O_8$, 837.37. found 837.4.

(19S)-19-(4-(((2,4-diaminopteridin-6-yl)methyl)(methyl)amino)benzamido)-1-((2-(2,6-dioxopiperidin-3-yl)-1,3-dioxoisoindolin-4-yl)oxy)-2,16-dioxo-6,9,12-trioxa-3,15-diazaicosan-20-oic acid (I-5)

I-1 +

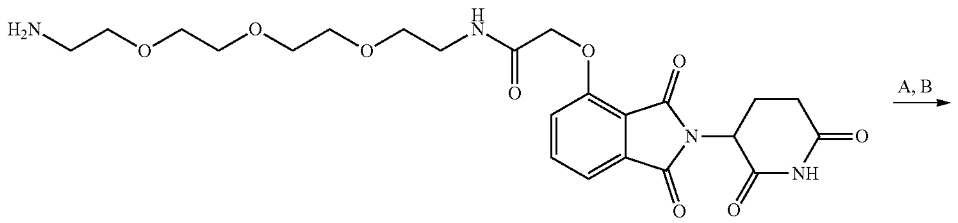

A-3

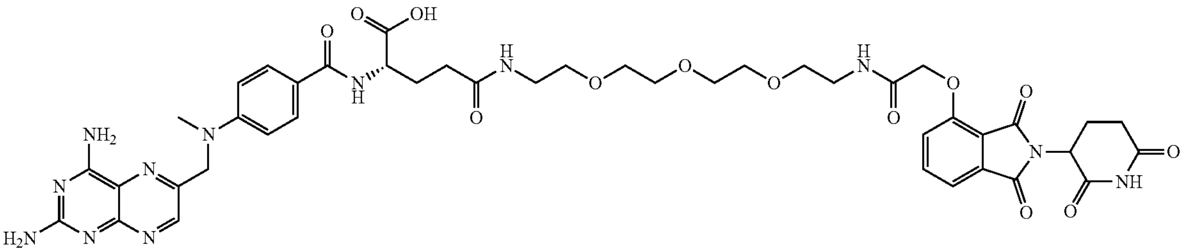

I-5

Made using N-(2-(2-(2-(2-aminoethoxy)ethoxy)ethoxy)ethyl)-2-((2-(2,6-dioxopiperidin-3-yl)-1,3-dioxoisoindolin-4-yl)oxy)acetamide (A-3) was purchased from MedChemExpress LLC.

$^1$H NMR (400 MHz, DMSO-$d_6$) δ 12.99 (s, 1H), 12.45 (s, 1H), 11.09 (s, 1H), 9.24 (s, 1H), 9.04 (s, 1H), 8.70 (s, 1H), 8.57 (s, 1H), 8.28 (d, J=7.4 Hz, 1H), 7.98 (t, J=5.7 Hz, 1H), 7.88 (t, J=5.6 Hz, 1H), 7.79 (t, J=7.9 Hz, 1H), 7.72 (d, J=8.7 Hz, 2H), 7.48 (d, J=7.3 Hz, 1H), 7.38 (d, J=8.5 Hz, 1H), 6.81 (d, J=8.8 Hz, 2H), 5.09 (dd, J=12.9, 5.4 Hz, 1H), 4.85 (s, 2H), 4.77 (s, 2H), 4.29-4.24 (m, 1H), 3.50-3.40 (m, 9H), 3.36-3.27 (m, 4H), 3.23 (s, 3H), 3.15 (q, J=6.0 Hz, 2H), 2.96-2.81 (m, 1H), 2.60-2.52 (m, 1H), 2.18 (t, J=7.6 Hz, 2H), 2.06-1.99 (m, 2H), 1.94-1.85 (m, 1H). MS (ESI); m/z [M+H]+: Calcd. for $C_{43}H_{50}N_{12}O_{13}$, 943.36. found 943.3.

(17S)-17-(4-(((2,4-diaminopteridin-6-yl)methyl)(methyl)amino)benzamido)-3-((4R)-4-hydroxy-2-((4-(4-methylthiazol-5-yl)benzyl)carbamoyl)pyrrolidine-1-carbonyl)-2,2-dimethyl-5,14-dioxo-7,10-dioxa-4,13-diazaoctadecan-18-oic acid (I-6)

I-1 +

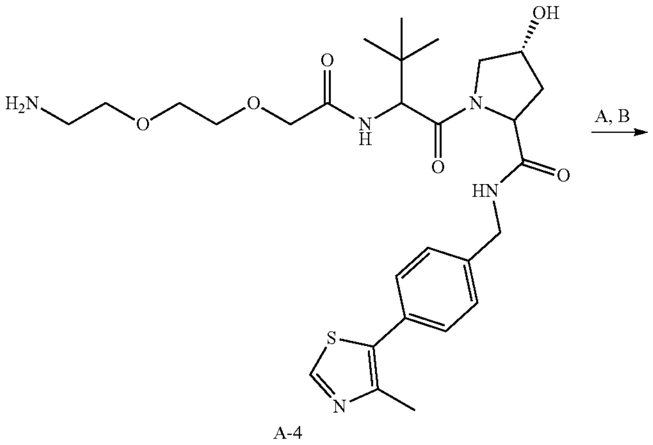

A-4

-continued

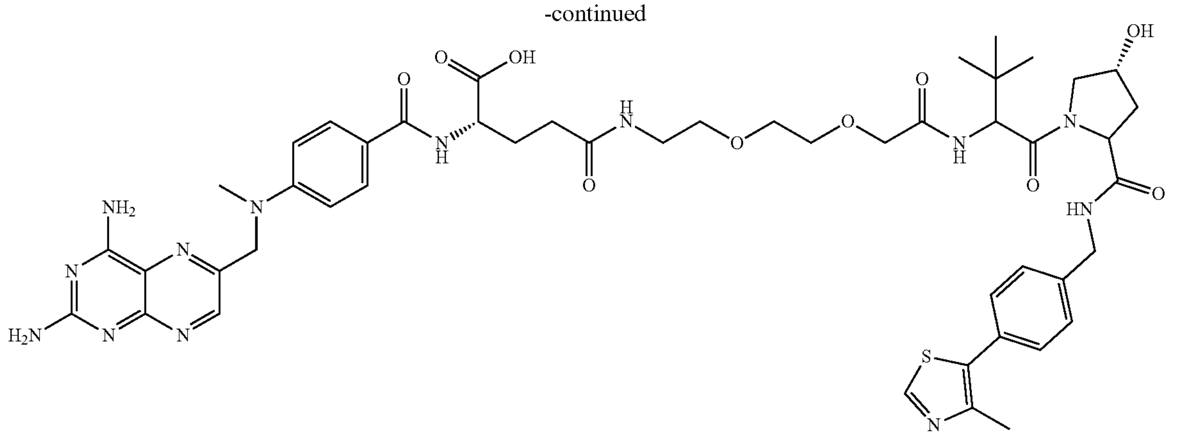

I-6

$^1$H NMR (400 MHz, DMSO-$d_6$) δ 12.98 (s, 1H), 12.44 (s, 1H), 9.25 (s, 1H), 9.05 (s, 1H), 8.95 (s, 1H), 8.69 (s, 1H), 8.62 (s, 1H), 8.56 (t, J=6.1 Hz, 1H), 8.29 (d, J=7.4 Hz, 1H), 7.89 (t, J=5.7 Hz, 1H), 7.72 (d, J=8.6 Hz, 2H), 7.41 (d, J=9.6 Hz, 1H), 7.37 (s, 4H), 6.80 (d, J=8.7 Hz, 2H), 5.13 (s, 1H), 4.85 (s, 2H), 4.55 (d, J=9.6 Hz, 1H), 4.46-4.22 (m, 5H), 3.94 (s, 2H), 3.66-3.47 (m, 7H), 3.39 (t, J=5.9 Hz, 2H), 3.23-3.11 (m, 1H), 2.52 (s, 1H), 2.42 (s, 3H), 2.18 (t, J=7.6 Hz, 2H), 2.09-1.96 (m, 2H), 1.88 (m, 2H), 0.91 (s, 9H). MS (ESI); m/z [M+H]+: Calcd. for $C_{48}H_{61}N_{13}O_{10}S$, 1012.44. found 1012.3, A-4 was purchased from MedChemExpress LLC.

(23S)-23-(4-(((2,4-diaminopteridin-6-yl)methyl)(methyl)amino)benzamido)-3-((4R)-4-hydroxy-2-((4-(4-methylthiazol-5-yl)benzyl)carbamoyl)pyrrolidine-1-carbonyl)-2,2-dimethyl-5,20-dioxo-7,10,13,16-tetraoxa-4,19-diazatetracosan-24-oic acid (I-7)

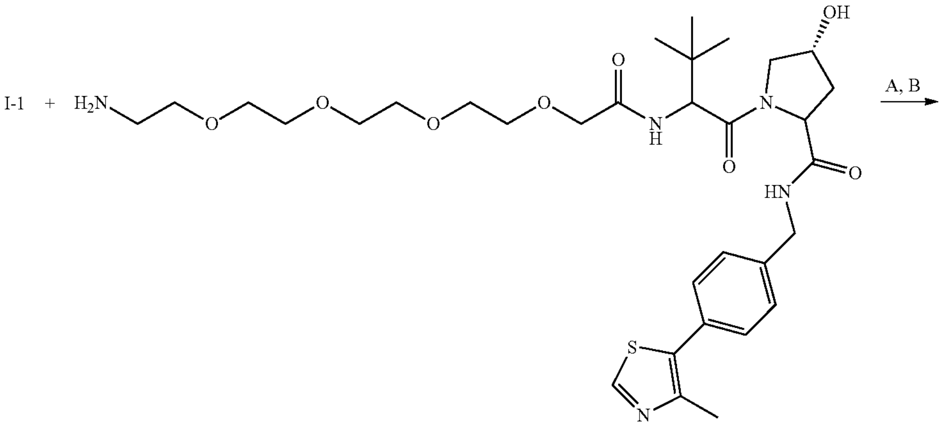

A-5

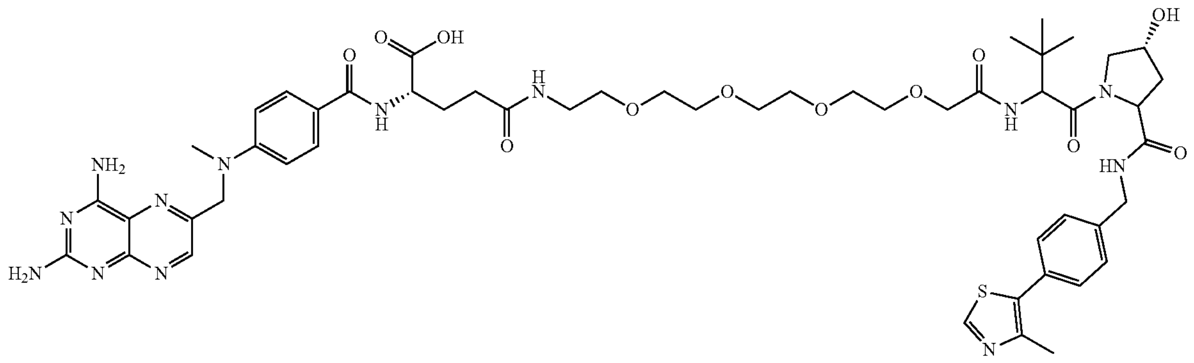

I-7

$^{1}$H NMR (400 MHz, DMSO-$d_6$) δ 12.97 (s, 1H), 12.45 (s, 1H), 9.26 (s, 1H), 9.06 (s, 1H), 8.96 (s, 1H), 8.70 (s, 1H), 8.57 (t, J=6.0 Hz, 1H), 8.28 (d, J=7.4 Hz, 1H), 7.88 (t, J=5.7 Hz, 1H), 7.72 (d, J=8.6 Hz, 2H), 7.49 (s, 1H), 7.44-7.33 (m, 1H), 7.38 (m, 4H), 6.81 (d, J=8.7 Hz, 2H), 4.86 (s, 2H), 4.55 (d, J=9.5 Hz, 1H), 4.44-4.39 (m, 2H), 4.33 (s, 1H), 4.31-4.18 (m, 2H), 3.95 (s, 2H), 3.65 (dd, J=10.7, 3.9 Hz, 1H), 3.62-3.50 (m, 4H), 3.54-3.45 (m, 3H), 3.34 (t, J=5.9 Hz, 2H), 3.23 (s, 2H), 3.15 (q, J=5.9 Hz, 2H), 2.42 (s, 3H), 2.18 (t, J=7.6 Hz, 2H), 2.07-1.85 (m, 4H), 0.91 (s, 9H). MS (ESI); m/z [M+H]+: Calcd. for $C_{52}H_{69}N_{13}O_{12}S$, 1100.49. found 1100.4 A-5 was purchased from MedChemExpress LLC.

N2-(4-(((2,4-diaminopteridin-6-yl)methyl)(methyl)amino)benzoyl)-N5-(8-((2-(2,6-dioxopiperidin-3-yl)-1-oxoisoindolin-4-yl)amino)octyl)-L-glutamine (I-8)

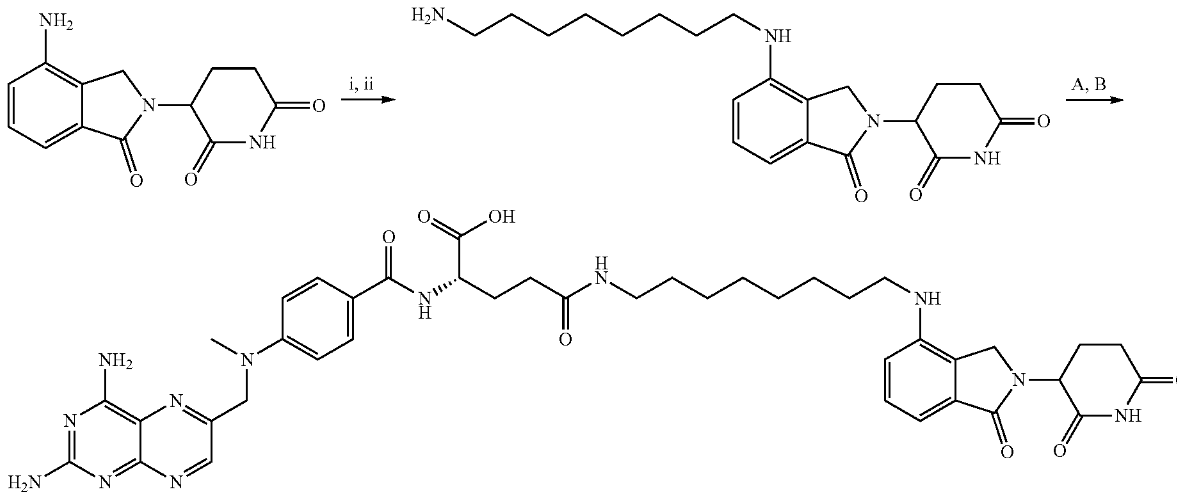

I-8

Step I & ii: The intermediate will be synthesized using the procedure reported in “Chemoselective Synthesis of Lenalidomide-Based PROTAC Library Using Alkylation Reaction paper” published in Organic Letters, 2019, 21, 3838-41

N2-(4-(((2,4-diaminopteridin-6-yl)methyl)(methyl)amino)benzoyl)-N5-(2-(2-(2-((2-(2,6-dioxopiperidin-3-yl)-1,3-dioxoisoindolin-4-yl)amino)ethoxy)ethoxy)ethyl)-L-glutamine (I-9)

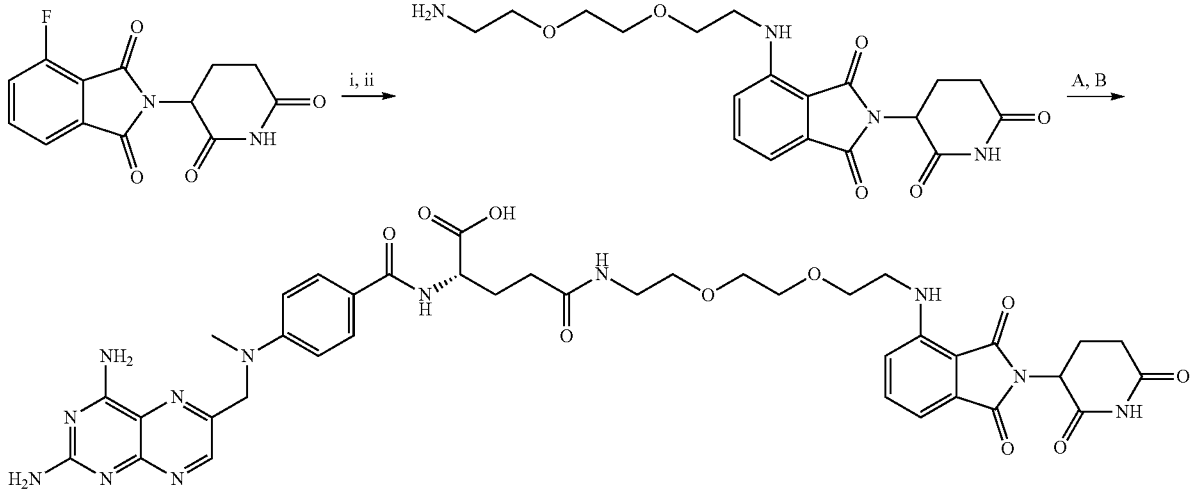

I-9

Amine intermediate will be purchased from Matrix Scientific.

N2-(4-(((2,4-diaminopteridin-6-yl)methyl)(methyl)amino)benzoyl)-N5-(2-(2-(2-((2-(2,6-dioxopiperidin-3-yl)-1-oxoisoindolin-4-yl)amino)ethoxy)ethoxy)ethyl)-L-glutamine (I-10)

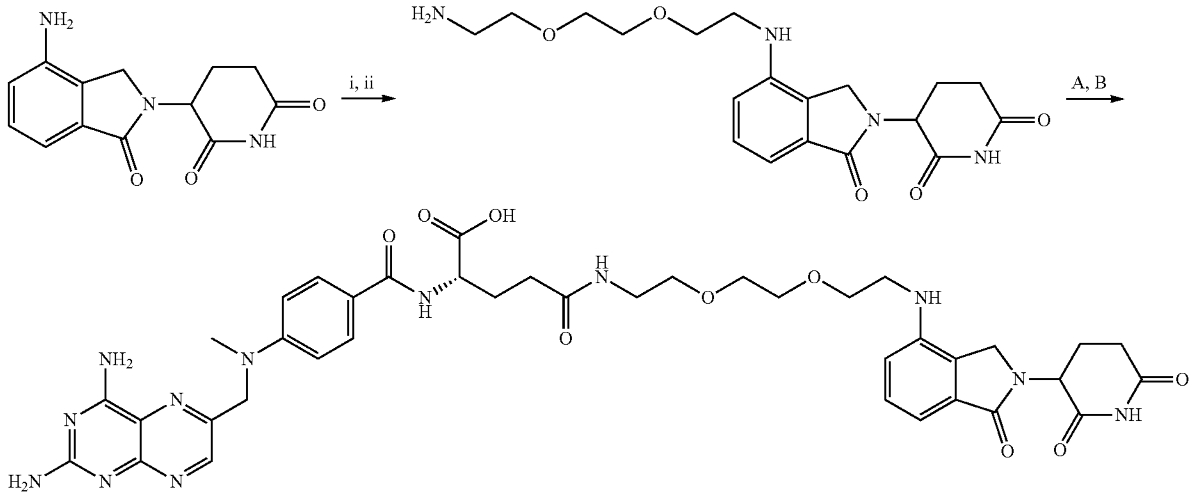

I-10

The intermediate will be synthesized using the procedure reported in "Chemoselective Synthesis of Lenalidomide-Based PROTAC Library Using Alkylation Reaction paper" published in Organic Letters, 2019, 21, 3838-41, using ter-t-butyl 2-[2-(2-bromoethoxy)ethoxy]ethylcarbamate starting material followed by the acid hydrolysis.

N2-(4-(((2,4-diaminopteridin-6-yl)methyl)(methyl)amino)benzoyl)-N5-(9-(2-(2,6-dioxopiperidin-3-yl)-1,3-dioxoisoindolin-4-yl)nonyl)-L-glutamine (I-11)

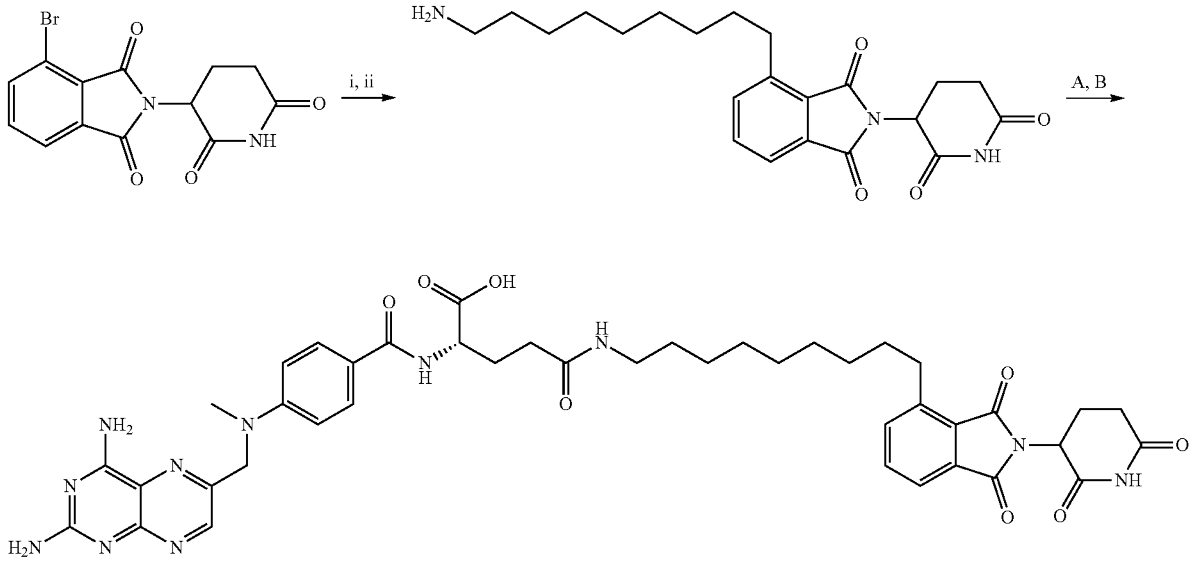

I-11

The intermediate will be synthesized using the procedure reported in US 2019/0192668 A1, incorporated herein by reference.

N2-(4-(((2,4-diaminopteridin-6-yl)methyl)(methyl)amino)benzoyl)-N5-(9-(2-(2,6-dioxopiperidin-3-yl)-1,3-dioxoisoindolin-4-yl)non-8-yn-1-yl)-L-glutamine (I-12)

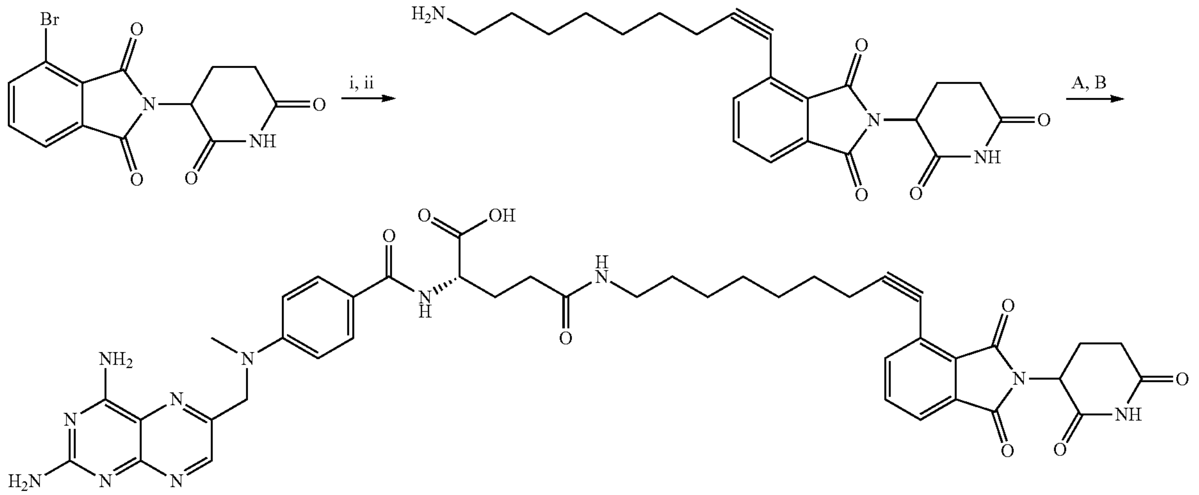

I-12

3-(4-bromo-1-oxoisoindolin-2-yl)piperidine-2,6-dione (1 eq) and tert-butyl non-8-yn-1-ylcarbamate (1.3 eq) in DMSO (3 ml) followed by addition of 2,2,6,6-tetramethylpiperidine (208 μl, 1.238 mmol). reaction will be vacuumed and purge Nitrogen. Chloro(crotyl)(tri-tert-butylphosphine)palladium(II) (0.05 eq) will be added followed by stirring at room temperature for 24 h. Crude will be dissolved in ethyl acetate and wash brine. Solvent will be evaporated followed by column chromatography will yield intermediate which will be taken in DCM and add 4N HCl in dioxane. Reaction mixture will be stirred under N2 at RT and monitored by LCMS.

N2-(4-(((2,4-diaminopteridin-6-yl)methyl)(methyl)amino)benzoyl)-N5-(9-(2-(2,6-dioxopiperidin-3-yl)-1-oxoisoindolin-4-yl)nonyl)-L-glutamine (I-13)

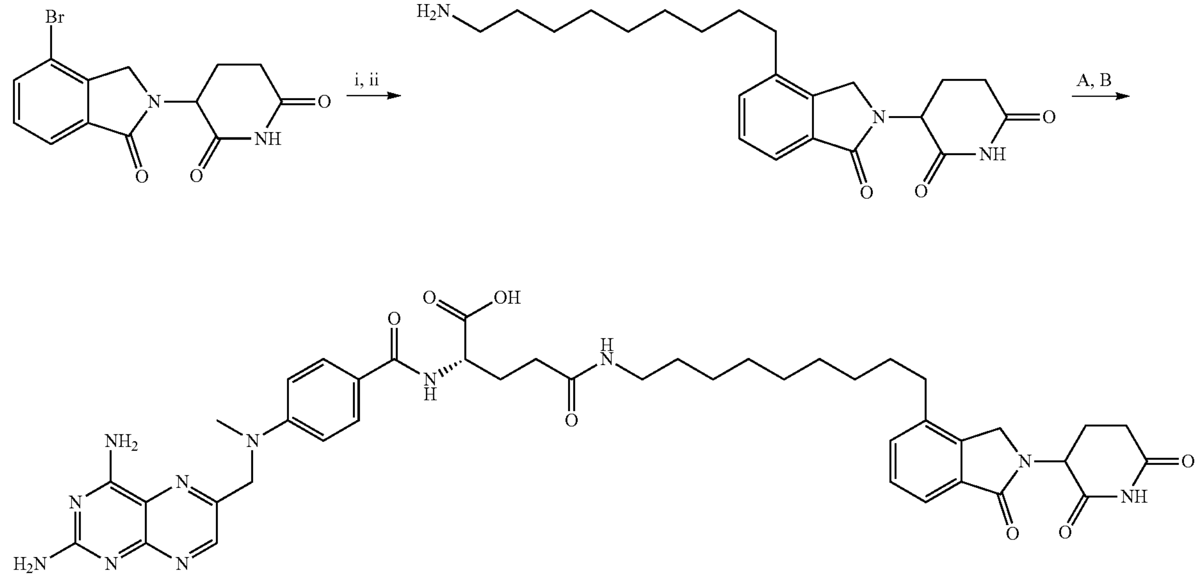

I-13

Intermediate prepared in previous will be subjected to 5% $H_2$/Pd in ethanol under hydrogenation conditions. Crude will be purified by column chromatography.

N2-(4-(((2,4-diaminopteridin-6-yl)methyl)(methyl)amino)benzoyl)-N5-(11-(2-((2-(2,6-dioxopiperidin-3-yl)-1,3-dioxoisoindolin-4-yl)oxy)acetamido)undecyl)-L-glutamine (I-14)

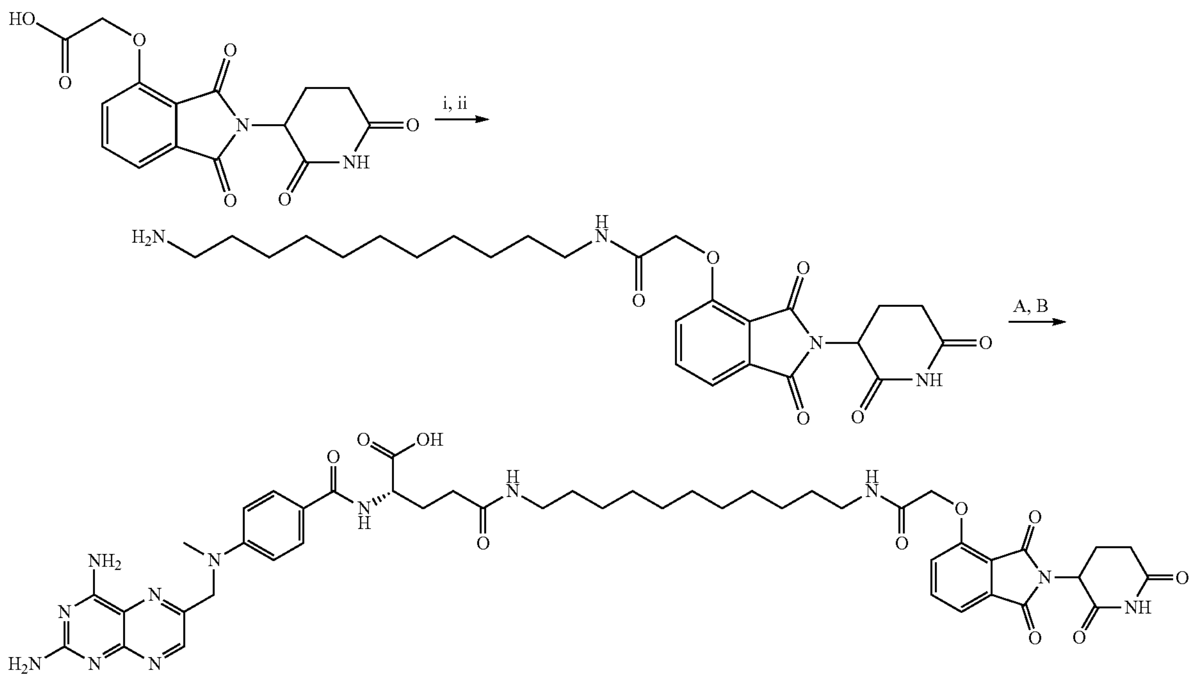

I-14

Commercially available starting material (1.0 eq) will be dissolved in DMF followed by addition of tert-butyl (1-aminoundecyl)carbamate (1.2 eq, HATU (2.0 eq), and DIEA (3.0 eq). The reaction will be monitored by LCMS. Upon completion, solvent will be removed, and crude will be purified by column chromatography. The intermediate will be dissolved in DCM followed by addition of excess of TFA. The crude will be purified by reverse phase HPLC to yield product.

(19S)-19-(4-(((2,4-diaminopteridin-6-yl)methyl)(methyl)amino)benzamido)-1-((2-(2,6-dioxopiperidin-3-yl)-1-oxoisoindolin-4-yl)oxy)-2,16-dioxo-6,9,12-trioxa-3,15-diazaicosan-20-oic acid (I-15)

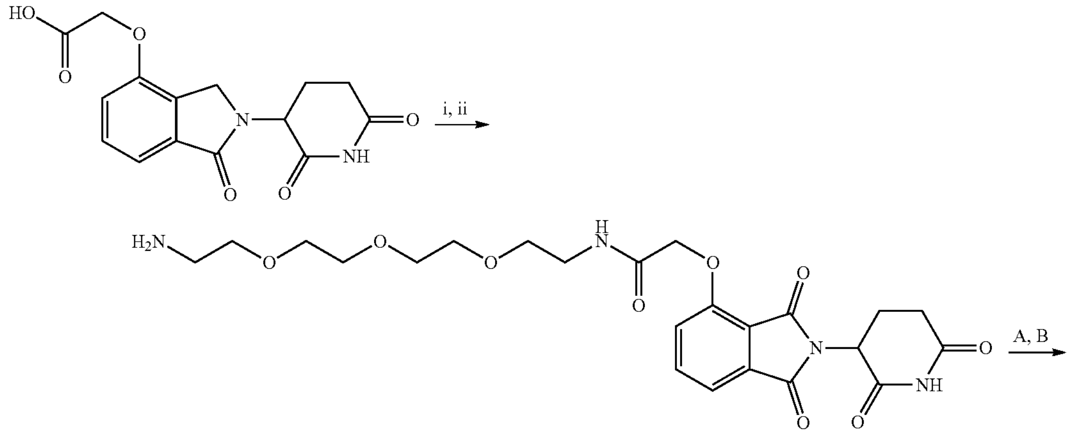

-continued

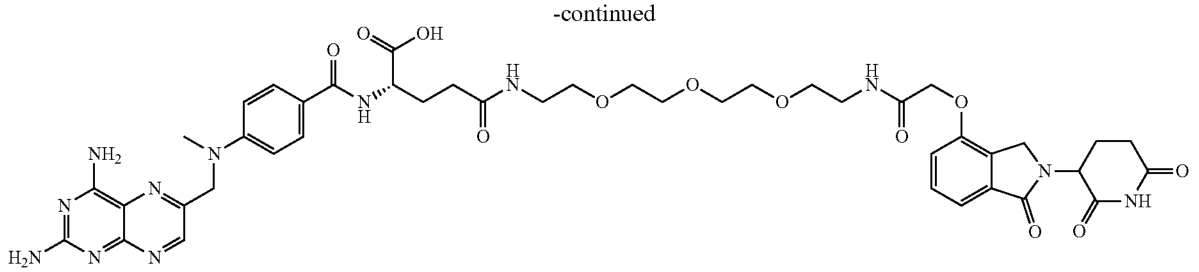

I-15

Commercially available starting material (1.0 eq) will be dissolved in DMF followed by addition of 5,8,11-Trioxa-2-azatridecanoic acid, 13-amino-, 1,1-dimethylethyl ester (12 eq), HATU (2.0 eq), and DIEA (3.0 eq). The reaction will be monitored by LCMS. Upon completion, solvent will be removed, and crude will be purified by column chromatography. The intermediate will be dissolved in DCM followed by addition of excess of TFA. The crude will be purified by reverse phase HPLC to yield product.

N2-(4-(((2,4-diaminopteridin-6-yl)methyl)(methyl)amino)benzoyl)-N5-(14-((2-(2,6-dioxopiperidin-3-yl)-1,3-dioxoisoindolin-4-yl)amino)tetradecyl)-L-glutamine (I-16)

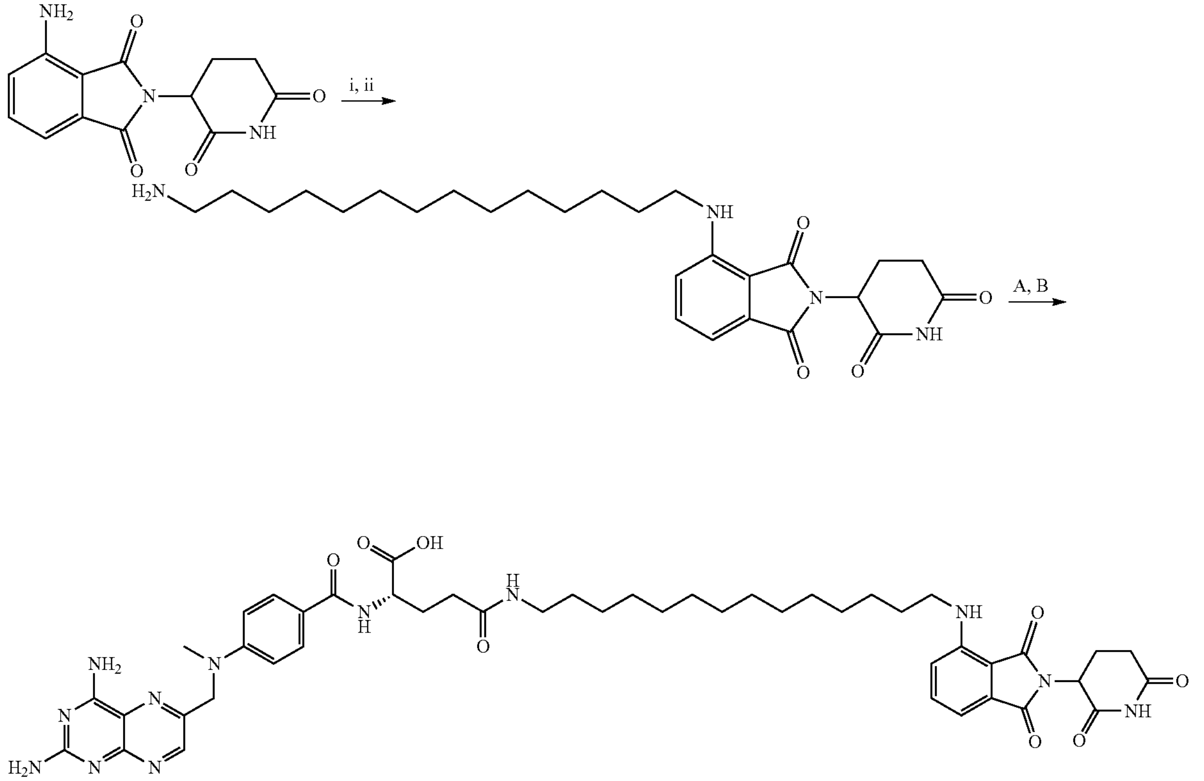

I-16

To a solution of 4-amino-2-(2,6-dioxopiperidin-3-yl)isoindoline-1,3-dione (1 eq) in methanol will be added 1 equivalent of tert-butyl (14-oxotetradecyl)carbamate (Chem. Eur. J. 2010, 16, 3594-3597) followed by addition of $NaBH_3CN$ (1.5 eq) and 1 drop acetic acid. Reaction will be stirred at 50 C overnight. The reaction will be monitored by LCMS and will be purified by column chromatography. The intermediate will be dissolved in DCM followed by addition of excess of TFA. The crude will be purified by reverse phase HPLC to yield product N2-(4-(((2,4-diaminopteridin-6-yl)methyl)(methyl)amino)benzoyl)-N5-(14-((2-(2,6-dioxopiperidin-3-yl)-1-oxoisoindolin-4-yl)amino)tetradecyl)-L-glutamine (I-17)

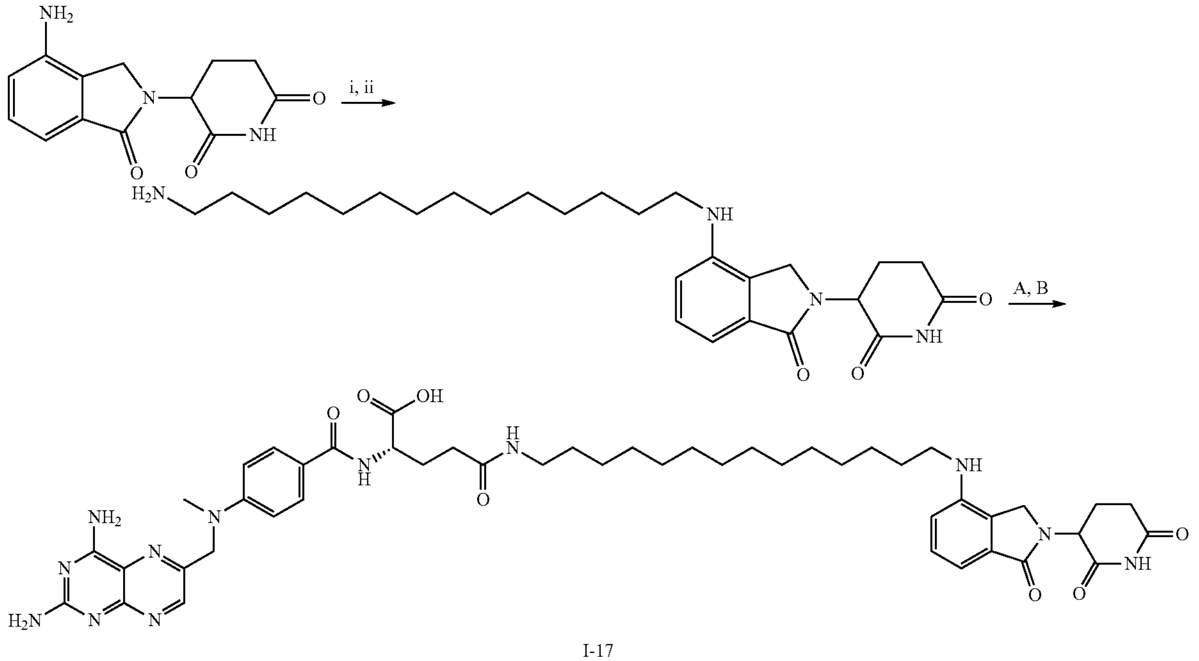

I-17

The intermediate will be synthesized by using 3-(4-amino-1-oxoisoindolin-2-yl)piperidine-2,6-dione starting material and the method reported for the synthesis of I-16.

(19S)-19-(4-(((2,4-diaminopteridin-6-yl)methyl)(methyl)amino)benzamido)-1-((2-(2,6-dioxopiperidin-3-yl)-1-oxoisoindolin-4-yl)amino)-16-oxo-3,6,9,12-tetraoxa-15-azaicosan-20-oic acid (I-18)

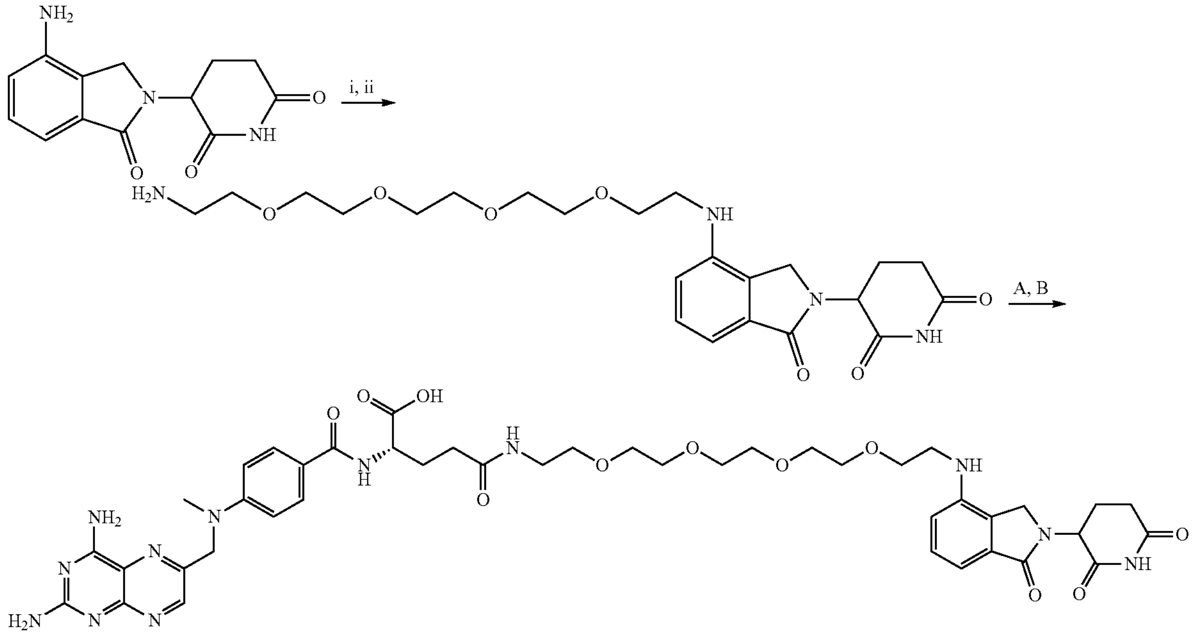

I-18

The intermediate will be synthesized by stirring 3-(4-amino-1-oxoisoindolin-2-yl)piperidine-2,6-dione (1 eq) in NMP followed by addition of DIEA (3.0 eq) and N-Boc-peg4-bromide (1.2 eq). The mixture will be stirred at 110° C. overnight. The crude will be purifies by reverse phase HPLC. The intermediate will be dissolved in DCM followed by addition of excess of TFA. The crude will be purified by reverse phase HPLC to yield product.

N2-(4-(((2,4-diaminopteridin-6-yl)methyl)(methyl)amino)benzoyl)-N5-(8-((2-(2,6-dioxopiperidin-3-yl)-1,3-dioxoisoindolin-5-yl)amino)octyl)-L-glutamine (I-19)

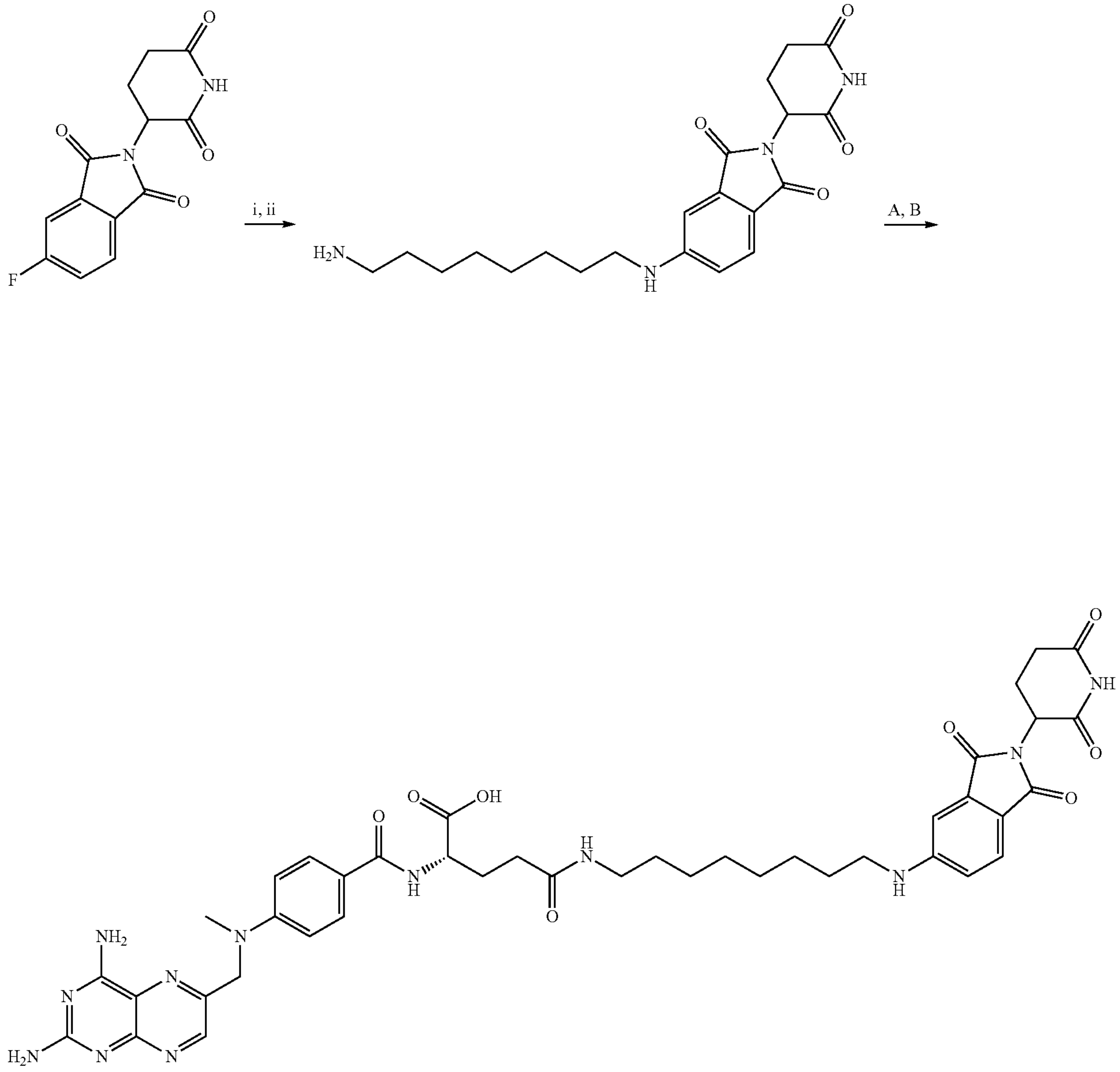

I-19

The intermediate will be synthesized based on the procedure reported Degradation of the BAF Complex Factor BRD9 by Heterobifunctional Ligands Angew Chem, 2017, 56, 5738-5743 using 2-((2,6-dioxopiperidin-3-yl)-5-fluoroisoindoline-1,3-dione and tert-butyl (8-aminooctyl)carbamate followed by acid hydrolysis.

(19S)-19-(4-(((2,4-diaminopteridin-6-yl)methyl)(methyl)amino)benzamido)-1-((2-(2,6-dioxopiperidin-3-yl)-1,3-dioxoisoindolin-5-yl)oxy)-2,16-dioxo-6,9,12-trioxa-3,15-diazaicosan-20-oic acid (I-20)

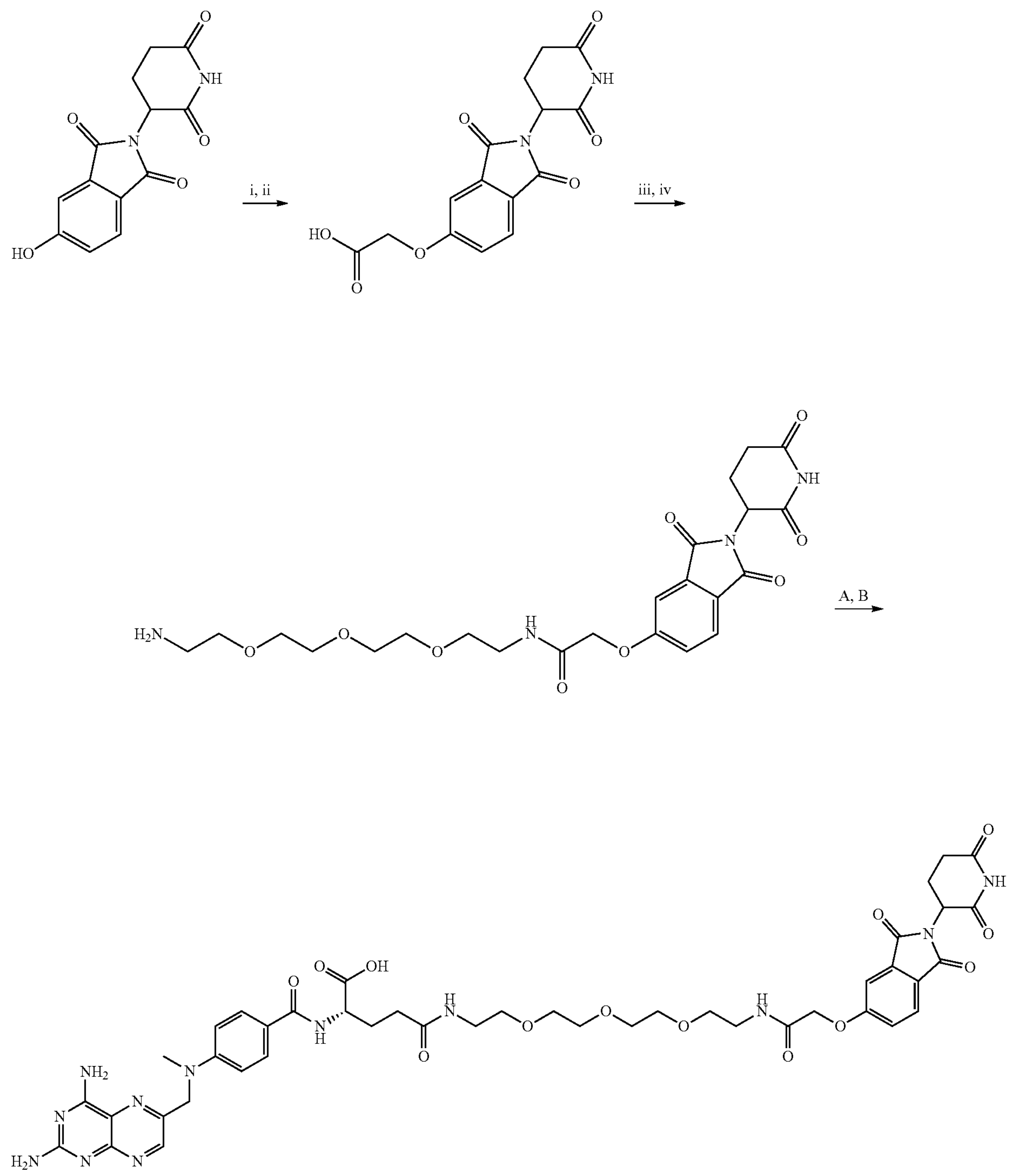

I-20

Commercially available 2-(2,6-dioxopiperidin-3-yl)-5-hydroxyisoindoline-1,3-dione will be treated with $K_2CO_3$ and tert-butyl 2-bromoacetate in DMF. The corresponding tert-butyl 2-((2-(2,6-dioxopiperidin-3-yl)-1,3-dioxoisoindolin-4-yl)oxy)acetate will be treated 4N HCl in dioxane to yield 2-((2-(2,6-dioxopiperidin-3-yl)-1,3-dioxoisoindolin-5-yl)oxy)acetic acid. The acid will be coupled with commercially available tert-butyl (2-(2-(2-(2-aminoethoxy)ethoxy)ethoxy)ethyl)carbamate followed by removal of t-butyl group under acidic condition.

Example 2

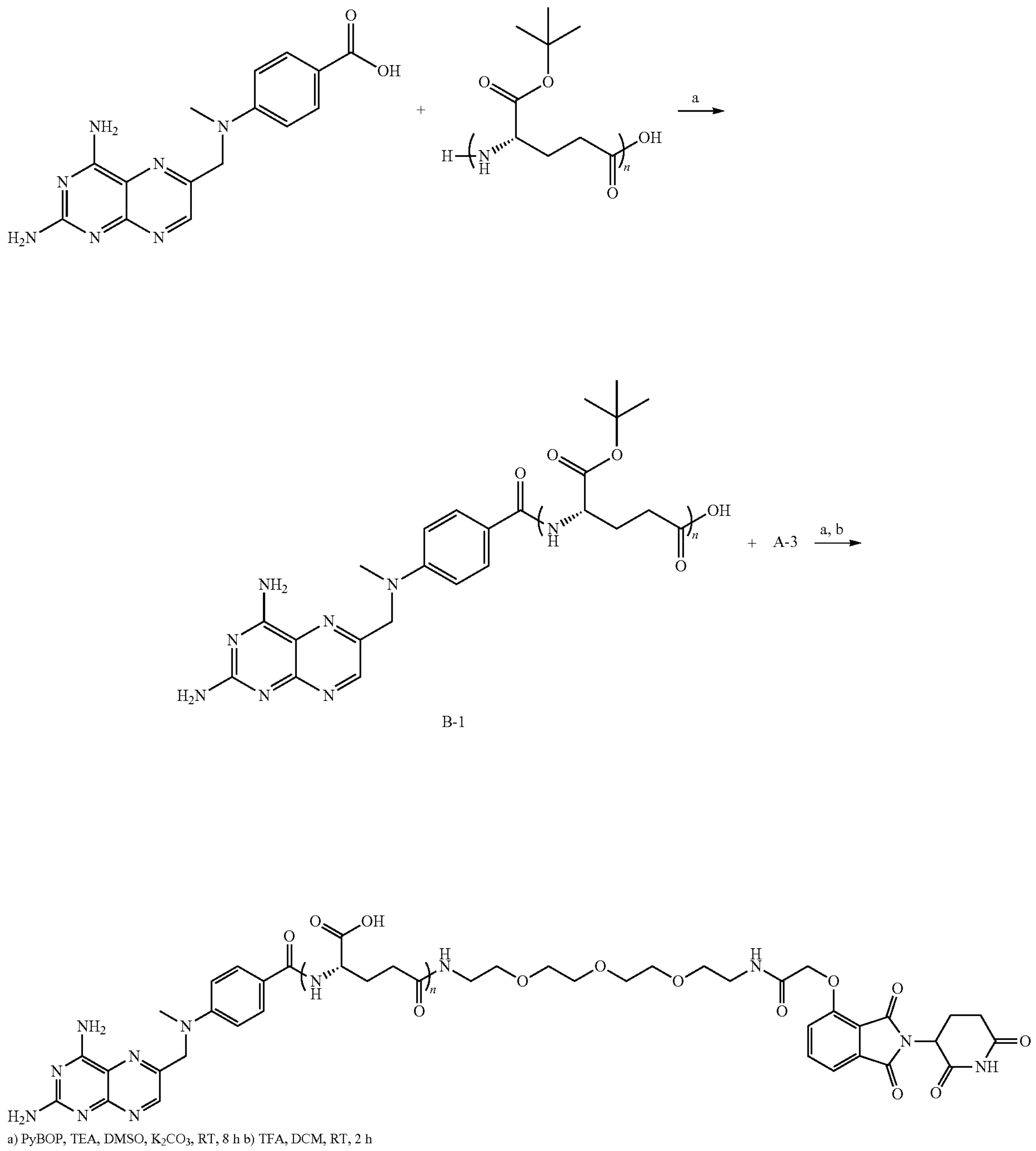

a) PyBOP, TEA, DMSO, $K_2CO_3$, RT, 8 h b) TFA, DCM, RT, 2 h

Step 1: To a solution of 4-(((2,4-diaminopteridin-6-yl)methyl)(methyl)amino) benzoic acid (100 mg, 0.307 mmol) in DMSO (3 ml) was added TEA (64.3 μl, 0.461 mmol) and PyBOP (192 mg, 0.369 mmol). The mixture was stirred at room temperature for 2 hours followed by addition of mono, di or tri t-Bu-Glutamic acid (0.369 mmol) and anhydrous K2CO3 (21.24 mg, 0.154 mmol). The resultant mixture was stirred at room temperature for additional 8 hours. Solvent was removed under reduced pressure and the crude was purifies by reverse phase HPLC to get pure B-1.

Step 2: The pure product B-1 from step 1 was coupled with A-3 following same procedure used in step 1 to obtain coupled product containing the t-butyl protecting groups which was purified by reverse phase HPLC.

Step 3: The above product from step 2 was dissolved in DCM (1 mL) followed by addition of TFA (1 mL). The progress of the reaction was monitored by LCMS (approximately 2 hours). The solvent was evaporated under reduced pressure and the crude was dissolved in DMF and purified by reverse phase preparative LCMS to give pure products.

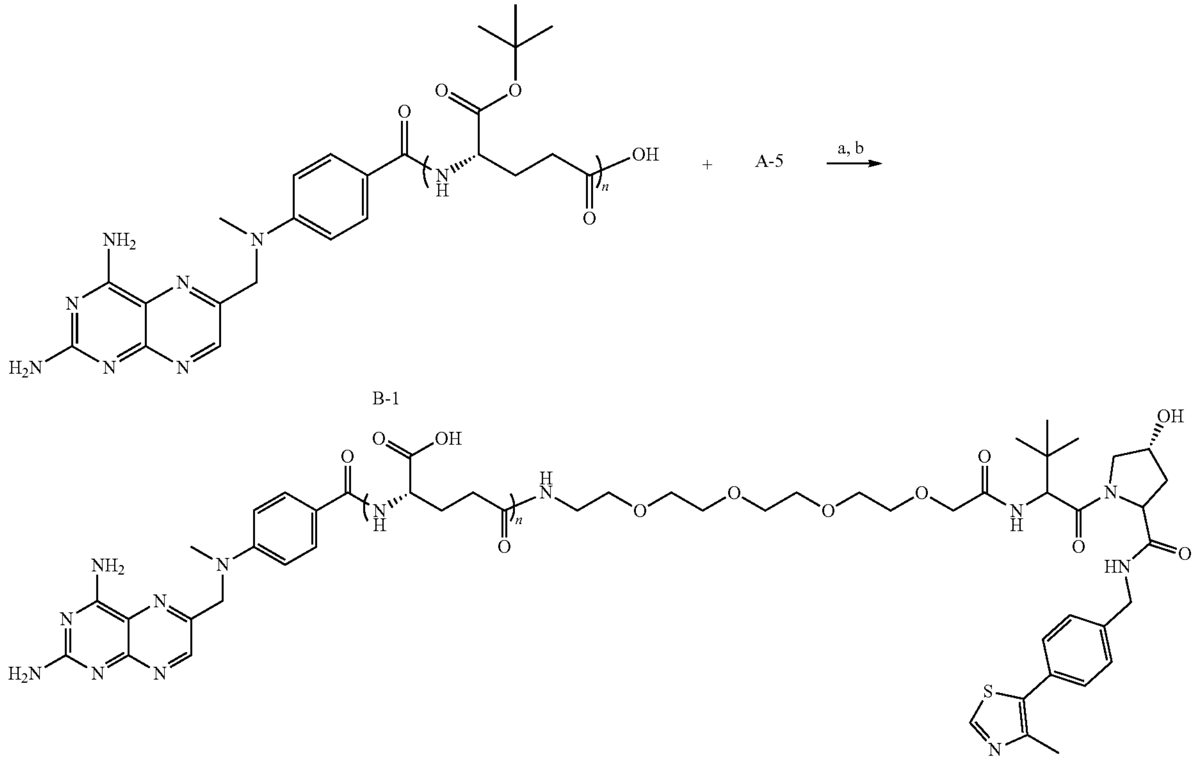

B-1 a) PyBOP, TEA, DMSO, $K_2CO_3$, RT, 8 h b) TFA, DCM, RT, 2 h

Step 1: To a solution of B-1 (0.307 mmol) in DMSO (3 ml) was added TEA (64.3 μl, 0.461 mmol) and PyBOP (192 mg, 0.369 mmol). The mixture was stirred at room temperature for 2 hours followed by addition of A-5 (0.369 mmol) and anhydrous K2CO3 (21.24 mg, 0.154 mmol). The resultant mixture was stirred at room temperature for additional 8 hours. Solvent was removed under reduced pressure and the crude was purifies by reverse phase HPLC.

Step 2: The above product from step 1 was dissolved in DCM (1 mL) followed by addition of TFA (1 mL). The progress of the reaction was monitored by LCMS (approximately 2 hours). The solvent was evaporated under reduced pressure and the crude was dissolved in DMF and purified by reverse phase preparative LCMS to give pure products.

Example 3

Scheme 4

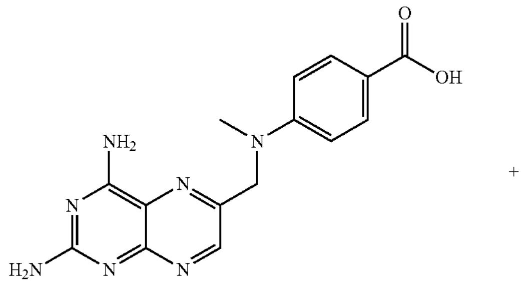

-continued

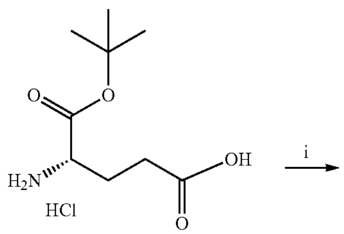

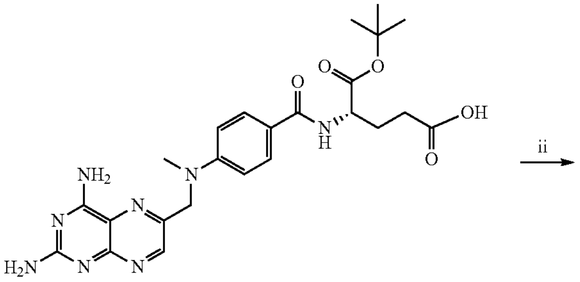

SAR003-016

-continued

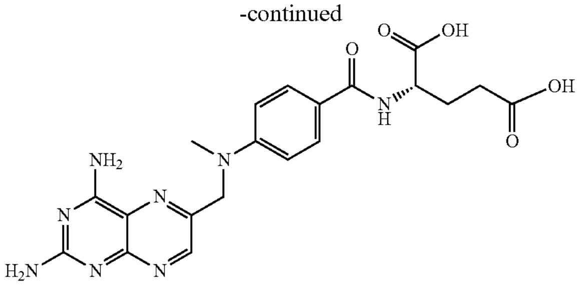

SAR003-021

(i) PyBOP, DIEA, DMSO; (ii) HATU, DIEA, DMF; (iii) $CF_3COOH$, DCM

(S)-5-(tert-butoxy)-4-(4-(((2,4-diaminopteridin-6-yl)methyl)(methyl)amino)benzamido)-5-oxopentanoic acid (SAR003-016)

To a solution of 4-(((2,4-diaminopteridin-6-yl)methyl)(methyl)amino)benzoic acid (100 mg, 0.307 mmol) in 3 ml of DMSO was added TEA (64.3 μl, 0.461 mmol) and PyBOP (192 mg, 0.369 mmol). The mixture was stirred at 30° C. for 2 hours resulting in dark brown solution. To that was added (S)-4-amino-5-(tert-butoxy)-5-oxopentanoic acid HCl (88.0 mg, 0.369 mmol) and $K_2CO_3$ (21.24 mg, 0.154 mmol). The reaction mixture was stirred for 18 hours. The crude was purified by reverse phase HPLC (10-100% $CH_3CN$ in water, 0.01% TFA).

LC-MS retention time: 2.69 min (method 1)

MS-ESI (+) calcd m/z for $C_{24}H_{30}N_8O_5^+$ 511.23 (M+H)+, found 511.3.

1H NMR (400 MHz, DMSO-d6) δ 12.12 (s, 1H), 8.57 (s, 1H), 8.17 (d, J=7.6 Hz, 1H), 7.89 (s, 1H), 7.75-7.68 (m, 2H), 7.67 (s, 1H), 6.85-6.77 (m, 4H), 4.78 (s, 2H), 4.26 (ddd, J=9.8, 7.4, 5.2 Hz, 1H), 3.20 (s, 3H), 2.30 (t, J=7.5 Hz, 2H), 2.06-1.94 (m, 1H), 1.88 (ddt, J=14.0, 9.4, 7.3 Hz, 1H), 1.37 (s, 9H).

(4-(((2,4-diaminopteridin-6-yl)methyl)(methyl)amino)benzoyl)-L-glutamic acid (SAR003-021; NCGC00025060)

(S)-5-(tert-butoxy)-4-(4-(((2,4-diaminopteridin-6-yl)methyl)(methyl)amino)benzamido)-5-oxopentanoic acid (20 mg, 0.039 mmol) was dissolved in DCM (1 mL) followed by addition of 1 mL of TFA. Reaction was stirred at the room temperature for 3 hours. Solvent was evaporated, and the crude compound was purified by reverse phase HPLC.

LC-MS retention time: 2.74 min (method 2)

MS (ESI); m/z [M+H]+: Calcd. for $C_{20}H_{22}N_8O_5$, 455.17 $(M+H)^+$. found 455.1.

1H NMR (400 MHz, DMSO-d6) δ 13.26 (s, 1H), 9.27 (s, 1H), 9.04 (s, 1H), 8.70 (s, 1H), 8.62-8.57 (m, 1H), 8.21 (dd, J=7.6, 3.7 Hz, 1H), 7.93 (s, 1H), 7.77-7.69 (m, 2H), 6.85-6.76 (m, 2H), 4.86 (s, 2H), 4.34 (ddd, J=9.9, 7.7, 4.9 Hz, 1H), 3.57 (d, J=20.1 Hz, 1H), 3.23 (s, 3H), 2.30 (t, J=7.5 Hz, 2H), 2.12-1.98 (m, 1H), 1.90 (ddt, J=13.9, 9.7, 7.0 Hz, 1H).

Example 4

Scheme 5

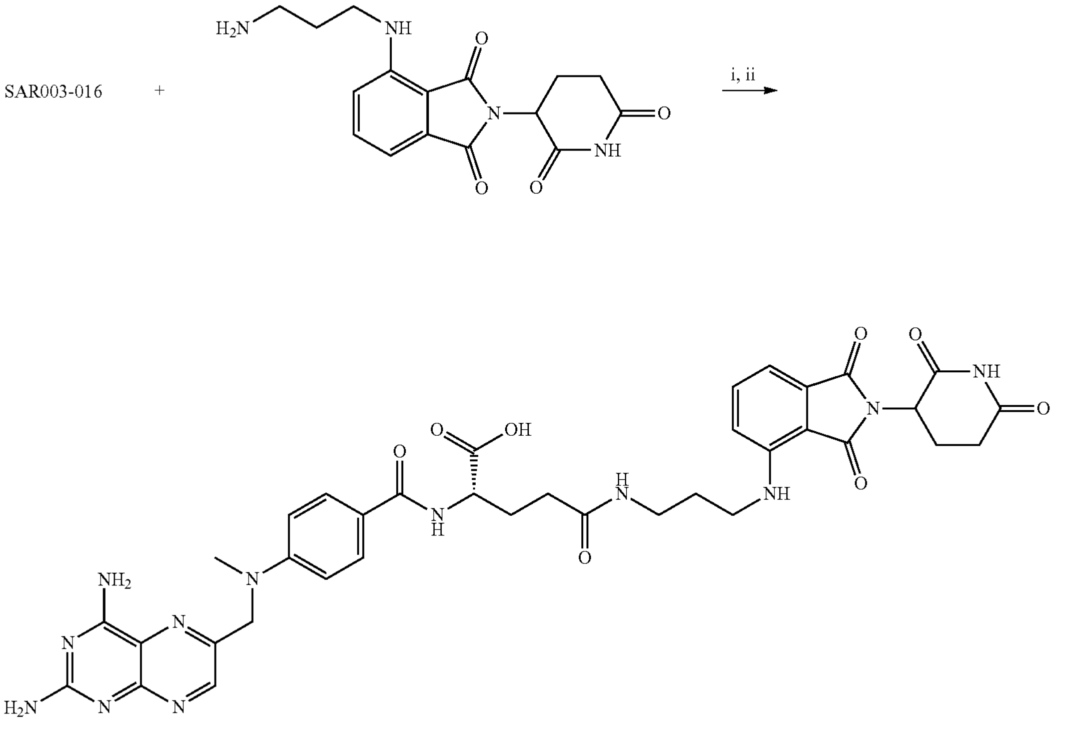

SAR003-018

(i) HATU, DIEA, DMF; (ii) $CF_3COOH$, DCM

N2-(4-(((2,4-diaminopteridin-6-yl)methyl)(methyl)amino)benzoyl)-N5-(3-((2-(2,6-dioxopiperidin-3-yl)-1,3-dioxoisoindolin-4-yl)amino)propyl)-L-glutamine·TFA (SAR003-018; NCGC00685938)

To a solution of SAR003-016 (15 mg, 0.029 mmol) and 4-((3-aminopropyl)amino)-2-(2,6-dioxopiperidin-3-yl)isoindoline-1,3-dione·TFA (10.68 mg, 0.032 mmol) (Li, Y. et al., *J Med Chem* 2019, 62 (2), 448-466, Zhou, B. et al., *J Med Chem* 2018, 61 (2), 462-481) in DMF (1 ml) was added HATU (22.34 mg, 0.059 mmol) followed by DIEA (51.3 µl, 0.294 mmol). The reaction mixture was stirred for 2 hours and compound was partially purified by silica gel column chromatography to yield tert-butyl N2-(4-(((2,4-diaminopteridin-6-yl)methyl)(methyl)amino)benzoyl)-N5-(3-((2-(2,6-dioxopiperidin-3-yl)-1,3-dioxoisoindolin-4-yl)amino)propyl)-L-glutaminate (10 mg, 41%) that was subjected to the next step. The partially purified compound was dissolved in DCM (1 mL) followed by the addition of 1 mL of TFA. The reaction was stirred at room temperature for 2 hours. The solvent was removed under reduced pressure and the crude was purified by reverse phase HPLC to the yield desired product as a TFA salt.

LC-MS retention time: 2.60 min (method 1)

MS-ESI (+) calcd m/z for $C_{36}H_{38}N_{12}O_8^+$ 767.29 (M+H)+, found 767.3.

Example 5

Scheme 6

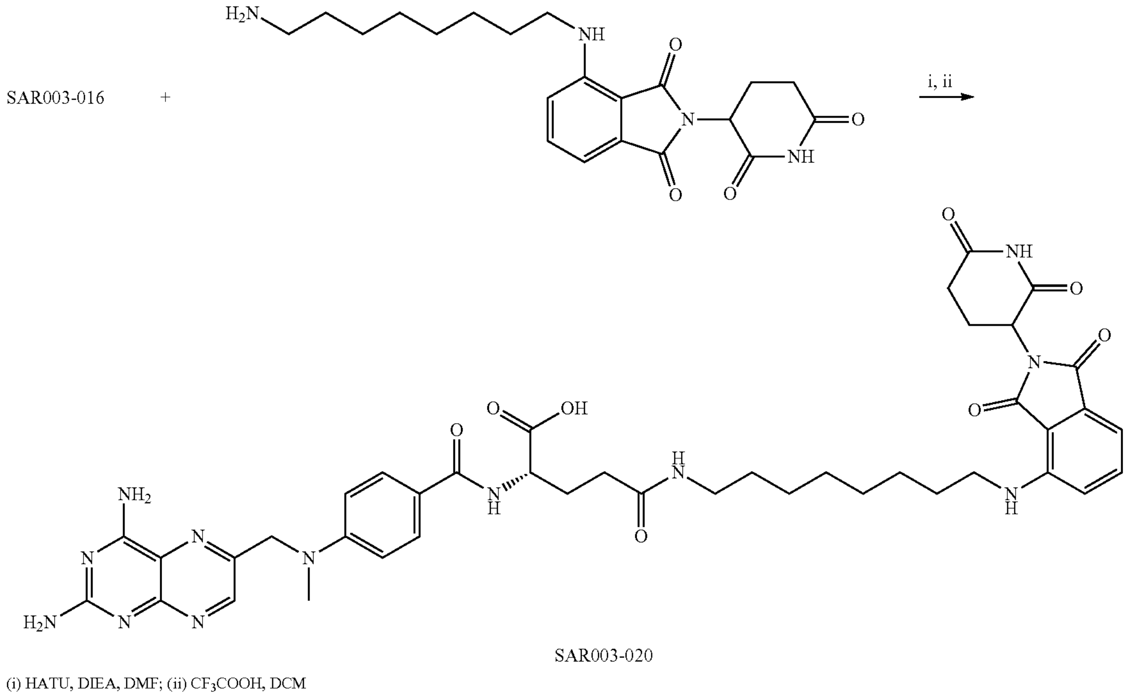

N2-(4-(((2,4-diaminopteridin-6-yl)methyl)(methyl)amino)benzoyl)-N5-(8-((2-(2,6-dioxopiperidin-3-yl)-1,3-dioxoisoindolin-4-yl)amino)octyl)-L-glutamine·TFA (SAR003-020; NCGC00685928)

This compound was synthesized with SAR003-016 and 4-((8-aminooctyl)amino)-2-(2,6-dioxopiperidin-3-yl)isoindoline-1,3-dione·TFA (Remillard, D et al. *Angew Chem Int Ed Engl* 2017, 56 (21), 5738-5743) using similar conditions reported for SAR003-018.

LC-MS retention time: 4.40 min (method 2)

MS-ESI (+) calcd m/z for $C_{41}H_{48}N_{12}O_8^+$ 837.37 (M+H)+, found 837.4.

$^1H$ NMR (400 MHz, DMSO-$d_6$) δ 12.98 (s, 1H), 12.44 (s, 1H), 11.07 (s, 1H), 9.21 (s, 1H), 9.00 (s, 1H), 8.69 (s, 1H), 8.28 (d, J=7.4 Hz, 1H), 7.78 (t, J=5.6 Hz, 1H), 7.72 (d, J=8.7 Hz, 2H), 7.55 (dd, J=8.6, 7.1 Hz, 1H), 7.06 (d, J=8.6 Hz, 1H), 7.00 (d, J=7.0 Hz, 1H), 6.80 (d, J=8.6 Hz, 2H), 6.49 (t, J=6.0 Hz, 1H), 5.03 (dd, J=12.8, 5.4 Hz, 1H), 4.85 (s, 2H), 4.27 (ddd, J=9.4, 7.4, 4.8 Hz, 1H), 3.26 (t, J=6.7 Hz, 2H), 3.22 (s, 3H), 2.98 (q, J=6.5 Hz, 2H), 2.86 (ddd, J=17.4, 14.0, 5.4 Hz, 1H), 2.62-2.50 (m, 2H), 2.16 (t, J=7.5 Hz, 2H), 2.06-1.98 (m, 2H), 1.96-1.83 (m, 1H), 1.57-1.50 (m, 2H), 1.37-1.20 (m, 12H).

Example 6

Scheme 7

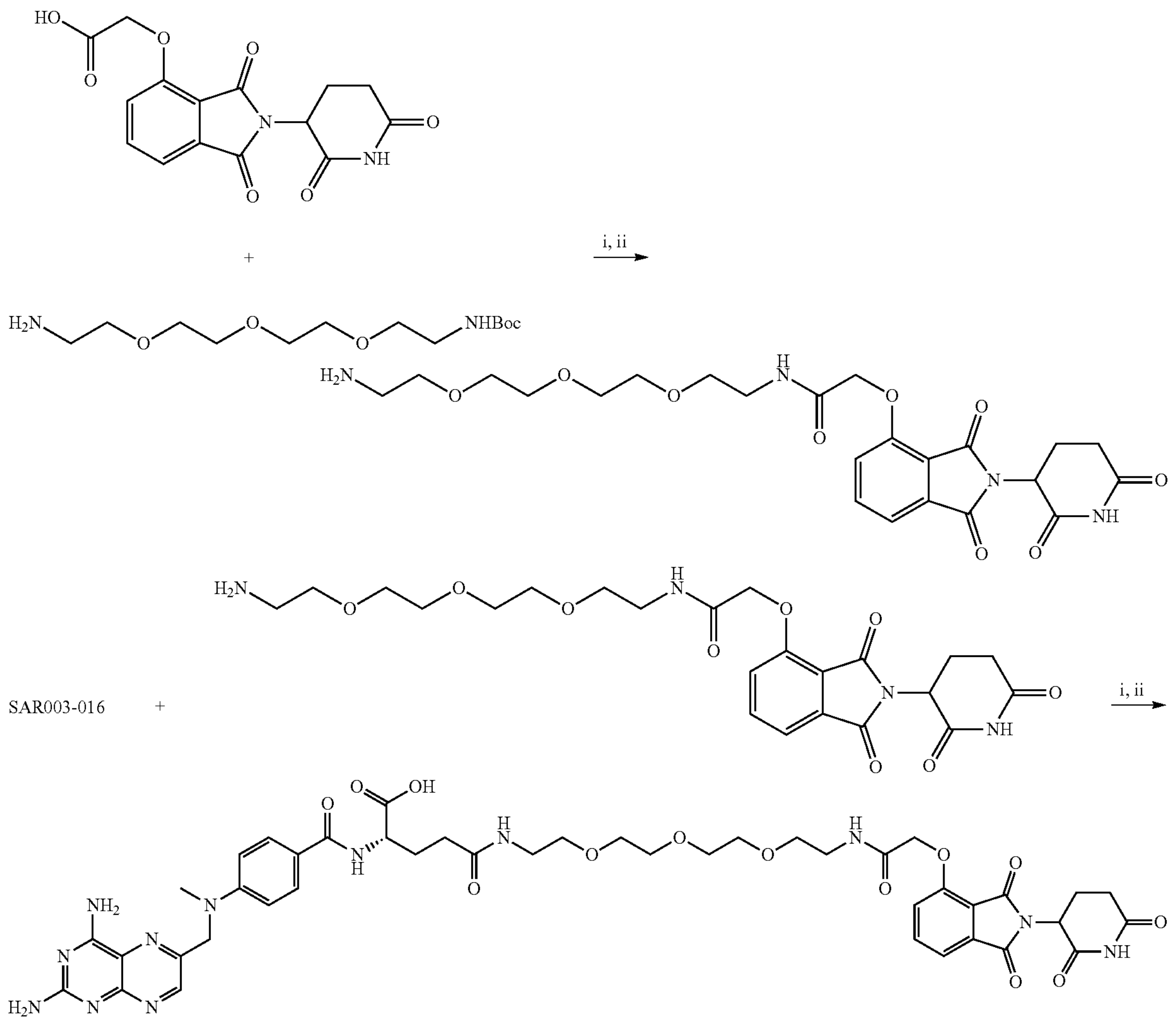

SAR003-027

(i) TCFH, NMI, $CH_3CN$; (ii) $CF_3COOH$, DCM (19S)-19-(4-(((2,4-diaminopteridin-6-yl)methyl)(methyl)amino)benzamido)-1-((2-(2,6-dioxopiperidin-3-yl)-1,3-dioxoisoindolin-4-yl)oxy)-2,16-dioxo-6,9,12-trioxa-3,15-diazaicosan-20-oic acid (SAR003-027; NCGC00685965)

Dissolve 2-((2-(2,6-dioxopiperidin-3-yl)-1,3-dioxoisoindolin-4-yl)oxy)acetic acid (300 mg, 0.903 mmol) and tert-butyl (2-(2-(2-(2-aminoethoxy)ethoxy)ethoxy)ethyl)carbamate (290 mg, 0.993 mmol) in acetonitrile (10 ml) followed by the addition of TCFH (381 mg, 1.354 mmol) and 1-methyl-1H-imidazole (222 mg, 2.71 mmol). The reaction was stirred for 2 hours. The solvent was evaporated under the reduced pressure and crude was purified by silica gel column chromatography to yield tert-butyl (1-((2-(2,6-dioxopiperidin-3-yl)-1,3-dioxoisoindolin-4-yl)oxy)-2-oxo-6,9,12-trioxa-3-azatetradecan-14-yl)carbamate (500 mg, 91% yield). MS-ESI (+) calcd m/z for $C_{28}H_{38}N_4O_{11}^+$ 607.25 (M+H)+, found 607.2; LC-MS retention time: 3.00 min (method 1).

The compound was dissolved in DCM (5 ml) followed by the addition of TFA (2 ml). The reaction was stirred at room temperature for 2 hours. The solvent was removed under reduced pressure to yield N-(2-(2-(2-(2-aminoethoxy)ethoxy)ethoxy)ethyl)-2-((2-(2,6-dioxopiperidin-3-yl)-1,3-dioxoisoindolin-4-yl)oxy)acetamide, TFA (470 mg, 0.757 mmol, 92% yield) which was used as such in the next step. MS-ESI (+) calcd m/z for $C_{23}H_{30}N_4O_9^+$ 607.20 (M+H)+, found 507.2; LC-MS retention time: 2.51 min (method 1).

SAR003-016 (411 mg, 0.806 mmol), N-(2-(2-(2-(2-aminoethoxy)ethoxy)ethoxy)ethyl)-2-((2-(2,6-dioxopiperidin-3-yl)-1,3-dioxoisoindolin-4-yl)oxy)acetamide, and TFA (500 mg, 0.806 mmol) were dissolved in anhydrous acetonitrile (10 ml) followed by the addition of TCFH (454 mg, 1.612 mmol) and 1-methyl-1H-imidazole (331 mg, 4.03 mmol). Reaction was stirred for 1 hours. The solvent was removed and the crude was purified by silica gel column chromatography to yield tert-butyl (19S)-19-(4-(((2,4-diaminopteridin-6-yl)methyl)(methyl)amino)benzamido)-1-((2-(2,6-dioxopiperidin-3-yl)-1,3-dioxoisoindolin-4-yl)oxy)-2,16-dioxo-6,9,12-trioxa-3,15-diazaicosan-20-oate, TFA (740 mg, 0.665 mmol, 83% yield) as red gel. MS-ESI (+) calcd m/z for $C_{47}H_{58}N_{12}O_{13}^+$ 999.42 (M+H)+, found 999.4; LC-MS retention time: 2.70 min (method 1).

The Boc protected acid was dissolved in DCM (1 mL) followed by the addition of 1 mL of TFA. The reaction was stirred at room temperature for 2 hours. The solvent was removed under reduced pressure and the crude was purified by reverse phase HPLC to the yield final product as a TFA salt.

LC-MS retention time: 3.39 min (method 2)

MS-ESI (+) calcd m/z for $C_{43}H_{50}N_{12}O_{13}^+$ 943.36 $(M+H)^+$. found 943.3.

$^1H$ NMR (400 MHz, DMSO-$d_6$) δ 12.99 (s, 1H), 12.45 (s, 1H), 11.09 (s, 1H), 9.24 (s, 1H), 9.04 (s, 1H), 8.70 (s, 1H), 8.57 (s, 1H), 8.28 (d, J=7.4 Hz, 1H), 7.98 (t, J=5.7 Hz, 1H), 7.88 (t, J=5.6 Hz, 1H), 7.79 (t, J=7.9 Hz, 1H), 7.72 (d, J=8.7 Hz, 2H), 7.48 (d, J=7.3 Hz, 1H), 7.38 (d, J=8.5 Hz, 1H), 6.81 (d, J=8.8 Hz, 2H), 5.09 (dd, J=12.9, 5.4 Hz, 1H), 4.85 (s, 2H), 4.77 (s, 2H), 4.29-4.24 (m, 1H), 3.50-3.40 (m, 9H), 3.36-3.27 (m, 4H), 3.23 (s, 3H), 3.15 (q, J=6.0 Hz, 2H), 2.96-2.81 (m, 1H), 2.60-2.52 (m, 1H), 2.18 (t, J=7.6 Hz, 2H), 2.06-1.99 (m, 2H), 1.94-1.85 (m, 1H).

Example 7

Scheme 8

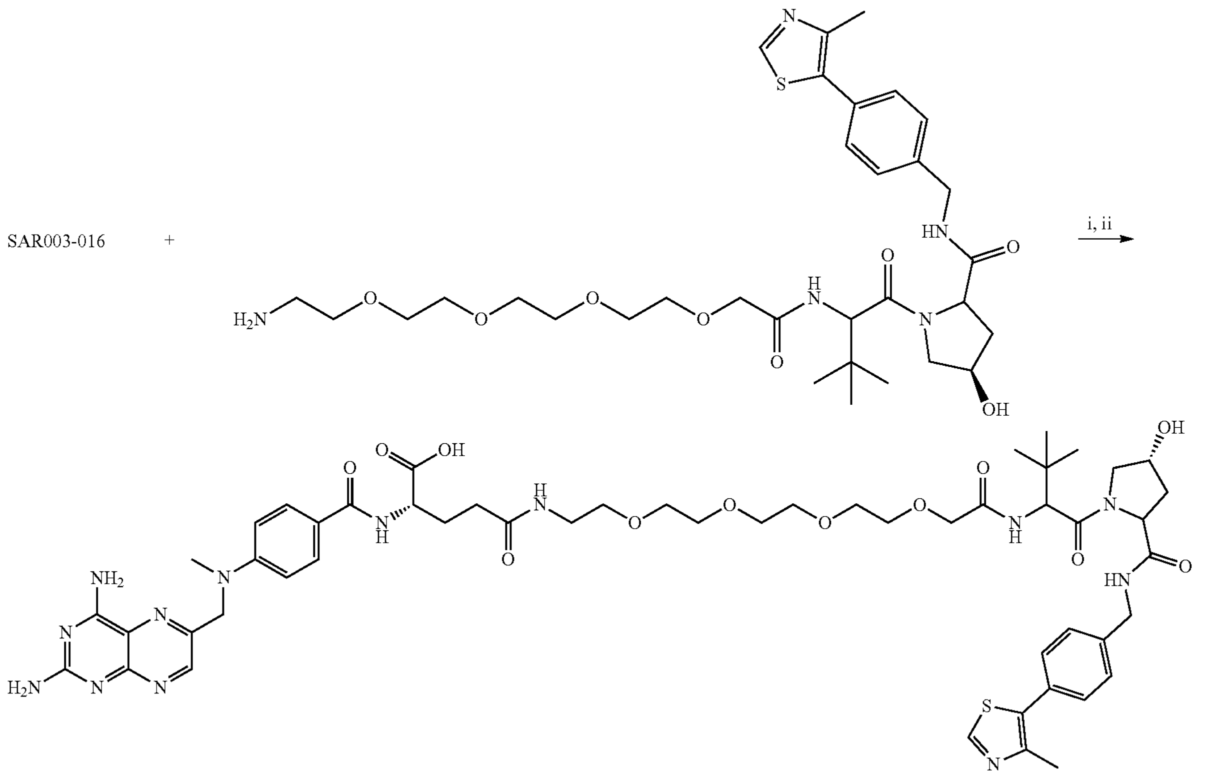

SAR003-026

(i) HATU, DIEA, DMF; (ii) $CF_3COOH$, DCM (23S)-23-(4-(((2,4-diaminopteridin-6-yl)methyl)(methyl)amino)benzamido)-3-((4R)-4-hydroxy-2-((4-(4-methylthiazol-5-yl)benzyl)carbamoyl)pyrrolidine-1-carbonyl)-2,2-dimethyl-5,20-dioxo-7,10,13,16-tetraoxa-4,19-diazatetracosan-24-oic acid (SAR003-026; NCGC00685964)

This compound was synthesized with (S)-5-(tert-butoxy)-4-(4-(((2,4-diaminopteridin-6-yl)methyl)(methyl)amino)benzamido)-5-oxopentanoic acid and (4R)-1-(17-amino-2-(tert-butyl)-4-oxo-6,9,12,15-tetraoxa-3-azaheptadecanoyl)-4-hydroxy-N-(4-(4-methylthiazol-5-yl)benzyl)pyrrolidine-2-carboxamide. HCl (medchemexpress) using similar conditions reported for SAR003-018.

LC-MS retention time: 3.89 min (method 2)

MS-ESI (+) calcd m/z for $Cs_2H_{69}N_{13}O_{12}S^+$ 1100.49 $(M+H)^+$. found 1100.4.

1H NMR (400 MHz, DMSO-d6) δ 12.97 (s, 1H), 12.45 (s, 1H), 9.26 (s, 1H), 9.06 (s, 1H), 8.96 (s, 1H), 8.70 (s, 1H), 8.57 (t, J=6.0 Hz, 1H), 8.28 (d, J=7.4 Hz, 1H), 7.88 (t, J=5.7 Hz, 1H), 7.72 (d, J=8.6 Hz, 2H), 7.49 (s, 1H), 7.44-7.33 (m, 1H), 7.38 (m, 4H), 6.81 (d, J=8.7 Hz, 2H), 4.86 (s, 2H), 4.55 (d, J=9.5 Hz, 1H), 4.44-4.39 (m, 2H), 4.33 (s, 1H), 4.31-4.18 (m, 2H), 3.95 (s, 2H), 3.65 (dd, J=10.7, 3.9 Hz, 1H), 3.62-3.50 (m, 4H), 3.54-3.45 (m, 3H), 3.34 (t, J=5.9 Hz, 2H), 3.23 (s, 2H), 3.15 (q, J=5.9 Hz, 2H), 2.42 (s, 3H), 2.18 (t, J=7.6 Hz, 2H), 2.07-1.85 (m, 4H), 0.91 (s, 9H).

Example 8

Scheme 9

SAR003-016 +

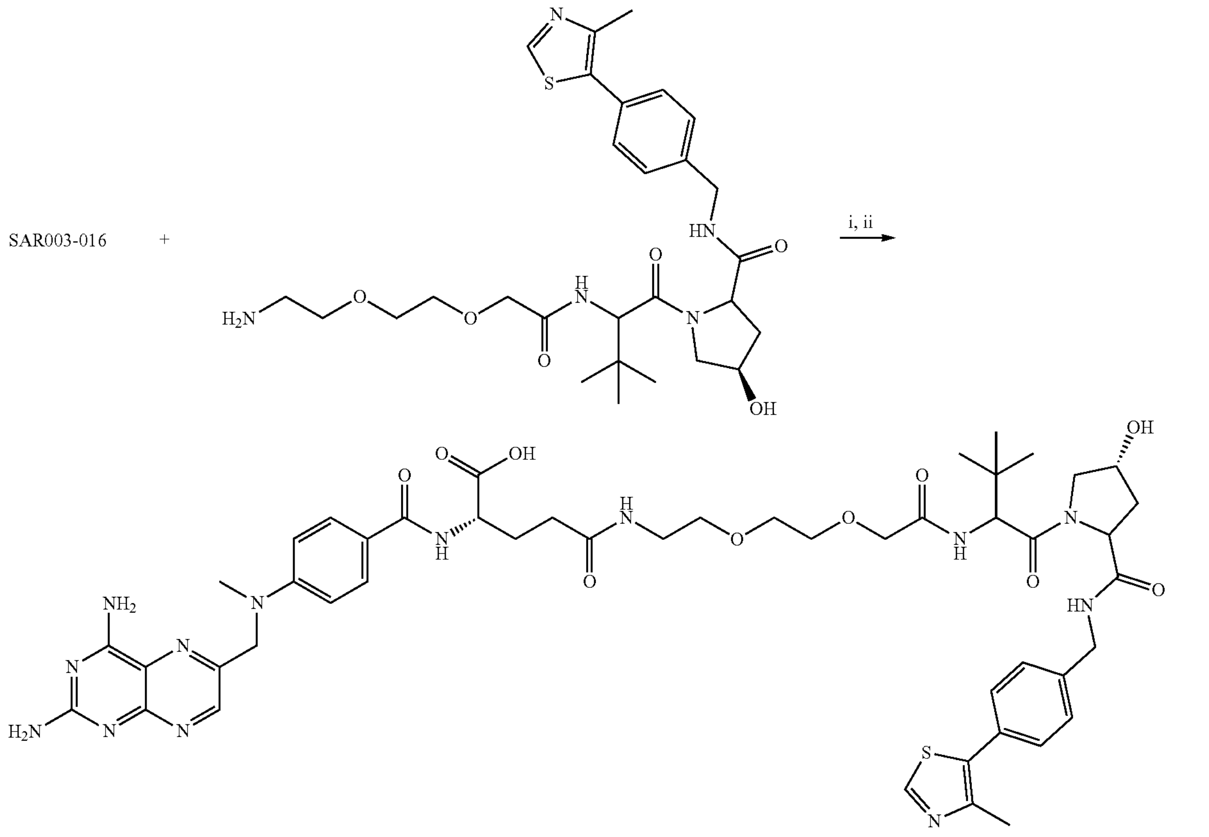

SAR003-030

(i) HATU, DIEA, DMF; (ii) $CF_3COOH$, DCM (17S)-17-(4-(((2,4-diaminopteridin-6-yl)methyl)(methyl)amino)benzamido)-3-((4R)-4-hydroxy-2-((4-(4-methylthiazol-5-yl)benzyl)carbamoyl)pyrrolidine-1-carbonyl)-2,2-dimethyl-5,14-dioxo-7,10-dioxa-4,13-diazaoctadecan-18-oic acid (SAR003-030; NCGC00685995)

This compound was synthesized with (S)-5-(tert-butoxy)-4-(4-(((2,4-diaminopteridin-6-yl)methyl)(methyl)amino)benzamido)-5-oxopentanoic acid and (4R)-1-(2-(2-(2-(2-aminoethoxy)ethoxy)acetamido)-3,3-dimethylbutanoyl)-4-hydroxy-N-(4-(4-methylthiazol-5-yl)benzyl)pyrrolidine-2-carboxamide·HCl (medchemexpress) using similar conditions reported for SAR003-018.

LC-MS retention time: 2.72 min (method 2)

MS-ESI (+) calcd m/z for $C_{48}H_{61}N_{13}O_{10}S^+$ 1012.44 $(M+H)^+$. found 1012.3. $^1H$ NMR (400 MHz, DMSO-$d_6$) δ 12.98 (s, 1H), 12.44 (s, 1H), 9.25 (s, 1H), 9.05 (s, 1H), 8.95 (s, 1H), 8.69 (s, 1H), 8.62 (s, 1H), 8.56 (t, J=6.1 Hz, 1H), 8.29 (d, J=7.4 Hz, 1H), 7.89 (t, J=5.7 Hz, 1H), 7.72 (d, J=8.6 Hz, 2H), 7.41 (d, J=9.6 Hz, 1H), 7.37 (s, 4H), 6.80 (d, J=8.7 Hz, 2H), 5.13 (s, 1H), 4.85 (s, 2H), 4.55 (d, J=9.6 Hz, 1H), 4.46-4.22 (m, 5H), 3.94 (s, 2H), 3.66-3.47 (m, 7H), 3.39 (t, J=5.9 Hz, 2H), 3.23-3.11 (m, 1H), 2.52 (s, 1H), 2.42 (s, 3H), 2.18 (t, J=7.6 Hz, 2H), 2.09-1.96 (m, 2H), 1.88 (m, 2H), 0.91 (s, 9H)

Example 9

Scheme 10

SAR003-016 +

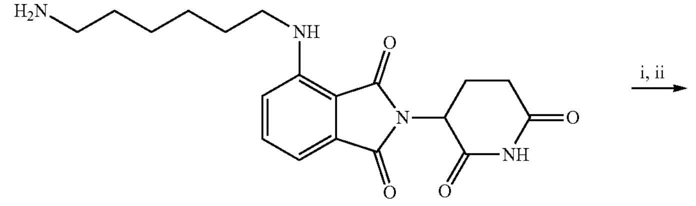

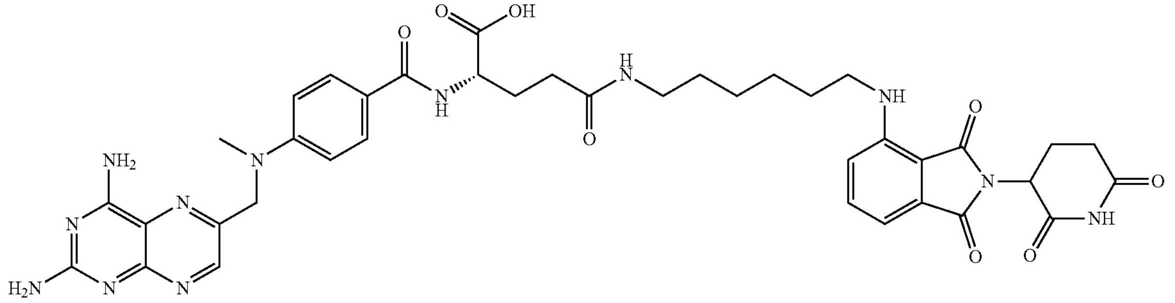

SAR004-099

(i) HATU, DIEA, DMF; (iii) $CF_3COOH$, DCM

N2-(4-(((2,4-diaminopteridin-6-yl)methyl)(methyl)amino)benzoyl)-N5-(6-((2-(2,6-dioxopiperidin-3-yl)-1,3-dioxoisoindolin-4-yl)amino)hexyl)-L-glutamine (SAR04-099; NCGC00687414)

This compound was synthesized with (S)-5-(tert-butoxy)-4-(4-(((2,4-diaminopteridin-6-yl)methyl)(methyl)amino)benzamido)-5-oxopentanoic acid and 4-((6-aminohexyl)amino)-2-(2,6-dioxopiperidin-3-yl)isoindoline-1,3-dione·TFA (medchemexpress) using similar conditions reported for SAR003-018.

LC-MS retention time: 3.90 min (method 2)

MS-ESI (+) calcd m/z for $C_{49}H_{44}N_{23}O_8^+$ 809.34 (M+H)+, found 809.4.

1H NMR (400 MHz, DMSO-d6) δ 12.95 (s, 1H), 12.44 (s, 1H), 11.07 (s, 1H), 9.23 (s, 1H), 9.02 (s, 1H), 8.69 (s, 1H), 8.56 (s, 1H), 8.28 (d, J=7.4 Hz, 1H), 7.79 (t, J=5.6 Hz, 1H), 7.75-7.67 (m, 2H), 7.55 (dd, J=8.6, 7.0 Hz, 1H), 7.05 (d, J=8.6 Hz, 1H), 6.99 (d, J=7.0 Hz, 1H), 6.84-6.77 (m, 2H), 6.48 (t, J=5.9 Hz, 1H), 5.03 (dd, J=12.8, 5.4 Hz, 1H), 4.85 (s, 2H), 4.27 (ddd, J=9.4, 7.3, 4.8 Hz, 1H), 3.22 (s, 3H), 2.99 (d, J=6.1 Hz, 2H), 2.89-2.81 (m, OH), 2.62-2.50 (m, 2H), 2.17 (t, J=7.5 Hz, 2H), 2.09-1.83 (m, 3H), 1.52 (p, J=7.1 Hz, 2H), 1.40-1.31 (m, 2H), 1.28 (s, 4H), 1.34-1.19 (m, 1H).

Example 10

Scheme 11

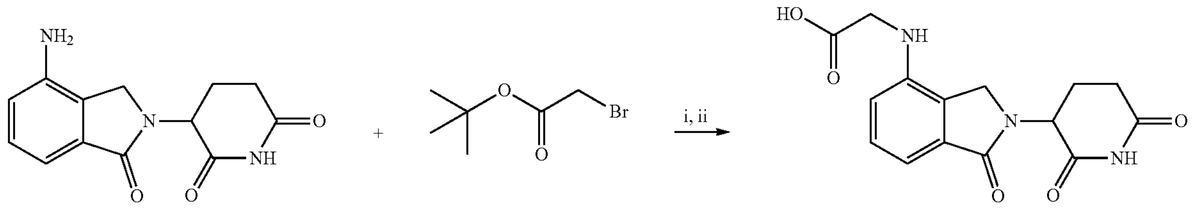

SAR004-088

SAR004-088

+

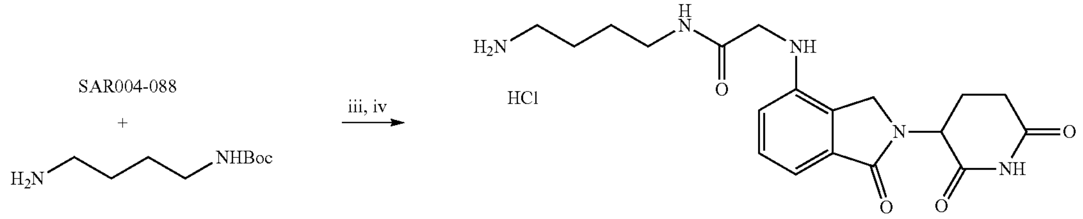

SAR004-096

SAR003-016 + SAR004-096 v, ii

-continued

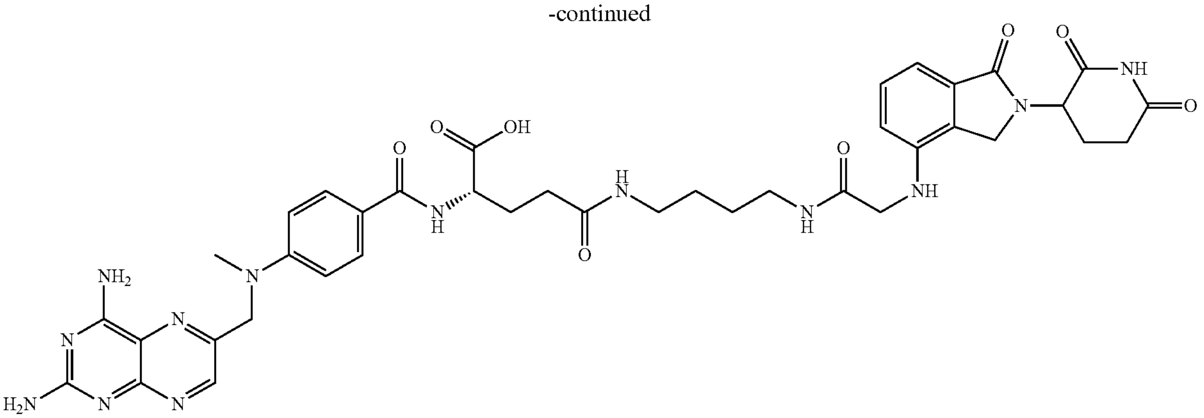

SAR005-007

(i) DIEA, DMF; (ii) $CF_3COOH$, DCM; (iii) TCFH, NMI, $CH_3CN$; (iv) 4N HCl in dioxane, DCM; (v) PyBOP, TEA, DMF.

N2-(4-(((2,4-diaminopteridin-6-yl)methyl)(methyl)amino)benzoyl)-N5-(4-(2-((2-(2,6-dioxopiperidin-3-yl)-1-oxoisoindolin-4-yl)amino)acetamido)butyl)-L-glutamine (SAR005-007; NCGC00687415)

2-(2,6-dioxopiperidin-3-yl)-1-oxoisoindolin-4-yl)glycine (SAR004-088) was synthesized using 3-(4-amino-1-oxoisoindolin-2-yl)piperidine-2,6-dione and tert-butyl 2-bromoacetate followed by deprotection of butyl group under acidic condition. MS-ESI (+) calcd m/z for $C_{15}H_{15}N_3O_5^+$ 318.10 $(M+H)^+$. found 318.1; LC-MS retention time: 2.27 min (method 1) (*Chemoselective Synthesis of Lenalidomide-Based PROTAC Library Using Alkylation Reaction" Org. Lett.* 2019, 21, 3838-3841).

Dissolved (2-(2,6-dioxopiperidin-3-yl)-1-oxoisoindolin-4-yl)glycine, TFA (180 mg, 0.417 mmol), and tert-butyl (4-aminobutyl)carbamate (86 mg, 0.459 mmol) in acetonitrile (5 ml) followed by addition of 1-methyl-1H-imidazole (103 mg, 1.252 mmol). Reaction was stirred for 10 minutes to make sure all components are dissolved in acetonitrile, followed by the addition of N-(chloro(dimethylamino)methylene)-N-methylmethanaminium hexafluorophosphate(V) (176 mg, 0.626 mmol). Reaction was stirred for an additional 1 hour. Solvent was removed and the crude mixture was purified by silica gel chromatography to yield tert-butyl (4-(2-((2-(2,6-dioxopiperidin-3-yl)-1-oxoisoindolin-4-yl)amino)acetamido)butyl)carbamate (160 mg, 0.328 mmol, 79% yield) which was dissolved in DCM (2 ml) and 4N HCl solution in dioxane (1.2 ml). Reaction was stirred for 8 hours and solvent was removed and the residue was washed with ether to yield N-(4-aminobutyl)-2-((2-(2,6-dioxopiperidin-3-yl)-1-oxoisoindolin-4-yl)amino)acetamide, HCl (SAR004-096). MS-ESI (+) calcd m/z for $C_{19}H_{25}N_5O_4^+$ 388.19 (M+H)+, found 388.2; LC: 2.07 min (method 1). It was used as such in next step without further purification.

To a solution of (S)-5-(tert-butoxy)-4-(4-(((2,4-diaminopteridin-6-yl)methyl)(methyl)amino)benzamido)-5-oxopentanoic acid (SAR003-016) (20 mg, 0.039 mmol) in DMF was added PyBOP (31 mg, 0.047 mmol) and TEA (12 mg, 0.118 mmol). Reaction was stirred for 30 minutes followed by the addition of N-(4-aminobutyl)-2-((2-(2,6-dioxopiperidin-3-yl)-1-oxoisoindolin-4-yl)amino)acetamide (18.21 mg, 0.047 mmol). Reaction was stirred for 24 hours. Removed solvent and silica gel column chromatography to yield tert-butyl N2-(4-(((2,4-diaminopteridin-6-yl)methyl)(methyl)amino)benzoyl)-N5-(4-(2-((2-(2,6-dioxopiperidin-3-yl)-1-oxoisoindolin-4-yl)amino)acetamido)butyl)-L-glutaminate which was dissolved in DCM and added excess of TFA (10 eq).

Reaction was stirred at room temperature for 3 hours. Solvent was removed and the compound was purified by reverse phase HPLC to give the final product.

LC-MS retention time: 3.06 min (method 2)

MS-ESI (+) calcd m/z for $C_{39}H_{45}N_{13}O_8^+$ 824.35 $(M+H)^+$. found 824.4.

1H NMR (400 MHz, DMSO-d6) δ 12.95 (s, 1H), 10.98 (s, 1H), 9.24 (s, 1H), 9.04 (s, 1H), 8.69 (s, 1H), 8.57 (s, 1H), 8.29 (d, J=7.4 Hz, 1H), 7.92 (t, J=5.9 Hz, 1H), 7.78 (t, J=5.6 Hz, 1H), 7.75-7.68 (m, 2H), 7.46 (s, 1H), 7.25 (t, J=7.7 Hz, 1H), 6.95 (d, J=7.4 Hz, 1H), 6.80 (d, J=8.5 Hz, 2H), 6.53 (d, J=8.1 Hz, 1H), 6.02 (s, 1H), 5.10 (dd, J=13.3, 5.1 Hz, 1H), 4.85 (s, 2H), 4.27 (dd, J=15.2, 8.7 Hz, 2H), 4.16 (d, J=17.0 Hz, 1H), 3.70 (s, 2H), 3.22 (s, 3H), 3.02 (p, J=6.1 Hz, 2H), 2.96 (d, J=6.6 Hz, 2H), 2.90 (td, J=13.5, 7.0 Hz, 1H), 2.65-2.56 (m, 1H), 2.27 (dd, J=13.3, 4.5 Hz, 1H), 2.16 (t, J=7.5 Hz, 2H), 2.02 (h, J=7.2, 6.3 Hz, 2H), 1.96-1.84 (m, 1H), 1.31 (q, J=6.9, 6.4 Hz, 4H).

Example 11

Scheme 12

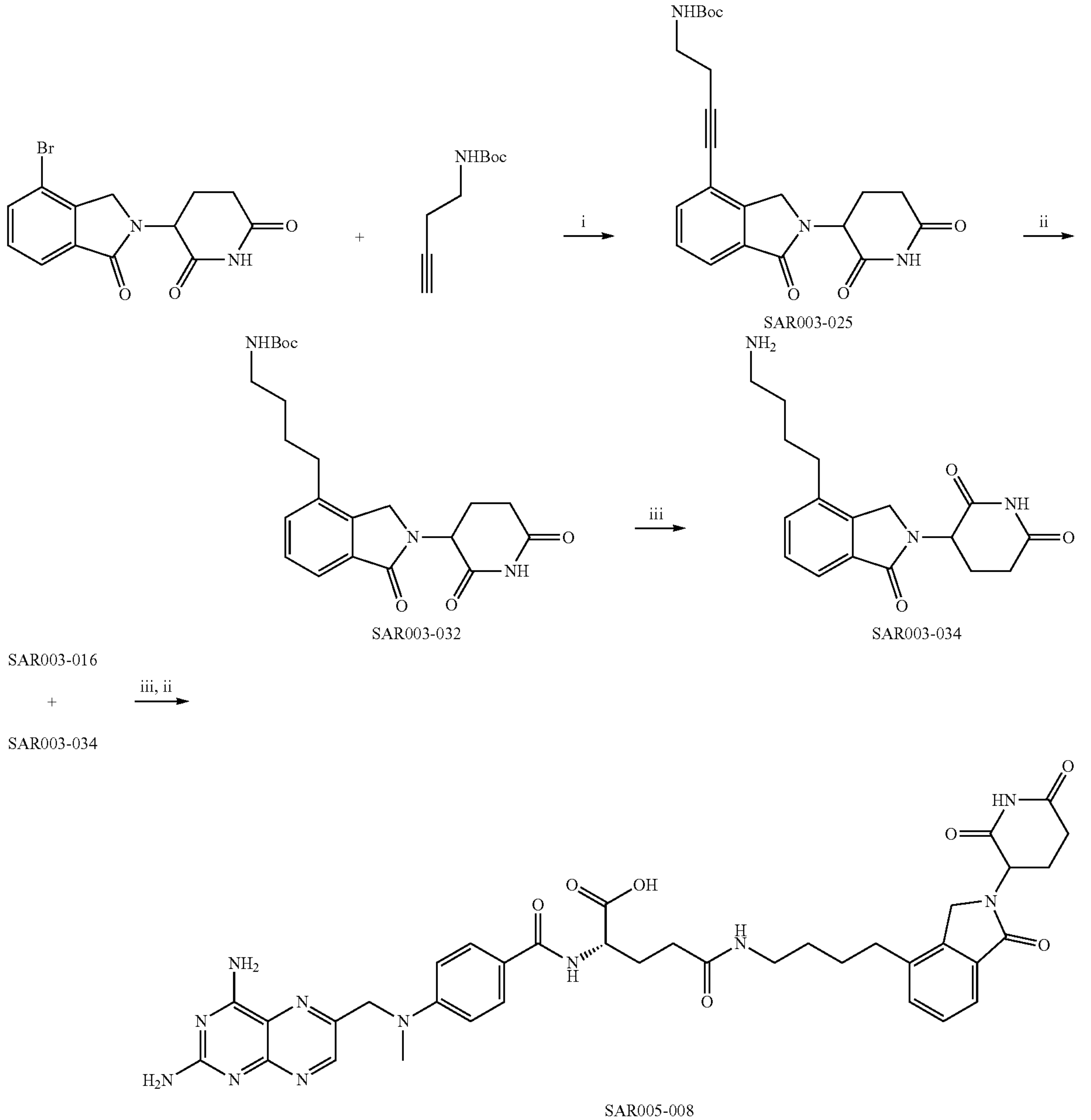

SAR003-016

SAR003-025

SAR003-032

SAR003-034

SAR003-016 + SAR003-034

SAR005-008

(i) 2,2,6,6-tetramethylpiperidine, Chloro(crotyl)(tri-tert-butylphosphine)palladium(II), DMSO; (ii) 5% Pd/C, Ethanol; (iii) 4N HCl in dioaxane, DCM; (iv) HATU, DIEA, DMF; (v) TFA, DCM N2-(4-(((2,4-diaminopteridin-6-yl)methyl)(methyl) amino)benzoyl)-N5-(4-(2-(2,6-dioxopiperidin-3-yl)-1-oxoisoindolin-4-yl)butyl)-L-glutamine (SAR005-008; NCGC00687417)

Taken 3-(4-bromo-1-oxoisoindolin-2-yl)piperidine-2,6-dione (200 mg, 0.619 mmol) and tert-butyl but-3-yn-1-ylcarbamate (136 mg, 0.805 mmol) in DMSO (3 ml) followed by addition of 2,2,6,6-tetramethylpiperidine (208 μl, 1.238 mmol). The reaction was vacuumed dried and purged nitrogen. Added chloro(crotyl)(tri-tert-butylphosphine)palladium(II) (12.39 mg, 0.031 mmol) and the reaction was stirred at room temperature overnight. The crude was dissolved in ethyl acetate and washed brine, dried $MgSO_4$ and purified by silica gel column chromatographed to yield tert-butyl (4-(2-(2,6-dioxopiperidin-3-yl)-1-oxoisoindolin-4-yl)but-3-yn-1-yl)carbamate (180 mg, 71%).

Subsequently, the compound (175 mg, 0.425 mmol) was dissolved in methanol (6 ml) followed by addition of 5% Pd/C (46 mg). Reaction mixture was vacuumed and purged hydrogen gas. The reaction was stirred at room temperature for 5 hours under hydrogen atmosphere. The mixture was filtered through celite and solvent was evaporated to yield tert-butyl (4-(2-(2,6-dioxopiperidin-3-yl)-1-oxoisoindolin-4-yl)butyl)carbamate (175 mg, 99%).

The compound (175 mg, 0.421 mmol) in subsequently dissolved in DCM (5 ml) followed by addition of 4N HCl (1280 µl, 42.1 mmol) in dioxane. Reaction mixture was stirred at room temperature for 5 hours. The crude was diluted with 20 mL hexane and filtered solid (140 mg. 94%) to yield 3-(4-(4-aminobutyl)-1-oxoisoindolin-2-yl)piperidine-2,6-dione (SAR003-034). MS-ESI (+) calcd m/z for $C_{17}H_{21}N_3O_3^+$ 316.16 $(M+H)^+$. found 316.2; LC: 2.58 min (method 2).

To a solution of (S)-5-(tert-butoxy)-4-(4-(((2,4-diaminopteridin-6-yl)methyl)(methyl)amino)benzamido)-5-oxopentanoic acid (20 mg, 0.039 mmol) in DMF (1 ml) followed by addition of PyBOP (30.6 mg, 0.059 mmol) and TEA (16.38 µl, 0.118 mmol). Reaction was stirred for 30 minutes followed by addition of N-(4-aminobutyl)-2-((2-(2,6-dioxopiperidin-3-yl)-1-oxoisoindolin-4-yl)amino)acetamide (18.21 mg, 0.047 mmol). The reaction was stirred for 24 hours. Following completion, the solvent was removed and the compound was purified by silica gel column chromatography to yield tert-butyl N2-(4-(((2,4-diaminopteridin-6-yl)methyl)(methyl)amino)benzoyl)-N5-(4-(2-((2-(2,6-dioxopiperidin-3-yl)-1-oxoisoindolin-4-yl)amino)acetamido)butyl)-L-glutaminate (12 mg, 34.8%) which was dissolved in DCM and added excess of TFA. Reaction was stirred at room temperature for 3 hours. Solvent was removed and the compound was purified by reverse phase HPLC to give the final product.

LC: 3.34 min (method 2)

MS-ESI (+) calcd m/z for $C_{37}H_{41}N_{11}O_7^+$ 752.32 (M+H)+, found 752.4.

1H NMR (400 MHz, DMSO-d6) δ 12.96 (s, 1H), 12.47 (s, 1H), 10.95 (s, 1H), 9.24 (s, 1H), 9.03 (s, 1H), 8.69 (s, 1H), 8.57 (s, 1H), 8.26 (d, J=7.4 Hz, 1H), 7.81 (t, J=5.7 Hz, 1H), 7.72 (d, J=8.5 Hz, 2H), 7.53 (dd, J=5.3, 3.3 Hz, 1H), 7.47 (s, 1H), 7.45-7.36 (m, 2H), 6.80 (d, J=8.6 Hz, 2H), 5.10 (dd, J=13.2, 5.1 Hz, 1H), 4.85 (s, 2H), 4.42 (d, J=17.2 Hz, 1H), 4.31-4.22 (m, 2H), 3.22 (s, 3H), 3.05 (p, J=6.3 Hz, 2H), 2.89 (ddd, J=18.1, 13.6, 5.4 Hz, 1H), 2.63-2.53 (m, 3H), 2.38 (td, J=13.3, 4.6 Hz, 1H), 2.16 (t, J=7.4 Hz, 2H), 2.01 (td, J=13.2, 11.8, 6.2 Hz, 2H), 1.90 (s, 1H), 1.55 (dq, J=15.7, 8.3, 7.2 Hz, 2H), 1.39 (p, J=7.1 Hz, 2H), 1.22 (s, 1H).

Example 12

Scheme 13

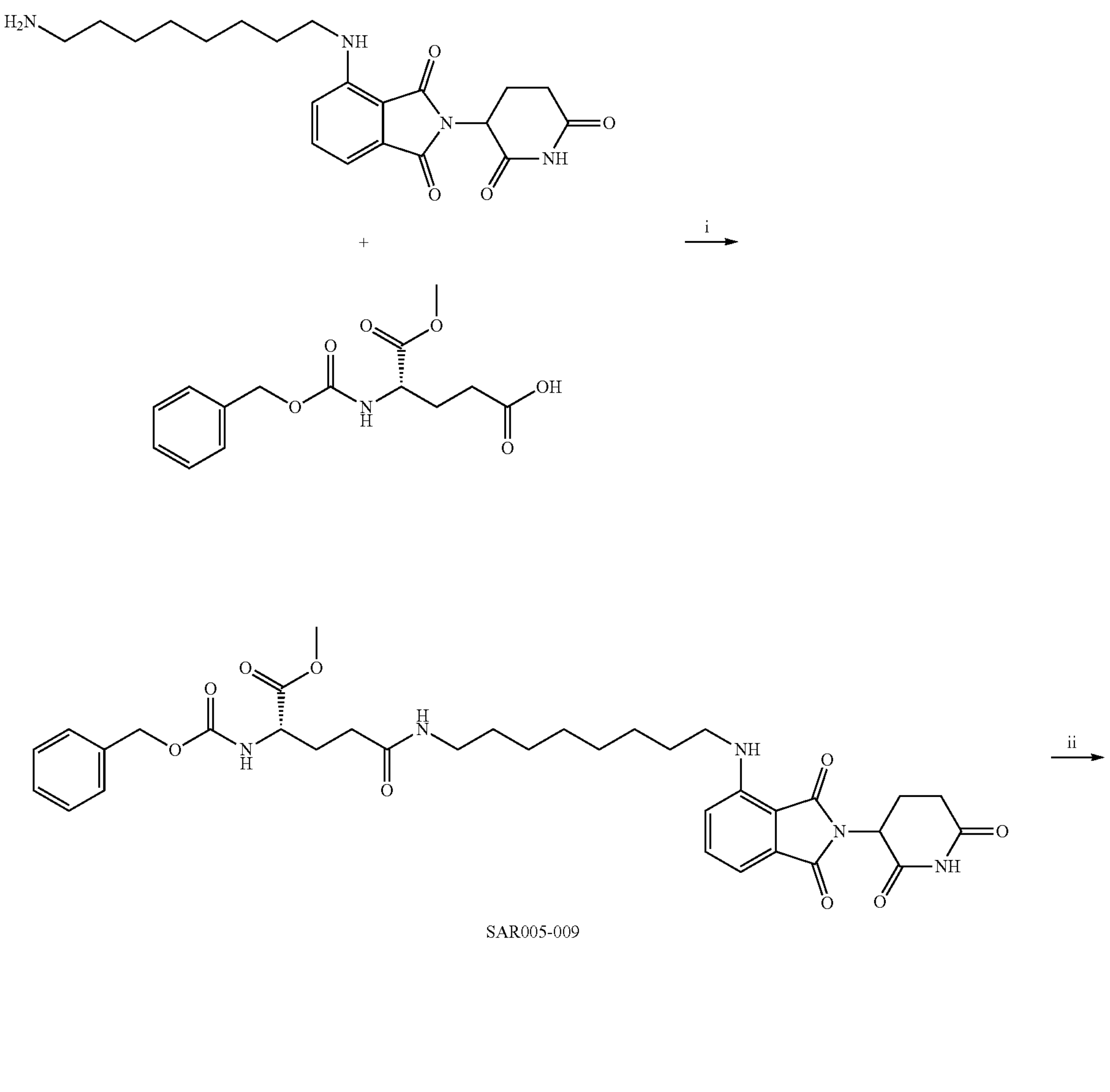

SAR005-009

-continued
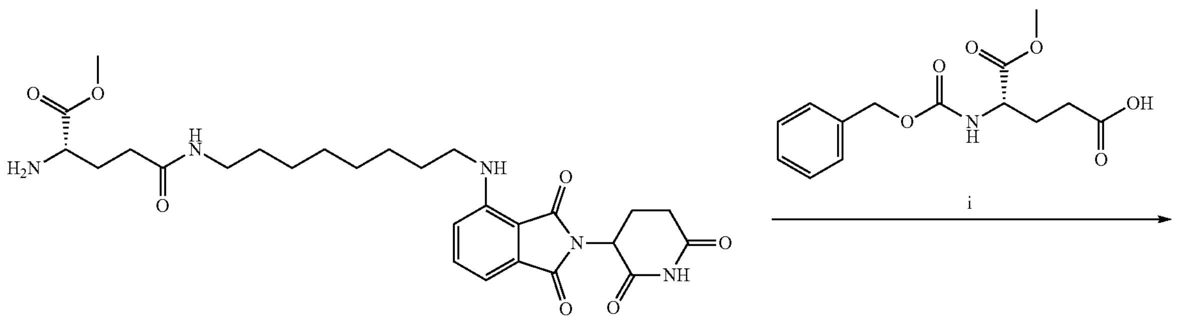
SAR005-011
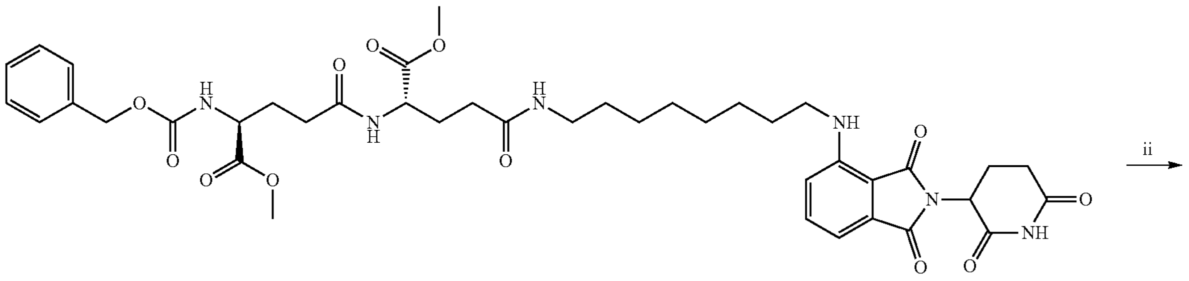
SAR005-013
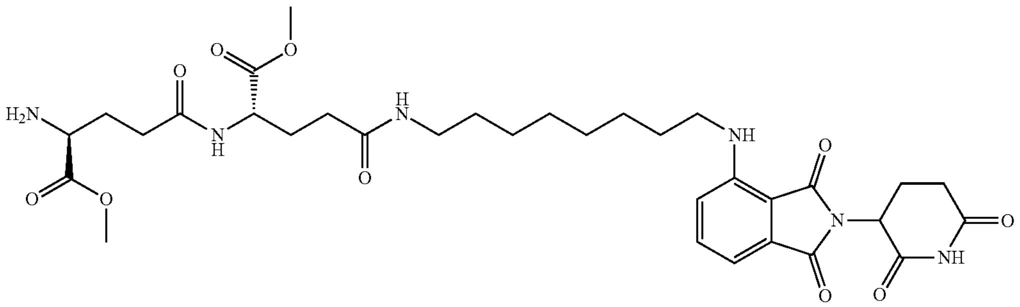
SAR005-015
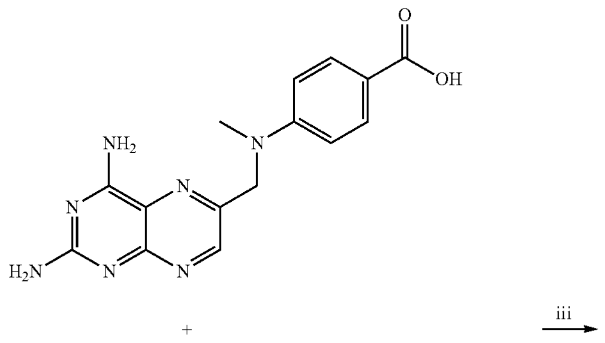
SAR005-015

-continued

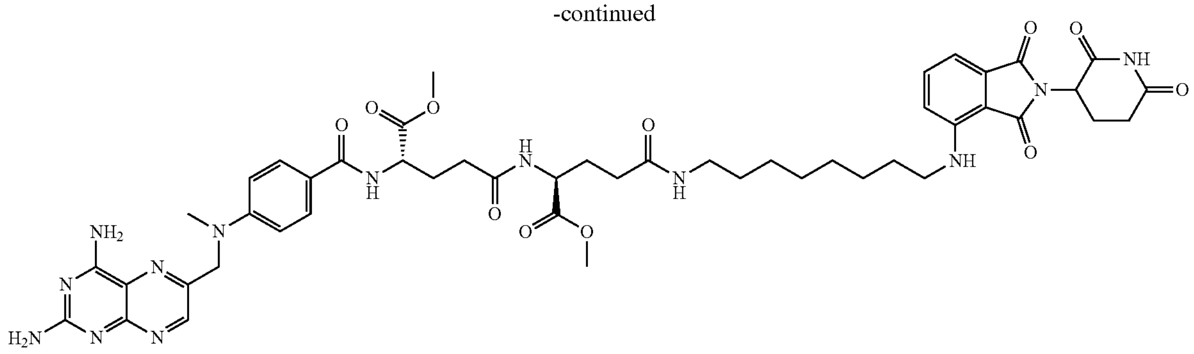

SAR005-019

(i) TCFH, NMI, $CH_3CN$; (ii) 5% Pd/C, Methanol; (iii) PyBOP, $NEt_3$, DMF

Methyl N2-((benzyloxy)carbonyl)-N5-(8-((2-(2,6-dioxopiperidin-3-yl)-1,3-dioxoisoindolin-4-yl)amino)octyl)-L-glutaminate (SAR005-009)

Taken (S)-4-(((benzyloxy)carbonyl)amino)-5-methoxy-5-oxopentanoic acid TFA (Aaron chemicals) (115 mg, 0.389 mmol) and (S)-4-(((benzyloxy)carbonyl)amino)-5-methoxy-5-oxopentanoic acid (115 mg, 0.389 mmol) in Acetonitrile (5 ml) followed by addition of 1-methyl-1H-imidazole (96 mg, 1.166 mmol). Reaction was stirred for 10 minutes followed by addition of N-(chloro(dimethylamino)methylene)-N-methylmethanaminium hexafluorophosphate (V) (142 mg, 0.505 mmol). Reaction was stirred for 1 h, Solvent was evaporated and purified by silica gel column chromatographed to yield desired product (110 mg, 42%).

LC-MS retention time: 3.32 min (method 1)

MS-ESI (+) calcd m/z for $C_{35}H_{43}N_5O_9^+$ 678.31 (M+H)$^+$. found 678.3.

1H NMR (400 MHz, DMSO-d6) δ 11.07 (s, 1H), 7.79-7.69 (m, 2H), 7.55 (t, J=7.8 Hz, 1H), 7.32 (q, J=8.6, 7.9 Hz, 4H), 7.06 (d, J=8.6 Hz, 1H), 6.99 (d, J=7.1 Hz, 1H), 6.51 (d, J=6.8 Hz, 1H), 5.73 (s, 1H), 5.07-4.99 (m, 1H), 5.00 (s, 2H), 4.00 (td, J=8.6, 5.1 Hz, 1H), 3.60 (s, 2H), 3.25 (s, 1H), 2.97 (q, J=6.5 Hz, 2H), 2.93-2.79 (m, 1H), 2.67 (s, 6H), 2.61-2.50 (m, 2H), 2.48 (d, J=5.7 Hz, 2H), 2.12 (t, J=7.5 Hz, 2H), 1.96 (ddt, J=34.0, 13.2, 5.5 Hz, 2H), 1.80-1.66 (m, 1H), 1.52 (dt, J=17.0, 8.5 Hz, 2H), 1.35 (s, 1H), 1.31 (dd, J=14.2, 7.9 Hz, 5H), 1.22 (d, J=6.0 Hz, 5H).

Methyl N5-(8-((2-(2,6-dioxopiperidin-3-yl)-1,3-dioxoisoindolin-4-yl)amino)octyl)-L-glutaminate (SAR005-011)

Taken methyl N2-((benzyloxy)carbonyl)-N5-(8-((2-(2,6-dioxopiperidin-3-yl)-1,3-dioxoisoindolin-4-yl)amino)octyl)-L-glutaminate (100 mg, 0.148 mmol) in methanol (5 ml) followed by addition of 10% Pd—C (15.70 mg, 0.015 mmol). Reaction was vacuumed 5 times followed by purging hydrogen. Reaction was stirred for 3 hours at the room temperature. The crude was filtered through celite and washed methanol. The solvent was evaporated to yield SAR005-011.

LC-MS retention time: 2.92 min (method 1).

MS-ESI (+) calcd m/z for $C_{27}H_{37}N_5O_7^+$ 544.27 (M+H)$^+$. found 544.3; 1H NMR (400 MHz, Methanol-d4) δ 7.53 (dd, J=8.5, 7.2 Hz, 1H), 7.01 (d, J=7.7 Hz, 2H), 5.05 (dd, J=12.6, 5.5 Hz, 1H), 3.71 (s, 2H), 3.47 (dd, J=7.2, 5.9 Hz, 1H), 3.30 (d, J=14.0 Hz, 1H), 3.14 (t, J=7.0 Hz, 2H), 2.93-2.83 (m, 1H), 2.80 (s, 9H), 2.79-2.63 (m, 2H), 2.33-2.18 (m, 2H), 2.15-1.79 (m, 2H), 1.65 (p, J=7.0 Hz, 2H), 1.48 (t, J=6.8 Hz, 1H), 1.46-1.31 (m, 6H).

Methyl N2-((benzyloxy)carbonyl)-N5-((2S)-5-((8-((2-(2,6-dioxopiperidin-3-yl)-1,3-dioxoisoindolin-4-yl)amino)octyl)amino)-1-methoxy-1,5-dioxopentan-2-yl)-L-glutaminate (SAR005-013)

Taken methyl N5-(8-((2-(2,6-dioxopiperidin-3-yl)-1,3-dioxoisoindolin-4-yl)amino)octyl)-L-glutaminate SAR005-011 (75 mg, 0.138 mmol) and (S)-4-(((benzyloxy)carbonyl)amino)-5-methoxy-5-oxopentanoic acid (48.9 mg, 0.166 mmol) in acetonitrile (5 ml) followed by addition of 1-methyl-1H-imidazole (34.0 mg, 0.414 mmol). Reaction was stirred for 10 minutes followed by addition of N-(chloro(dimethylamino)methylene)-N-methylmethanaminium hexafluorophosphate(V) (46.5 mg, 0.166 mmol). Reaction was stirred for 1 hour. After completion of the reaction, the solvent was under the reduced pressure and the compound was purified by silica gel column chromatographed to yield SAR005-013 product. MS-ESI (+) calcd m/z for $C_{41}H_{52}N_6O_{12}^+$ 821.36 (M+H)$^+$. found 821.4; LC: 3.28 min (method 1).

Methyl N5-((2S)-5-((8-((2-(2,6-dioxopiperidin-3-yl)-1,3-dioxoisoindolin-4-yl)amino)octyl)amino)-1-methoxy-1,5-dioxopentan-2-yl)-L-glutaminate (SAR005-015)

Taken methyl N2-((benzyloxy)carbonyl)-N5-((2S)-5-((8-((2-(2,6-dioxopiperidin-3-yl)-1,3-dioxoisoindolin-4-yl)amino)octyl)amino)-1-methoxy-1,5-dioxopentan-2-yl)-L-glutaminate (70 mg, 0.085 mmol) in methanol (4 ml) followed by addition of 10% Pd—C (9.07 mg, 8.53 μmol). Reaction was vacuumed followed by purging hydrogen. Reaction was stirred under hydrogen for additional 3 hours. The compound was filtered through silica and was used as such in the next step. MS-ESI (+) calcd m/z for $C_{33}H_{46}N_6O_{10}^+$ 687.33 (M+H)$^+$, found 687.3; LC: 2.95 min (method 1).

Methyl N2-(4-(((2,4-diaminopteridin-6-yl)methyl)(methyl)amino)benzoyl)-N5-((2S)-5-((8-((2-(2,6-dioxopiperidin-3-yl)-1,3-dioxoisoindolin-4-yl)amino)octyl)amino)-1-methoxy-1,5-dioxopentan-2-yl)-L-glutaminate (SAR005-019; NCGC00687567)

Dissolved 4-(((2,4-diaminopteridin-6-yl)methyl)(methyl)amino)benzoic acid (8.53 mg, 0.026 mmol), and methyl N5-((2S)-5-((8-((2-(2,6-dioxopiperidin-3-yl)-1,3-dioxoisoindolin-4-yl)amino)octyl)amino)-1-methoxy-1,5-dioxopentan-2-yl)-L-glutaminate (18 mg, 0.026 mmol) in DMF (1 ml) followed by the addition of TEA (18.27 μl, 0.131 mmol) and PyBOP (20.46 mg, 0.039 mmol). Reaction mixture was stirred for 24 hours, dilute with $NaHCO_3$ and extracted with ethyl acetate. The solvent was dried under $MgSO_4$ and purified by reverse phase HPLC.

LC-MS retention time: 4.48 min (method 2)

MS-ESI (+) calcd m/z for $C_{48}H_{59}N_{13}O_{11}^+$ 994.45 $(M+H)^+$. found 994.5.

Example 13

Scheme 14

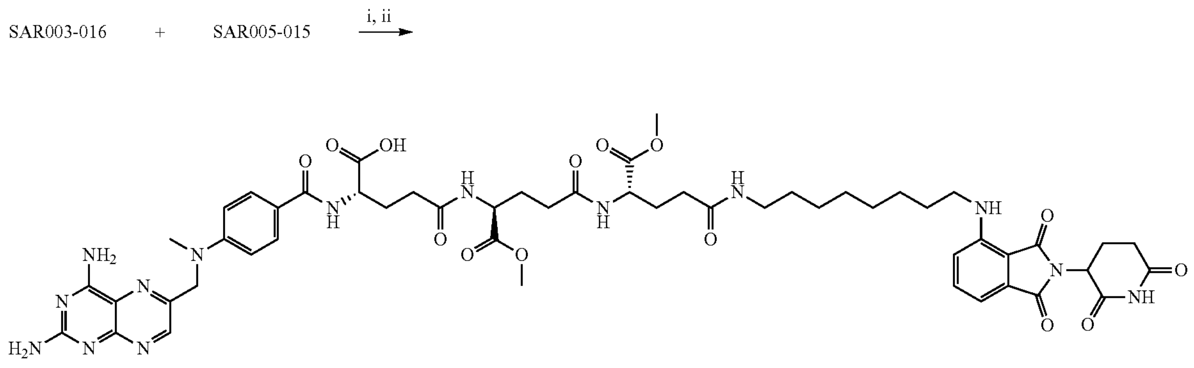

SAR005-022

(i) HATU, DIEA, DMF; (ii) $CF_3COOH$, DCM

N2-(4-(((2,4-diaminopteridin-6-yl)methyl)(methyl)amino)benzoyl)-N5-((2S)-5-(((2S)-5-((8-((2-(2,6-dioxopiperidin-3-yl)-1,3-dioxoisoindolin-4-yl)amino)octyl)amino)-1-methoxy-1,5-dioxopentan-2-yl)amino)-1-methoxy-1,5-dioxopentan-2-yl)-L-glutamine (SAR005-022; NCGC00687569)

This compound was synthesized with (S)-5-(tert-butoxy)-4-(4-(((2,4-diaminopteridin-6-yl)methyl)(methyl)amino)benzamido)-5-oxopentanoic acid and Methyl N5-((2S)-5-((8-((2-(2,6-dioxopiperidin-3-yl)-1,3-dioxoisoindolin-4-yl)amino)octyl)amino)-1-methoxy-1,5-dioxopentan-2-yl)-L-glutaminate using similar conditions reported for SAR003-018.

LC-MS retention time: 4.34 min (method 2)

MS-ESI (+) calcd m/z for $C_{53}H_{66}N_{14}O_{14}^+$ 1123.49 $(M+H)^+$. found 1123.5.

1H NMR (400 MHz, DMSO-d6) δ 12.98 (s, 1H), 12.48 (s, 1H), 11.06 (s, 1H), 9.18 (s, 1H), 8.97 (s, 1H), 8.68 (s, 1H), 8.49 (s, 1H), 8.25 (dd, J=17.0, 7.6 Hz, 3H), 7.73 (t, J=7.3 Hz, 3H), 7.54 (q, J=6.5, 5.0 Hz, 1H), 7.06 (d, J=8.6 Hz, 1H), 6.99 (d, J=7.0 Hz, 1H), 6.80 (d, J=8.6 Hz, 2H), 6.49 (t, J=6.1 Hz, 1H), 5.03 (dd, J=12.9, 5.4 Hz, 1H), 4.85 (s, 2H), 4.32 (td, J=9.1, 4.9 Hz, 1H), 4.17 (dt, J=13.3, 6.1 Hz, 2H), 3.57 (d, J=4.1 Hz, 6H), 3.46 (s, 2H), 3.26 (d, J=6.7 Hz, 2H), 2.98 (q, J=6.9 Hz, 2H), 2.93-2.77 (m, 1H), 2.58 (d, J=3.5 Hz, 1H), 2.53 (d, J=10.0 Hz, 1H), 2.25 (t, J=7.6 Hz, 2H), 2.21-1.98 (m, 5H), 1.96 (s, 8H), 1.92 (qd, J=15.1, 14.3, 4.9 Hz, 2H), 1.71 (s, 2H), 1.77-1.62 (m, 1H), 1.53 (q, J=7.2 Hz, 3H), 1.45 (s, 1H), 1.37-1.25 (m, 7H), 1.25-1.19 (m, 6H).

Example 14
Scheme 15
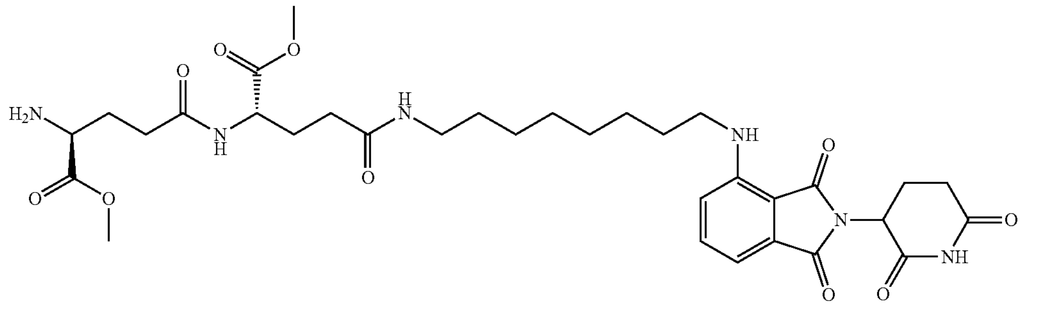
+
SAR005-015
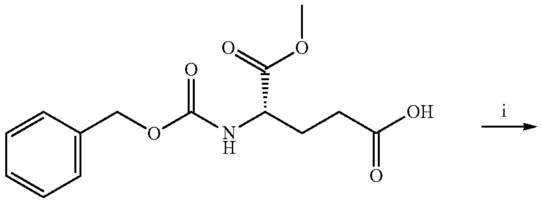
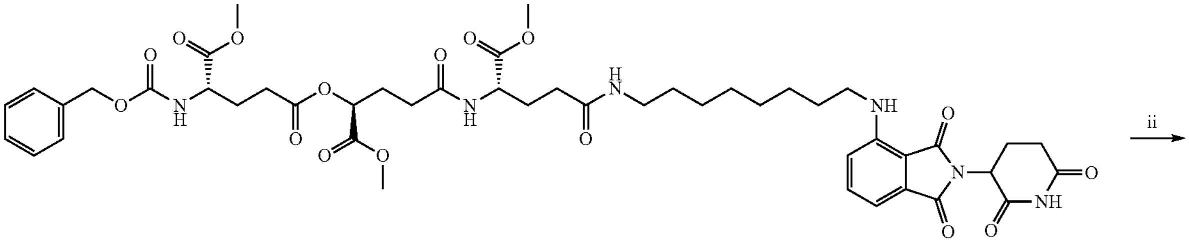
SAR005-036
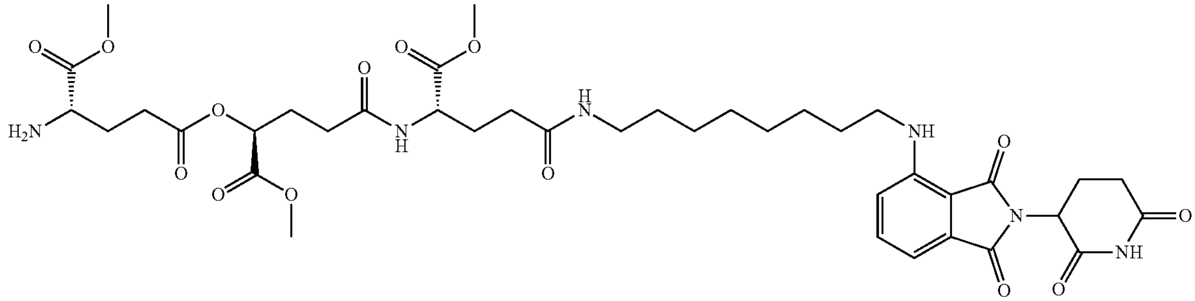
SAR005-040
SAR003-016
+
iii, iv
SAR005-040
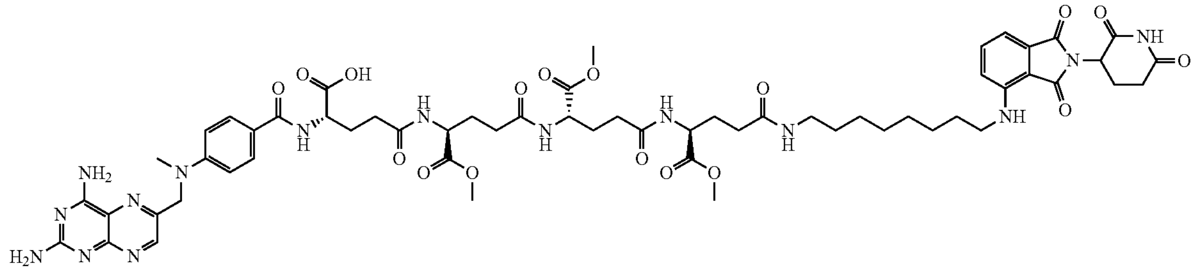
SAR005-044
(i) TCFH, NMI, $CH_3CN$; (ii) 5% Pd/C, Methanol; (iii) PyBOP, $NEt_3$, DMF; (iv) $CF_3COOH$, DCM 5-((2S)-5-(((2S)-5-((8-((2-(2,6-dioxopiperidin-3-yl)-1,3-dioxoisoindolin-4-yl)amino)octyl)amino)-1-methoxy-1,5-dioxopentan-2-yl)amino)-1-methoxy-1,5-dioxopentan-2-yl) 1-methyl((benzyloxy)carbonyl)-L-glutamate (SAR005-036)

The compound was synthesized using procedure reported for SAR005-013.

LC-MS retention time: 3.26 min (method 1)

MS-ESI (+) calcd m/z for $C_{47}H_{60}N_6O_{16}^+$ 965.41 $(M+H)^+$. found 965.4.

1H NMR (400 MHz, Methanol-d4) δ 8.58 (s, 1H), 7.53 (dd, J=8.5, 7.1 Hz, 1H), 7.49-7.40 (m, 2H), 7.40-7.29 (m, 4H), 7.32-7.23 (m, 1H), 7.05-6.98 (m, 2H), 5.10 (s, 2H), 5.04 (dd, J=12.5, 5.5 Hz, 1H), 4.41 (dd, J=9.9, 3.6 Hz, 2H), 4.23 (dd, J=10.2, 4.4 Hz, 1H), 3.90 (s, 3H), 3.69 (d, J=3.4 Hz, 8H), 3.30 (d, J=14.4 Hz, 1H), 3.14 (hept, J=6.7 Hz, 2H), 2.92-2.79 (m, 1H), 2.83-2.63 (m, 3H), 2.38 (hept, J=6.3, 5.7 Hz, 2H), 2.31-2.15 (m, 6H), 2.19-2.04 (m, 1H), 2.00 (s, 1H), 1.93-1.73 (m, 3H), 1.64 (p, J=7.0 Hz, 2H), 1.47 (t, J=6.8 Hz, 2H), 1.44-1.37 (m, 1H), 1.37 (s, 1H), 1.33 (d, J=3.5 Hz, 5H), 1.23 (t, J=7.1 Hz, 1H).

5-((2S)-5-(((2S)-5-((8-((2-(2,6-dioxopiperidin-3-yl)-1,3-dioxoisoindolin-4-yl)amino)octyl)amino)-1-methoxy-1,5-dioxopentan-2-yl)amino)-1-methoxy-1,5-dioxopentan-2-yl) 1-methyl L-glutamate (SAR005-040)

The compound was synthesized using procedure reported for SAR005-015.

LC-MS retention time: 2.96 min (method 1)

MS-ESI (+) calcd m/z for $C_{39}H_{54}N_6O_{14}^+$ 831.37 $(M+H)^+$. found 831.4.

1H NMR (400 MHz, Methanol-d4) δ 7.93 (s, 2H), 7.53 (dd, J=8.5, 7.1 Hz, 1H), 7.20 (s, 2H), 7.11 (s, 2H), 7.02 (dd, J=7.9, 3.5 Hz, 2H), 5.05 (dd, J=12.4, 5.4 Hz, 1H), 4.39 (ddd, J=13.3, 9.1, 4.9 Hz, 2H), 3.99 (q, J=6.7 Hz, 1H), 3.80 (d, J=15.5 Hz, 8H), 3.73-3.63 (m, 7H), 3.31 (dd, J=15.0, 8.2 Hz, 4H), 3.14 (dt, J=8.3, 4.2 Hz, 2H), 2.93-2.79 (m, 1H), 2.83-2.63 (m, 2H), 2.50 (td, J=7.2, 2.2 Hz, 2H), 2.35 (t, J=7.2 Hz, 2H), 2.25 (t, J=7.4 Hz, 2H), 2.13 (ddt, J=25.2, 14.1, 7.1 Hz, 3H), 1.92 (tq, J=15.5, 7.8, 7.2 Hz, 2H), 1.65 (p, J=7.0 Hz, 2H), 1.49 (d, J=6.9 Hz, 1H), 1.48-1.37 (m, 1H), 1.38 (s, 1H), 1.36-1.25 (m, 6H).

(2S,7S,12S,17S)-2-(4-(((2,4-diaminopteridin-6-yl)methyl)(methyl)amino)benzamido)-29-((2-(2,6-dioxopiperidin-3-yl)-1,3-dioxoisoindolin-4-yl)amino)-7,12,17-tris(methoxycarbonyl)-5,10,15,20-tetraoxo-6,11,16,21-tetraazanonacosanoic acid (SAR005-044; NCGC00687807)

This compound was synthesized with (S)-5-(tert-butoxy)-4-(4-(((2,4-diaminopteridin-6-yl)methyl)(methyl)amino)benzamido)-5-oxopentanoic acid and methyl N5-((2S)-5-(((2S)-5-((8-((2-(2,6-dioxopiperidin-3-yl)-1,3-dioxoisoindolin-4-yl)amino)octyl)amino)-1-methoxy-1,5-dioxopentan-2-yl)amino)-1-methoxy-1,5-dioxopentan-2-yl)-L-glutaminate using similar conditions reported for SAR003-018.

LC-MS retention time: 2.97 min (method 1)

MS-ESI (+) calcd m/z for $C_{59}H_{74}N_{14}O_{18}^+$ 1267.53 $(M+H)^+$. found 1267.5.

Example 15

Scheme 16

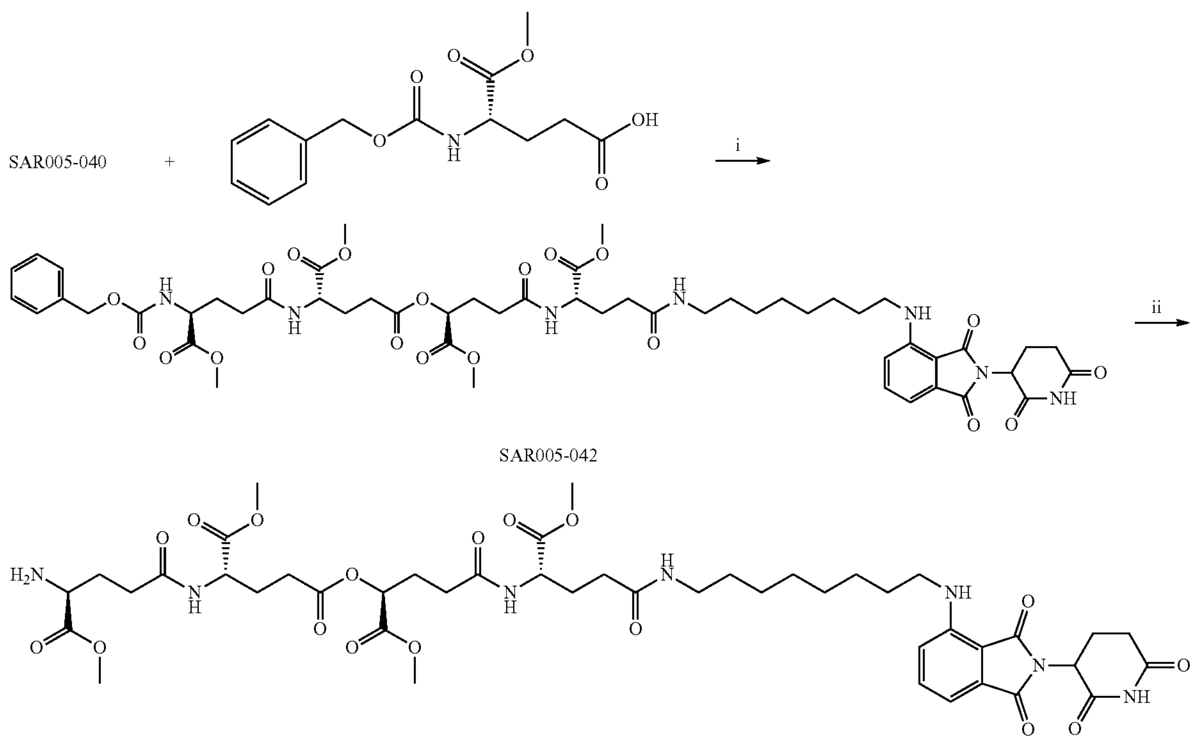

SAR005-042

SAR005-043

-continued

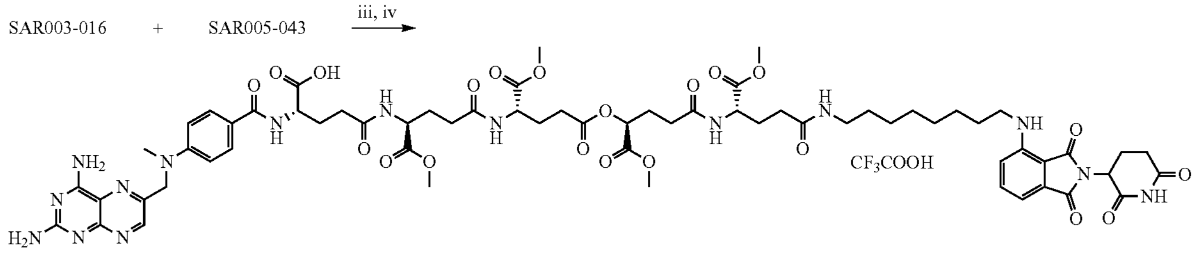

SAR005-046

(i) TCFH, NMI, $CH_3CN$; (ii) 5% Pd/C, Methanol; (iii) HATU, DIEA, DMF; (iv) $CF_3COOH$, DCM 5-((2S)-5-(((2S)-5-((8-((2-(2,6-dioxopiperidin-3-yl)-1,3-dioxoisoindolin-4-yl)amino)octyl)amino)-1-methoxy-1,5-dioxopentan-2-yl)amino)-1-methoxy-1,5-dioxopentan-2-yl) 1-methyl ((S)-4-(((benzyloxy)carbonyl)amino)-5-methoxy-5-oxopentanoyl)-L-glutamate (SAR005-042)

Taken 5-((2S)-5-(((2S)-5-((8-((2-(2,6-dioxopiperidin-3-yl)-1,3-dioxoisoindolin-4-yl)amino)octyl)amino)-1-methoxy-1,5-dioxopentan-2-yl)amino)-1-methoxy-1,5-dioxopentan-2-yl) 1-methyl L-glutamate (67 mg, 0.081 mmol) and (S)-4-(((benzyloxy)carbonyl)amino)-5-methoxy-5-oxopentanoic acid (28.6 mg, 0.097 mmol) in acetonitrile (3 ml) followed by addition of 1-methyl-1H-imidazole (19.86 mg, 0.242 mmol). The reaction was stirred for 10 minutes followed by addition of N-(chloro(dimethylamino)methylene)-N-methylmethanaminium hexafluorophosphate(V) (33.9 mg, 0.121 mmol). Reaction was stirred for an additional 1 hour. The solvent was evaporated and purified by silica gel column chromatography. MS-ESI (+) calcd m/z for $C_{53}H_{69}N_7O_{19}^+$ 1108.46 $(M+H)^+$. found 1108.4; LC-MS retention time: 3.23 min (method 1).

5-((2S)-5-(((2S)-5-((8-((2-(2,6-dioxopiperidin-3-yl)-1,3-dioxoisoindolin-4-yl)amino)octyl)amino)-1-methoxy-1,5-dioxopentan-2-yl)amino)-1-methoxy-1,5-dioxopentan-2-yl) 1-methyl ((S)-4-amino-5-methoxy-5-oxopentanoyl)-L-glutamate (SAR005-043)

Taken 5-((2S)-5-(((2S)-5-((8-((2-(2,6-dioxopiperidin-3-yl)-1,3-dioxoisoindolin-4-yl)amino)octyl)amino)-1-methoxy-1,5-dioxopentan-2-yl)amino)-1-methoxy-1,5-dioxopentan-2-yl) 1-methyl ((S)-4-(((benzyloxy)carbonyl)amino)-5-methoxy-5-oxopentanoyl)-L-glutamate (90 mg, 0.081 mmol) in methanol (3 ml) followed by addition of 10% Pd—C (0.864 mg, 8.12 μmol). Reaction was vacuumed and purged hydrogen three times. The reaction was stirred at room temperature for additional 2 hours. The reaction was filtered through celite and used as such in the next step. MS-ESI (+) calcd m/z for $C_{45}H_{63}N_7O_{17}^+$ 974.43 $(M+H)^+$. found 974.4.

LC-MS retention time: 2.98 min (method 1).

(2S,7S,12S,17S,22S)-2-(4-(((2,4-diaminopteridin-6-yl)methyl)(methyl)amino)benzamido)-34-((2-(2,6-dioxopiperidin-3-yl)-1,3-dioxoisoindolin-4-yl)amino)-7,12,17,22-tetrakis(methoxycarbonyl)-5,10,15,20,25-pentaoxo-6,11,16,21,26-pentaazatetratriacontanoic acid (SAR005-046; NCGC00687811)

This compound was synthesized with (S)-5-(tert-butoxy)-4-(4-(((2,4-diaminopteridin-6-yl)methyl)(methyl)amino)benzamido)-5-oxopentanoic acid and tetramethyl (1S,6S,11S,16S)-1-amino-28-((2-(2,6-dioxopiperidin-3-yl)-1,3-dioxoisoindolin-4-yl)amino)-4,9,14,19-tetraoxo-5,10,15,20-tetraazaoctacosane-1,6,11,16-tetracarboxylate using similar conditions reported for SAR003-018.

LC-MS retention time: 4.42 min (method 2)

MS-ESI (+) calcd m/z for $C_{65}H_{83}N_{15}O_{21}^+$ 1410.59 $(M+H)^+$. found 1410.4.

Example 16

Scheme 17

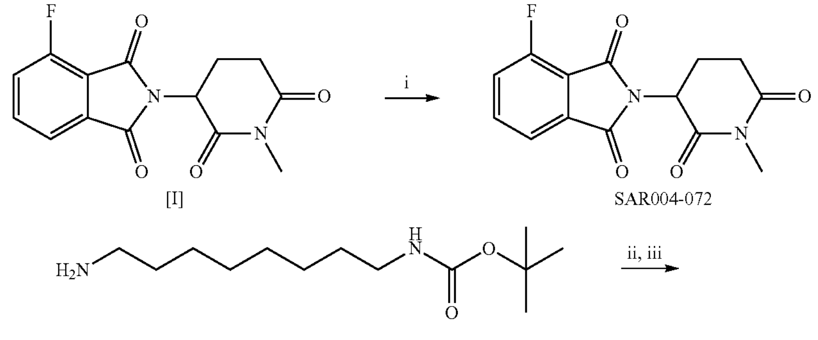

-continued

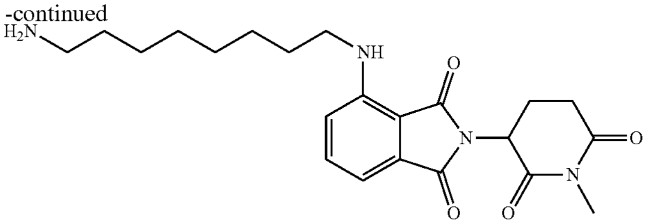

SAR005-018

SAR003-016

+

SAR005-018

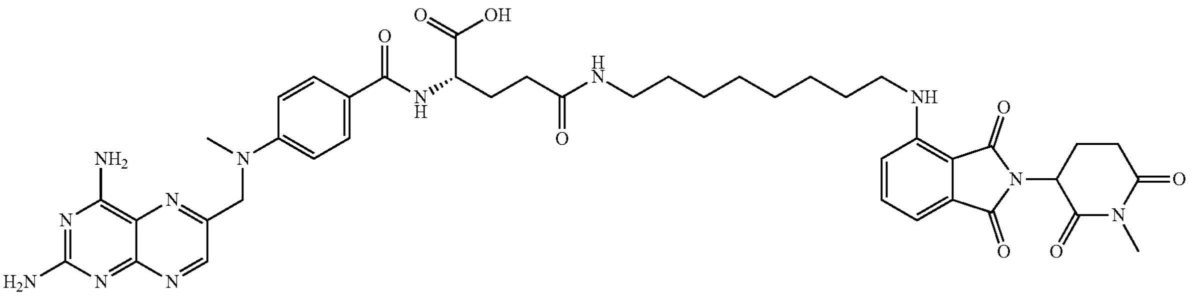

SAR005-054

(i) NaH, $CH_3I$, DMF; (ii) DIEA, DMF; (iii) 4N HCl in dioxane, DCM; (iv) HATU, DIEA, DMF; (v) $CF_3COOH$, DCM 4-fluoro-2-(1-methyl-2,6-dioxopiperidin-3-yl)isoindoline-1,3-dione (SAR004-072)

To a cooled solution of 2-(2,6-dioxopiperidin-3-yl)-4-fluoroisoindoline-1,3-dione (500 mg, 1.810 mmol) in DMF (5 ml) followed by addition of sodium hydride (109 mg, 2.72 mmol). The reaction was stirred for 30 minutes followed by the addition of iodomethane (170 μl, 2.72 mmol). Reaction was stirred for an additional 18 hours. The crude mixture was diluted with ethyl acetate and washed with brine, dried ($MgSO_4$) and concentrated under reduced pressure. The crude was purified by silica gel chromatography to give product.

MS-ESI (+) calcd m/z for $C_{14}H_{11}FN_2O_4^+$ 291.07 $(M+H)^+$. found 291.1; LC-MS retention time: 2.75 min (method 1).

4-((8-aminooctyl)amino)-2-(1-methyl-2,6-dioxopiperidin-3-yl)isoindoline-1,3-dione (SAR005-018)

In a microwave vial, taken 4-fluoro-2-(1-methyl-2,6-dioxopiperidin-3-yl)isoindoline-1,3-dione (100 mg, 0.345 mmol) in DMF (2 ml) followed by the addition of tert-butyl (8-aminooctyl)carbamate (101 mg, 0.413 mmol) and N-ethyl-N-isopropylpropan-2-amine (301 μl, 1.723 mmol). The reaction mixture was heated in a microwave reactor at 110° C. for 2 hours. The crude was washed with $NaHCO_3$ and extract with ethyl acetate, dried $MgSO_4$, and concentrated under reduced pressure. The crude was purified by silica gel chromatography to give tert-butyl (8-((2-(1-methyl-2,6-dioxopiperidin-3-yl)-1,3-dioxoisoindolin-4-yl)amino)octyl)carbamate (72 mg, 0.140 mmol). The compound was further dissolved in DCM (2 ml) followed by addition of HCl (350 μl, 1.399 mmol). The reaction was stirred overnight. Added hexane to the reaction mixture, and sonicated for 30 minutes, followed by filtration to yield product. MS-ESI (+) calcd m/z for $C_{22}H_{30}N_4O_4^+$ 415.23 $(M+H)^+$. found 415.2; LC-MS retention time: 2.93 min (method 1).

N2-(4-(((2,4-diaminopteridin-6-yl)methyl)(methyl)amino)benzoyl)-N5-(8-((2-(1-methyl-2,6-dioxopiperidin-3-yl)-1,3-dioxoisoindolin-4-yl)amino)octyl)-L-glutamine (SAR005-054; NCGC00687847)

This compound was synthesized with (S)-5-(tert-butoxy)-4-(4-(((2,4-diaminopteridin-6-yl)methyl)(methyl)amino)benzamido)-5-oxopentanoic acid and 4-((8-aminooctyl)amino)-2-(1-methyl-2,6-dioxopiperidin-3-yl)isoindoline-1,3-dione (24.36 mg, 0.059 mmol) using similar conditions reported for SAR003-018.

LC-MS retention time: 4.55 min (method 2)

MS-ESI (+) calcd m/z for $C_{42}H_{50}N_{12}O_8^+$ 851.39 $(M+H)^+$. found 851.4.

1H NMR (400 MHz, DMSO-d6) δ 13.00 (s, 1H), 12.43 (s, 1H), 9.23 (s, 1H), 9.01 (s, 1H), 8.69 (s, 1H), 8.55 (s, 1H), 8.27 (d, J=7.4 Hz, 1H), 7.78 (t, J=5.6 Hz, 1H), 7.72 (d, J=8.5 Hz, 2H), 7.56 (t, J=7.8 Hz, 1H), 7.06 (d, J=8.6 Hz, 1H), 7.00 (d, J=7.0 Hz, 1H), 6.80 (d, J=8.5 Hz, 2H), 6.49 (t, J=5.9 Hz, 1H), 5.09 (dd, J=13.0, 5.4 Hz, 1H), 4.85 (s, 2H), 4.26 (td, J=8.4, 8.0, 4.9 Hz, 1H), 3.25 (d, J=6.6 Hz, 2H), 3.22 (s, 3H), 2.98 (d, J=8.5 Hz, 5H), 2.98-2.86 (m, 1H), 2.73 (dt, J=17.3, 3.5 Hz, 1H), 2.54 (dd, J=13.0, 4.3 Hz, 1H), 2.49 (s, 3H), 2.16 (t, J=7.4 Hz, 2H), 2.02 (qt, J=7.8, 4.2 Hz, 2H), 1.90 (dt, J=14.0, 7.2 Hz, 1H), 1.53 (p, J=7.1 Hz, 2H), 1.33 (d, J=6.3 Hz, 1H), 1.33-1.24 (m, 4H), 1.23 (d, J=12.8 Hz, 6H).

Example 17

Scheme 18

SAR003-016 +

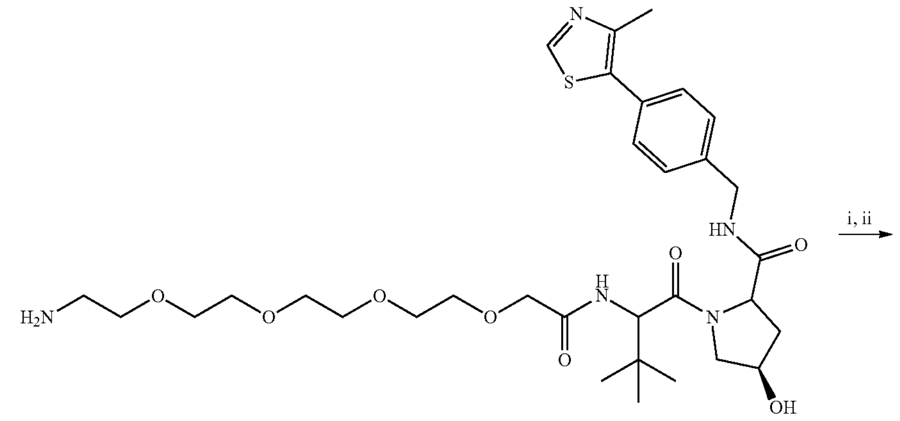

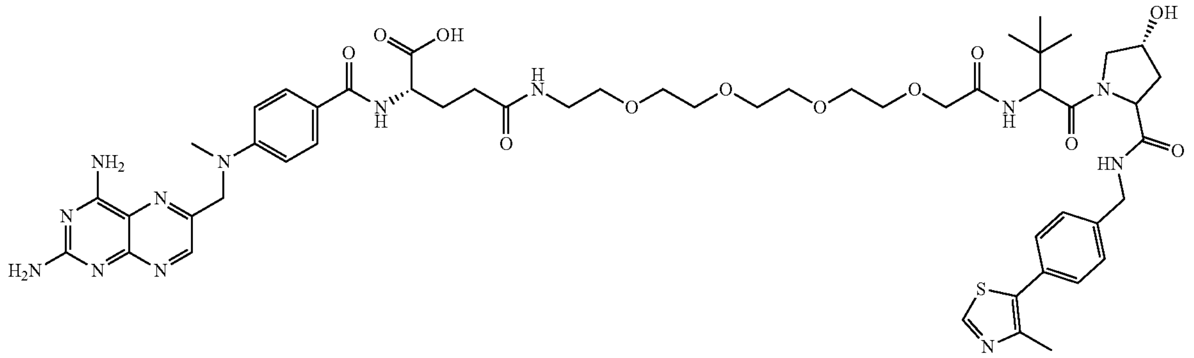

SAR005-055

(i) HATU, DIEA, DMF; (ii) $CF_3COOH$, DCM (23S)-23-(4-(((2,4-diaminopteridin-6-yl)methyl)(methyl)amino)benzamido)-3-((4R)-4-hydroxy-2-((4-(4-methylthiazol-5-yl)benzyl)carbamoyl)pyrrolidine-1-carbonyl)-2,2-dimethyl-5,20-dioxo-7,10,13,16-tetraoxa-4,19-diazatetracosan-24-oic acid (SAR003-026; NCGC00685964 second batch)

This compound was synthesized with (S)-5-(tert-butoxy)-4-(4-(((2,4-diaminopteridin-6-yl)methyl)(methyl)amino)benzamido)-5-oxopentanoic acid and (4R)-1-(17-amino-2-(tert-butyl)-4-oxo-6,9,12,15-tetraoxa-3-azaheptadecanoyl)-4-hydroxy-N-(4-(4-methylthiazol-5-yl)benzyl)pyrrolidine-2-carboxamide·HCl (medchemexpress) using similar conditions reported for SAR003-018.

LC-MS retention time: 2.74 min (method 1)

MS-ESI (+) calcd m/z for $C_{62}H_{59}N_{13}O_{12}S^+$ 1100.49 $(M+H)^+$. found 1100.5.

1H NMR (400 MHz, DMSO-d6) δ 12.97 (s, 1H), 12.43 (s, 1H), 9.26 (s, 1H), 9.06 (s, 1H), 8.96 (s, 1H), 8.69 (s, 1H), 8.56 (t, J=6.1 Hz, 1H), 8.52 (s, 1H), 8.28 (d, J=7.4 Hz, 1H), 7.88 (t, J=5.7 Hz, 1H), 7.72 (d, J=8.5 Hz, 2H), 7.49 (s, 1H), 7.40 (d, J=9.4 Hz, 1H), 7.37 (s, 4H), 6.80 (d, J=8.6 Hz, 2H), 4.85 (s, 2H), 4.54 (d, J=9.5 Hz, 1H), 4.38 (dt, J=27.4, 6.9 Hz, 3H), 4.31-4.18 (m, 2H), 3.94 (s, 2H), 3.61 (s, 1H), 3.69-3.44 (m, 14H), 3.33 (t, J=5.8 Hz, 2H), 3.22 (s, 3H), 3.15 (q, J=5.8 Hz, 2H), 2.42 (s, 3H), 2.18 (t, J=7.6 Hz, 2H), 2.03 (dt, J=15.0, 7.9 Hz, 2H), 1.89 (ddt, J=13.1, 8.4, 4.7 Hz, 2H), 0.92 (s, 9H).

Example 18

Scheme 19

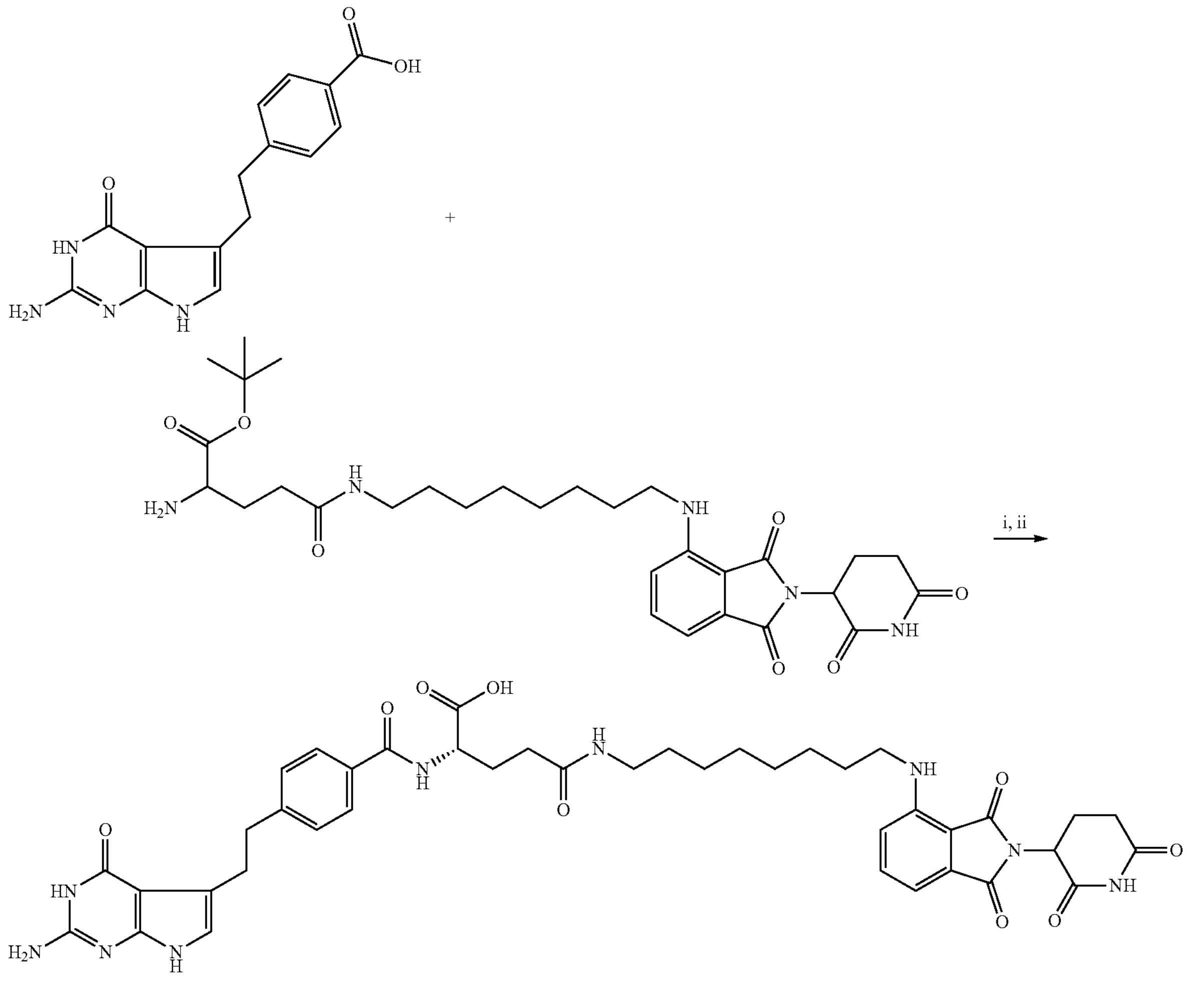

SAR005-057

(i) PyBOP, DIEA, DMSO; (ii) $CF_3COOH$, DCM

N2-(4-(2-(2-amino-4-oxo-4,7-dihydro-3H-pyrrolo[2,3-d]pyrimidin-5-yl)ethyl)benzoyl)-N5-(8-((2-(2,6-dioxopiperidin-3-yl)-1,3-dioxoisoindolin-4-yl)amino)octyl)-L-glutamine (SAR005-057; NCGC00687877)

4-(2-(2-amino-4-oxo-4,7-dihydro-3H-pyrrolo[2,3-d]pyrimidin-5-yl)ethyl)benzoic acid (50 mg, 0.168 mmol) and tert-butyl N5-(8-((2-(2,6-dioxopiperidin-3-yl)-1,3-dioxoisoindolin-4-yl)amino)octyl)glutaminate (118 mg, 0.201 mmol) (A1 Bio Chem Labs) in DMF (1 ml) followed by addition of DIEA (146 µl, 0.838 mmol) and PyBOP (174 mg, 0.335 mmol). Reaction mixture was stirred for 24 hours. Solvent was evaporated and the crude was purified by silica gel column chromatography using 70% ethyl acetate in hexane to yield tert-butyl N2-(4-(((2,4-diaminopteridin-6-yl)methyl)(methyl)amino)benzoyl)-N5-((2S)-5-((8-((2-(2,6-dioxopiperidin-3-yl)-1,3-dioxoisoindolin-4-yl)amino)octyl)amino)-1-methoxy-1,5-dioxopentan-2-yl)-L-glutaminate (60 mg, 41%). The BOC protected acid was dissolved in DCM followed by the addition of excess of TFA. Reaction was stirred for 3 hours. Solvent was evaporated, and crude mixture was purified by reverse phase HPLC to yield desired product as a TFA salt.

LC-MS retention time: 4.45 min (method 2)

MS-ESI (+) calcd m/z for $C_{41}H_{47}N_9O_9^+$ 810.35 $(M+H)^+$. found 811.3.

1H NMR (400 MHz, DMSO-d6) δ 11.06 (s, 1H), 10.23 (s, 1H), 8.54 (d, J=8.0 Hz, 1H), 7.76 (d, J=8.3 Hz, 3H), 7.54 (d, J=8.2 Hz, 1H), 7.26 (d, J=8.1 Hz, 2H), 7.05 (d, J=8.8 Hz, 1H), 6.99 (d, J=7.2 Hz, 1H), 6.48 (s, 1H), 6.30 (s, 1H), 6.10 (s, 2H), 5.02 (dd, J=12.9, 5.6 Hz, 1H), 4.30 (s, 1H), 3.80 (s, 4H), 3.24 (s, 4H), 2.99 (t, J=5.7 Hz, 11H), 2.94 (d, J=8.5 Hz, 4H), 2.84 (q, J=12.6, 7.5 Hz, 4H), 2.56 (d, J=16.1 Hz, 1H), 2.44 (s, 6H), 2.17 (d, J=8.0 Hz, 2H), 2.09-1.96 (m, 3H), 1.91 (s, 2H), 1.70 (q, J=10.1, 8.3 Hz, 11H), 1.52 (q, J=8.5, 7.8 Hz, 3H), 1.31 (t, J=14.7 Hz, 4H), 1.22 (s, 10H), 0.82 (s, 1H).

Example 19

Scheme 20

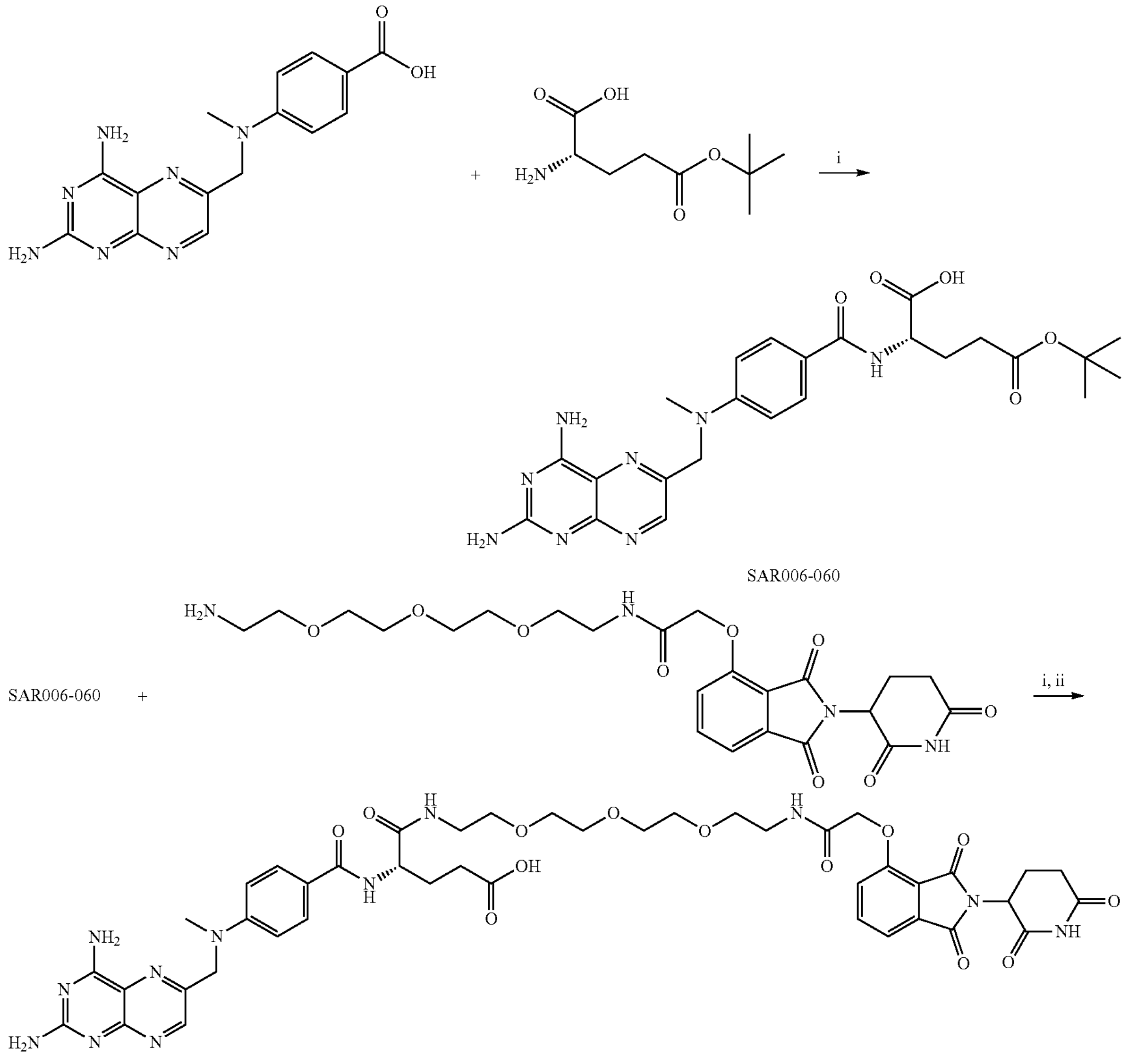

SAR006-060

SAR006-060 +

SAR006-069

(i) HATU, DIEA, DMF; (ii) $CF_3COOH$, DCM (S)-5-(tert-butoxy)-2-(4-(((2,4-diaminopteridin-6-yl)methyl)(methyl)amino)benzamido)-5-oxopentanoic acid (SAR006-060)

Taken 4-(((2,4-diaminopteridin-6-yl)methyl)(methyl)amino)benzoic acid (100 mg, 0.307 mmol) in DMF followed by the addition of HATU (175 mg, 0.461 mmol) and DIEA (268 μl, 1.537 mmol). The reaction was stirred for 15 min followed by the addition of (S)-2-amino-5-(tert-butoxy)-5-oxopentanoic acid (75.0 mg, 0.369 mmol). The reaction mixture was stirred at the room temperature for 24 h. The solvent was removed, and the crude was purified by silica gel column chromatography to yield product as brown solid (100 mg, 0.196 mmol, 63.7% yield).

LC-MS retention time: 2.60 min (method 1)

MS-ESI (+) calcd m/z for $C_{24}H_{30}N_8O_5^+$ 511.23 $(M+H)^+$. found 511.2.

N2-(4-(2-(2-amino-4-oxo-4,7-dihydro-3H-pyrrolo[2,3-d]pyrimidin-5-yl)ethyl)benzoyl)-N5-(2-(2-(2-((2-(2,6-dioxopiperidin-3-yl)-1,3-dioxoisoindolin-4-yl)amino)ethoxy)ethoxy)ethyl)-L-glutamine (SAR005-069; NCGC00689137)

This compound was synthesized using SAR006-060 and N-(2-(2-(2-(2-aminoethoxy)ethoxy)ethoxy)ethyl)-2-((2-(2,6-dioxopiperidin-3-yl)-1,3-dioxoisoindolin-4-yl)oxy)acetamide using conditions reported for SAR005-057.

LC-MS retention time: 3.66 min (method 2)

MS-ESI (+) calcd m/z for $C_{39}H_{43}N_9O_{11}^+$ 814.31 $(M+H)^+$. found 814.3.
1H NMR (400 MHz, DMSO-d6) δ 11.06 (s, 1H), 10.66 (s, 1H), 10.30 (s, 1H), 8.54 (d, J=7.5 Hz, 1H), 7.87 (t, J=5.7 Hz, 1H), 7.76 (d, J=7.9 Hz, 2H), 7.55 (t, J=7.8 Hz, 1H), 7.26 (d, J=8.0 Hz, 2H), 7.11 (d, J=8.6 Hz, 1H), 7.01 (d, J=7.0 Hz, 1H), 6.57 (s, 1H), 6.31 (d, J=2.1 Hz, 1H), 6.18 (s, 2H), 5.03 (dd, J=13.0, 5.3 Hz, 1H), 4.35-4.25 (m, 1H), 3.60-3.41 (m, 11H), 3.36 (t, J=5.9 Hz, 2H), 3.16 (d, J=6.9 Hz, 3H), 2.95 (dd, J=9.4, 6.1 Hz, 2H), 2.91-2.79 (m, 3H), 2.61-2.50 (m, 2H), 2.20 (t, J=7.5 Hz, 2H), 2.12-1.96 (m, 2H), 2.02 (s, 1H), 1.96-1.86 (m, 1H), 1.22 (s, 1H).
Example 720
Scheme 21
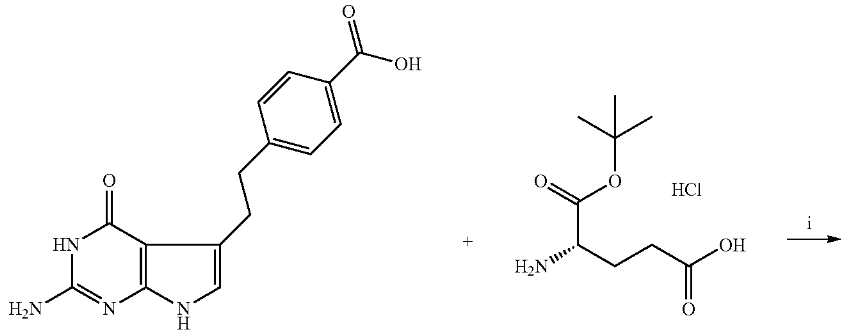
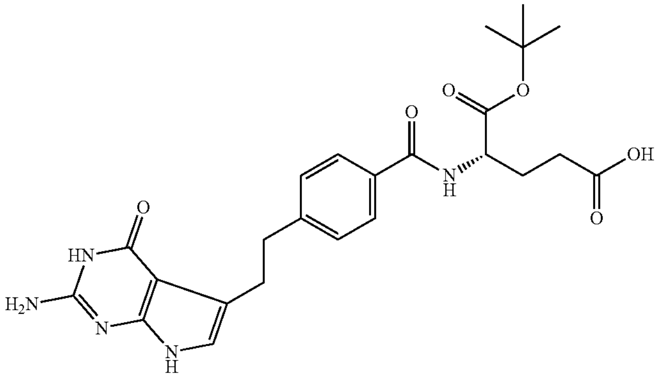
SAR005-073
SAR005-073 +
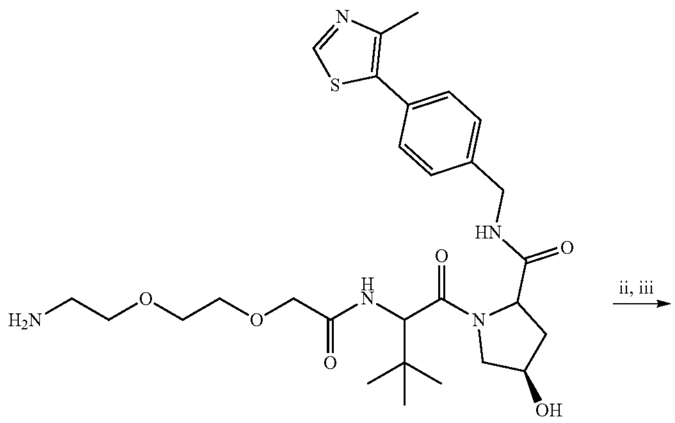

-continued

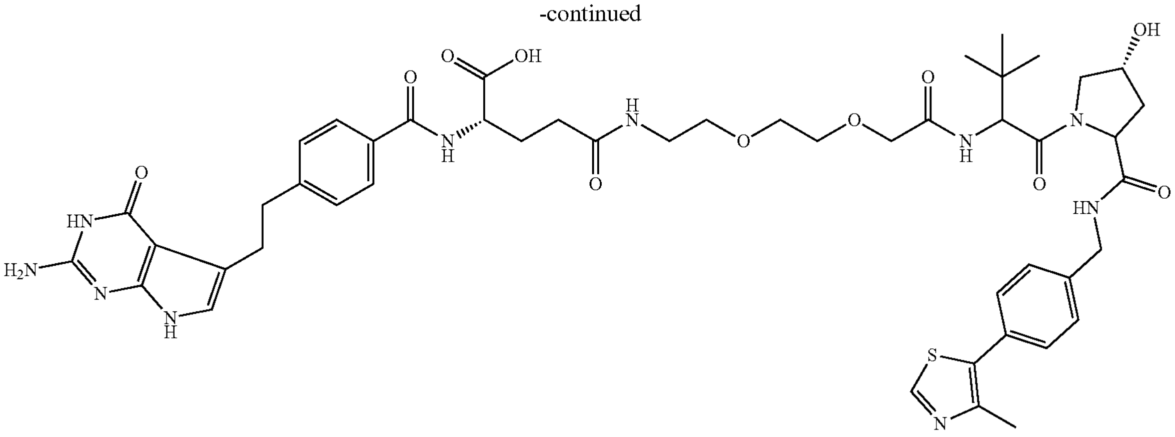

SAR005-083

(i) PyBOP, DIEA, DMSO; (ii) HATU, DIEA, DMF; (iii) $CF_3COOH$, DCM (4S)-4-(4-(2-(2-amino-4-oxo-4,4a,7,7a-tetrahydro-3H-pyrrolo[2,3-d]pyrimidin-5-yl)ethyl)benzamido)-5-(tert-butoxy)-5-oxopentanoic acid (SAR005-073)

To a solution of 4-(2-(2-amino-4-oxo-4,4a,7,7a-tetrahydro-3H-pyrrolo[2,3-d]pyrimidin-5-yl)ethyl)benzoic acid (600 mg, 1.998 mmol) in DMF (3 ml) was added TEA (1392 μl, 9.99 mmol) and PyBOP (1560 mg, 3.00 mmol). The mixture was stirred at 30° C. for 2 hours which resulted in dark brown color solution. In another vial, taken (S)-4-amino-5-(tert-butoxy)-5-oxopentanoic acid HCl (575 mg, 2.397 mmol) in DMF (3 ml) followed by addition of $K_2CO_3$ (276 mg, 1.998 mmol). To this vial was added activated acid and the reaction mixture was stirred at 30° C. for 18 hours. Solvent was evaporated under reduced pressure and the crude was purified by reverse phase HPLC to yield product (300 mg, 25%).

LC-MS retention time: 2.70 min (method 1)

MS-ESI (+) calcd m/z for $C_{24}H_{29}N_5O_6^+$ 484.21 $(M+H)^+$. found 484.2.

(17S)-17-(4-(2-(2-amino-4-oxo-4,4a,7,7a-tetrahydro-3H-pyrrolo[2,3-d]pyrimidin-5-yl)ethyl)benzamido)-3-((4R)-4-hydroxy-2-((4-(4-methylthiazol-5-yl)benzyl)carbamoyl)pyrrolidine-1-carbonyl)-2,2-dimethyl-5,14-dioxo-7,10-dioxa-4,13-diazaoctadecan-18-oic acid (SAR005-083; NCGC00689630)

Taken (S)-4-(4-(2-(2-amino-4-oxo-4,7-dihydro-3H-pyrrolo[2,3-d]pyrimidin-5-yl)ethyl)benzamido)-5-(tert-butoxy)-5-oxopentanoic acid (20 mg, 0.041 mmol) and (4R)-1-(2-(2-(2-(2-aminoethoxy)ethoxy)acetamido)-3,3-dimethylbutanoyl)-4-hydroxy-N-(4-(4-methylthiazol-5-yl)benzyl)pyrrolidine-2-carboxamide·TFA (28.4 mg, 0.041 mmol) in DMF (1 ml) followed by the addition of HATU (23.5 mg, 0.062 mmol) and DIEA (26.6 mg, 0.206 mmol). Reaction was stirred overnight followed by purification via silica gel column chromatography to yield tert-butyl (17S)-17-(4-(2-(2-amino-4-oxo-4,4a,7,7a-tetrahydro-3H-pyrrolo[2,3-d]pyrimidin-5-yl)ethyl)benzamido)-3-((4R)-4-hydroxy-2-((4-(4-methylthiazol-5-yl)benzyl)carbamoyl)pyrrolidine-1-carbonyl)-2,2-dimethyl-5,14-dioxo-7,10-dioxa-4,13-diazaoctadecan-18-oate (20 mg, 0.019 mmol, 46.5% yield). In the subsequent step, Boc protected acid was dissolved in DCM followed by the addition of 10 eq of TFA. Reaction was stirred for 3 h, solvent was evaporated and was purified by reverse phase HPLC for yield final product as a TFA salt.

LC-MS retention time: 3.82 min (method 2)

MS-ESI (+) calcd m/z for $C_{48}H_{60}N_{10}O_{11}S^+$ 985.43 $(M+H)^+$. found 985.4.

1H NMR (400 MHz, DMSO-d6) δ 12.44 (s, 1H), 8.96 (s, 1H), 8.57 (q, J=7.0, 6.4 Hz, 1H), 7.91 (d, J=6.0 Hz, 1H), 7.79 (d, J=7.9 Hz, 1H), 7.41 (d, J=9.4 Hz, 1H), 7.37 (s, 3H), 7.24 (dd, J=12.2, 8.0 Hz, 1H), 6.84 (s, 1H), 4.55 (d, J=9.5 Hz, 1H), 4.40 (dt, J=13.9, 7.0 Hz, 1H), 4.33 (d, J=5.6 Hz, 2H), 4.25 (dd, J=15.9, 5.5 Hz, 1H), 3.94 (s, 2H), 3.61 (dt, J=26.6, 5.6 Hz, 3H), 3.52 (d, J=4.4 Hz, 2H), 3.42-3.35 (m, 2H), 3.24-3.13 (m, 2H), 2.42 (s, 3H), 2.21 (s, 2H), 2.04 (dd, J=13.2, 7.6 Hz, 2H), 1.96-1.83 (m, 2H), 0.92 (s, 7H).

Example 21

Scheme 22

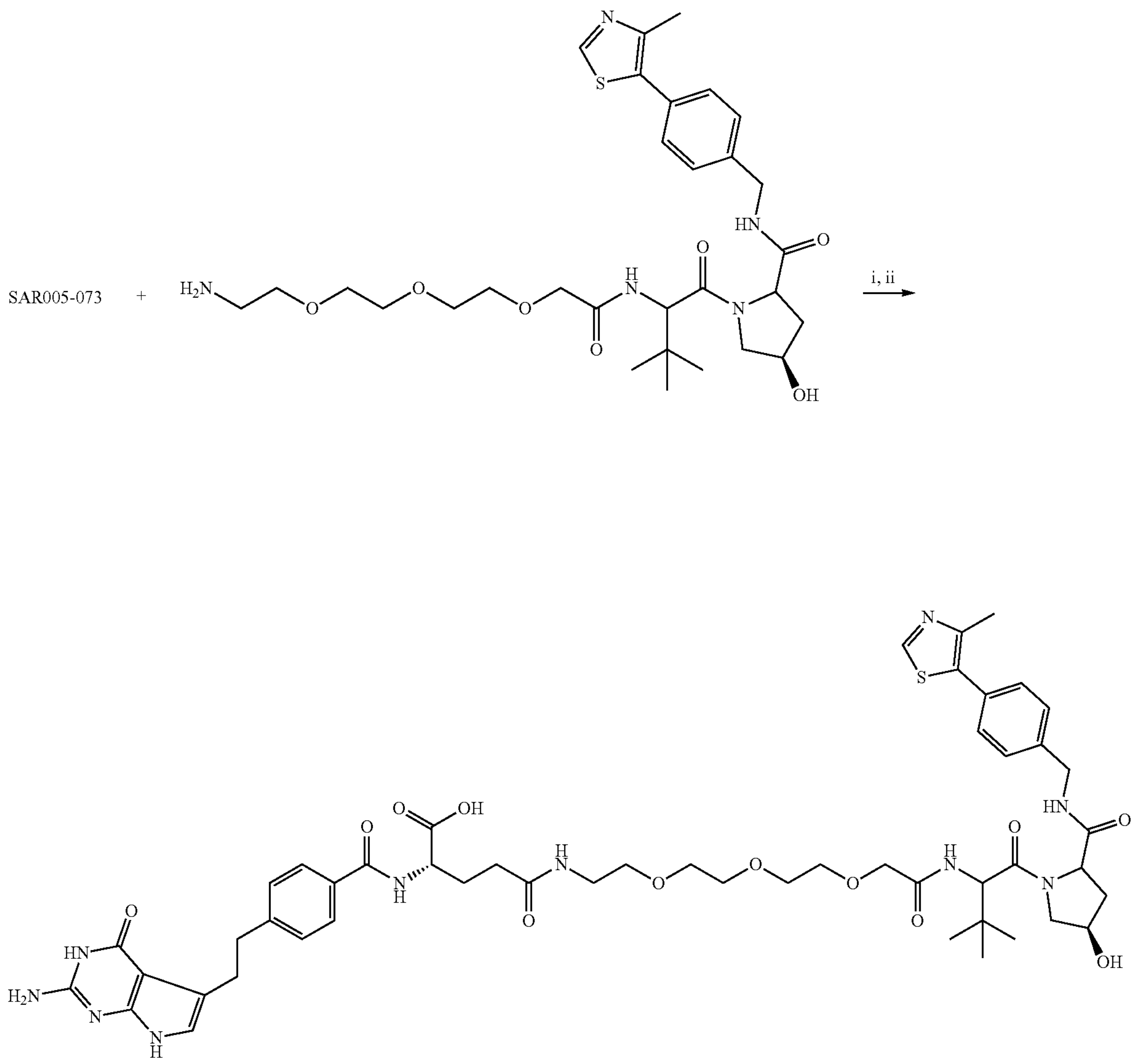

SAR005-084

(i) HATU, DIEA, DMF; (ii) $CF_3COOH$, DCM (20S)-20-(4-(2-(2-amino-4-oxo-4,4a,7,7a-tetrahydro-3H-pyrrolo[2,3-d]pyrimidin-5-yl)ethyl)benzamido)-3-((4R)-4-hydroxy-2-((4-(4-methylthiazol-5-yl)benzyl)carbamoyl)pyrrolidine-1-carbonyl)-2,2-dimethyl-5,17-dioxo-7,10,13-trioxa-4,16-diazahenicosan-21-oic acid (SAR005-084; NCGC00689208)

This compound was synthesized using SAR005-073 and (4R)-1-(14-amino-2-(tert-butyl)-4-oxo-6,9,12-trioxa-3-aza-tetradecanoyl)-4-hydroxy-N-(4-(4-methylthiazol-5-yl)benzyl)pyrrolidine-2-carboxamide·TFA (medchemexpress) using conditions reported for SAR005-083.

LC-MS retention time: 3.83 min (method 2)

MS-ESI (+) calcd m/z for $C_{50}H_{64}N_{10}O_{12}S^+$ 1029.44 $(M+H)^+$. found 1029.4.

1H NMR (400 MHz, DMSO-d6) δ 12.41 (s, 1H), 8.96 (s, 1H), 8.56 (q, J=7.7, 6.8 Hz, 2H), 7.89 (d, J=5.8 Hz, 1H), 7.78 (t, J=7.9 Hz, 2H), 7.40 (d, J=9.6 Hz, 1H), 7.37 (s, 4H), 7.33-7.14 (m, 2H), 6.88 (s, 2H), 6.21 (s, 1H), 4.54 (d, J=9.5 Hz, 1H), 4.46-4.31 (m, 5H), 4.24 (dd, J=15.8, 5.6 Hz, 1H), 3.94 (s, 2H), 3.67 (s, 1H), 3.65-3.44 (m, 9H), 3.39-3.30 (m, 1H), 3.15 (dd, J=7.5, 4.0 Hz, 2H), 2.95 (t, J=7.6 Hz, 1H), 2.84 (d, J=8.3 Hz, 1H), 2.42 (s, 4H), 2.21 (s, 3H), 2.09-1.99 (m, 2H), 1.88 (td, J=12.9, 11.0, 4.6 Hz, 1H), 0.92 (s, 9H).

Example 22

Scheme 23

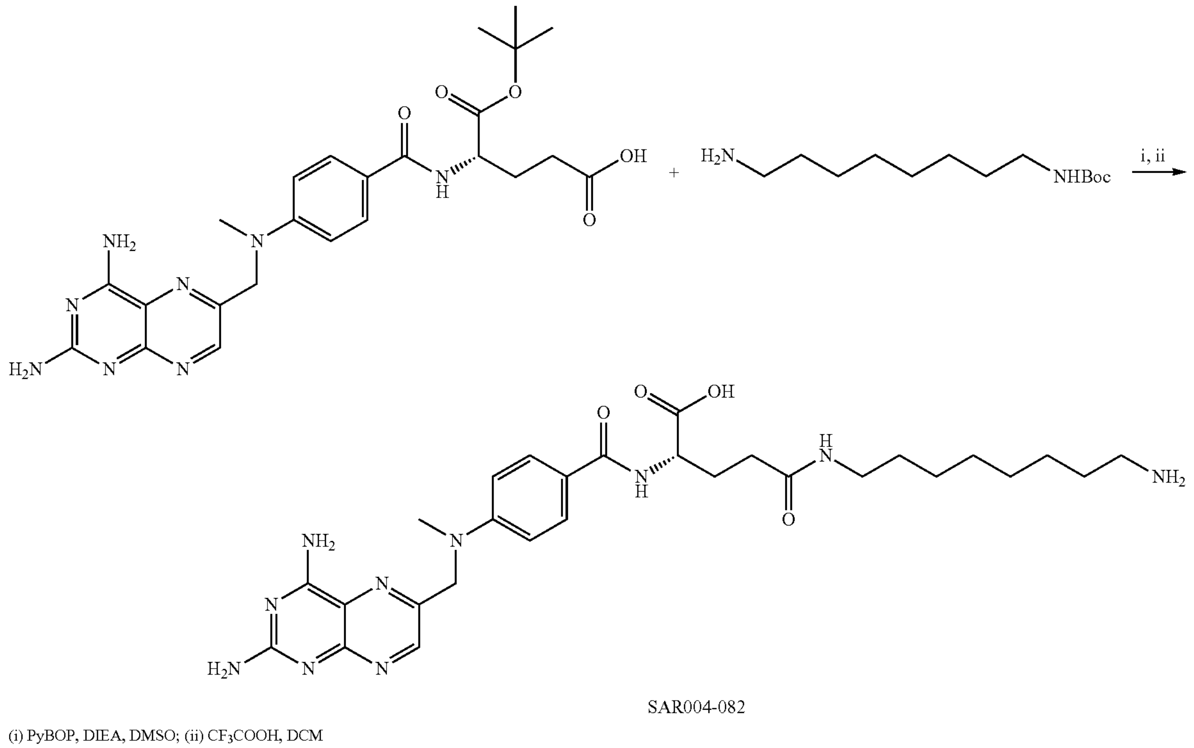

SAR004-082

N5-(8-aminooctyl)-N2-(4-(((2,4-diaminopteridin-6-yl)methyl)(methyl)amino)benzoyl)-L-glutamine (SAR004-082)

(S)-5-(tert-butoxy)-4-(4-(((2,4-diaminopteridin-6-yl)methyl)(methyl)amino)benzamido)-5-oxopentanoic acid (20 mg, 0.039 mmol) and tert-butyl (8-aminooctyl)carbamate (10.53 mg, 0.043 mmol) in DMF (1 ml) followed by addition of DIEA (54.7 μl, 0.313 mmol) and HATU (29.8 mg, 0.078 mmol). Reaction mixture was stirred for 2 h and column chromatographed (18 mg, 62%). Partially purified compound was dissolved in DCM followed by the addition of 10 eq of TFA. Reaction was stirred for 3 h, solvent was evaporated, and the crude was purified by reverse phase HPLC for yield final product as a TFA salt.

LC-MS retention time: 2.06 min (method 1)

MS-ESI (+) calcd m/z for $C_{28}H_{40}N_{10}O_4^+$ 581.32 $(M+H)^+$. found 581.4.

Example 23

Scheme 24

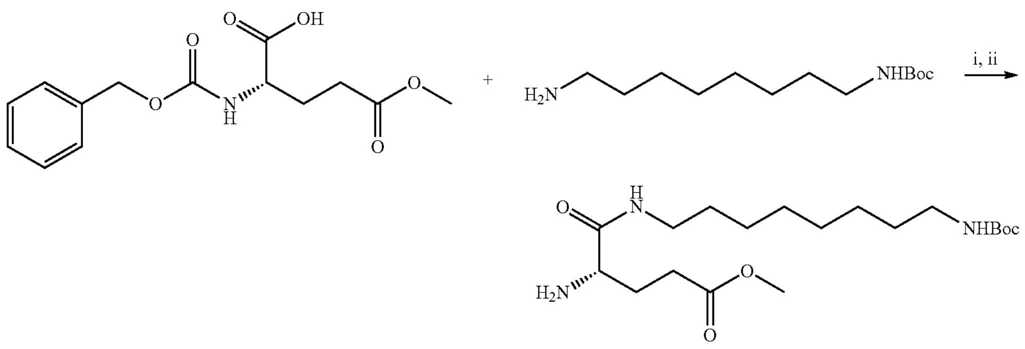

SAR005-089

-continued

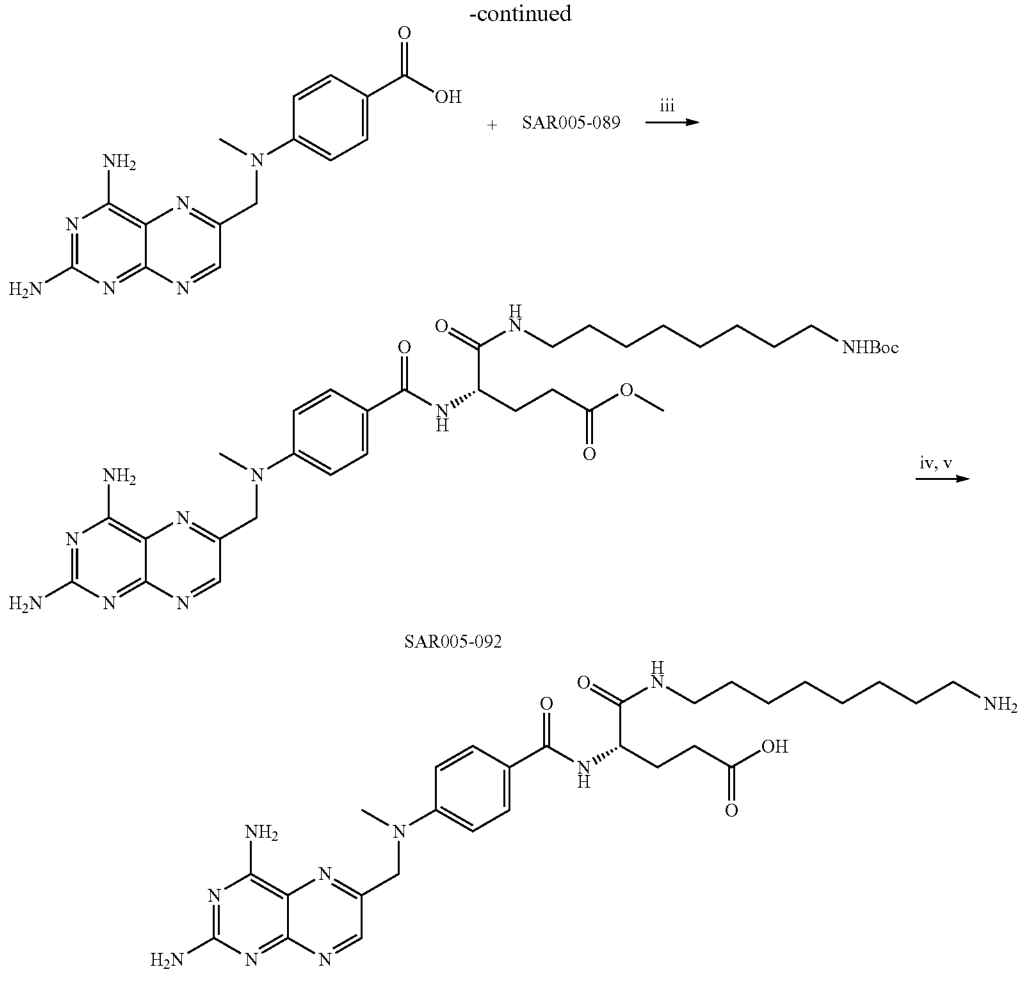

SAR005-096

(i) TCFH, NMI, $CH_3CN$; (ii) Pd/C. MeOH; (iii) PyBOP, DIEA, DMF; (iv) LiOH, MeOH; (v) $CF_3COOH$, DCM Methyl (S)-4-amino-5-((8-((tert-butoxycarbonyl)amino)octyl)amino)-5-oxopentanoate (SAR005-089)

Taken (S)-2-(((benzyloxy)carbonyl)amino)-5-methoxy-5-oxopentanoic acid (300 mg, 1.016 mmol) and tert-butyl (8-aminooctyl)carbamate (248 mg, 1.016 mmol) in Acetonitrile (5 ml) followed by the addition of 1-methyl-1H-imidazole (250 mg, 3.05 mmol) and N-(chloro(dimethylamino)methylene)-N-methylmethanaminium hexafluorophosphate(V) (342 mg, 1.219 mmol). Reaction was stirred at the room temperature for 1 h. Solvent was removed, and the crude was dissolved in DCM and washed brine. The crude was purified by silica gel column chromatography to yield product (330 mg, 62%).

Taken methyl (S)-4-(((benzyloxy)carbonyl)amino)-5-((8-((tert-butoxycarbonyl)amino)octyl)amino)-5-oxopentanoate (310 mg, 0.594 mmol) in methanol (6 ml) followed by the addition of 10% Pd—C (63.2 mg, 0.059 mmol). Reaction was vacuumed and purged with $H_2$ gas. The reaction was stirred for 3 hours and filtered through celite to yield product as an off-white solid (180 mg, 78%)

LC-MS retention time: 3.18 min (method 1)

MS-ESI (+) calcd m/z for $C_{19}H_{37}N_3O_5^+$ 388.27 $(M+H)^+$. found 388.2.

1H NMR (400 MHz, DMSO-d6) δ 7.76 (q, J=5.0, 4.4 Hz, 1H), 6.72 (t, J=5.8 Hz, 1H), 3.55 (s, 2H), 3.03 (ddq, J=19.0, 12.8, 6.4, 5.8 Hz, 3H), 2.86 (q, J=6.6 Hz, 2H), 2.31 (t, J=7.8 Hz, 2H), 1.77 (tdd, J=11.2, 8.1, 4.3 Hz, 2H), 1.63-1.48 (m, 1H), 1.35 (s, 9H), 1.34 (q, J=7.0 Hz, 4H), 1.21 (s, 8H), 1.18 (d, J=6.0 Hz, 1H).

Methyl (S)-5-((8-((tert-butoxycarbonyl)amino)octyl)amino)-4-(4-(((2,4-diaminopteridin-6-yl)methyl)(methyl)amino)benzamido)-5-oxopentanoate (SAR005-092)

To a solution of 4-(((2,4-diaminopteridin-6-yl)methyl)(methyl)amino)benzoic acid (50 mg, 0.154 mmol) in DMF (3 ml) was added TEA (107 μl, 0.768 mmol) and PyBOP (120 mg, 0.231 mmol). The reaction mixture was stirred at 30° C. for 30 minutes resulting in dark brown solution. To this was added a solution of methyl (S)-4-amino-5-((8-((tert-butoxycarbonyl)amino)octyl)amino)-5-oxopentanoate (59.6 mg, 0.154 mmol) in DMF (1 mL). The resulting reaction mixture was stirred for an additional 24 hours. Solvent was removed under reduced pressure and the crude was purified by column chromatography.

(S)-5-((8-aminooctyl)amino)-4-(4-(((2,4-diaminopteridin-6-yl)methyl)(methyl)amino)benzamido)-5-oxopentanoic acid (SAR005-096; NCGC00689560)

The partially purified compound was dissolved in methanol and added 10 eq of LiOH in water. Reaction was stirred for 3 hours. The solvent was evaporated, and the crude was dissolved in DCM and followed by the addition of 10 eq of TFA. Reaction was stirred for 3 hours and solvent was evaporated. The crude was purified by reverse phase HPLC to yield desired product as a TFA salt.

LC-MS retention time: 2.92 min (method 2)

MS-ESI (+) calcd m/z for $C_{28}H_{40}N_{10}O_4^+$ 581.32 $(M+H)^+$. found 581.3.

Example 24

Scheme 25

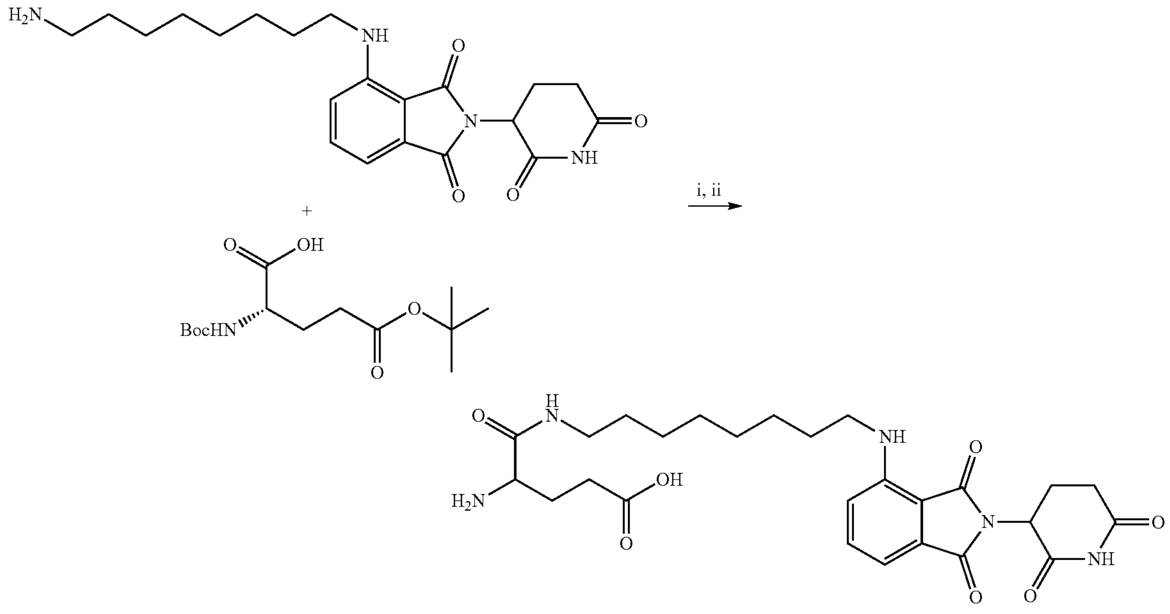

SAR006-036

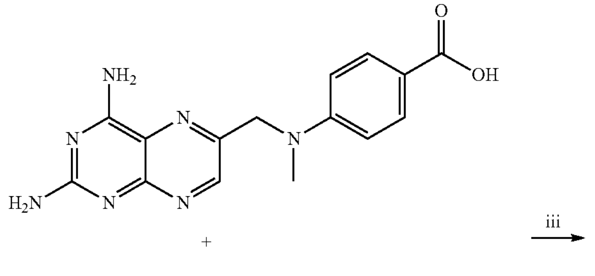

SAR006-036

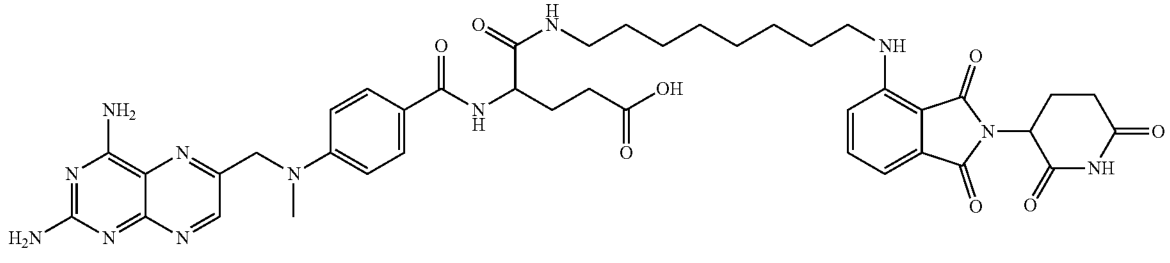

SAR006-037

(i) HATU, DIEA, DMF; (ii) $CF_3COOH$, DCM; (iii) PyBOP, DIEA, DMSO 4-amino-5-((8-((2-(2,6-dioxopiperidin-3-yl)-1,3-dioxoisoindolin-4-yl)amino)octyl)amino)-5-oxopentanoic acid (SAR006-036)

Taken 4-((8-aminooctyl)amino)-2-(2,6-dioxopiperidin-3-yl)isoindoline-1,3-dione (96 mg, 0.240 mmol) and (S)-5-(tert-butoxy)-2-((tert-butoxycarbonyl)amino)-5-oxopentanoic acid·TFA (100 mg, 0.240 mmol) in DMF (2 ml) followed by the addition of HATU (137 mg, 0.359 mmol) and DIEA (209 µl, 1.198 mmol). Reaction was stirred overnight. The crude mixture was dissolved in ethyl acetate and washed with $NH_4Cl$ and brine. The solvent was evaporated and the crude was purified by silica gel column chromatography to yield product (164 mg, 43%). The compound was further dissolved in DCM and added 10 eq. of TFA. Reaction was stirred for 3 h, solvent was removed and used as such in next step.

4-(4-(((2,4-diaminopteridin-6-yl)methyl)(methyl)amino)benzamido)-5-((8-((2-(2,6-dioxopiperidin-3-yl)-1,3-dioxoisoindolin-4-yl)amino)octyl)amino)-5-oxopentanoic acid (SAR006-037; NCGC00690075)

Taken 4-(((2,4-diaminopteridin-6-yl)methyl)(methyl)amino)benzoic acid (15.16 mg, 0.047 mmol) in DMSO (1 ml) followed by the addition of TEA (32.5 µl, 0.233 mmol) and PyBOP (48.5 mg, 0.093 mmol). Reaction was stirred for 30 min. In another vial, taken 4-amino-5-((8-((2-(2,6-dioxopiperidin-3-yl)-1,3-dioxoisoindolin-4-yl)amino)octyl)amino)-5-oxopentanoic acid, TFA (30 mg, 0.047 mmol) in DMSO (1 ml) and added activated acid to it. The reaction was stirred for 24 hours and the crude was purified by reverse phase HPLC to yield product as a TFA salt.

LC-MS retention time: 4.36 min (method 2)

MS-ESI (+) calcd m/z for $C_{41}H_{48}N_{12}O_8^+$ 837.37 $(M+H)^+$. found 837.4.

1H NMR (400 MHz, DMSO-d6) δ 12.95 (s, 1H), 11.07 (s, 1H), 9.26 (s, 1H), 9.06 (s, 1H), 8.69 (s, 1H), 8.60 (s, 2H), 7.98 (d, J=7.9 Hz, 1H), 7.82 (t, J=5.7 Hz, 1H), 7.73 (d, J=8.5 Hz, 2H), 7.55 (t, J=7.8 Hz, 1H), 7.47 (s, 1H), 7.05 (d, J=8.5 Hz, 1H), 6.99 (d, J=7.0 Hz, 1H), 6.79 (d, J=8.6 Hz, 2H), 6.49 (d, J=6.0 Hz, 1H), 5.03 (dd, J=12.9, 5.3 Hz, 1H), 4.85 (s, 2H), 4.33 (td, J=8.5, 5.4 Hz, 1H), 3.24 (d, J=13.6 Hz, 5H), 3.12-3.04 (m, 1H), 3.00 (td, J=6.6, 3.7 Hz, 49H), 2.92-2.81 (m, 1H), 2.57 (d, J=17.6 Hz, 2H), 2.27-2.18 (m, 2H), 2.01 (dt, J=12.4, 4.6 Hz, 2H), 1.94 (t, J=7.3 Hz, 1H), 1.86-1.78 (m, 1H), 1.77-1.66 (m, 47H), 1.52 (q, J=7.2 Hz, 3H), 1.36 (t, J=6.2 Hz, 2H), 1.28 (s, 5H), 1.28-1.20 (m, 7H).

Example 25

Scheme 26

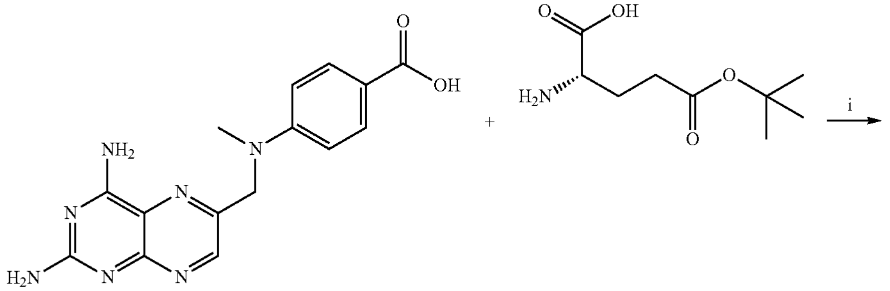

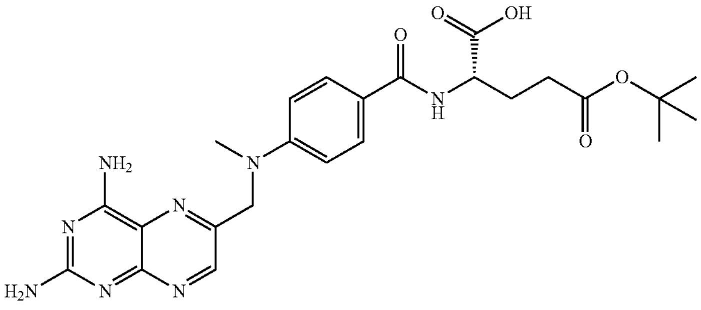

SAR006-060

SAR006-060 +

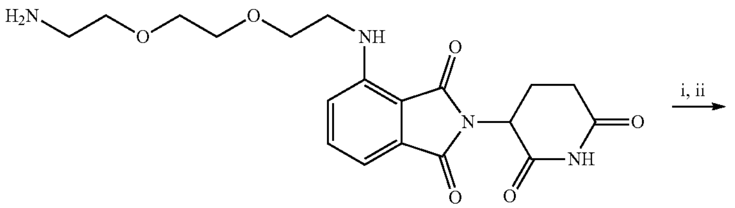

-continued

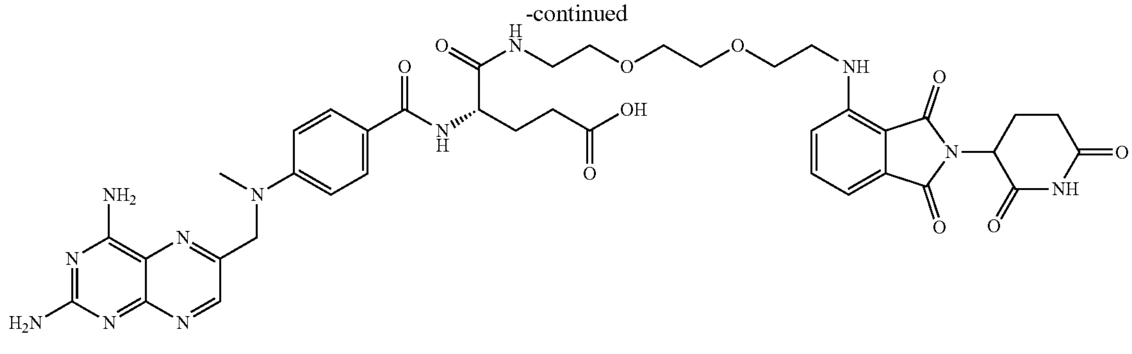

SAR006-067

(i) HATU, DIEA, DMF; (ii) $CF_3COOH$, DCM ((S)-5-(tert-butoxy)-2-(4-(((2,4-diaminopteridin-6-yl)methyl)(methyl)amino)benzamido)-5-oxopentanoic acid (SAR006-060)

Taken 4-(((2,4-diaminopteridin-6-yl)methyl)(methyl)amino)benzoic acid (100 mg, 0.307 mmol) in DMF (2 ml) and added HATU (175 mg, 0.461 mmol) and DIEA (268 µl, 1.537 mmol). Reaction was stirred for 15 minutes followed by the addition of (S)-2-amino-5-(tert-butoxy)-5-oxopentanoic acid (75.0 mg, 0.369 mmol). Continue stirring for additional 24 hours. Solvent was removed and the crude was purified by column chromatography to yield product as a brown solid (100 mg, 64%). LC: 2.66 min (method 1). MS-ESI (+) calcd m/z for $C_{24}H_{30}N_8O_5^+$ 511.23 $(M+H)^+$. found 511.2.

(4S)-4-(4-(((2,4-diaminopteridin-6-yl)methyl)(methyl)amino)benzamido)-5-((2-(2-(2-((2-(2,6-dioxopiperidin-3-yl)-1,3-dioxoisoindolin-4-yl)amino)ethoxy)ethoxy)ethyl)amino)-5-oxopentanoic acid (SAR006-067; NCGC00690407)

Taken (S)-5-(tert-butoxy)-2-(4-(((2,4-diaminopteridin-6-yl)methyl)(methyl)amino)benzamido)-5-oxopentanoic acid (30 mg, 0.059 mmol) in DMF (2 ml) followed by the addition of HATU (33.5 mg, 0.088 mmol) and DIEA (51.3 µl, 0.294 mmol). The reaction was stirred for 15 minutes followed by the addition of 4-((3-aminopropyl)amino)-2-(2,6-dioxopiperidin-3-yl)isoindoline-1,3-dione (19.41 mg, 0.059 mmol). Reaction was stirred overnight. Solvent was removed under reduced pressure and the crude was purified by silica gel column chromatography. Partially purified compound was dissolved in DCM followed by the addition of 10 eq of TFA. Reaction was stirred for 3 h, solvent was evaporated and purified by reverse phase HPLC for yield DP as TFA salt.

LC-MS retention time: 3.42 min (method 2)

MS-ESI (+) calcd m/z for $C_{39}H_{44}N_{12}O_{10}^+$ 841.33 $(M+H)^+$. found 841.4.

1H NMR (400 MHz, DMSO-d6) δ 13.00 (s, 1H), 12.03 (s, 1H), 11.06 (s, 1H), 9.24 (s, 1H), 9.03 (s, 1H), 8.69 (s, 1H), 8.57 (s, 1H), 8.01 (d, J=8.0 Hz, 1H), 7.86 (t, J=5.9 Hz, 1H), 7.73 (d, J=8.5 Hz, 2H), 7.55 (t, J=7.8 Hz, 1H), 7.10 (d, J=8.6 Hz, 1H), 7.01 (d, J=7.0 Hz, 1H), 6.79 (d, J=8.6 Hz, 2H), 6.60-6.46 (m, 1H), 5.03 (dd, J=13.0, 5.3 Hz, 1H), 4.85 (s, 2H), 4.36 (td, J=8.5, 5.4 Hz, 1H), 3.57 (t, J=5.3 Hz, 2H), 3.54-3.47 (m, 4H), 3.46-3.35 (m, 4H), 3.22 (s, 3H), 3.16 (td, J=13.3, 6.7 Hz, 1H), 2.86 (ddd, J=19.0, 14.3, 5.4 Hz, 1H), 2.56 (dd, J=19.4, 6.3 Hz, 2H), 2.27-2.18 (m, 2H), 1.99 (ddt, J=23.8, 14.7, 5.6 Hz, 2H), 1.83 (dq, J=15.5, 8.4 Hz, 1H).

Example 26

Scheme 27

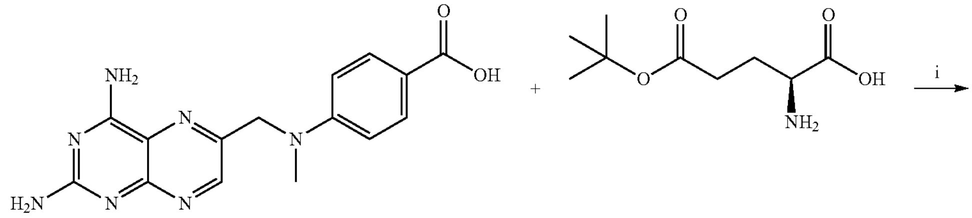

-continued

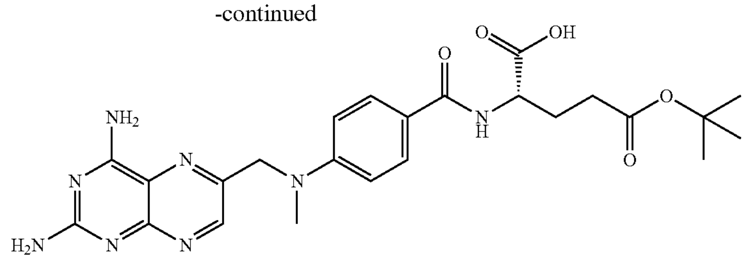

SAR006-060

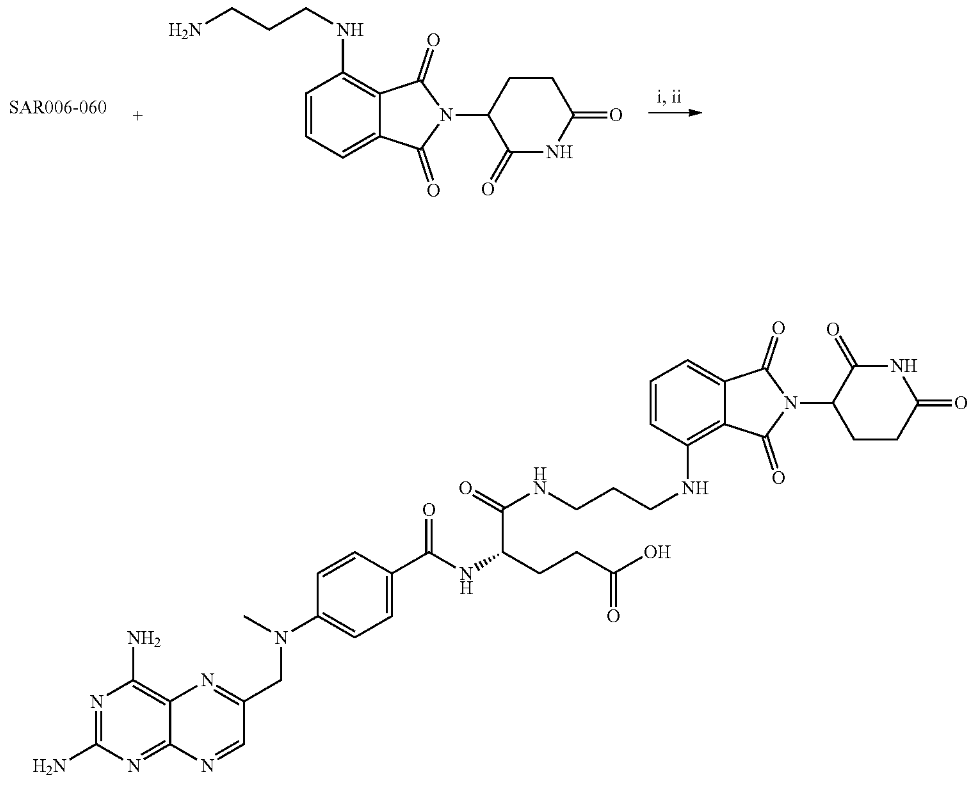

SAR006-068

(i) HATU, DIEA, DMF; (ii) $CF_3COOH$, DCM (4S)-4-(4-(((2,4-diaminopteridin-6-yl)methyl)(methyl)amino)benzamido)-5-((3-((2-(2,6-dioxopiperidin-3-yl)-1,3-dioxoisoindolin-4-yl)amino)propyl)amino)-5-oxopentanoic acid (SAR006-068; NCGC00690412)

Taken (S)-5-(tert-butoxy)-2-(4-(((2,4-diaminopteridin-6-yl)methyl)(methyl)amino)benzamido)-5-oxopentanoic acid (30 mg, 0.059 mmol) in DMF (2 ml) followed by the addition of HATU (33.5 mg, 0.088 mmol) and DIEA (51.3 µl, 0.294 mmol). Reaction was stirred for 15 minutes followed by the addition of 4-((3-aminopropyl)amino)-2-(2,6-dioxopiperidin-3-yl)isoindoline-1,3-dione (19.41 mg, 0.059 mmol). Reaction was stirred overnight. and purified by column chromatography. Partially purified compound was dissolved in DCM followed by the addition of 10 eq of TFA. Reaction was stirred for 3 hours, solvent was evaporated and purified by reverse phase HPLC for yield DP as TFA salt.

LC-MS retention time: 3.41 min (method 2)

MS-ESI (+) calcd m/z for $C_{36}H_{38}N_{12}O_8^+$ 767.29 $(M+H)^+$. found 767.3.

1H NMR (400 MHz, DMSO-d6) δ 12.98 (s, 1H), 12.05 (s, 1H), 11.06 (s, 1H), 9.25 (s, 1H), 9.04 (s, 1H), 8.69 (s, 1H), 8.57 (s, 1H), 8.05 (d, J=7.7 Hz, 1H), 7.99 (t, J=5.9 Hz, 1H), 7.75 (d, J=8.5 Hz, 2H), 7.51 (t, J=7.8 Hz, 1H), 7.05 (d, J=8.5 Hz, 1H), 6.98 (d, J=7.0 Hz, 1H), 6.80 (d, J=8.7 Hz, 2H), 6.67 (t, J=6.3 Hz, 1H), 5.02 (dd, J=12.9, 5.4 Hz, 1H), 4.85 (s, 2H), 4.33 (td, J=8.5, 5.6 Hz, 1H), 3.31-3.23 (m, 2H), 3.12 (dd, J=14.4, 8.0 Hz, 3H), 2.85 (dt, J=18.8, 7.0 Hz, 2H), 2.61-2.52 (m, 1H), 2.24 (dt, J=13.5, 8.6 Hz, 2H), 2.05-1.76 (m, 4H), 1.64 (h, J=6.7 Hz, 2H).

Example 27

Scheme 28

SAR006-060

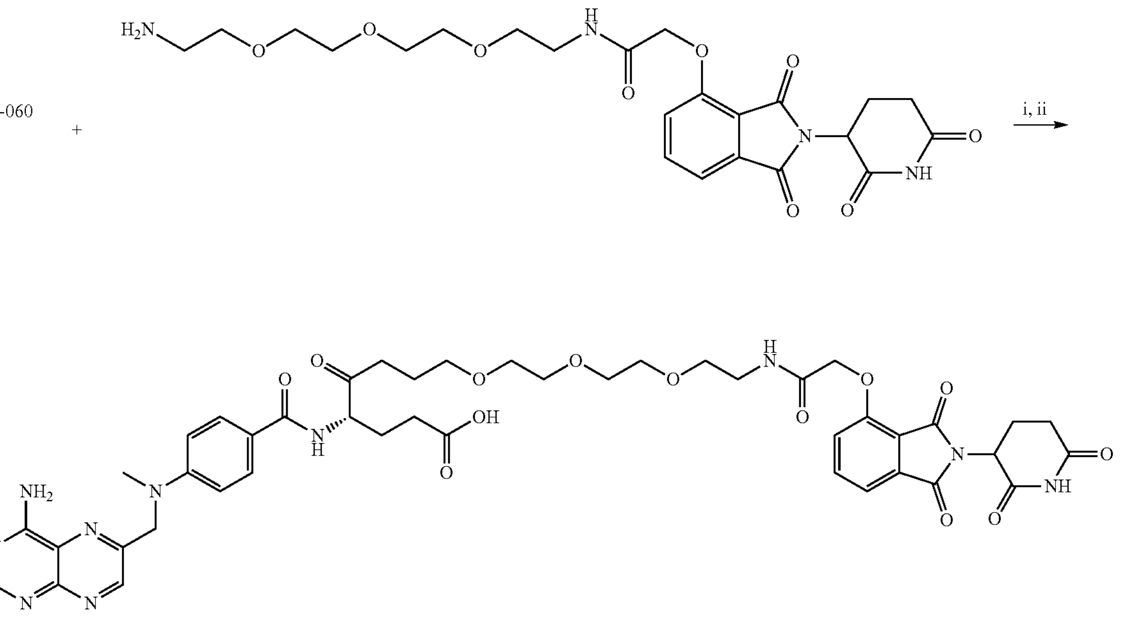

SAR006-069

(i) HATU, DIEA, DMF; (ii) $CF_3COOH$, DCM (17S)-17-(4-(((2,4-diaminopteridin-6-yl)methyl)(methyl)amino)benzamido)-1-((2-(2,6-dioxopiperidin-3-yl)-1,3-dioxoisoindolin-4-yl)oxy)-2,16-dioxo-6,9,12-trioxa-3,15-diazaicosan-20-oic acid (SAR006-069; NCGC00690069)

The compound was synthesized using similar procedure reported for SAR006-068 using (S)-5-(tert-butoxy)-2-(4-(((2,4-diaminopteridin-6-yl)methyl)(methyl)amino)benzamido)-5-oxopentanoic acid and N-(2-(2-(2-(2-aminoethoxy)ethoxy)ethoxy)ethyl)-2-((2-(2,6-dioxopiperidin-3-yl)-1,3-dioxoisoindolin-4-yl)oxy)acetamide·TFA salt.

LC-MS retention time: 2.50 min (method 1)

MS-ESI (+) calcd m/z for $C_{43}H_{50}N_{12}O_{13}^+$ 943.36 $(M+H)^+$. found 943.3.

1H NMR (400 MHz, DMSO-d6) δ 12.97 (s, 1H), 12.01 (s, 1H), 11.09 (s, 1H), 9.25 (s, 1H), 9.05 (s, 1H), 8.69 (s, 1H), 8.58 (s, 1H), 7.99 (q, J=6.7, 5.5 Hz, 2H), 7.89 (q, J=7.6, 5.7 Hz, 1H), 7.77 (dd, J=17.8, 9.8 Hz, 2H), 7.72 (s, 1H), 7.47 (d, J=7.3 Hz, 2H), 7.37 (d, J=8.5 Hz, 1H), 6.79 (d, J=8.6 Hz, 2H), 5.09 (dd, J=12.9, 5.4 Hz, 1H), 4.85 (s, 2H), 4.77 (s, 2H), 4.36 (td, J=8.5, 5.3 Hz, 1H), 3.46 (d, J=7.1 Hz, 11H), 3.44-3.33 (m, 3H), 3.29 (q, J=5.7 Hz, 2H), 3.22 (s, 2H), 3.27-3.08 (m, 2H), 2.94-2.81 (m, 1H), 2.62-2.51 (m, 2H), 2.23 (td, J=8.9, 4.3 Hz, 2H), 2.08-1.89 (m, 2H), 1.83 (dq, J=15.4, 8.3 Hz, 1H).

Example 28

Scheme 29

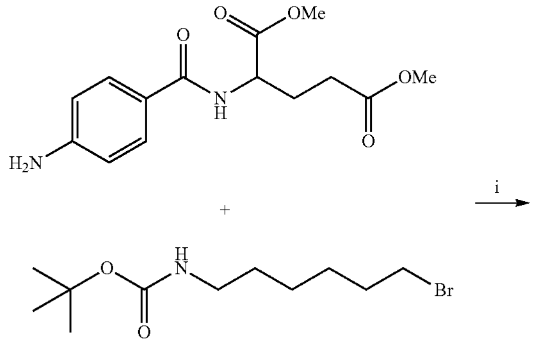

-continued
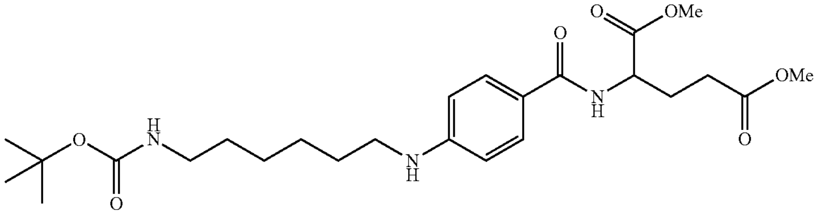
SAR006-003
SAR006-018 +
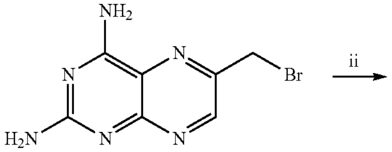
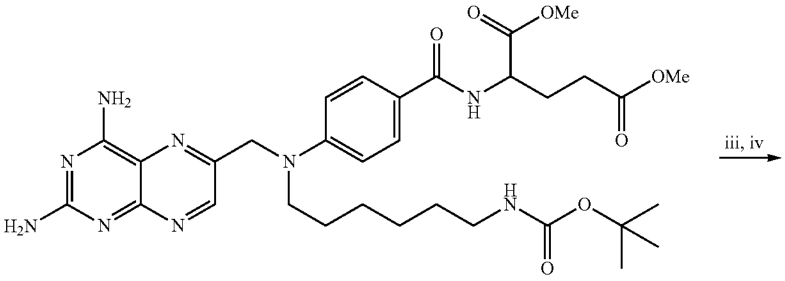
SAR006-019
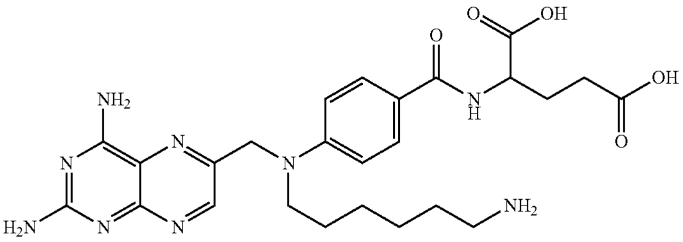
SAR006-022
SAR006-094 +
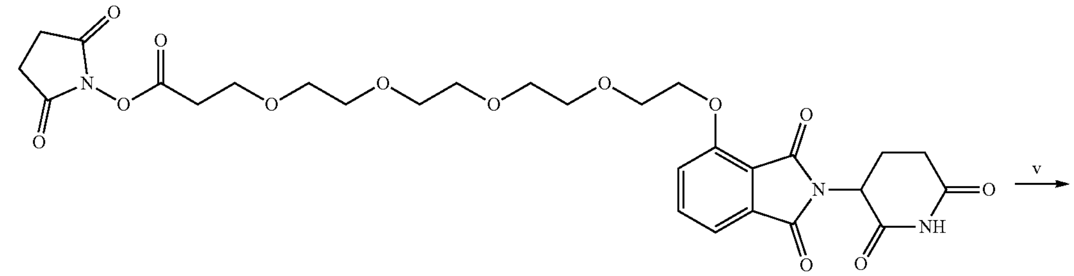
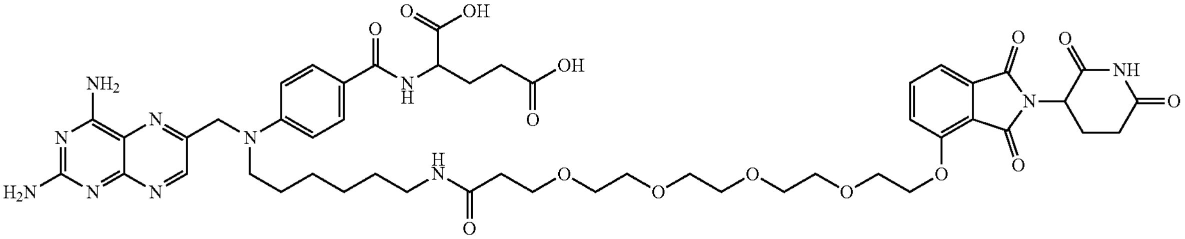
SAR007-001
(i) DIEA, DMF; (ii) DMA; (iii) 1N NaOH, THF: Water; (iv) $CF_3COOH$, DCM; (v) DIEA, DMF dimethyl (4-((6-((tert-butoxycarbonyl)amino)hexyl)amino)benzoyl)glutamate (SAR006-003)

Taken dimethyl (4-aminobenzoyl)glutamate (270 mg, 0.917 mmol) and tert-butyl (6-bromohexyl)carbamate (308 mg, 1.101 mmol) in DMF (3 ml) followed by the addition of DIEA (801 μl, 4.59 mmol). Reaction was stirred at 65° C. for one week. Solvent was evaporated under reduced pressure and the crude was purified by silica gel column chromatography to give product as a reddish brown solid (220 mg, 49%).

LC-MS retention time: 3.13 min (method 1)

MS-ESI (+) calcd m/z for $C_{25}H_{39}N_3O_7^+$ 540.26 $(M+H)^+$. found 494.3.

Dimethyl (4-((6-((tert-butoxycarbonyl)amino)hexyl)((2,4-diaminopteridin-6-yl)methyl)amino)benzoyl)glutamate (SAR 006-019)

Taken 6-(bromomethyl)pteridine-2,4-diamine, HBr (47.6 mg, 0.142 mmol) and dimethyl (4-((6-((tert-butoxycarbonyl)amino)hexyl)amino)benzoyl) glutamate (70 mg, 0.142 mmol) in DMA (2 ml) and stir at 70° C. for 24 hours. Solvent was evaporated under reduced pressure and the crude was purified by silica gel column chromatography to give product as Light green solid (45 mg, 48%).

LC-MS retention time: 2.97 min (method 1)

MS-ESI (+) calcd m/z for $C_{32}H_{45}N_9O_7^+$ 668.34 $(M+H)^+$. found 668.3.

(4-((6-aminohexyl)((2,4-diaminopteridin-6-yl)methyl)amino)benzoyl)glutamic acid (SAR006-022)

Taken dimethyl (4-((6-((tert-butoxycarbonyl)amino)hexyl)((2,4-diaminopteridin-6-yl)methyl)amino)benzoyl)glutamate in dissolved in THF:Water (1:1) followed by the addition of 5 equivalents of 1N NaOH. Reaction was stirred for 3 hours. Solvent was evaporated under reduced pressure and the compound was dissolved in DCM and added 10 eq of TFA. Reaction was stirred for 3 hours. Solvent was removed, and the crude was purified by reverse phase HPLC to yield product as TFA salt.

LC-MS retention time: 2.53 min (method 2)

MS-ESI (+) calcd m/z for $C_{25}H_{33}N_9O_5^+$ 540.26 $(M+H)^+$. found 540.3.

(4-(((2,4-diaminopteridin-6-yl)methyl)(1-((2-(2,6-dioxopiperidin-3-yl)-1,3-dioxoisoindolin-4-yl)oxy)-15-oxo-3,6,9,12-tetraoxa-16-azadocosan-22-yl)amino)benzoyl)glutamic acid (SAR007-001; NCGC00690395)

Taken (4-((6-aminohexyl)((2,4-diaminopteridin-6-yl)methyl)amino)benzoyl)glutamic acid (10 mg, 0.019 mmol) in DMF (1.5 ml) followed by the addition of DIEA (32.4 μl, 0.185 mmol). Reaction was stirred for 10 minutes followed by the addition of solution of 2,5-dioxopyrrolidin-1-yl 1-((2-(2,6-dioxopiperidin-3-yl)-1,3-dioxoisoindolin-4-yl)oxy)-3,6,9,12-tetraoxapentadecan-15-oate (11.48 mg, 0.019 mmol) in DMF. Reaction was stirred overnight and the crude was purified by reverse phase HPLC to give product as a TFA salt.

LC-MS retention time: 2.60 min (method 1)

MS-ESI (+) calcd m/z for $C_{49}H_{61}N_{11}O_{15}^+$ 1044.46 $(M+H)^+$. found 1044.3.

1H NMR (400 MHz, DMSO-d6) δ 12.16 (s, 2H), 11.08 (s, 1H), 8.51 (s, OH), 7.79 (td, J=7.8, 3.5 Hz, 1H), 7.72 (dd, J=20.3, 7.0 Hz, 1H), 7.51 (dd, J=8.6, 5.7 Hz, 1H), 7.44 (dd, J=7.3, 2.1 Hz, 1H), 6.75 (d, J=8.6 Hz, 1H), 5.06 (dd, J=12.8, 5.3 Hz, 1H), 4.80 (s, 1H), 4.32 (p, J=4.1, 3.6 Hz, 2H), 3.78 (q, J=4.1 Hz, 2H), 3.66-3.41 (m, 13H), 3.00 (q, J=6.5 Hz, 1H), 2.86 (ddd, J=16.8, 13.9, 5.4 Hz, 1H), 2.61-2.50 (m, 2H), 2.41 (t, J=6.3 Hz, 1H), 2.27 (dt, J=13.1, 7.0 Hz, 2H), 2.01 (q, J=7.0, 5.4 Hz, 1H), 1.60 (s, 1H), 1.43-1.27 (m, 3H).

Example 29

Scheme 30

SAR006-094 +

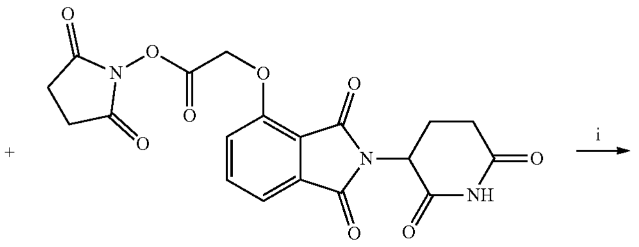

-continued

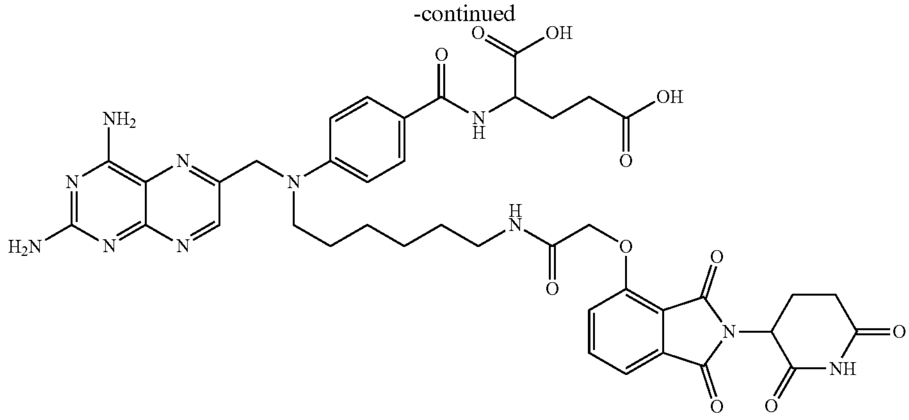

SAR007-002

(i) DIEA, DMF (4-(((2,4-diaminopteridin-6-yl)methyl)(6-(2-((2-(2,6-dioxopiperidin-3-yl)-1,3-dioxoisoindolin-4-yl)oxy)acetamido)hexyl)amino)benzoyl)glutamic acid (SAR007-002; NCGC00690396): Taken 1 eq of (4-((6-aminohexyl)((2,4-diaminopteridin-6-yl)methyl)amino)benzoyl)glutamic acid and 1 eq of 2,5-dioxopyrrolidin-1-yl 2-((2-(2,6-dioxopiperidin-3-yl)-1,3-dioxoisoindolin-4-yl)oxy)acetate in DMF followed by the addition of 3 eq of DIEA. Reaction was stirred overnight and the crude was purified by reverse phase HPLC to give product as a TFA salt.

LC-MS retention time: 3.58 min (method 2)

MS-ESI (+) calcd m/z for $C_{40}H_{43}N_{11}O_{11}^+$ 854.31 $(M+H)^+$. found 854.2.

Example 30

Scheme 31

SAR006-094 +

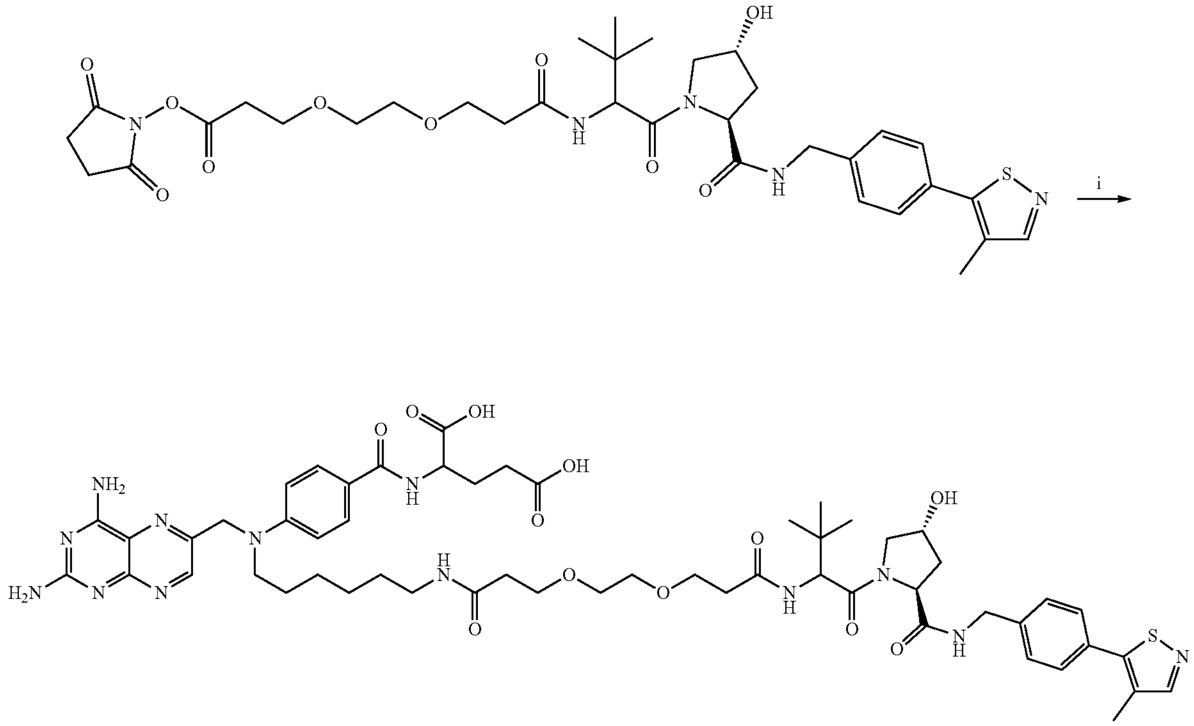

SAR007-006

(i) DIEA, DMF (4-(((2,4-diaminopteridin-6-yl)methyl)(3-((2S,4R)-4-hydroxy-2-((4-(4-methylthiazol-5-yl)benzyl)carbamoyl)pyrrolidine-1-carbonyl)-2,2-dimethyl-5,14-dioxo-8,11-dioxa-4,15-diazahenicosan-21-yl)amino)benzoyl)glutamic acid (SAR007-006; NCGC00690397)

Taken 1 eq of (4-((6-aminohexyl)((2,4-diaminopteridin-6-yl)methyl)amino)benzoyl)glutamic acid and 1 eq of 2,5-dioxopyrrolidin-1-yl 3-(2-(3-((1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-3-oxopropoxy)ethoxy)propanoate in DMF followed by the addition of 3 eq of DIEA. Reaction was stirred overnight and the crude was purified by reverse phase HPLC to give product as a TFA salt.

LC-MS retention time: 2.68 min (method 1)

MS-ESI (+) calcd m/z for $C_{55}H_{73}N_{13}O_{12}S^+$ 1140.52 $(M+H)^+$. found 1140.4.

1H NMR (400 MHz, DMSO-d6) δ 12.96 (s, 1H), 12.32 (s, 2H), 9.27 (s, 1H), 9.09 (s, 1H), 8.96 (s, 1H), 8.64 (s, 1H), 8.54 (t, J=6.1 Hz, 1H), 8.17 (d, J=7.8 Hz, 1H), 7.89 (d, J=9.3 Hz, 1H), 7.76 (t, J=5.6 Hz, 1H), 7.66 (dd, J=24.4, 8.5 Hz, 2H), 7.38 (q, J=8.1 Hz, 4H), 6.75 (d, J=8.5 Hz, 2H), 6.52 (d, J=8.4 Hz, OH), 5.07 (s, 1H), 4.81 (s, 2H), 4.53 (d, J=9.3 Hz, 1H), 4.48-4.15 (m, 6H), 3.65 (dd, J=10.5, 4.1 Hz, 1H), 3.61 (s, 6H), 3.59 (d, J=2.6 Hz, 1H), 3.55 (t, J=7.0 Hz, 5H), 3.43 (d, J=2.4 Hz, 4H), 3.04 (dq, J=33.9, 6.5, 5.7 Hz, 3H), 2.52 (s, 1H), 2.42 (s, 4H), 2.38-2.22 (m, 5H), 2.03 (dt, J=13.9, 7.2 Hz, 2H), 1.88 (ddd, J=12.9, 9.0, 4.5 Hz, 2H), 1.60 (s, 2H), 1.51 (t, J=7.3 Hz, 1H), 1.37 (t, J=6.8 Hz, 2H), 1.31 (s, 6H), 1.24-1.12 (m, 1H), 0.91 (s, 9H).

Example 31

Scheme 32

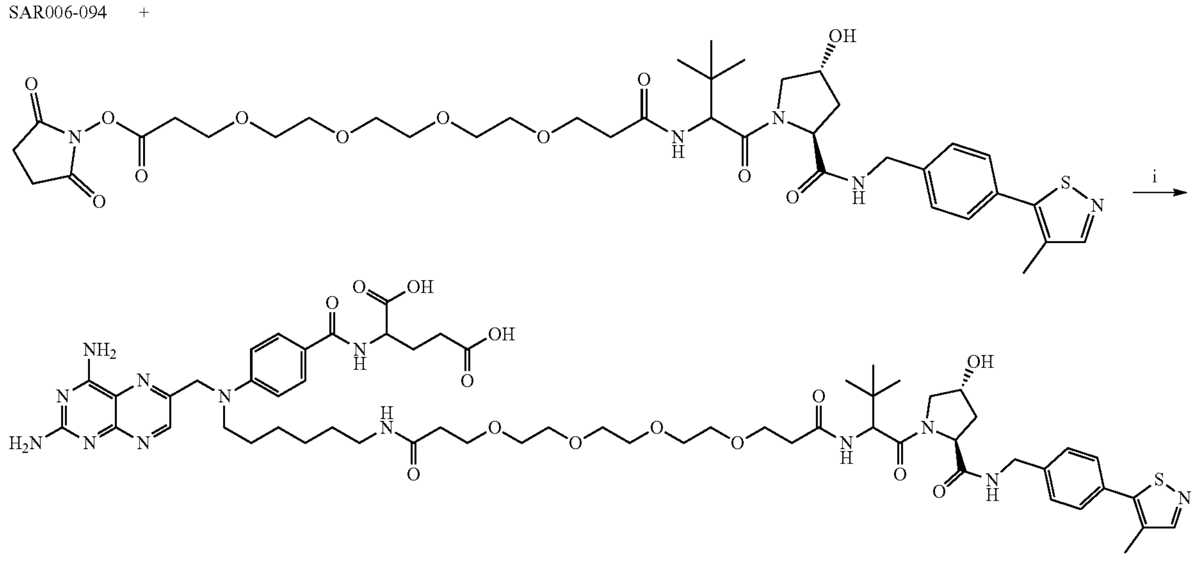

SAR007-007

(i) DIEA, DMF (4-(((2,4-diaminopteridin-6-yl)methyl)(3-((2S,4R)-4-hydroxy-2-((4-(4-methylthiazol-5-yl)benzyl)carbamoyl)pyrrolidine-1-carbonyl)-2,2-dimethyl-5,20-dioxo-8,11,14,17-tetraoxa-4,21-diazaheptacosan-27-yl)amino)benzoyl)glutamic acid (SAR007-007; NCGC00690398)

Taken 1 eq of (4-((6-aminohexyl)((2,4-diaminopteridin-6-yl)methyl)amino)benzoyl)glutamic acid and 1 eq of 2,5-dioxopyrrolidin-1-yl 18-((2S,4R)-4-hydroxy-2-((4-(4-methylthiazol-5-yl)benzyl)carbamoyl)pyrrolidine-1-carbonyl)-19,19-dimethyl-16-oxo-4,7,10,13-tetraoxa-17-azaicosanoate in DMF followed by the addition of 3 eq of DIEA. Reaction was stirred overnight and the crude was purified by reverse phase HPLC to give product as a TFA salt.

LC-MS retention time: 2.69 min (method 1)

MS-ESI (+) calcd m/z for $C_{59}H_{81}N_{13}O_{14}S^+$ 1228.57 $(M+H)^+$. found 1228.5.

Example 32

Scheme 33

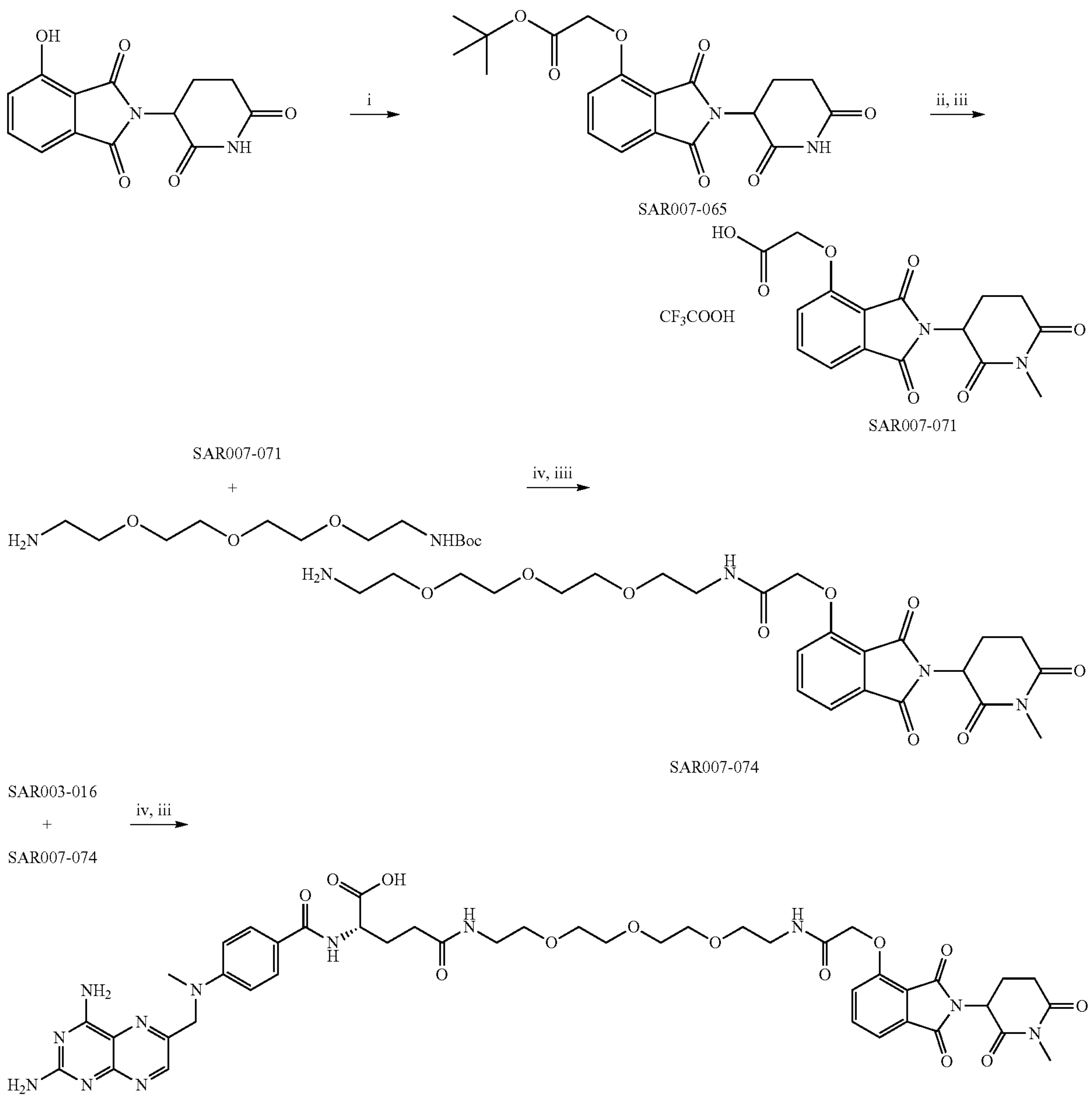

SAR007-065

SAR007-071

SAR007-071 +

SAR007-074

SAR003-016 + SAR007-074

SAR007-087

(i) $BrCH_2COO$-t-Bu, $K_2CO_3$, DMF; (ii) MeI, $K_2CO_3$, DMF; (iii) $CF_3COOH$, DCM; (iv) TCFH, NMI, $CH_3CN$ tert-butyl 2-((2-(2,6-dioxopiperidin-3-yl)-1,3-dioxoisoindolin-4-yl)oxy)acetate (SAR007-065)

Taken 2-(2,6-dioxopiperidin-3-yl)-4-hydroxyisoindoline-1,3-dione (500 mg, 1.823 mmol) in DMF (5 ml) followed by the addition of $K_2CO_3$ (378 mg, 2.73 mmol) and t-butyl 2-bromoacetate (261 μl, 2.006 mmol). Reaction was stirred for 12 hours and diluted with ethyl acetate, washed with brine and dried $MgSO_4$. The solvent was removed under reduced pressure and the crude was purified by silica gel column chromatography to give product (670 mg, 95%).

LC-MS retention time: 3.08 min (method 1)

MS-ESI (+) calcd m/z for $C_{19}H_{20}N_2O_7^+$ 389.13 $(M+H)^+$. found 333.1 (M/Z-t-Bu).

2-((2-(1-methyl-2,6-dioxopiperidin-3-yl)-1,3-dioxoisoindolin-4-yl)oxy)acetic acid (SAR007-071)

Taken tert-butyl 2-((2-(2,6-dioxopiperidin-3-yl)-1,3-dioxoisoindolin-4-yl)oxy)acetate (670 mg, 1.725 mmol) in DMF followed by the addition of $K_2CO_3$ (477 mg, 3.45 mmol) and iodomethane (537 μl, 8.63 mmol). Reaction was stirred at 50° C. for 24 hours. Reaction was stirred for 12 hours and diluted with ethyl acetate, washed with brine and dried $MgSO_4$. The solvent was removed under reduced pressure to yield white solid which was dissolved in DCM and added 10 eq of TFA. Reaction was stirred for 3 hours. Solvent was removed under reduced pressure and was used as such in next step without further purification.

LC-MS retention time: 2.64 min (method 1)

MS-ESI (+) calcd m/z for $C_{16}H_{14}N_2O_7^+$ 347.08 (M+H)$^+$. found 347.2.

1H NMR (400 MHz, DMSO-d6) δ 7.78 (t, J=7.9 Hz, 1H), 7.46 (d, J=7.3 Hz, 1H), 7.38 (d, J=8.6 Hz, 1H), 5.19-5.06 (m, 1H), 4.96 (s, 2H), 3.00 (s, 3H), 2.99-2.86 (m, 1H), 2.74 (dt, J=17.2, 3.8 Hz, 1H), 2.59-2.48 (m, 1H), 2.04 (ddt, J=12.5, 7.6, 3.6 Hz, 1H).

N-(2-(2-(2-(2-aminoethoxy)ethoxy)ethoxy)ethyl)-2-((2-(1-methyl-2,6-dioxopiperidin-3-yl)-1,3-dioxoisoindolin-4-yl)oxy)acetamide (SAR007-074)

Taken 2-((2-(1-methyl-2,6-dioxopiperidin-3-yl)-1,3-dioxoisoindolin-4-yl)oxy)acetic acid, TFA (180 mg, 0.391 mmol) and tert-butyl (2-(2-(2-(2-aminoethoxy)ethoxy)ethoxy)ethyl)carbamate (126 mg, 0.430 mmol) in acetonitrile (5 ml) followed by the addition of TCFH (165 mg, 0.587 mmol) and 1-methyl-1H-imidazole (96 mg, 1.173 mmol). Reaction was stirred for 1 hour. The solvent was removed under reduced pressure and the crude was purified by silica gel column chromatography to give product (180 mg, 74%), which was dissolved in DCM (2 ml) and 10 eq of TFA. Reaction was stirred for 3 hours. Remove solvent and used as such in next step (180 mg, 98%).

LC-MS retention time: 3.11 min (method 1)

MS-ESI (+) calcd m/z for $C_{24}H_{32}N_4O_9$+521.22 (M+H)$^+$. found 521.2.

(19S)-19-(4-(((2,4-diaminopteridin-6-yl)methyl)(methyl)amino)benzamido)-1-((2-(1-methyl-2,6-dioxopiperidin-3-yl)-1,3-dioxoisoindolin-4-yl)oxy)-2,16-dioxo-6,9,12-trioxa-3,15-diazaicosan-20-oic acid (SAR007-087; NCGC00842358)

Taken (S)-5-(tert-butoxy)-4-(4-(((2,4-diaminopteridin-6-yl)methyl)(methyl)amino)benzamido)-5-oxopentanoic acid (121 mg, 0.236 mmol), N-(2-(2-(2-(2-aminoethoxy)ethoxy)ethoxy)ethyl)-2-((2-(1-methyl-2,6-dioxopiperidin-3-yl)-1,3-dioxoisoindolin-4-yl)oxy)acetamide, TFA (150 mg, 0.236 mmol) in anhydrous acetonitrile (10 ml) followed by the addition of TCFH (133 mg, 0.473 mmol) and 1-methyl-1H-imidazole (97 mg, 1.182 mmol). Reaction was stirred for 1 hour. The solvent was removed under reduced pressure and the crude was purified by silica gel column chromatography to give partial purified product which was dissolved in DCM (2 ml) and 10 eq of TFA. Reaction was stirred for 3 hours. Removed solvent and the crude was purified by reverse phase HPLC to give product as a TFA salt.

LC-MS retention time: 3.62 min (method 2)

MS-ESI (+) calcd m/z for $C_{44}H_{52}N_{12}O_{13}^+$ 957.38 (M+H)$^+$. found 957.3.

1H NMR (400 MHz, DMSO-d6) δ 13.03 (s, 1H), 12.46 (s, 1H), 9.26 (s, 1H), 9.05 (s, 1H), 8.69 (s, 1H), 8.59 (s, 1H), 8.26 (dd, J=14.4, 7.5 Hz, 1H), 7.98 (t, J=5.6 Hz, 1H), 7.88 (t, J=5.6 Hz, 1H), 7.79 (dd, J=8.5, 7.3 Hz, 1H), 7.76-7.67 (m, 2H), 7.56 (s, 1H), 7.48 (d, J=7.2 Hz, 1H), 7.38 (d, J=8.5 Hz, 1H), 6.85-6.73 (m, 2H), 5.16 (dd, J=13.0, 5.4 Hz, 1H), 4.85 (s, 2H), 4.76 (s, 2H), 4.27 (ddd, J=9.4, 7.4, 4.9 Hz, 1H), 3.48-3.40 (m, 6H), 3.38-3.20 (m, 6H), 3.15 (q, J=3.8, 3.4 Hz, 3H), 3.00 (s, 3H), 2.99-2.87 (m, 1H), 2.75 (ddd, J=17.2, 4.5, 2.6 Hz, 1H), 2.60-2.49 (m, 1H), 2.18 (t, J=7.7 Hz, 2H), 2.04 (ddt, J=13.7, 6.5, 2.7 Hz, 1H), 1.90 (ddd, J=13.1, 8.9, 6.7 Hz, 1H).

Example 33

Scheme 34

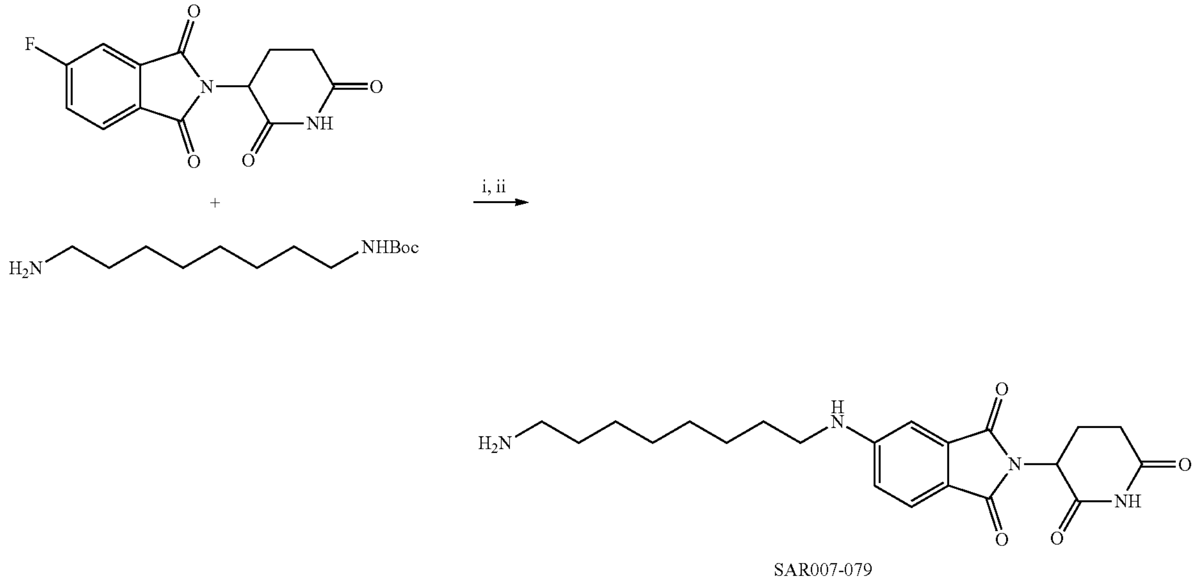

SAR007-079

SAR003-016

\+ iii, ii

SAR007-079

-continued

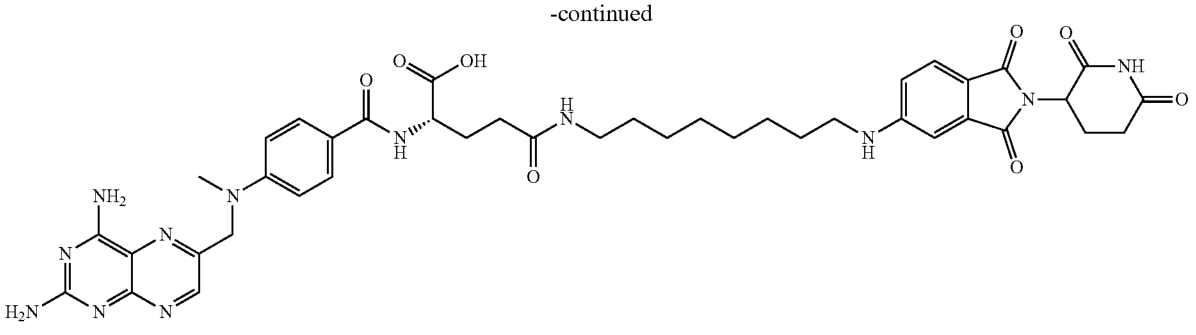

SAR007-094

(i) DIEA, DMF; (ii) $CF_3COOH$, DCM; (iii) TCFH, NMI, $CH_3CN$ 5-((8-aminooctyl)amino)-2-(2,6-dioxopiperidin-3-yl) isoindoline-1,3-dione (SAR007-079)

Taken 2-(2,6-dioxopiperidin-3-yl)-5-fluoroisoindoline-1,3-dione (200 mg, 0.724 mmol) and tert-butyl (8-aminooctyl) carbamate (212 mg, 0.869 mmol) in DMF (2 ml) followed by the addition of DIEA (632 µl, 3.62 mmol). Reaction was stirred at 90° C. for 24 hours. The reaction mixture was diluted with ethyl acetate, washed with brine and dried $MgSO_4$. The solvent was removed under reduced pressure and the crude was purified by silica gel column chromatography to give product. Subsequently, the compound was dissolved in DCM and added 10 eq of TFA. Reaction was stirred for 3 hours and used as such in next step.

LC-MS retention time: 2.65 min (method 1)

MS-ESI (+) calcd m/z for $C_{21}H_{28}N_4O_4^+$ 401.21 $(M+H)^+$. found 401.3.

1H NMR (400 MHz, DMSO-d6) δ 11.04 (s, 2H), 7.64 (s, 7H), 7.54 (d, J=8.3 Hz, 2H), 7.11 (s, 1H), 6.91 (s, 2H), 6.82 (d, J=8.3 Hz, 2H), 5.00 (dd, J=12.9, 5.3 Hz, 2H), 3.13 (t, J=7.0 Hz, 4H), 2.84 (d, J=12.6 Hz, 1H), 2.75 (q, J=6.7 Hz, 4H), 2.60-2.51 (m, 3H), 1.97 (dt, J=11.9, 5.1 Hz, 2H), 1.52 (dp, J=21.6, 7.2 Hz, 9H), 1.37 (s, 1H), 1.35 (s, 1H), 1.35-1.24 (m, 15H).

N2-(4-(((2,4-diaminopteridin-6-yl)methyl)(methyl) amino)benzoyl)-N5-(8-((2-(2,6-dioxopiperidin-3-yl)-1,3-dioxoisoindolin-5-yl)amino)octyl)-L-glutamine (SAR007-094; NCGC00842344)

Amide coupling was done using TCFH and NMI and the crude was dissolved in DCM and added 10 eq of TFA. Solvent was removed and crude was purified by reverse phase HPLC as reported for SAR007-087.

LC-MS retention time: 4.09 min (method 2)

MS-ESI (+) calcd m/z for $C_{41}H_{48}N_{12}O_8^+$ 837.37 $(M+H)^+$. found 837.4.

1H NMR (400 MHz, DMSO-d6) δ 12.97 (s, 1H), 12.43 (s, 1H), 11.03 (s, 1H), 9.24 (s, 1H), 9.03 (s, 1H), 8.69 (s, 1H), 8.28 (d, J=7.4 Hz, 1H), 7.78 (t, J=5.6 Hz, 1H), 7.75-7.69 (m, 2H), 7.53 (d, J=8.3 Hz, 1H), 7.47 (s, 1H), 7.06 (s, 1H), 6.91 (d, J=2.1 Hz, 1H), 6.85-6.77 (m, 3H), 5.00 (dd, J=12.9, 5.4 Hz, 1H), 4.85 (s, 2H), 4.26 (ddd, J=9.5, 7.4, 4.8 Hz, 1H), 3.22 (s, 3H), 3.11 (s, 2H), 2.98 (q, J=6.6 Hz, 2H), 2.91-2.79 (m, 1H), 2.61-2.49 (m, 2H), 2.16 (t, J=7.4 Hz, 2H), 1.97 (ddddd, J=30.6, 23.1, 16.4, 8.0, 4.3 Hz, 2H), 1.53 (p, J=7.0 Hz, 2H), 1.28 (dt, J=40.5, 5.7 Hz, 11H).

Example 34

Scheme 35

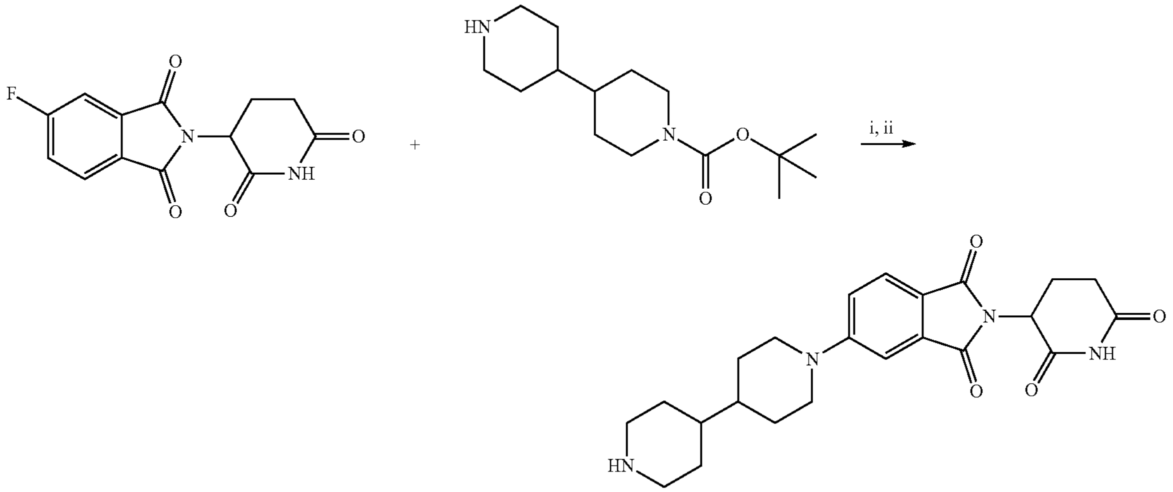

SAR007-092

-continued

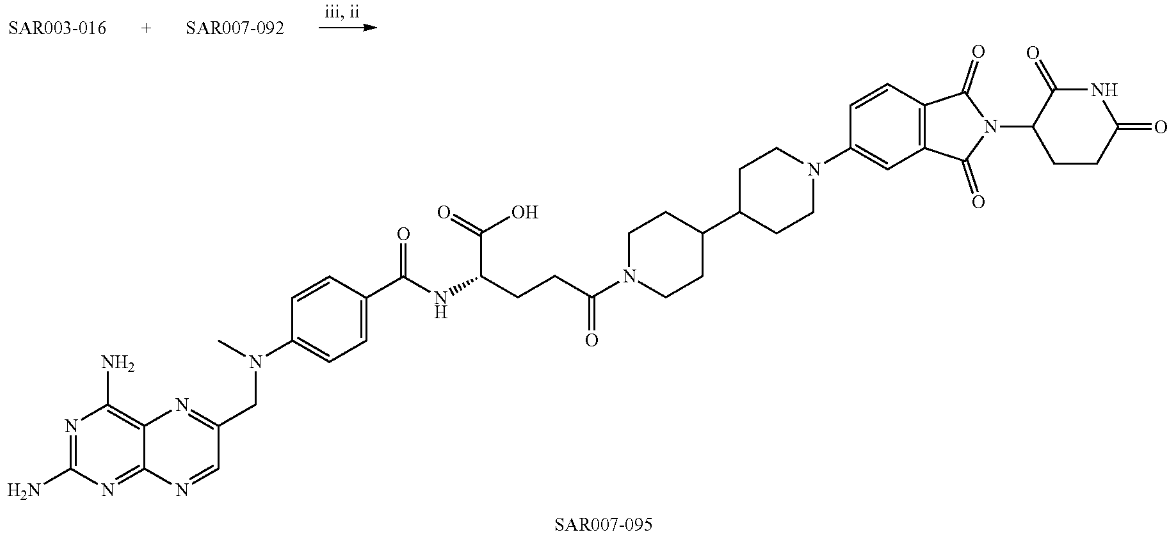

SAR007-095

(i) DIEA, NMP; (ii) $CF_3COOH$, DCM; (iii) TCFH, NMI, $CH_3CN$

5-([4,4'-bipiperidin]-1-yl)-2-(2,6-dioxopiperidin-3-yl)isoindoline-1,3-dione (SAR007-092)

Similar procedure as SAR007-087.

LC-MS retention time: 2.55 min (method 1)

MS-ESI (+) calcd m/z for $C_{23}H_{28}N_4O_4^+$ 425.21 $(M+H)^+$. found 425.3.

(2S)-2-(4-(((2,4-diaminopteridin-6-yl)methyl)(methyl)amino)benzamido)-5-(1'-(2-(2,6-dioxopiperidin-3-yl)-1,3-dioxoisoindolin-5-yl)-[4,4'-bipiperidin]-1-yl)-5-oxopentanoic acid (SAR007-095; NCGC00842354)

LC-MS retention time: 4.04 min (method 2)

MS-ESI (+) calcd m/z for $C_{43}H_{48}N_{12}O_8^+$ 861.37 $(M+H)^+$. found 861.4.

1H NMR (400 MHz, DMSO-d6) δ 12.97 (s, 1H), 12.44 (s, 1H), 11.05 (s, 1H), 9.23 (s, 1H), 9.03 (s, 1H), 8.69 (s, 1H), 8.23 (dd, J=11.8, 7.5 Hz, 1H), 7.72 (dd, J=8.9, 4.5 Hz, 2H), 7.63 (dd, J=8.6, 1.7 Hz, 1H), 7.48 (s, 1H), 7.26 (dd, J=6.6, 2.3 Hz, 1H), 7.23-7.14 (m, 1H), 6.85-6.78 (m, 2H), 5.04 (dd, J=12.9, 5.4 Hz, 1H), 4.85 (s, 2H), 4.41 (d, J=12.7 Hz, 1H), 4.32 (dq, J=9.3, 5.7, 4.3 Hz, 1H), 4.04 (d, J=12.1 Hz, 2H), 3.79 (s, 1H), 3.22 (s, 3H), 2.93-2.82 (m, 2H), 2.82 (d, J=5.9 Hz, 2H), 2.62-2.49 (m, 2H), 2.38 (dq, J=14.8, 8.6 Hz, 3H), 2.00 (dddd, J=21.8, 14.4, 10.7, 5.7 Hz, 2H), 1.65 (q, J=11.8, 10.5 Hz, 4H), 1.27 (s, 2H), 1.16 (s, 1H).

Example 35

Scheme 36

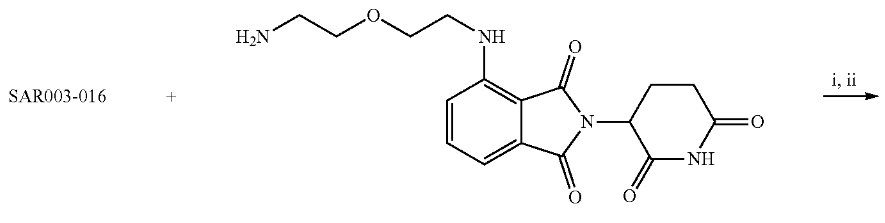

-continued

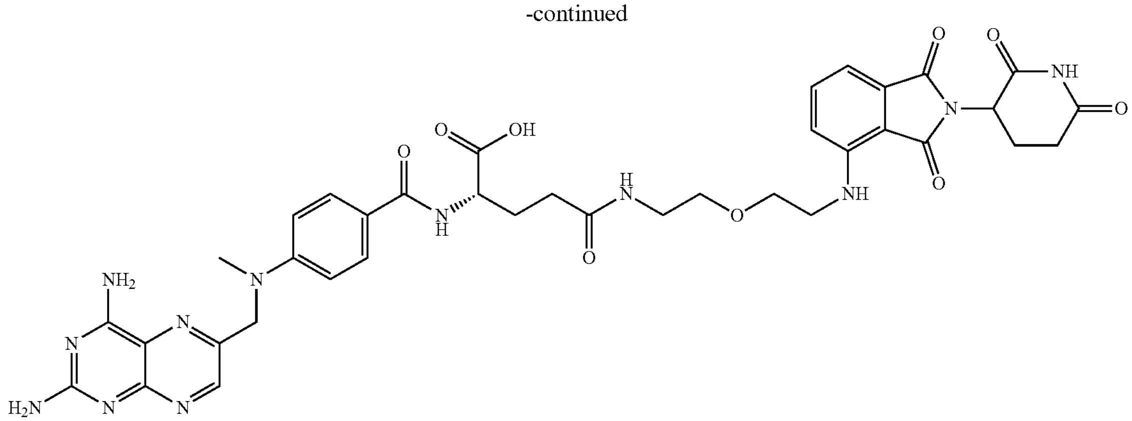

SAR008-001

(i) TCFH, NMI, $CH_3CN$; (ii) $CF_3COOH$, DCM

N2-(4-(((2,4-diaminopteridin-6-yl)methyl)(methyl)amino)benzoyl)-N5-(2-(2-((2-(2,6-dioxopiperidin-3-yl)-1,3-dioxoisoindolin-4-yl)amino)ethoxy)ethyl)-L-glutamine (SAR008-001; NCGC00687572)

Amide coupling was done using TCFH and NMI and the crude was dissolved in DCM and added 10 eq of TFA. Solvent was removed and crude was purified by reverse phase HPLC.

LC-MS retention time: 3.53 min (method 2)

MS-ESI (+) calcd m/z for $C_{37}H_{40}N_{12}O_9^+$ 797.30 $(M+H)^+$. found 797.3.

1H NMR (400 MHz, DMSO-d6) δ 12.99 (s, 1H), 12.46 (s, 1H), 11.06 (s, 1H), 9.24 (s, 1H), 9.03 (s, 1H), 8.69 (s, 1H), 8.57 (s, 1H), 8.30-8.24 (m, 1H), 7.87 (t, J=5.6 Hz, 1H), 7.72 (d, J=8.6 Hz, 2H), 7.55 (dd, J=8.6, 7.1 Hz, 1H), 7.51-7.45 (m, 1H), 7.10 (d, J=8.6 Hz, 1H), 7.01 (d, J=7.0 Hz, 1H), 6.80 (d, J=8.8 Hz, 2H), 6.56 (t, J=5.7 Hz, 1H), 5.03 (ddd, J=12.7, 5.4, 1.9 Hz, 1H), 4.85 (s, 2H), 4.28 (dtd, J=9.3, 5.7, 4.9, 1.6 Hz, 1H), 3.56 (t, J=5.4 Hz, 2H), 3.45-3.37 (m, 10H), 3.24-3.13 (m, 5H), 2.86 (ddd, J=17.4, 14.0, 5.4 Hz, 1H), 2.61-2.50 (m, 2H), 2.19 (t, J=7.4 Hz, 2H), 2.09-1.83 (m, 3H).

Example 36

Scheme 37

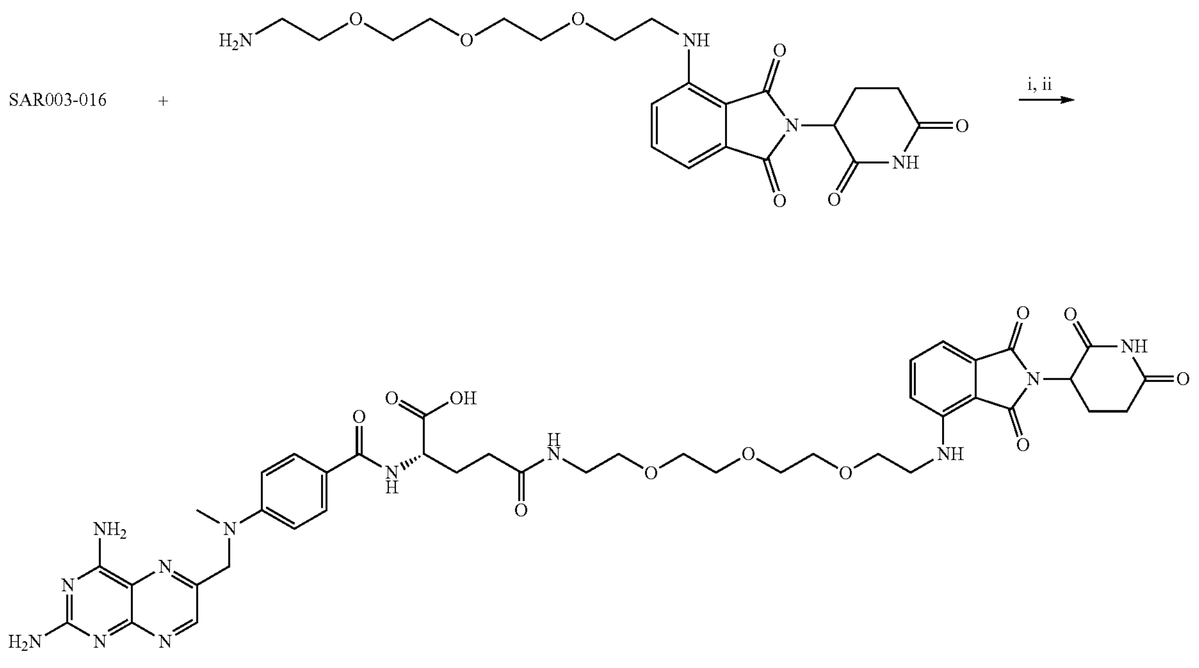

SAR008-002

(i) TCFH, NMI, $CH_3CN$; (ii) $CF_3COOH$, DCM (16S)-16-(4-(((2,4-diaminopteridin-6-yl)methyl)(methyl)amino)benzamido)-1-((2-(2,6-dioxopiperidin-3-yl)-1,3-dioxoisoindolin-4-yl)amino)-13-oxo-3,6,9-trioxa-12-azaheptadecan-17-oic acid (SAR008-002; NCGC00842350)

Amide coupling was done using TCFH and NMI and the crude was dissolved in DCM and added 10 eq of TFA. Solvent was removed and crude was purified by reverse phase HPLC.

LC-MS retention time: 3.66 min (method 2)

MS-ESI (+) calcd m/z for $C_{41}H_{48}N_{12}O_{11}^+$ 885.36 $(M+H)^+$. found 885.4.

1H NMR (400 MHz, DMSO-d6) δ 12.99 (s, 1H), 12.46 (s, 1H), 11.07 (s, 1H), 9.24 (s, 1H), 9.04 (s, 1H), 8.69 (s, 1H), 8.57 (s, 1H), 8.28 (d, J=7.4 Hz, 1H), 7.87 (t, J=5.6 Hz, 1H), 7.72 (d, J=8.9 Hz, 2H), 7.55 (dd, J=8.6, 7.1 Hz, 1H), 7.49 (s, 1H), 7.11 (d, J=8.6 Hz, 1H), 7.02 (d, J=7.0 Hz, 1H), 6.80 (d, J=9.0 Hz, 2H), 6.57 (t, J=5.8 Hz, 1H), 5.03 (dd, J=12.9, 5.4 Hz, 1H), 4.85 (s, 2H), 4.27 (ddd, J=9.5, 7.4, 4.9 Hz, 1H), 3.59 (t, J=5.4 Hz, 2H), 3.56-3.41 (m, 9H), 3.22 (s, 3H), 3.19-3.10 (m, 2H), 2.86 (ddd, J=17.5, 14.1, 5.4 Hz, 1H), 2.62-2.49 (m, 2H), 2.18 (t, J=7.6 Hz, 2H), 2.09-1.96 (m, 2H), 1.91 (ddd, J=13.6, 9.2, 6.8 Hz, 1H).

Example 37

Scheme 38

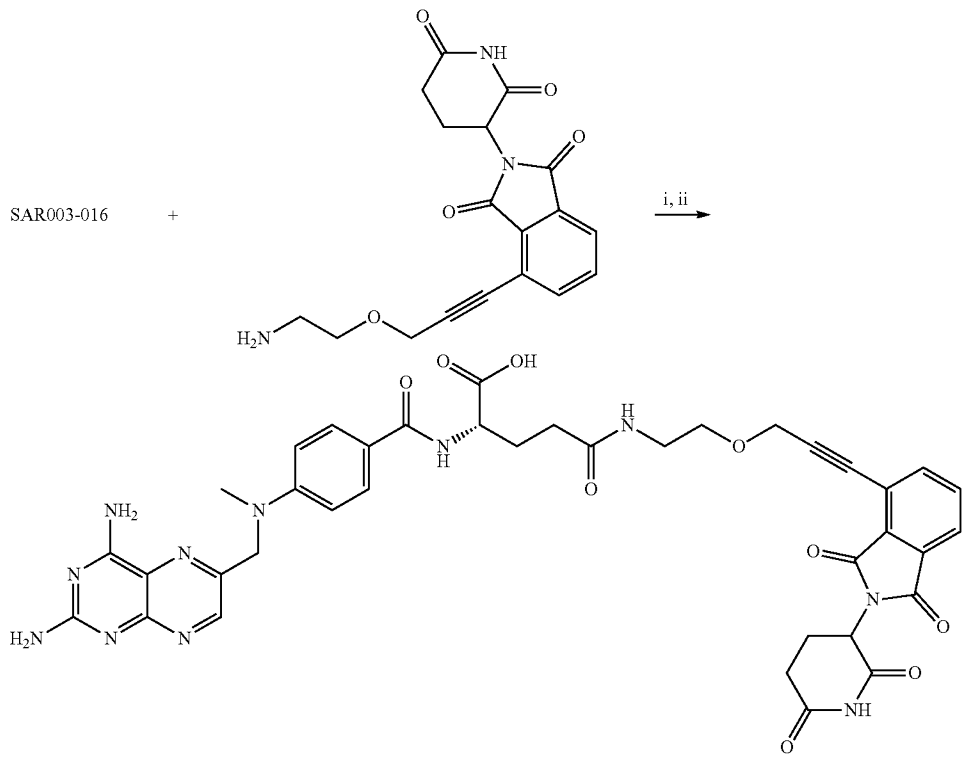

SAR008-011

(i) TCFH, NMI, $CH_3CN$; (ii) $CF_3COOH$, DCM

N2-(4-(((2,4-diaminopteridin-6-yl)methyl)(methyl)amino)benzoyl)-N5-(2-((3-(2-(2,6-dioxopiperidin-3-yl)-1,3-dioxoisoindolin-4-yl)prop-2-yn-1-yl)oxy)ethyl)-L-glutamine (SAR008-011; NCGC00842346)

Amide coupling was done using TCFH and NMI and the crude was dissolved in DCM and added 10 eq of TFA. Solvent was removed and crude was purified by reverse phase HPLC.

LC: 3.55 min (method 2)

MS-ESI (+) calcd m/z for $C_{38}H_{37}N_{11}O_9^+$ 792.28 $(M+H)^+$. found 814.2 (M+Na)

1H NMR (400 MHz, DMSO-d6) δ 12.95 (s, 1H), 12.46 (s, 1H), 11.11 (s, 1H), 9.21 (s, 1H), 9.01 (s, 1H), 8.69 (s, 1H), 8.53 (s, 1H), 8.27 (d, J=7.4 Hz, 1H), 7.96 (t, J=5.6 Hz, 1H), 7.90 (dd, J=6.4, 2.1 Hz, 1H), 7.90-7.79 (m, 2H), 7.75-7.69 (m, 2H), 7.46 (s, 1H), 6.84-6.77 (m, 2H), 5.13 (dd, J=12.7, 5.4 Hz, 1H), 4.85 (s, 2H), 4.45 (s, 2H), 4.27 (ddd, J=9.5, 7.4, 4.8 Hz, 1H), 3.57 (t, J=5.7 Hz, 2H), 3.24 (d, J=13.0 Hz, 4H), 3.15 (s, OH), 2.90-2.80 (m, 1H), 2.64-2.49 (m, 2H), 2.20 (t, J=7.7 Hz, 2H), 2.09-1.97 (m, 2H), 1.90 (ddd, J=16.4, 13.9, 7.6 Hz, 1H).

Example 38

Scheme 39

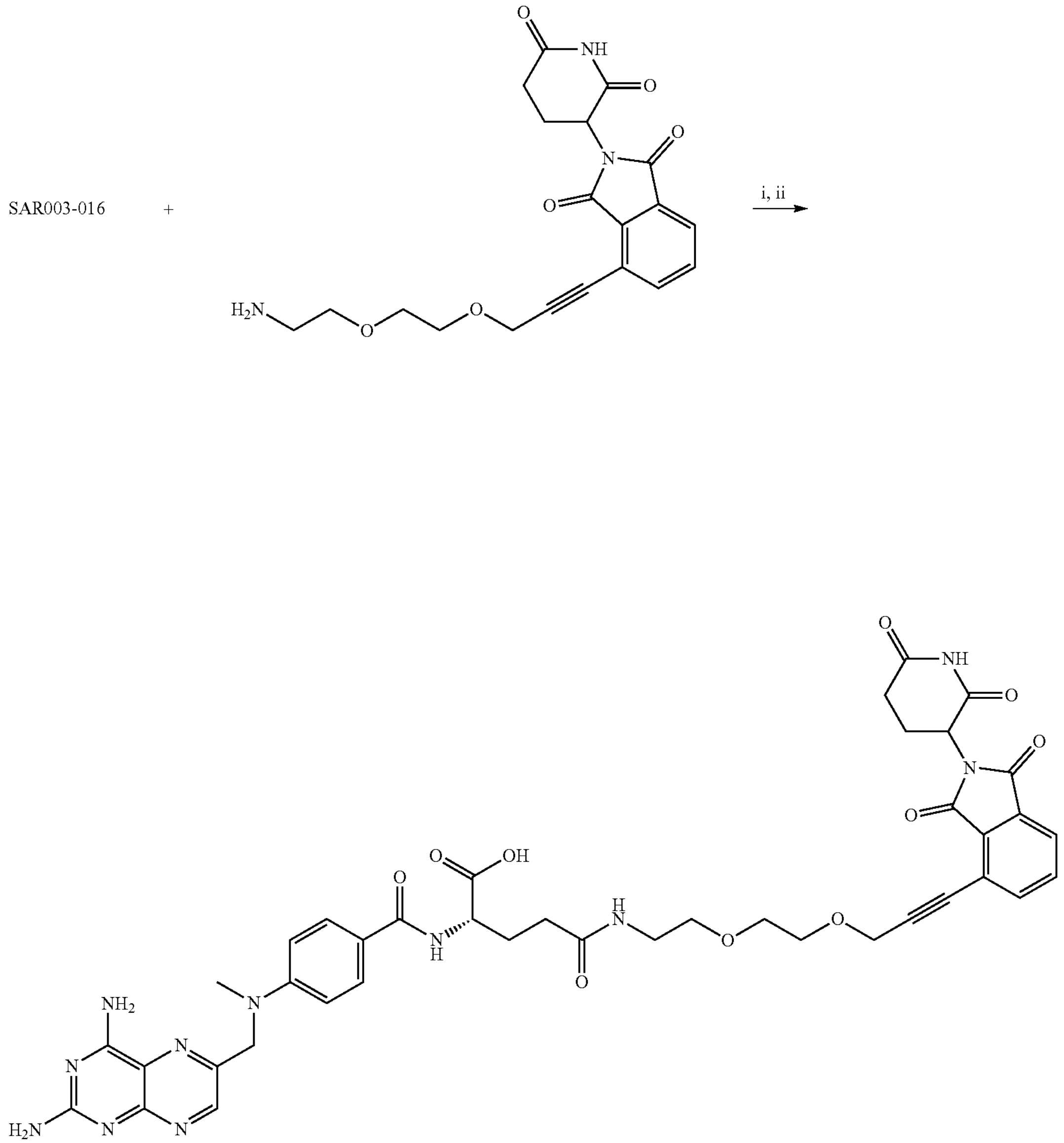

SAR008-009

(i) TCFH, NMI, $CH_3CN$; (ii) $CF_3COOH$, DCM

N2-(4-(((2,4-diaminopteridin-6-yl)methyl)(methyl)amino)benzoyl)-N5-(2-(2-((3-(2-(2,6-dioxopiperidin-3-yl)-1,3-dioxoisoindolin-4-yl)prop-2-yn-1-yl)oxy)ethoxy)ethyl)-L-glutamine (SAR008-009; NCGC00842342)

Amide coupling was done using TCFH and NMI and the crude was dissolved in DCM and added 10 eq of TFA. Solvent was removed and crude was purified by reverse phase HPLC.

LC-MS retention time: 3.61 min (method 2)

MS-ESI (+) calcd m/z for $C_{40}H_{41}N_{11}O_{10}^+$ 836.30 $(M+H)^+$. found 836.3.

1H NMR (400 MHz, DMSO-d6) δ 12.98 (s, 1H), 12.46 (s, 1H), 11.11 (s, 1H), 9.25 (s, 1H), 9.05 (s, 1H), 8.69 (s, 1H), 8.57 (s, 1H), 8.25 (dd, J=15.0, 7.5 Hz, 1H), 7.94-7.80 (m, 4H), 7.75-7.67 (m, 2H), 7.48 (s, 1H), 6.84-6.73 (m, 2H), 5.13 (dd, J=12.7, 5.4 Hz, 1H), 4.85 (s, 2H), 4.47 (s, 2H), 4.27 (ddd, J=9.5, 7.4, 4.9 Hz, 1H), 3.69 (dd, J=5.8, 3.6 Hz, 2H), 3.54 (dd, J=5.8, 3.6 Hz, 2H), 3.38 (s, 2H), 3.25-3.13 (m, 6H), 2.95-2.80 (m, 1H), 2.64-2.49 (m, 2H), 2.19 (t, J=7.6 Hz, 2H), 2.04 (ddt, J=13.3, 11.1, 3.6 Hz, 2H), 1.91 (ddd, J=13.2, 9.0, 6.7 Hz, 1H).

Example 39

Scheme 40

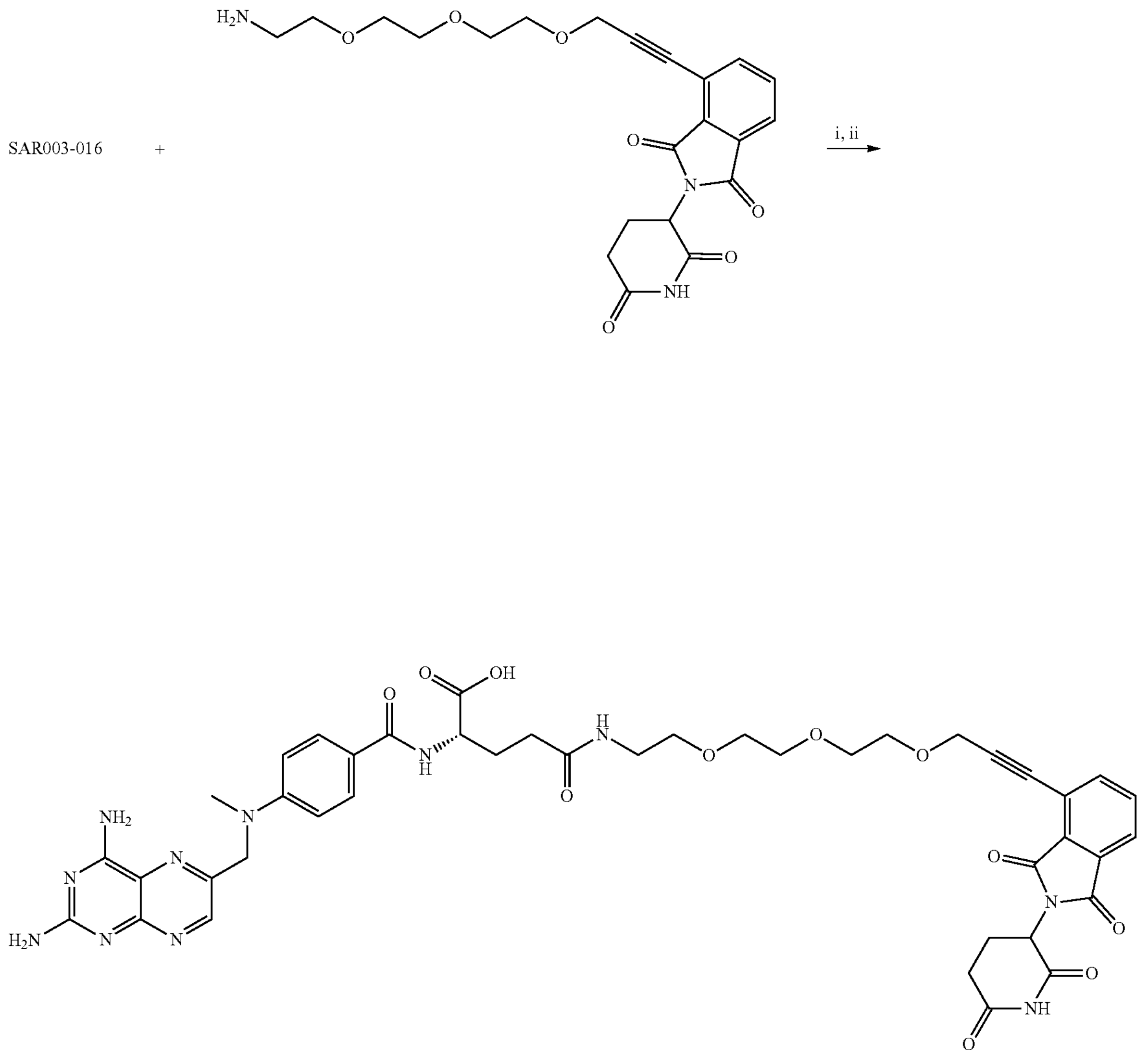

SAR008-012

(i) TCFH, NMI, $CH_3CN$; (ii) $CF_3COOH$, DCM (17S)-17-(4-(((2,4-diaminopteridin-6-yl)methyl)(methyl)amino)benzamido)-1-(2-(2,6-dioxopiperidin-3-yl)-1,3-dioxoisoindolin-4-yl)-14-oxo-4,7,10-trioxa-13-azaoctadec-1-yn-18-oic acid (SAR008-012; NCGC00842343)

Amide coupling was done using TCFH and NMI and the crude was dissolved in DCM and added 10 eq of TFA. Solvent was removed and crude was purified by reverse phase HPLC. LC-MS retention time: 3.67 min (method 2) MS-ESI (+) calcd m/z for $C_{42}H_{45}N_{11}O_{11}^+$ 880.33 $(M+H)^+$. found 880.3.

1H NMR (400 MHz, DMSO-d6) δ 12.98 (s, 1H), 12.46 (s, 1H), 11.11 (s, 1H), 9.24 (s, 1H), 9.04 (s, 1H), 8.69 (s, 1H), 8.57 (s, 1H), 8.27 (d, J=7.4 Hz, 1H), 7.95-7.80 (m, 4H), 7.72 (d, J=8.5 Hz, 2H), 7.48 (s, 1H), 6.80 (d, J=8.6 Hz, 2H), 5.13 (dd, J=12.7, 5.4 Hz, 1H), 4.85 (s, 2H), 4.47 (s, 2H), 4.27 (dq, J=8.8, 5.3 Hz, 1H), 3.69 (dd, J=5.9, 3.5 Hz, 2H), 3.59-3.44 (m, 8H), 3.23 (s, 3H), 3.16 (q, J=5.8 Hz, 3H), 2.95-2.80 (m, 3H), 2.63-2.50 (m, 2H), 2.18 (t, J=7.5 Hz, 2H), 2.10-1.95 (m, 2H), 1.90 (s, 1H).

Example 40

Scheme 41

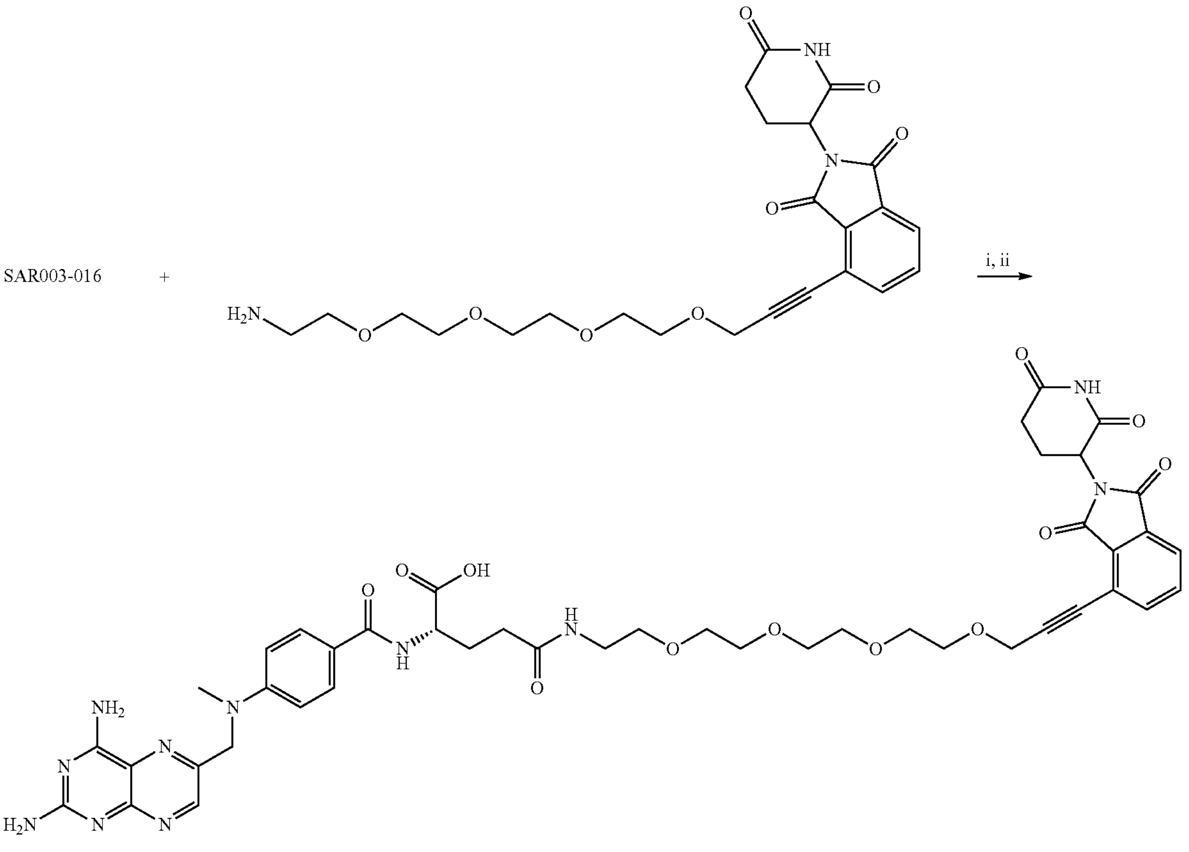

SAR008-013

(i) TCFH, NMI, $CH_3CN$; (ii) $CF_3COOH$, DCM (20S)-20-(4-(((2,4-diaminopteridin-6-yl)methyl)(methyl)amino)benzamido)-1-(2-(2,6-dioxopiperidin-3-yl)-1,3-dioxoisoindolin-4-yl)-17-oxo-4,7,10,13-tetraoxa-16-azahenicos-1-yn-21-oic acid (SAR008-013; NCGC00842356)

Amide coupling was done using TCFH and NMI and the crude was dissolved in DCM and added 10 eq of TFA. Solvent was removed and crude was purified by reverse phase HPLC.

LC-MS retention time: 3.70 min (method 2)

MS-ESI (+) calcd m/z for $C_{44}H_{49}N_{11}O_{12}^+$ 924.36 $(M+H)^+$. found 924.3.

1H NMR (400 MHz, DMSO-d6) δ 12.98 (s, 1H), 12.50 (s, 1H), 11.11 (s, 1H), 9.24 (s, 1H), 9.03 (s, 1H), 8.69 (s, 1H), 8.57 (s, 1H), 8.27 (d, J=7.4 Hz, 1H), 7.96-7.80 (m, 4H), 7.76-7.68 (m, 2H), 6.85-6.75 (m, 2H), 5.13 (dd, J=12.7, 5.4 Hz, 1H), 4.85 (s, 2H), 4.48 (s, 2H), 4.27 (ddd, J=9.4, 7.4, 4.8 Hz, 1H), 3.69 (dd, J=5.8, 3.6 Hz, 2H), 3.61-3.46 (m, 7H), 3.46 (dq, J=4.2, 2.5, 2.0 Hz, 4H), 3.23 (s, 3H), 3.20-3.11 (m, 3H), 2.95-2.80 (m, 3H), 2.64-2.50 (m, 2H), 2.18 (t, J=7.6 Hz, 2H), 2.11-1.97 (m, 2H), 1.91 (ddd, J=13.3, 9.1, 6.7 Hz, 1H).

Example 41

Scheme 42

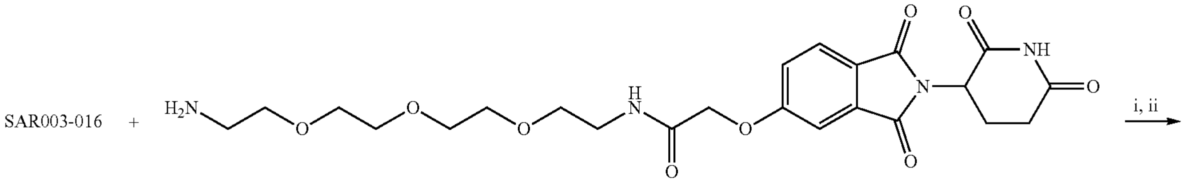

-continued

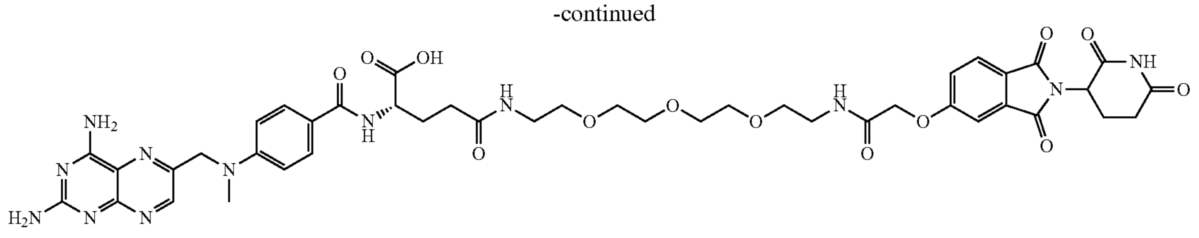

SAR008-016

(i) TCFH, NMI, $CH_3CN$; (ii) $CF_3COOH$, DCM (19S)-19-(4-(((2,4-diaminopteridin-6-yl)methyl)(methyl)amino)benzamido)-1-((2-(2,6-dioxopiperidin-3-yl)-1,3-dioxoisoindolin-5-yl)oxy)-2,16-dioxo-6,9,12-trioxa-3,15-diazaicosan-20-oic acid (SAR008-016; NCGC00842349)

Amide coupling was done using TCFH and NMI and the crude was dissolved in DCM and added 10 eq of TFA. Solvent was removed and crude was purified by reverse phase HPLC.

LC-MS retention time: 3.39 min (method 2)

MS-ESI (+) calcd m/z for $C_{43}H_{50}N_{12}O_{13}^+$ 943.36 $(M+H)^+$. found 943.3.

1H NMR (400 MHz, DMSO-d6) δ 12.99 (s, 1H), 12.46 (s, 1H), 11.09 (s, 1H), 9.25 (s, 1H), 9.05 (s, 1H), 8.69 (s, 1H), 8.63 (s, OH), 8.57 (s, 1H), 8.31-8.19 (m, 2H), 7.92-7.80 (m, 2H), 7.72 (d, J=8.8 Hz, 2H), 7.52 (s, 1H), 7.41 (d, J=2.4 Hz, 1H), 7.36 (dd, J=8.3, 2.3 Hz, 1H), 6.80 (d, J=8.8 Hz, 2H), 5.10 (dd, J=12.8, 5.4 Hz, 1H), 4.85 (s, 2H), 4.71 (s, 2H), 4.27 (ddd, J=9.4, 7.3, 4.8 Hz, 1H), 3.48 (s, 10H), 3.42 (d, J=11.5 Hz, 1H), 3.34 (d, J=5.9 Hz, 1H), 3.25 (d, J=20.8 Hz, 4H), 3.20-3.11 (m, 2H), 2.95-2.80 (m, 1H), 2.63-2.50 (m, 2H), 2.18 (t, J=7.5 Hz, 2H), 2.03 (dtd, J=11.2, 6.4, 3.2 Hz, 2H), 1.90 (ddd, J=16.5, 13.9, 7.8 Hz, 1H).

Example 42

Scheme 43

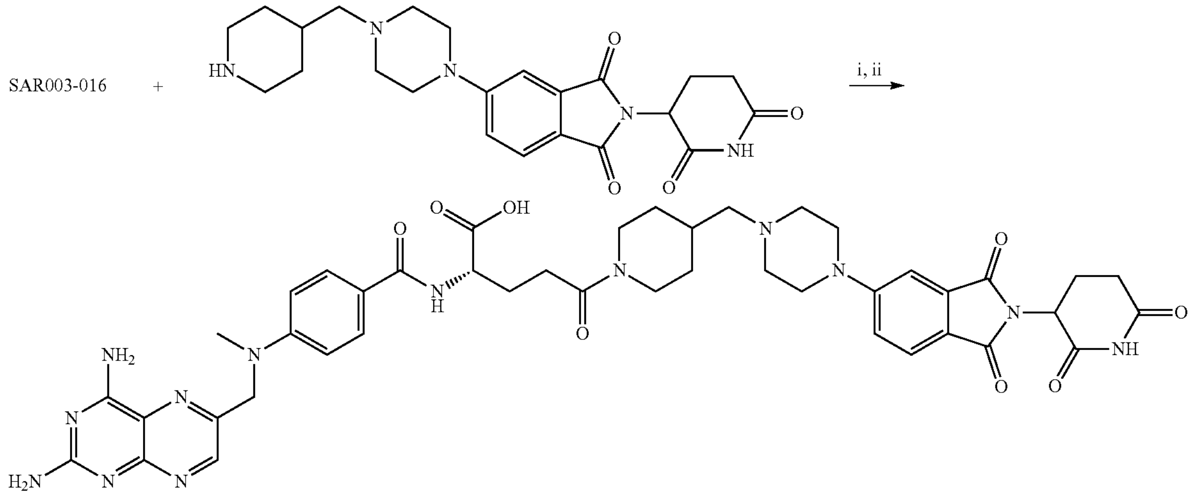

SAR008-019

(i) HATU, DIEA, DMF; (ii) $CF_3COOH$, DCM (2S)-2-(4-(((2,4-diaminopteridin-6-yl)methyl)(methyl)amino)benzamido)-5-(4-((4-(2-(2,6-dioxopiperidin-3-yl)-1,3-dioxoisoindolin-5-yl)piperazin-1-yl)methyl)piperidin-1-yl)-5-oxopentanoic acid (SAR008-019)

Amide coupling was done using TCFH and NMI and the crude was dissolved in DCM and added 10 eq of TFA. Solvent was removed and crude was purified by reverse phase HPLC.

LC-MS retention time: 3.15 min (method 2)

MS-ESI (+) calcd m/z for $C_{43}H_{49}N_{13}O_8^+$ 876.38 $(M+H)^+$. found 877.4.

1H NMR (400 MHz, DMSO-d6) δ 11.07 (s, 1H), 9.16 (d, J=7.8 Hz, 1H), 8.95 (s, 1H), 8.69 (s, 1H), 8.26 (d, J=7.4 Hz, 1H), 7.74 (t, J=8.6 Hz, 3H), 7.55 (s, 1H), 7.46 (d, J=2.3 Hz, 1H), 7.33 (dd, J=8.6, 2.3 Hz, 1H), 6.84-6.78 (m, 2H), 5.07 (dd, J=12.9, 5.4 Hz, 1H), 4.85 (s, 2H), 4.41-4.28 (m, 2H), 3.23 (s, 3H), 2.97 (d, J=12.2 Hz, 2H), 2.62-2.50 (m, 3H), 2.39 (d, J=8.6 Hz, 2H), 2.09-1.97 (m, 2H), 1.97-1.91 (m, 1H), 1.74 (d, J=12.2 Hz, 2H), 1.02 (dt, J=27.1, 11.3 Hz, 3H).

Example 43

Scheme 44

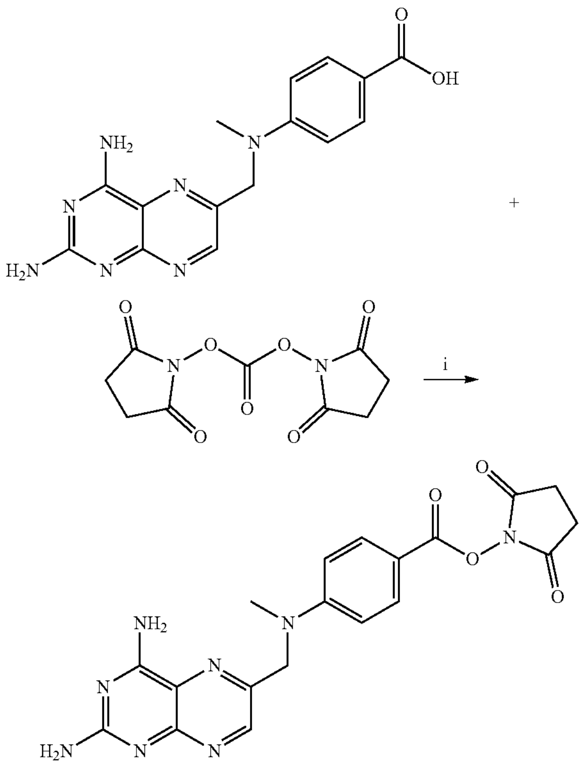

SAR008-040

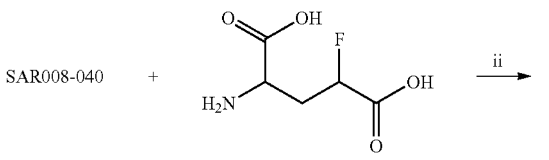

-continued

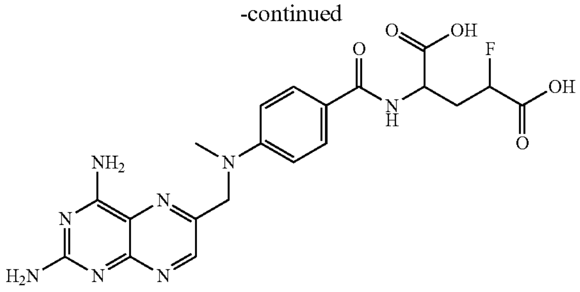

SAR008-042

(i) DIEA, DMSO; (ii) DIEA, DMF 2,5-dioxopyrrolidin-1-yl 4-(((2,4-diaminopteridin-6-yl)methyl)(methyl)amino)benzoate (SAR008-040)

Taken 4-(((2,4-diaminopteridin-6-yl)methyl)(methyl)amino)benzoic acid (50 mg, 0.154 mmol) in DMSO (1 ml) followed by the addition of bis(2,5-dioxopyrrolidin-1-yl) carbonate (118 mg, 0.461 mmol) and triethylamine (105 μl, 0.768 mmol). Reaction was heat to 50° C. for 1 hour. Reaction was washed with $NaHCO_3$ and extract with ethyl acetate, washed brine, dried $MgSO_4$, concentrated under reduced pressure to yield SAR008-040 as a yellow solid (36 mg, 56%).

LC-MS retention time: 2.55 min (method 1)

MS-ESI (+) calcd m/z for $C_{19}H_{18}N_8O_4^+$ 423.15 $(M+H)^+$. found 423.2.

1H NMR (400 MHz, DMSO-d6) δ 13.17 (s, 1H), 9.28 (s, 1H), 8.99 (s, 1H), 8.78 (s, 1H), 8.66 (s, 1H), 7.87 (s, 1H), 7.81 (d, J=7.7 Hz, 2H), 6.93 (d, J=8.0 Hz, 2H), 4.92 (s, 2H), 3.30 (s, 3H), 2.81 (s, 4H).

2-(4-(((2,4-diaminopteridin-6-yl)methyl)(methyl)amino)benzamido)-4-fluoropentanedioic Acid (SAR008-042)

Dissolve crude 2,5-dioxopyrrolidin-1-yl 4-(((2,4-diaminopteridin-6-yl)methyl)(methyl)amino)benzoate in DMF followed by the addition of 1.5 eq of 2-amino-4-fluoropentanedioic acid and 10 eq. of DIEA. Reaction was heated at 50° C. for 5 days and progress of the rection was monitored by HPLC. The crude was purified by reverse phase HPLC to yield product as a TFA salt.

LC-MS retention time: 2.22 min (method 1)

MS-ESI (+) calcd m/z for $C_{20}H_{21}FN_8O_5^+$ 473.16 $(M+H)^+$. found 473.2.

Example 44

Scheme 45

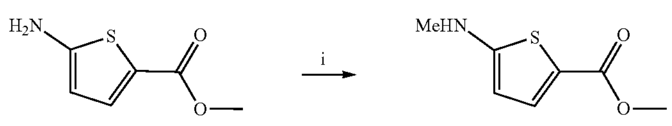

[I] SAR008-034

-continued

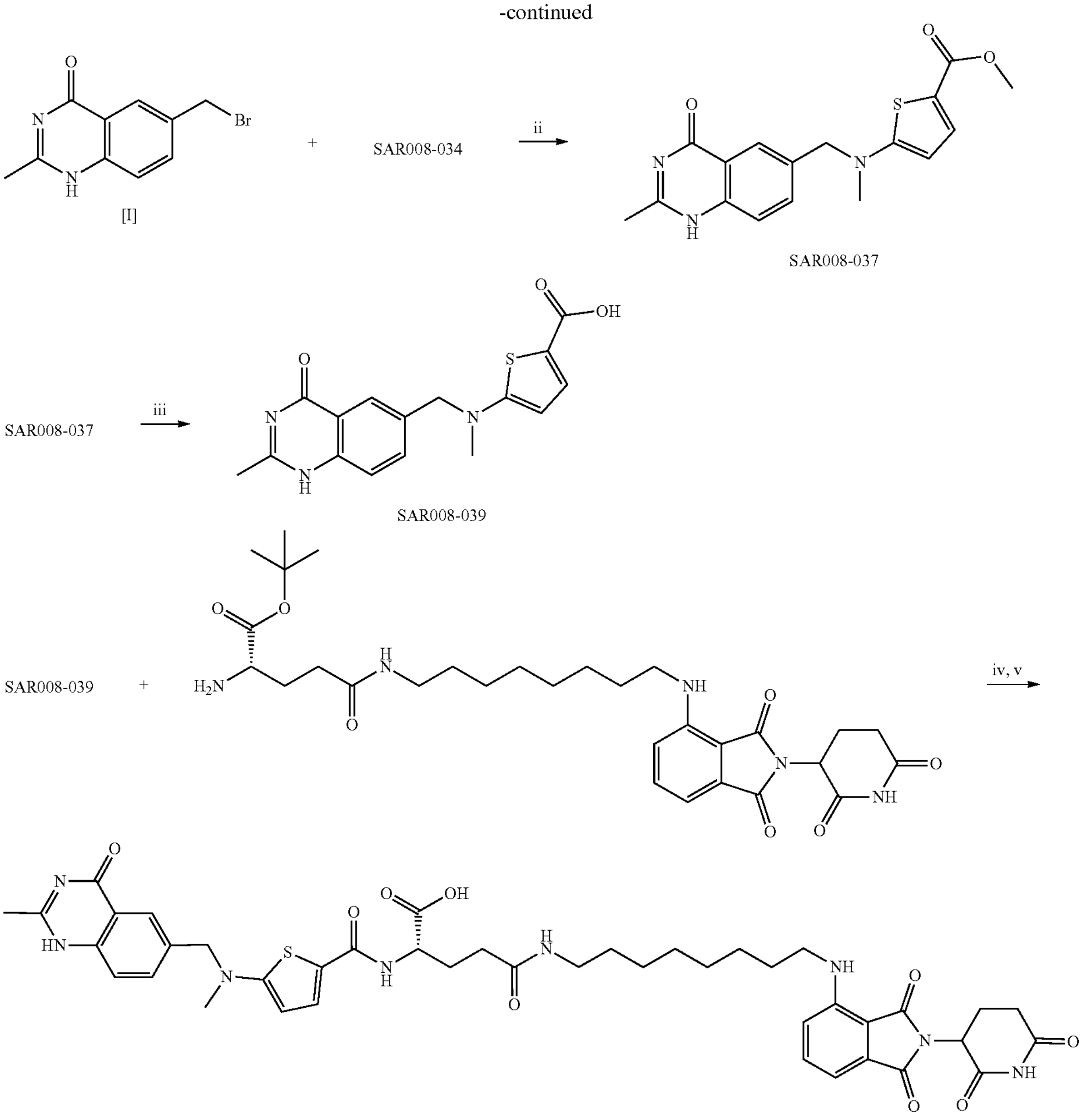

SAR008-046

(i) $CH_3I$, 2,6-lutidine, DMF; (ii) 2,6-lutidine, DMF; (iii) 1N NaOH, THF:Water; (iv) EDCl, HOAT, NMM, DMSO; (v TFA, DCM)

Methyl 5-(methylamino)thiophene-2-carboxylate (SAR008-034)

Dissolve methyl 5-aminothiophene-2-carboxylate (300 mg, 1.909 mmol) in DMF (3 ml) followed by the addition of 2,6-lutidine (389 µl, 3.34 mmol) and iodomethane (143 µl, 2.290 mmol). Reaction was stirred at heat 140° C. for 6 hours in a microwave reactor. Solvent was removed and the compound was purified by silica gel chromatography to yield product as brown solid (115 mg, 35%).

LC-MS retention time: 2.97 min (method 1)

MS-ESI (+) calcd m/z for $C_7H_9N_2S^+$ 172.04 $(M+H)^+$. found 172.0.

1H NMR (400 MHz, DMSO-d6) δ 7.41 (d, J=4.2 Hz, 1H), 7.30 (q, J=4.8 Hz, 1H), 5.86 (d, J=4.3 Hz, 1H), 3.66 (s, 3H), 2.74 (d, J=4.9 Hz, 3H).

Methyl 5-(methyl((2-methyl-4-oxo-1,4-dihydroquinazolin-6-yl)methyl)amino)thiophene-2-carboxylate (SAR008-037)

Dissolve 6-(bromomethyl)-2-methylquinazolin-4(4aH)-one (185 mg, 0.732 mmol) and methyl 5-aminothiophene-2-carboxylate (115 mg, 0.732 mmol) in DMF (3 ml) followed by the addition of 2,6-lutidine (85 µl, 0.732 mmol). Reaction was stirred at 80° C. for 48 hours. Solvent was removed under reduced pressure and the crude was purified by silica gel chromatography to yield product as white solid (85 mg, 34%).

LC-MS retention time: 2.75 min (method 1)

MS-ESI (+) calcd m/z for $C_{17}H_{17}N_3O_3S^+$ 344.10 $(M+H)^+$. found 344.1.

1H NMR (400 MHz, DMSO-d6) δ 12.20 (s, 1H), 7.91 (d, J=2.1 Hz, 1H), 7.64 (dd, J=8.4, 2.1 Hz, 1H), 7.54 (d, J=8.4 Hz, 1H), 7.47 (d, J=4.3 Hz, 1H), 6.05 (d, J=4.3 Hz, 1H), 4.68 (s, 2H), 3.67 (s, 3H), 3.07 (s, 3H), 2.32 (s, 3H).

5-(methyl((2-methyl-4-oxo-1,4-dihydroquinazolin-6-yl)methyl)amino)thiophene-2-carboxylic acid (SAR008-039)

Dissolve methyl 5-(methyl((2-methyl-4-oxo-4,4a-dihydroquinazolin-6-yl)methyl)amino)thiophene-2-carboxylate (80 mg, 0.233 mmol) in THF (1 ml) and Water (1.00 ml) followed by 1N NaOH (2 ml). Reaction was heated at 50° C. for 24 hours. Solvent was removed under the reduced pressure and the crude was purified by reverse phase HPLC to yield product as off-white solid.

LC-MS retention time: 2.53 min (method 1)

MS-ESI (+) calcd m/z for $C_{16}H_{15}N_3O_3S^+$ 330.08 $(M+H)^+$. found 330.1.

N5-(8-((2-(2,6-dioxopiperidin-3-yl)-1,3-dioxoisoindolin-4-yl)amino)octyl)-N2-(5-(methyl((2-methyl-4-oxo-1,4-dihydroquinazolin-6-yl)methyl)amino)thiophene-2-carbonyl)-L-glutamine (SAR008-046)

Taken 5-(methyl((2-methyl-4-oxo-1,4-dihydroquinazolin-6-yl)methyl)amino)thiophene-2-carboxylic acid, TFA (20 mg, 0.045 mmol) and tert-butyl N5-(8-((2-(2,6-dioxopiperidin-3-yl)-1,3-dioxoisoindolin-4-yl)amino)octyl)-L-glutaminate (31.7 mg, 0.054 mmol) (ABCL—A1 Bio Chem Labs) in DMSO (2 ml) followed by the addition of EDCI (17.23 mg, 0.090 mmol), HOAT (12.27 mg, 0.090 mmol) and NMM (20.00 μl, 0.180 mmol). The mixture was stirred at room temperature and the crude was partially purified with silica gel column chromatography to yield tert-butyl N5-(8-((2-(2,6-dioxopiperidin-3-yl)-1,3-dioxoisoindolin-4-yl)amino)octyl)-N2-(5-(methyl((2-methyl-4-oxo-1,4-dihydroquinazolin-6-yl)methyl)amino)thiophene-2-carbonyl)-L-glutaminate (22 mg, 0.025 mmol, 54.4% yield) which was dissolved in DCM and excess of TFA. The mixture was stirred at room temperature for 3 h. The solvent was removed, and the crude was purified by reverse phase HPLC to yield product.

LC retention time: 3.00 min (method 1)

MS-ESI (+) calcd m/z for $C_{42}H_{48}N_8O_9S^+$ 841.33 $(M+H)^+$. found 841.3.

Example 45

Scheme 46

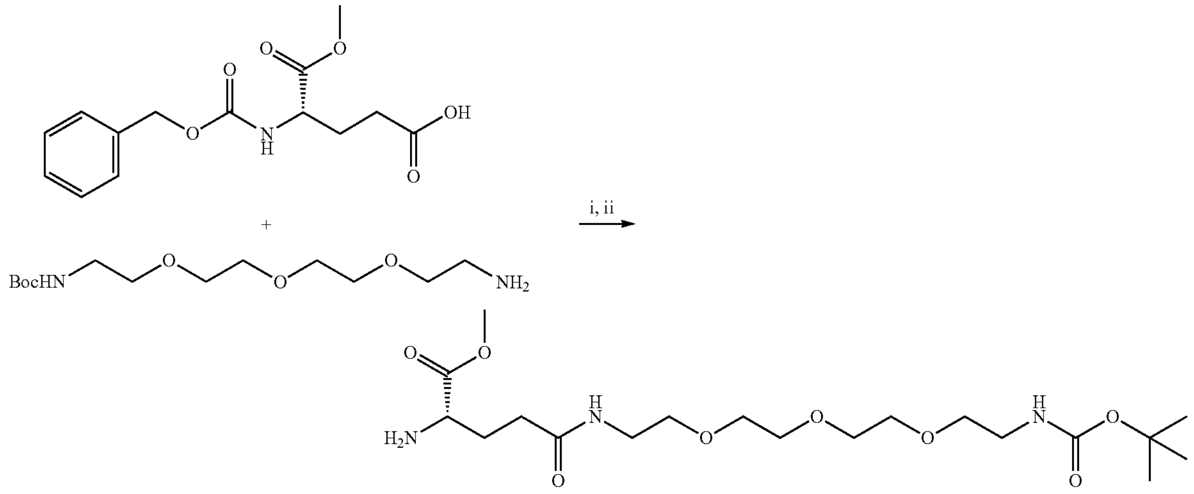

SAR008-032

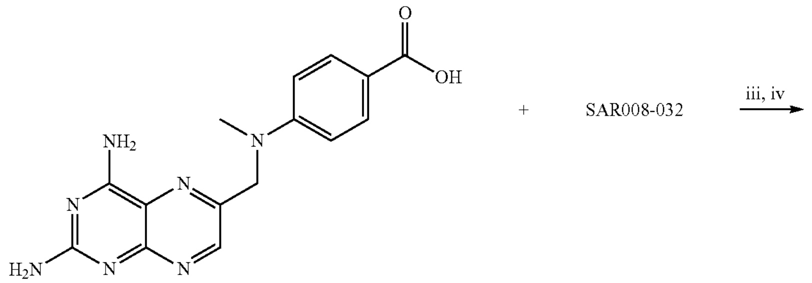

+ SAR008-032

-continued

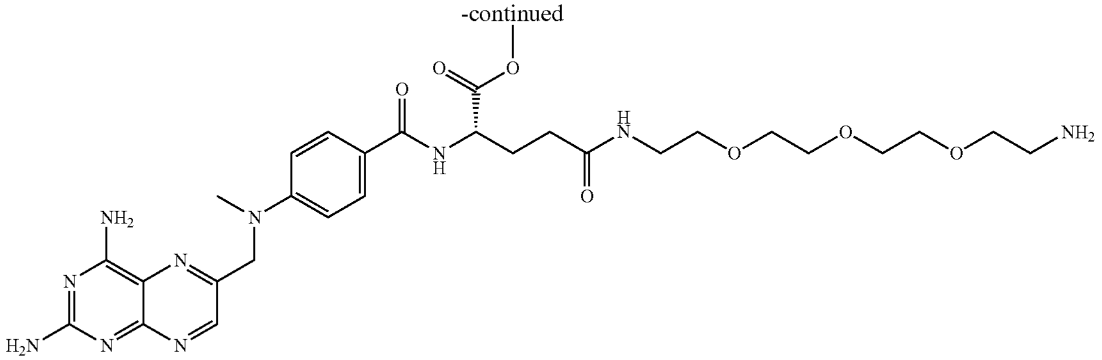

SAR008-035

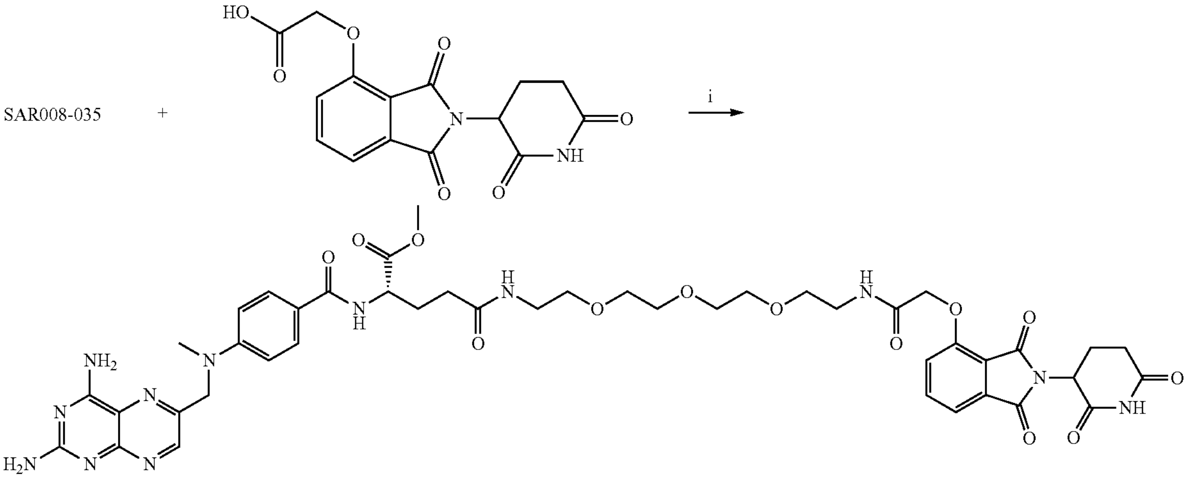

SAR008-036

(i) TCFH, NMI, $CH_3CN$; (ii) 10% Pd-C, $CH_3OH$; (iii) EDCI, HOAT, NMM, DMSO; (iv) TFA, DCM

Methyl (S)-21-amino-2,2-dimethyl-4,18-dioxo-3,8,11,14-tetraoxa-5,17-diazadocosan-22-oate (SAR008-032)

Taken (S)-4-(((benzyloxy)carbonyl)amino)-5-methoxy-5-oxopentanoic acid (330 mg, 1.118 mmol), and tert-butyl (2-(2-(2-(2-aminoethoxy)ethoxy)ethoxy)ethyl)carbamate, HCl (367 mg, 1.118 mmol) in acetonitrile (5 ml) followed by addition of 1-methyl-1H-imidazole (275 mg, 3.35 mmol). Reaction was stirred for 10 minutes followed by addition of N-(chloro(dimethylamino)methylene)-N-methylmethanaminium hexafluorophosphate(V) (408 mg, 1.453 mmol). Reaction was stirred for 1 hour. Solvent was removed under reduced pressure and the crude was purified by silica gel column chromatography to give methyl (S)-21-(((benzyloxy)carbonyl)amino)-2,2-dimethyl-4,18-dioxo-3,8,11,14-tetraoxa-5,17-diazadocosan-22-oate (600 mg, 1.053 mmol, 94% yield) as colorless oil. MS-ESI (+) calcd m/z for $C_{27}H_{43}N_3O_{10}^+$ 570.29 $(M+H)^+$, found 570.3; LC retention time: 3.20 min (method 1). Dissolve methyl (S)-21-(((benzyloxy)carbonyl)amino)-2,2-dimethyl-4,18-dioxo-3,8,11,14-tetraoxa-5,17-diazadocosan-22-oate (600 mg, 1.053 mmol) was dissolved in methanol (10 ml) followed by addition of 5% Pd/C (46 mg). Reaction mixture was vacuumed and purged hydrogen gas. The reaction was stirred at room temperature for 5 hour under hydrogen atmosphere. The mixture was filtered through the celite, and the solvent was evaporated to yield methyl (S)-21-amino-2,2-dimethyl-4,18-dioxo-3,8,11,14-tetraoxa-5,17-diazadocosan-22-oate (380 mg, 0.873 mmol, 83% yield). LC retention time: 3.20 min (method 1). MS-ESI (+) calcd m/z for $C_{19}H_{37}N_3O_8^+$ 436.26 $(M+H)^+$. found 436.3.

Methyl (S)-1-amino-16-(4-(((2,4-diaminopteridin-6-yl)methyl)(methyl)amino)benzamido)-13-oxo-3,6,9-trioxa-12-azaheptadecan-17-oate (SAR008-035)

To a solution of 4-(((2,4-diaminopteridin-6-yl)methyl)(methyl)amino)benzoic acid (50 mg, 0.154 mmol) in DMSO (2 ml) was added methyl (S)-21-amino-2,2-dimethyl-4,18-dioxo-3,8,11,14-tetraoxa-5,17-diazadocosan-22-oate (80 mg, 0.184 mmol), EDCI (58.7 mg, 0.307 mmol), HOAT (41.8 mg, 0.307 mmol) and NMM (68.2 μl, 0.615 mmol). The reaction was stirred for 24 hours. The crude was purified by reverse phase HPLC to yield methyl (S)-21-(4-(((2,4-diaminopteridin-6-yl)methyl)(methyl)amino)benzamido)-2,2-dimethyl-4,18-dioxo-3,8,11,14-tetraoxa-5,17-diazadocosan-22-oate (65 mg, 0.088 mmol, 56.9% yield). MS-ESI (+) calcd m/z for $C_{34}H_{50}N_{10}O_9^+$ 743.38 $(M+H)^+$. found 743.4; LC retention time: 2.69 min (method 1). The compound was dissolved in DCM and added 10 equivalents of TFA. The reaction was stirred for 3 h and the solvent was removed under the reduced pressure. The crude was used as such in the next step without further purification. MS-ESI (+) calcd m/z for $C_{29}H_{42}N_{10}O_7^+$ 643.32 $(M+H)^+$. found 643.4; LC retention time: 2.33 min (method 1).

Methyl (19S)-19-(4-(((2,4-diaminopteridin-6-yl)methyl)(methyl)amino)benzamido)-1-((2-(2,6-dioxopiperidin-3-yl)-1,3-dioxoisoindolin-4-yl)oxy)-2,16-dioxo-6,9,12-trioxa-3,15-diazaicosan-20-oate (SAR008-036; NCGC00842394)

Dissolve methyl (S)-1-amino-16-(4-(((2,4-diaminopteridin-6-yl)methyl)(methyl)amino)benzamido)-13-oxo-3,6,9-trioxa-12-azaheptadecan-17-oate, TFA (50 mg, 0.066 mmol) in acetonitrile (4 ml) followed by the addition of 2-((2-(2,6-dioxopiperidin-3-yl)-1,3-dioxoisoindolin-4-yl)oxy)acetic acid (21.95 mg, 0.066 mmol), TCFH (37.1 mg, 0.132 mmol), and NMI (27.1 mg, 0.330 mmol). The reaction was stirred for 12 hours. The solvent was removed and the crude was purified by reverse phase HPLC to give product as a TFA salt.

LC retention time: 2.58 min (method 1).

MS-ESI (+) calcd m/z for $C_{44}H_{52}N_{12}O_{13}^{+}$ 957.38 $(M+H)^{+}$. found 957.3.

Example 46

MTX-Mediated Proteasomal Targeting of Cellular DHFR

DHFR is a monomeric protein (186 AA, 21544 Da) and has been crystallized with MTX inhibitor (PDB code, 2INQ, FIG. 1A). The pteridine rings occupy deep hydrophobic pocket whereas the polar glutamate chain is bent outward and is solvent exposed (FIGS. 1A and 1B). In addition, studies have shown that long chain polyglutamates of MTX (n=2-5) have equal affinity for DHFR. This suggests that terminal solvent exposed carboxylic acid could serve as an optimal position for linker conjugation.

The x-ray crystal structure of phthalimide based analogs in a complex with CRBN (FIG. 1C) suggests that the $NH_2$ position is solvent exposed and thus amenable to modification to conjugate different linkers (FIG. 1D). PROTACs (5 and 7, NCGC00685938 and NCGC00685928, respectively) of varying linker lengths were synthesized. Also, studies have shown that other phthalimide based compound such as thalidomide binds to CRBN in similar fashion. MTX-PROTAC 9 (NCGC00685965) was synthesized by tethering MTX via a long PEG based linker (Table 1).

In addition to the CRBN/Cullin 4A E3 ligase complex, the von Hippel-Lindau protein 1 (VHL-1)/Cullin 2 E3 ligase system has been employed for the design of PROTAC degraders against several target proteins (Bai et al., *Cancer Cell* 36(5):498-511, 2019). We further tested whether VHL-1/cullin 2 E3 ligase could be hijacked to degrader DHFR protein. Based on X-ray crystal structural information of VHL E3 ligase in complex with VHL-1 ligand (FIG. 1E), the terminal methyl group is solvent exposed, making it the site suitable for linker conjugation for potential DHFR degraders which has been reported previously to develop VHL based PROTAC degraders. Two DHFR degraders were synthesized using the VHL-1 ligand and Methotrexate with linkers of different lengths and chemical compositions.

TABLE 1

Exemplary MTX-PROTAC compounds

| $R_1$—$R_2$—$R_3$ | $R_1$ | $R_2$ | $R_3$ |
|---|---|---|---|
| $R_1$ = MTX, $R_2$ = 1, $R_3$ = 1 MTX-PROTAC 5 | 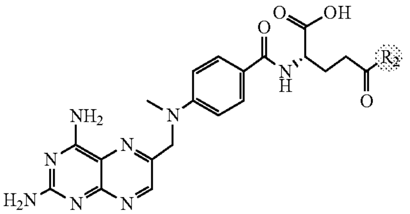 | 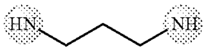 1 | 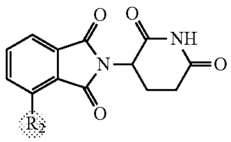 1 |
| $R_1$ = MTX, $R_2$ = 2, $R_3$ = 1 MTX-PROTAC 7 | | 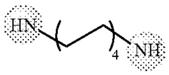 2 | |
| $R_1$ = MTX, $R_2$ = 3, $R_3$ = 1 MTX-PROTAC 9 | | 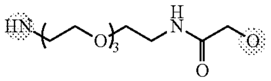 3 | 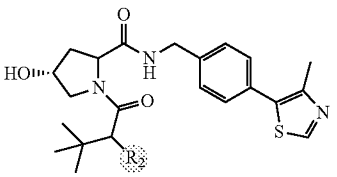 2 |
| $R_1$ = MTX, $R_2$ = 4, $R_3$ = 2 MTX-PROTAC 11 | | 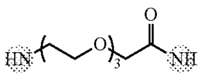 4 | |
| $R_1$ = MTX, $R_2$ = 5, $R_3$ = 2 MTX-PROTAC 13 | | 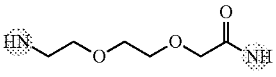 5 | |

MTX-PROTAC 5: NCGC00685938
MTX-PROTAC 7: NCGC00685928
MTX-PROTAC 9: NCGC00685965
MTX-PROTAC 11: NCGC00685964
MTX-PROTAC 13: NCGC00685995

Figure 2A:
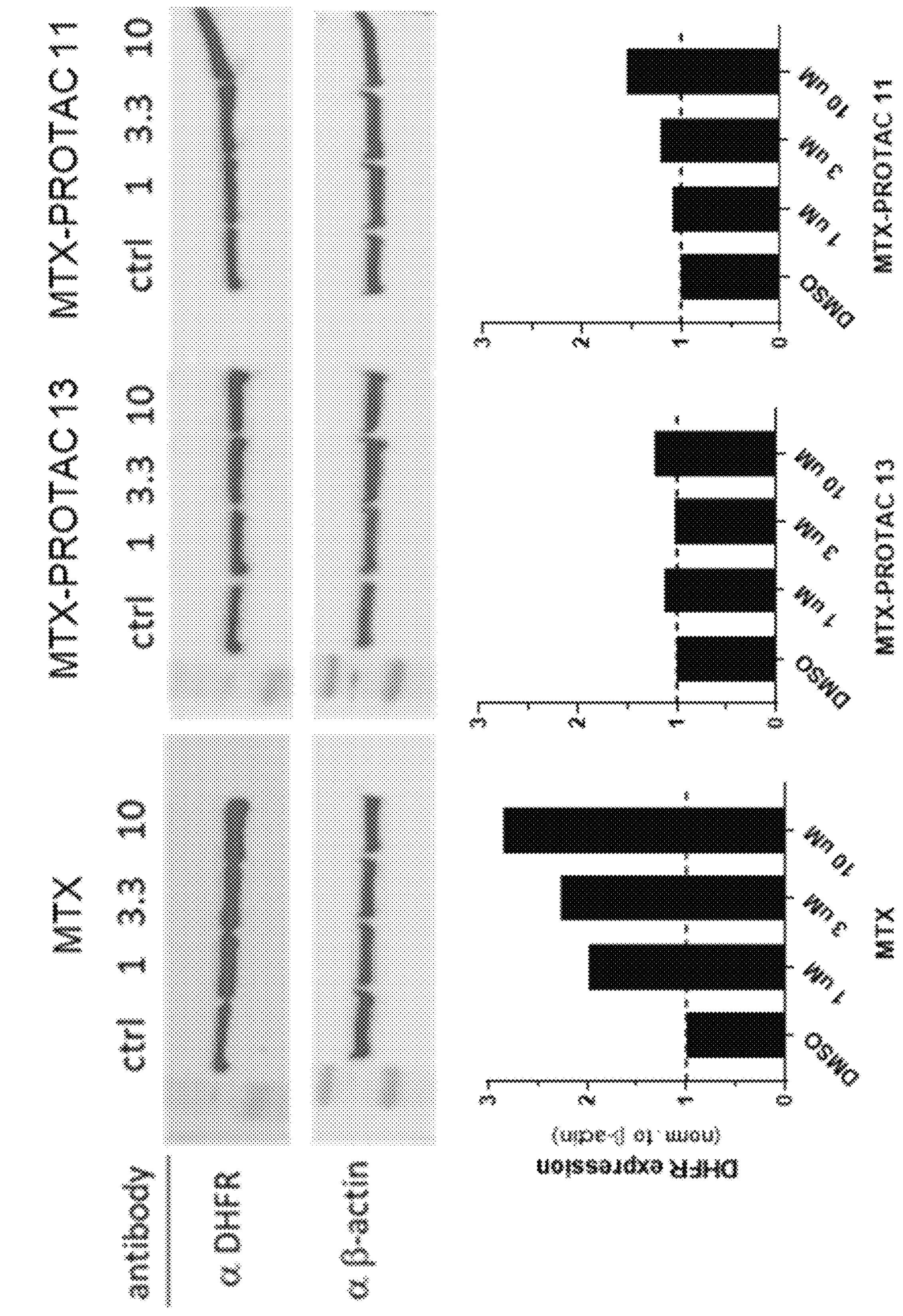
FIGS. 2A-2C show MTX and MTX-PROTACs effect on HBL1 cell DHFR levels. For each panel, top shows Western blot detection of DHFR levels after treatment of HBL1 cells for 16 h at the indicated concentrations of MTX or MTX-PROTAC and bottom shows quantification of protein levels as determined by densitometry and normalized to β-actin levels. Untreated control DHFR protein level was set to 1.0. Concentrations are in μM.
Figure 2B:
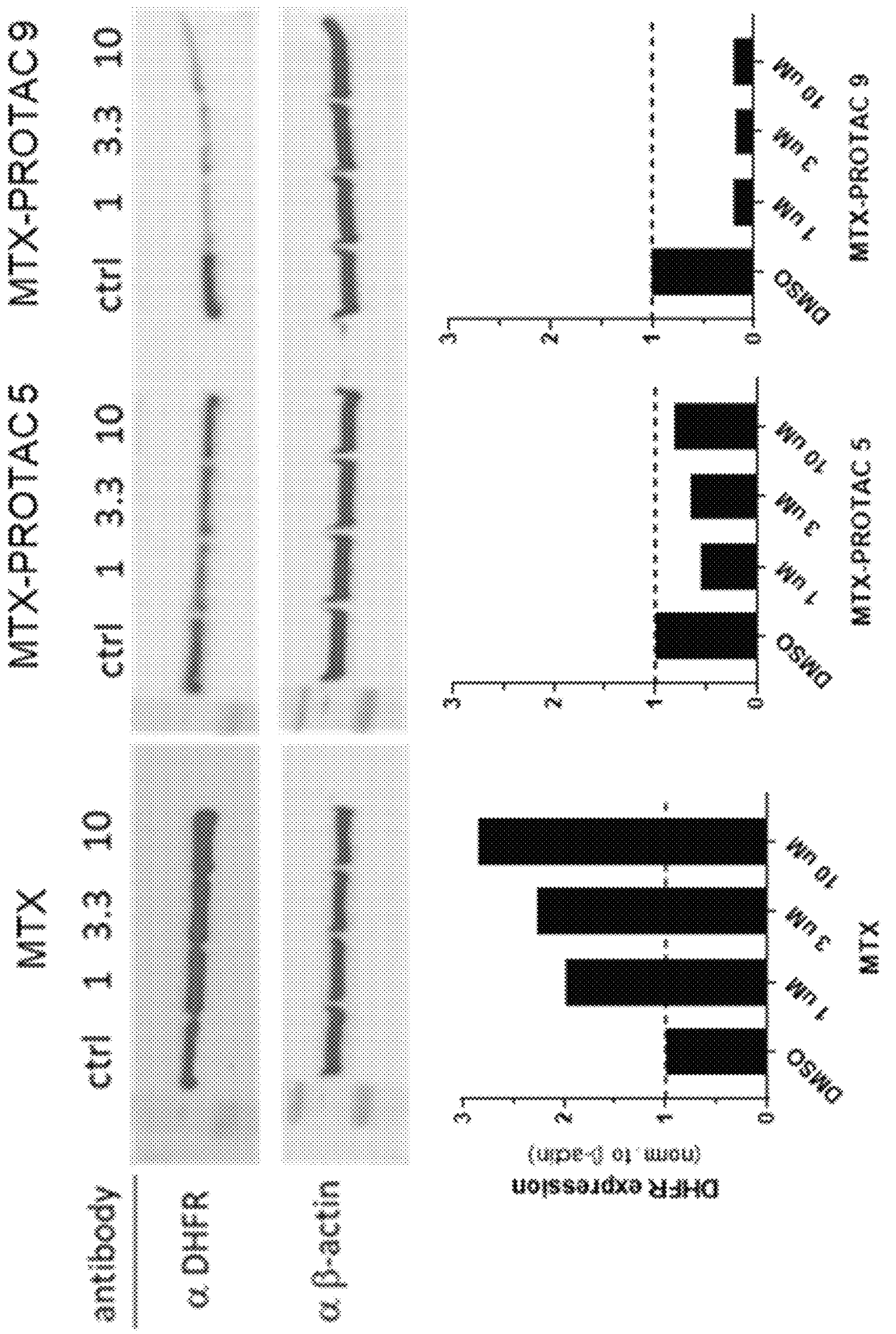
Figure 2C:
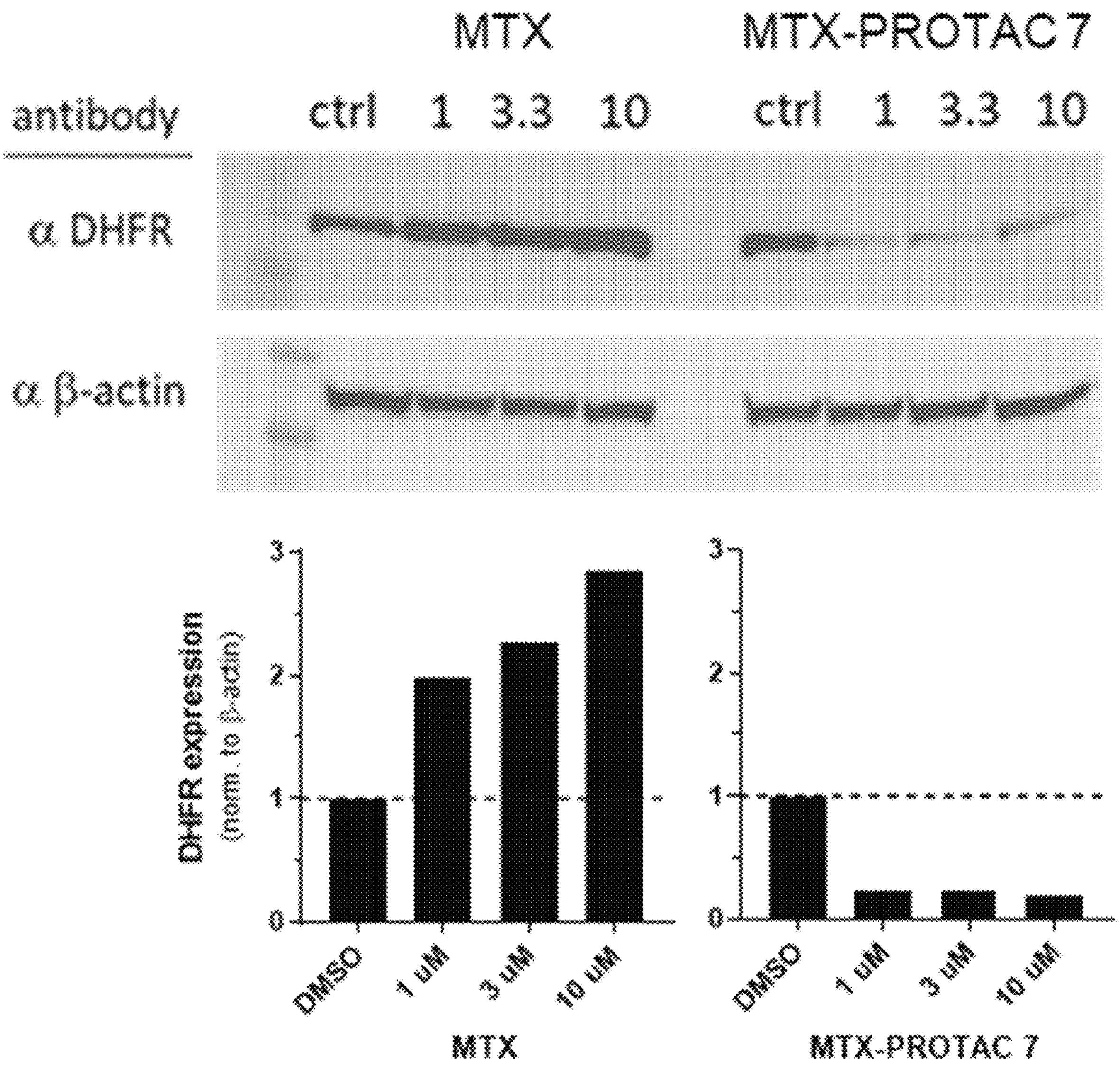

The initial western blot data from HBL1 cell lysates showed robust DHFR depletion using MTX-PROTAC 9 (NCGC00685965) and MTX-PROTAC 7 (NCGC00685928) suggesting recruitment of CRBN E3 ligase to DHFR, followed by ubiquitination and subsequent proteasomal degradation (FIGS. 2B and 2C). Strikingly, the effect of MTX-PROTAC 9 (NCGC00685965) or MTX-PROTAC 7 (NCGC00685928) on cellular levels of DHFR differed in kind and not just degree compared to identical MTX concentrations. The lowest concentration used in this experiment, 1 μM, suggested that the concentrations used were significantly higher than the concentration needed to effectively degrade 50% of the DHFR, or its $EC_{50}$. Interestingly, treatment of HBL1 cells with MTX-PROTACs 11 (NCGC00685964) and 13 (NCGC00685995) showed no alterations in DHFR protein levels (FIG. 2A). These preliminary studies suggest CRBN E3 ligase can be used to develop DHFR degraders.

Figure 3A:
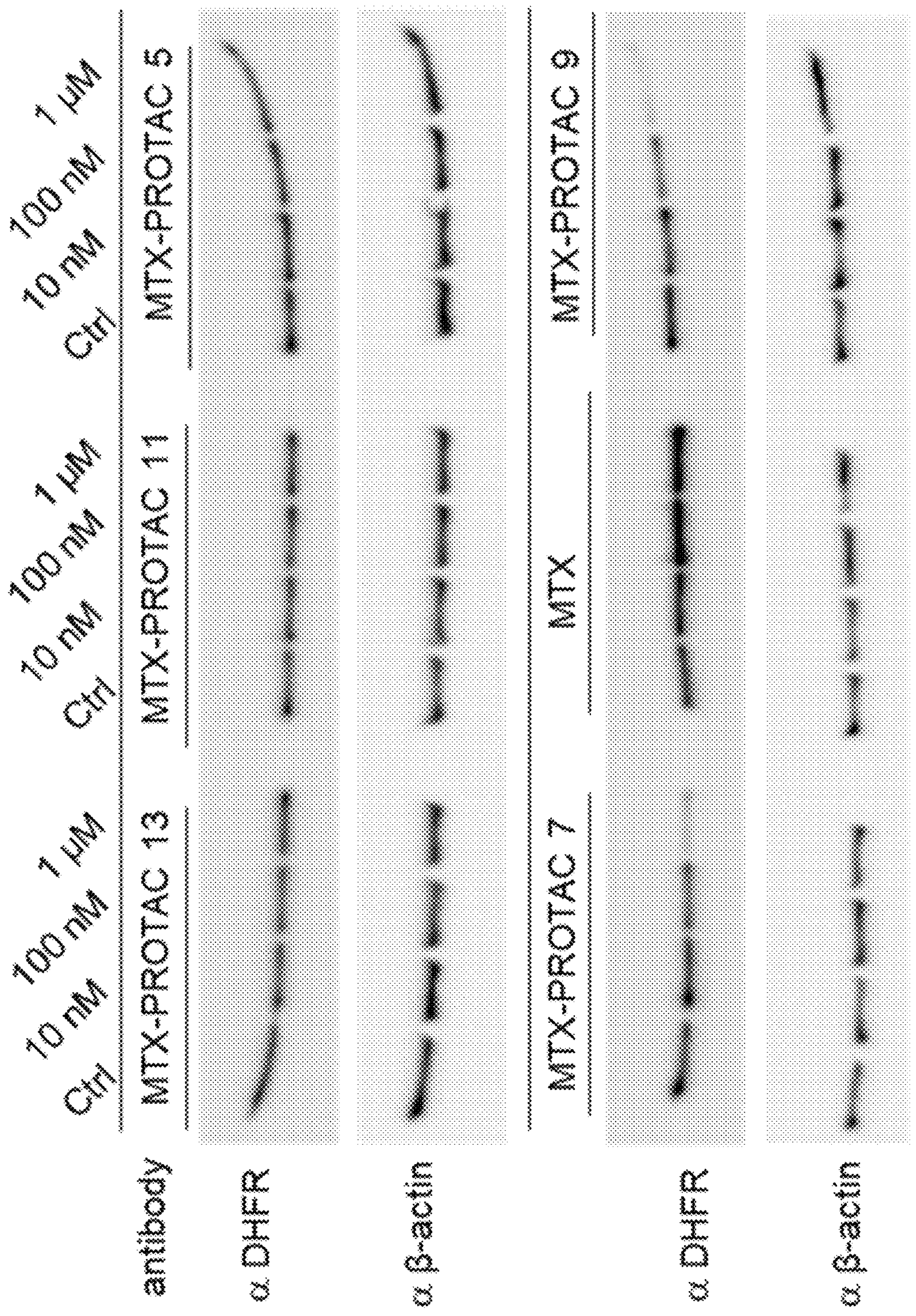
FIGS. 3A and 3B show MTX and MTX-PROTACs effect on HBL1 cell DHFR levels.
Figure 3B:
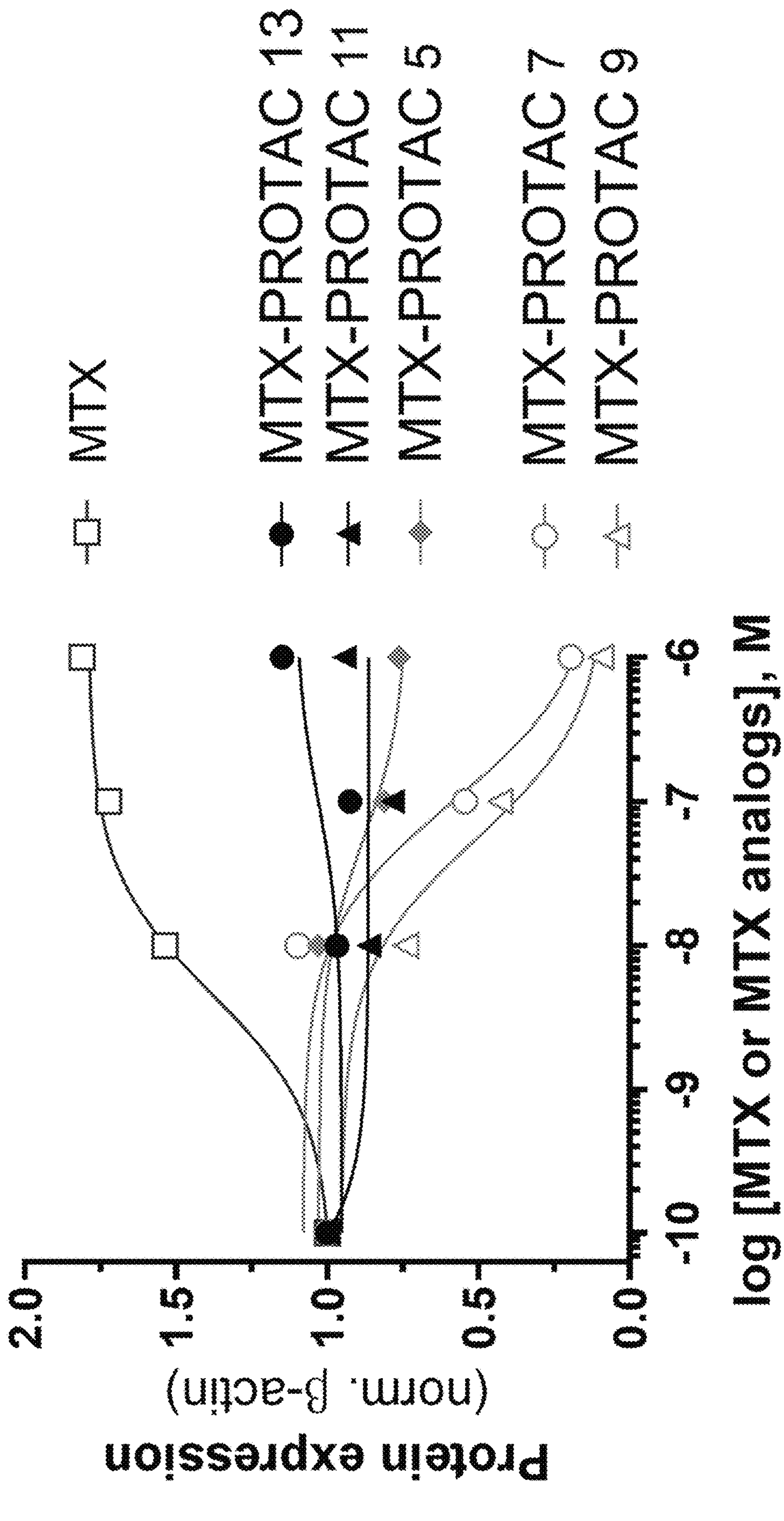

To further investigate the potency of MTX-PROTACs the experiments in HBL1 cells were repeated beginning at 1 μM and titrating the MTX-PROTAC down to 10 nM (FIG. 3A). Quantifying the western blot data and plotting it vs the treatment concentration demonstrated that the $EC_{50}$ values for MTX-PROTACs 9 (NCGC00685965) and 7 (NCGC00685928) were near or below 100 nM (FIG. 3B). In addition, robust MTX-dependent increase in DHFR levels was observed.

Figure 4A:
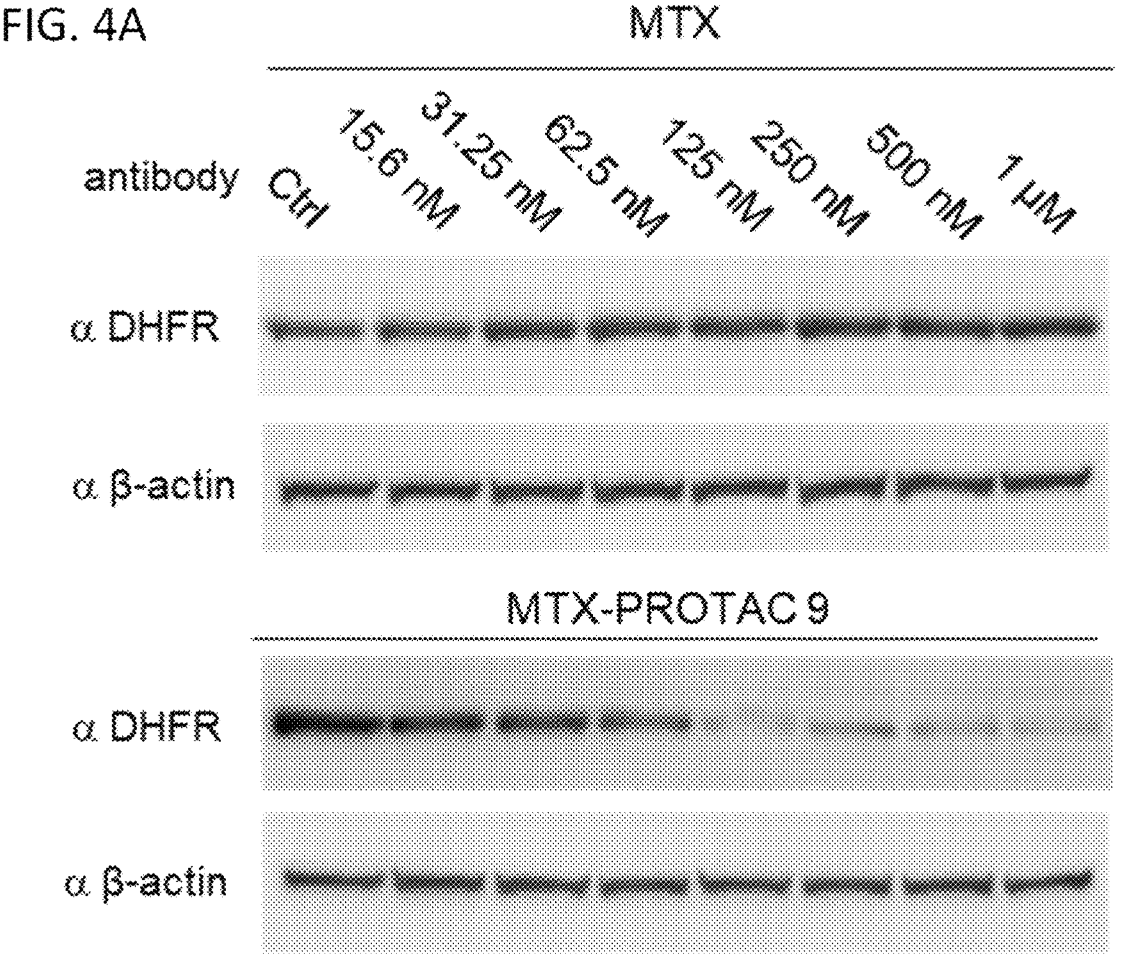
FIGS. 4A and 4B show DHFR levels resulting from MTX vs MTX-PROTAC 9 (NCGC00685965) in HBL1 cells.
Figure 4B:
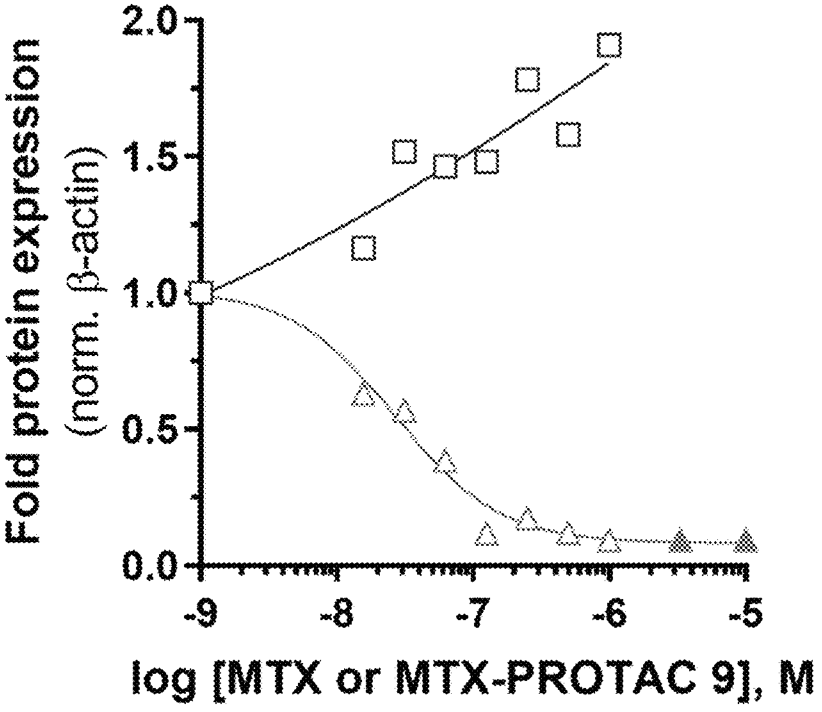

To determine precise $EC_{50}$ values for the most active MTX-PROTAC, 9 the number of concentrations in the HBL1 cell assay was increased (FIG. 4A). Results from this experiment indicated that the $EC_{50}$ of MTX-PROTAC 9 (NCGC00685965) is 27 nM (FIG. 4B).

Figure 5A:
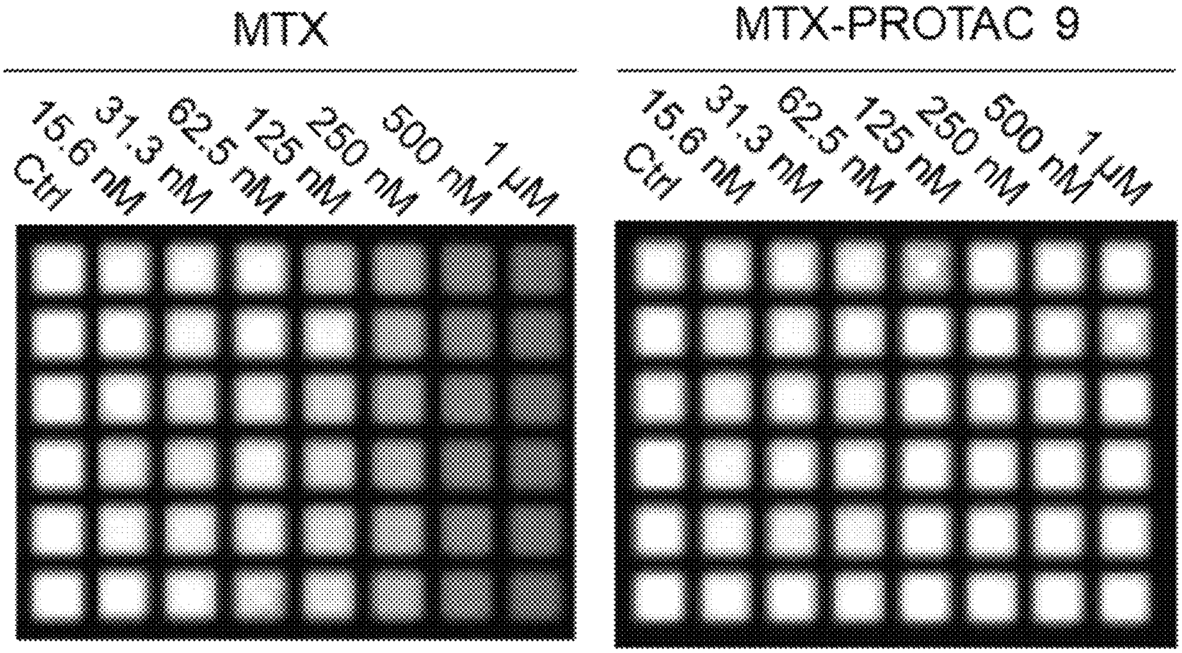
FIGS. 5A and 5B show effect of MTX or MTX-PROTAC 9 (NCGC00685965) on cellular ATP levels in HBL1 cells.
Figure 5B:
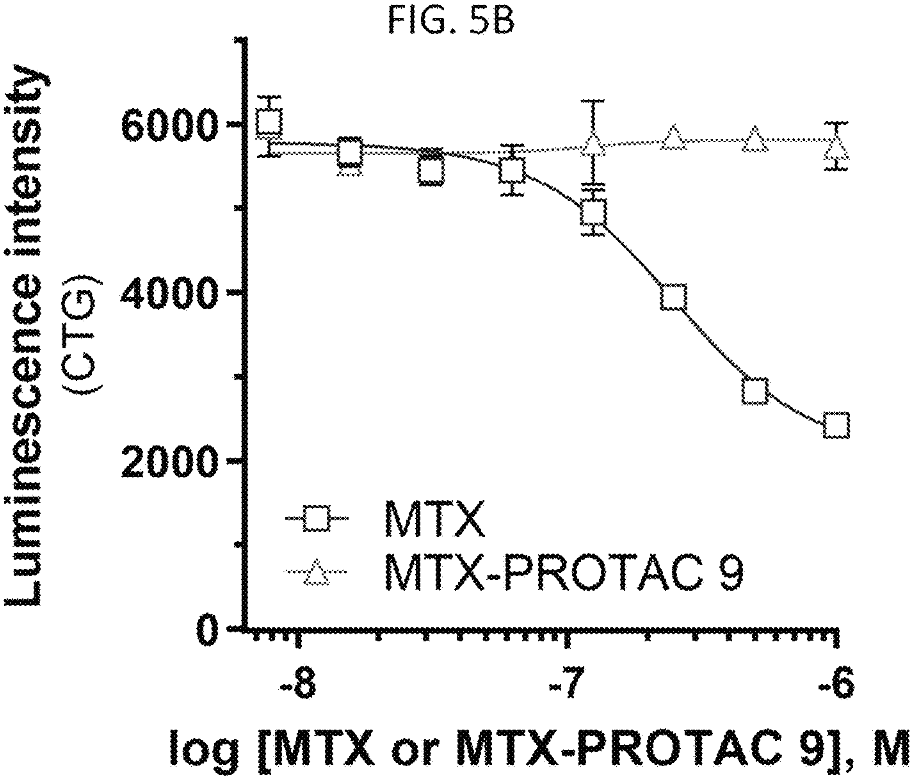

To determine the effect of our MTX-PROTAC on acute cellular toxicity the CellTiter-Glo luminescent cell viability assay, which employs cellular ATP levels as an indicator of cell viability, was used. Strikingly, ATP levels were not affected by MTX-PROTAC 9 (NCGC00685965) even at concentrations clearly demonstrated to deplete DHFR from the HBL1 cell. However, at equivalent levels, MTX significantly depleted ATP levels (FIG. 5A). The luminescent output of the CellTiter-Glo assay is quantified on a CCD-based imager as shown in FIG. 5B. The $IC_{50}$ for cellular ATP-depletion by MTX is 200 nM, while MTX-PROTAC 9 (NCGC00685965) did not significantly alter ATP levels even up to 1 μM.

Figures 6A, 6B, 6C:
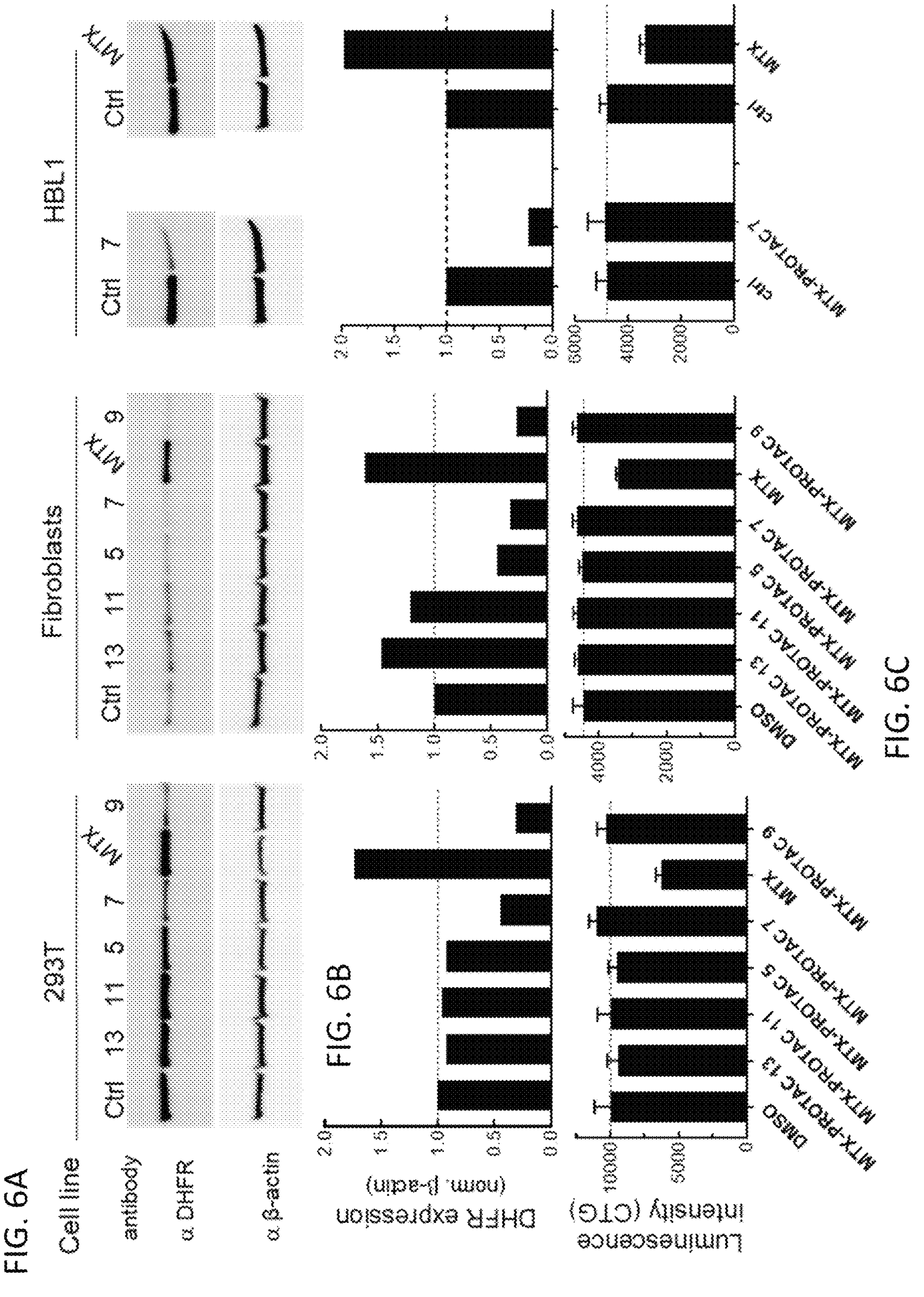
FIGS. 6A-6C show cell-type dependence of MTX and MTX-PROTACs on DHFR protein levels.

The generality of the DHFR degrading effect of MTX-PROTACs based on the thalidomide CRBN E3 ligase ligand and whether the VHL ligand would promote DHFR degradation in other cell types was next examined. Cultured A293 and fibroblast cell lines were tested under similar conditions used in the HBL1 cell line studies. Interestingly, not only did the same MTX-PROTACs affect the DHFR levels in different cell types, but there appeared to be an enhanced effect in fibroblasts such that MTX-PROTAC 5 (NCGC00685938), which was essentially inactive in HBL1 and 293T cells, showed a significant degradation of DHFR. In fibroblasts there appeared to be an MTX-like stabilization of DHFR by MTX-PROTAC 13 (NCGC00685995), a VHL ligand-based PROTAC (FIGS. 6A-6C). Additionally, the ATP-depleting properties of MTX in 293T and fibroblast cell lines were observed, and this effect was again not observed with the MTX-PROTAC, including the MTX-PROTAC 13 (NCGC00685995), which appears to share DHFR stabilizing activity with MTX.

Figure 7A:
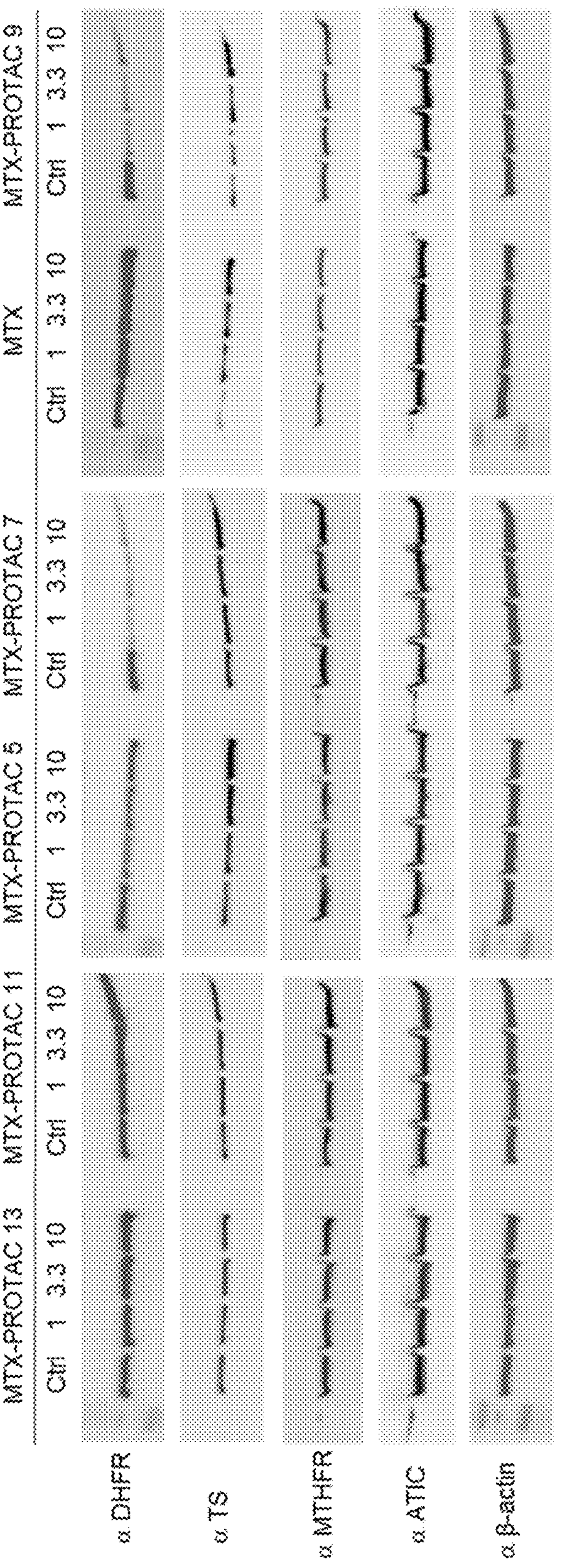
FIGS. 7A and 7B show effects of MTX or MTX-PROTAC analogs on folate-cofactor utilizing enzymes in HBL1 cells. Western blot detection of folate-cofactor dependent enzyme levels after treatment of HBL1 cells (FIG. 7A) or 293T cells, HBL1, or fibroblasts (FIG. 7B) for 16 h at the indicated concentrations of MTX or MTX-PROTAC. Antibodies (a) used were for the following enzymes: DHFR, dihydrofolate reductase; TS, thymidylate synthase; MTHFR, methylenetetrahydrofolate reductase; ATIC, 5-amino-4-imidazolecarboxamide ribonucleotide transformylase; and β-actin was used for protein normalization. Concentrations are in micromolar.
Figure 7B:
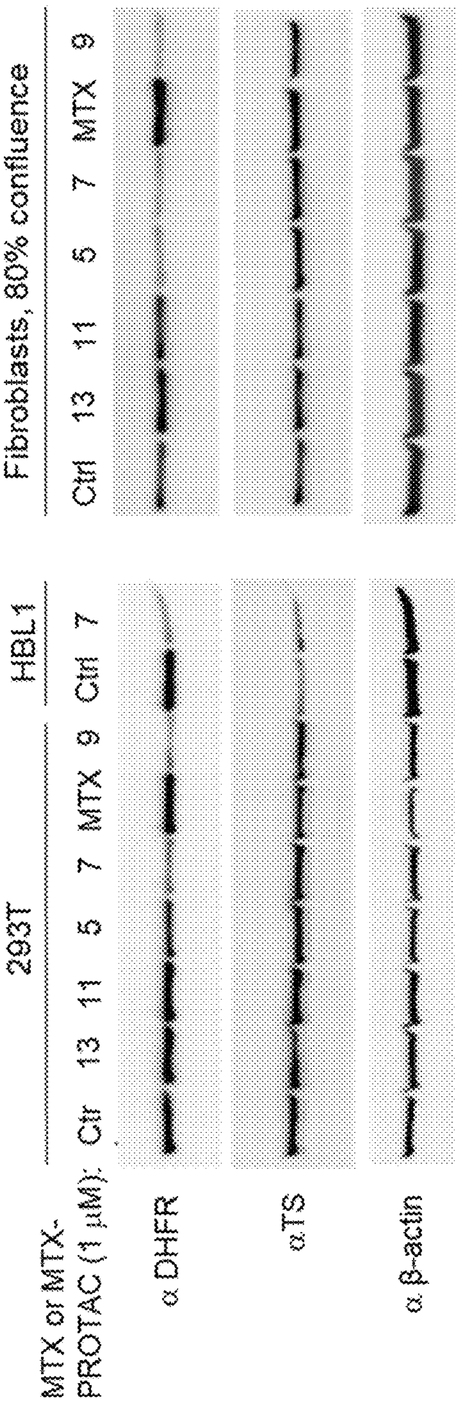

MTX and its polyglutamylated forms are known to inhibit other reduced folate cofactor-utilizing enzymes. The effect of 1 μM MTX or MTX-PROTACs on the protein levels in HBL1 cells for thymidylate synthase (TS), methylenetetrahydrofolate reductase (MTHFR) and 5-amino-4-imidazolecarboxamide ribonucleotide transformylase (ATIC) was also investigated. Western blots in FIG. 7A show that there is no discernable effect of the MTX-PROTACs vs. MTX on the levels of MTHFR or ATIC, however MTX-PROTAC 5 (NCGC00685938) and to a lesser extent MTX-PROTAC 7 (NCGC00685928) and 9 (NCGC00685965) showed a slight increase in TS similar to that observed for MTX. Exploring this effect on TS further in 293T and fibroblasts (FIG. 7B) low but detectable increases in TS by MTX and MTX-PROTAC 5 (NCGC00685938) and 7 (NCGC00685928), were observed, while in 293T cells there was no significant change in TS levels.

Figure 8A:
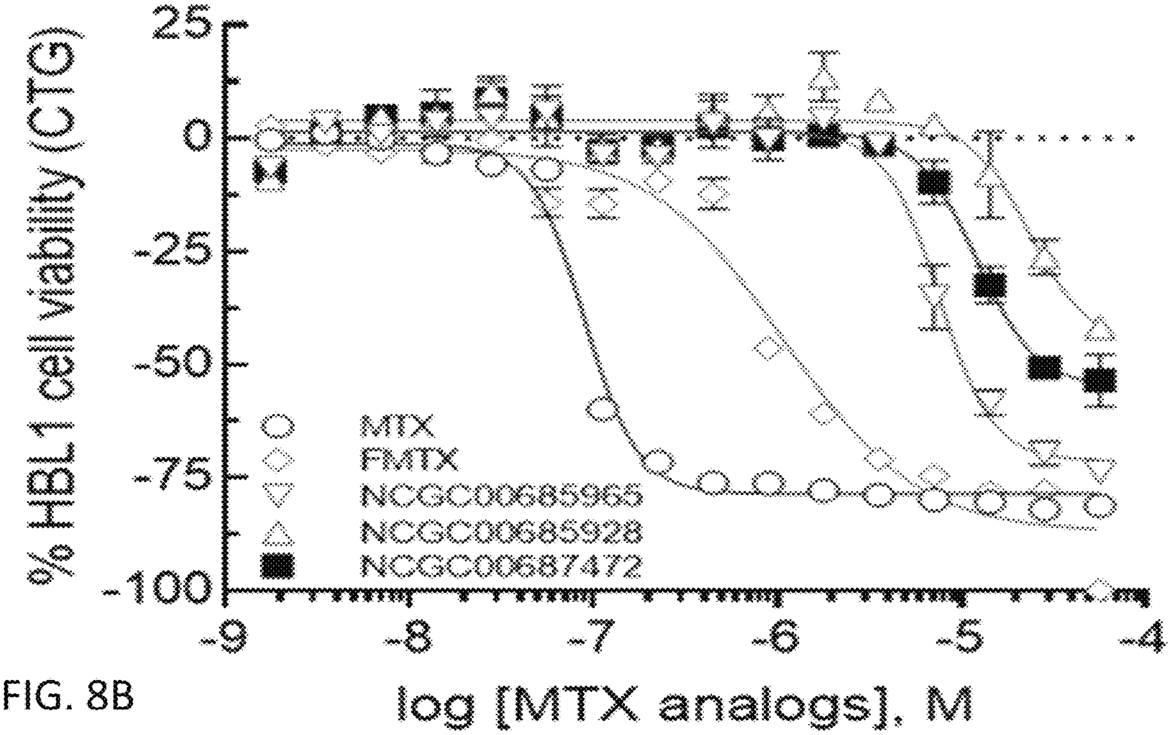
FIGS. 8A-8C show cellular toxicity of representative MTX-PROTACs. Cell viability as measured by the CellTiter-Glo assay (Promega) after 72 hours treatment with MTX, FMTX, and MTX-PROTACs NCGC00685965, NCGC00685928, and NCGC00687472 on the HBL1 cell line (FIG. 8A) and the MTX-resistant HBL1 cell line obtained from prolonged culture in 5 μM MTX (FIG. 8B).

To determine the effect of additional MTX-PROTACs on cellular proliferation the CellTiter-Glo luminescent cell viability assay, which employs cellular ATP levels as an indicator of cell viability (Riss et al., Cell Viability Assays, In *Assay Guidance Manual*, Bethesda, MD 2004), was used. Strikingly the viability of an HBL1 cell line was not significantly affected by the MTX-PROTACs as compared to MTX or the γ-polyglutamylation-resistant MTX analog, FMTX (Galivan et al., *Proc. Natl. Acad. Sci. USA* 82:2598-2602, 1984), at concentration below 10 μM (FIG. 8A and Table 2). An MTX-resistant HBL1 cell line was subsequently developed by culturing HBL1 cells with increasing MTX concentrations over several months.

Figure 8B:
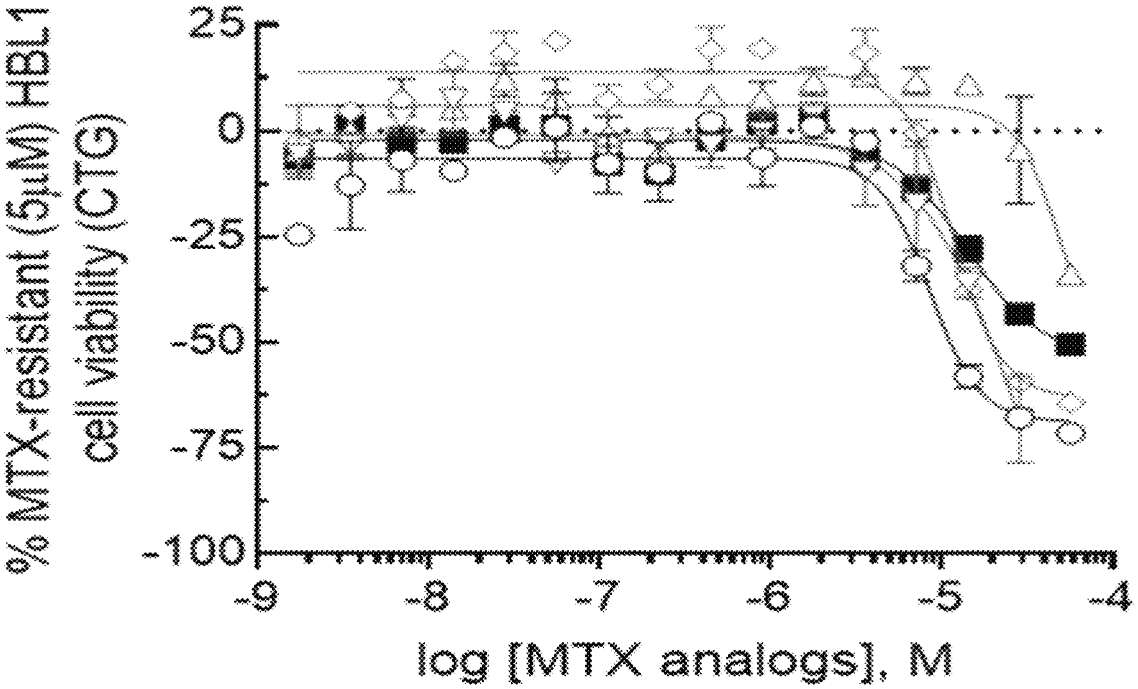
Figure 8C:
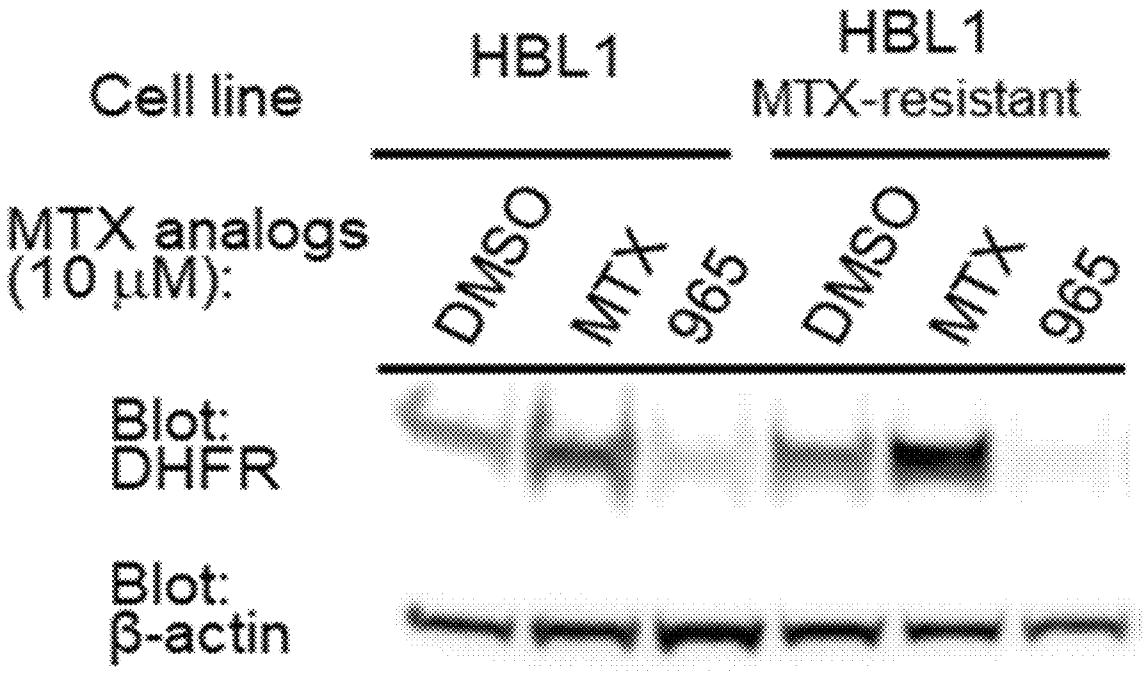

In this cell line, both MTX and FMTX cellular toxicities greatly decreased to overlap with that of the MTX-PROTACs (FIG. 8B), while interestingly, the ability of the MTX-PROTACs, as represented by NCGC00685965 remained capable of depleting cellular DHFR in both cell lines (FIG. 8C).

Example 47

Efficacy of MTX-PROTACs in Cancer

Analysis is conducted in a MCF-7 breast cancer xenograft mouse model to establish the safety and the efficacy of MTX-PROTAC compared to MTX on tumor growth inhibition. This protocol is based at least partly on previously performed in vivo experiments with mice (see e.g., Khan et al., *Nature Medicine* 25:1938-1947, 2019; Cheng et al., Acta Pharmacol. Sin. 34:951-959, 2013). Female BALB/c nude mice (6 weeks old) are purchased from commercial vendors and acclimated in the laboratories for seven days prior to experimentation. MCF-7 cells (2×106) are suspended in 200 μL PBS and inoculated subcutaneously in the right flank. The treatment is started once the average tumor volume reaches ~100 $mm^3$. The mice are randomly divided into control, MTX, and MTX-PROTAC, with eight mice each. The doses used are as follows: 25 mg/kg MTX; 50 mg/kg MTX; 100 mg/kg MTX; 25 mg/kg MTX-PROTAC; 50 mg/kg MTX-PROTAC; 100 mg/kg MTX-PROTAC. The control group receives vehicle alone (PBS pH 7.4). All treatments are given by intraperitoneal injection once weekly for 3 weeks.

Mice are weighed three times a week and toxicity is assessed by the lethality of tumor-bearing mice and body weight loss. To assess drug effect on xenografts growth, caliper measurements of tumors are performed three times a week. Tumor volume is determined using the formula ((L×W2)×0.5), where L is length in mm and W is the width in mm. The antitumor activity is calculated by comparing the tumor volume of the treated group (T) on the treatment day with the control group (C), or with the initial tumor volume (T0), resulting in T/C values (percentages) and T/To values (percentages). Tumor-doubling time of test and control groups is defined as the period required to double the initial tumor volume (200%). All the animals are euthanized in accordance with institutional policy, and various tissues are collected. Tumors are weighed and used for DHFR and other folate ligands expression by immunoblotting. Livers ae collected and assessed for markers of toxicity.

Example 48

Evaluation of Compounds for Efficacy in Collagen-Induced Arthritis DBA/1 Mouse Model This protocol is based at least partly on previously performed in vivo experiments with mice (see e.g., Brand et al., *Nature Protocols* 2:1269-1275, 2007; Cannon et al., *Agents Actions* 29:315-323, 1990). DBA/1 mice 8-10 weeks of age are obtained from commercial vendors and maintained in the animal facility with freely available chow and water. The compound dosing solutions are prepared fresh using pharmaceutically acceptable formulation vehicles and water/saline as the diluent before the animal experiments. Mice ae randomly divided into following 6 groups (n=10 each group) Group 1: Bovine type II collagen (CII) emulsified in complete Freund's adjuvant (CFA); Group 2: CII in CFA+treatment with normal vehicle used to dissolve test compounds as control (daily vehicle dosing); Group 3: CII in CFA+treatment of methotrexate (oral dose of 1 mg/kg daily); Group 4: CII in CFA+treatment of methotrexate (oral dose of 10 mg/kg); Group 5: CII in CFA+treatment of MTX-PROTAC (oral dose of 1 mg/kg daily); Group 6: CII in CFA+treatment of MTX-PROTAC (oral dose of 10 mg/kg daily). Mice are immunized with a 50 μl volume of CII in CFA intradermally (i.d.) into the tail for all six groups. Mice are monitored daily for the onset of disease and are weighed weekly, for the assessment of overall health status and clinical score to each of their paws from day 0. Arthritis affected animals are clinically assessed five times per week to examine each limb of each mouse for the appearance of arthritis in each limb by paw measurements using a plethysmometer. Mice without signs of arthritis ten weeks after treatments are considered disease negative.

After the end of the tenth week, animals are sacrificed and histopathology. ELISA assays are performed to determine anti-type II collagen antibody levels and total immunoglobulin levels. Spleen and lymph nodes are removed and single-cell suspensions are prepared. Mitogen responses to collagen and antigen proliferative responses to type II collagen are determined using standard techniques. The analysis is conducted to assess the influence of the compound on (i) disease incidence, (ii) time of disease onset, (iii) individual paw swelling, and (iv) disease progression based on cumulative arthritis score. The immunological data are analyzed to examine the therapeutic effects of the compounds.

Example 49

Effect of MTX-PROTACs on Viruses

The effect of MTX-PROTAC vs MTX on intact virus or viral RNA and DNA replication can be tested using a variety of assay methods such as reporter-gene containing recombinant infectious virus or subgenomic replicons, respectively.

Viral replication in cell culture. In some examples, the system described by Liu et al., 2020 is used to test such combinations for their ability to inhibit dengue virus replication using the pDENV-Luc infectious clone originally derived from dengue serotype 2 (DENV-2) strain 16681 (Marceau et al., *Nature* 535:159-163, 2016). Here the pDENV-Luc replicon plasmid is linearized, RNA generated, purified, and transfected into Vero E6 cells to generate and quantify supernatants containing infectious DENV-Luc virus by standard methods (Paillet et al., Vaccine 26:6464-6467, 2009; Segura et al., *Viral Vectors for Gene Therapy: Methods and Protocols* 737:89-116, 2011). Assays to evaluate the effect of MTX-PROTAC or MTX are conducted in A549 cells plated overnight in 96-well plates (5,000 cells per well), 384 well plates (1,250 cells per well), or 1536 well plates (300-500 cells per well) in complete DMEM supplemented with 20 μM uridine, incubated at 37° C. for 24 hr, followed by treatment with MTX-PROTAC or MTX. After drug treatment (1-6 hr) cells are infected with DENV-Luc virus at a MOI=0.04. After the prescribed time (24-72 hr), DENV-Luc replication is monitored using a substrate for the specific luciferase being expressed, for example, *Renilla* luciferase which can be measured using commercial detection kits, such as *Renilla*-Glo Luciferase Assay System (Promega Corp.) by following manufacturer instructions. General cellular toxicity can also be measured in a parallel replicate experiment by measuring cell viability using any number of assays, for example total cell number or ATP levels (see, e.g., Riss et al., Cell Viability Assays. *Assay Guidance Manual.* G. S. Sittampalam, et al., 2004).

RNA replication measured by subgenomic replicons. Replication of viral nucleic acid from a subgenomic replicon can be monitored using known measurements (see e.g., Lohmann, *Methods Mol Biol* 510:145-163, 2009). For example, a hepatitis C subgenomic RNA replicon can be used to express β-lactamase in place of the HCV structural proteins as a reporter for viral replication in the permissive Huh-7 cell, MR-2 as previously described (e.g., Zuck et al., *Anal. Biochem.* 334:344-355, 2004). Here a beta-lactamase reporter-containing HCV subgenomic replicon (HCV-bla) sequence is linearized, RNA synthesized using a T7 in vitro transcription, purified, and quantified by 260 nm absorbance. Assays to evaluate the effect of MTX-PROTAC or MTX can be conducted in MR-2 cells pre-transfected with HCV-bla RNA under optimized conditions, aliquoted, and frozen. For the assay, cells are thawed and seeded into 384-well at 40,000 cells/well in CellGro DMEM supplemented with 10% fetal bovine serum, nonessential amino acids, Penicillin-streptomycin solution, glutamine, 20 μM uridine and allowed to recover for at least 6 hr at 37° C. prior to compound testing. After addition of MTX-PROTAC or MTX, cells are incubated for 24 hr at 37° C. followed by addition of a pro-fluorescent beta-lactamase substrate for example, CCF4-AM (Zuck et al., *Anal. Biochem.* 334:344-355, 2004) or Fluorocillin (Rukavishnikov et al., *Anal. Biochem.* 419(1):9-16. 2011) with fluorescence measured in a plate-based spectrophotometer (340 nm excitation, 530 nm emissions) to obtain % inhibition.

Example 50

High-Throughput DHFR Abundance Assay

Reagents and antibodies: Anti-DHFR antibody was from Abcam and anti-β-actin mAb was purchased from Cell Signaling. Peroxidase-conjugated goat anti-mouse and goat anti-rabbit sera were from Thermo Scientific. The Nano-Glo® HiBiT Lytic Detection System for bioluminescent protein detection and the Nano-Glo® HiBiT Blotting System used to quantify protein expression on western blots were from Promega.

CellTiter-Glo viability assays: Five μL of cells (2500 cells) from the 12-well plate culture were plated into white 1536-well plates (Greiner, Monroe, NC, 789173-F) in 6 replicates. CellTiter-Glo Luminescent Cell Viability Assay (CTG) (Promega, G7572), 2.5 μL/well reagent was added with a BioRAPTR FRD (Beckman Coulter, Sykesville, MD), plates were incubated in the dark at ambient temperature for 10 min, and luminescence measured with a ViewLux 1430 Ultra HTS (Perkin Elmer, Waltham, MA).

Production of DHFR-HiBiT: The human DHFR-HiBiT fusion protein was constructed to have the HiBiT tag (VSGWRLFKKIS; SEQ ID NO: 1) sequence (Dixon et al. (2016) *ACS Chem. Biol.* 11(2):400-408) located in C-terminus of DHFR. The human DHFR-HiBiT construct was synthetized (Bio Basic) and cloned into the retroviral vector pBMN-Ires-Lyt-2 (provided by G. Nolan, Stanford University, Stanford, CA) which expresses the coding region of mouse CD8a (Lyt-2) using the restriction sites BamHI/XhoI. All constructs were sequenced to validate authenticity. Infected cells were positively selected based on murine CD8a expression using magnetic beads (Miltenyi Biotech).

Cell culture: Human embryonic kidney HEK293T cells were maintained in DMEM (Gibco) supplemented with 10% fetal bovine serum (Hyclone), 2 mmol/L 1-glutamine, HEPES (Gibco) and 100 U/mL penicillin/streptomycin (Invitrogen). The lymphoma cell line HBL1 were maintained in RPMI (Life Technology) supplemented with 5% fetal bovine serum (Hyclone), 2 mmol/L L-glutamine, HEPES (Gibco) and 100 U/mL penicillin/streptomycin (Invitrogen). For efficient retroviral infection and transduction, HBL1 cells were engineered to express the murine ecotropic retroviral receptor (provided by L. Staudt, NIH, NCI, Bethesda, MD), (Ngo, et al., *Nature* 441:106-110 (2006)). Cells were cultured in incubators maintained at 37° C., with 5% $CO_2$ and 85% humidity.

Transfection and retroviral infections: Transfections were performed using Lipofectamine 2000 (Invitrogen) according to the manufacturer's protocol. For retroviral infections, viruses were produced in HEK293T cells and used to infect HBL1 cell line. The retroviral construct delivering DHFR-HiBiT was co-transfected into 293T cells with the mutant ecotropic envelope-expressing plasmid pHIT/EA6×3* and the MLV gag-pol expression plasmid pHIT60n (kind gifts of Dr. Louis Staudt, National Cancer Institute, USA) as previously reported (Ngo, et al., *Nature* 441:106-110 (2006)). Supernatants containing the retrovirus were collected and filtered at 48- and 72-hours post-transfection. HBL1 cells were centrifuged and then resuspended with the retroviral supernatant with 8 μg/ml of polybrene. The cells were spin-infected twice on consecutive days at 2,500 rpm, at RT, for 90 minutes.

Protein expression analysis: Cells were collected and homogenized in lysis buffer (20 mM Tris-HCl (pH 7.5), 150 mM NaCl, 1 mM $Na_2EDTA$, 1 mM EGTA 1% Triton, 2.5 mM sodium pyrophosphate) with freshly added protease inhibitors (50 mM HEPES, pH 7.6, 150 mM NaCl, 20 mM EDTA, 10 mM sodium orthovanadate (Vanadate, $Na_3VO_4$), 100 mM NaF, 2% Triton X-100, 10 μg/ml aprotinin, 10 μg/ml leupeptin, 0.5 mm phenylmethyl sulfonyl fluoride). Cell debris was removed by centrifugation and normalized amounts of protein were separated by 12% SDS-PAGE and transferred onto nitrocellulose. The membrane was immunoblotted with rabbit polyclonal anti-DHFR or mouse anti-β-actin antibodies. The immune complexes were detected by horseradish peroxidase-conjugated secondary antibodies (Thermo Scientific) and developed using a ChemiDoc MP Imager (Bio-Rad). To detect HiBiT-tagged proteins, the membrane was rinsed for 1 h in TBST and then incubated in LgBiT/buffer solution overnight. Nano-Glo® Luciferase Assay Substrate furimazine was added and incubated 5 minutes, and the blot was exposed on the imager.

Lytic HiBiT Detection: Cells were plated in solid white 1536-well tissue culture plates (Greiner), at the concentration of 2000 cells/well. After treatment, an equal volume of Nano-Glo HiBiT Lytic Reagent (Promega) containing the substrate furimazine and Large BiT (LgBiT) was added to the cells according to the manufacturer's protocol. Cells were incubated for 10 min at room temperature, and luminescence was measured using a Perkin Elmer ViewLux microplate imager with 30 seconds of exposure time.

Figure 9A:
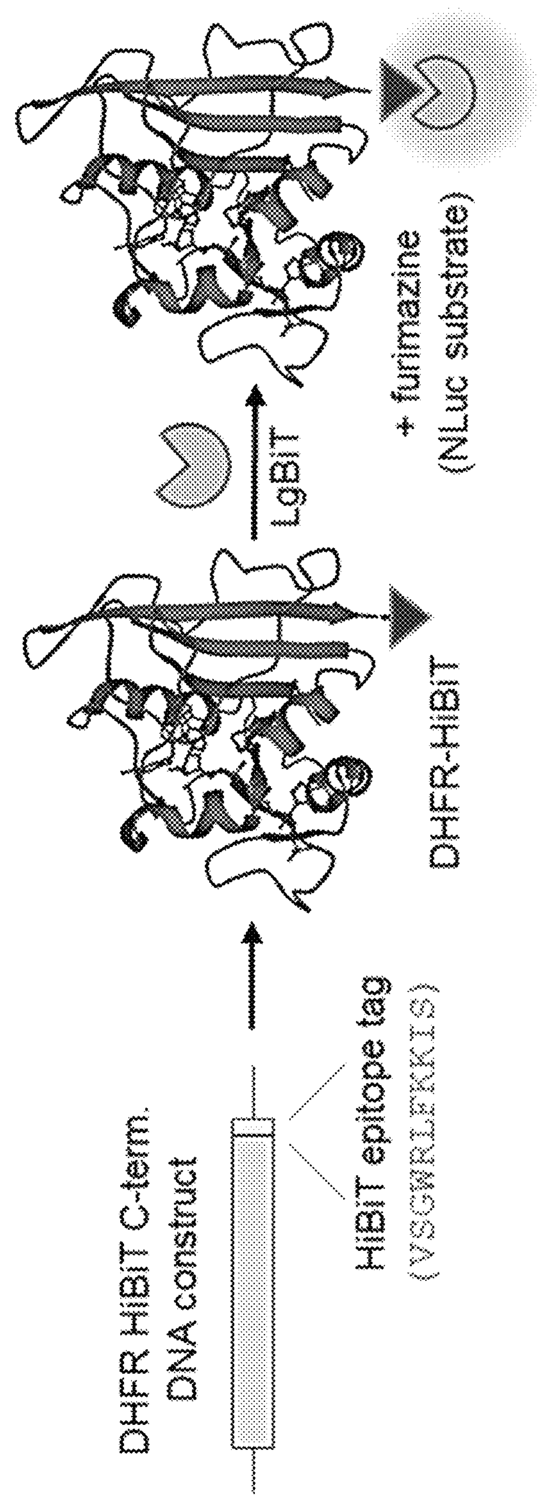
FIGS. 9A-9C show detection of HiBiT-tagged DHFR protein.
Figure 9B:
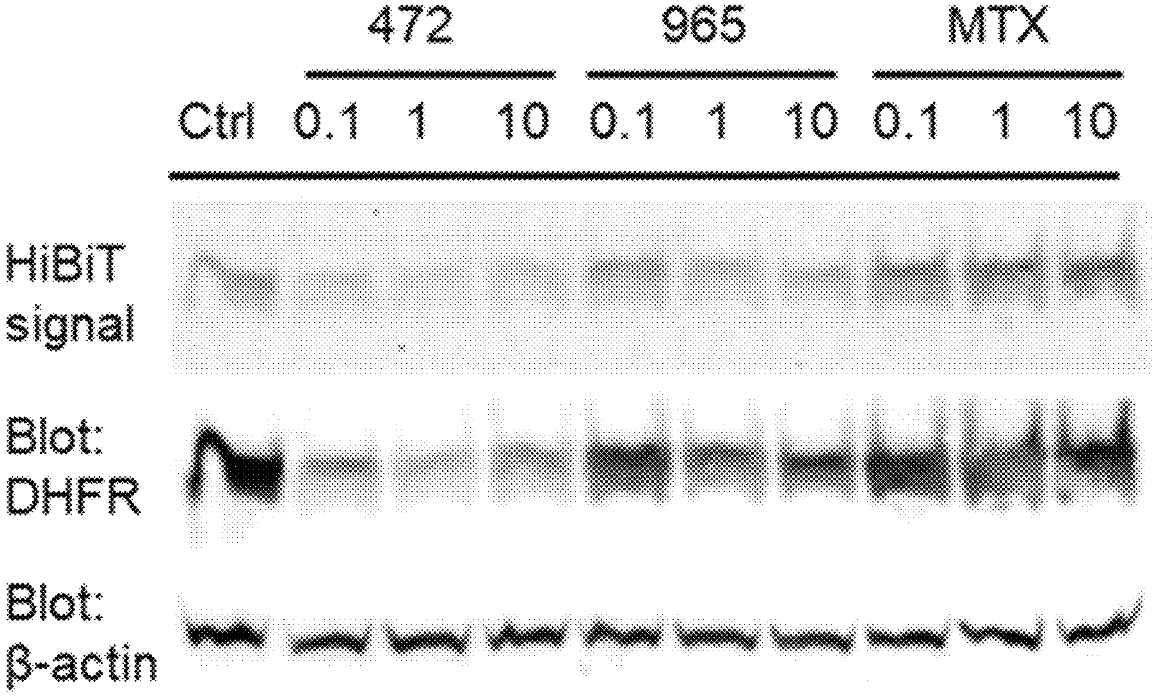
Figure 9C:
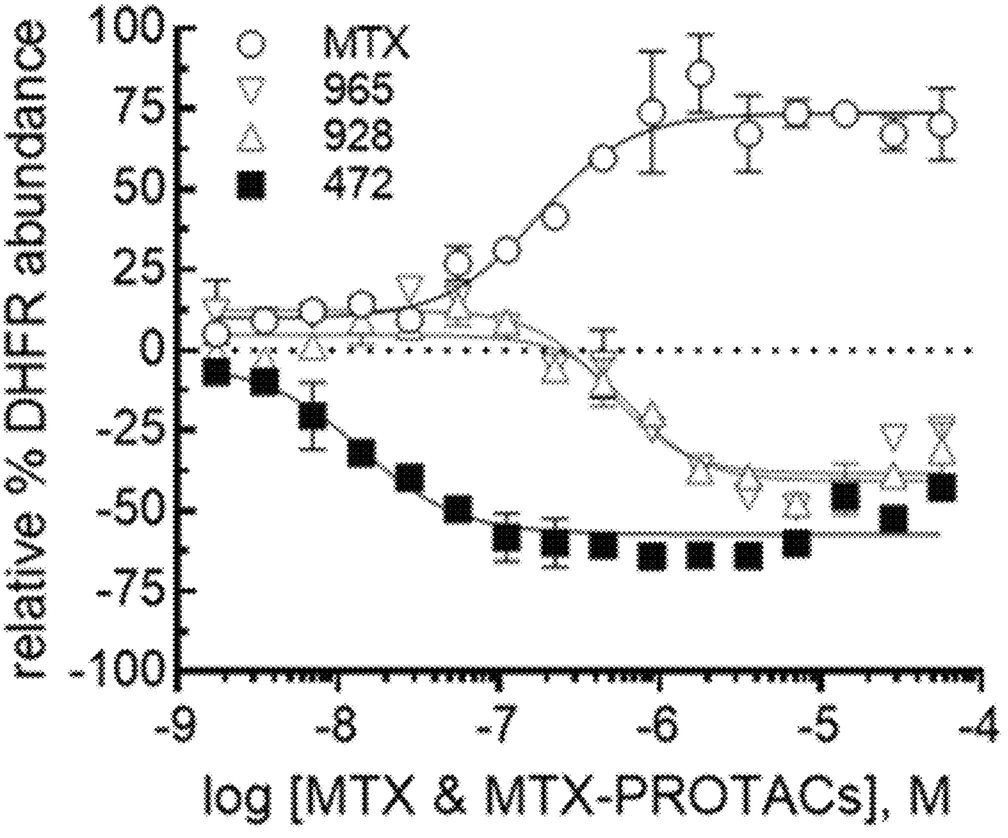

DHFR-HiBiT expressing cell line for quantification of DHFR: To enable a consistent and facile method to measure and compare the potency and efficacy of MTX-PROTAC analogs, a DHFR-HiBiT cell line was constructed (FIG. 9A) to allow a direct measure of cellular DHFR levels. In this assay, the cellular level of DHFR in an HBL1 cell line was determined by measuring the bioluminescence resulting from the complementation of DHFR-HiBiT with exogenously added LgBiT fragment (Dixon et al. (2016) *ACS Chem. Biol.* 11(2):400-408). The resulting bioluminescence was shown to parallel the cellular DHFR level as measured by western blot analysis (FIG. 9B). Utilizing the DHFR-HiBiT assay, the potency and efficacy, plotted as % change in untreated cellular DHFR level (control) could be measured as illustrated for MTX, NCGC00685928, and NCGC00687472 in FIG. 9C. Table 2 summarizes degradation or stabilization potency and efficacy of a panel of MTX-PROTACs measured using the DHFR-HiBiT assay.

TABLE 2

Degradation or stabilization potency and efficacy for MTX, FMTX and MTX-PROTACs as measured by the DHFR-HiBiT assay

| NCGC ID | Cell line | Linker attachment | E3 ligase ligand | Ave $EC_{50}$ (M) | s.d. (M) | efficacy (%) | s.d. (%) | cytotox |
|---|---|---|---|---|---|---|---|---|
| MTX | HBL1 | NA | NA | 1.17E−07 | 7.86E−08 | 118.2 | 45.4 | 5.71E−08 |
| FMTX | HBL1 | NA | NA | 2.80E−07 | 3.44E−08 | 115.1 | 50.9 | 1.10E−06 |
| NCGC00687847 | HBL1 | γ-COOH | CRBN-Inac. | 3.00E−06 | 1.84E−06 | 93.2 | 31.1 | 2.54E−05 |
| NCGC00685995 | HBL1 | γ-COOH | VHL | NA | NA | NA | NA | 2.02E−05 |
| NCGC00685964 | HBL1 | γ-COOH | VHL | NA | NA | NA | NA | 2.15E−05 |
| NCGC00685938 | HBL1 | γ-COOH | CRBN | NA | NA | NA | NA | 1.66E−06 |
| NCGC00685965 | HBL1 | γ-COOH | CRBN | 7.15E−07 | 2.37E−07 | −64.2 | 10.6 | 5.91E−06 |
| NCGC00685928 | HBL1 | γ-COOH | CRBN | 2.72E−07 | 5.13E−08 | −65.0 | 10.1 | 2.37E−05 |
| NCGC00687472 | HBL1 | γ-COOH | CRBN | 1.55E−08 | 2.17E−09 | −62.9 | 5.5 | 1.22E−05 |
| NCGC00687555 | HBL1 | γ-COOH | CRBN | 2.45E−07 | 1.07E−07 | −56.9 | 15.1 | 3.93E−06 |

TABLE 2-continued

Degradation or stabilization potency and efficacy for MTX, FMTX and MTX-PROTACs as measured by the DHFR-HiBiT assay

| NCGC ID | Cell line | Linker attachment | E3 ligase ligand | Ave $EC_{50}$ (M) | s.d. (M) | efficacy (%) | s.d. (%) | cytotox |
|---|---|---|---|---|---|---|---|---|
| NCGC00687576 | HBL1 | γ-COOH | CRBN | 9.28E−08 | 9.34E−09 | −62.3 | 16.9 | 1.70E−05 |
| NCGC00687569 | HBL1 | γ-COOH | CRBN | 9.95E−08 | 2.23E−08 | −53.9 | 17.7 | 2.15E−05 |
| NCGC00687807 | HBL1 | γ-COOH | CRBN | 2.04E−07 | 7.25E−08 | −48.1 | 21.8 | 2.08E−05 |
| NCGC00687811 | HBL1 | γ-COOH | CRBN | 4.04E−07 | 1.29E−07 | −40.5 | 22.1 | 2.24E−05 |
| NCGC00842394 | HBL1 | γ-COOH | CRBN | 5.29E−07 | — | −27.6 | — | 3.39E−05 |
| NCGC00690395 | HBL1 | N10 | CRBN | 2.55E−06 | 7.48E−07 | −32.8 | 9.0 | 3.34E−05 |
| NCGC00690396 | HBL1 | N10 | CRBN | NA | NA | NA | NA | 2.66E−05 |
| NCGC00690397 | HBL1 | N10 | VHL | 1.20E−06 | 2.51E−07 | −64.1 | 9.8 | 2.87E−05 |
| NCGC00690398 | HBL1 | N10 | VHL | 2.61E−06 | 2.75E−07 | −26.0 | 16.8 | 3.67E−05 |
| NCGC00690069 | HBL1 | α-COOH | CRBN | NA | NA | NA | NA | 3.58E−05 |
| NCGC00690075 | HBL1 | α-COOH | CRBN | NA | NA | NA | NA | 7.00E−05 |
| NCGC00690407 | HBL1 | α-COOH | CRBN | NA | NA | NA | NA | 3.29E−05 |
| NCGC00690412 | HBL1 | α-COOH | CRBN | NA | NA | NA | NA | 3.86E−05 |

Data represent average of N = 2-5 independent experiments.
NA, not applicable; NE, no effect.

In view of the many possible embodiments to which the principles of the disclosure may be applied, it should be recognized that the illustrated embodiments are only examples and should not be taken as limiting the scope of the invention. Rather, the scope of the invention is defined by the following claims. We therefore claim as our invention all that comes within the scope and spirit of these claims.

We claim:

1. A compound having a structure according to Formula I

Formula I

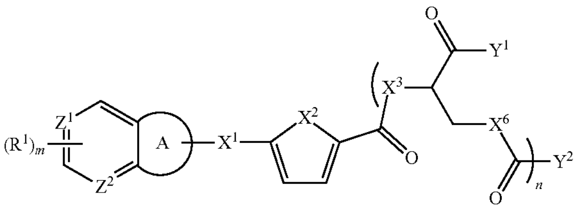

or a pharmaceutically acceptable salt, N-oxide, or hydrate thereof, wherein:

each of $Z^1$ and $Z^2$ independently is N or CH;

each $R^1$ independently is optionally substituted $C_{1-6}$alkyl, $C_{1-4}$haloalkyl, OH, cyano, amino, or SH;

m is 0, 1, 2, 3 or 4;

n is 1, 2, 3, 4, or 5;

ring A is 5- or 6-membered heterocyclyl containing nitrogen;

$X^1$ is $-CH_2NY^3-$;

$R^2$ is H, optionally substituted aliphatic, or $R^2$ together with the atoms to which it is attached, forms a 5-membered optionally substituted heterocyclic ring that is fused to ring A;

$X^2$ is $CH{=}CR^3$;

each $X^3$ independently is $NR^4$;

each $X^6$ independently is $CH_2$, or CHF;

each of $Y^1$ and $Y^2$ independently is OH, $OC_{1-6}$alkyl or -Linker-$E_3$ Ligand;

$Y^3$ is H or $C_{1-6}$alkyl;

with the provision that at least one of $Y^1$ or $Y^2$ is or comprises -Linker-$E_3$ Ligand;

$R^3$ is H;

each $R^4$ independently is H or optionally substituted $C_{1-6}$alkyl, or $C_{3-6}$cycloalkyl;

$E_3$ Ligand is selected from

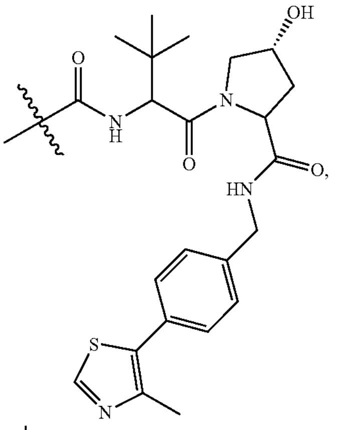

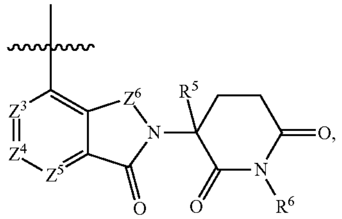

or

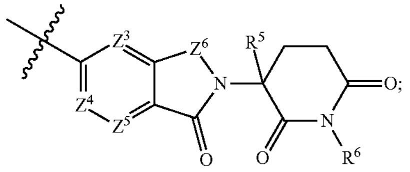

wherein each of $Z^3$, $Z^4$, and $Z^5$ independently is CH or N;

$Z^6$ is $CH_2$ or C═O;

$R^5$ is H, D, $C_{1-6}$alkyl or halogen; and $R^6$ is H, $C_{1-6}$alkyl or

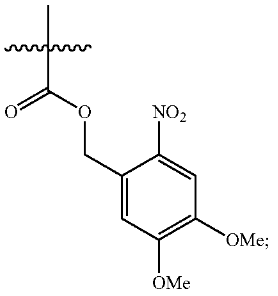 [SMILES: *C(=O)OCc1cc(OC)c(OC)cc1[N+](=O)[O-]]

and

Linker has a formula

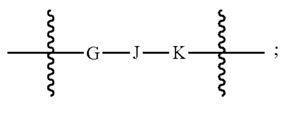

wherein G is a bond, $NR^7$, —$NR^7C$(═O)—, or $CH_2$;

$R^7$ is H, or optionally substituted $C_{1-4}$alkyl;

K is a bond, O, optionally substituted $C_{1-4}$alkyl, $NR^8$, C(O)$NR^8$, NHC(O), $NHCO_2CH_2$, $CH_2C$(O)NH, NHC(O)$CH_2$O, NHC(O)$CH_2$NH, C(O)$CH_2$O, C≡C, S, or S(═O);

$R^8$ is H, or optionally substituted $C_{1-6}$alkyl; and

J is optionally substituted $C_{1-12}$alkyl, $(CH_2)_n$—O—$(CH_2)_p$ where n is 1-6 and p is 1-6, $(—CH_2CH_2O—)_q$, $(—CH_2CH_2O—)_qCH_2—$, $(—CH_2CH_2O—)_qCH_2CH_2—$ where q is 1-6, $(CH_2CH_2)_r$—O—$(CH_2CH_2)_s$ where r is 2-6 and s is 1-6, or —$(CH_2)_x$-M-$(CH_2)_y$— where M is optionally substituted phenyl, optionally substituted cycloalkyl, optionally substituted spirocycloalkyl, or optionally substituted heterocyclyl, where x is 0-8 and y is 0-8; and wherein each optional substituent is independently selected from $C_{1-6}$alkyl, $C_{3-6}$cycloalkyl, halogen, haloalkyl, aryl, heteroaryl, heterocycloaliphatic, carboxy, carboxyl ester, or amino.

2. The compound of claim 1, wherein:

$R^4$ is H, methyl, ethyl, or cyclopropyl.

3. The compound of claim 1, wherein the

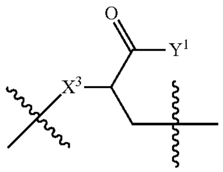

moiety is

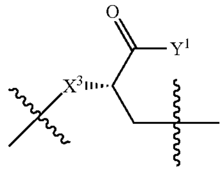

or

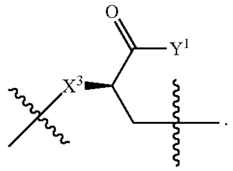

.

4. The compound of claim 1, wherein the compound has a formula II

Formula II

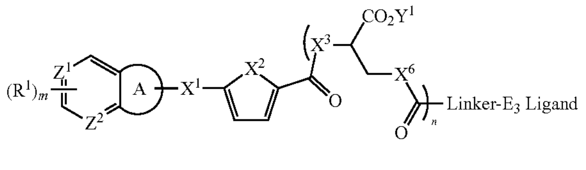

or a pharmaceutically acceptable salt, N-oxide, or hydrate thereof, wherein:

each $Y^1$ independently is OH or $OC_{1-6}$alkyl.

5. The compound of claim 4, wherein:

n is 1 and $Y^1$ is OH; or n is 2-5 and one $Y^1$ is OH and the remainder are $OC_{1-6}$alkyl.

6. The compound of claim 4, wherein the compound has a formula

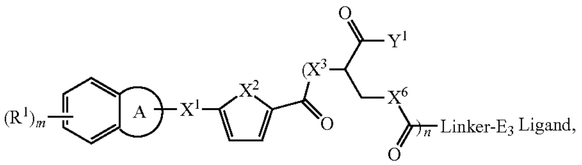
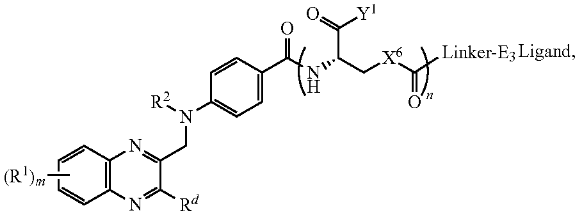
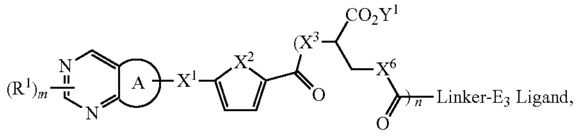
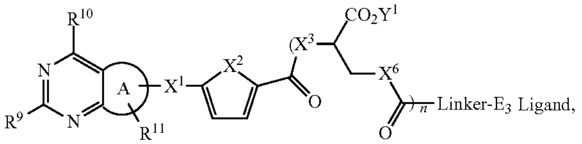
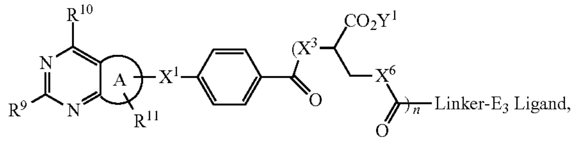
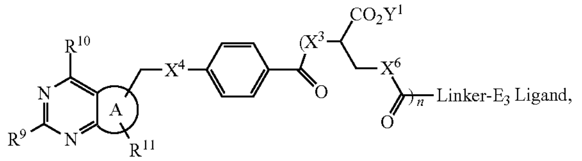
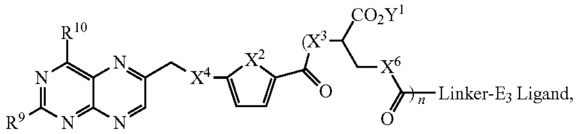
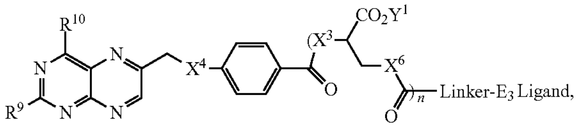
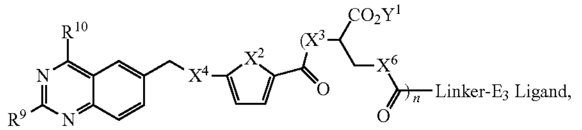

or

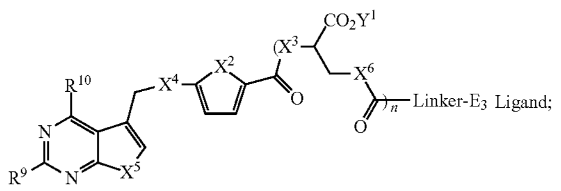

or a pharmaceutically acceptable salt, N-oxide, or hydrate thereof, wherein, if present, $R^d$ is H, $CF_3$ or methyl;

each of $R^9$, $R^{10}$ and $R^{11}$ independently is optionally substituted $C_{1-6}$alkyl, $C_{1-4}$haloalkyl, OH, cyano, amino, or SH; and $X^4$ is NH, $N(CH_3)$, $N(CH(CH_3)_2)$, or $N(CH_2CH_3)$; and $X^5$ is NH.

7. The compound of claim 6, wherein:

$R^9$ is $NH_2$, $CH_3$ or $CF_3$;

$R^{10}$ is OH, $NH_2$, SH, $CF_2H$, or $CF_3$; and $R^{11}$ is H, $CH_3$ or $CF_3$.

8. The compound of claim 7, wherein:

$R^{10}$ is $NH_2$, SH, $CF_2H$, $CF_3$ or OH;

$R^{11}$ is H; or a combination thereof.

9. The compound of claim 7, wherein:

$R^9$ is $NH_2$ and $R^{10}$ is $NH_2$; or $R^9$ is $NH_2$ and $R^{10}$ is OH.

10. The compound of claim 1, wherein $X^6$ is $CH_2$ or

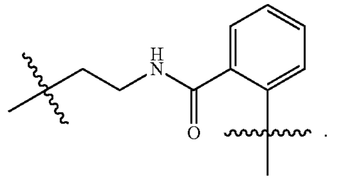 [SMILES: *CCNC(=O)c1ccccc1*]

11. The compound of claim 1, wherein $E_3$ Ligand is

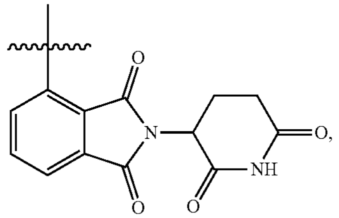
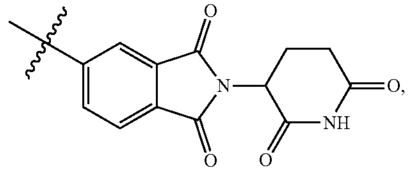
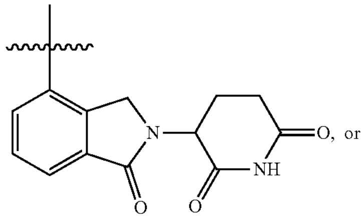

or

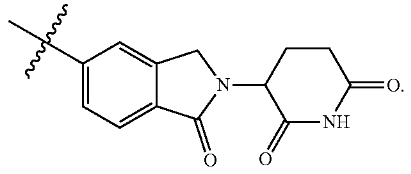

12. The compound of claim 1, wherein J is
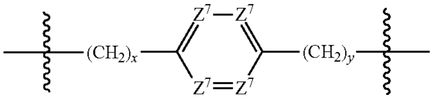
,
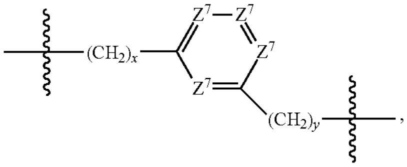
,
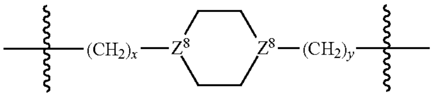
,
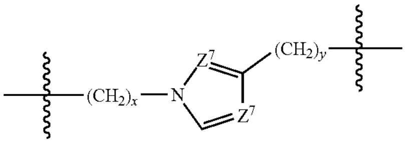
,
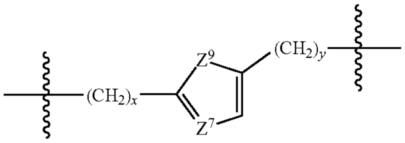
,
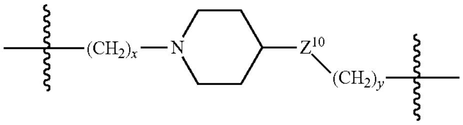
,
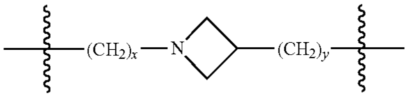
,
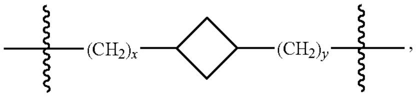
,
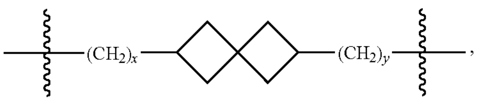
,
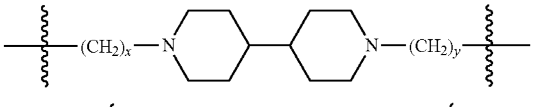
, or
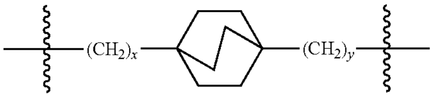
,
where each $Z^7$ independently is CH or N,
$Z^8$ is CH, N or NC (O);
$Z^9$ is $CH_2$, S, NH, $NR^c$ or O, where $R^c$ is $C_{1-6}$alkyl, $C_{3-6}$cycloalkyl, or $C_{1-6}$haloalkyl; and
$Z^{10}$ is O, NH, S or S(═O).
13. The compound of claim 1, wherein the -Linker-$E_3$ Ligand moiety is selected from:
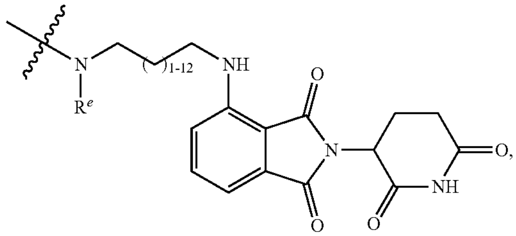
,
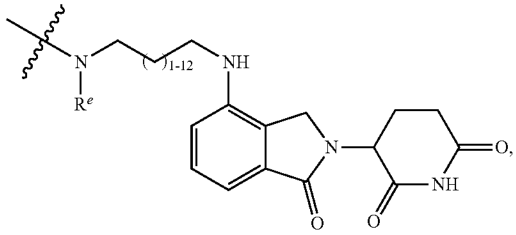
,
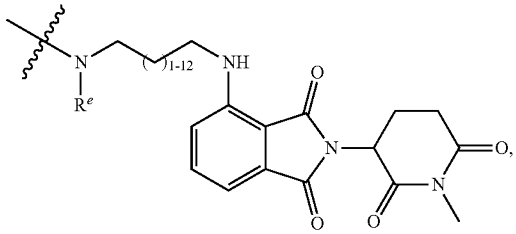
,
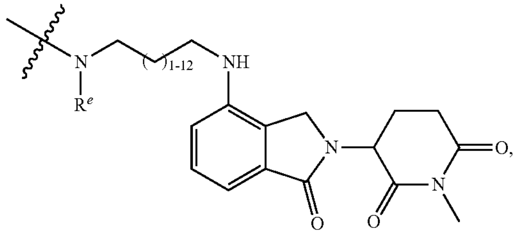
,
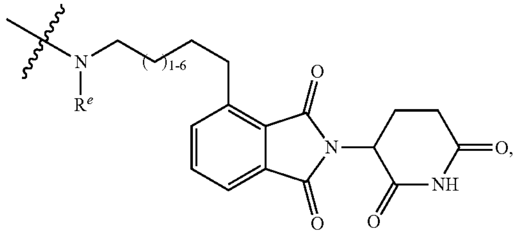
,
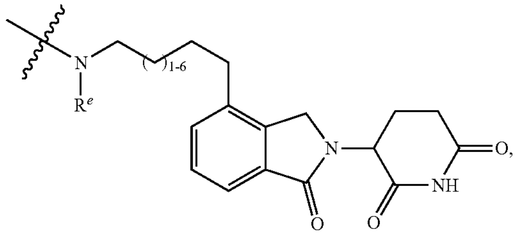
,
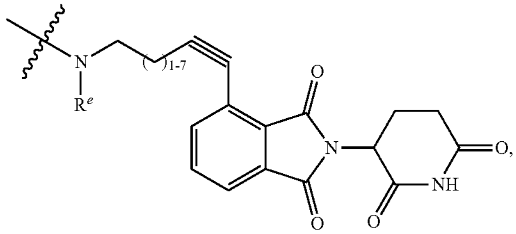
, -continued
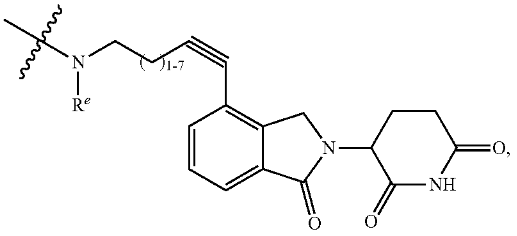
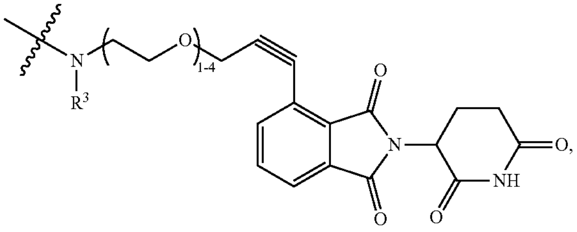
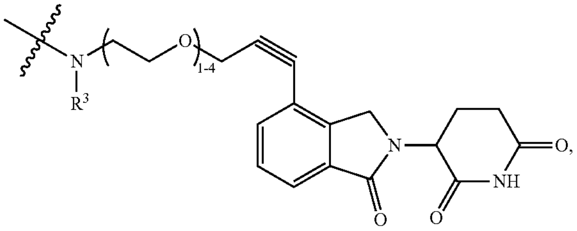
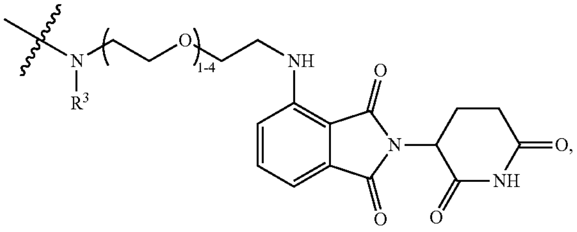
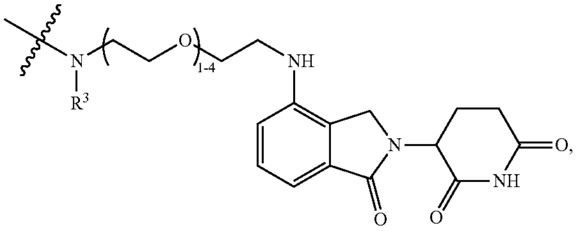
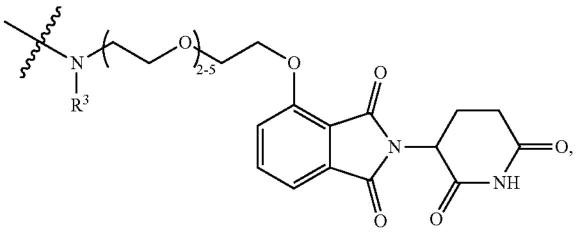
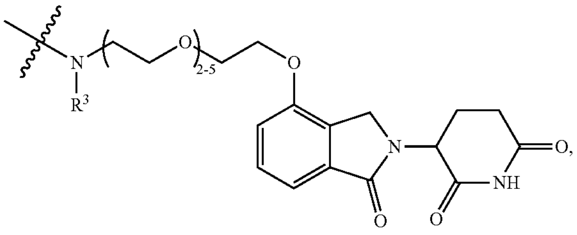
-continued
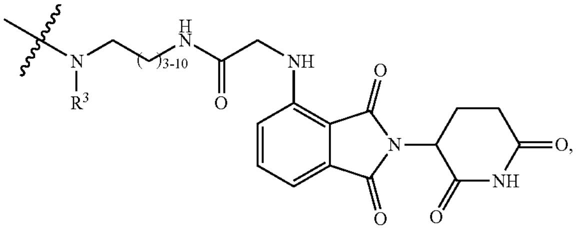
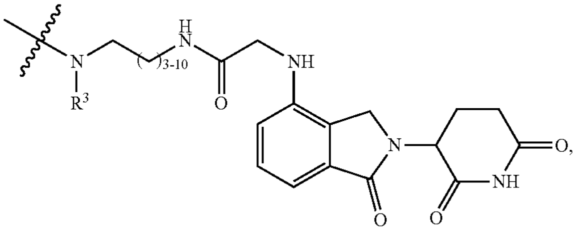
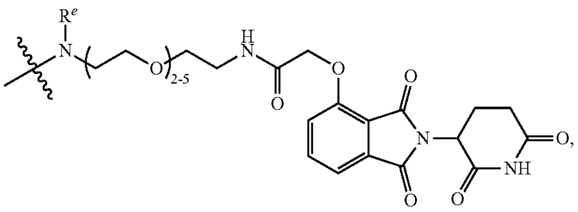
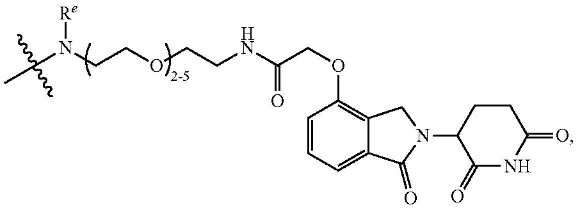
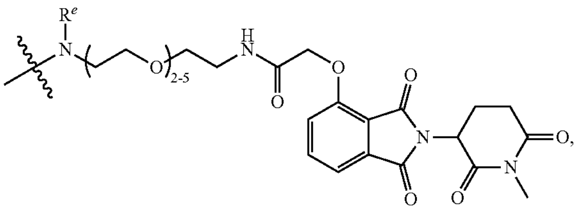
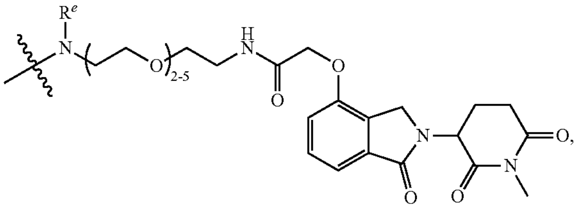
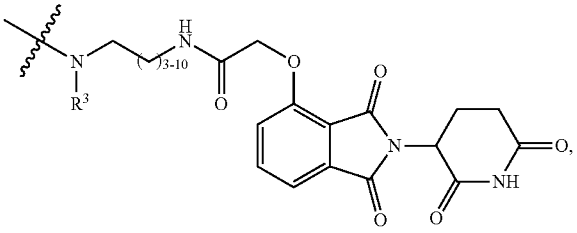

-continued
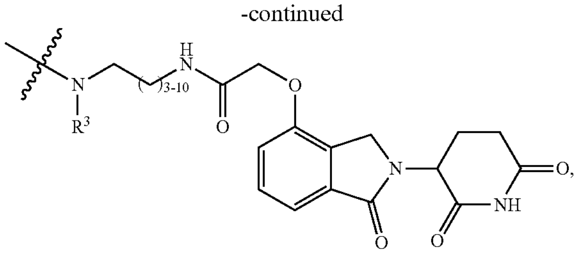
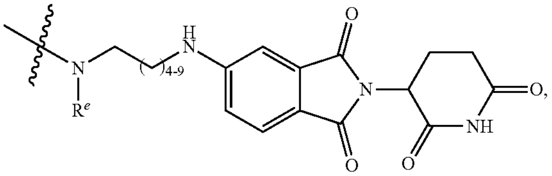
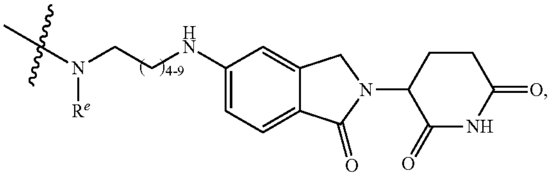
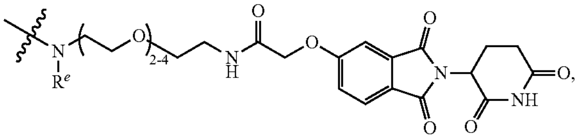
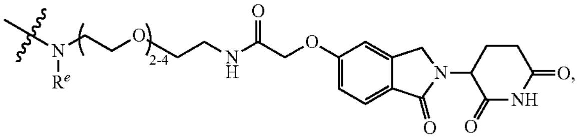
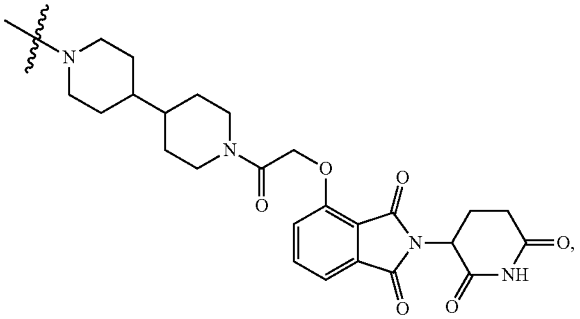
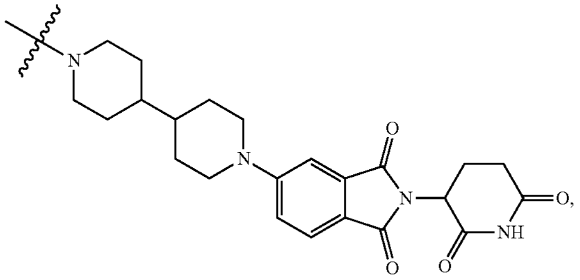
-continued
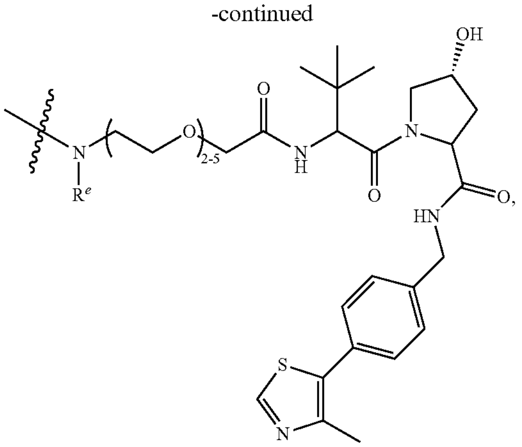
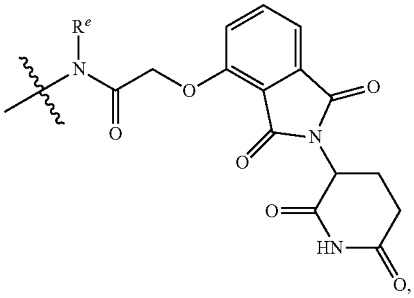
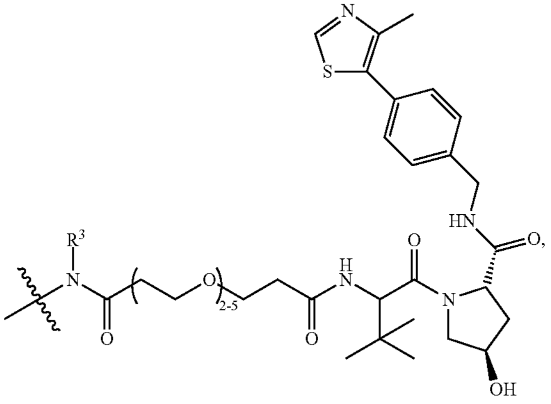
or
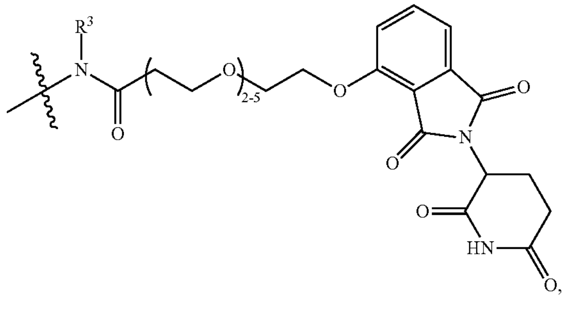
where $R^e$ is H, or $C_{1-6}$alkyl.
14. The compound of claim 1, wherein the compound is selected from:

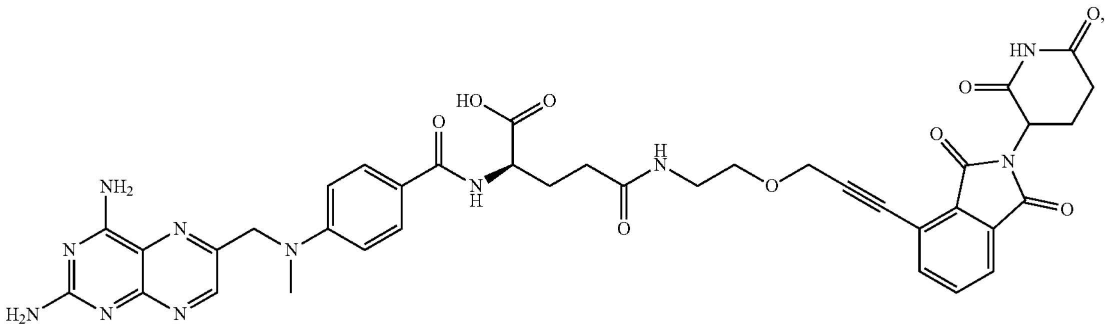
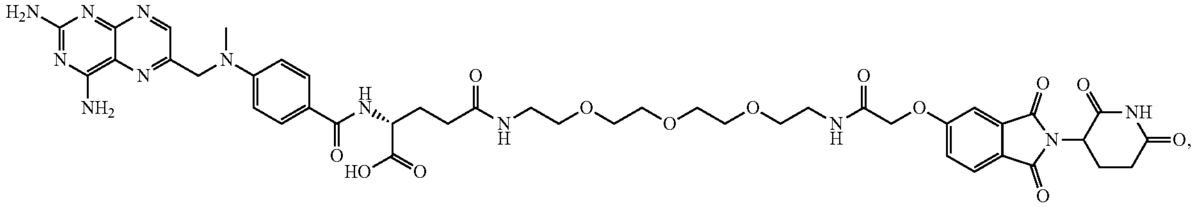
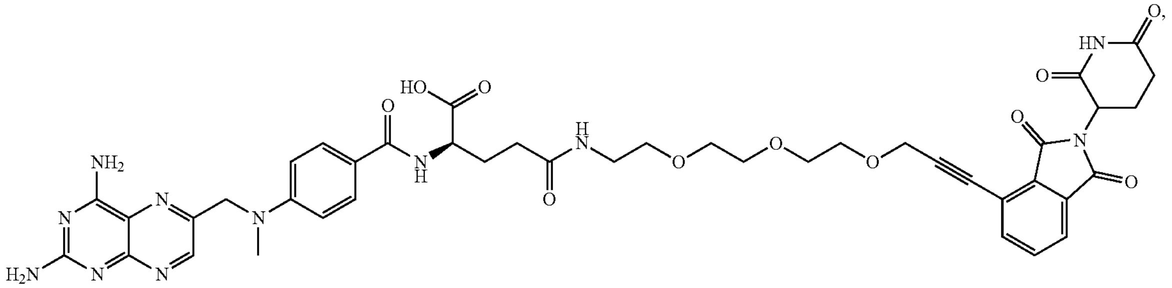
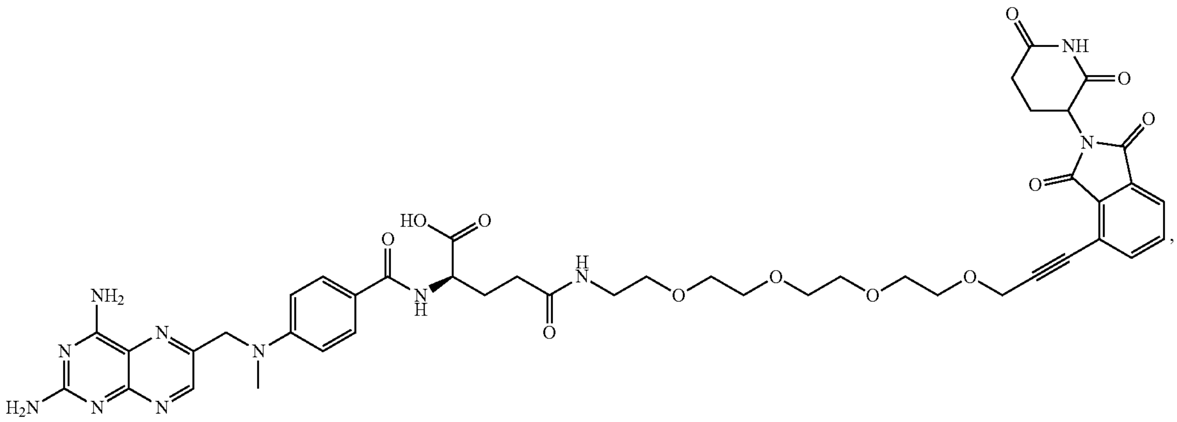
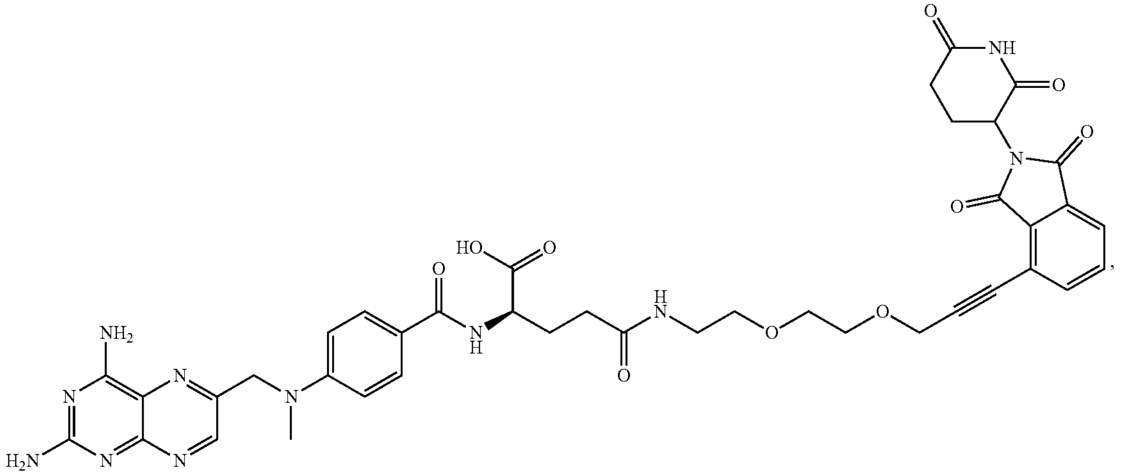

-continued
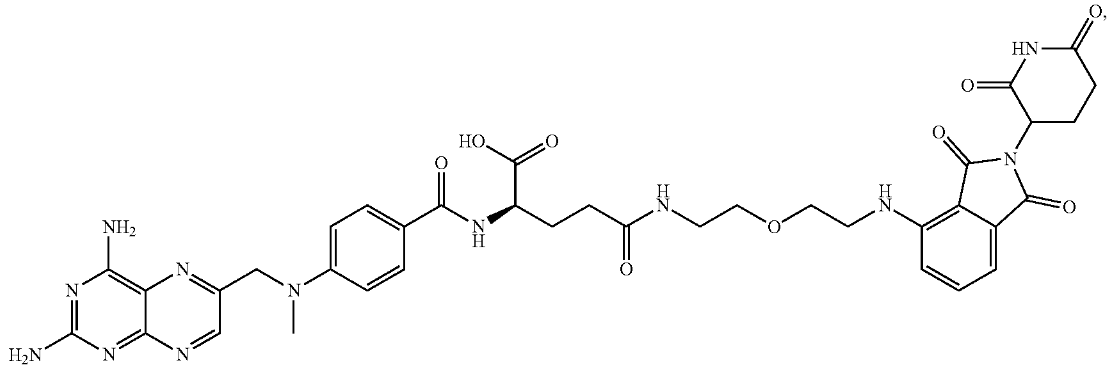
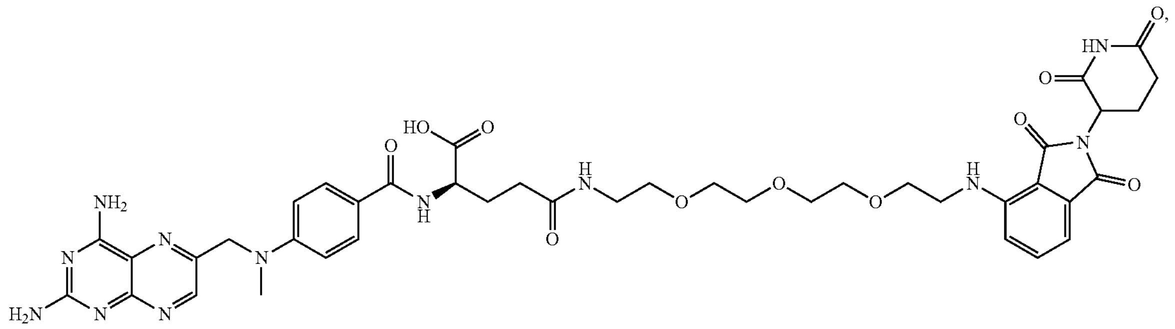
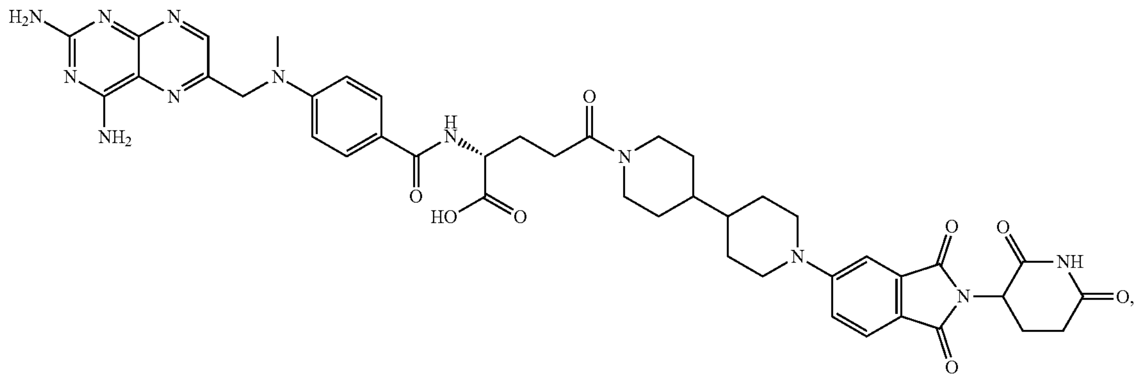
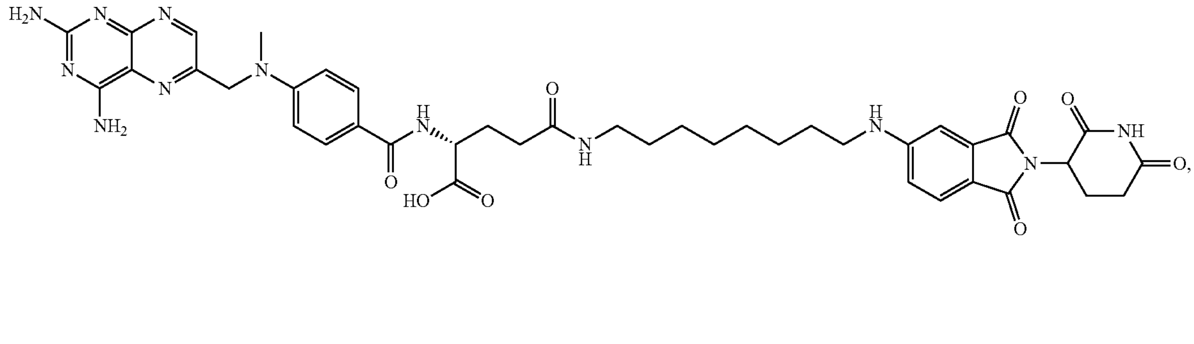

-continued
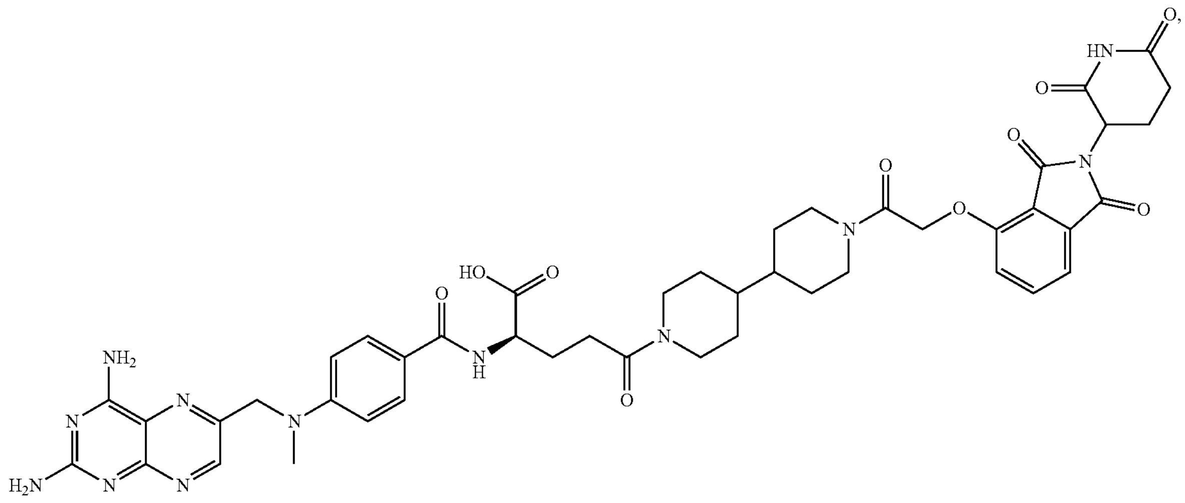
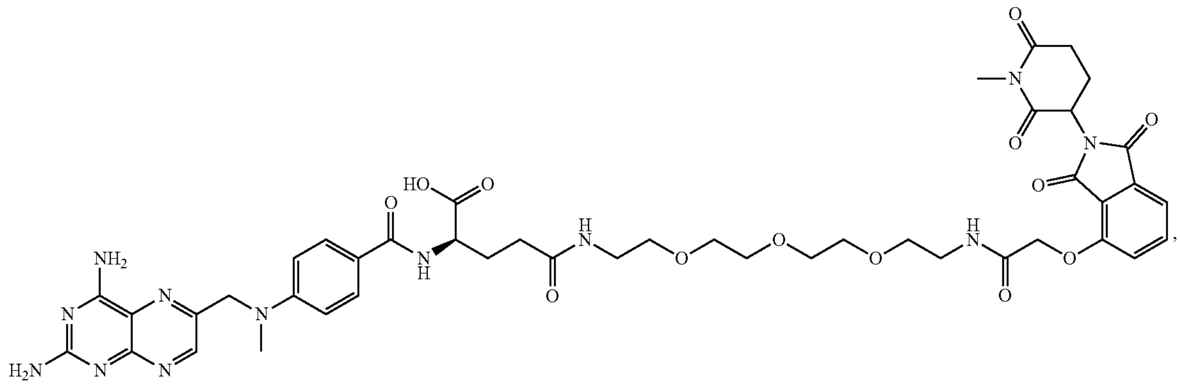
,
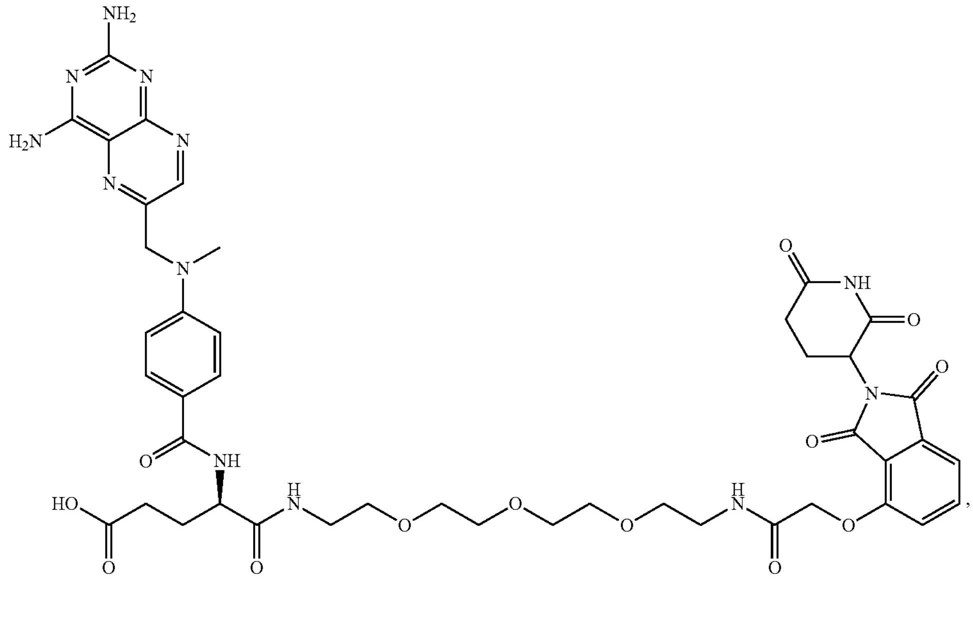
,

-continued
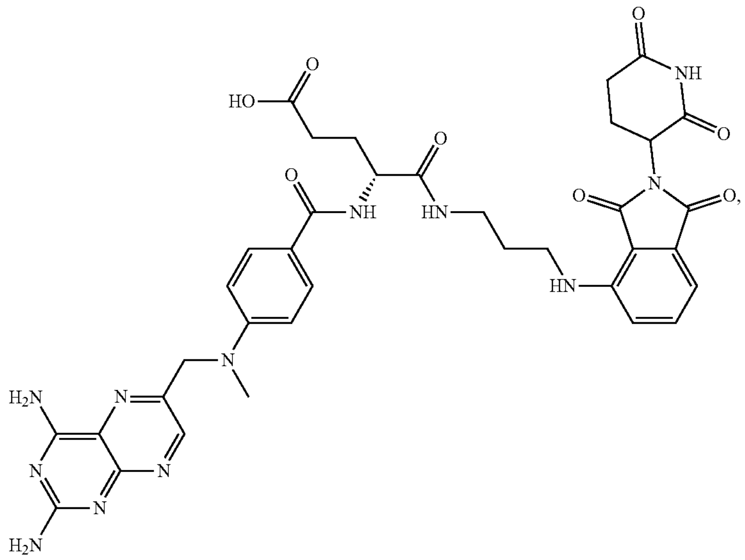
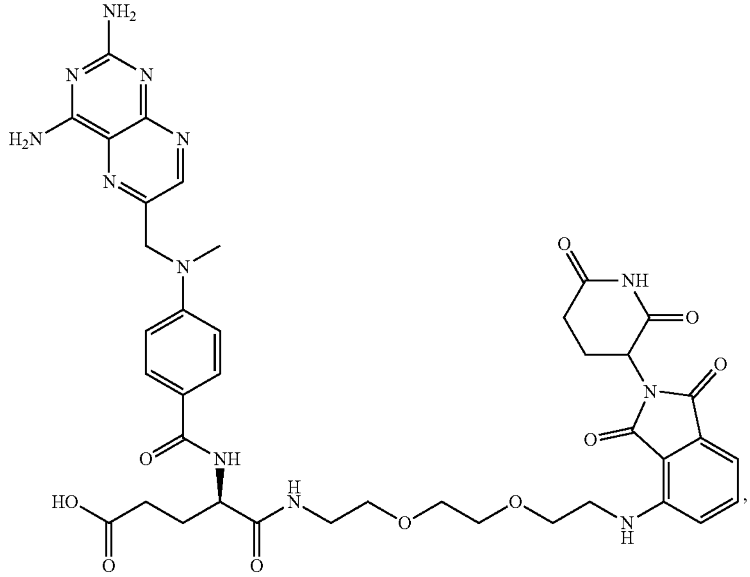
,
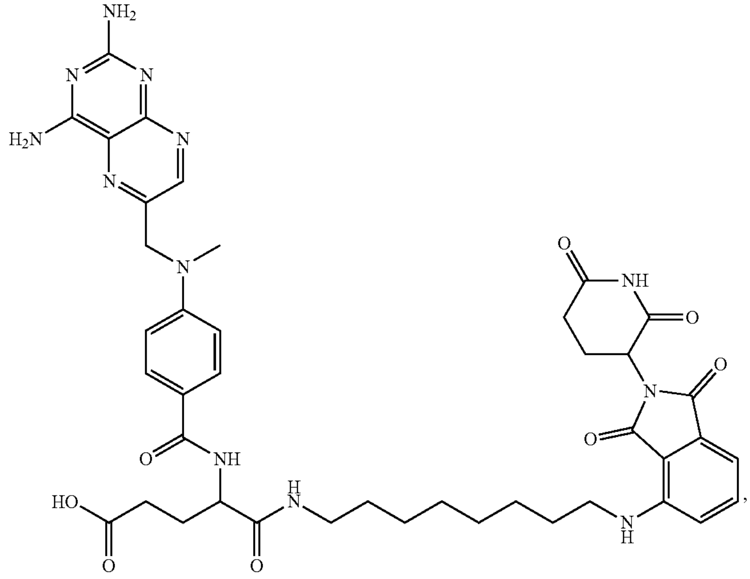
,

-continued
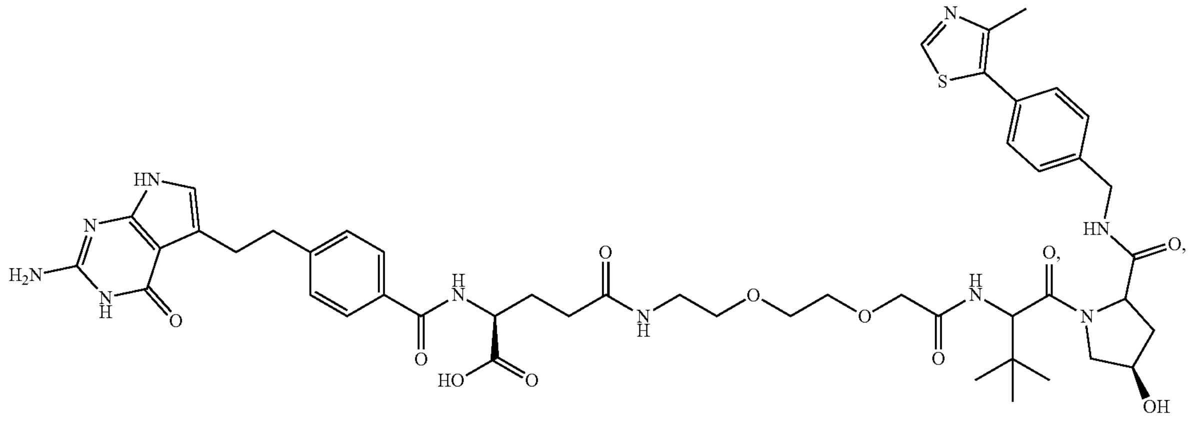
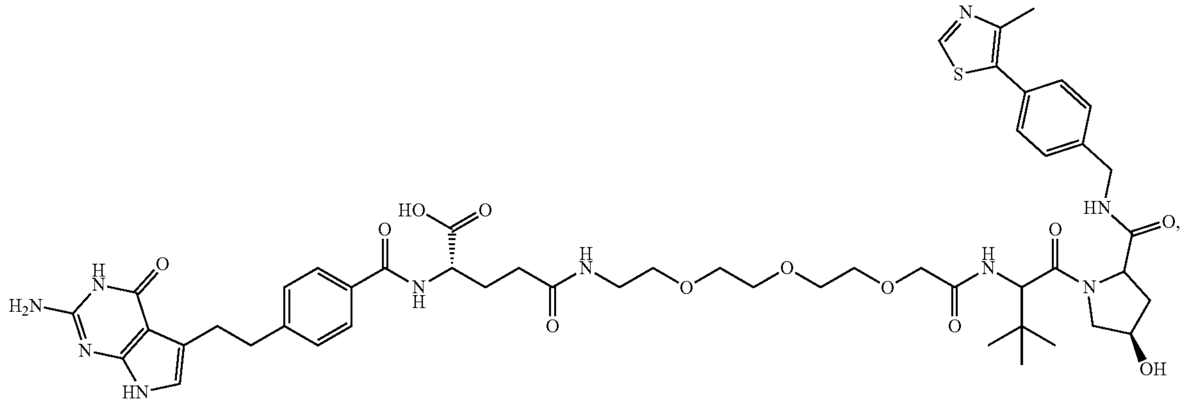
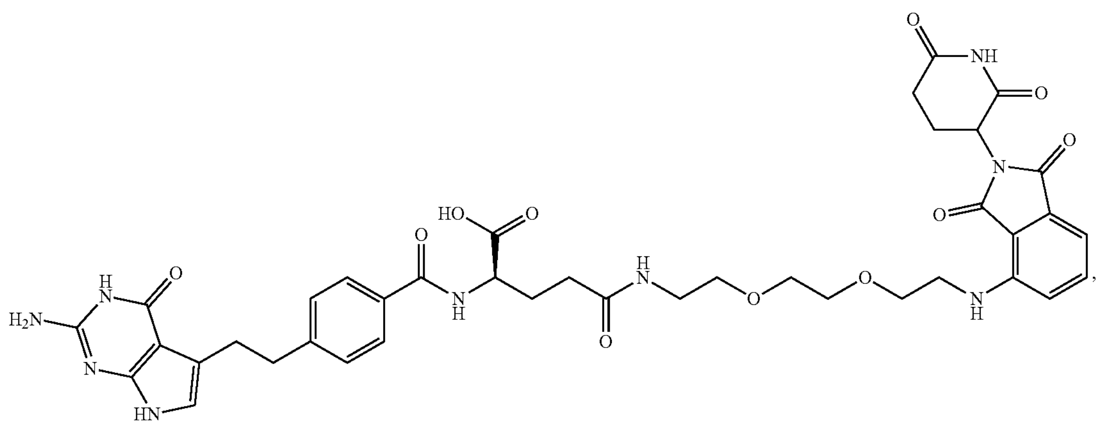

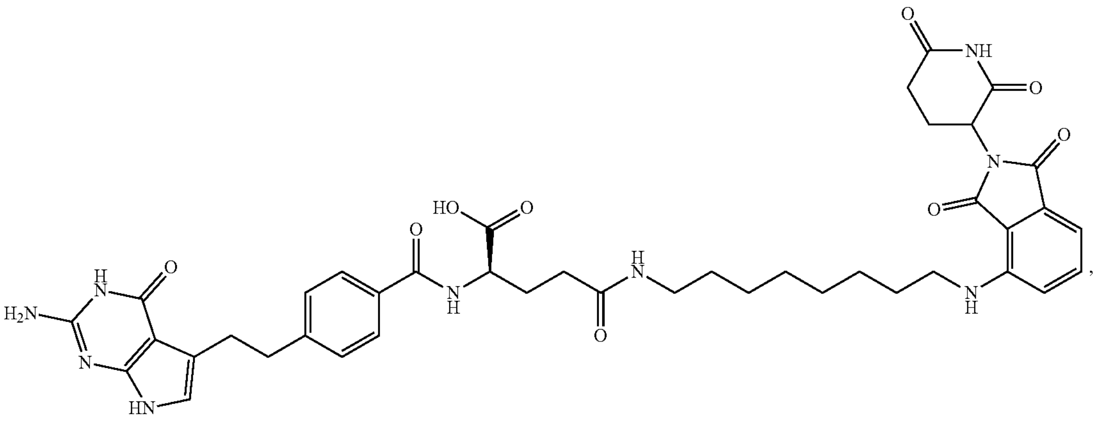
,
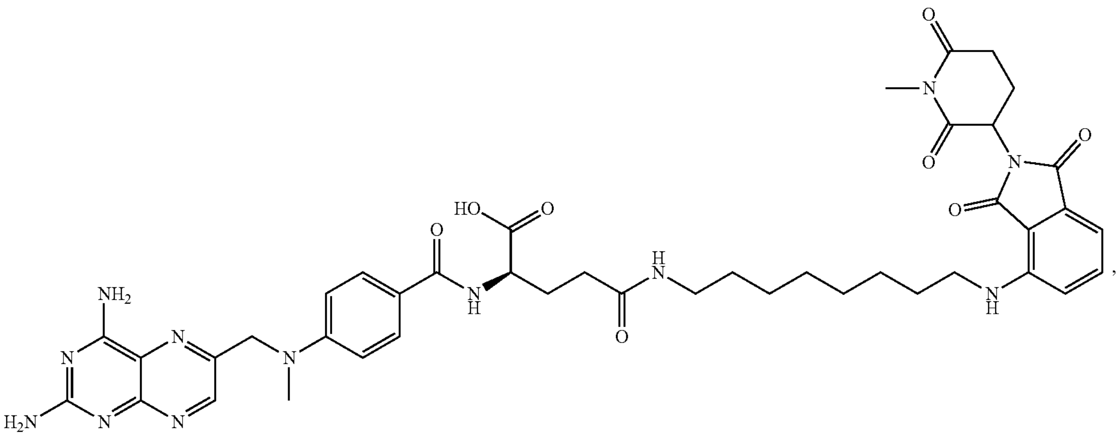
,
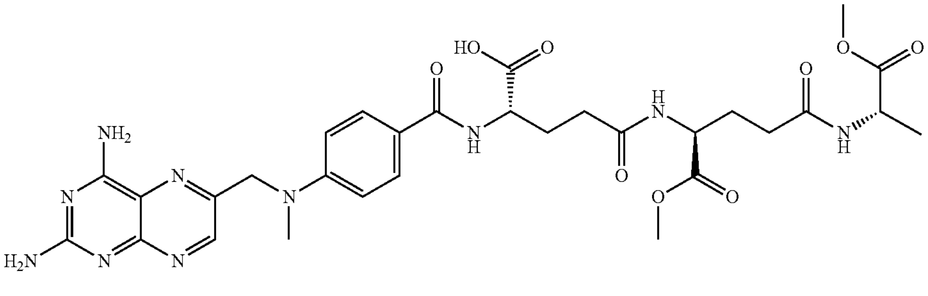
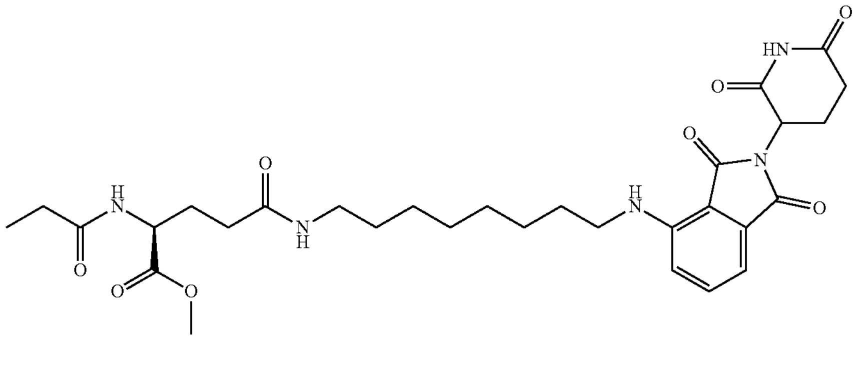

-continued
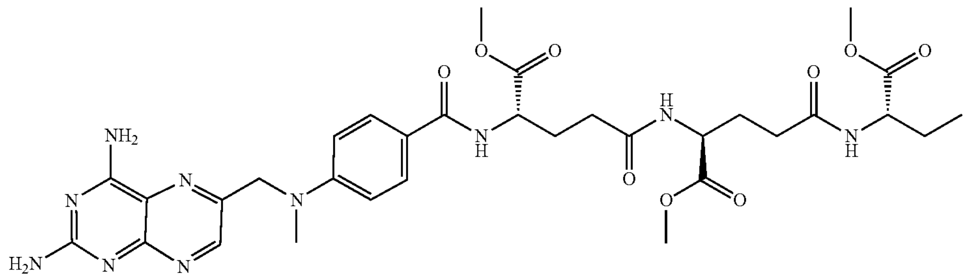
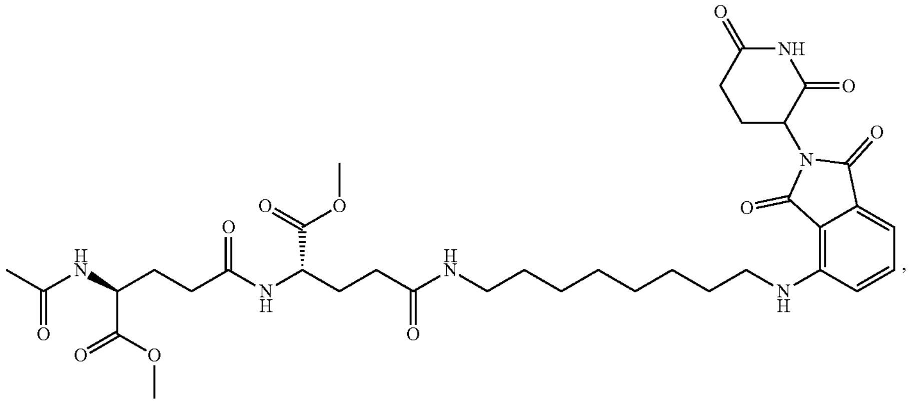
,
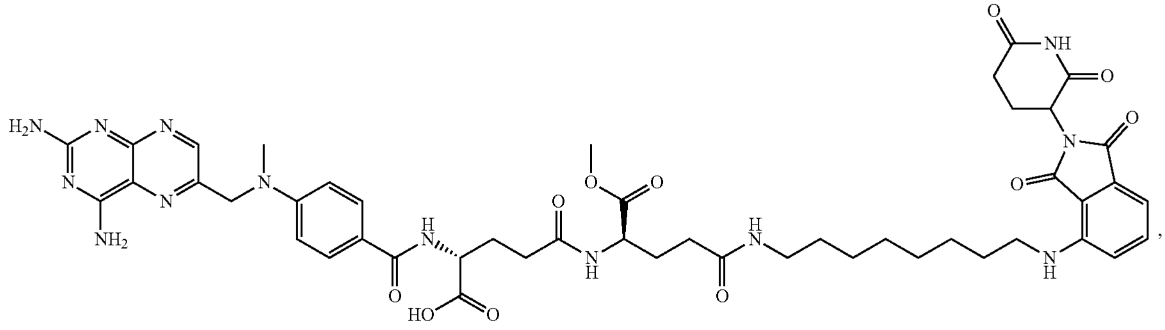
,
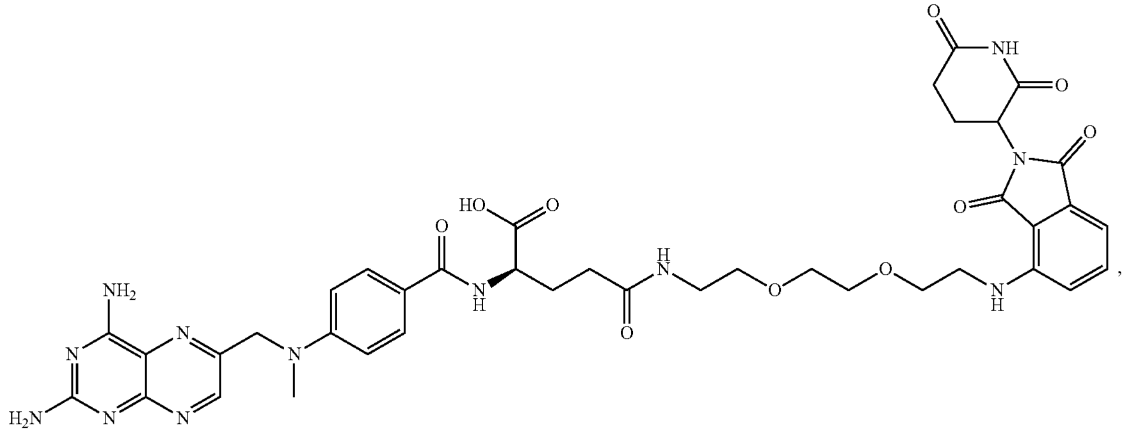
,

-continued
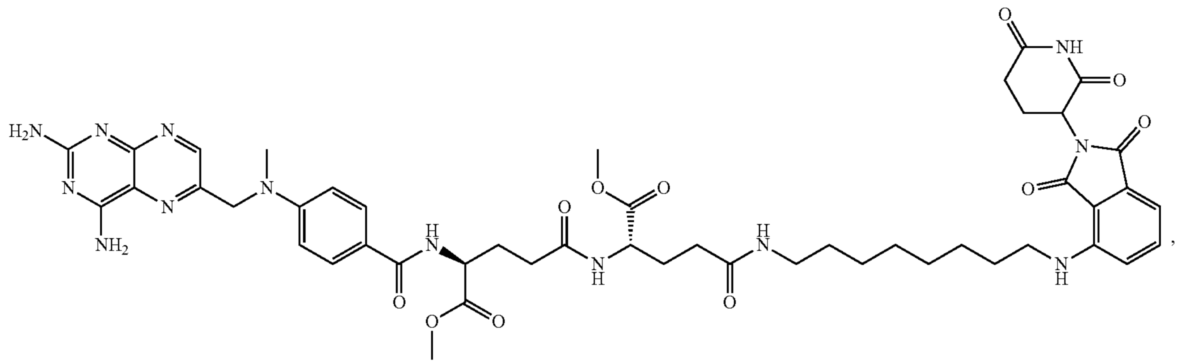
,
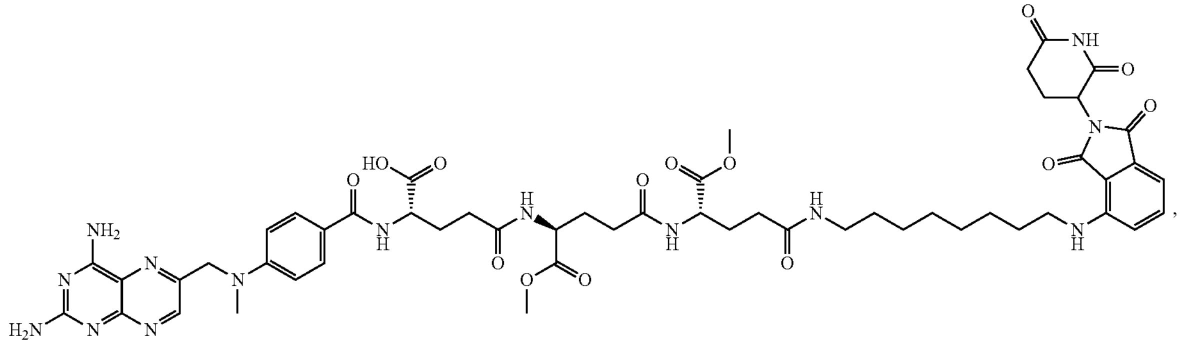
,
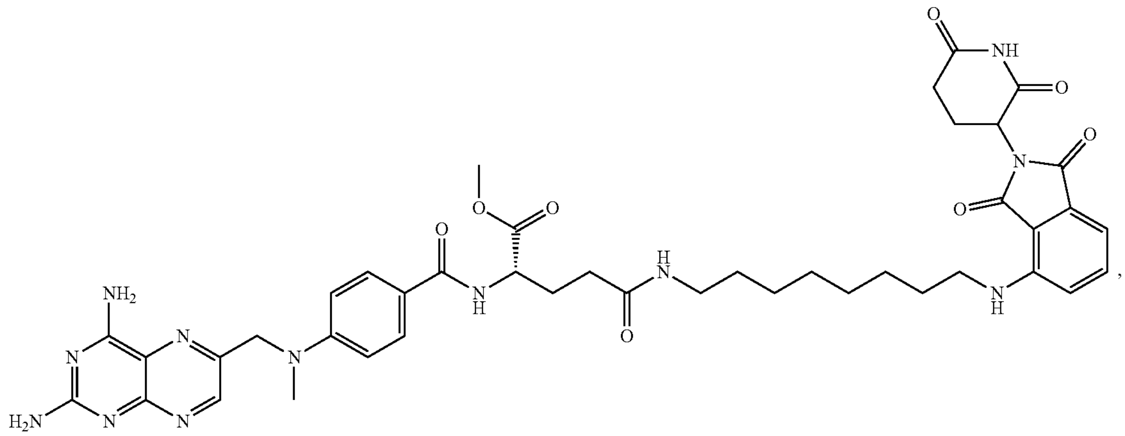
,
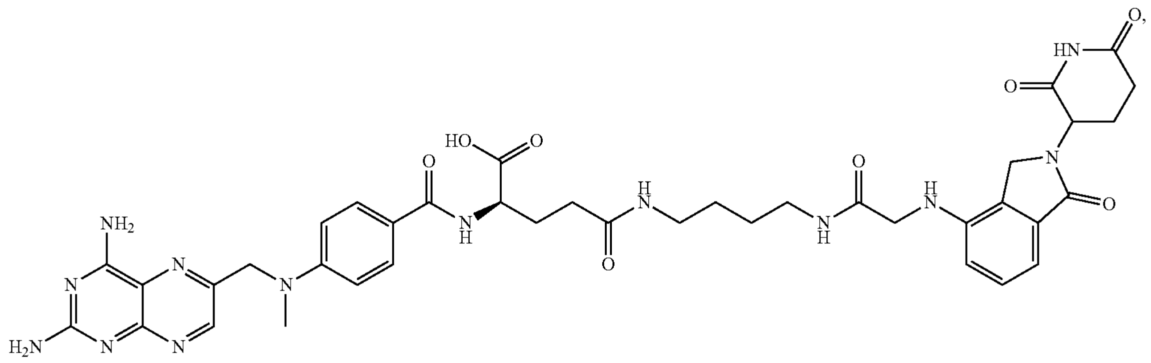
,

-continued
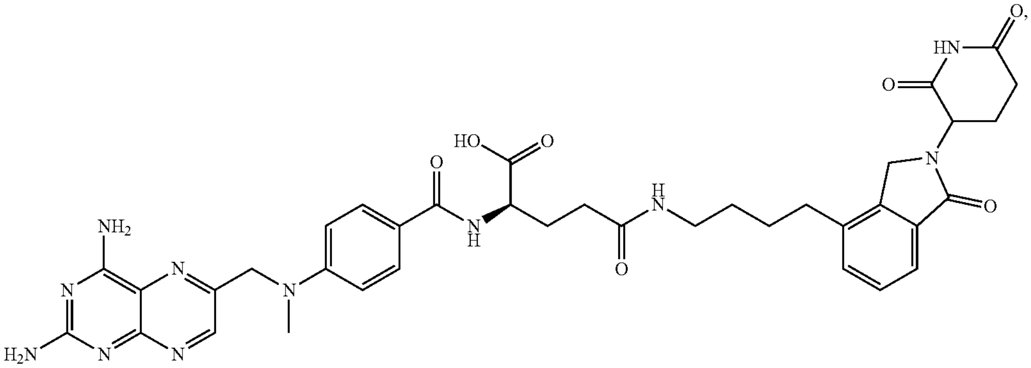
,
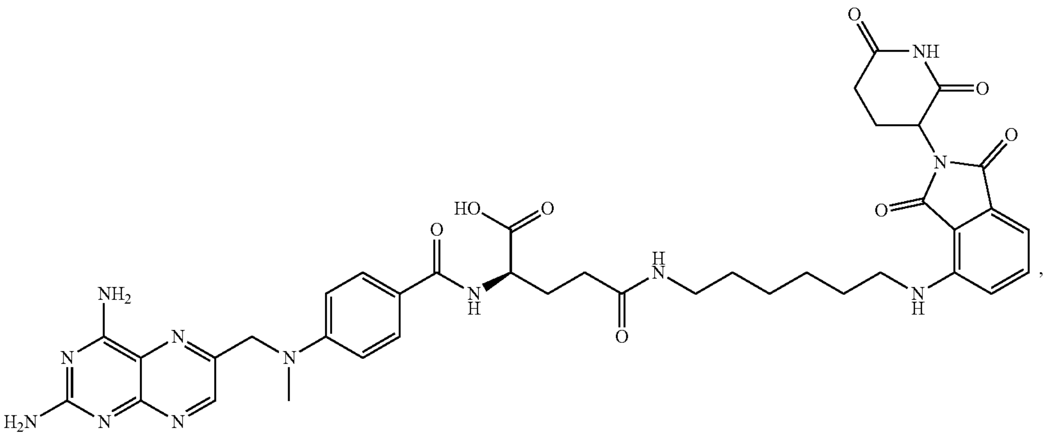
,
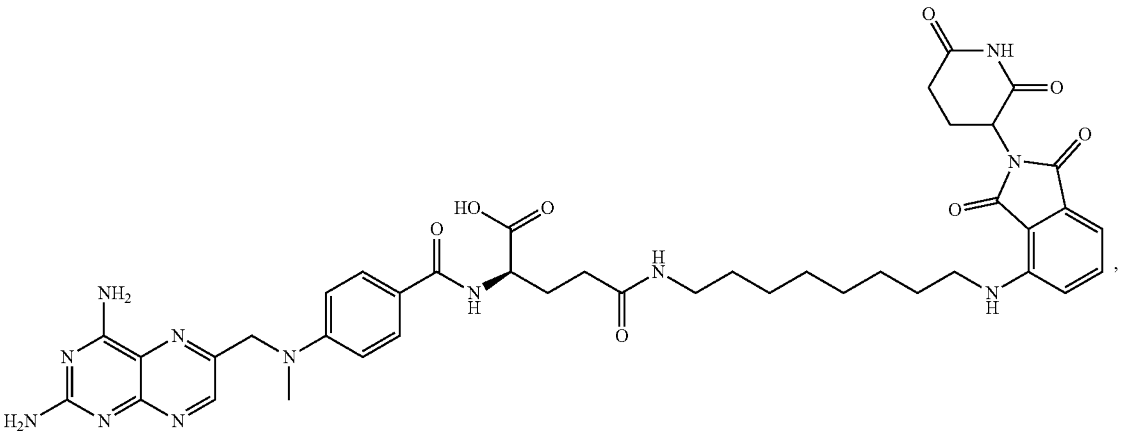
,
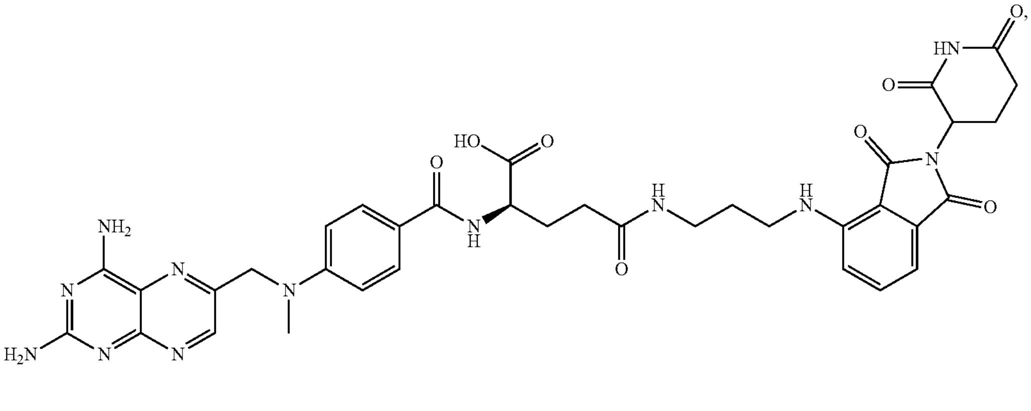
,

-continued
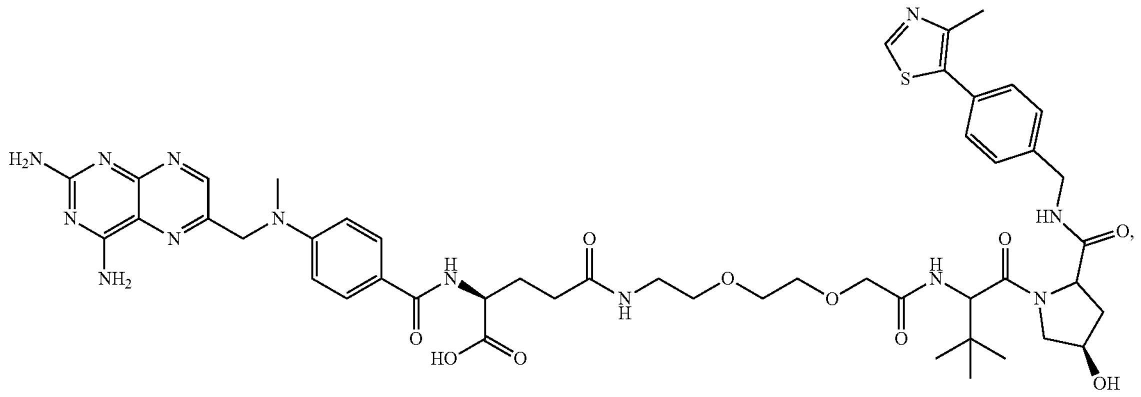
,
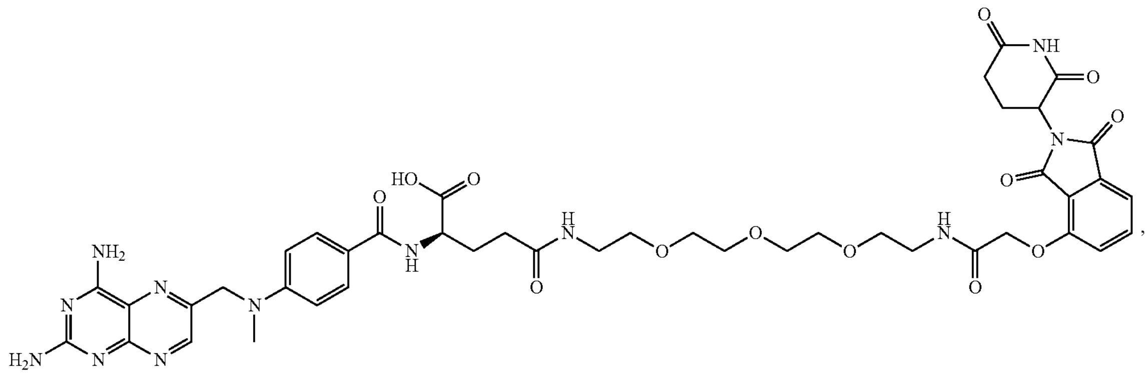
,
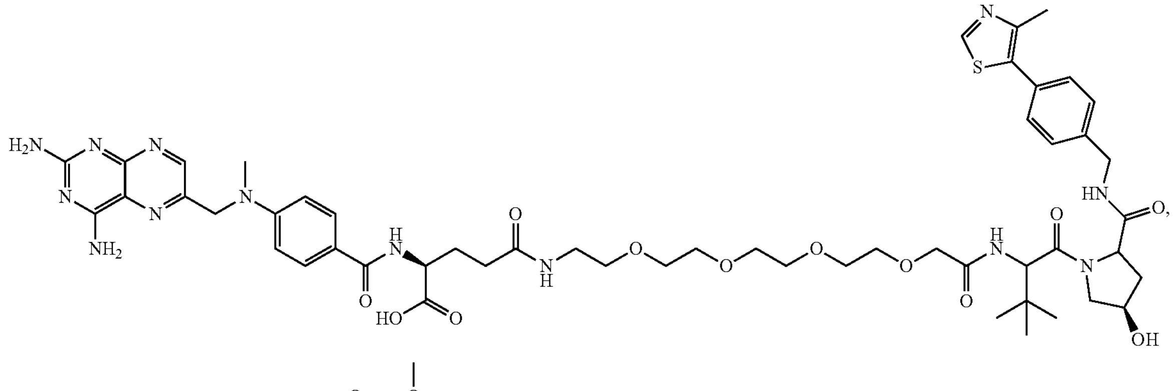
,
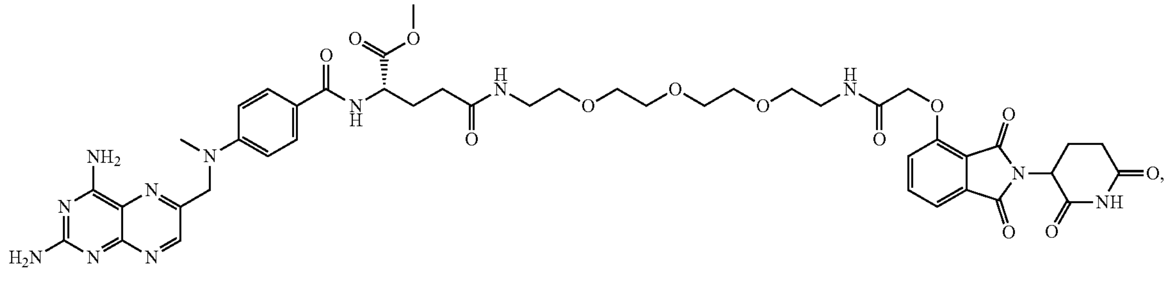
,

-continued
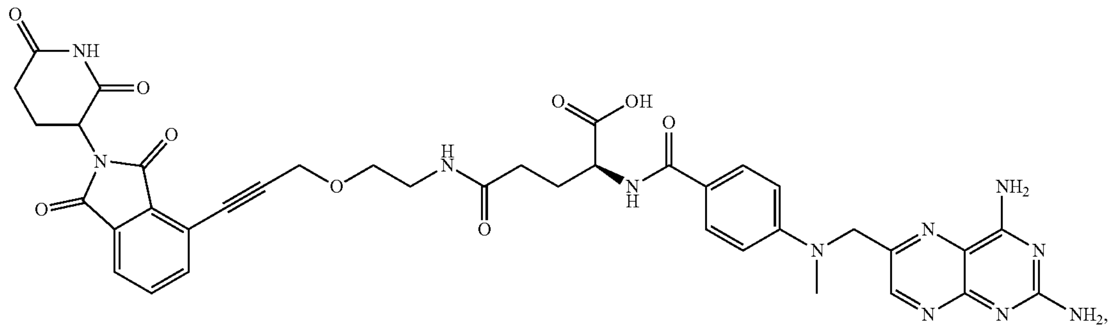
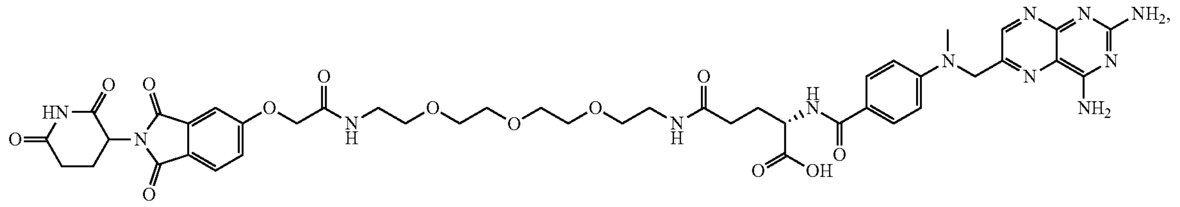
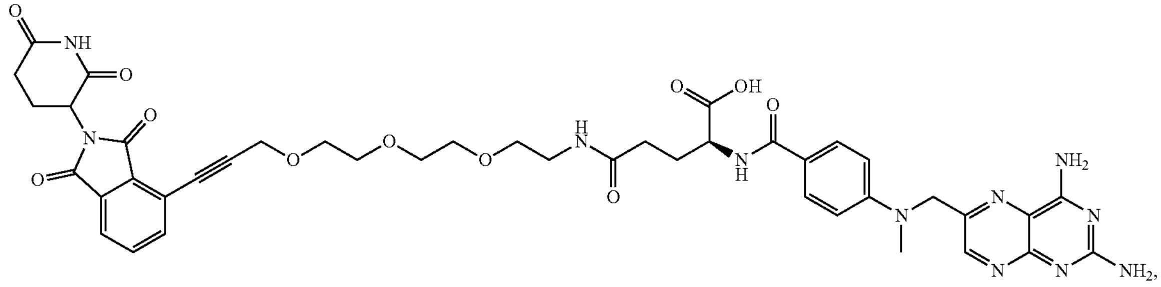
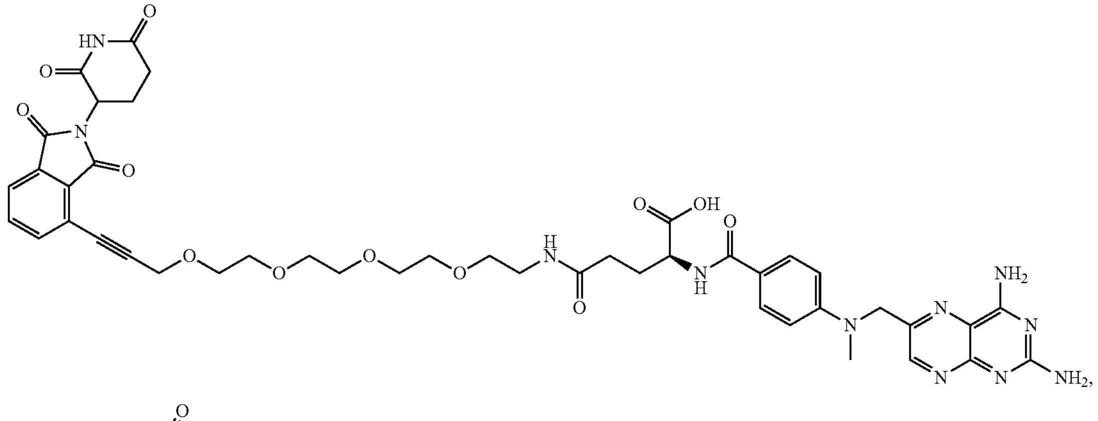
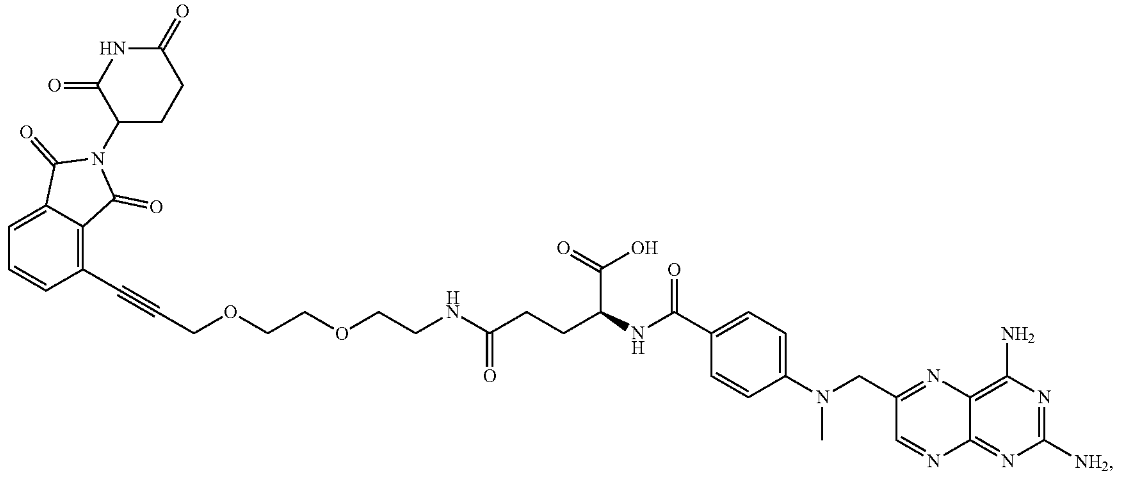

-continued
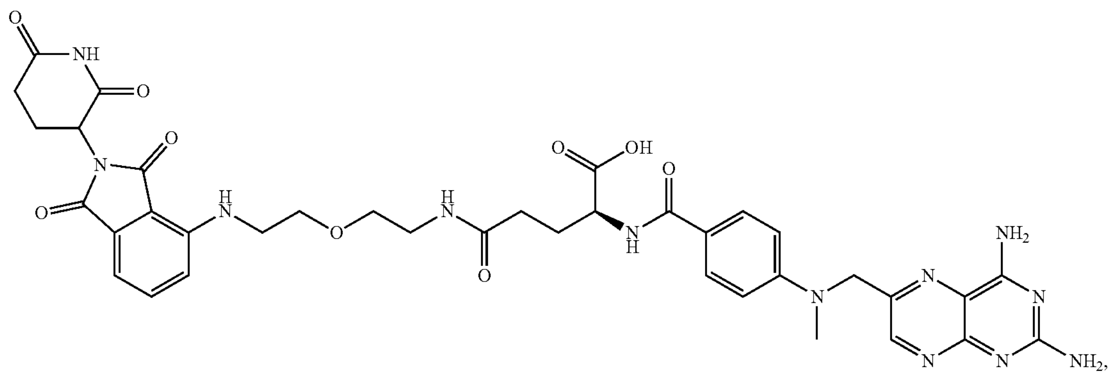
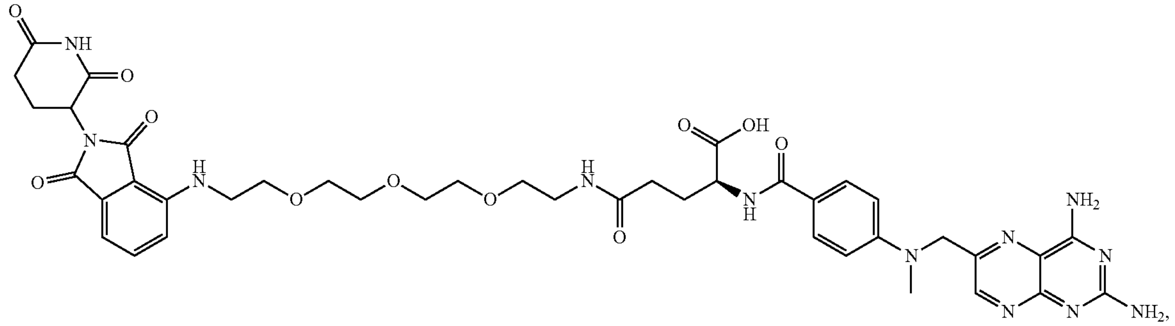
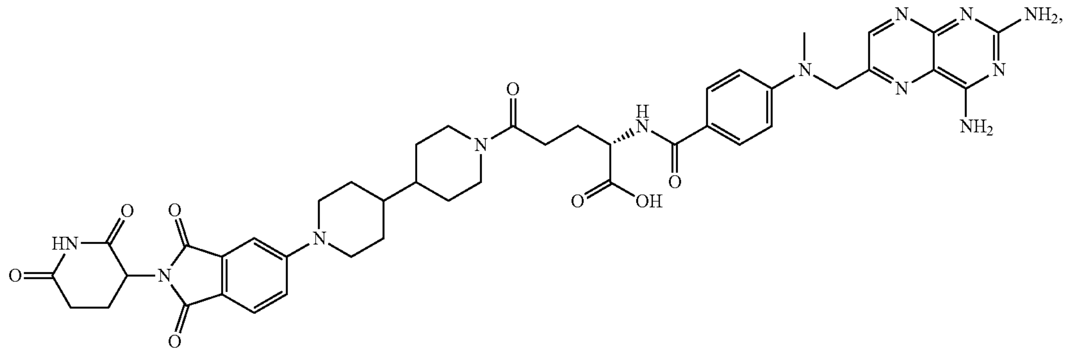
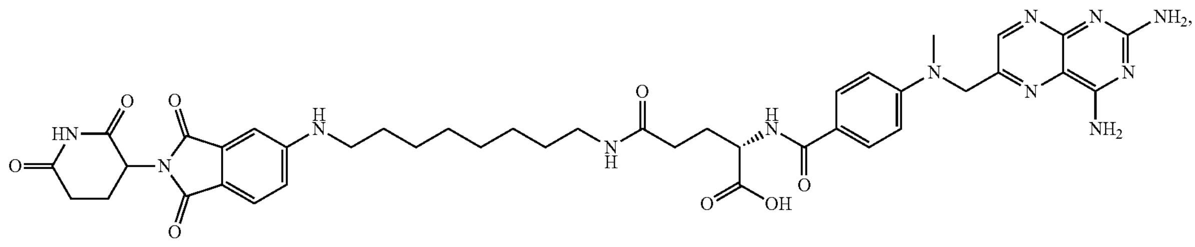

-continued
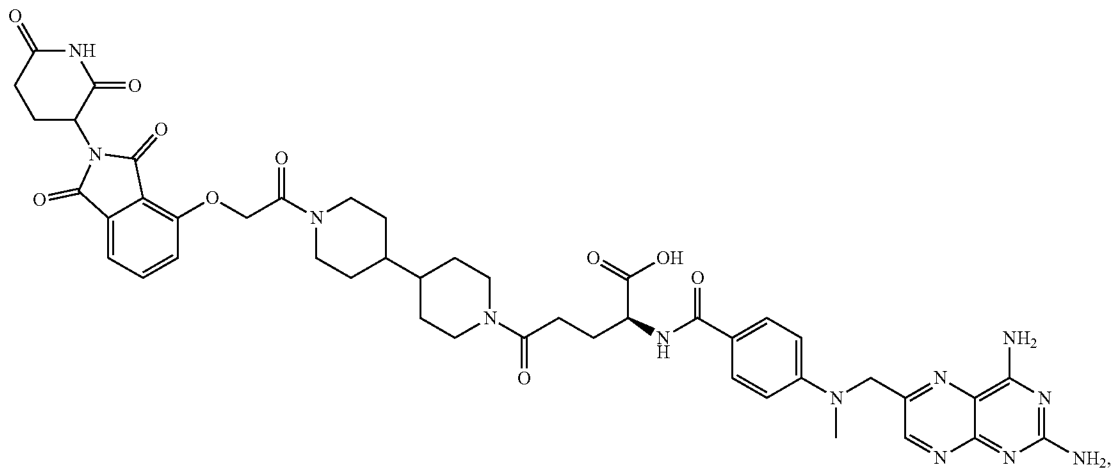
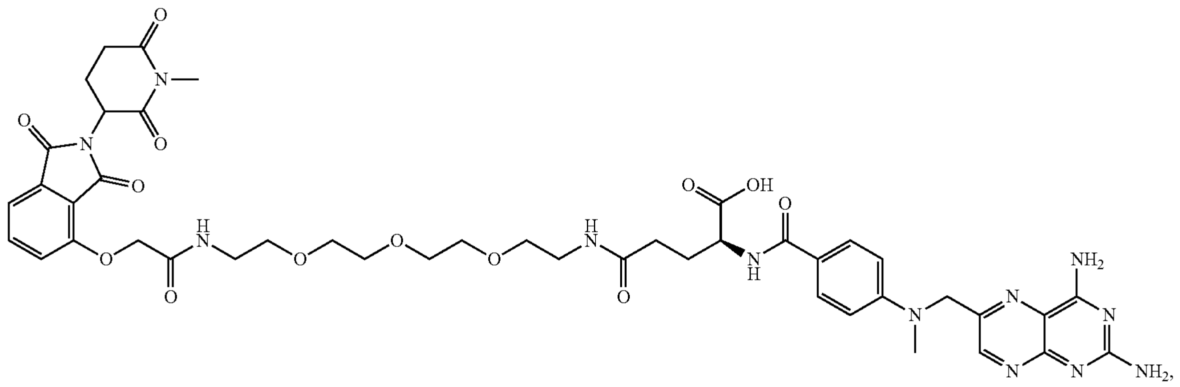
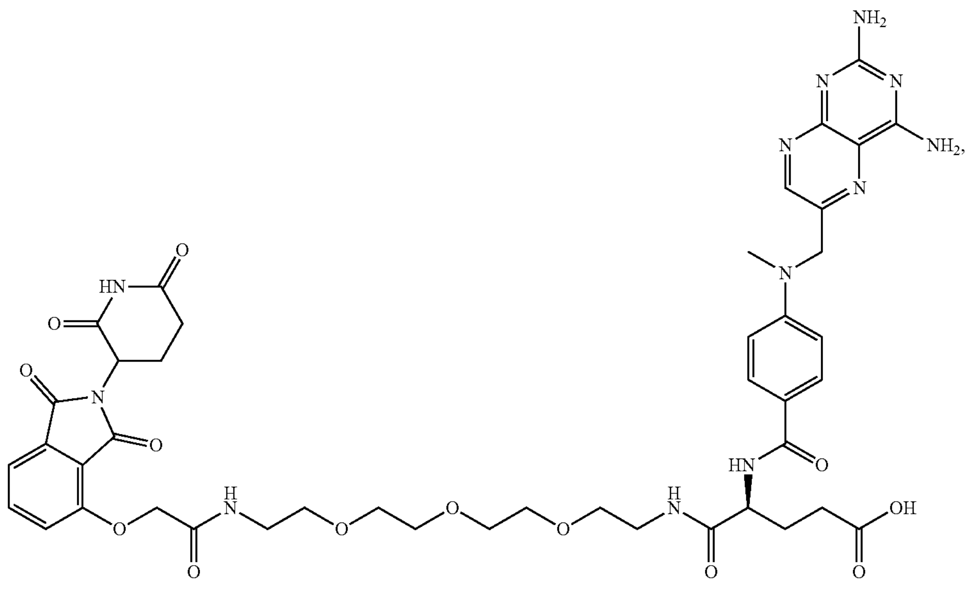

-continued
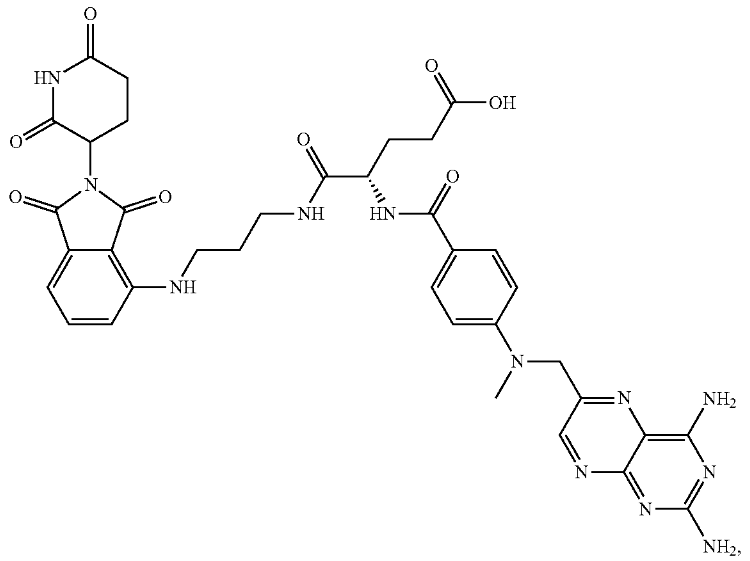
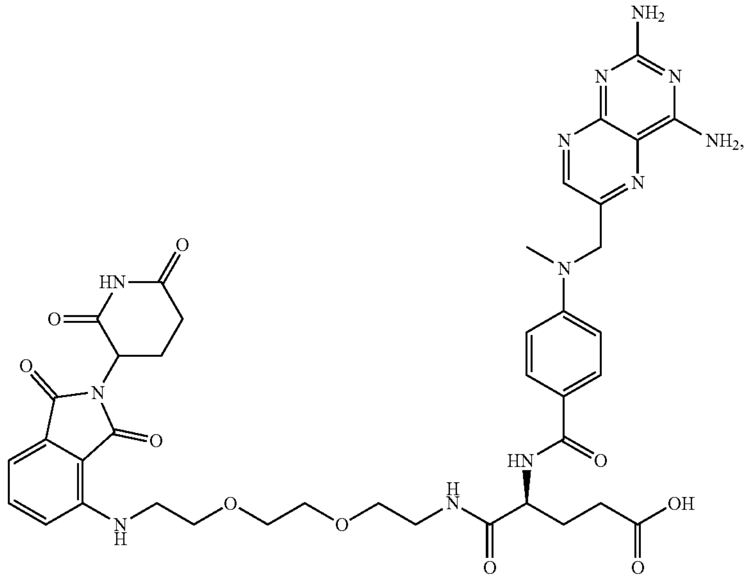

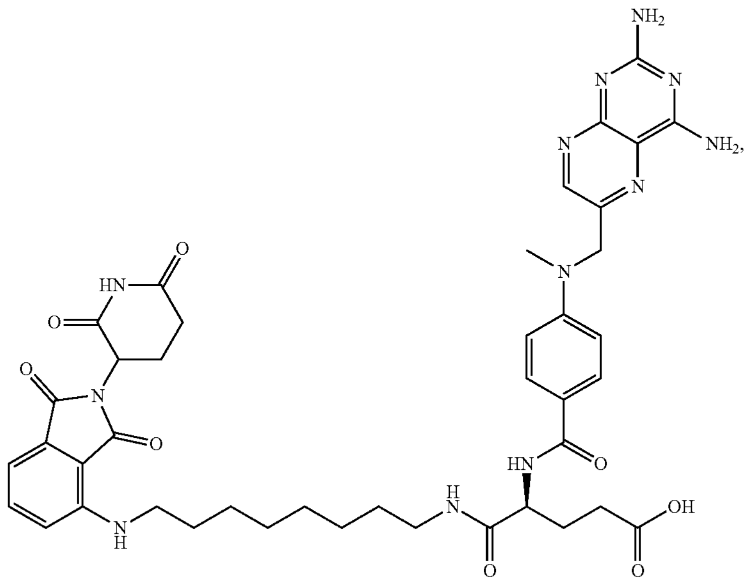
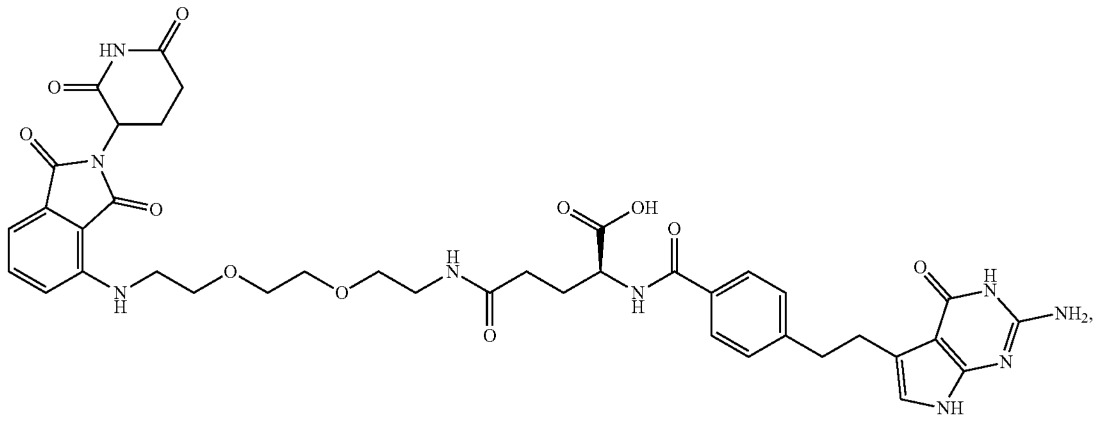
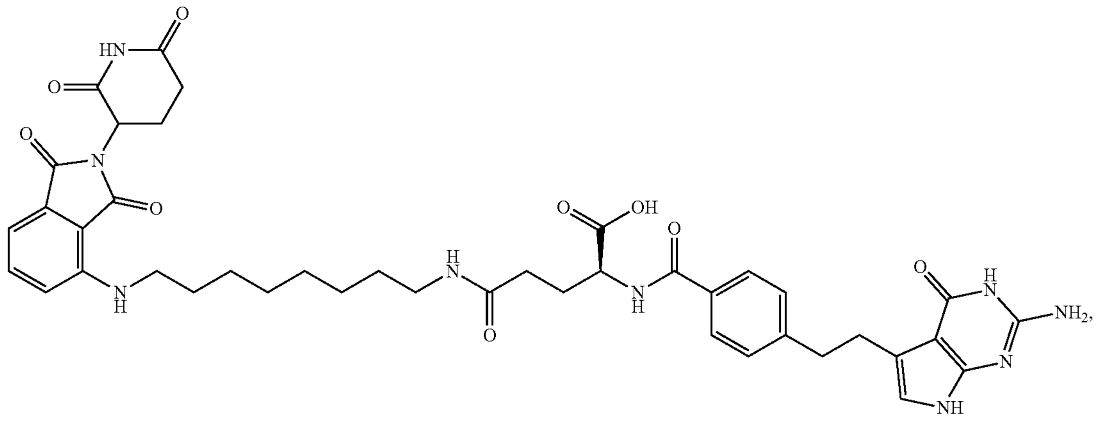

-continued
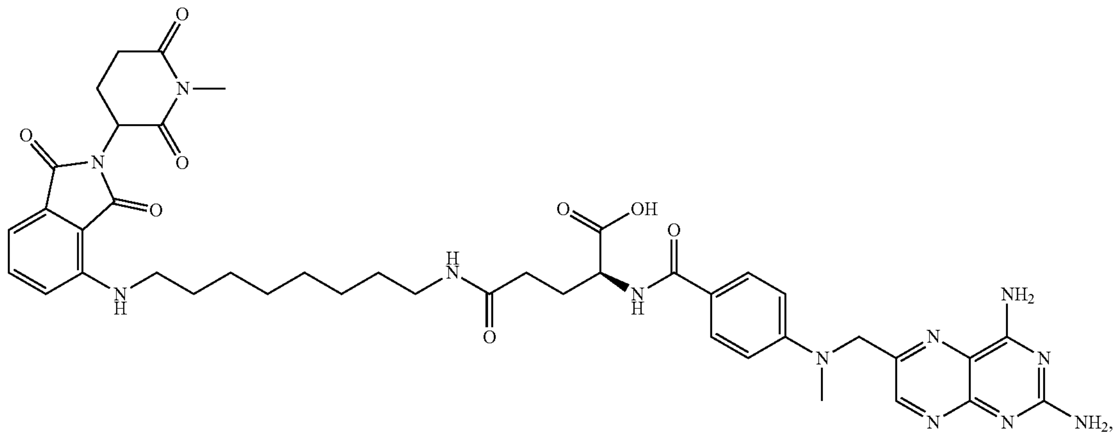
,
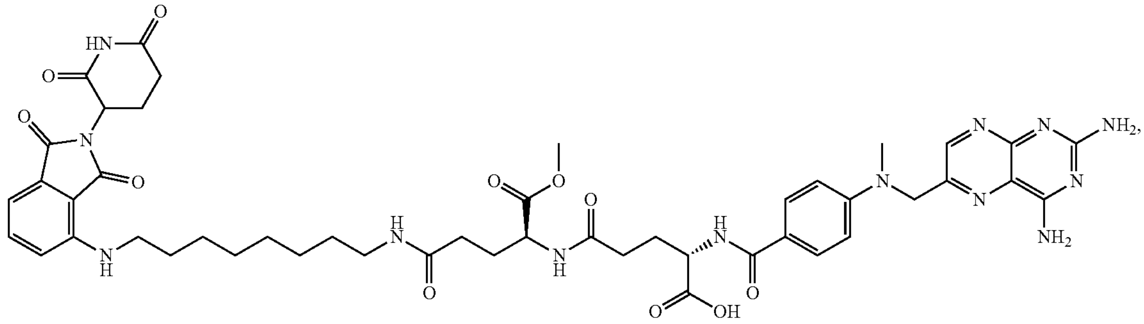
,
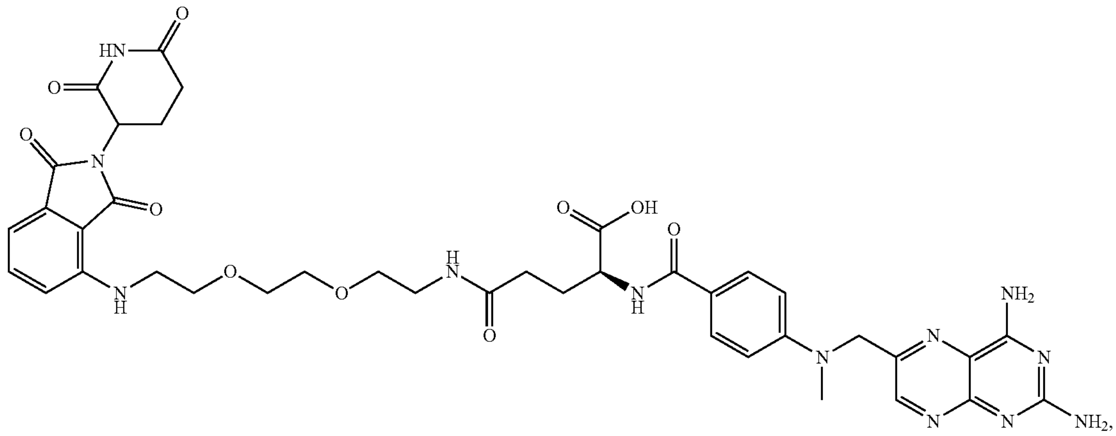
,
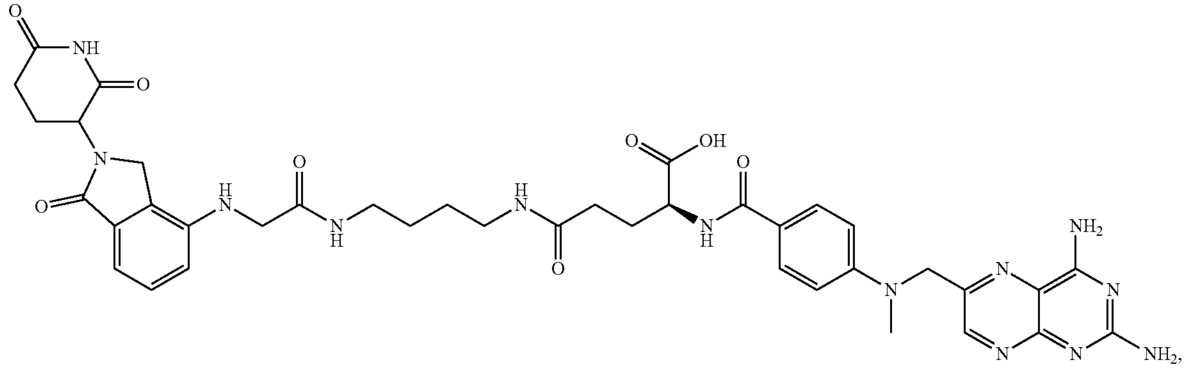
,

-continued
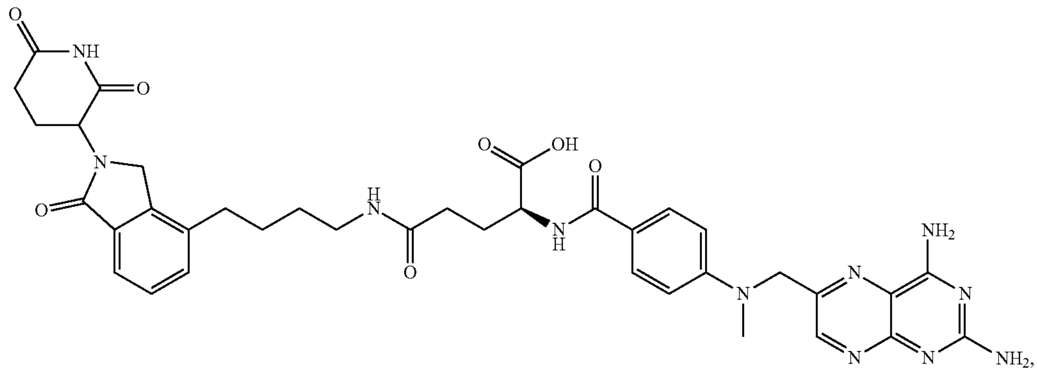
,
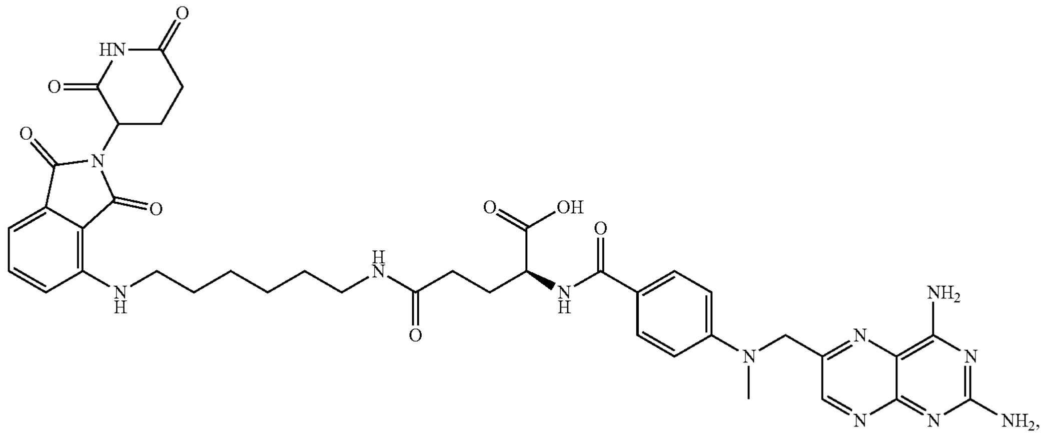
,
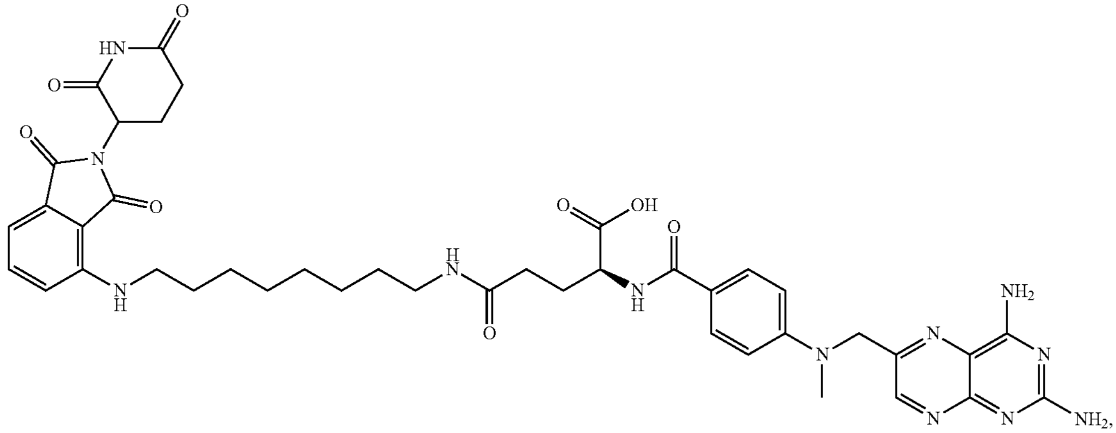
,
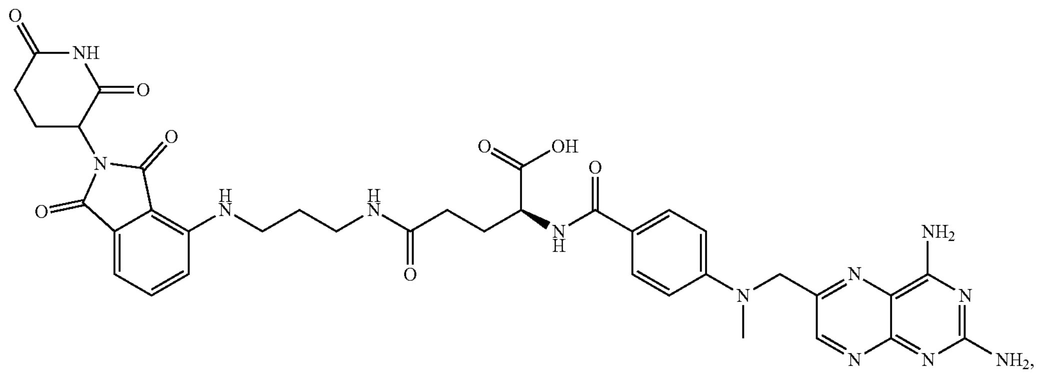
,

-continued
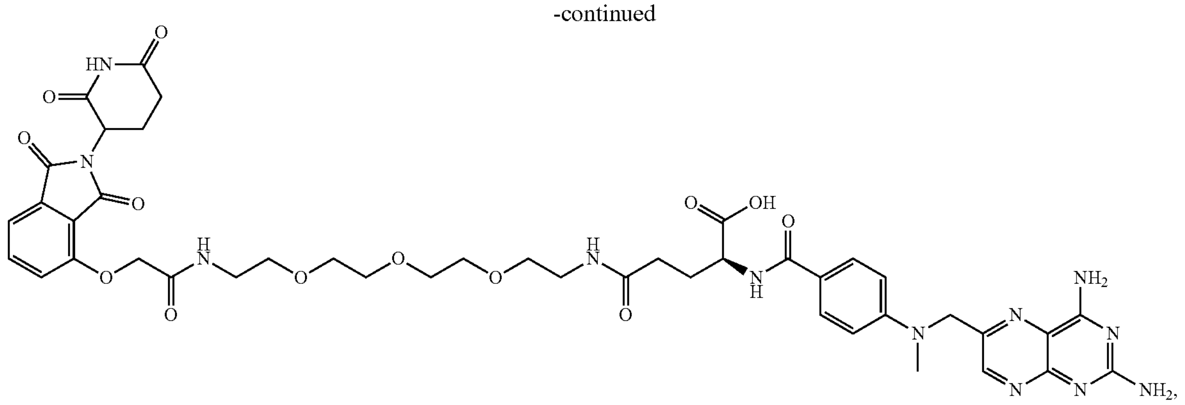
or a pharmaceutically acceptable salt, N-oxide, or hydrate thereof.
15. A pharmaceutical composition, comprising a compound according to claim 1, and a pharmaceutically acceptable excipient.
16. A method of treating a subject with leukemia, comprising administering to the subject an effective amount of the compound of claim 1.
17. A compound selected from:
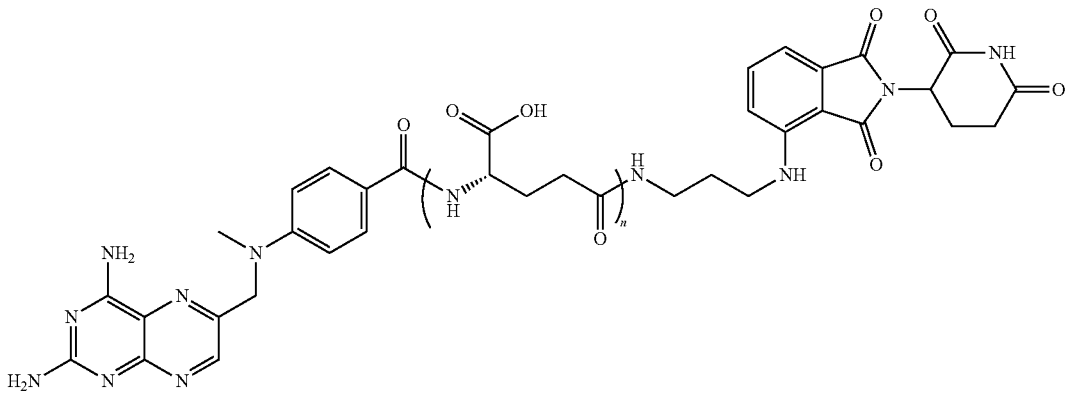
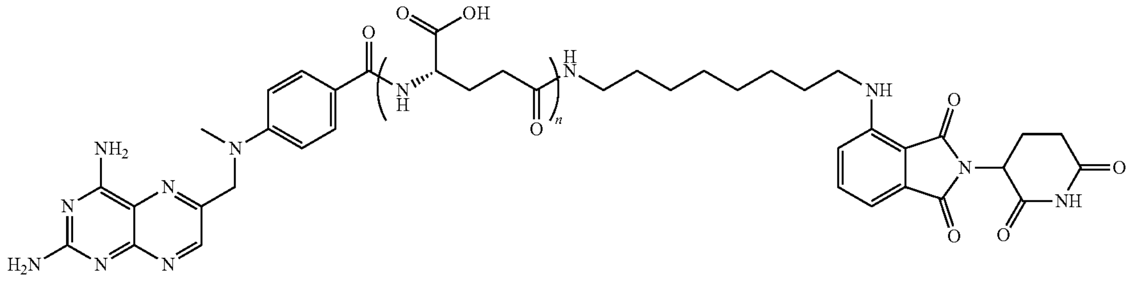
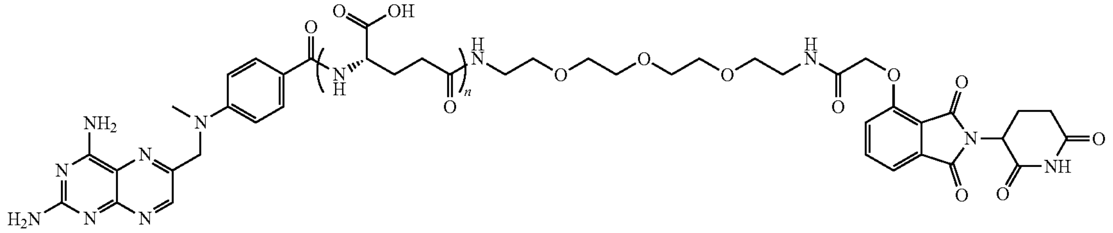

-continued
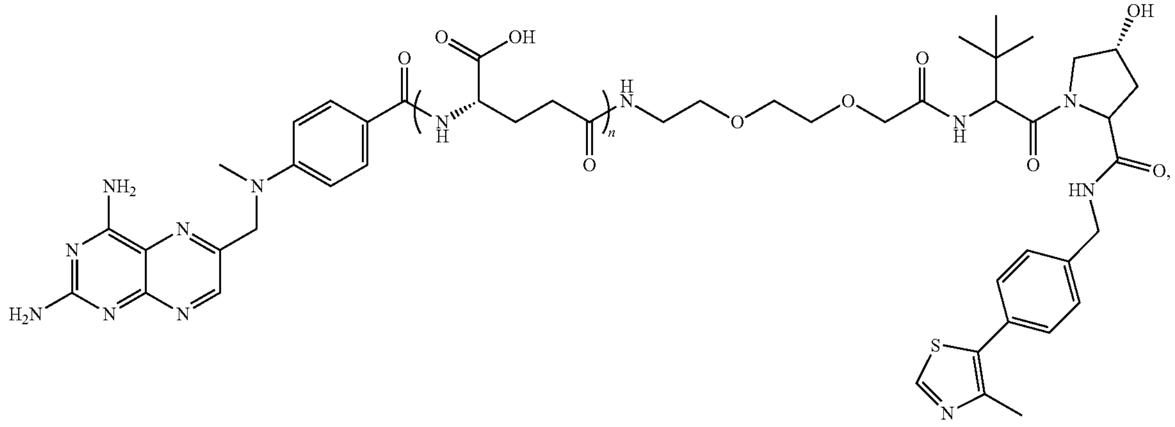
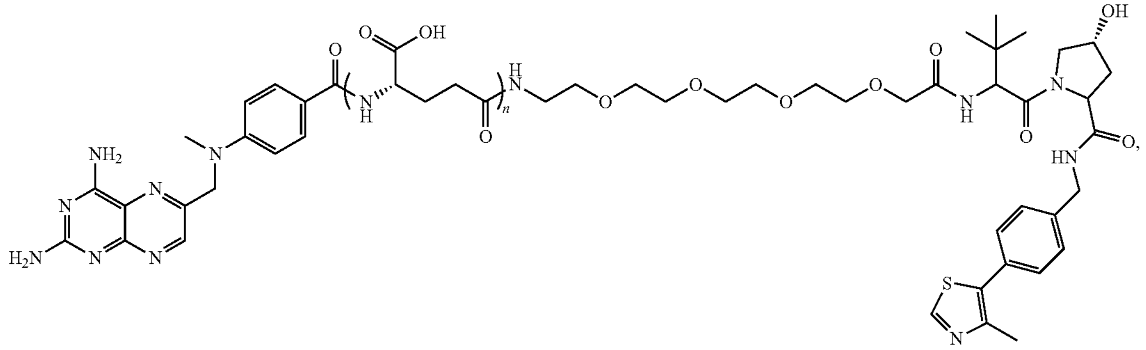
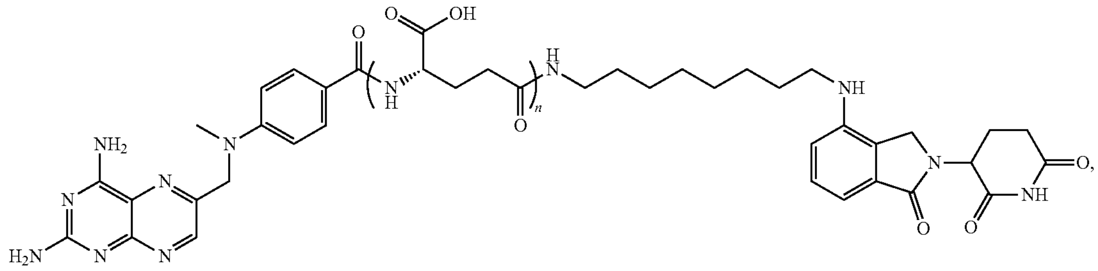
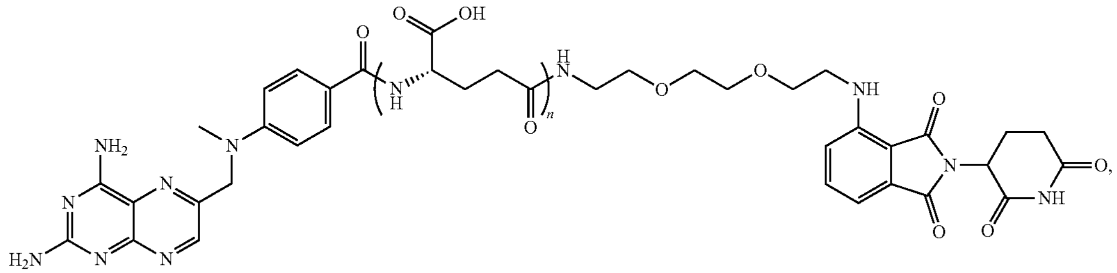
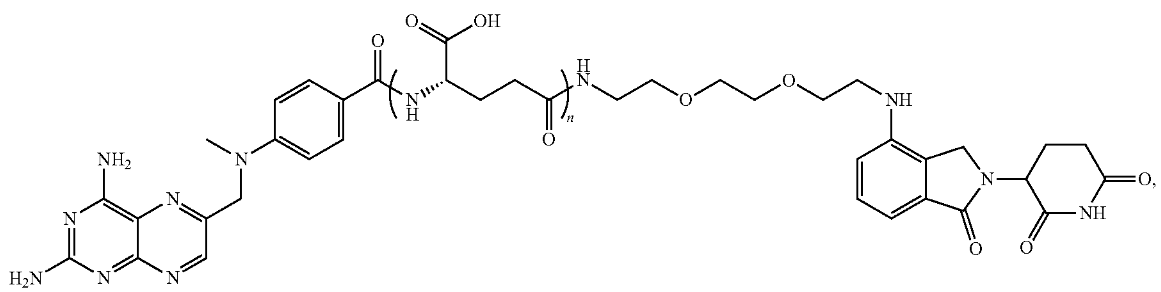

-continued
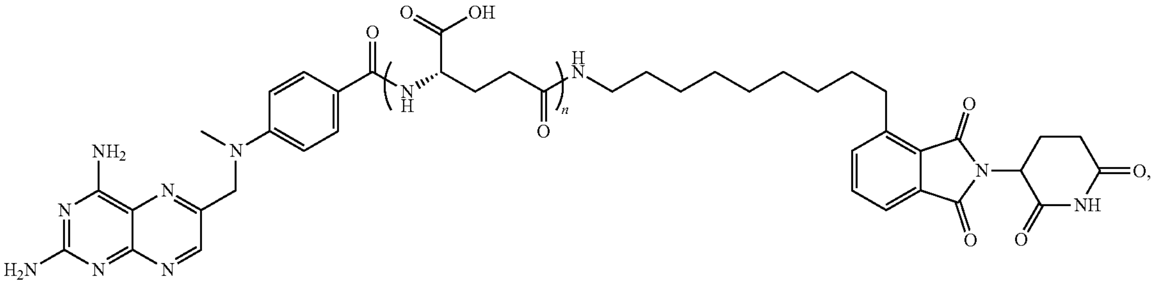
,
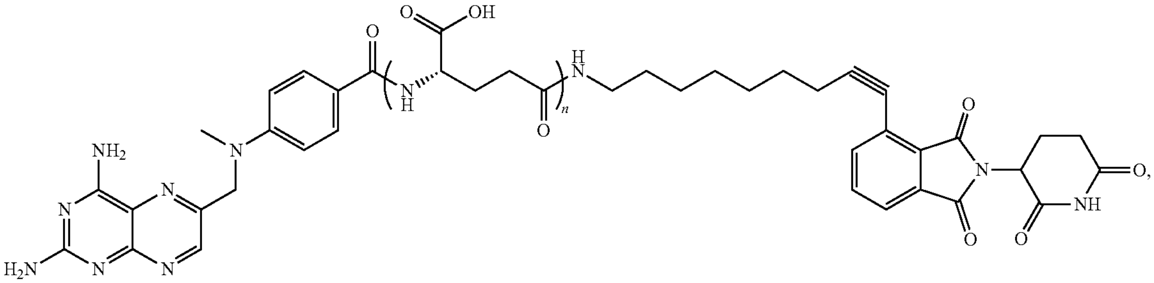
,
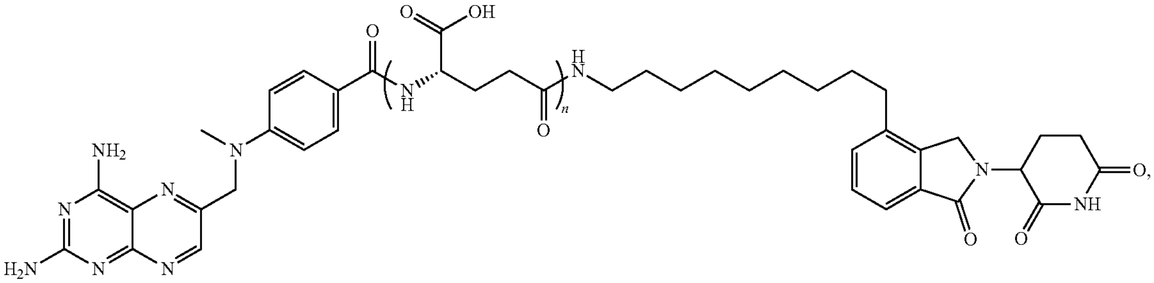
,
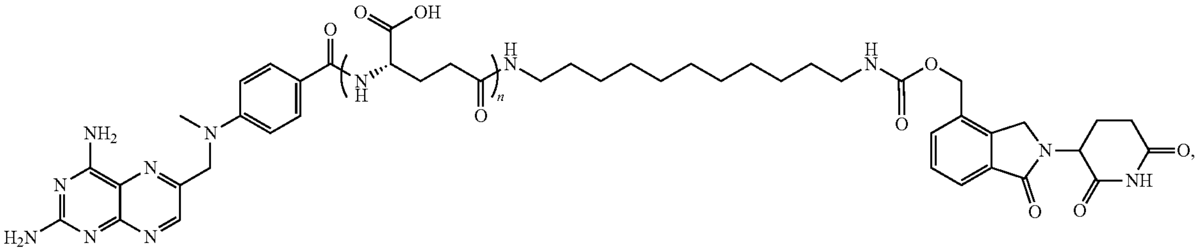
,
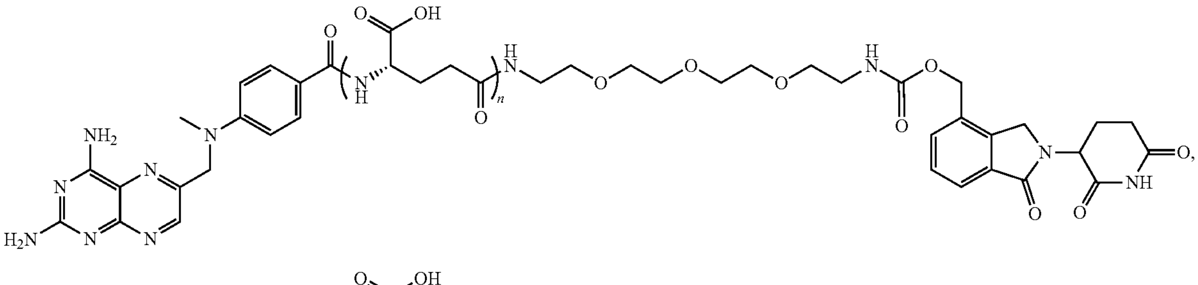
,
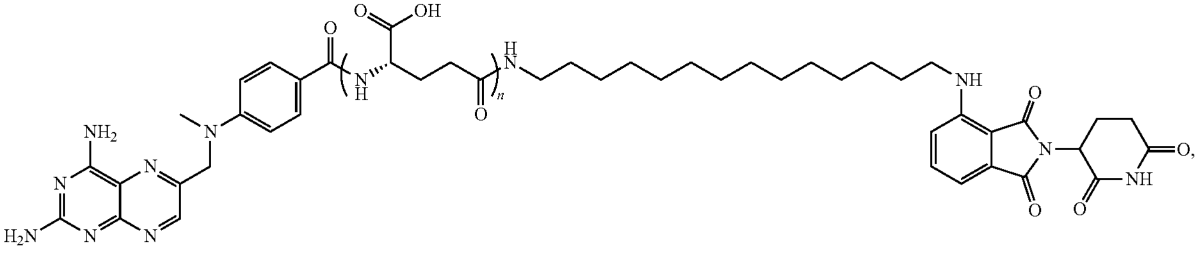
, -continued
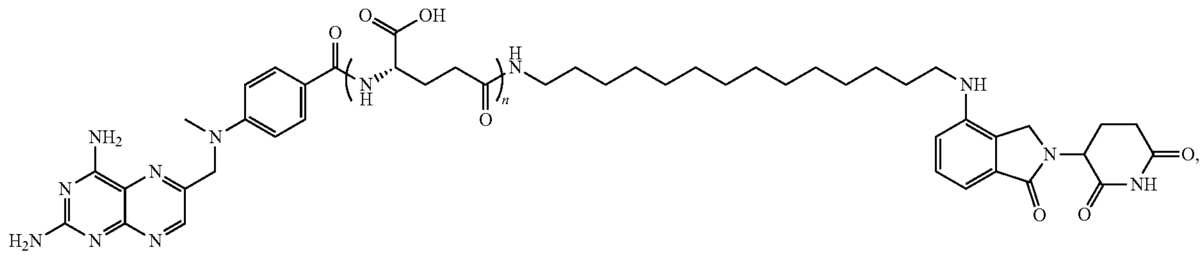
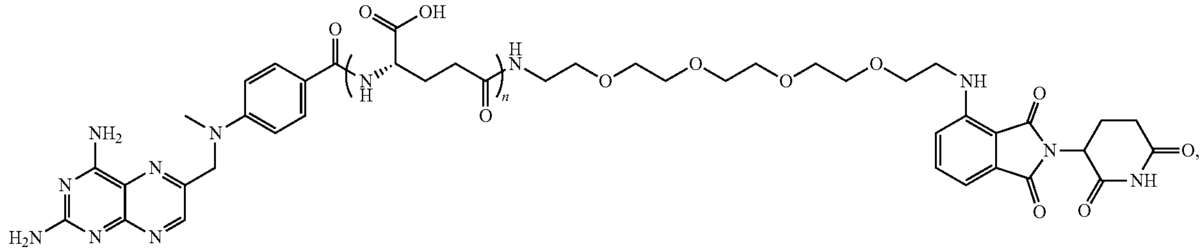
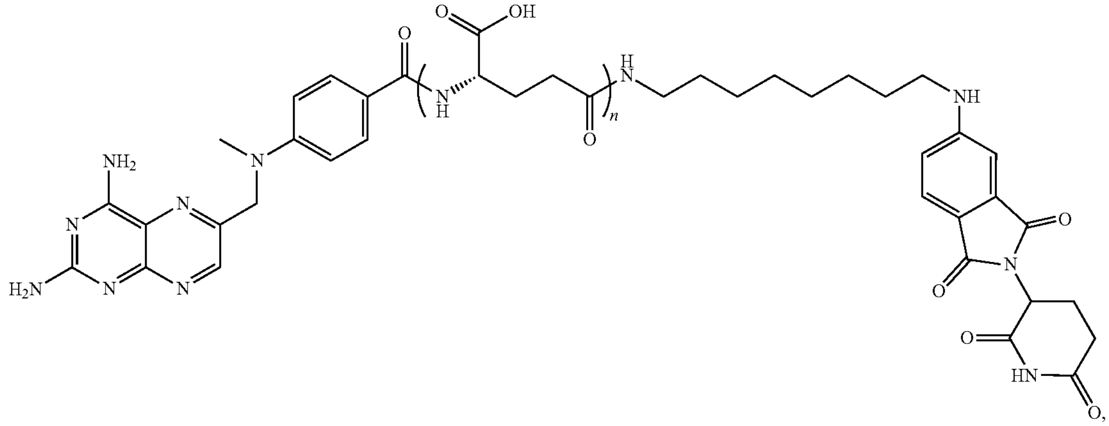
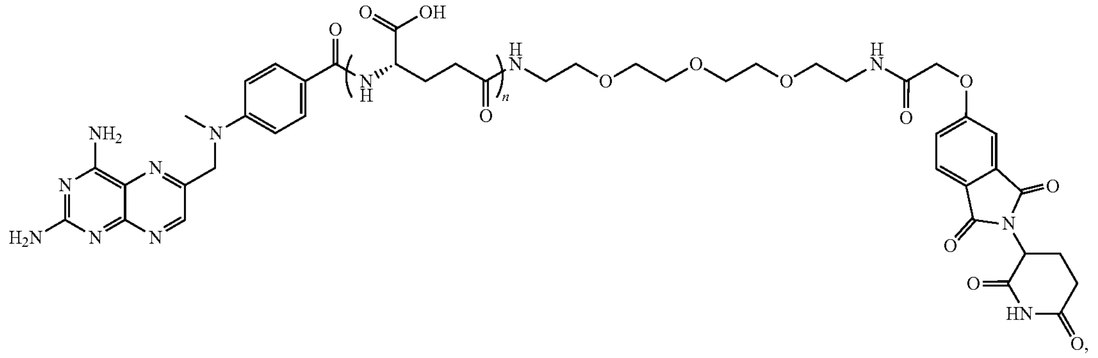
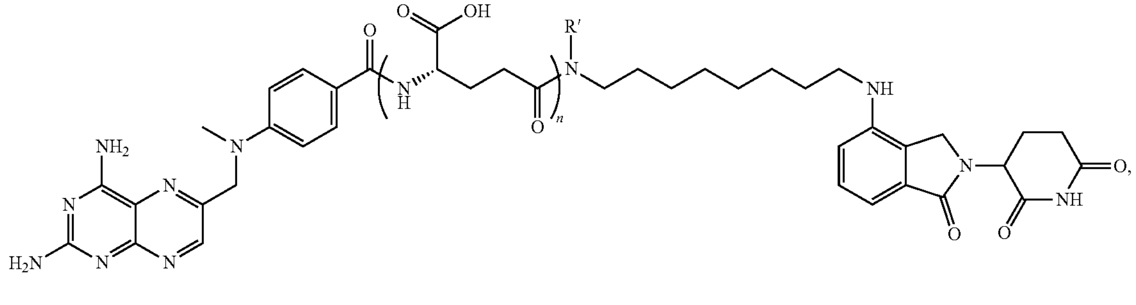

-continued
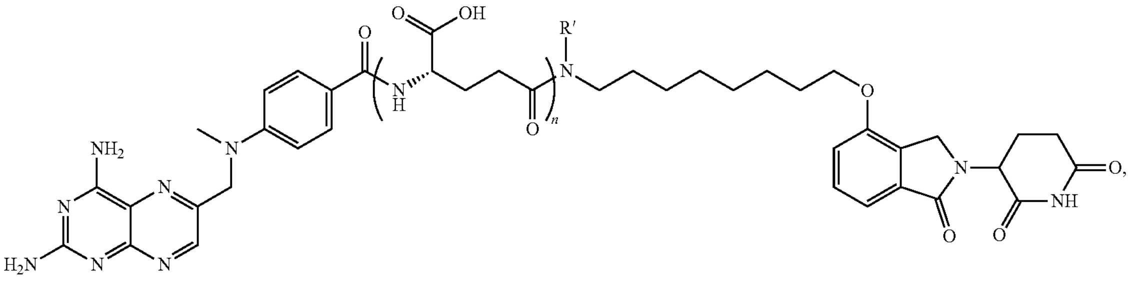
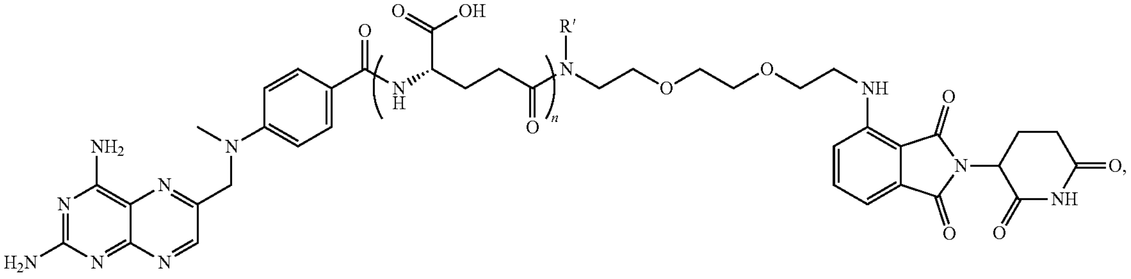
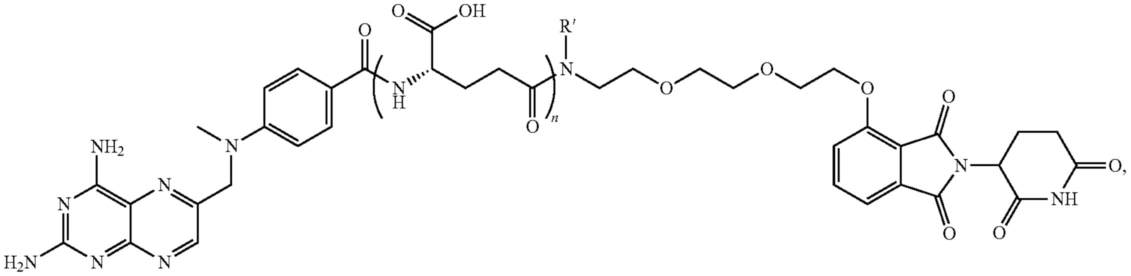
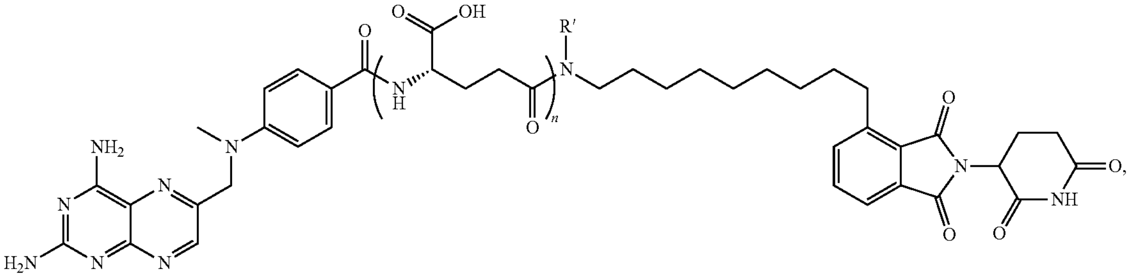
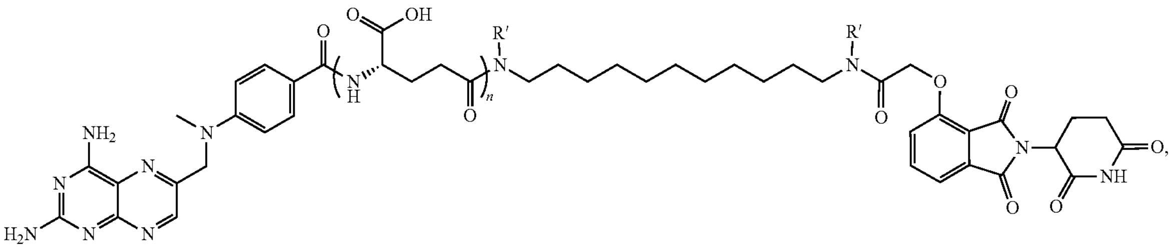
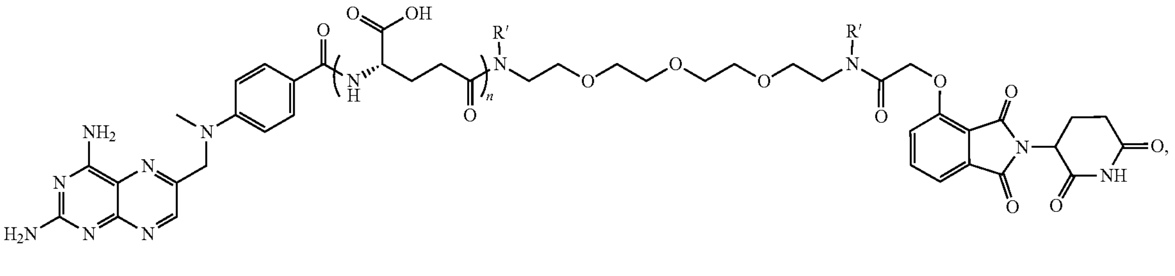

-continued
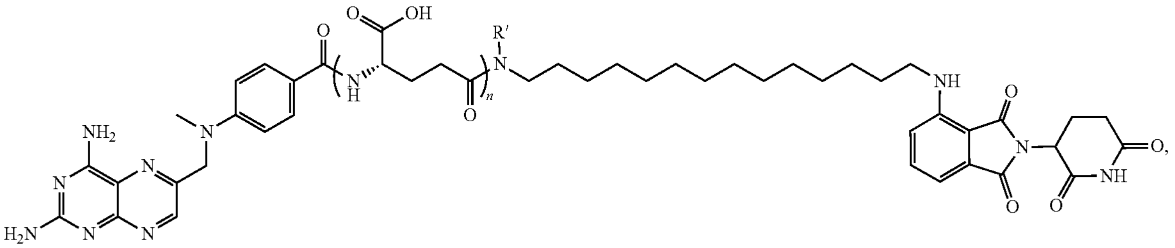
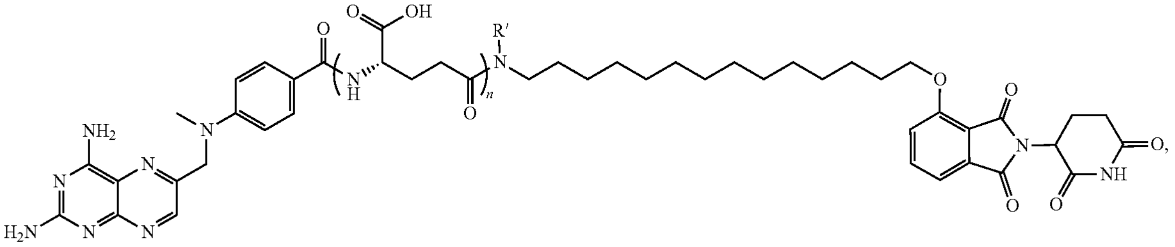
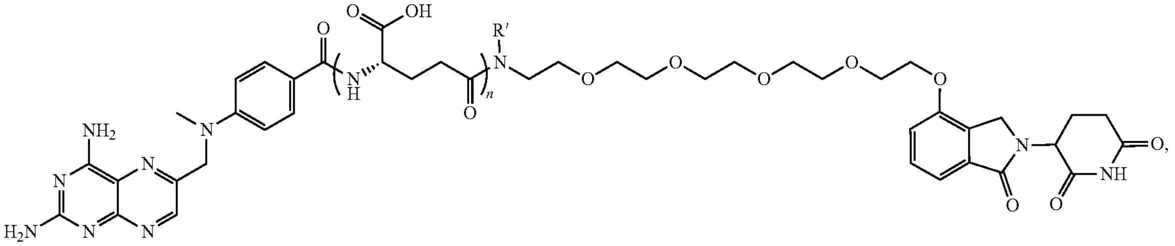
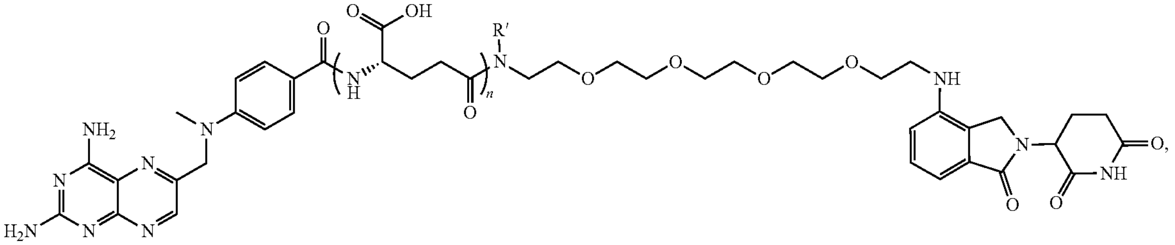
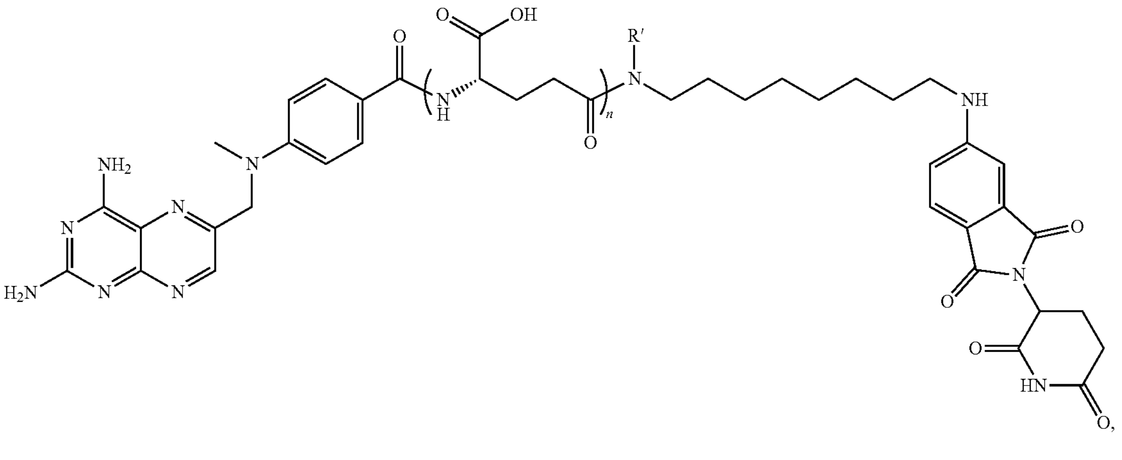
or

-continued
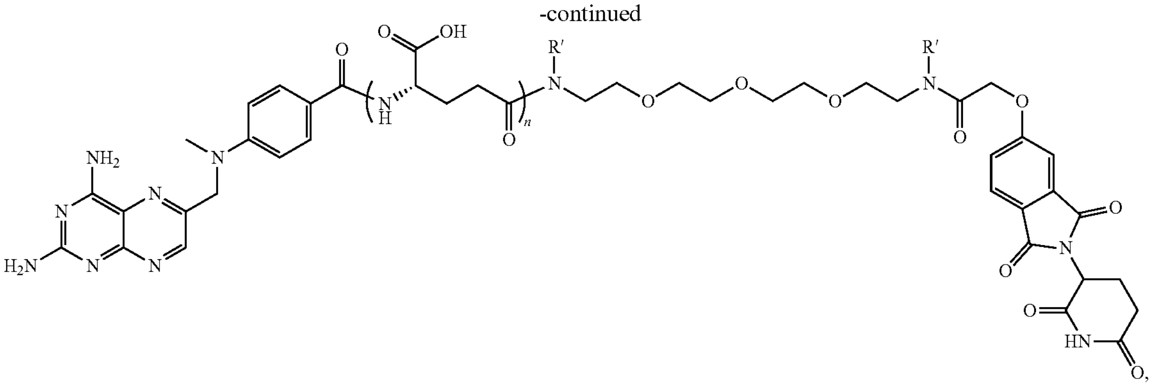
or a pharmaceutically acceptable salt, N-oxide, or hydrate thereof, wherein:
each R' independently is H, methyl, ethyl, n-propyl, or isopropyl, and at least one R' is not H; and
n is 1, 2, 3, 4, or 5.
* * * * *